(12) United States Patent
Coelho et al.

(10) Patent No.: US 10,202,620 B2
(45) Date of Patent: Feb. 12, 2019

(54) SYNTHESIS OF OLEFINIC ALCOHOLS VIA ENZYMATIC TERMINAL HYDROXYLATION

(71) Applicant: PROVIVI, INC., Santa Monica, CA (US)

(72) Inventors: Pedro Coelho, Santa Monica, CA (US); Mike M. Y. Chen, Santa Monica, CA (US); Peter Meinhold, Santa Monica, CA (US); Catherine Mee-Hie Cho, Santa Monica, CA (US); Vu Bui, Santa Monica, CA (US); Thomas Heel, Santa Monica, CA (US)

(73) Assignee: PROVIVI, INC., Santa Monica, CA (US)

( * ) Notice: Subject to any disclaimer, the term of this patent is extended or adjusted under 35 U.S.C. 154(b) by 0 days.

(21) Appl. No.: 14/845,212

(22) Filed: Sep. 3, 2015

(65) Prior Publication Data
US 2016/0108436 A1    Apr. 21, 2016

Related U.S. Application Data

(63) Continuation of application No. PCT/US2015/031219, filed on May 15, 2015.

(60) Provisional application No. 61/994,662, filed on May 16, 2014, provisional application No. 62/060,469, filed on Oct. 6, 2014, provisional application No. 62/062,758, filed on Oct. 10, 2014, provisional application No. 62/082,555, filed on Nov. 20, 2014, provisional application No. 62/096,417, filed on Dec. 23, 2014, provisional application No. 62/096,429, filed on Dec. 23, 2014.

(51) Int. Cl.

| | | |
|---|---|---|
| *C12P 7/04* | (2006.01) | |
| *C12P 33/06* | (2006.01) | |
| *C07C 29/32* | (2006.01) | |
| *C07C 67/14* | (2006.01) | |
| *C07C 45/29* | (2006.01) | |
| *C07C 51/235* | (2006.01) | |
| *C07C 1/34* | (2006.01) | |
| *C07C 2/86* | (2006.01) | |
| *C07C 5/09* | (2006.01) | |
| *C07C 6/04* | (2006.01) | |
| *C12P 5/02* | (2006.01) | |
| *C12P 7/64* | (2006.01) | |
| *C12N 9/02* | (2006.01) | |
| *C12N 9/10* | (2006.01) | |

(52) U.S. Cl.
CPC  *C12P 7/04* (2013.01); *C07C 1/34* (2013.01); *C07C 2/861* (2013.01); *C07C 5/09* (2013.01); *C07C 6/04* (2013.01); *C07C 29/32* (2013.01); *C07C 45/29* (2013.01); *C07C 51/235* (2013.01); *C07C 67/14* (2013.01); *C12P 5/026* (2013.01); *C12P 7/6418* (2013.01); *C07C 2523/44* (2013.01); *C07C 2531/22* (2013.01); *C07C 2531/24* (2013.01)

(58) Field of Classification Search
CPC ..... C07C 29/32; C07C 67/14; C07C 2531/24; C07C 1/34; C12P 7/04
USPC .................. 435/157, 135; 560/233
See application file for complete search history.

(56) References Cited

U.S. PATENT DOCUMENTS

| | | |
|---|---|---|
| 4,455,373 A | 6/1984 | Higgins |
| 4,473,643 A | 9/1984 | Higgins |
| 5,104,504 A | 4/1992 | Tanaka et al. |
| 5,593,872 A | 1/1997 | Gabelman et al. |
| 5,783,429 A | 7/1998 | Gabelman et al. |
| 6,034,028 A | 3/2000 | Hayashi et al. |
| 6,215,019 B1 | 4/2001 | Pederson et al. |
| 6,331,420 B1 | 12/2001 | Wilson et al. |
| 6,540,991 B2 | 4/2003 | Klassen et al. |

(Continued)

FOREIGN PATENT DOCUMENTS

| | | |
|---|---|---|
| EP | 2 617 703 A1 | 7/2013 |
| WO | 00/002837 A1 | 1/2000 |

(Continued)

OTHER PUBLICATIONS

Devos et al., (Proteins: Structure, Function and Genetics, 2000, vol. 41: 98-107).*

(Continued)

*Primary Examiner* — Robert B Mondesi
*Assistant Examiner* — Mohammad Y Meah
(74) *Attorney, Agent, or Firm* — Kilpatrick Townsend & Stockton LLP

(57) ABSTRACT

In certain aspects, the present invention provides methods for producing terminally hydroxylated alkenes and alkynes by contacting an unsaturated or saturated hydrocarbon substrate with a hydroxylase enzyme. Exemplary terminal hydroxylases useful for carrying out the methods of the invention exhibit strong selectivity towards one terminal carbon of a hydrocarbon substrate and include, but are not limited to, non-heme diiron alkane monooxygenases, cytochromes P450 (e.g., cytochromes P450 of the CYP52 and CYP153 family), as well as long chain alkane hydroxylases. In some embodiments, the terminally hydroxylated alkene or alkyne is further converted to a terminal alkenal. In certain embodiments, terminally hydroxylated alkenes and alkynes are useful as insect pheromones which modify insect behavior. In other embodiments, terminally hydroxylated alkenes and alkynes are useful intermediates for producing pheromones via acetylation or oxidation of the alcohol moiety.

19 Claims, 2 Drawing Sheets
Specification includes a Sequence Listing.

(56) References Cited

U.S. PATENT DOCUMENTS

| | | |
|---|---|---|
| 7,405,063 B2 | 7/2008 | Eirich et al. |
| 7,524,664 B2 | 4/2009 | Arnold et al. |
| 8,143,034 B2 | 3/2012 | Gross et al. |
| 8,158,391 B2 | 4/2012 | Gross et al. |
| 8,309,333 B1 | 11/2012 | Koch et al. |
| 8,361,769 B1 | 1/2013 | Koch et al. |
| 8,597,923 B2 | 12/2013 | Ness et al. |
| 2002/0022741 A1 | 2/2002 | Pederson et al. |
| 2002/0146387 A1 | 10/2002 | Klassen et al. |
| 2003/0022947 A1 | 1/2003 | McAtee et al. |
| 2007/0142680 A1 | 6/2007 | Ayoub et al. |
| 2008/0057577 A1 | 3/2008 | Arnold et al. |
| 2009/0054610 A1 | 2/2009 | Gross et al. |
| 2009/0137850 A1 | 5/2009 | Yanagawa et al. |
| 2012/0271085 A1 | 10/2012 | Nesterenko et al. |
| 2013/0085288 A1 | 4/2013 | Snead et al. |
| 2013/0274529 A1 | 10/2013 | Del Cardayre |
| 2014/0004598 A1 | 1/2014 | Picataggio et al. |
| 2014/0186905 A1 | 7/2014 | Schaffer et al. |
| 2015/0010968 A1 | 1/2015 | Engel et al. |

FOREIGN PATENT DOCUMENTS

| | | |
|---|---|---|
| WO | 2011/008232 A2 | 1/2011 |
| WO | 2014/079683 A1 | 5/2014 |
| WO | 2014/201474 A1 | 12/2014 |
| WO | 2015/014644 A1 | 2/2015 |

OTHER PUBLICATIONS

Witkowski et al., (Biochemistry 38:11643-11650, 1999.*
Kisselev L., (Structure, 2002, vol. 10: 8-9.*
Whisstock et al., (Quarterly Reviews of Biophysics 2003, vol. 36 (3): 307-340.*
Catterjee etal. JACS 2003, 125, p. 11360-11370.*
Abghari, A. and Chen, S., "Yarrowia lipolytica as an oleaginous cell factory platform for the production of fatty acid-based biofuel and bioproducts," Front. Energy Res. 2(2):1-21, 2014.
Abramovitch, R. et al., "1,2-Benzisothiazole 1,1-dioxide: a convenient synthesis. The question of the possible aromaticity of 1,2-benzothiazepine 1,1-dioxides," J. Chem. Soc., Chem. Commun., 520-521, 1983.
Albrecht, M. et al., "Expression of a ketolase gene mediates the synthesis of canthaxanthin in Synechococcus leading to tolerance against photoinhibition, pigment degradation and UV-B sensitivity of photosynthesis," Photochem Photobiol, 73(5):551-555, 2001.
Ando, T. et al., "Insecticidal activity of new fluorinated pyrethroids and their stability toward chemical oxidation and photoreaction," Pestic. Sci., 40:307-312, 1994.
Andrus, M. and Zhou, Z., "Highly Enantioselective Copper-Bisoxazoline-Catalyzed Allylic Oxidation of Cyclic Olefins with tert-Butyl p-nitroperbenzoate," J. Am. Chem. Soc., 124:8806-8807, 2002.
Arterburn, J., "Selective oxidation of secondary alcohols," Tetrahedron, 57(49), 9765-9788, 2001.
Bae, J. et al., "Development of a recombinant *Escherichia coli*-based biocatalyst to enable high styrene epoxidation activity with high product yield on energy source," Process Biochem., 45:147-152, 2010.
Balasubramanian, R. et al., "Oxidation of methane by a biological dicopper centre," Nature, 465:115-119, 2010.
Baldwin, C. and Woodley, J., "On oxygen limitation in a whole cell biocatalytic Baeyer-Villiger oxidation process," Biotechnol. Bioeng., 95:362-369, 2006.
Banthorpe, D., "Purification and properties of alcohol oxidase from Tanacetum vulgare," Phytochemistry, 15:391-394, 1976.
Beier, A. et al., "Metabolism of alkenes and ketones by Candida maltosa and related yeasts," AMB Express, 4:75, 2014.
Bell, S. et al., "Butane and propane oxidation by engineered cytochrome P450cam," Chem. Commun., 490-491, 2002.
Boddupalli, S. et al., "Fatty acid monooxygenation by cytochrome P-450BM-3," J. Biol. Chem., 265:4233-4239, 1990.
Boetius, A. et al., "A marine microbial consortium apparently mediating anaerobic oxidation of methane," Nature, 407:623-626, 2000.
Bogdan, A. and McQuade, D., "A biphasic oxidation of alcohols to aldehydes and ketones using a simplified packed-bed microreactor," Beilstein Journal of Organic Chemistry, 5:17, 2009.
Boll, M. et al., "Anaerobic oxidation of aromatic compounds and hydrocarbons," Curr. Opin. Chem. Biol., 6:604-611, 2002.
Bordeaux, M. et al., "A Regioselective Biocatalyst for Alkane Activation under Mild Conditions," Angew. Chemie-International Ed, 50:2075-2079, 2011.
Bordeaux, M. et al., "Catalytic, mild, and selective oxyfunctionalization of linear alkanes: current challenges," Angew Chem Int Ed Engl, 51:10712-10723, 2012.
Bosetti, A. et al., "Production of primary aliphatic alcohols with a recombinant Pseudomonas strain, encoding the alkane hydroxylase enzyme system," Enzym. Microb. Technol., 14:702-708, 1992.
Braun, A. et al., "Steroid biotransformation in biphasic systems with Yarrowia lipolytica expressing human liver cytochrome P450 genes," Microb. Cell Fact., 11:106, 2012.
Bronner, S. et al., "Ru-based Z-selective metathesis catalysts with modified cyclometalated carbene ligands," Chem Sci, 5:4091-4098, 2014.
Buck, M. and Chong, J., "Alkylation of 1-alkynes in THF," Tetrahedron Lett, 42:5825-5827, 2001.
Buhler, B. and Schmid, A., "Process implementation aspects for biocatalytic hydrocarbon oxyfunctionalization," J. Biotechnol., 113:183-210, 2004.
Cannon, J. and Grubbs, R., "Alkene Chemoselectivity in Ruthenium-Catalyzed Z-Selective Olefin Metathesis," Angew Chemie Int Ed, 52:9001-9004, 2013.
Cao, Z. et al., "Engineering the acetyl-CoA transportation system of candida tropicalis enhances the production of dicarboxylic acid," Biotechnol. J., 1:68-74, 2006.
Cappaert, L. and Larroche, C., "Oxidation of a mixture of 2-(R) and 2-(S)-heptanol to 2-heptanone by *Saccharomyces cerevisiae* in a biphasic system," Biocatal. Biotransformation, 22:291-296, 2004.
Cappelletti, M. et al., "Analyses of both the alkB Gene Transcriptional Start Site and alkB Promoter-Inducing Properties of *Rhodococcus* sp Strain BCP1 Grown on n-Alkanes," Appl. Environ. Microbiol., 77(5):1619-1627, 2011.
Cardemil, E., "Alcohol-oxidizing enzymes from various organisms," Comp Biochem Physiol B, 60B:1-7, 1978.
Caron, S. et al., "Large-Scale Oxidations in the Pharmaceutical Industry," Chemical Reviews, 106(7):2943-2989, 2006.
Chatterjee, A. et al., "A general model for selectivity in olefin cross metathesis," Journal of the American Chemical Society, 125(37):11360-11370, 2003.
Chen, M. and White, M., "A Predictably Selective Aliphatic C—H Oxidation Reaction for Complex Molecule Synthesis," Science, 318:783-787, 2007.
Chen, M. et al., "Utilizing Terminal Oxidants to Achieve P450-Catalyzed Oxidation of Methane," Adv. Synth. Catal., 354:964-968, 2012.
Cheng, Q. et al., "*Candida* yeast long chain fatty alcohol oxidase is a c-type haemoprotein and plays an important role in long chain fatty acid metabolism," Biochim et Biophysica Acta, 1735:192-203, 2005.
Cheng, Q. et al., "Functional identification of AtFao3, a membrane bound long chain alcohol oxidase in *Arabidopsis thaliana*," FEBS Lett, 574:62-68, 2004.
Chrobok, A. et al., "Supported ionic liquid phase catalysis for aerobic oxidation of primary alcohols," Applied Catalysis, A: General, 389(1-2):179-185, 2010.
Ciriminna, R. and Pagliaro, M., "Industrial Oxidations with Organocatalyst TEMPO and Its Derivatives," Organic Process Research & Development, 14(1):245-251, 2010.
Cornelissen, S. et al., "Cell physiology rather than enzyme kinetics can determine the efficiency of cytochrome P450-catalyzed C—H oxyfunctionalization," J. Ind. Microbiol. Biotechnol., 38:1359-1370, 2011.

(56) References Cited

OTHER PUBLICATIONS

Cornelissen, S. et al., "Whole-cell-based CYP153A6-catalyzed (S)-limonene hydroxylation efficiency depends on host background and profits from monoterpene uptake via AlkL," Biotechnology and Bioengineering, 110:1282-1292, 2013.
Craft, D. et al., "Identification and Characterization of the CYP52 Family of Candida tropicalis ATCC 20336, Important for the Conversion of Fatty Acids and Alkanes to α,ω-Dicarboxylic Acids," Appl. Environ. Microbiol., 69(10):5983-5991, 2003.
Crow, J., "Dichlorodihydrofluorescein and dihydrorhodamine 123 are sensitive indicators of peroxynitrite in vitro: implications for intracellular measurement of reactive nitrogen and oxygen species," Nitric Oxide: Biology and Chemistry, 1(2):145-157, 1997.
D'Acunzo, F. et al., "A mechanistic survey of the oxidation of alcohols and ethers with the enzyme laccase and its mediation by TEMPO," European Journal of Organic Chemistry, 24:4195-4201, 2002.
Daff, S. et al., "Redox control of the catalytic cycle of flavocytochrome P-450 BM3," Biochemistry, 36:13816-13823, 1997.
De Smidt, O. et al., "The alcohol dehydrogenases of Saccharomyces cerevisiae: a comprehensive review," FEMS Yeast Res, 8:967-978, 2008.
Dellomonaco, C. et al., "Engineered reversal of the β-oxidation cycle for the synthesis of fuels and chemicals," Nature, 476:355-359, 2011.
Dickinson, F. and Dack, S., "The activity of yeast ADH I and ADH II with long-chain alcohols and diols," Chem. Biol. Interact., 130-132:417-423, 2001.
Dickinson, F. and Wadforth, C., "Purification and some properties of alcohol oxidase from alkane-grown candida-tropicalis," Biochem. J., 282:325-331, 1992.
Dong, Y. et al., "Engineering of LadA for enhanced hexadecane oxidation using random- and site-directed mutagenesis," Appl. Microbiol. Biotechnol., 94:1019-1029, 2012.
Duff, S. and Murray W., "Production and application of methylotrophic yeast Pichia-pastoris," Biotechnol Bioeng, 31:44-49, 1988.
Eirich, L. et al., "Cloning and characterization of three fatty alcohol oxidase genes from Candida tropicalis strain ATCC 20336," Appl Environ Microbiol, 70(8):4872-4879, 2004.
Endo, K. and Grubbs, R., "Chelated ruthenium catalysts for Z-selective olefin metathesis," J Am Chem Soc, 133(22):8525-8527, 2011.
Ernst, M. et al., "Enantioselective reduction of carbonyl compounds by whole-cell biotransformation, combining a formate dehydrogenase and a (R)-specific alcohol dehydrogenase," Appl Microbiol Biotechnol, 66:629-634, 2005.
Eschenfeldt, W. et al., "Transformation of fatty acids catalyzed by cytochrome P450 monooxygenase enzymes of Candida tropicalis," Appl. Environ. Microbiol. 69(10):5992-5999, 2003.
Farinas, E. et al., "Alkene epoxidation catalyzed by cytochrome P450 BM-3 139-3," Tetrahedron, 60:525-528, 2004.
Farinas, E. et al., "Directed evolution of a cytochrome P450 monooxygenase for alkane oxidation," Advanced Synth. Catal., 343:601-606, 2001.
Fasan, R., "Tuning P450 Enzymes as Oxidation Catalysts," ACS Catal., 2:647-666, 2012.
Favre-Bulle, O. and Witholt, B., "Biooxidation of n-octane by a recombinant Escherichia coli in a two-liquid-phase system: Effect of medium components on cell growth and alkane oxidation activity," Enzym. Microb. Technol., 14:931-937, 1992.
Feng, L. et al., "Genome and proteome of long-chain alkane degrading Geobacillus thermodenitrificans NG80-2 isolated from a deep-subsurface oil reservoir," Proc. Natl. Acad. Sci. U. S. A., 104(13):5602-5607, 2007.
Fickers, P. et al., "Hydrophobic substrate utilisation by the yeast Yarrowia lipolytica, and its potential applications," FEMS Yeast Res., 5:527-543, 2005.
Fishman, A. et al., "Controlling the Regiospecific Oxidation of Aromatics via Active Site Engineering of Toluene para-Monooxygenase of Ralstonia pickettii PKO1," J. Biol. Chem., 280(1):506-514, 2005.
Flook, M. et al., "Z-selective olefin metathesis processes catalyzed by a molybdenum hexaisopropylterphenoxide monopyrrolide complex," Journal of the American Chemical Society, 131(23):7962-3, 2009.
Fontan, N. et al., "Synthesis of C40-Symmetrical Fully-Conjugated Carotenoids by Olefin Metathesis," Eur. J. Org. Chem., 2011(33):6704-6712, 2011.
Friedrich, H., "The oxidation of alcohols to aldehydes or ketones high oxidation state ruthenium compounds as catalysts," Platinum Metals Review, 43(3):94-102, 1999.
Fujii, T. et al., "Biotransformation of various alkanes using the Escherichia coli expressing an alkane hydroxylase system from Gordonia sp TF6," Biosci. Biotechnol. Biochem., 68(10):2171-2177, 2004.
Fujii, T. et al., "Production of α,ω-alkanediols using Escherichia coli expressing a cytochrome p450 from Acinetobacter sp OC4," Biosci. Biotechnol. Biochem., 70(6):1379-1385, 2006.
Fujita, N. et al., "Comparison of Two Vectors for Functional Expression of a Bacterial Cytochrome P450 Gene in Escherichia coli Using CYP153 Genes," Biosci. Biotechnol. Biochem., 73(8):1825-1830, 2009.
Funhoff, E. et al., "CYP153A6, a soluble P450 oxygenase catalyzing terminal-alkane hydroxylation," J. Bacteriol., 188(14):5220-5227, 2006.
Funhoff, E. et al., "Hydroxylation and epoxidation reactions catalyzed by CYP153 enzymes," Enzyme and Microbial Technology, 40:806-812, 2007.
Garikipati, S. et al., "Whole-Cell Biocatalysis for 1-Naphthol Production in Liquid-Liquid Biphasic Systems," Appl. Environ. Microbiol., 75(20):6545-6552, 2009.
Girhard, M. et al., "Characterization of the versatile monooxygenase CYP109B1 from Bacillus subtilis," Appl Microbiol Biotechnol, 87:595-607, 2010.
Goswami, P. et al., "An overview on alcohol oxidases and their potential applications," Applied Microbiology and Biotechnology, 97:4259-4275, 2013.
Grant, C. et al., "Identification and use of an alkane transporter plug-in for applications in biocatalysis and whole-cell biosensing of alkanes," Sci. Rep. 4:5844, 9 pages, 2014.
Grant, C. et al., "Whole-cell bio-oxidation of n-dodecane using the alkane hydroxylase system of P-putida GPo1 expressed in E-coil," Enzyme Microb. Technol., 48:480-486, 2011.
Griffin, B. et al., "Radical mechanism of aminopyrine oxidation by cumene hydroperoxide catalyzed by purified liver microsomal cytochrome P-450," Arch. Biochem. Biophys., 205(2):543-553, 1980.
Griffin, K. and Matthey, J., "Selective oxidation of alcohols to carbonyls," Innovations in Pharmaceutical Technology, 02(10), 110,112,114, 2002.
Groothaert, M. et al., "Selective Oxidation of Methane by the Bis(µ-oxo)dicopper Core Stabilized on ZSM-5 and Mordenite Zeolites," J. Am. Chem. Soc., 127:1394-1395, 2005.
Gross, R. et al., "Engineered catalytic biofilms for continuous large scale production of n-octanol and (S)-styrene oxide," Biotechnol. Bioeng., 110(2):424-436, 2013.
Groves, J. and Roman, J., "Nitrous Oxide Activation by a Ruthenium Porphyrin," J. Am. Chem. Soc., 117:5594-5595, 1995.
Groves, J., "High-valent iron in chemical and biological oxidations," J. Inorg. Biochem., 100:434-447, 2006.
Gudiminchi, R. et al., "Screening for cytochrome P450 expression in Pichia pastoris whole cells by P450-carbon monoxide complex determination," Biotechnol. J., 8:146-152, 2013.
Gudiminchi, R. et al., "Whole-cell hydroxylation of n-octane by Escherichia coli strains expressing the CYP153A6 operon," Appl. Microbiol. Biotechnol., 96:1507-1516, 2012.
Guengerich, F. et al., "Evidence for a 1-electron oxidation mechanism in N-dealkylation of N,N-dialkylanilines by cytochrome P450 2B1," J. Biol. Chem., 271(44):27321-27329, 1996.

(56) References Cited

OTHER PUBLICATIONS

Guengerich, F., "Oxidation-reduction properties of rat liver cytochromes P-450 and NADPH-cytochrome P-450 reductase related to catalysis in reconstituted systems," Biochemistry, 22:2811-2820, 1983.
Hagstrom, A. et al., "A moth pheromone brewery: production of (Z)-11-hexadecenol by heterologous co-expression of two biosynthetic genes from a noctuid moth in a yeast cell factory," Microb. Cell Fact., 12:125, 11 pages, 2013.
Hagstrom, A. et al., "Semi-Selective Fatty Acyl Reductases from Four Heliothine Moths Influence the Specific Pheromone Composition," PLoS One, 7(5):e37230, 11 pages, 2012.
Hamberg, M. et al., "α-Dioxygenases," Biochem. Biophys. Res. Commun., 338:169-174, 2005.
Hara, A. et al., "Cloning and functional analysis of alkB genes in Alcanivorax borkumensis SK2," Environ. Microbiol., 6(3):191-197, 2004.
Hartmans, S. et al., "Microbial metabolism of short-chain unsaturated hydrocarbons," FEMS Microbiol Rev, 5:235-264, 1989.
Hartung, J. and Grubbs, R., "Highly Z-selective and enantioselective ring-opening/cross-metathesis catalyzed by a resolved stereogenic-at-Ru complex," J Am Chem Soc, 135(28):10183-10185, 2013.
Hartung, J. et al., "Enantioselective Olefin Metathesis with Cyclometalated Ruthenium Complexes," Journal of the American Chemical Society, 136(37):13029-13037, 2014.
Herbert, M. et al., "Concise syntheses of insect pheromones using Z-selective cross metathesis," Angew Chem Int Ed Engl, 52:310-314, 2013.
Hommel, R. and Ratledge, C., "Evidence for two fatty alcohol oxidases in the biosurfactant-producing yeast *Candida* (Torulopsis) bombicola," FEMS Microbiol Lett, 58:183-186, 1990.
Hommel, R. et al., "The inducible microsomal fatty alcohol oxidase of Candida (Torulopsis) apicola," Appl Microbiol Biotechnol, 40:729-734, 1994.
Hoover, J. et al., "Copper(I)/TEMPO-catalyzed aerobic oxidation of primary alcohols to aldehydes with ambient air," Nature Protocols, 7(6):1161-1166, S1161/1-S1161/5, 2012.
Hou, C. et al., "Thermostable NAD-linked secondary alcohol-dehydrogenase from propane-grown pseudomonas-fluorescens NRRL-B-1244," Appl Environ Microbiol, 46(1):98-105, 1983.
Hua, F. et al., "Trans-membrane transport of n-octadecane by *Pseudomonas* sp DG17," J. Microbiol., 51(6):791-799, 2013.
Huang, F. et al., "Expression and Characterization of CYP52 Genes Involved in the Biosynthesis of Sophorolipid and Alkane Metabolism from Starmerella bombicola," Appl. Environ. Microbiol., 80:766-776, 2014.
Iida, T. et al., "The cytochrome P450ALK multigene family of an n-alkane-assimilating yeast, *Yarrowia lipolytica*: cloning and characterization of genes coding for new CYP52 family members," Yeast, 16:1077-1087, 2000.
Ji, Y. et al., "Structural insights into diversity and n-alkane biodegradation mechanisms of alkane hydroxylases," Front. Microbiol., 4(58):1-13, 2013.
Jiang, A. et al., "Highly Z-Selective Metathesis Homocoupling of Terminal Olefins," Journal of the American Chemical Society, 131(46):16630-16631, 2009.
Johnson Matthey PLC, The Catalyst Technical Handbook, West Deptford, NJ, USA, 94 pages, 2005.
Johnson Matthey PLC, The Catalyst Technical Handbook, Platinum Metals Review, 45(3), 110, 2001.
Jones, D. and Howe, R., "Microbiological oxidation of long-chain aliphatic compounds. I. Alkanes and 1-alkenes," J. Chem. Soc. C, 2801-2808, 1968.
Jones, N. et al., "Engineering the selectivity of aliphatic C—H bond oxidation catalyzed by cytochrome P450cam," Chem. Commun., 2413-2414, 1996.
Jordann, M. et al., "Experimental and DFT investigation of the 1-octene metathesis reaction mechanism with the Grubbs 1 precatalyst," J. Mol. Catal. A: Chem., 254:145-154, 2006.

Julsing, M. et al., "Outer Membrane Protein AlkL Boosts Biocatalytic Oxyfunctionalization of Hydrophobic Substrates in *Escherichia coli*," Appl. Environ. Microbiol., 78(16):5724-5733, 2012.
Kaehne, F. et al., "A recombinant α-dioxygenase from rice to produce fatty aldehydes using *E. coli*," Appl Microbiol Biotechnol, 90:989-995, 2011.
Kajikawa, T. et al., "Olefin metathesis in carotenoid synthesis," Org. Biomol. Chem., 7(22):4586-4589, 2009.
Karimi, B. et al., "Green, transition-metal-free aerobic oxidation of alcohols using a highly durable supported organocatalyst," Angewandte Chemie, International Edition, 46(38):7210-7213, 2007.
Karra-Chaabouni M. et al., "Biooxidation of n-Hexanol by Alcohol Oxidase and Catalase in Biphasic and Micellar Systems Without Solvent," Biotechnol Bioeng, 81:27-32, 2003.
Katopodis, A. et al., "Mechanistic studies on non-heme iron monooxygenase catalysis: epoxidation, aldehyde formation and demethylation by the ω-hydroxylation system of Pseudomonas oleovorans," J. Am. Chem. Soc., 106:7928-7935, 1984.
Kedziora, K. et al., "Laccase/TEMPO-mediated system for the thermodynamically disfavored oxidation of 2,2-dihalo-1-phenylethanol derivatives," Green Chemistry, 16(5):2448-2453, 2014.
Keitz, B. et al., "Cis-selective ring-opening metathesis polymerization with ruthenium catalysts," J Am Chem Soc, 134(4):2040-2043, 2012.
Keitz, B. et al., "Improved ruthenium catalysts for Z-selective olefin metathesis," J Am Chem Soc, 134(1):693-699, 2012.
Kemp, G. et al., "Activity and substrate-specificity of the fatty alcohol oxidase of candida-tropicalis in organic-solvents," Appl Microbiol Biotechnol, 34:441-445, 1991.
Kemp, G. et al., "Inducible long-chain alcohol oxidase from alkane-grown candida-tropicalis," Appl Microbiol Biotechnol, 29:370-374, 1988.
Kemp, G. et al., "Light sensitivity of the n-alkane-induced fatty alcohol oxidase from Candida tropicalis and Yarrowia lipolytica," Appl Microbiol Biotechnol, 32:461-464, 1990.
Khan, R. et al., "Readily accessible and easily modifiable Ru-based catalysts for efficient and Z-selective ring-opening metathesis polymerization and ring-opening/cross-metathesis," J Am Chem Soc, 135:10258-10261, 2013.
Kille, S. et al., "Regio- and stereoselectivity of P450-catalysed hydroxylation of steroids controlled by laboratory evolution," Nat Chem, 3:738-743, 2011.
Kim, D. et al., "Functional expression and characterization of cytochrome P450 52A21 from Candida albicans," Arch. Biochem. Biophys., 464:213-220, 2007.
Kirmair, L. and Skerra, A., "Biochemical Analysis of Recombinant AlkJ from Pseudomonas putida Reveals a Membrane-Associated, Flavin Adenine Dinucleotide-Dependent Dehydrogenase Suitable for the Biosynthetic Production of Aliphatic Aldehydes," Appl. Environ. Microbiol., 80(8):2468-2477, 2014.
Koch, D. et al., "In vivo evolution of butane oxidation by terminal alkane hydroxylases AlkB and CYP153A6," Appl. Environ. Microbiol., 75(2):337-344, 2009.
Kotani, H. et al., "Photocatalytic Generation of a Non-Heme Oxoiron(IV) Complex with Water as an Oxygen Source," J. Am. Chem. Soc., 133:3249-3251, 2011.
Krebs, C. et al., "Non-Heme Fe(IV)-Oxo Intermediates," Acc. Chem. Res., 40:484-492, 2007.
Kubo, T. et al., "Enantioselective epoxidation of terminal alkenes to (R)- and (S)-epoxides by engineered cytochromes P450 BM-3," Chem. Eur. J., 12:1216-1220, 2006.
Kubota, M. et al., "Isolation and functional analysis of cytochrome P450 CYP153A genes from various environments," Biosci Biotechnol Biochem, 69(12):2421-2430, 2005.
Kumar A. and Goswami, P., "Functional characterization of alcohol oxidases from Aspergillus terreus MTCC 6324," Appl Microbiol Biotechnol, 72:906-911, 2006.
Labinger, J., "Selective alkane oxidation: hot and cold approaches to a hot problem," J. Mol. Catal. A Chem., 220:27-35, 2004.
Lewis, J. and Arnold, F., "Catalysts on demand. selective oxidations by laboratory-evolved cytochrome P450 BM3," Chimia (Aarau), 63(6):309-312, 2009.

(56) References Cited

OTHER PUBLICATIONS

Lewis, J. et al., "Combinatorial Alanine Substitution Enables Rapid Optimization of Cytochrome P450$_{BM3}$ for Selective Hydroxylation of Large Substrates," Chembiochem, 11:2502-2505, 2010.
Li, L. et al., "Crystal Structure of Long-Chain Alkane Monooxygenase (LadA) in Complex with Coenzyme FMN: Unveiling the Long-Chain Alkane Hydroxylase," J. Mol. Biol., 376:453-465, 2008.
Lipscomb, J. et al., "Methane monooxygenase and compound Q: lessons in oxygen activation," Int. Congr. Ser., 1233:205-212, 2002.
Liu, S. et al., "Optimal pH control strategy for high-level production of long-chain α,ω-dicarboxylic acid by Candida tropicalis," Enzyme Microb. Technol., 34:73-77, 2004.
Liu, X. et al., "Two novel metal-independent long-chain alkyl alcohol dehydrogenases from Geobacillus thermodenitrificans NG80-2," Microbiology, 155:2078-2085, 2009.
Liu, Y. et al., "Isolation of an alkane-degrading *Alcanivorax* sp strain 2B5 and cloning of the alkB gene," Bioresour. Technol., 101:310-316, 2010.
Lo Piccolo, L. et al., "Involvement of an Alkane Hydroxylase System of *Gordonia* sp Strain SoCg in Degradation of Solid n-Alkanes," Appl. Environ. Microbiol., 77(4):1204-1213, 2011.
Lu, W. et al., "Biosynthesis of Monomers for Plastics from Renewable Oils," J. Am. Chem. Soc., 132:15451-15455, 2010.
Lucio Anelli, P. et al., "Fast and selective oxidation of primary alcohols to aldehydes or to carboxylic acids and of secondary alcohols to ketones mediated by oxoammonium salts under two-phase conditions," Journal of Organic Chemistry, 52(12):2559-2562, 1987.
Malca, S. et al., "Bacterial CYP153A monooxygenases for the synthesis of omega-hydroxylated fatty acids," Chemical Communications, 48:5115-5117, 2012.
Malca, S., "Substrate characterization and protein engineering of bacterial cytochrome P450 monooxygenases for the bio-based synthesis of omega-hydroxylated aliphatic compounds," Institute of Technical Biochemistry at the University of Stuttgart (University of Stuttgart, 2013).
Marinescu, S. et al., "Isolation of pure disubstituted E olefins through Mo-catalyzed Z-selective ethenolysis of stereoisomeric mixtures," Journal of the American Chemical Society, 133(30):11512-4, 2011.
Martinez, C. and Rupashinghe, S., "Cytochrome P450 bioreactors in the pharmaceutical industry: challenges and opportunities," Curr Top Med Chem, 13:1470-1490, 2013.
Marx, V. et al., "Stereoselective access to Z and E macrocycles by ruthenium-catalyzed Z-selective ring-closing metathesis and ethenolysis," J Am Chem Soc, 135(1): 94-97, 2013.
Marzorati, M. et al., "Selective laccase-mediated oxidation of sugars derivatives," Green Chemistry, 7(5):310-315, 2005.
Masuda, H. et al., "Characterization of three propane-inducible oxygenases in *Mycobacterium* sp. strain ENV421," Lett. Appl. Microbiol., 55:175-181, 2012.
Mathys, R. et al., "Integrated two-liquid phase bioconversion and product-recovery processes for the oxidation of alkanes: process design and economic evaluation," Biotechnol Bioeng, 64:459-477, 1999.
Matsuyama, H. et al., "A new n-alkane oxidation system from Pseudomonas aeruginosa S7B1," Agric. Biol. Chem., 45(1):9-14, 1981.
Mauersberger, S. et al., "Substrate-specificity and stereo selectivity of fatty alcohol oxidase from the yeast candida-maltosa," Appl. Microbiol. Biotechnol., 37:66-73, 1992.
Maurer, S. et al., "Catalytic hydroxylation in biphasic systems using CYP102A1 mutants," Adv. Synth. Catal., 347:1090-1098, 2005.
May, S. and Schwartz, R., "Stereoselective epoxidation of octadiene catalyzed by an enzyme system of Pseudomonas oleovorans," J. Am. Chem. Soc., 96:4031-4032, 1974.
Mayoral, J. et al., "NADP(+)-dependent farnesol dehydrogenase, a corpora allata enzyme involved in juvenile hormone synthesis," Proc. Natl. Acad. Sci. U. S. A., 106:21091-21096, 2009.

Meinhold, P. et al., "Engineering cytochrome P450 BM3 for terminal alkane hydroxylation," Adv. Synth. Catal., 348:763-772, 2006.
Moreau, R. and Huang, A., "Oxidation of fatty alcohol in the cotyledons of jojoba seedlings," Arch Biochem Biophys, 194(2):422-430, 1979.
Mori, K., "Synthesis of all the six components of the female-produced contact sex pheromone of the German cockroach, *Blattella germanica* (L.)," Tetrahedron, 64:4060-4071, 2008.
Munzer, D. et al., "Stereoselective hydroxylation of an achiral cyclopentanecarboxylic acid derivative using engineered P450s BM-3," Chem. Commun., 2597-2599, 2005.
Murray, W. and Duff, S., "Biooxidation of aliphatic and aromatic high-molecular-weight alcohols by pichia-pastoris alcohol oxidase," Appl. Microbiol. Biotechnol., 33:202-205, 1990.
Nguyen, H. et al., "Metabolic Engineering of Seeds Can Achieve Levels of ω-7 Fatty Acids Comparable with the Highest Levels Found in Natural Plant Sources," Plant Physiology, 154(4):1897-1904, 2010.
Nie, Y. et al., "Diverse alkane hydroxylase genes in microorganisms and environments," Sci. Rep., 4(4968) :1-11, 2014.
Nodate, M. et al., "Functional expression system for cytochrome P450 genes using the reductase domain of self-sufficient P450RhF from *Rhodococcus* sp NCIMB 9784," Appl. Microbiol.Biotechnol., 71:455-462, 2006.
Olaofe, O. et al., "The influence of microbial physiology on biocatalyst activity and efficiency in the terminal hydroxylation of n-octane using *Escherichia coli* expressing the alkane hydroxylase, CYP153A6," Microb. Cell Fact., 12:8, 12 pages, 2013.
Oprean, I. et al., "Synthesis of cis-7,8-epoxyoctadecane, species-specific component of the sex pheromone of nun moth *Lymantria monacha* (Lepidoptera, Limantriidae)," Stud Univ Babes-Bolyai, Chem, 51:33-38, 2006.
Ozimek, P. et al., "Alcohol oxidase: A complex peroxisomal, oligomeric flavoprotein," FEMS Yeast Res, 5:975-983, 2005.
Pagliaro, M. et al., "Ru-based oxidation catalysis," Chemical Society Reviews, 34(10):837-845, 2005.
Pederson, R. et al., "Applications of olefin cross metathesis to commercial products," Advanced Synthesis & Catalysis, 344(6-7):728-735,2002.
Peryshkov, D. et al., "Z-Selective olefin metathesis reactions promoted by tungsten oxo alkylidene complexes," Journal of the American Chemical Society, 133(51):20754-7, 2011.
Peter, S. et al., "Selective hydroxylation of alkanes by an extracellular fungal peroxygenase," FEBS J., 278(19):3667-3675, 2011.
Peters, M. et al., "Regio- and Enantioselective Alkane Hydroxylation with Engineered Cytochromes P450 BM-3," J. Am. Chem. Soc., 125:13442-13450, 2003.
Pflug, S. et al., "Development of a fed-batch process for the production of the cytochrome P450 monooxygenase CYP102A1 from Bacillus megaterium in *E. coli*," J Biotechnol, 129:481-488, 2007.
Pham, S. et al., "Evolving P450pyr hydroxylase for highly enantioselective hydroxylation at non-activated carbon atom," Chem. Commun., 48:4618-4620, 2012.
Presecki, A. et al., "Coenzyme Regeneration in Hexanol Oxidation Catalyzed by Alcohol Dehydrogenase," Appl. Biochem. Biotechnol., 167:595-611, 2012.
Pribisko, M. et al., "Z-Selective ruthenium metathesis catalysts: Comparison of nitrate and nitrite X-type ligands," Polyhedron Ahead of Print. doi: 10.1016/j.poly.2014.06.055, Published in final edited form as: Polyhedron. Dec. 14, 2014; 84: 144-149.
Qian, W. et al., "Clean and selective oxidation of alcohols catalyzed by ion-supported TEMPO in water," Tetrahedron, 62(4):556-562,2006.
Quigley, B. and Grubbs, R., "Ruthenium-catalysed Z-selective cross metathesis of allylic-substituted olefins," Chemical Science, 5(2):501-506, 2014.
Rickert, A. et al., "Enzymatic allylic oxidations with a lyophilisate of the edible fungus *Pleurotus sapidus*," Green Chem., 14:639-644, 2012.

(56) References Cited

OTHER PUBLICATIONS

Roiban, G. et al., "Stereo- and regioselectivity in the P450-catalyzed oxidative tandem difunctionalization of 1-methylcyclohexene," Tetrahedron, 69:5306-5311, 2013.
Rosebrugh, L. et al., "Highly active ruthenium metathesis catalysts exhibiting unprecedented activity and Z-selectivity," J Am Chem Soc, 135(4):1276-1279, 2013.
Rui, Z. et al., "Microbial biosynthesis of medium-chain 1-alkenes by a nonheme iron oxidase," Proc. Natl. Acad. Sci. U. S. A., 111(51):18237-18242, 2014.
Ryland, B. and Stahl, S., "Practical Aerobic Oxidations of Alcohols and AMINES with Homogeneous Copper/TEMPO and Related Catalyst Systems," Angew Chemie Int Ed, 53:8824-8838, 2014.
Sarmah, P. et al., "Copper(II) catalysed oxidation of alcohols in aqueous medium," Indian Journal of Chemistry, Section A: Inorganic, Bio-Inorganic, Physical, Theoretical & Analytical Chemistry, 48A(5):637-644, 2009.
Sato, S. et al., "Selective Dehydration of Alkanediols into Unsaturated Alcohols over Rare Earth Oxide Catalysts," ACS Catal, 3:721-734, 2013.
Savitha, J. and Ratledge, C., "Alcohol oxidase of Aspergillus flavipes grown on hexadecanol," FEMS Microbiol Lett, 80:221-224, 1991.
Scheller, U. et al., "Characterization of the n-alkane and fatty acid hydroxylating cytochrome P450 forms 52A3 and 52A4," Arch. Biochem. Biophys., 328(2):245-254, 1996.
Scheller, U. et al., "Generation of the soluble and functional cytosolic domain of microsomal cytochrome P450 52A3," J. Biol. Chem., 269(17):12779-12783, 1994.
Scheller, U. et al., "Oxygenation cascade in conversion of n-alkanes to $\alpha,\omega$-dioic acids catalyzed by cytochrome p450 52A3," J. Biol. Chem., 273(49):32528-32534, 1998.
Scheps, D. et al., "Regioselective $\omega$-hydroxylation of medium-chain n-alkanes and primary alcohols by CYP153 enzymes from *Mycobacterium marinum* and *Polaromonas* sp strain J5666," Org. Biomol. Chem., 9:6727-6733, 2011.
Scheps, D. et al., "Synthesis of $\omega$-hydroxy dodecanoic acid based on an engineered CYP153A fusion construct," Microb. Biotechnol., 6(6):694-707, 2013.
Scheps, D., "Cytochrome P450 monooxygenases: a study of the synthesis of industrial relevant aliphatic $\omega$-hydroxy products," Institute of Technical Biochemistry at the University of Stuttgart, 130 pages, 2013.
Schrewe, M. et al., "Kinetic Analysis of Terminal and Unactivated C—H Bond Oxyfunctionalization in Fatty Acid Methyl Esters by Monooxygenase-Based Whole-Cell Biocatalysis," Advanced Synthesis & Catalysis, 353:3485-3495, 2011.
Schrewe, M. et al., "Whole-cell biocatalysis for selective and productive C—O functional group introduction and modification," Chem. Soc. Rev., 42:6346-6377, 2013.
Schroer, K. et al., "Continuous asymmetric ketone reduction processes with recombinant *Escherichia coli*," J. Biotechnol., 132:438-444, 2007.
Seghezzi, W. et al., "Characterization of a second alkane-inducible cytochrome P450-encoding gene, CYP52A2, from Candida tropicalis," Gene, 106:51-60, 1991.
Seghezzi, W. et al., "Identification and characterization of additional members of the cytochrome-p450 multigene family CYP52 of Candida-tropicalis," DNA Cell Biol., 11(10):767-780, 1992.
Shahane, S. et al., "Z Selectivity: Recent Advances in one of the Current Major Challenges of Olefin Metathesis," ChemCatChem, 5:3436-3459, 2013.
Smith, A. et al., "Evolution of a Gram-Scale Synthesis of (+)-Discodermolide," J Am Chem Soc, 122:8654-8664, 2000.
Smits, T. et al., "Functional analysis of alkane hydroxylases from gram-negative and gram-positive bacteria," J. Bacteriol., 184(6):1733-42, 2002.
Smits, T. et al., "Functional characterization of genes involved in alkane oxidation by Pseudomonas aeruginosa," Antonie Van Leeuwenhoek, 84:193-200, 2003.
Smits, T. et al., "New alkane-responsive expression vectors for *Escherichia coli* and Pseudomonas," Plasmid, 46:16-24, 2001.
Sugimoto, K. et al "Intake and transformation to a glycoside of (Z)-3-hexenol from infested neighbors reveals a mode of plant odor reception and defense," Proc Natl Acad Sci, 111(19):7144-7149, 2014.
Takai, H. et al., "Construction and characterization of a Yarrowia lipolytica mutant lacking genes encoding cytochromes P450 subfamily 52," Fungal Genet. Biol., 49:58-64, 2012.
Tani, A. et al., "Thermostable NADP(+)-dependent medium-chain alcohol dehydrogenase from *Acinetobacter* sp strain M-1: Purification and characterization and gene expression in *Escherichia coli*," Appl Environ Microbiol, 66(12):5231-5235, 2000.
Thevenieau, F. et al., "Characterization of Yarrowia lipolytica mutants affected in hydrophobic substrate utilization," Fungal Genet. Biol., 44:531-542, 2007.
Townsend, E. et al., "Z-selective metathesis homocoupling of 1,3-dienes by molybdenum and tungsten monoaryloxide pyrrolide (MAP) complexes," Journal of the American Chemical Society, 134(28):11334-7, 2012.
Uchio, R. and Shiio, I., "Tetradecane-1,14-dicarboxylic acid production from n-hexadecane by Candida cloacae" Agric. Biol. Chem., 36(8):1389-1397, 1972.
Urlacher, V. et al., "Biotransformation of β-ionone by engineered cytochrome P450 BM-3," Appl Microbiol Biotechnol, 70:53-59, 2006.
Urlacher, V. et al., "Microbial P450 enzymes in biotechnology," Appl. Microbiol. Biotechnol., 64:317-325, 2004.
Van Beilen, J. and Funhoff, E., "Alkane hydroxylases involved in microbial alkane degradation," Appl. Microbiol. Biotechnol., 74:13-21, 2007.
Van Beilen, J. and Funhoff, E., "Expanding the alkane oxygenase toolbox: new enzymes and applications," Curr. Opin. Biotechnol., 16:308-314, 2005.
Van Beilen, J. et al., "Characterization of two alkane hydroxylase genes from the marine hydrocarbonoclastic bacterium Alcanivorax borkumensis," Environ. Microbiol., 6(3):264-273, 2004.
Van Beilen, J. et al., "Cytochrome P450 alkane hydroxylases of the CYP153 family are common in alkane-degrading eubacteria lacking integral membrane alkane hydroxylases," Appl. Environ. Microbiol., 72(1):59-65, 2006.
Van Beilen, J. et al., "Diversity of alkane hydroxylase systems in the environment," Oil Gas Sci. Technol, 58(4):427-440, 2003.
Van Beilen, J. et al., "Identification of an amino acid position that determines the substrate range of integral membrane alkane hydroxylases," J. Bacteriol., 187(1):85-91, 2005.
Van Beilen, J. et al., "Practical issues in the application of oxygenases," Trends Biotechnol., 21(4):170-177, 2003.
Van Beilen, J. et al., "Substrate-specificity of the alkane hydroxylase system of Pseudomonas-oleovorans GPO1," Enzyme Microb. Technol., 16:904-911, 1994.
Van Der Gryp, P. et al., "Experimental, DFT and kinetic study of 1-octene metathesis with Hoveyda-Grubbs second generation precatalyst," Journal of Molecular Catalysis A: Chemical, 355:85-95, 2012.
Van Der Klei, I. et al., "Biosynthesis and assembly of alcohol oxidase, a peroxisomal matrix protein in methylotrophic yeasts: a review," Yeast, 7:195-209, 1991.
Vangnai, A. and Arp, D., "An inducible 1-butanol dehydrogenase, a quinohaemoprotein, is involved in the oxidation of butane by 'Pseudomonas butanovora,'" Microbiology, 147:745-756, 2001.
Vanhanen, S. et al., "A consensus sequence for long-chain fatty-acid alcohol oxidases from Candida identifies a family of genes involved in lipid $\omega$-oxidation in yeast with homologues in plants and bacteria," J Biol Chem, 275(6):4445-4452, 2000.
Wang, C. et al., "Mo-Based Complexes with Two Aryloxides and a Pentafluoroimido Ligand Catalysts for Efficient Z-Selective Synthesis of a Macrocyclic Trisubstituted Alkene by Ring-Closing Metathesis," Angewandte Chemie International Edition, 52(7):1939-1943, 2013.
Wang, L. et al., "Gene diversity of CYP153A and AlkB alkane hydroxylases in oil-degrading bacteria isolated from the Atlantic Ocean," Env. Microbiol, 12(5):1230-1242, 2010.

(56) References Cited

OTHER PUBLICATIONS

Weissbart, D. et al., "Regioselectivity of a plant lauric acid omega hydroxylase. Omega hydroxylation of cis and trans unsaturated lauric acid analogs and epoxygenation of the terminal olefin by plant cytochrome P-450," Biochimica et Biophysica Acta, 1124:135-142, 1992.

Wentzel, A. et al., "Bacterial metabolism of long-chain n-alkanes," Appl. Microbiol. Biotechnol., 76:1209-1221, 2007.

Whitehouse, C. et al., "$P450_{BM3}$ (CYP102A1): connecting the dots," Chem. Soc. Rev., 41:1218-1260, 2012.

Youngquist, J. et al., "Production of medium chain length fatty alcohols from glucose in *Escherichia coli*," Metab. Eng., 20:177-186, 2013.

Yu, A. et al., "Production of Fatty Acid-Derived Valuable Chemicals in Synthetic Microbes," Front. Bioeng. Biotechnol., 2(78):1-12, 2014.

Zampolli, J. et al., "Biodegradation of variable-chain-length n-alkanes in Rhodococcus opacus R7 and the involvement of an alkane hydroxylase system in the metabolism," AMB Express, 4:73, 9 pages, 2014.

Zehentgruber, D. et al., "Studies on the enantioselective oxidation of β-ionone with a whole *E. coli* system expressing cytochrome P450 monooxygenase BM3," J. Mol. Catal. B Enzym., 84:62-64, 2012.

Zhang, H. et al., "Preparation of Macrocyclic Z Enoates and (E,Z)- or (Z,E) Dienoates through Catalytic Stereoselective Ring-Closing Metathesis," Journal of the American Chemical Society, 136(47):16493-16496, 2014.

Zhao, S. et al., "Cloning and characterization of long-chain fatty alcohol oxidase LjFAO1 in Lotus japonicas," Biotechnol. Prog., 24:773-779, 2008.

Zimmer, T. et al., "The CYP52 multigene family of Candida maltosa encodes functionally diverse n-alkane-inducible cytochromes P450," Biochem. Biophys. Res. Commun., 224:784-789, 1996.

Zotova, N. et al., "Catalysis in flow: the practical and selective aerobic oxidation of alcohols to aldehydes and ketones," Green Chemistry, 12(12):2157-2163, 2010.

\* cited by examiner

SEQUENCE LISTING

<160> NUMBER OF SEQ ID NOS: 93

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide 1406_provivi 023

<400> SEQUENCE: 1
agccatcatc atcatcatca cagcagc                                          27

<210> SEQ ID NO 2
<211> LENGTH: 34
<212> TYPE: DNA
<213> ORGANISM: Artificial Sequence
<220> FEATURE:
<223> OTHER INFORMATION: synthetic oligonucleotide 1406_provivi 024

<400> SEQUENCE: 2
cactataggg gaattgtgag cggataacaa ttcc                                  34

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide 1406_provivi 025

<400> SEQUENCE: 3 ctataggga attgtgagcg gataacaatt ccc                                    33

<210> SEQ ID NO 4
<211> LENGTH: 34
<212> TYPE: DNA
<213> ORGANISM: Artificial Sequence
<220> FEATURE:
<223> OTHER INFORMATION: synthetic oligonucleotide 1406_provivi 026

<400> SEQUENCE: 4
tggtggtgct cgagtgcggc cgcaagcttc taat                               34

<210> SEQ ID NO 5
<211> LENGTH: 35
<212> TYPE: DNA
<213> ORGANISM: Artificial Sequence
<220> FEATURE:
<223> OTHER INFORMATION: synthetic forward primer oPV001

<400> SEQUENCE: 5
cttaaatctc gtagcgacta atttaataaa aattg                              35

<210> SEQ ID NO 6
<211> LENGTH: 24
<212> TYPE: DNA
<213> ORGANISM: Artificial Sequence
<220> FEATURE:
<223> OTHER INFORMATION: synthetic reverse primer oPV002

<400> SEQUENCE: 6
aaacagaagc ttggctgcag gtcg                                          24

<210> SEQ ID NO 7
<211> LENGTH: 25
<212> TYPE: DNA
<213> ORGANISM: Artificial Sequence
<220> FEATURE:
<223> OTHER INFORMATION: synthetic forward primer oPV003

<400> SEQUENCE: 7
cttattcctg aggattggtg ctgcc                                         25

<210> SEQ ID NO 8
<211> LENGTH: 25
<212> TYPE: DNA
<213> ORGANISM: Artificial Sequence
<220> FEATURE:
<223> OTHER INFORMATION: synthetic reverse primer oPV004

<400> SEQUENCE: 8
ggcagcacca atcctcagga ataag                                         25

<210> SEQ ID NO 9
<211> LENGTH: 23
<212> TYPE: DNA
<213> ORGANISM: Artificial Sequence
<220> FEATURE:
<223> OTHER INFORMATION: synthetic forward primer oPV005

<400> SEQUENCE: 9
gatgccgctg gatctggcct aga                                           23

<210> SEQ ID NO 10
<211> LENGTH: 23
<212> TYPE: DNA
<213> ORGANISM: Artificial Sequence
<220> FEATURE:
<223> OTHER INFORMATION: synthetic CYP52A13 forward primer OPV 0042

<400> SEQUENCE: 10
atgacggttc atgacatcat cgc                                             23

<210> SEQ ID NO 11
<211> LENGTH: 20
<212> TYPE: DNA
<213> ORGANISM: Artificial Sequence
<220> FEATURE:
<223> OTHER INFORMATION: synthetic CYP52A13/A3 reverse primer OPV 0043

<400> SEQUENCE: 11
ctgacatcct cttgagcggc                                                 20

<210> SEQ ID NO 12
<211> LENGTH: 25
<212> TYPE: DNA
<213> ORGANISM: Artificial Sequence
<220> FEATURE:
<223> OTHER INFORMATION: synthetic CYP52A3 forward primer OPV 0044

<400> SEQUENCE: 12
atggctattg agcagattat cgaag                                           25

<210> SEQ ID NO 13
<211> LENGTH: 8374
<212> TYPE: DNA
<213> ORGANISM: Artificial Sequence
<220> FEATURE:
<223> OTHER INFORMATION: synthetic sequence of the linearized construct
      for expressing CYP52A3/CPR

<400> SEQUENCE: 13

| | | | | | |
|---|---|---|---|---|---|
| agatccaatt | cccgctttga | ctgcctgaaa | tctccatcgc | ctacaatgat | gacatttgga | 60 |
| tttggttgac | tcatgttggt | attgtgaaat | agacgcagat | cgggaacact | gaaaaataca | 120 |
| cagttattat | tcatttaaat | aacatccaaa | gacgaaaggt | tgaatgaaac | cttttttgcca | 180 |
| tccgacatcc | acaggtccat | tctcacacat | aagtgccaaa | cgcaacagga | ggggatacac | 240 |
| tagcagcaga | ccgttgcaaa | cgcaggacct | ccactcctct | tctcctcaac | acccactttt | 300 |
| gccatcgaaa | aaccagccca | gttattgggc | ttgattggag | ctcgctcatt | ccaattcctt | 360 |
| ctattaggct | actaacacca | tgactttatt | agcctgtcta | tcctggcccc | cctggcgagg | 420 |
| ttcatgtttg | tttatttccg | aatgcaacaa | gctccgcatt | acacccgaac | atcactccag | 480 |
| atgagggctt | tctgagtgtg | gggtcaaata | gtttcatgtt | ccccaaatgg | cccaaaactg | 540 |
| acagtttaaa | cgctgtcttg | gaacctaata | tgacaaaagc | gtgatctcat | ccaagatgaa | 600 |
| ctaagtttgg | ttcgttgaaa | tgctaacggc | cagttggtca | aaaagaaact | tccaaaagtc | 660 |
| ggcataccgt | ttgtcttgtt | tggtattgat | tgacgaatgc | tcaaaaataa | tctcattaat | 720 |
| gcttagcgca | gtctctctat | cgcttctgaa | ccccggtgca | cctgtgccga | aacgcaaatg | 780 |
| gggaaacacc | cgcttttggg | atgattatgc | attgtctcca | cattgtatgc | ttccaagatt | 840 |
| ctggtgggaa | tactgctgat | agcctaacgt | tcatgatcaa | aatttaactg | ttctaacccc | 900 |
| tacttgacag | caatatataa | acagaaggaa | gctgccctgt | cttaaacctt | ttttttttatc | 960 |
| atcattatta | gcttactttc | ataattgcga | ctggttccaa | ttgacaagct | tttgatttta | 1020 |
| acgactttta | acgacaactt | gagaagatca | aaaacaaact | aattattgaa | agaattccga | 1080 |
| aacgatggct | ttgataagt | tggatttgta | cgtcatcatt | gttcttgctg | ttgctgttgc | 1140 |
| tgcctacttt | gctaaaaacc | agttcttgga | tcaacctcag | gacactggtt | tcttgtcaaa | 1200 |

```
cgatacagct ggtggaaata gtagagatat ccttgaaact ttgaagaaaa acaataagaa    1260
cacattgctt ttgttcggat ctcaaaccgg tactgctgag gactacgcca ataagctttc    1320
aagagaaatc catagtagat tcggattgaa aactatggtt gccgatttcg cagattacga    1380
ctgggataac tttggtgaca tccctaacga tatcttggtt ttctttatcg tcgccaccta    1440
tggagaggga gaaccaactg acaacgcaga tgagtttcac acctggttga ctgacgaagc    1500
tgatacactt tccaccttga gatacaccgt tttcggtttg ggaaactcaa cttacgaatt    1560
ttacaacgct atcggtagaa agtttgacag acttttggaa gagaaaggtg gagagagatt    1620
tgctgattat ggtgaaggag atgacggtac aggaacccctt gacgaggatt tcttgacatg    1680
gaaggacaac gttttcgata cccttaaaaa cgatttgaac ttcgaagaga gagagttgaa    1740
gtacgaacct aacgttaagc ttacagaaag agatgacttg accgttgatg actctgaggt    1800
ctccttggga gaaccaaata agaaatacat ccaatctgaa gagatcgact tgacaaaggg    1860
tccttttgat catacccacc catatcttgc aaagatctct aagactagag agttgtttgc    1920
ttccaaggaa agaaactgtg ttcatgtcga gttcgatgtt tctgaatcca atcttaagta    1980
cactacagga gaccacttgg ccgttttggcc atcaaacagt gatgagaata ttgcaaagtt    2040
catcaaatgc tttggtttgg atgacaagat taacactgtt ttcgaactta aagccttgga    2100
ttctacatac caaattccat tccctaatcc aatcacctat ggagcagttg tcagacatca    2160
cttggaaatt tcaggtcctg ttagtagaca gttttttcctt gctatcgccg gattcgctcc    2220
agacgaagag actaagaaaa cttttacaag aatcggtaac gataagcaag aatttgccaa    2280
caagatcaca agaaagaaat tgaacgttgc agacgctctt ttgtttgctt caaatggtag    2340
accttggagt gatgttccat ttgagttcat tatcgaaaac gtccctcatt tgcaaccaag    2400
atactactct atctcttcct caagtttgtc cgagaagcag actattaata tcacagctgt    2460
tgtcgaagtt gaagaggaag cagacggaag agctgtcacc ggtgttgtca ctaacctttt    2520
gaagaatatt gagatcgaac agaacaagac tggagaaaaa cctgttgtcc attacgattt    2580
gtctggtcca agaaacaagt ttaacaagtt taagttgcct gttcacgtca gaagatccaa    2640
ctttaagctt cctaaaaata ccactacacc agttattttg atcggtcctg gaactggtgt    2700
tgctccactt agaggtttcg tcagagagag agttcaacag gtcaagaacg gagttaacgt    2760
cggtaaaact gttttgtttt atggatgtag aaacgaacat gatgacttct tgtacaagca    2820
agagtggtct gaatatgctt ccgttttggg agagaatttt gaaatgttca ctgccttttc    2880
tagacaagac ccatccaaga aagtttacgt ccaggataag attgcagaaa actctaaagt    2940
tgtcaacgat cttttgaacg aaggagctat catctatgtt tgcggtgacg cctcaagaat    3000
ggcaagagat gttcaaagta ctattgctaa gatcgtcgcc aaacacagag agattcagga    3060
agataaagct gtcgagttgg ttaaatcctg gaaagttcag aatagatatc aagaagatgt    3120
ttggtaagcg gccgctcaag aggatgtcag aatgccattt gcctgagaga tgcaggcttc    3180
atttttgata cttttttatt tgtaacctat atagtatagg attttttttg tcattttgtt    3240
tcttctcgta cgagcttgct cctgatcagc ctatctcgca gcagatgaat atcttgtggt    3300
aggggttggg gaaaatcatt cgagtttgat gttttttcttg gtatttccca ctcctcttca    3360
gagtacagaa gattaagtga gaccttcgtt tgtgcggatc caacatccaa agacgaaagg    3420
ttgaatgaaa ccttttttgcc atccgacatc cacaggtcca ttctcacaca taagtgccaa    3480
acgcaacagg aggggataca ctagcagcag accgttgcaa acgcaggacc tccactcctc    3540
```

```
ttctcctcaa cacccacttt tgccatcgaa aaaccagccc agttattggg cttgattgga    3600
gctcgctcat tccaattcct tctattaggc tactaacacc atgactttat tagcctgtct    3660
atcctggccc ccctggcgag gttcatgttt gtttatttcc gaatgcaaca agctccgcat    3720
tacacccgaa catcactcca gatgagggct ttctgagtgt ggggtcaaat agtttcatgt    3780
tccccaaatg gcccaaaact gacagtttaa acgctgtctt ggaacctaat atgacaaaag    3840
cgtgatctca tccaagatga actaagtttg gttcgttgaa atgctaacgg ccagttggtc    3900 aaaagaaac ttccaaaagt cggcataccg tttgtcttgt ttggtattga ttgacgaatg    3960
ctcaaaaata atctcattaa tgcttagcgc agtctctcta tcgcttctga accccggtgc    4020
acctgtgccg aaacgcaaat ggggaaacac ccgcttttg gatgattatg cattgtctcc    4080
acattgtatg cttccaagat tctggtggga atactgctga tagcctaacg ttcatgatca    4140
aaatttaact gttctaaccc ctacttgaca gcaatatata aacagaagga agctgccctg    4200
tcttaaacct tttttttat catcattatt agcttacttt cataattgcg actggttcca    4260
attgacaagc ttttgatttt aacgactttt aacgacaact tgagaagatc aaaaaacaac    4320
taattattga agaattccg aaacgatggc tattgagcag attatcgaag aggttttgcc    4380
ttacttgact aaatggtaca ctatccttt tggtgccgct ttcacatact ttttgtcaat    4440
cgcacttaga aacaaatact acgagtacaa gttgaagtgt gaaaacccac cttacttcaa    4500
gactgctgga ttcgttggta tccctggatt gattgatgtc atcaaggcta agaacgctgg    4560
taaattggcc gattacgcag accaaacatt tgacgaatac cctcatcaca gtttctatat    4620
gaccgttgct ggaatgttga aaattgttct tactgtcgat ccagaaaaca tcaaggctgt    4680
tcttgccaca cagtttaatg acttcgcatt gggtgctaga catgcccact tgatccatt    4740 gcttggagac ggtattttca ccttggatgg agaaggttgg aaacattcca gagcaatgtt    4800
gagacctcaa tttgctagag agcagattgc ccatgttaag gcattggaac cacacgttca    4860
agtccttgcc aagcagatca aattgaacaa gggagagaca ttcgatttgc aagaattgtt    4920
tttcagattc accgttgaca cagctaccga gttttgttc ggagaatcag ttcacagtct    4980
ttacgatgag aaattgggtg tcccacctcc aaacaatatt cctggaagag aaaactttgc    5040
taaggccttc aatacctcac aacattattt ggctactaga acatacagtc agatgttcta    5100
tttcttgact aacccaaagg agtttagaga ctgcaatgcc aaagttcaca gcttgcaca    5160 atacttcgtc aataaggcat tggatgcttc tgaagacgag gttgctgaga agtccaaagg    5220
tggatacgtt ttcttgtatg aacttgtcaa acagactaga gatcctaagg ttttgcaaga    5280
ccagttgctt aacattatgg tcgctggtag agatactaca gccggattgc tttcttttgc    5340
aatgttcgag cttgctagaa acccaaagat ctggaataag ttgagagaag agatcgaagt    5400
taattttgga cttggtgaag aggccagagt cgacgaaatc tcattcgaga ctttgaagaa    5460
atgcgagtac ttgaaggcag ttcttaacga acattgaga atgtatccta gtgttccagt    5520
caattttaga accgctacta gagataccac tttgcctaga ggtggtggta agacggtac    5580 ttctcctatt ttcgttccaa agggatcttc cgttgtctac acagtctata aacccatag    5640 attggaagag tactatggta agatgcttta cgagtttaga cctgagagat ggttcgaacc    5700
atccactaga aaattgggtt gggcctatgt tcctttaat ggaggtccaa gaatttgcct    5760
tggacaacag ttcgctttga ctgaggcctc ttacgttatc acaagacttg ctcaaatgtt    5820
tgaacacttg gagtccaagg atgaaactta tcctccaaac aagtgtatcc atttgactat    5880
gaatcacaac gaaggagttt ttatttctgc taagtaggcg gccgctcaag aggatgtcag    5940
```

```
aatgccattt gcctgagaga tgcaggcttc attttttgata cttttttatt tgtaacctat   6000
atagtatagg atttttttg tcattttgtt tcttctcgta cgagcttgct cctgatcagc    6060
ctatctcgca gcagatgaat atcttgtggt aggggtttgg gaaaatcatt cgagtttgat   6120 gttttcttg gtatttccca ctcctcttca gagtacagaa gattaagtga gaccttcgtt   6180
tgtgcggatc cttcagtaat gtcttgtttc ttttgttgca gtggtgagcc attttgactt   6240
cgtgaaagtt tctttagaat agttgtttcc agaggccaaa cattccaccc gtagtaaagt   6300
gcaagcgtag gaagaccaag actggcataa atcaggtata agtgtcgagc actggcaggt   6360
gatcttctga aagtttctac tagcagataa gatccagtag tcatgcatat ggcaacaatg   6420
taccgtgtgg atctaagaac gcgtcctact aaccttcgca ttcgttggtc cagtttgttg   6480
ttatcgatca acgtgacaag gttgtcgatt ccgcgtaagc atgcataccc aaggacgcct   6540
gttgcaattc caagtgagcc agttccaaca atctttgtaa tattagagca cttcattgtg   6600
ttgcgcttga aagtaaaatg cgaacaaatt aagagataat ctcgaaaccg cgacttcaaa   6660
cgccaatatg atgtgcggca cacaataagc gttcatatcc gctgggtgac tttctcgctt   6720
taaaaaatta tccgaaaaaa ttttctagag tgttgttact ttatacttcc ggctcgtata   6780
atacgacaag gtgtaaggag gactaaacca tggctaaact cacctctgct gttccagtcc   6840
tgactgctcg tgatgttgct ggtgctgttg agttctggac tgatagactc ggtttctccc   6900
gtgacttcgt agaggacgac tttgccggtg ttgtacgtga cgacgttacc ctgttcatct   6960
ccgcagttca ggaccaggtt gtgccagaca acactctggc atgggtatgg gttcgtggtc   7020
tggacgaact gtacgctgag tggtctgagg tcgtgtctac caacttccgt gatgcatctg   7080
gtccagctat gaccgagatc ggtgaacagc cctggggtcg tgagtttgca ctgcgtgatc   7140
cagctggtaa ctgcgtgcat ttcgtcgcag aagagcagga ctaacaattg acaccttacg   7200
attatttaga gagtatttat tagttttatt gtatgtatac ggatgtttta ttatctattt   7260
atgcccttat attctgtaac tatccaaaag tcctatctta tcaagccagc aatctatgtc   7320
cgcgaacgtc aactaaaaat aagcttttta tgctcttctc tcttttttttc ccttcggtat   7380 aattatacct tgcatccaca gattctcctg ccaaattttg cataatcctt tacaacatgg   7440
ctatatggga gcacttagcg ccctccaaaa cccatattgc ctacgcatgt ataggtgttt   7500
tttccacaat atttctctg tgctctcttt ttattaaaga gaagctctat atcggagaag   7560
cttctgtggc cgttatattc ggccttatcg tgggaccaca ttgcctgaat tggtttgccc   7620
cggaagattg gggaaacttg gatctgatta ccttagctgc aggtaccact gagcgtcaga   7680
ccccgtagaa aagatcaaag gatcttcttg agatccttttt tttctgcgcg taatctgctg   7740
cttgcaaaca aaaaaaccac cgctaccagc ggtggtttgt ttgccggatc aagagctacc   7800
aactcttttt ccgaaggtaa ctggcttcag cagagcgcag ataccaaata ctgttcttct   7860
agtgtagccg tagttaggcc accacttcaa gaactctgta gcaccgccta catacctcgc   7920
tctgctaatc ctgttaccag tggctgctgc cagtggcgat aagtcgtgtc ttaccgggtt   7980
ggactcaaga cgatagttac cggataaggc gcagcggtcg ggctgaacgg ggggttcgtg   8040
cacacagccc agcttggagc gaacgaccta caccgaactg agatacctac agcgtgagct   8100
atgagaaagc gccacgcttc ccgaagggag aaaggcggac aggtatccgg taagcggcag   8160
ggtcggaaca ggagagcgca cgagggagct tccaggggga aacgcctggt atctttatag   8220
tcctgtcggg tttcgccacc tctgacttga gcgtcgattt ttgtgatgct cgtcagggggg  8280
```

```
gcggagccta tggaaaaacg ccagcaacgc ggccttttta cggttcctgg ccttttgctg    8340
gccttttgct cacatgttct ttcctgcggt accc                                8374
```

<210> SEQ ID NO 14
<211> LENGTH: 8369
<212> TYPE: DNA
<213> ORGANISM: Artificial Sequence
<220> FEATURE:
<223> OTHER INFORMATION: synthetic sequence of the linearized construct
      for expressing CYP52A13/CPR

<400> SEQUENCE: 14

```
agatccaatt cccgctttga ctgcctgaaa tctccatcgc ctacaatgat gacatttgga      60
tttggttgac tcatgttggt attgtgaaat agacgcagat cgggaacact gaaaaataca     120
cagttattat tcatttaaat aacatccaaa gacgaaaggt tgaatgaaac ctttttgcca     180
tccgacatcc acaggtccat tctcacacat aagtgccaaa cgcaacagga ggggatacac     240
tagcagcaga ccgttgcaaa cgcaggacct ccactcctct tctcctcaac acccactttt     300
gccatcgaaa aaccagccca gttattgggc ttgattggag ctcgctcatt ccaattcctt     360
ctattaggct actaacacca tgactttatt agcctgtcta tcctggcccc cctggcgagg     420
ttcatgtttg tttatttccg aatgcaacaa gctccgcatt acacccgaac atcactccag     480
atgagggctt tctgagtgtg gggtcaaata gtttcatgtt ccccaaatgg cccaaaactg     540
acagtttaaa cgctgtcttg gaacctaata tgacaaaagc gtgatctcat ccaagatgaa     600
ctaagtttgg ttcgttgaaa tgctaacggc cagttggtca aaaagaaact tccaaaagtc     660
ggcataccgt ttgtcttgtt tggtattgat tgacgaatgc tcaaaaataa tctcattaat     720
gcttagcgca gtctctctat cgcttctgaa ccccggtgca cctgtgccga aacgcaaatg     780
gggaaacacc cgcttttgg atgattatgc attgtctcca cattgtatgc ttccaagatt      840
ctggtgggaa tactgctgat agcctaacgt tcatgatcaa aatttaactg ttctaacccc     900
tacttgacag caatatataa acagaaggaa gctgccctgt cttaaacctt ttttttatc      960 atcattatta gcttactttc ataattgcga ctggttccaa ttgacaagct tttgattta     1020 acgactttta acgacaactt gagaagatca aaaaacaact aattattgaa agaattcaaa    1080
acgatggcac ttgataaact agatttgtac gtgattatca ccttagtggt tgctatcgct    1140
gcctacttcg ctaaaaacca atttctggac caacagcagg acactggatt tttgaatact    1200
gattccggtg atggtaactc cagagacatt ttacaagcac ttaagaagaa taacaaaaat    1260
actctactgt tatttggatc acaaactggt acagctgaag attacgccaa caaactgtcc    1320
cgtgaattac attcgaggtt tggattgaaa acaatggttg cagacttcgc tgattatgac    1380
ttcgagaatt tcggtgatat tacagaggac attttggtct ttttcatagt cgccactat     1440 ggtgaaggtg aaccgactga taatgctgac gagttccaca cttggctgac cgaggaggct    1500 gatacttga gtacactgaa gtacacagtt tttggattgg gtaattctac ttacgaattt     1560
ttcaacgcta ttggtaggaa gttcgacaga ttactgggtg agaaaggtgg cgacagattt    1620
gctgaatacg tgaaggcga cgacggtact ggaactttgg atgaagattt ccttgcttgg    1680
aaggacaacg tctttgattc attgaaaaat gatttgaatt tcgaggagaa agagcttaag    1740
tatgaaccaa acgtaaaatt gaccgaaagg gacgatttga gcggtaatga tccagatgta    1800
tctctaggtg aacctaatgt gaaatacatc aaaagtgaag gtgtgaccct taccaaagga    1860
cctttcgacc atacccatcc cttttttggca aggatcgtga aaacaaaaga gttgttcaca    1920
```

```
agcgaagata gacactgtgt tcatgtagag tttgacatat ccgaatcaaa ccttaagtac    1980
acaacaggtg accatctggc aatctggcca tcaaattctg atgagaatat caagcaattt    2040
gccaagtgtt ttggactgga ggataagctc gacactgtca ttgaattgaa ggcattggac    2100
tcaacgtatt ctattccatt tccaaatcct atcacctacg gtgcagttat cagacaccat    2160
ctagaaataa gtggtcctgt ctcaagacaa ttttttcctct ccatcgccgg atttgctcca    2220
gatgaggaga ctaaaaagtc cttcactaga attggtggag acaaacagga gttcgccagc    2280
aaggtaacta gacgtaagtt taacatcgct gatgcccttt tgttcgcttc caacaatcgt    2340
ccgtggtctg acgttccatt cgagtttcta attgaaaatg ttcaacactt gacaccacgt    2400
tattactcta tttcctcaag ctccctatca gaaaaacaga ccattaatgt tacagctgtg    2460
gttgaagctg aggaggaagc agacggcagg cctgttacgg gagttgtgac aaatctgctt    2520
aaaaacattg aaattgaaca aaataagacg ggagaaactc ctatggttca ctatgacttg    2580
aatggtccaa gaggtaagtt ctccaagttc agactgcccg ttcacgttag aagatccaac    2640
tttaagctcc caagaactc gactacaccc gtcatcttga ttggtccagg tacaggtgtt    2700
gccccttga gaggattcgt tagagaacgt gtacagcaag tgaaaaacgg tgtcaatgtg    2760
ggtaaaacgg ttttgttta tggatgtaga aattccgaac aagacttcct gtacaagcag    2820
gaatggtctg agtatgcttc ggtgctaggt gagaactttg agatgttcaa tgcattcagt    2880
cgtcaagacc ctactaaaaa ggtgtacgtt caagataaaa tcttagaaaa ttctgcactt    2940
gtagatgagt tgctctcttc tggagccata atctacgtgt gcggagatgc tagtcgtatg    3000
gcaagagatg tccaagcagc tatcgctaaa atcgtcgcta agtcacgaga catccatgaa    3060
gataaggccg cagagttggt gaagagctgg aaagttcaaa atcgttatca ggaggatgtt    3120
tggtaagcgg ccgctcaaga ggatgtcaga atgccatttg cctgagagat gcaggcttca    3180
ttttttgatac ttttttattt gtaacctata tagtatagga ttttttttgt cattttgttt    3240
cttctcgtac gagcttgctc ctgatcagcc tatctcgcag cagatgaata tcttgtggta    3300
ggggttgggg aaaatcattc gagtttgatg ttttttcttgg tatttcccac tcctcttcag    3360
agtacagaag attaagtgag accttcgttt gtgcggatcc aacatccaaa gacgaaaggt    3420
tgaatgaaac ctttttgcca tccgacatcc acaggtccat tctcacacat aagtgccaaa    3480
cgcaacagga ggggatacac tagcagcaga ccgttgcaaa cgcaggacct ccactcctct    3540
tctcctcaac acccactttt gccatcgaaa aaccagccca gttattgggc ttgattggag    3600
ctcgctcatt ccaattcctt ctattaggct actaacacca tgactttatt agcctgtcta    3660
tcctggcccc cctggcgagg ttcatgtttg tttatttccg aatgcaacaa gctccgcatt    3720
acacccgaac atcactccag atgagggctt tctgagtgtg gggtcaaata gtttcatgtt    3780
ccccaaatgg cccaaaactg acagtttaaa cgctgtcttg aacctaata tgacaaaagc    3840
gtgatctcat ccaagatgaa ctaagtttgg ttcgttgaaa tgctaacggc cagttggtca    3900
aaaagaaact tccaaaagtc ggcataccgt ttgtcttgtt tggtattgat tgacgaatgc    3960
tcaaaaataa tctcattaat gcttagcgca gtctctctat cgcttctgaa ccccggtgca    4020
cctgtgccga aacgcaaatg gggaaacacc cgcttttttgg atgattatgc attgtctcca    4080
cattgtatgc ttccaagatt ctggtgggaa tactgctgat agcctaacgt tcatgatcaa    4140
aatttaactg ttctaacccc tacttgacag caatatataa acagaaggaa gctgccctgt    4200
cttaaacctt tttttttatc atcattatta gcttactttc ataattgcga ctggttccaa    4260
ttgacaagct tttgatttta acgacttta acgacaactt gagaagatca aaaaacaact    4320
```

```
aattattgaa agaattcaaa acgatgacgg ttcatgacat catcgctact tacttcacaa    4380
agtggtacgt tatcgttcct ttagccctta ttgcatacag agtgctggat tacttctatg    4440
gtaggtactt aatgtataag ttgggtgcaa aaccatttt ccagaaacag accgacggtt     4500
gtttcggttt taaggctcct ttggaattgc ttaaaaagaa atcagacggt actctgatcg    4560
actttacatt gcaaaggata cacgatctgg atagacctga cattcccact tttactttc    4620
cagtattcag cattaatctt gttaacactc tcgaaccaga gaacataaaa gctattttgg    4680
caacgcaatt caatgatttc tccttgggta ccagacactc ccactttgct ccactcctcg    4740
gtgatggtat tttcacactg gacggtgcag gatggaagca ttctagatcc atgctaaggc    4800
cacaatttgc aagagagcag atttcccatg tgaagctgtt ggagccacat gtgcaggtct    4860
ttttcaagca cgtccgtaag gctcaaggaa aaacttttga tattcaggag ttgttttca    4920
gattgactgt tgattcagcc accgaatttt tgttcggaga aagtgttgaa tcgctgcgtg    4980
acgaatcaat tggaatgagc atcaacgcac ttgatttcga tggtaaagca ggttttgctg    5040
atgcttttaa ctactctcaa aactaccttg cttcaagagc tgtgatgcaa caactgtact    5100
gggttttgaa tggtaaaaag tttaaggaat gcaatgccaa ggtacacaag ttcgctgact    5160
attatgttaa caaagctctt gatctaacac ctgagcaatt ggaaaaacaa gacggctacg    5220
ttttcctata tgagttggtt aaacaaacta gagacaaaca agtttacgt gatcagttgt     5280
tgaatatcat ggtagctggc cgagatacaa cagcaggact gttgtcgttc gtcttttcg     5340
aactggccag aaatcccgaa gtcacaaaca aactgagaga agagatcgag acaagtttg     5400
gtttaggtga gaatgctagt gttgaggaca tcagctttga atctttaaag tcctgtgagt    5460
acttgaaggc tgtgctgaat gaaactttgc gtttatatcc atctgttcct caaaattc      5520
gtgtcgctac caaaaatacg acattgccaa gaggaggagg caaagacggt ctgagtcctg    5580
tactagtcag aaaaggtcag actgtgatct acggagttta tgcagcccat agaaatcctg    5640
ccgtatatgg aaaagatgct ttggagttc gtccggagag atggtttgaa ccagaaacca    5700
aaaagctcgg atgggctttc cttccattca atggtggtcc caggatatgt ttaggtcaac    5760
aattcgcttt aactgaagca tcctacgtga cagtgcgttt gttacaagag tttgcacatc    5820
tttccatgga cccagacact gagtatcctc ctaaaaagat gtctcatttg actatgtctt    5880
tgttcgatgg tgcaaacatt gaaatgtatt aagcggccgc tcaagaggat gtcagaatgc    5940
catttgcctg agagatgcag gcttcatttt tgatactttt ttatttgtaa cctatatagt    6000
ataggatttt ttttgtcatt ttgtttcttc tcgtacgagc ttgctcctga tcagcctatc    6060
tcgcagcaga tgaatatctt gtggtagggg tttgggaaaa tcattcgagt ttgatgtttt    6120
tcttggtatt tcccactcct cttcagagta cagaagatta agtgagacct tcgtttgtgc    6180
ggatccttca gtaatgtctt gttctttg ttgcagtggt gagccatttt gacttcgtga     6240
aagtttcttt agaatagttg tttccagagg ccaaacattc cacccgtagt aaagtgcaag    6300
cgtaggaaga ccaagactgg cataaatcag gtataagtgt cgagcactgg caggtgatct    6360
tctgaaagtt tctactagca gataagatcc agtagtcatg catatggcaa caatgtaccg    6420
tgtggatcta agaacgcgtc ctactaacct tcgcattcgt tggtccagtt tgttgttatc    6480
gatcaacgtg acaaggttgt cgattccgcg taagcatgca tacccaagga cgcctgttgc    6540
aattccaagt gagccagttc caacaatctt tgtaatatta gagcacttca ttgtgttgcg    6600
cttgaaagta aaatgcgaac aaattaagag ataatctcga aaccgcgact tcaaacgcca    6660
```

```
atatgatgtg cggcacacaa taagcgttca tatccgctgg gtgactttct cgctttaaaa    6720
aattatccga aaaaatttc tagagtgttg ttactttata cttccggctc gtataatacg    6780
acaaggtgta aggaggacta aaccatggct aaactcacct ctgctgttcc agtcctgact    6840
gctcgtgatg ttgctggtgc tgttgagttc tggactgata gactcggttt ctcccgtgac    6900
ttcgtagagg acgactttgc cggtgttgta cgtgacgacg ttaccctgtt catctccgca    6960
gttcaggacc aggttgtgcc agacaacact ctggcatggg tatgggttcg tggtctggac    7020
gaactgtacg ctgagtggtc tgaggtcgtg tctaccaact ccgtgatgc atctggtcca    7080
gctatgaccg agatcggtga acagccctgg ggtcgtgagt ttgcactgcg tgatccagct    7140
ggtaactgcg tgcatttcgt cgcagaagag caggactaac aattgacacc ttacgattat    7200
ttagagagta tttattagtt ttattgtatg tatacggatg ttttattatc tatttatgcc    7260
cttatattct gtaactatcc aaaagtccta tcttatcaag ccagcaatct atgtccgcga    7320
acgtcaacta aaaataagct ttttatgctc ttctctcttt ttttcccttc ggtataatta    7380
taccttgcat ccacagattc tcctgccaaa ttttgcataa tcctttacaa catggctata    7440
tgggagcact tagcgccctc caaaacccat attgcctacg catgtatagg tgttttttcc    7500
acaatatttt ctctgtgctc tcttttttatt aaagagaagc tctatatcgg agaagcttct    7560
gtggccgtta tattcggcct tatcgtggga ccacattgcc tgaattggtt tgccccggaa    7620
gattggggaa acttggatct gattacctta gctgcaggta ccactgagcg tcagaccccg    7680
tagaaaagat caaaggatct tcttgagatc cttttttct gcgcgtaatc tgctgcttgc    7740
aaacaaaaaa accaccgcta ccagcggtgg tttgtttgcc ggatcaagag ctaccaactc    7800
tttttccgaa ggtaactggc ttcagcagag cgcagatacc aaatactgtt cttctagtgt    7860
agccgtagtt aggccaccac ttcaagaact ctgtagcacc gcctacatac ctcgctctgc    7920
taatcctgtt accagtggct gctgccagtg gcgataagtc gtgtcttacc gggttggact    7980
caagacgata gttaccggat aaggcgcagc ggtcgggctg aacggggggt tcgtgcacac    8040
agcccagctt ggagcgaacg acctacaccg aactgagata cctacagcgt gagctatgag    8100
aaagcgccac gcttcccgaa gggagaaagg cggacaggta tccggtaagc ggcagggtcg    8160
gaacaggaga gcgcacgagg gagcttccag ggggaaacgc ctggtatctt tatagtcctg    8220
tcgggtttcg ccacctctga cttgagcgtc gatttttgtg atgctcgtca ggggggcgga    8280
gcctatggaa aaacgccagc aacgcggcct ttttacggtt cctggccttt tgctggcctt    8340
ttgctcacat gttctttcct gcggtaccc                                      8369
```

<210> SEQ ID NO 15
<211> LENGTH: 416
<212> TYPE: PRT
<213> ORGANISM: Sphingomonas macrogoltabidus

<400> SEQUENCE: 15

Met Glu His Thr Gly Gln Ser Ala Ala Thr Met Pro Leu Asp Ser
1               5                   10                  15

Ile Asp Val Ser Ile Pro Glu Leu Phe Tyr Asn Asp Ser Val Gly Glu
            20                  25                  30

Tyr Phe Lys Arg Leu Arg Lys Asp Asp Pro Val His Tyr Cys Ala Asp
        35                  40                  45

Ser Ala Phe Gly Pro Tyr Trp Ser Ile Thr Lys Tyr Asn Asp Ile Met
    50                  55                  60

His Val Asp Thr Asn His Asp Ile Phe Ser Ser Asp Ala Gly Tyr Gly

```
                65                  70                  75                  80
Gly Ile Ile Ile Asp Asp Gly Ile Gln Lys Gly Gly Asp Gly Gly Leu
                    85                  90                  95

Asp Leu Pro Asn Phe Ile Ala Met Asp Arg Pro Arg His Asp Glu Gln
                100                 105                 110

Arg Lys Ala Val Ser Pro Ile Ala Pro Ala Asn Leu Ala Ala Leu
                115                 120                 125

Glu Gly Thr Ile Arg Glu Arg Val Ser Lys Thr Leu Asp Gly Leu Pro
            130                 135                 140

Val Gly Glu Glu Phe Asp Trp Val Asp Arg Val Ser Ile Glu Ile Thr
145                 150                 155                 160

Thr Gln Met Leu Ala Thr Leu Phe Asp Phe Pro Phe Glu Arg Arg
                165                 170                 175

Lys Leu Thr Arg Trp Ser Asp Val Thr Thr Ala Ala Pro Gly Gly Gly
                180                 185                 190

Val Val Glu Ser Trp Asp Gln Arg Lys Thr Glu Leu Leu Glu Cys Ala
            195                 200                 205

Ala Tyr Phe Gln Val Leu Trp Asn Glu Arg Val Asn Lys Asp Pro Gly
210                 215                 220

Asn Asp Leu Ile Ser Met Leu Ala His Ser Pro Ala Thr Arg Asn Met
225                 230                 235                 240

Thr Pro Glu Glu Tyr Leu Gly Asn Val Leu Leu Ile Val Gly Gly
                245                 250                 255

Asn Asp Thr Thr Arg Asn Ser Met Thr Gly Gly Val Leu Ala Leu His
                260                 265                 270

Lys Asn Pro Asp Gln Phe Ala Lys Leu Lys Ala Asn Pro Ala Leu Val
            275                 280                 285

Glu Thr Met Val Pro Glu Ile Ile Arg Trp Gln Thr Pro Leu Ala His
            290                 295                 300

Met Arg Arg Thr Ala Ile Ala Asp Ser Glu Leu Gly Gly Lys Thr Ile
305                 310                 315                 320

Arg Lys Gly Asp Lys Val Val Met Trp Tyr Tyr Ser Gly Asn Arg Asp
                325                 330                 335

Asp Glu Val Ile Asp Arg Pro Glu Glu Phe Ile Ile Asp Arg Pro Arg
                340                 345                 350

Pro Arg Gln His Leu Ser Phe Gly Phe Gly Ile His Arg Cys Val Gly
                355                 360                 365

Asn Arg Leu Ala Glu Met Gln Leu Arg Ile Leu Trp Glu Glu Ile Leu
            370                 375                 380

Thr Arg Phe Ser Arg Ile Glu Val Met Ala Glu Pro Glu Arg Val Arg
385                 390                 395                 400

Ser Asn Phe Val Arg Gly Tyr Ala Lys Met Met Val Arg Val His Ala
                405                 410                 415

<210> SEQ ID NO 16
<211> LENGTH: 420
<212> TYPE: PRT
<213> ORGANISM: Mycobacterium sp. ENV421

<400> SEQUENCE: 16

Met Thr Glu Met Thr Val Ala Ala Ser Asp Ala Thr Asn Ala Ala Tyr
1               5                   10                  15

Gly Met Ala Leu Glu Asp Ile Asp Val Ser Asn Pro Val Leu Phe Arg
                20                  25                  30
```

Asp Asn Thr Trp His Pro Tyr Phe Lys Arg Leu Arg Glu Asp Pro
            35                  40                  45

Val His Tyr Cys Lys Ser Ser Met Phe Gly Pro Tyr Trp Ser Val Thr
 50                  55                  60

Lys Tyr Arg Asp Ile Met Ala Val Glu Thr Asn Pro Lys Val Phe Ser
 65                  70                  75                  80

Ser Glu Ala Lys Ser Gly Gly Ile Thr Ile Met Asp Asp Asn Ala Ala
                 85                  90                  95

Ala Ser Leu Pro Met Phe Ile Ala Met Asp Pro Lys His Asp Val
                100                 105                 110

Gln Arg Lys Thr Val Ser Pro Ile Val Ala Pro Glu Asn Leu Ala Thr
            115                 120                 125

Met Glu Ser Val Ile Arg Gln Arg Thr Gly Asp Leu Leu Asp Gly Leu
130                 135                 140

Pro Ile Asn Glu Glu Phe Asp Trp Val His Arg Val Ser Ile Asp Leu
145                 150                 155                 160

Thr Thr Lys Met Leu Ala Thr Leu Phe Asp Phe Pro Trp Asp Asp Arg
                165                 170                 175

Ala Lys Leu Thr Arg Trp Ser Asp Val Thr Thr Ala Leu Pro Gly Gly
            180                 185                 190

Gly Ile Ile Asp Ser Glu Glu Gln Arg Met Ala Glu Leu Met Glu Cys
        195                 200                 205

Ala Thr Tyr Phe Thr Glu Leu Trp Asn Gln Arg Val Asn Ala Glu Pro
    210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Val Val Leu Leu Ile Val Gly
                245                 250                 255

Gly Asn Asp Thr Thr Arg Asn Ser Met Thr Gly Gly Val Leu Ala Leu
            260                 265                 270

Asn Glu Phe Pro Asp Glu Tyr Arg Lys Leu Ser Ala Asn Pro Ala Leu
        275                 280                 285

Ile Ser Ser Met Val Ser Glu Ile Ile Arg Trp Gln Thr Pro Leu Ser
    290                 295                 300

His Met Arg Arg Thr Ala Leu Glu Asp Ile Glu Phe Ala Gly Lys His
305                 310                 315                 320

Ile Arg Gln Gly Asp Lys Val Val Met Trp Tyr Val Ser Gly Asn Arg
                325                 330                 335

Asp Pro Glu Ala Ile Asp Asn Pro Asp Thr Phe Ile Ile Asp Arg Ala
            340                 345                 350

Lys Pro Arg Gln His Leu Ser Phe Gly Phe Gly Ile His Arg Cys Val
        355                 360                 365

Gly Asn Arg Leu Ala Glu Leu Gln Leu Asn Ile Leu Trp Glu Glu Ile
    370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                405                 410                 415

Arg Ile Asn Ala
            420

<210> SEQ ID NO 17
<211> LENGTH: 281
<212> TYPE: PRT

<213> ORGANISM: Unknown
<220> FEATURE:
<223> OTHER INFORMATION: cytochrome P450 alkane hydroxylase from uncultured bacterium

<400> SEQUENCE: 17

```
Met Phe Ile Ala Met Asp Pro Pro Lys His Asp Val Gln Arg Arg Ser
1               5                   10                  15

Val Gln Asn Val Val Ala Pro Gln Asn Leu Lys Glu Met Glu Gly Leu
            20                  25                  30

Ile Arg Thr Arg Thr Ala Glu Val Leu Glu Ser Leu Pro Arg Asn Glu
        35                  40                  45

Val Phe Asn Trp Val Pro Ala Val Ser Lys Glu Leu Thr Gly Arg Met
    50                  55                  60

Leu Ala Thr Leu Leu Asp Phe Pro Tyr Glu Glu Arg His Lys Leu Ile
65                  70                  75                  80

Glu Trp Ser Asp Gln Met Ala Gly Thr Ala Ala Thr Gly Gly Glu
                85                  90                  95

Phe Glu Asp Glu Glu Ser Met Phe Glu Ala Ala Ala Asp Met Ala Trp
            100                 105                 110

Ser Phe Ser Arg Leu Trp Arg Asp Lys Lys Ala Arg Ala Ala Gly
            115                 120                 125

Glu Ala Pro Gly Phe Asp Leu Ile Ser Leu Leu Gln Ser Gly Glu Asp
130                 135                 140

Thr Gln Asp Leu Ile Asn Arg Pro Met Glu Phe Ile Gly Asn Leu Ala
145                 150                 155                 160

Leu Leu Ile Val Gly Gly Asn Asp Thr Thr Arg Asn Ser Met Ser Gly
                165                 170                 175

Gly Val Leu Ala Met Asn Gln Phe Pro Ala Glu Phe Ala Lys Leu Lys
            180                 185                 190

Ala Asn Pro Lys Leu Leu Pro Asn Met Val Ser Glu Ile Ile Arg Trp
        195                 200                 205

Gln Thr Pro Leu Ala His Met Arg Arg Val Ala Thr Gln Asp Val Glu
    210                 215                 220

Leu Arg Gly Gln Thr Ile Lys Lys Gly Asp Arg Val Leu Met Trp Tyr
225                 230                 235                 240

Ala Ser Gly Asn Arg Asp Glu Arg Lys Phe Glu Lys Pro Asp Asp Phe
                245                 250                 255

Ile Ile Asp Arg Glu Gly Ala Arg Asn His Ile Ala Phe Gly Tyr Gly
            260                 265                 270

Ile His Arg Cys Met Gly Asn Arg Leu
        275                 280
```

<210> SEQ ID NO 18
<211> LENGTH: 281
<212> TYPE: PRT
<213> ORGANISM: Unknown
<220> FEATURE:
<223> OTHER INFORMATION: cytochrome P450 alkane hydroxylase from uncultured bacterium

<400> SEQUENCE: 18

```
Met Phe Ile Ala Met Asp Pro Pro Lys His Asp Val Gln Arg Arg Ala
1               5                   10                  15

Val Gln Gly Val Val Ala Pro Lys Asn Leu Lys Glu Met Glu Gly Leu
            20                  25                  30

Ile Arg Ser Arg Ala Ala Glu Val Leu Asp Ser Leu Pro Leu Asp Lys
```

```
            35                  40                  45
Pro Phe Asp Trp Val Pro Ala Val Ser Lys Glu Leu Thr Gly Arg Met
 50                  55                  60

Leu Ala Thr Leu Leu Asp Phe Pro Tyr Glu Asp Arg His Lys Leu Val
65                  70                  75                  80

Glu Trp Ser Asp Arg Leu Ser Gly Ala Ala Ser Ala Thr Gly Gly Glu
                85                  90                  95

Phe Thr Asp Glu Asp Val Met Phe Asp Asp Ala Ala Asp Met Ala Arg
            100                 105                 110

Ala Phe Ser Arg Leu Trp Arg Asp Lys Glu Ala Arg Arg Ala Ser Gly
        115                 120                 125

Glu Glu Pro Gly Phe Asp Leu Ile Ser Met Leu Gln Ser Asn Glu Asp
    130                 135                 140

Thr Lys Asp Leu Ile Asn Arg Pro Met Glu Phe Ile Gly Asn Leu Ala
145                 150                 155                 160

Leu Leu Ile Val Gly Gly Asn Asp Thr Thr Arg Asn Ser Met Ser Gly
                165                 170                 175

Gly Val Leu Ala Leu Asn Gln Phe Pro Glu Glu Phe Arg Lys Leu Lys
            180                 185                 190

Ala Lys Pro Glu Leu Ile Pro Asn Met Val Ser Glu Ile Ile Arg Trp
        195                 200                 205

Gln Thr Pro Leu Ala Asn Met Arg Arg Val Ala Thr Gln Asp Val Glu
    210                 215                 220

Leu Arg Gly Gln Thr Ile Lys Lys Gly Asp Arg Val Leu Met Trp Tyr
225                 230                 235                 240

Ala Ser Gly Asn Arg Asp Glu Arg Lys Phe Glu Asn Pro Asp Gln Leu
                245                 250                 255

Ile Ile Asp Arg Lys Asp Ala Arg Asn His Ile Ser Phe Gly Tyr Gly
            260                 265                 270

Ile His Arg Cys Met Gly Asn Arg Leu
        275                 280

<210> SEQ ID NO 19
<211> LENGTH: 470
<212> TYPE: PRT
<213> ORGANISM: Marinobacter hydrocarbonoclasticus VT8

<400> SEQUENCE: 19

Met Pro Thr Leu Pro Arg Thr Phe Asp Asp Ile Gln Ser Arg Leu Ile
1               5                   10                  15

Asn Ala Thr Ser Arg Val Val Pro Met Gln Arg Gln Ile Gln Gly Leu
                20                  25                  30

Lys Phe Leu Met Ser Ala Lys Arg Lys Thr Phe Gly Pro Arg Arg Pro
            35                  40                  45

Met Pro Glu Phe Val Glu Thr Pro Ile Pro Asp Val Asn Thr Leu Ala
        50                  55                  60

Leu Glu Asp Ile Asp Val Ser Asn Pro Phe Leu Tyr Arg Gln Gly Gln
65                  70                  75                  80

Trp Arg Ala Tyr Phe Lys Arg Leu Arg Asp Glu Ala Pro Val His Tyr
                85                  90                  95

Gln Lys Asn Ser Pro Phe Gly Pro Phe Trp Ser Val Thr Arg Phe Glu
            100                 105                 110

Asp Ile Leu Phe Val Asp Lys Ser His Asp Leu Phe Ser Ala Glu Pro
        115                 120                 125
```

```
Gln Ile Ile Leu Gly Asp Pro Pro Glu Gly Leu Ser Val Glu Met Phe
    130                 135                 140

Ile Ala Met Asp Pro Pro Lys His Asp Val Gln Arg Ser Ser Val Gln
145                 150                 155                 160

Gly Val Val Ala Pro Lys Asn Leu Lys Glu Met Glu Gly Leu Ile Arg
                165                 170                 175

Ser Arg Thr Gly Asp Val Leu Asp Ser Leu Pro Thr Asp Lys Pro Phe
            180                 185                 190

Asn Trp Val Pro Ala Val Ser Lys Glu Leu Thr Gly Arg Met Leu Ala
        195                 200                 205

Thr Leu Leu Asp Phe Pro Tyr Glu Glu Arg His Lys Leu Val Glu Trp
    210                 215                 220

Ser Asp Arg Met Ala Gly Ala Ser Ala Thr Gly Gly Glu Phe Ala
225                 230                 235                 240

Asp Glu Asn Ala Met Phe Asp Ala Ala Asp Met Ala Arg Ser Phe
                245                 250                 255

Ser Arg Leu Trp Arg Asp Lys Glu Ala Arg Ala Ala Gly Glu Glu
            260                 265                 270

Pro Gly Phe Asp Leu Ile Ser Leu Leu Gln Ser Asn Lys Glu Thr Lys
        275                 280                 285

Asp Leu Ile Asn Arg Pro Met Glu Phe Ile Gly Asn Leu Thr Leu Leu
    290                 295                 300

Ile Val Gly Gly Asn Asp Thr Thr Arg Asn Ser Met Ser Gly Gly Leu
305                 310                 315                 320

Val Ala Met Asn Glu Phe Pro Arg Glu Phe Glu Lys Leu Lys Ala Lys
                325                 330                 335

Pro Glu Leu Ile Pro Asn Met Val Ser Glu Ile Ile Arg Trp Gln Thr
            340                 345                 350

Pro Leu Ala Tyr Met Arg Arg Ile Ala Lys Gln Asp Val Glu Leu Gly
        355                 360                 365

Gly Gln Thr Ile Lys Lys Gly Asp Arg Val Val Met Trp Tyr Ala Ser
    370                 375                 380

Gly Asn Arg Asp Glu Arg Lys Phe Asp Asn Pro Asp Gln Phe Ile Ile
385                 390                 395                 400

Asp Arg Lys Asp Ala Arg Asn His Met Ser Phe Gly Tyr Gly Val His
                405                 410                 415

Arg Cys Met Gly Asn Arg Leu Ala Glu Leu Gln Leu Arg Ile Leu Trp
            420                 425                 430

Glu Glu Ile Leu Lys Arg Phe Asp Asn Ile Glu Val Val Glu Glu Pro
        435                 440                 445

Glu Arg Val Gln Ser Asn Phe Val Arg Gly Tyr Ser Arg Leu Met Val
    450                 455                 460

Lys Leu Thr Pro Asn Ser
465                 470

<210> SEQ ID NO 20
<211> LENGTH: 401
<212> TYPE: PRT
<213> ORGANISM: Pseudomonas aeruginosa

<400> SEQUENCE: 20

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
            20                  25                  30
```

Met Ile Gly Ile Trp Leu Ala Asn Glu Thr Gly Trp Gly Ile Phe Tyr
                35                  40                  45

Gly Leu Val Leu Leu Val Trp Tyr Gly Ala Leu Pro Leu Leu Asp Ala
 50                  55                  60

Met Phe Gly Glu Asp Phe Asn Asn Pro Pro Glu Glu Val Val Pro Lys
 65                  70                  75                  80

Leu Glu Lys Glu Arg Tyr Tyr Arg Val Leu Thr Tyr Leu Thr Val Pro
                 85                  90                  95

Met His Tyr Ala Ala Leu Ile Val Ser Ala Trp Trp Val Gly Thr Gln
                100                 105                 110

Pro Met Ser Trp Leu Glu Ile Gly Ala Leu Ala Leu Ser Leu Gly Ile
                115                 120                 125

Val Asn Gly Leu Ala Leu Asn Thr Gly His Glu Leu Gly His Lys Lys
130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
                180                 185                 190

Lys Phe Ser Ile Arg Glu Ile Pro Gly Ala Phe Ile Arg Ala Trp Gly
                195                 200                 205

Leu Glu Glu Gln Arg Leu Ser Arg Arg Gly Gln Ser Val Trp Ser Phe
                210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
                260                 265                 270

His Tyr Gly Leu Leu Arg Gln Lys Met Glu Asp Gly Arg Tyr Glu His
                275                 280                 285

Gln Lys Pro His His Ser Trp Asn Ser Asn His Ile Val Ser Asn Leu
                290                 295                 300

Val Leu Phe His Leu Gln Arg His Ser Asp His His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
                340                 345                 350

Arg Ser Val Met Asp Pro Lys Val Val Asp Trp Ala Gly Gly Asp Leu
                355                 360                 365

Asn Lys Ile Gln Ile Asp Asp Ser Met Arg Glu Thr Tyr Leu Lys Lys
                370                 375                 380

Phe Gly Thr Ser Ser Ala Gly His Ser Ser Thr Ser Ala Val Ala
385                 390                 395                 400

Ser

<210> SEQ ID NO 21
<211> LENGTH: 402
<212> TYPE: PRT
<213> ORGANISM: Pseudomonas putida

<400> SEQUENCE: 21

```
Met Asn Gly Lys Ser Ser Val Leu Asp Ser Ala Pro Glu Tyr Val Asp
1               5                   10                  15

Lys Lys Lys Tyr Phe Trp Ile Leu Ser Thr Phe Trp Pro Ala Thr Pro
            20                  25                  30

Met Ile Gly Ile Trp Leu Ala Asn Glu Thr Gly Trp Gly Ile Phe Tyr
        35                  40                  45

Gly Leu Val Leu Ala Val Trp Tyr Gly Val Leu Pro Leu Leu Asp Ala
    50                  55                  60

Met Phe Gly Glu Asp Phe Asn Asn Pro Pro Glu Glu Val Val Glu Lys
65                  70                  75                  80

Leu Glu Lys Glu Arg Tyr Tyr Arg Val Leu Thr Tyr Leu Thr Val Pro
                85                  90                  95

Met His Tyr Ala Ala Leu Ile Val Ser Ala Trp Trp Val Gly Thr Gln
                100                 105                 110

Ser Met Ser Trp Phe Glu Ile Val Ala Leu Ala Leu Ser Leu Gly Ile
        115                 120                 125

Val Asn Gly Leu Ala Leu Asn Thr Gly His Glu Leu Gly His Lys Lys
    130                 135                 140

Glu Ala Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Asn Ile Tyr
                180                 185                 190

Lys Phe Ser Thr Arg Glu Ile Pro Gly Ala Phe Arg Arg Ala Trp Gly
        195                 200                 205

Leu Glu Glu Gln Arg Leu Ser Arg Arg Gly Gln Ser Val Trp Ser Phe
210                 215                 220

Asp Asn Glu Ile Leu Gln Pro Met Val Ile Thr Val Val Leu Tyr Thr
225                 230                 235                 240

Leu Leu Leu Ala Phe Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
                260                 265                 270

His Tyr Gly Leu Leu Arg Glu Lys Met Ala Asp Gly Arg Tyr Glu His
                275                 280                 285

Gln Lys Pro His His Ser Trp Asn Ser Asn His Ile Val Ser Asn Leu
    290                 295                 300

Val Leu Phe His Leu Gln Arg His Ser Asp His His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
                340                 345                 350

Arg Ser Val Met Asp Pro Lys Val Asn Trp Ala Asn Gly Asp Leu
                355                 360                 365

Ser Lys Ile Gln Ile Glu Asp Ser Met Arg Ala Glu Tyr Ile Lys Lys
    370                 375                 380

Phe Thr His Asn Val Gly Ala Asp Asp Lys Arg Gly Ala Thr Ala Val
385                 390                 395                 400

Ala Ser
```

```
<210> SEQ ID NO 22
<211> LENGTH: 404
<212> TYPE: PRT
<213> ORGANISM: Alcanivorax borkumensis

<400> SEQUENCE: 22

Met Ser Glu Asn Ile Leu Thr Glu Pro Pro Arg Ser Asp Ala Asp Asn
1               5                   10                  15

Glu Gly Tyr Val Asp Arg Lys Arg His Leu Trp Ile Leu Ser Val Leu
            20                  25                  30

Trp Pro Ala Thr Pro Ile Ile Gly Leu Tyr Leu Val Ser Gln Thr Gly
        35                  40                  45

Trp Ser Ile Trp Tyr Gly Leu Val Leu Ile Leu Trp Tyr Gly Leu Val
    50                  55                  60

Pro Leu Ile Asp Thr Met Leu Gly Glu Asp Tyr Ser Asn Pro Pro Glu
65                  70                  75                  80

Ser Val Val Pro Lys Leu Glu Gln Asp Arg Tyr Tyr Lys Val Leu Thr
                85                  90                  95

Tyr Leu Thr Val Pro Ile His Tyr Ala Ala Leu Ile Ile Ser Ala Trp
            100                 105                 110

Trp Val Ser Thr Gln Pro Ile Gly Val Phe Glu Phe Leu Ala Leu Ala
        115                 120                 125

Leu Ser Leu Gly Ile Val Asn Gly Leu Ala Leu Asn Thr Gly His Glu
130                 135                 140

Leu Gly His Lys Lys Glu Thr Phe Asp Arg Trp Met Ala Lys Leu Val
145                 150                 155                 160

Leu Ala Val Val Gly Tyr Gly His Phe Phe Ile Glu His Asn Lys Gly
                165                 170                 175

His His Arg Asp Val Ala Thr Pro Met Asp Pro Ala Thr Ser Arg Met
            180                 185                 190

Gly Glu Ser Ile Tyr Thr Phe Ser Leu Arg Glu Ile Pro Gly Ala Phe
        195                 200                 205

Lys Arg Ala Trp Gly Leu Glu Glu Gln Arg Leu Ser Arg Cys Gly Lys
    210                 215                 220

Ser Val Trp Ser Leu Asp Asn Glu Val Leu Gln Pro Met Ile Leu Thr
225                 230                 235                 240

Val Val Leu Tyr Ala Ala Leu Leu Ala Phe Phe Gly Pro Leu Met Leu
                245                 250                 255

Ile Phe Leu Pro Ile Gln Met Ala Phe Gly Trp Trp Gln Leu Thr Ser
            260                 265                 270

Ala Asn Tyr Ile Glu His Tyr Gly Leu Leu Arg Glu Lys Leu Pro Asn
        275                 280                 285

Gly Arg Tyr Glu His Gln Lys Pro His His Ser Trp Asn Ser Asn His
    290                 295                 300

Val Met Ser Asn Leu Ile Leu Phe His Leu Gln Arg His Ser Asp His
305                 310                 315                 320

His Ala His Pro Thr Arg Ser Tyr Gln Ser Leu Arg Asp Phe Ser Asp
                325                 330                 335

Leu Pro Thr Leu Pro Thr Gly Tyr Pro Gly Met Phe Phe Val Ala Phe
            340                 345                 350

Phe Pro Ser Trp Phe Arg Ser Leu Met Asp Asp Arg Val Met Glu Trp
        355                 360                 365

Ala His Gly Asp Ile Asn Lys Ile Gln Ile Gln Pro Gly Met Arg Glu
    370                 375                 380
```

```
Phe Tyr Glu Gln Lys Phe Gly Val Lys Gly Ser Glu Ser Pro Asp Thr
385                 390                 395                 400

Thr Val Ala Lys
```

<210> SEQ ID NO 23
<211> LENGTH: 522
<212> TYPE: PRT
<213> ORGANISM: Candida tropicalis

<400> SEQUENCE: 23

```
Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
                20                  25                  30

Gly Arg Tyr Leu Met Tyr Lys Leu Gly Ala Lys Pro Phe Phe Gln Lys
            35                  40                  45

Gln Thr Asp Gly Cys Phe Gly Phe Lys Ala Pro Leu Glu Leu Leu Lys
    50                  55                  60

Lys Lys Ser Asp Gly Thr Leu Ile Asp Phe Thr Leu Gln Arg Ile His
65                  70                  75                  80

Asp Leu Asp Arg Pro Asp Ile Pro Thr Phe Thr Phe Pro Val Phe Ser
                85                  90                  95

Ile Asn Leu Val Asn Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Val Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
            260                 265                 270

Tyr Tyr Val Asn Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
    290                 295                 300

Lys Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350
```

```
Gly Leu Gly Glu Asn Ala Ser Val Glu Asp Ile Ser Phe Glu Ser Leu
            355                 360                 365

Lys Ser Cys Glu Tyr Leu Lys Ala Val Leu Asn Glu Thr Leu Arg Leu
370                 375                 380

Tyr Pro Ser Val Pro Gln Asn Phe Arg Val Ala Thr Lys Asn Thr Thr
385                 390                 395                 400

Leu Pro Arg Gly Gly Lys Asp Gly Leu Ser Pro Val Leu Val Arg
            405                 410                 415

Lys Gly Gln Thr Val Ile Tyr Val Tyr Ala Ala His Arg Asn Pro
            420                 425                 430

Ala Val Tyr Gly Lys Asp Ala Leu Glu Phe Arg Pro Glu Arg Trp Phe
            435                 440                 445

Glu Pro Glu Thr Lys Lys Leu Gly Trp Ala Phe Leu Pro Phe Asn Gly
            450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ala His Leu Ser Met Asp
                485                 490                 495

Pro Asp Thr Glu Tyr Pro Pro Lys Lys Met Ser His Leu Thr Met Ser
            500                 505                 510

Leu Phe Asp Gly Ala Asn Ile Glu Met Tyr
            515                 520

<210> SEQ ID NO 24
<211> LENGTH: 523
<212> TYPE: PRT
<213> ORGANISM: Candida maltosa

<400> SEQUENCE: 24

Met Ala Ile Glu Gln Ile Ile Glu Glu Val Leu Pro Tyr Leu Thr Lys
1               5                   10                  15

Trp Tyr Thr Ile Leu Phe Gly Ala Ala Phe Thr Tyr Phe Leu Ser Ile
                20                  25                  30

Ala Leu Arg Asn Lys Tyr Tyr Glu Tyr Lys Leu Lys Cys Glu Asn Pro
            35                  40                  45

Pro Tyr Phe Lys Thr Ala Gly Phe Val Gly Ile Pro Gly Leu Ile Asp
        50                  55                  60

Val Ile Lys Ala Lys Asn Ala Gly Lys Leu Ala Asp Tyr Ala Asp Gln
65                  70                  75                  80

Thr Phe Asp Glu Tyr Pro His His Ser Phe Tyr Met Thr Val Ala Gly
                85                  90                  95

Met Leu Lys Ile Val Leu Thr Val Asp Pro Glu Asn Ile Lys Ala Val
            100                 105                 110

Leu Ala Thr Gln Phe Asn Asp Phe Ala Leu Gly Ala Arg His Ala His
            115                 120                 125

Phe Asp Pro Leu Leu Gly Asp Gly Ile Phe Thr Leu Asp Gly Glu Gly
        130                 135                 140

Trp Lys His Ser Arg Ala Met Leu Arg Pro Gln Phe Ala Arg Glu Gln
145                 150                 155                 160

Ile Ala His Val Lys Ala Leu Glu Pro His Val Gln Val Leu Ala Lys
                165                 170                 175

Gln Ile Lys Leu Asn Lys Gly Glu Thr Phe Asp Leu Gln Glu Leu Phe
            180                 185                 190

Phe Arg Phe Thr Val Asp Thr Ala Thr Glu Phe Leu Phe Gly Glu Ser
            195                 200                 205
```

Val His Ser Leu Tyr Asp Glu Lys Leu Gly Val Pro Pro Asn Asn
    210                 215                 220

Ile Pro Gly Arg Glu Asn Phe Ala Lys Ala Phe Asn Thr Ser Gln His
225                 230                 235                 240

Tyr Leu Ala Thr Arg Thr Tyr Ser Gln Met Phe Tyr Phe Leu Thr Asn
                245                 250                 255

Pro Lys Glu Phe Arg Asp Cys Asn Ala Lys Val His Lys Leu Ala Gln
                260                 265                 270

Tyr Phe Val Asn Lys Ala Leu Asp Ala Ser Glu Asp Glu Val Ala Glu
                275                 280                 285

Lys Ser Lys Gly Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Met Phe Glu Leu
                325                 330                 335

Ala Arg Asn Pro Lys Ile Trp Asn Lys Leu Arg Glu Glu Ile Glu Val
                340                 345                 350

Asn Phe Gly Leu Gly Glu Glu Ala Arg Val Asp Glu Ile Ser Phe Glu
    355                 360                 365

Thr Leu Lys Lys Cys Glu Tyr Leu Lys Ala Val Leu Asn Glu Thr Leu
370                 375                 380

Arg Met Tyr Pro Ser Val Pro Val Asn Phe Arg Thr Ala Thr Arg Asp
385                 390                 395                 400

Thr Thr Leu Pro Arg Gly Gly Lys Asp Gly Thr Ser Pro Ile Phe
                405                 410                 415

Val Pro Lys Gly Ser Ser Val Val Tyr Thr Val Tyr Lys Thr His Arg
                420                 425                 430

Leu Glu Glu Tyr Tyr Gly Lys Asp Ala Tyr Glu Phe Arg Pro Glu Arg
                435                 440                 445

Trp Phe Glu Pro Ser Thr Arg Lys Leu Gly Trp Ala Tyr Val Pro Phe
    450                 455                 460

Asn Gly Gly Pro Arg Ile Cys Leu Gly Gln Gln Phe Ala Leu Thr Glu
465                 470                 475                 480

Ala Ser Tyr Val Ile Thr Arg Leu Ala Gln Met Phe Glu His Leu Glu
                485                 490                 495

Ser Lys Asp Glu Thr Tyr Pro Pro Asn Lys Cys Ile His Leu Thr Met
                500                 505                 510

Asn His Asn Glu Gly Val Phe Ile Ser Ala Lys
    515                 520

<210> SEQ ID NO 25
<211> LENGTH: 401
<212> TYPE: PRT
<213> ORGANISM: Pseudomonas oleovorans

<400> SEQUENCE: 25

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
                20                  25                  30

Met Ile Gly Ile Trp Leu Ala Asn Glu Thr Gly Trp Gly Ile Phe Tyr
                35                  40                  45

Gly Leu Val Leu Leu Val Trp Tyr Gly Ala Leu Pro Leu Leu Asp Ala

```
                50                  55                  60
Met Phe Gly Glu Asp Phe Asn Asn Pro Pro Glu Val Val Pro Lys
 65                  70                  75                  80

Leu Glu Lys Glu Arg Tyr Tyr Arg Val Leu Thr Tyr Leu Thr Val Pro
                 85                  90                  95

Met His Tyr Ala Ala Leu Ile Val Ser Ala Trp Trp Val Gly Thr Gln
                100                 105                 110

Pro Met Ser Trp Leu Glu Ile Gly Ala Leu Ala Leu Ser Leu Gly Ile
            115                 120                 125

Val Asn Gly Leu Ala Leu Asn Thr Gly His Glu Leu Gly His Lys Lys
130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
            195                 200                 205

Leu Glu Glu Gln Arg Leu Ser Arg Arg Gly Gln Ser Val Trp Ser Phe
210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
            275                 280                 285

Gln Lys Pro His His Ser Trp Asn Ser Asn His Ile Val Ser Asn Leu
290                 295                 300

Val Leu Phe His Leu Gln Arg His Ser Asp His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
            340                 345                 350

Arg Ser Val Met Asp Pro Lys Val Val Asp Trp Ala Gly Gly Asp Leu
            355                 360                 365

Asn Lys Ile Gln Ile Asp Asp Ser Met Arg Glu Thr Tyr Leu Lys Lys
370                 375                 380

Phe Gly Thr Ser Ser Ala Gly His Ser Ser Ser Thr Ser Ala Val Ala
385                 390                 395                 400

Ser

<210> SEQ ID NO 26
<211> LENGTH: 402
<212> TYPE: PRT
<213> ORGANISM: Pseudomonas putida

<400> SEQUENCE: 26

Met Asn Gly Lys Ser Ser Val Leu Asp Ser Ala Pro Glu Tyr Val Asp
 1               5                  10                  15

Lys Lys Lys Tyr Phe Trp Ile Leu Ser Thr Phe Trp Pro Ala Thr Pro
```

```
            20                  25                  30
Met Ile Gly Ile Trp Leu Ala Asn Glu Thr Gly Trp Gly Ile Phe Tyr
        35                  40                  45
Gly Leu Val Leu Ala Val Trp Tyr Gly Val Leu Pro Leu Leu Asp Ala
 50                  55                  60
Met Phe Gly Glu Asp Phe Asn Asn Pro Pro Glu Val Val Glu Lys
 65                  70                  75                  80
Leu Glu Lys Glu Arg Tyr Tyr Arg Val Leu Thr Tyr Leu Thr Val Pro
                85                  90                  95
Met His Tyr Ala Ala Leu Ile Val Ser Ala Trp Trp Val Gly Thr Gln
                100                 105                 110
Ser Met Ser Trp Phe Glu Ile Val Ala Leu Ala Leu Ser Leu Gly Ile
                115                 120                 125
Val Asn Gly Leu Ala Leu Asn Thr Gly His Glu Leu Gly His Lys Lys
                130                 135                 140
Glu Ala Phe Asp Arg Trp Met Ala Lys Ile Val Leu Ala Val Val Gly
145                 150                 155                 160
Tyr Gly His Phe Phe Ile Glu His Asn Lys Gly His His Arg Asp Val
                165                 170                 175
Ala Thr Pro Met Asp Pro Ala Thr Ser Arg Met Gly Glu Asn Ile Tyr
                180                 185                 190
Lys Phe Ser Thr Arg Glu Ile Pro Gly Ala Phe Arg Arg Ala Trp Gly
                195                 200                 205
Leu Glu Glu Gln Arg Leu Ser Arg Arg Gly Gln Ser Val Trp Ser Phe
                210                 215                 220
Asp Asn Glu Ile Leu Gln Pro Met Val Ile Thr Val Val Leu Tyr Thr
225                 230                 235                 240
Leu Leu Leu Ala Phe Phe Gly Pro Lys Met Leu Val Phe Leu Pro Ile
                245                 250                 255
Gln Met Ala Phe Gly Trp Trp Gln Leu Thr Ser Ala Asn Tyr Ile Glu
                260                 265                 270
His Tyr Gly Leu Leu Arg Glu Lys Met Ala Asp Gly Arg Tyr Glu His
                275                 280                 285
Gln Lys Pro His His Ser Trp Asn Ser Asn His Ile Val Ser Asn Leu
                290                 295                 300
Val Leu Phe His Leu Gln Arg His Ser Asp His His Ala His Pro Thr
305                 310                 315                 320
Arg Ser Tyr Gln Ser Leu Arg Asp Phe Pro Gly Leu Pro Ala Leu Pro
                325                 330                 335
Thr Gly Tyr Pro Gly Ala Phe Leu Met Ala Met Ile Pro Gln Trp Phe
                340                 345                 350
Arg Ser Val Met Asp Pro Lys Val Asn Trp Ala Asn Gly Asp Leu
                355                 360                 365
Ser Lys Ile Gln Ile Glu Asp Ser Met Arg Ala Glu Tyr Ile Lys Lys
                370                 375                 380
Phe Thr His Asn Val Gly Ala Asp Asp Lys Arg Gly Ala Thr Ala Val
385                 390                 395                 400
Ala Ser

<210> SEQ ID NO 27
<211> LENGTH: 404
<212> TYPE: PRT
<213> ORGANISM: Alcanivorax borkumensis
```

<400> SEQUENCE: 27

Met Ser Glu Asn Ile Leu Thr Glu Pro Pro Arg Ser Asp Ala Asp Asn
1               5                   10                  15

Glu Gly Tyr Val Asp Arg Lys Arg His Leu Trp Ile Leu Ser Val Leu
            20                  25                  30

Trp Pro Ala Thr Pro Ile Ile Gly Leu Tyr Leu Val Ser Gln Thr Gly
        35                  40                  45

Trp Ser Ile Trp Tyr Gly Leu Val Leu Ile Leu Trp Tyr Gly Leu Val
    50                  55                  60

Pro Leu Ile Asp Thr Met Leu Gly Glu Asp Tyr Ser Asn Pro Pro Glu
65                  70                  75                  80

Ser Val Val Pro Lys Leu Glu Gln Asp Arg Tyr Tyr Lys Val Leu Thr
                85                  90                  95

Tyr Leu Thr Val Pro Ile His Tyr Ala Ala Leu Ile Ile Ser Ala Trp
            100                 105                 110

Trp Val Ser Thr Gln Pro Ile Gly Val Phe Glu Phe Leu Ala Leu Ala
        115                 120                 125

Leu Ser Leu Gly Ile Val Asn Gly Leu Ala Leu Asn Thr Gly His Glu
    130                 135                 140

Leu Gly His Lys Lys Glu Thr Phe Asp Arg Trp Met Ala Lys Leu Val
145                 150                 155                 160

Leu Ala Val Val Gly Tyr Gly His Phe Phe Ile Glu His Asn Lys Gly
                165                 170                 175

His His Arg Asp Val Ala Thr Pro Met Asp Pro Ala Thr Ser Arg Met
            180                 185                 190

Gly Glu Ser Ile Tyr Thr Phe Ser Leu Arg Glu Ile Pro Gly Ala Phe
        195                 200                 205

Lys Arg Ala Trp Gly Leu Glu Glu Gln Arg Leu Ser Arg Cys Gly Lys
    210                 215                 220

Ser Val Trp Ser Leu Asp Asn Glu Val Leu Gln Pro Met Ile Leu Thr
225                 230                 235                 240

Val Val Leu Tyr Ala Ala Leu Leu Ala Phe Phe Gly Pro Leu Met Leu
                245                 250                 255

Ile Phe Leu Pro Ile Gln Met Ala Phe Gly Trp Trp Gln Leu Thr Ser
            260                 265                 270

Ala Asn Tyr Ile Glu His Tyr Gly Leu Leu Arg Glu Lys Leu Pro Asn
        275                 280                 285

Gly Arg Tyr Glu His Gln Lys Pro His His Ser Trp Asn Ser Asn His
    290                 295                 300

Val Met Ser Asn Leu Ile Leu Phe His Leu Gln Arg His Ser Asp His
305                 310                 315                 320

His Ala His Pro Thr Arg Ser Tyr Gln Ser Leu Arg Asp Phe Ser Asp
                325                 330                 335

Leu Pro Thr Leu Pro Thr Gly Tyr Pro Gly Met Phe Phe Val Ala Phe
            340                 345                 350

Phe Pro Ser Trp Phe Arg Ser Leu Met Asp Asp Arg Val Met Glu Trp
        355                 360                 365

Ala His Gly Asp Ile Asn Lys Ile Gln Ile Gln Pro Gly Met Arg Glu
    370                 375                 380

Phe Tyr Glu Gln Lys Phe Gly Val Lys Gly Ser Glu Ser Pro Asp Thr
385                 390                 395                 400

Thr Val Ala Lys

<210> SEQ ID NO 28
<211> LENGTH: 398
<212> TYPE: PRT
<213> ORGANISM: Alcanivorax dieselolei

<400> SEQUENCE: 28

Met Ser Lys Ala Gly Glu Phe Thr Gly Pro Ser Gly Val Val Tyr Arg
1               5                   10                  15

Asp Arg Lys Arg His Leu Trp Phe Ser Ser Ile Phe Val Pro Ala Ile
            20                  25                  30

Val Phe Ile Gly Pro Leu Leu Tyr Leu Ala Asn Gly Asn Ala Leu Met
        35                  40                  45

Leu Trp Ile Pro Leu Val Phe Tyr Tyr Leu Ala Val Pro Val Leu Asp
    50                  55                  60

Met Leu Ile Gly Glu Asp Arg Ser Asn Pro Pro Glu Glu Val Val Pro
65                  70                  75                  80

Gln Leu Glu Glu Asp Pro Tyr Tyr Arg Trp Val Thr Tyr Ala Leu Val
                85                  90                  95

Pro Val Ile Trp Gly Ala Trp Phe Phe Gly Ala Trp Phe Val Gly Thr
            100                 105                 110

Gln Asp Leu Pro Trp His Gly Leu Leu Ala Met Ile Leu Leu Leu Gly
        115                 120                 125

Gly Thr Cys Gly Val Gly Ile Asn Leu Gly His Glu Leu Gly His Lys
    130                 135                 140

Lys Gly Lys Gly Glu Arg Trp Leu Ala Lys Phe Val Leu Ala Pro Cys
145                 150                 155                 160

Ala Tyr Gly His Phe Phe Ile Glu His Asn Lys Gly His His Arg Asp
                165                 170                 175

Val Ala Thr Pro Glu Asp Pro Ala Ser Ser Arg Met Gly Glu Ser Ile
            180                 185                 190

Trp Lys Phe Val Leu Arg Glu Ile Pro Gly Ala Ala Arg Arg Ala Trp
        195                 200                 205

Lys Leu Glu Gln Glu Arg Leu Glu Ser Arg Gly Lys Ser Val Trp Ser
    210                 215                 220

Leu Asp Asn Glu Ile Ile Gln Pro Ala Ile Ile Thr Ala Ile Ala Trp
225                 230                 235                 240

Gly Val Val Leu Ala Leu Phe Gly Ile Gly Ile Leu Pro Tyr Ile Leu
                245                 250                 255

Gly Thr Ala Phe Trp Gly Ala Phe Gln Leu Thr Ser Ala Asn Tyr Ile
            260                 265                 270

Glu His Tyr Gly Leu Leu Arg His Lys Thr Lys Thr Gly Arg Tyr Glu
        275                 280                 285

Arg Thr Gln Pro Tyr His Ser Trp Asn Ser Asn His Met Phe Ser Asn
    290                 295                 300

Trp Ala Thr Phe His Leu Gln Arg His Ser Asp His Ala His Pro
305                 310                 315                 320

Thr Arg Arg Tyr Gln Ser Leu Arg His Phe Asp Asp Val Pro Ser Leu
                325                 330                 335

Pro Ser Gly Tyr Phe Gly Met Phe Leu Val Ser Tyr Ile Pro Pro Leu
            340                 345                 350

Trp Tyr Arg Leu Met Asp Lys Arg Leu Leu Glu His Ala Gly Tyr Asp
        355                 360                 365

Ala Arg Asn Ile Asn Phe Asp Pro Asp Lys Arg Glu Ala Leu Ile Arg
    370                 375                 380

Lys Tyr Gly Ile Gln His Gly Asp Ala Pro Pro Arg Ile Val
385                 390                 395

<210> SEQ ID NO 29
<211> LENGTH: 440
<212> TYPE: PRT
<213> ORGANISM: Geobacillus thermodenitrificans

<400> SEQUENCE: 29

Met Thr Lys Lys Ile His Ile Asn Ala Phe Glu Met Asn Cys Val Gly
1               5                   10                  15

His Ile Ala His Gly Leu Trp Arg His Pro Glu Asn Gln Arg His Arg
            20                  25                  30

Tyr Thr Asp Leu Asn Tyr Trp Thr Glu Leu Ala Gln Leu Leu Glu Lys
        35                  40                  45

Gly Lys Phe Asp Ala Leu Phe Leu Ala Asp Val Val Gly Ile Tyr Asp
    50                  55                  60

Val Tyr Arg Gln Ser Arg Asp Thr Ala Val Arg Glu Ala Val Gln Ile
65                  70                  75                  80

Pro Val Asn Asp Pro Leu Met Leu Ile Ser Ala Met Ala Tyr Val Thr
                85                  90                  95

Lys His Leu Ala Phe Ala Val Thr Phe Ser Thr Thr Tyr Glu His Pro
            100                 105                 110

Tyr Gly His Ala Arg Arg Met Ser Thr Leu Asp His Leu Thr Lys Gly
        115                 120                 125

Arg Ile Ala Trp Asn Val Val Thr Ser His Leu Pro Ser Ala Asp Lys
    130                 135                 140

Asn Phe Gly Ile Lys Lys Ile Leu Glu His Asp Glu Arg Tyr Asp Leu
145                 150                 155                 160

Ala Asp Glu Tyr Leu Glu Val Cys Tyr Lys Leu Trp Glu Gly Ser Trp
                165                 170                 175

Glu Asp Asn Ala Val Ile Arg Asp Ile Glu Asn Asn Ile Tyr Thr Asp
            180                 185                 190

Pro Ser Lys Val His Glu Ile Asn His Ser Gly Lys Tyr Phe Glu Val
        195                 200                 205

Pro Gly Pro His Leu Cys Glu Pro Ser Pro Gln Arg Thr Pro Val Ile
    210                 215                 220

Tyr Gln Ala Gly Met Ser Glu Arg Gly Arg Glu Phe Ala Ala Lys His
225                 230                 235                 240

Ala Glu Cys Val Phe Leu Gly Gly Lys Asp Val Glu Thr Leu Lys Phe
                245                 250                 255

Phe Val Asp Asp Ile Arg Lys Arg Ala Lys Lys Tyr Gly Arg Asn Pro
            260                 265                 270

Asp His Ile Lys Met Phe Ala Gly Ile Cys Val Ile Val Gly Lys Thr
        275                 280                 285

His Asp Glu Ala Met Glu Lys Leu Asn Ser Phe Gln Lys Tyr Trp Ser
    290                 295                 300

Leu Glu Gly His Leu Ala His Tyr Gly Gly Gly Thr Gly Tyr Asp Leu
305                 310                 315                 320

Ser Lys Tyr Ser Ser Asn Asp Tyr Ile Gly Ser Ile Ser Val Gly Glu
                325                 330                 335

Ile Ile Asn Asn Met Ser Lys Leu Asp Gly Lys Trp Phe Lys Leu Ser
            340                 345                 350

Val Gly Thr Pro Lys Lys Val Ala Asp Glu Met Gln Tyr Leu Val Glu

```
                    355                 360                 365
Glu Ala Gly Ile Asp Gly Phe Asn Leu Val Gln Tyr Val Ser Pro Gly
                370                 375                 380

Thr Phe Val Asp Phe Ile Glu Leu Val Val Pro Glu Leu Gln Lys Arg
385                 390                 395                 400

Gly Leu Tyr Arg Val Asp Tyr Glu Glu Gly Thr Tyr Arg Glu Lys Leu
                    405                 410                 415

Phe Gly Lys Gly Asn Tyr Arg Leu Pro Asp Asp His Ile Ala Ala Arg
                420                 425                 430

Tyr Arg Asn Ile Ser Ser Asn Val
                435                 440

<210> SEQ ID NO 30
<211> LENGTH: 440
<212> TYPE: PRT
<213> ORGANISM: Geobacillus stearothermophilus

<400> SEQUENCE: 30

Met Thr Lys Glu Ile His Ile Asn Ala Phe Glu Lys Asn Cys Val Gly
1               5                   10                  15

His Ile Ala His Gly Leu Trp Arg His Pro Glu Asn Gln Arg His Arg
                20                  25                  30

Tyr Thr Asp Leu Asn Tyr Trp Thr Glu Leu Ala Gln Leu Leu Glu Lys
            35                  40                  45

Gly Lys Phe Asp Ala Leu Phe Leu Ala Asp Val Val Gly Ile Tyr Asp
        50                  55                  60

Val Tyr Arg Gln Ser Arg Asp Thr Ala Val Arg Glu Ala Val Gln Ile
65                  70                  75                  80

Pro Val Asn Asp Pro Leu Met Leu Ile Ser Ala Met Ala Tyr Val Thr
                85                  90                  95

Lys His Leu Ala Phe Ala Val Thr Phe Ser Thr Thr Tyr Glu His Pro
                100                 105                 110

Tyr Gly His Ala Arg Arg Met Ser Thr Leu Asp His Leu Thr Lys Gly
            115                 120                 125

Arg Ile Ala Trp Asn Val Val Thr Ser His Leu Pro Ser Ala His Lys
        130                 135                 140

Asn Phe Gly Ile Lys Lys Ile Leu Glu His Asp Glu Arg Tyr Asp Leu
145                 150                 155                 160

Ala Asp Glu Tyr Leu Glu Val Cys Tyr Lys Leu Trp Glu Gly Ser Trp
                165                 170                 175

Glu Asp Asn Ala Val Ile Arg Asp Ile Glu Asn Asn Ile Tyr Thr Asp
                180                 185                 190

Pro Ser Lys Val His Glu Ile Asn His Ser Gly Lys Tyr Phe Glu Val
            195                 200                 205

Pro Gly Pro His Leu Cys Glu Pro Ser Pro Gln Arg Thr Pro Val Ile
        210                 215                 220

Tyr Gln Ala Gly Met Ser Glu Arg Gly Arg Glu Phe Ala Ala Lys His
225                 230                 235                 240

Ala Glu Thr Val Phe Leu Gly Gly Thr Asp Val Glu Thr Leu Lys Phe
                245                 250                 255

Phe Val Asp Asp Ile Arg Lys Arg Ala Lys Lys Tyr Gly Arg Asn Pro
                260                 265                 270

Asp His Ile Lys Met Phe Ala Gly Ile Cys Val Ile Val Gly Lys Thr
            275                 280                 285
```

-continued

```
His Asp Glu Ala Met Glu Lys Leu Asn Ser Phe Gln Lys Tyr Trp Ser
            290                 295                 300

Leu Glu Gly His Leu Ala His Tyr Gly Gly Thr Gly Tyr Asp Leu
305                 310                 315                 320

Ser Lys Tyr Ser Ser Asn Asp Tyr Ile Gly Ser Ile Ser Val Gly Glu
                    325                 330                 335

Ile Ile Asn Asn Met Ser Lys Leu Asp Gly Lys Trp Phe Lys Leu Ser
                340                 345                 350

Val Gly Thr Pro Lys Lys Val Ala Asp Glu Met Gln Tyr Leu Val Glu
                355                 360                 365

Glu Ala Gly Ile Asp Gly Phe Asn Leu Val Gln Tyr Val Ser Pro Gly
370                 375                 380

Thr Phe Val Asp Phe Ile Glu Leu Val Val Pro Glu Leu Gln Lys Arg
385                 390                 395                 400

Gly Leu Tyr Arg Val Asp Tyr Glu Glu Gly Thr Tyr Arg Glu Lys Leu
                405                 410                 415

Phe Gly Lys Gly Asn Tyr Arg Leu Pro Asp Asp His Ile Ala Ala Arg
                420                 425                 430

Tyr Arg Asn Ile Ser Ser Asn Val
                435                 440

<210> SEQ ID NO 31
<211> LENGTH: 464
<212> TYPE: PRT
<213> ORGANISM: Bacillus methanolicus

<400> SEQUENCE: 31

Met Gly Lys Gln Ile Ile Leu Asn Ala Phe Glu Met Thr Ser Ala Met
1               5                   10                  15

His Asn Ser His Gly Leu Trp Lys His Pro Glu Ser Lys Arg Gln Arg
                20                  25                  30

Arg Tyr Lys Asp Leu Asp Tyr Trp Ile Glu Met Ala Lys Leu Leu Glu
            35                  40                  45

Arg Gly Lys Phe Asp Ala Val Phe Phe Ala Asp Val Leu Gly Val Tyr
50                  55                  60

Asp Thr Tyr Lys Gln Ser Lys Glu Pro Ser Ile Arg Asp Gly Met Gln
65                  70                  75                  80

Ile Pro Leu Ile Asp Ala Ala Leu Val Ile Pro Val Met Ala Ser Val
                85                  90                  95

Thr Lys His Leu Ser Phe Ala Phe Thr Val Ser Thr Thr Tyr Glu Pro
                100                 105                 110

Pro Phe Ala His Ala Arg Arg Phe Ser Thr Leu Asp His Leu Thr Gln
            115                 120                 125

Gly Arg Ile Ala Trp Asn Val Val Thr Ser Tyr Leu Pro Asn Ala Ala
            130                 135                 140

Arg Asn Phe Gly Leu Pro Glu Met Ile Lys His Asp Arg Arg Tyr Asp
145                 150                 155                 160

Ile Ala Asp Glu Tyr Leu Glu Val Cys Tyr Lys Leu Trp Glu Leu Ser
                165                 170                 175

Trp Glu Asp Gly Ala Val Ile Glu Asp Val Lys Asn Gly Ile Leu Val
                180                 185                 190

Asp Pro Ser Lys Val His Glu Ile Asn His Ser Gly Glu Phe Phe His
            195                 200                 205

Val Glu Gly Pro His Leu Ser Glu Pro Ser Leu Gln Arg Thr Pro Val
210                 215                 220
```

Leu Tyr Gln Ala Gly Val Ser Glu Arg Gly Arg Glu Phe Ala Ala Lys
225                 230                 235                 240

His Ala Glu Cys Val Phe Val Gly Gly Pro Thr Pro Glu Arg Ile Arg
            245                 250                 255

Phe Tyr Thr Glu Asp Ile Lys Gln Arg Ala Glu Lys Tyr Gly Arg Asn
        260                 265                 270

Pro Asp Asn Ile Lys Val Phe Ser Phe Leu Thr Val Ile Val Gly Glu
    275                 280                 285

Thr Thr Glu Glu Ala Glu Arg Lys Tyr Gln Glu Leu Asn Arg Leu Trp
290                 295                 300

Ser Pro Asp Ala Ala Lys Ala Gln Phe Gly Gly Ala Ser Gly Tyr Asp
305                 310                 315                 320

Leu Ser Gln Tyr Glu Lys Ser Asp Leu Asp Gln Pro Phe Glu Phe Lys
                325                 330                 335

Pro Thr Glu His Gly His Tyr Lys Ala Ala Ser Leu Thr Lys Asp Ala
            340                 345                 350

Ser Lys Lys Leu Lys Ile Gly Glu Ala Leu Ser Arg Leu Glu Asn Ile
        355                 360                 365

Asp Arg Glu Gln Val Ile Val Gly Asn Pro Ile Glu Val Ala Asp Ala
    370                 375                 380

Ile Gln Tyr Gln Phe Glu Ala Ser Gly Val Asp Gly Phe Asn Leu Asn
385                 390                 395                 400

His Leu Ile Thr Pro Gly Ser Leu Glu Asp Phe Ile Asp Leu Val Val
                405                 410                 415

Pro Ile Leu Gln Glu Arg Gly Leu Tyr Lys Thr Glu Tyr Lys Glu Gly
            420                 425                 430

Thr Leu Arg Gln Lys Leu Phe Gly His Gly Ser Asn Leu Leu Pro Glu
        435                 440                 445

Asp His Pro Gly Ser Lys Tyr Arg Arg Ile Tyr Ser Ser Val Asn Asn
    450                 455                 460

<210> SEQ ID NO 32
<211> LENGTH: 464
<212> TYPE: PRT
<213> ORGANISM: Pseudomonas cichorii

<400> SEQUENCE: 32

Met Ala Lys Lys Lys Ile Leu Leu Asn Ala Phe Asn Met Asn Cys Ile
1               5                   10                  15

Gly His Ile Asn His Gly Leu Trp Thr His Pro Arg Asp Asn Ser Thr
            20                  25                  30

Gln Tyr Lys Thr Leu Glu Tyr Trp Thr Glu Leu Ala Gln Leu Leu Glu
        35                  40                  45

Arg Gly Leu Phe Asp Gly Leu Phe Ile Ala Asp Ile Val Gly Val Tyr
    50                  55                  60

Asp Val Tyr Gln Asn Ser Val Asp Val Thr Leu Lys Glu Ser Ile Gln
65                  70                  75                  80

Leu Pro Val Asn Asp Pro Leu Leu Val Ser Ala Met Ala Ala Val
                85                  90                  95

Thr Arg Asn Leu Gly Phe Gly Leu Thr Ala Asn Leu Thr Tyr Glu Thr
            100                 105                 110

Pro Tyr Leu Phe Ala Arg Arg Met Ser Thr Leu Asp His Leu Ser Arg
        115                 120                 125

Gly Arg Val Gly Trp Asn Ile Val Thr Gly Tyr Leu Asp Ser Ala Ala

```
        130                 135                 140
Arg Ala Met Gly Leu Thr Glu Gln Val Glu His Asp Arg Arg Tyr Asp
145                 150                 155                 160

Gln Ala Asp Glu Tyr Leu Glu Val Leu Tyr Lys Leu Trp Glu Gly Ser
                165                 170                 175

Trp Glu Asp Gly Ala Val Ile Asn Asp Arg Glu Gln Arg Val Tyr Ala
                180                 185                 190

Arg Pro Asp Lys Val His Lys Val Arg His Lys Gly Glu Phe Tyr Gln
                195                 200                 205

Val Glu Gly Tyr His Leu Cys Glu Pro Ser Pro Gln Arg Thr Pro Val
            210                 215                 220

Leu Phe Gln Ala Gly Ser Glu Arg Gly Leu Gln Phe Ala Gly Gln
225                 230                 235                 240

Asn Ala Glu Cys Val Phe Ile Ser Gly Gln Asn Lys Ala Ala Thr Arg
                245                 250                 255

Glu Gln Val Asp Lys Val Arg Ala Ser Ala Val Ala Ala Gly Arg Asn
                260                 265                 270

Pro Asp Gly Ile Lys Val Phe Met Gly Leu Asn Val Ile Val Gly Ala
            275                 280                 285

Thr Glu Ala Ile Ala Arg Glu Lys Tyr Ala Glu Tyr Arg Ser Tyr Ala
290                 295                 300

Ser Ala Glu Ala Gly Val Ala His Phe Ala Ala Ser Thr Gly Ile Asp
305                 310                 315                 320

Phe Ala Glu Tyr Glu Leu Asp Glu Pro Ile Gln Tyr Val Lys Ser Asn
                325                 330                 335

Ala Ile Gln Ser Ala Thr Lys Asn Leu Lys Asn Asn Asp Trp Thr Arg
                340                 345                 350

Gln Arg Leu Leu Asp Gln His Ala Leu Gly Gly Arg Tyr Ile Thr Leu
            355                 360                 365

Val Gly Ser Pro Glu Gln Val Ala Asp Glu Leu Glu Ser Trp Ile Glu
            370                 375                 380

Glu Thr Gly Leu Asp Gly Phe Asn Leu Thr Arg Ile Val Thr Pro Glu
385                 390                 395                 400

Ser Tyr Val Asp Phe Ile Asp Leu Val Ile Pro Glu Leu Gln Arg Arg
                405                 410                 415

Gly Ser Tyr Lys Thr Ala Tyr Glu Asp Gly Ser Leu Arg Lys Lys Leu
                420                 425                 430

Phe Pro Glu Gly Asn Ala His Leu Pro Asp Asn His Ala Gly Ser Arg
            435                 440                 445

His Arg His His Gly Phe Ala Thr Glu Val Ala Leu Thr His Ser Pro
450                 455                 460

<210> SEQ ID NO 33
<211> LENGTH: 523
<212> TYPE: PRT
<213> ORGANISM: Candida tropicalis

<400> SEQUENCE: 33

Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
                20                  25                  30

Asn Ile Lys Asn Tyr Val Lys Ala Lys Lys Leu Lys Cys Val Asp Pro
            35                  40                  45
```

```
Pro Tyr Leu Lys Asp Ala Gly Leu Thr Gly Ile Ser Ser Leu Ile Ala
    50              55                  60

Ala Ile Lys Ala Lys Asn Asp Gly Arg Leu Ala Asn Phe Ala Asp Glu
65              70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
                100                 105                 110

Leu Ala Thr Gln Phe Thr Asp Phe Ser Leu Gly Thr Arg His Ala His
            115                 120                 125

Phe Ala Pro Leu Leu Gly Asp Gly Ile Phe Thr Leu Asp Gly Glu Gly
130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415

Ile Pro Lys Gly Ser Thr Val Ala Tyr Val Val Tyr Lys Thr His Arg
            420                 425                 430

Leu Glu Glu Tyr Tyr Gly Lys Asp Ala Asn Asp Phe Arg Pro Glu Arg
        435                 440                 445

Trp Phe Glu Pro Ser Thr Lys Lys Leu Gly Trp Ala Tyr Val Pro Phe
    450                 455                 460

Asn Gly Gly Pro Arg Val Cys Leu Gly Gln Gln Phe Ala Leu Thr Glu
```

```
                465                 470                 475                 480
Ala Ser Tyr Val Ile Thr Arg Leu Ala Gln Met Phe Glu Thr Val Ser
                    485                 490                 495

Ser Asp Pro Gly Leu Glu Tyr Pro Pro Lys Cys Ile His Leu Thr
                500                 505                 510

Met Ser His Asn Asp Gly Val Phe Val Lys Met
                515                 520

<210> SEQ ID NO 34
<211> LENGTH: 523
<212> TYPE: PRT
<213> ORGANISM: Candida tropicalis

<400> SEQUENCE: 34

Met Ala Thr Gln Glu Ile Ile Asp Ser Ala Leu Pro Tyr Leu Thr Lys
1               5                   10                  15

Trp Tyr Thr Val Ile Thr Leu Ala Ala Leu Val Phe Leu Ile Ser Ser
                20                  25                  30

Asn Ile Lys Asn Tyr Val Lys Ala Lys Lys Leu Lys Cys Arg Asp Pro
            35                  40                  45

Pro Tyr Phe Lys Gly Ala Gly Trp Thr Gly Ile Ser Pro Leu Ile Glu
        50                  55                  60

Ile Ile Lys Val Lys Gly Asn Gly Arg Leu Ala Asp Phe Ala Asp Lys
65              70                  75                  80

Thr Phe Asp Asp Tyr Pro Asn His Thr Phe Tyr Met Ser Ile Ile Gly
                85                  90                  95

Ala Leu Lys Ile Val Leu Thr Val Asp Pro Glu Asn Ile Lys Ala Val
                100                 105                 110

Leu Ala Thr Gln Phe Thr Asp Phe Ser Leu Gly Thr Arg His Ala His
                115                 120                 125

Phe Tyr Pro Leu Leu Gly Asp Gly Ile Phe Thr Leu Asp Gly Glu Gly
        130                 135                 140

Trp Lys His Ser Arg Ala Met Leu Arg Pro Gln Phe Ala Arg Asp Gln
145             150                 155                 160

Ile Gly His Val Lys Ala Leu Glu Pro His Ile Gln Ile Leu Ala Lys
                165                 170                 175

Gln Ile Lys Leu Asn Lys Gly Lys Thr Phe Asp Ile Gln Glu Leu Phe
                180                 185                 190

Phe Arg Phe Thr Val Asp Thr Ala Thr Glu Phe Leu Phe Gly Glu Ser
            195                 200                 205

Val His Ser Leu Tyr Asp Glu Lys Leu Gly Ile Pro Thr Pro Asn Glu
        210                 215                 220

Ile Pro Gly Arg Asp Asn Phe Ala Thr Ala Phe Asn Thr Ser Gln His
225             230                 235                 240

Tyr Leu Ala Thr Arg Thr Tyr Ser Gln Thr Phe Tyr Phe Leu Thr Asn
                245                 250                 255

Pro Lys Glu Phe Arg Asp Cys Asn Ala Lys Val His Tyr Leu Ala Lys
            260                 265                 270

Tyr Phe Val Asn Lys Ala Leu Asn Phe Thr Pro Glu Glu Ile Glu Glu
        275                 280                 285

Lys Ser Lys Ser Gly Tyr Val Phe Leu Tyr Glu Leu Val Lys Gln Thr
            290                 295                 300

Arg Asp Pro Lys Val Leu Gln Asp Gln Leu Leu Asn Ile Met Val Ala
305             310                 315                 320
```

```
Gly Arg Asp Thr Thr Ala Gly Leu Leu Ser Phe Ala Met Phe Glu Leu
                325                 330                 335

Ala Arg His Pro Glu Ile Trp Ser Lys Leu Arg Glu Glu Ile Glu Val
            340                 345                 350

Asn Phe Gly Val Gly Glu Glu Ser Arg Val Glu Glu Ile Thr Phe Glu
        355                 360                 365

Ser Leu Lys Arg Cys Glu Tyr Leu Lys Ala Ile Leu Asn Glu Thr Leu
    370                 375                 380

Arg Met Tyr Pro Ser Val Pro Val Asn Ser Arg Thr Ala Thr Arg Asp
385                 390                 395                 400

Thr Thr Leu Pro Arg Gly Gly Pro Asn Gly Thr Asp Pro Ile Phe
                405                 410                 415

Ile Pro Lys Gly Ser Thr Val Ala Tyr Ile Val Tyr Lys Thr His Arg
                420                 425                 430

Leu Glu Glu Tyr Tyr Gly Lys Asp Ala Asp Asp Phe Arg Pro Glu Arg
            435                 440                 445

Trp Phe Glu Pro Ser Thr Lys Lys Leu Gly Trp Ala Tyr Val Pro Phe
        450                 455                 460

Asn Gly Gly Pro Arg Ile Cys Leu Gly Gln Gln Phe Ala Leu Thr Glu
465                 470                 475                 480

Ala Ser Tyr Val Ile Thr Arg Leu Val Gln Met Phe Glu Thr Val Ser
                485                 490                 495

Ser Ser Pro Asp Val Glu Tyr Pro Pro Lys Cys Ile His Leu Thr
                500                 505                 510

Met Ser His Asp Asp Gly Val Phe Val Lys Met
            515                 520

<210> SEQ ID NO 35
<211> LENGTH: 523
<212> TYPE: PRT
<213> ORGANISM: Candida maltosa

<400> SEQUENCE: 35

Met Ala Ile Glu Gln Ile Ile Glu Glu Val Leu Pro Tyr Leu Thr Lys
1               5                   10                  15

Trp Tyr Thr Ile Leu Phe Gly Ala Ala Phe Thr Tyr Phe Leu Ser Ile
                20                  25                  30

Ala Leu Arg Asn Lys Tyr Tyr Glu Tyr Lys Leu Lys Cys Glu Asn Pro
            35                  40                  45

Pro Tyr Phe Lys Thr Ala Gly Phe Val Gly Ile Pro Gly Leu Ile Asp
        50                  55                  60

Val Ile Lys Ala Lys Asn Ala Gly Lys Leu Ala Asp Tyr Ala Asp Gln
65                  70                  75                  80

Thr Phe Asp Glu Tyr Pro His His Ser Phe Tyr Met Thr Val Ala Gly
                85                  90                  95

Met Leu Lys Ile Val Leu Thr Val Asp Pro Glu Asn Ile Lys Ala Val
            100                 105                 110

Leu Ala Thr Gln Phe Asn Asp Phe Ala Leu Gly Ala Arg His Ala His
        115                 120                 125

Phe Asp Pro Leu Leu Gly Asp Gly Ile Phe Thr Leu Asp Gly Glu Gly
    130                 135                 140

Trp Lys His Ser Arg Ala Met Leu Arg Pro Gln Phe Ala Arg Glu Gln
145                 150                 155                 160

Ile Ala His Val Lys Ala Leu Glu Pro His Val Gln Val Leu Ala Lys
                165                 170                 175
```

```
Gln Ile Lys Leu Asn Lys Gly Glu Thr Phe Asp Leu Gln Glu Leu Phe
            180                 185                 190

Phe Arg Phe Thr Val Asp Thr Ala Thr Glu Phe Leu Phe Gly Glu Ser
            195                 200                 205

Val His Ser Leu Tyr Asp Glu Lys Leu Gly Val Pro Pro Asn Asn
210                 215                 220

Ile Pro Gly Arg Glu Asn Phe Ala Lys Ala Phe Asn Thr Ser Gln His
225                 230                 235                 240

Tyr Leu Ala Thr Arg Thr Tyr Ser Gln Met Phe Tyr Phe Leu Thr Asn
            245                 250                 255

Pro Lys Glu Phe Arg Asp Cys Asn Ala Lys Val His Lys Leu Ala Gln
            260                 265                 270

Tyr Phe Val Asn Lys Ala Leu Asp Ala Ser Glu Asp Glu Val Ala Glu
            275                 280                 285

Lys Ser Lys Gly Gly Tyr Val Phe Leu Tyr Glu Leu Val Lys Gln Thr
            290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Met Phe Glu Leu
            325                 330                 335

Ala Arg Asn Pro Lys Ile Trp Asn Lys Leu Arg Glu Glu Ile Glu Val
            340                 345                 350

Asn Phe Gly Leu Gly Glu Glu Ala Arg Val Asp Glu Ile Ser Phe Glu
            355                 360                 365

Thr Leu Lys Lys Cys Glu Tyr Leu Lys Ala Val Leu Asn Glu Thr Leu
            370                 375                 380

Arg Met Tyr Pro Ser Val Pro Val Asn Phe Arg Thr Ala Thr Arg Asp
385                 390                 395                 400

Thr Thr Leu Pro Arg Gly Gly Lys Asp Gly Thr Ser Pro Ile Phe
            405                 410                 415

Val Pro Lys Gly Ser Ser Val Val Tyr Thr Val Tyr Lys Thr His Arg
            420                 425                 430

Leu Glu Glu Tyr Tyr Gly Lys Asp Ala Tyr Glu Phe Arg Pro Glu Arg
            435                 440                 445

Trp Phe Glu Pro Ser Thr Arg Lys Leu Gly Trp Ala Tyr Val Pro Phe
            450                 455                 460

Asn Gly Gly Pro Arg Ile Cys Leu Gly Gln Gln Phe Ala Leu Thr Glu
465                 470                 475                 480

Ala Ser Tyr Val Ile Thr Arg Leu Ala Gln Met Phe Glu His Leu Glu
            485                 490                 495

Ser Lys Asp Glu Thr Tyr Pro Pro Asn Lys Cys Ile His Leu Thr Met
            500                 505                 510

Asn His Asn Glu Gly Val Phe Ile Ser Ala Lys
            515                 520

<210> SEQ ID NO 36
<211> LENGTH: 526
<212> TYPE: PRT
<213> ORGANISM: Candida parapsilosis

<400> SEQUENCE: 36

Met Ser Ser Ile Leu Asp Gln Ala Ser Asp Phe Gly Glu Lys Leu Leu
1               5                   10                  15

Pro Tyr Leu Thr Lys Trp Tyr Ser Ile Val Phe Ile Ile Leu Leu Thr
```

```
                20                  25                  30
Tyr Ile Pro Leu Leu Asn Ile Arg Asn Ala Tyr Val Gly Trp Lys Leu
            35                  40                  45

Gly Cys Gln Asp Pro Lys Phe Arg Lys Ala Gly Phe Thr Gly Val
    50                  55                  60

Phe Ala Leu Ile Glu Ala Val Lys Lys Lys Asn Gln Gly Arg Leu Val
65                  70                  75                  80

Asp Trp Gly Asp Glu Gln Phe Asp Glu Tyr Pro Asn His Ser Met Tyr
                85                  90                  95

Leu Asn Val Thr Gly Leu Leu Lys Ile Val Leu Thr Val Asp Pro Glu
            100                 105                 110

Asn Ile Lys Ala Val Leu Ala Thr Gln Phe Asn Asp Phe Ser Leu Gly
            115                 120                 125

Thr Arg His Ala His Phe Ala Pro Leu Leu Gly Asp Gly Ile Phe Thr
            130                 135                 140

Leu Asp Gly Asn Gly Trp Lys Asp Ser Arg Ala Met Leu Arg Pro Gln
145                 150                 155                 160

Phe Ala Arg Glu Gln Ile Ala His Val Lys Ser Leu Glu Pro His Leu
                165                 170                 175

Gln Ile Leu Ala Lys His Ile Lys Ser Thr Asn Phe Gln Thr Phe Asp
            180                 185                 190

Leu Gln Glu Leu Phe Phe Lys Phe Thr Val Asp Thr Ala Thr Glu Phe
            195                 200                 205

Leu Phe Gly Glu Ser Val His Ser Leu Tyr Asp Asp Lys Leu Gly Ile
            210                 215                 220

Ala Pro Pro Asn Asp Ile Pro Gly Arg Glu His Phe Ala Asp Ala Phe
225                 230                 235                 240

Asn Lys Ser Gln Lys Tyr Leu Ala Thr Arg Thr Tyr Leu Gln Met Phe
                245                 250                 255

Tyr Phe Leu Ile Asn Pro Lys Glu Phe Arg Asp Cys Asn Lys Lys Val
            260                 265                 270

Gln His Leu Ala Gln Tyr Phe Val Asn Lys Ala Leu Asn Phe Thr Pro
            275                 280                 285

Glu Glu Leu Glu Glu Lys Ser Lys Asp Gly Tyr Ile Phe Leu Tyr Glu
            290                 295                 300

Leu Val Lys Gln Thr Lys Asn Pro Gln Val Leu Gln Asp Gln Leu Leu
305                 310                 315                 320

Asn Ile Met Val Ala Gly Arg Asp Thr Thr Ala Gly Leu Leu Ser Phe
                325                 330                 335

Thr Met Tyr Glu Leu Ala Arg Asn Pro Gln Val Trp Gln Lys Leu Arg
            340                 345                 350

Gln Glu Ile Val Glu Asn Phe Gly Asp Gly Glu Asp Ala Arg Val Glu
            355                 360                 365

Ser Ile Thr Phe Glu Thr Leu Lys Lys Cys Glu Tyr Leu Lys Ala Val
            370                 375                 380

Leu Asn Glu Thr Leu Arg Leu Tyr Pro Ser Val Pro Val Asn Phe Arg
385                 390                 395                 400

Thr Ala Thr Arg Asp Thr Thr Leu Pro Arg Gly Gly Gly Ala Asp Gly
                405                 410                 415

Thr Lys Pro Ile Phe Val Pro Lys Gly Ser Thr Val Ala Tyr Thr Val
            420                 425                 430

Tyr Lys Thr His Arg Leu Glu Glu Tyr Tyr Gly Lys Asp Ser Lys Glu
            435                 440                 445
```

```
Phe Lys Pro Glu Arg Trp Glu Asn Ile Lys Arg Leu Gly Trp Ala Tyr
    450                 455                 460

Leu Pro Phe Asn Gly Gly Pro Arg Ile Cys Leu Gly Gln Gln Phe Ala
465                 470                 475                 480

Leu Thr Glu Ala Ser Tyr Val Ala Arg Leu Val Gln Met Phe Pro
                485                 490                 495

Thr Leu Glu Ser Gln Asp Asp Thr Tyr Pro Pro Lys Lys Cys Val His
                500                 505                 510

Leu Thr Met Asn Leu Asp Glu Gly Val Phe Val Lys Met Lys
            515                 520                 525

<210> SEQ ID NO 37
<211> LENGTH: 528
<212> TYPE: PRT
<213> ORGANISM: Lodderomyces elongisporus

<400> SEQUENCE: 37

Met Ser Ser Thr Phe Val Gln Gln Val Ala Ser Leu Gly Gln Glu Ile
1               5                   10                  15

Val Pro Tyr Phe Thr Lys Trp Tyr Thr Val Leu Ile Leu Leu Val Val
            20                  25                  30

Thr Tyr Ile Ala Ala Phe Asn Ile Lys Asp Ala Tyr Met Thr Trp Lys
        35                  40                  45

Leu Gly Cys Lys Asn Pro Leu Tyr Tyr Lys Pro Ala Gly Tyr Thr Gly
    50                  55                  60

Val Tyr Ser Leu Tyr Glu Ile Ile Gln Arg Lys Asn Lys Gly Glu Leu
65                  70                  75                  80

Ala Glu Phe Ala Gln Glu Ala Phe Asp Glu Tyr Thr Thr Asn Thr Val
                85                  90                  95

Tyr Val Lys Ile Gly Gly Leu Met Lys Ile Met Phe Thr Val Asp Pro
            100                 105                 110

Glu Asn Ile Lys Ala Val Leu Ala Thr Gln Phe Asn Asp Phe Ser Leu
        115                 120                 125

Gly Ile Arg His Ala His Phe Ala Pro Leu Leu Gly Asp Gly Ile Phe
    130                 135                 140

Thr Leu Asp Gly Asp Gly Trp Lys Asp Ser Arg Ala Met Leu Arg Pro
145                 150                 155                 160

Gln Phe Ala Arg Glu Gln Ile Ala His Val Lys Ala Leu Glu Pro His
                165                 170                 175

Val Leu Met Leu Ala Lys Gln Ile Ala Asn Thr Lys Tyr Glu Thr Phe
            180                 185                 190

Asp Leu Gln Glu Leu Phe Phe Arg Phe Thr Val Asp Thr Ser Thr Glu
        195                 200                 205

Phe Leu Phe Gly Glu Ser Val His Thr Leu Tyr Asp Asp Lys Ile Gly
    210                 215                 220

Val Ala Pro Pro Asn Asp Ile Pro Gly Arg Glu Ala Phe Ala Asp Ala
225                 230                 235                 240

Phe Asn Phe Ser Gln His Tyr Leu Ala Thr Arg Thr Tyr Ser Gln Val
                245                 250                 255

Phe His Trp Leu Phe Asn Ser Lys Glu Phe Arg Glu Asn Asn Ala Lys
            260                 265                 270

Val His His Leu Ala Gln Tyr Phe Val Lys Lys Ala Leu Asn Phe Thr
        275                 280                 285

Pro Glu Glu Leu Glu Glu Lys Ser Gln Asp Gly Tyr Thr Phe Leu Tyr
```

```
            290                 295                 300
Glu Leu Val Lys Gln Thr Arg Asn Pro Lys Thr Leu Gln Asp Gln Leu
305                 310                 315                 320

Leu Asn Ile Met Val Ala Gly Arg Asp Thr Thr Ala Gly Leu Leu Ser
                325                 330                 335

Phe Cys Met Phe Glu Leu Ala Arg Asn Pro Glu Ile Trp Gln Arg Leu
            340                 345                 350

Arg Thr Glu Val Leu Asp Asn Phe Gly Asp Gly Ser Thr Lys Glu Gln
        355                 360                 365

Ile Asp Ser Ile Thr Phe Glu Asn Leu Lys Lys Cys Glu Phe Leu Lys
    370                 375                 380

Ser Val Leu Asn Glu Thr Leu Arg Leu Tyr Pro Ser Val Pro Ile Asn
385                 390                 395                 400

Phe Arg Thr Ala Thr Arg Asp Thr Thr Leu Pro His Gly Gly Gly Ser
                405                 410                 415

Asp Gly Ser Lys Pro Ile Phe Val Pro Lys Gly Ser Thr Val Ala Tyr
            420                 425                 430

Ala Ile Tyr Lys Thr His Arg Leu Glu Glu Tyr Tyr Gly Lys Asp Ser
        435                 440                 445

Gln Glu Phe Lys Pro Asp Arg Trp Thr Asp Met Lys Arg Leu Gly Trp
    450                 455                 460

Ala Tyr Leu Pro Phe Asn Gly Gly Pro Arg Ile Cys Leu Gly Gln Gln
465                 470                 475                 480

Phe Ala Leu Thr Glu Ala Ser Tyr Val Leu Ala Arg Leu Ala Gln Leu
                485                 490                 495

Phe Pro Thr Leu Gln Ser Arg Asp Glu Thr Tyr Pro Pro Lys Lys Cys
            500                 505                 510

Ile His Leu Thr Met Asn His Ala Glu Gly Val Phe Val Gly Met Lys
        515                 520                 525

<210> SEQ ID NO 38
<211> LENGTH: 517
<212> TYPE: PRT
<213> ORGANISM: Candida tropicalis

<400> SEQUENCE: 38

Met Ile Glu Gln Leu Leu Glu Tyr Trp Tyr Val Val Pro Val Leu
1               5                   10                  15

Tyr Ile Ile Lys Gln Leu Leu Ala Tyr Thr Lys Thr Arg Val Leu Met
                20                  25                  30

Lys Lys Leu Gly Ala Ala Pro Val Thr Asn Lys Leu Tyr Asp Asn Ala
            35                  40                  45

Phe Gly Ile Val Asn Gly Trp Lys Ala Leu Gln Phe Lys Lys Glu Gly
        50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140
```

```
Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Arg Phe Thr Val Asp
            180                 185                 190

Ser Ala Thr Glu Phe Leu Phe Gly Glu Ser Val His Ser Leu Lys Asp
            195                 200                 205

Glu Ser Ile Gly Ile Asn Gln Asp Asp Ile Asp Phe Ala Gly Arg Lys
            210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Ser Val His Lys Phe Thr Asn Tyr Tyr Val Gln Lys
                260                 265                 270

Ala Leu Asp Ala Ser Pro Glu Glu Leu Glu Lys Gln Ser Gly Tyr Val
            275                 280                 285

Phe Leu Tyr Glu Leu Val Lys Gln Thr Arg Asp Pro Asn Val Leu Arg
290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
            355                 360                 365

Leu Lys Ala Phe Leu Asn Glu Thr Leu Arg Ile Tyr Pro Ser Val Pro
            370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
            435                 440                 445

Lys Leu Gly Trp Ala Tyr Leu Pro Phe Asn Gly Gly Pro Arg Ile Cys
450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515

<210> SEQ ID NO 39
<211> LENGTH: 521
<212> TYPE: PRT
<213> ORGANISM: Candida parapsilosis

<400> SEQUENCE: 39
```

-continued

```
Met Ser Asp Leu Thr Leu Phe Asp Tyr Ala Thr Lys Trp Tyr Val Leu
1               5                   10                  15

Ala Pro Ala Leu Ile Val Leu Tyr Ala Val Tyr Ile Gln Val Tyr Asn
            20                  25                  30

Ala Tyr Leu Ile Lys Lys Leu Gly Ala Ala Lys Glu Ala Asn Cys Glu
            35                  40                  45

Gly Asp Gly Leu Phe Gly Phe Arg Leu Pro Phe Trp Leu Ile Glu Arg
50                      55                  60

Lys Glu Asn Gly Thr Val Val Asp Tyr Val Ala Glu Arg Phe Asp Glu
65                  70                  75                  80

Val Ser His Pro Ser Ile Pro Thr Phe Ser Ile Arg Ile Phe Met Val
                85                  90                  95

Lys Leu Trp Met Thr Lys Asp Pro Glu Asn Ile Lys Ala Leu Leu Ala
                100                 105                 110

Thr Gln Phe Asn Asp Phe Cys Leu Gly Thr Arg His Ala Gln Phe Lys
            115                 120                 125

Pro Leu Leu Gly Asp Gly Ile Phe Thr Leu Asp Gly Gln Gly Trp Lys
        130                 135                 140

Glu Ser Arg Gln Met Leu Arg Pro Gln Phe Ala Arg Asp Gln Ile Ser
145                 150                 155                 160

His Val Lys Met Leu Glu Pro His Ile Gln Val Leu Phe Lys Gln Ile
                165                 170                 175

His Lys Asn Lys Gly Gln Val Phe Asp Leu Gln Glu Leu Phe Phe Arg
            180                 185                 190

Phe Thr Val Asp Ser Ala Thr Glu Phe Leu Phe Gly Glu Ser Val Asp
            195                 200                 205

Ser Leu Lys Asp Ala Ser Ile Gly Met Gln Ala Val Ser Asn Glu Val
    210                 215                 220

Glu Gly Lys Glu Gln Phe Ala Lys Ser Phe Asn Phe Ser Gln Asn Tyr
225                 230                 235                 240

Leu Ala Ser Arg Thr Thr Met Gln Gly Leu Tyr Trp Leu Leu Asn Ser
            245                 250                 255

Lys Lys Phe Arg Asp Asn Asn Ala Val Val His Lys Phe Ala Gln Tyr
        260                 265                 270

Tyr Val Lys Arg Ala Leu Ser Leu Thr Pro Glu Glu Leu Glu Lys Gln
    275                 280                 285

Asn Gly Tyr Val Phe Leu Tyr Glu Leu Ala Lys His Thr Arg Asp Pro
    290                 295                 300

Lys Val Leu Gln Asp Gln Leu Leu Asn Ile Leu Val Ala Gly Arg Asp
305                 310                 315                 320

Thr Thr Ala Gly Leu Leu Ser Phe Val Phe Glu Leu Ala Arg Ser
                325                 330                 335

Pro Ala Val Leu Thr Lys Leu Arg Glu Glu Ile Gly Ala Lys Phe Gly
            340                 345                 350

Leu Asp Lys Glu Ala Arg Val Asp Glu Ile Thr Phe Glu Ser Leu Lys
        355                 360                 365

Asn Cys Glu Tyr Leu Lys Ala Val Leu Asn Glu Cys Leu Arg Leu Tyr
    370                 375                 380

Pro Ser Val Pro Gln Asn Phe Arg Val Ala Thr Lys Asn Thr Thr Leu
385                 390                 395                 400

Pro Arg Gly Gly Gly Pro Asp Gly Met Ser Pro Ile Phe Val Thr Lys
                405                 410                 415
```

```
Gly Gln Ile Val Gln Tyr Cys Val Tyr Ala Thr His Arg Met Glu Glu
                420             425                 430

Phe Tyr Gly Lys Asn Ala Asn Glu Phe Arg Pro Glu Arg Trp Phe Glu
            435                 440                 445

Pro Gln Thr Arg Lys Leu Gly Trp Ala Phe Val Pro Phe Asn Gly Gly
450                 455                 460

Pro Arg Ile Cys Leu Gly Gln Gln Phe Ala Leu Thr Glu Ala Ser Tyr
465                 470                 475                 480

Val Thr Thr Arg Leu Val Gln Glu Phe Ser Ser Leu Trp Met Asp Pro
                485                 490                 495

Asn Thr Gln Tyr Pro Pro His Lys Met Ser His Leu Thr Met Ser Leu
            500                 505                 510

Tyr Asp Gly Cys Asn Val Lys Met Glu
            515                 520

<210> SEQ ID NO 40
<211> LENGTH: 521
<212> TYPE: PRT
<213> ORGANISM: Candida parapsilosis

<400> SEQUENCE: 40

Met Ser Asp Phe Asp Ile Met Glu Tyr Ser Thr Lys Trp Tyr Ile Ile
1               5                   10                  15

Ala Pro Ala Leu Ile Val Phe Tyr Val Val Tyr Lys Lys Ile Asn Glu
            20                  25                  30

Ala Tyr Leu Met Lys Lys Leu Gly Ala Val Arg Glu Thr Asn Pro Glu
        35                  40                  45

Gly Asp Gly Tyr Leu Gly Phe Lys Leu Pro Phe Trp Leu Ile Glu Arg
50                  55                  60

Lys Lys Asn Gly Thr Leu Val Asp Phe Ser Gln Arg Phe His Glu
65                  70                  75                  80

Ile Ser His Pro Glu Val Pro Thr Leu Ser Met Arg Ile Phe Thr Val
                85                  90                  95

Lys Leu Trp Ala Thr Lys Asp Pro Glu Asn Ile Lys Ala Leu Leu Ala
            100                 105                 110

Thr Gln Phe Asn Asp Phe Ser Leu Gly Thr Arg His Pro Gln Phe Lys
        115                 120                 125

Pro Leu Leu Gly Asp Gly Ile Phe Thr Leu Asp Asn Gln Gly Trp Lys
130                 135                 140

Asp Ser Arg Gln Met Leu Arg Pro Gln Phe Ala Arg Glu Gln Ile Ser
145                 150                 155                 160

His Val Lys Met Leu Glu Pro His Ile Gln Val Leu Phe Lys His Val
                165                 170                 175

Arg Lys Asn Lys Gly Gln Val Phe Asp Leu Gln Glu Leu Phe Arg
            180                 185                 190

Phe Thr Val Asp Ser Ala Thr Glu Phe Leu Phe Gly Glu Ser Val Asp
        195                 200                 205

Ser Leu Lys Asp Ala Ser Val Gly Met Gln Ala Asp Ser Asn Glu Ile
210                 215                 220

Asp Gly Lys Glu Gln Phe Ala Glu Ser Phe Asn Phe Ser Gln Asn Tyr
225                 230                 235                 240

Leu Ala Ser Arg Ala Val Met Gln Gly Leu Tyr Trp Leu Leu Asn Ser
                245                 250                 255

Lys Lys Phe Arg Asp Ser Asn Ala Val Val His Arg Phe Ala Gln His
            260                 265                 270
```

```
Tyr Val Lys Arg Ala Leu Ser Leu Ser Pro Glu Glu Leu Glu Lys Gln
            275                 280                 285

Asn Gly Tyr Val Phe Leu Tyr Glu Leu Ala Lys His Thr Arg Asp Pro
        290                 295                 300

Lys Val Leu Gln Asp Gln Leu Leu Asn Ile Leu Val Ala Gly Arg Asp
305                 310                 315                 320

Thr Thr Ala Gly Leu Leu Ser Phe Val Phe Glu Leu Ala Arg Asn
                325                 330                 335

Pro Ala Val Leu Ala Lys Leu Arg Glu Glu Ile Gly Thr Lys Phe Gly
                340                 345                 350

Leu Gly Lys Glu Ala Arg Ile Glu Glu Ile Thr Phe Glu Ser Leu Lys
            355                 360                 365

Asn Cys Glu Tyr Leu Lys Ala Val Leu Asn Glu Cys Leu Arg Leu Tyr
        370                 375                 380

Pro Ser Val Pro Gln Asn Phe Arg Val Ala Thr Arg Asn Thr Thr Leu
385                 390                 395                 400

Pro Arg Gly Gly Gly Pro Asp Gly Met Ser Pro Ile Leu Ile Thr Lys
                405                 410                 415

Gly Gln Thr Val Asn Tyr Ser Val Tyr Ala Thr His Arg Ser Glu Glu
            420                 425                 430

Tyr Tyr Gly Lys Asp Ala Asn Glu Phe Arg Pro Glu Arg Trp Phe Glu
        435                 440                 445

Pro Gln Thr Arg Lys Leu Gly Trp Ala Phe Val Pro Phe Asn Gly Gly
    450                 455                 460

Pro Arg Ile Cys Leu Gly Gln Gln Phe Ala Leu Thr Glu Ala Ser Tyr
465                 470                 475                 480

Val Thr Thr Arg Leu Val Gln Glu Phe Ser Ser Leu Trp Met Asp Pro
                485                 490                 495

Asn Thr Gln Tyr Pro Pro His Lys Met Ser His Leu Thr Met Ser Leu
            500                 505                 510

Tyr Asp Gly Cys Asn Val Lys Met Glu
        515                 520

<210> SEQ ID NO 41
<211> LENGTH: 526
<212> TYPE: PRT
<213> ORGANISM: Candida maltosa

<400> SEQUENCE: 41

Met Thr Ser Asp Ser Thr Ile His Glu Leu Ile Gln Ser Tyr Ile Thr
1               5                   10                  15

Lys Trp Tyr Val Ile Val Pro Leu Ala Ile Ile Tyr Lys Val Phe
            20                  25                  30

Asp Tyr Phe Tyr Val Leu Ser Leu Arg Lys Arg Leu Gly Ala Ala Val
        35                  40                  45

Pro Thr Asn Glu Glu Thr Asp Gly Tyr Phe Gly Phe His Leu Pro Phe
    50                  55                  60

Val Leu Met Ser Lys Lys Lys Asp Gly Thr Ile Ile Asp Phe Ser Ile
65                  70                  75                  80

Glu Arg Tyr Pro Glu Leu Lys His Pro Glu Thr Pro Thr Phe Glu Phe
                85                  90                  95

Pro Ile Phe Thr Val Lys Leu Ile Ser Thr Ile Asp Pro Glu Asn Ile
            100                 105                 110

Lys Ala Ile Leu Ala Thr Gln Phe Ser Asp Phe Ser Leu Gly Thr Arg
```

-continued

```
                115                 120                 125
His Ala His Phe Ala Pro Leu Ile Gly Asp Gly Ile Phe Thr Leu Asp
    130                 135                 140
Gly Ala Gly Trp Lys His Ser Arg Ala Met Leu Arg Pro Gln Phe Ala
145                 150                 155                 160
Arg Glu Gln Val Gly His Val Lys Leu Leu Glu Pro His Val Gln Val
                165                 170                 175
Leu Phe Lys His Ile Arg Lys Asn Lys Gly Arg Glu Phe Asp Leu Gln
            180                 185                 190
Glu Leu Phe Phe Arg Phe Thr Val Asp Ser Ala Thr Glu Phe Leu Phe
        195                 200                 205
Gly Glu Ser Val Glu Ser Leu Arg Asp Ala Ser Ile Gly Met Thr Ser
    210                 215                 220
Lys Ser Lys Asp Val Asp Gly Ile Glu Asp Phe Thr Gly Ala Phe Asn
225                 230                 235                 240
Tyr Ser Gln Asn Tyr Leu Ala Ser Arg Ser Ile Met Gln Gln Phe Tyr
                245                 250                 255
Trp Ile Leu Asn Gly Lys Lys Phe Arg Glu Cys Asn Ala Ile Val His
            260                 265                 270
Lys Phe Ala Asp His Tyr Val Gln Lys Ala Leu Asn Leu Thr Glu Ala
        275                 280                 285
Asp Leu Glu Lys Gln Ala Gly Tyr Val Phe Leu Tyr Glu Leu Val Lys
    290                 295                 300
Gln Thr Arg Asp Pro Gln Val Leu Arg Asp Gln Leu Leu Asn Ile Leu
305                 310                 315                 320
Val Ala Gly Arg Asp Thr Thr Ala Gly Leu Leu Ser Phe Val Phe Phe
                325                 330                 335
Glu Leu Ala Arg Asn Pro Asp Val Val Ala Lys Leu Lys Asp Glu Ile
            340                 345                 350
Asp Thr Lys Phe Gly Leu Gly Glu Asp Ala Arg Ile Glu Glu Ile Thr
        355                 360                 365
Phe Glu Ser Leu Lys Gln Cys Glu Tyr Leu Lys Ala Val Leu Asn Glu
    370                 375                 380
Cys Leu Arg Leu Tyr Pro Ser Val Pro Gln Asn Phe Arg Val Ala Thr
385                 390                 395                 400
Lys Asn Thr Thr Leu Pro Arg Gly Gly Lys Asp Gly Leu Ser Pro
                405                 410                 415
Ile Leu Val Arg Lys Gly Gln Thr Val Met Tyr Ser Val Tyr Ala Thr
            420                 425                 430
His Arg Met Glu Ser Val Tyr Gly Lys Asp Ala Thr Thr Phe Arg Pro
        435                 440                 445
Glu Arg Trp Phe Glu Pro Glu Thr Arg Lys Leu Gly Trp Ala Phe Val
    450                 455                 460
Pro Phe Asn Gly Gly Pro Arg Ile Cys Leu Gly Gln Gln Phe Ala Leu
465                 470                 475                 480
Thr Glu Ala Ser Tyr Val Thr Val Arg Leu Leu Gln Glu Phe Ser Thr
                485                 490                 495
Leu Thr Leu Asp Pro Asn Leu Glu Tyr Pro Pro Lys Lys Met Ser His
            500                 505                 510
Leu Thr Met Ser Leu Phe Asp Gly Thr Asn Val Gln Met Tyr
        515                 520                 525

<210> SEQ ID NO 42
```

```
<211> LENGTH: 522
<212> TYPE: PRT
<213> ORGANISM: Candida tropicalis

<400> SEQUENCE: 42
```

| | | | | | | | | | | | | | | |
|---|---|---|---|---|---|---|---|---|---|---|---|---|---|---|
| Met | Thr | Val | His | Asp | Ile | Ile | Ala | Thr | Tyr | Phe | Thr | Lys | Trp | Tyr | Val |
| 1 | | | | 5 | | | | | 10 | | | | | 15 | |

Ile Val Pro Leu Ala Leu Ile Ala Tyr Arg Val Leu Asp Tyr Phe Tyr
            20                  25                  30

Gly Arg Tyr Leu Met Tyr Lys Leu Gly Ala Lys Pro Phe Phe Gln Lys
        35                  40                  45

Gln Thr Asp Gly Cys Phe Gly Phe Lys Ala Pro Leu Glu Leu Leu Lys
    50                  55                  60

Lys Lys Ser Asp Gly Thr Leu Ile Asp Phe Thr Leu Gln Arg Ile His
65                  70                  75                  80

Asp Leu Asp Arg Pro Asp Ile Pro Thr Phe Thr Phe Pro Val Phe Ser
                85                  90                  95

Ile Asn Leu Val Asn Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Val Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
            260                 265                 270

Tyr Tyr Val Asn Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
    290                 295                 300

Lys Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Ser Val Glu Asp Ile Ser Phe Glu Ser Leu
        355                 360                 365

Lys Ser Cys Glu Tyr Leu Lys Ala Val Leu Asn Glu Thr Leu Arg Leu
    370                 375                 380

Tyr Pro Ser Val Pro Gln Asn Phe Arg Val Ala Thr Lys Asn Thr Thr

```
                    385                 390                 395                 400
Leu Pro Arg Gly Gly Gly Lys Asp Gly Leu Ser Pro Val Leu Val Arg
                405                 410                 415

Lys Gly Gln Thr Val Ile Tyr Gly Val Tyr Ala Ala His Arg Asn Pro
            420                 425                 430

Ala Val Tyr Gly Lys Asp Ala Leu Glu Phe Arg Pro Glu Arg Trp Phe
            435                 440                 445

Glu Pro Glu Thr Lys Lys Leu Gly Trp Ala Phe Leu Pro Phe Asn Gly
        450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ala His Leu Ser Met Asp
                485                 490                 495

Pro Asp Thr Glu Tyr Pro Pro Lys Lys Met Ser His Leu Thr Met Ser
            500                 505                 510

Leu Phe Asp Gly Ala Asn Ile Glu Met Tyr
        515                 520

<210> SEQ ID NO 43
<211> LENGTH: 526
<212> TYPE: PRT
<213> ORGANISM: Candida parapsilosis

<400> SEQUENCE: 43

Met Ile Asp Ser Ala Ile Ala Thr Tyr Trp Tyr Ile Thr Ile Pro Ser
1               5                   10                  15

Val Phe Leu Leu Tyr Ile Ile Ser Tyr Ile Asn Glu Gln Tyr Leu
            20                  25                  30

Met Arg Lys Phe Lys Ala Lys Pro Phe Thr Asn Tyr Ile Ser Gly Gly
        35                  40                  45

Phe Phe Gly Phe Gln Glu Gly Ile Ala Ala Leu Lys His Lys Lys Ala
    50                  55                  60

Gly Thr Ala Ile Glu Arg Tyr Arg Asp Leu Tyr Glu Glu Leu Pro Asn
65                  70                  75                  80

Pro Asp Val Pro Thr Tyr Lys Ser Phe Val Phe Gly Thr Pro Leu Val
                85                  90                  95

Phe Thr Lys Asp Pro Glu Asn Ile Lys Ala Ile Leu Ala Thr Gln Phe
            100                 105                 110

Asn Asp Phe Ser Leu Gly Ile Arg His Ala His Phe Asp Pro Leu Leu
        115                 120                 125

Gly Asp Gly Ile Phe Thr Leu Asp His Gln Gly Trp Lys Asp Ser Arg
    130                 135                 140

Ala Met Leu Arg Pro Gln Phe Ala Arg Asp Gln Ile Ala His Val Lys
145                 150                 155                 160

Ala Leu Glu Pro His Phe Gln Phe Leu Leu Arg His Ile Glu Lys Asn
                165                 170                 175

Asn Gly Gln Phe Phe Asp Ile Gln Glu Leu Phe Arg Phe Thr Val
            180                 185                 190

Asp Ser Ala Thr Glu Phe Leu Phe Gly Ser Ser Val Ser Ser Leu Gln
        195                 200                 205

Asp Glu Ser Ile Gly Cys Asp Thr Thr Glu Leu Asp Phe Val Gly Arg
    210                 215                 220

Lys Glu Phe Pro Glu Ala Phe Asn Lys Ser Gln Leu Ile Leu Ser Thr
225                 230                 235                 240
```

Arg Ala Leu Leu Gln Lys Met Tyr Trp Ile Tyr Asn Pro Lys Glu Phe
            245                 250                 255

Lys Lys Cys Asn Ala Ile Val His Gln Phe Ser Asp Tyr Tyr Ile Asn
        260                 265                 270

Lys Val Leu Ser Cys Thr Pro Glu Glu Ile Glu Lys Gln Ser Gly Tyr
    275                 280                 285

Val Phe Leu Tyr Glu Leu Val Lys Gln Thr Arg Asn Pro Lys Val Leu
290                 295                 300

Arg Asp Gln Ala Leu Asn Ile Leu Val Ala Gly Arg Asp Thr Thr Ala
305                 310                 315                 320

Gly Leu Leu Ser Phe Val Leu Phe Glu Leu Ala Arg Asn Pro Asp Ile
                325                 330                 335

Tyr Lys Lys Leu Arg Asp Glu Ile Leu Asp Lys Phe Gly Thr Ser Asn
            340                 345                 350

Leu Glu Glu Ile Thr Phe Glu Ser Leu Lys Lys Cys Glu Tyr Leu Lys
        355                 360                 365

Ala Val Leu Asn Glu Ala Leu Arg Met Tyr Pro Ser Val Pro Arg Asn
    370                 375                 380

Tyr Arg Val Ser Thr Arg Asn Thr Thr Leu Pro Arg Gly Gly Gly Ser
385                 390                 395                 400

Asp Gly Thr Ser Pro Ile Phe Ile Pro Lys Gly Arg Ser Val Ile Tyr
                405                 410                 415

Asn Ile Ala Ala Thr His Met Asp Pro Arg Tyr Tyr Gly Lys Asp Val
            420                 425                 430

Glu Glu Phe Arg Pro Glu Arg Trp Phe Glu Glu Ser Thr Lys Lys Leu
        435                 440                 445

Gly Trp Ala Tyr Leu Pro Phe Asn Gly Gly Pro Arg Ile Cys Leu Gly
    450                 455                 460

Gln Gln Phe Ala Leu Thr Glu Ala Ser Tyr Val Val Ala Arg Leu Ala
465                 470                 475                 480

Gln Thr Ile Ser Lys Leu Glu Leu Lys Asp Gly Tyr Thr Tyr Pro Pro
                485                 490                 495

Lys Lys Met Thr His Leu Thr Met Cys Met Phe Asp Gly Val Tyr Val
            500                 505                 510

Lys Met Glu Lys Asp Ala Thr Ala Ala Ala Lys Ser Gly
        515                 520                 525

<210> SEQ ID NO 44
<211> LENGTH: 512
<212> TYPE: PRT
<213> ORGANISM: Candida tropicalis

<400> SEQUENCE: 44

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Lys Ala Lys Ser Ala Gly
    50                  55                  60

Arg Ser Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

```
Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
            115                 120                 125

Thr Leu Asp Ala Glu Gly Trp Lys His Ser Arg Ala Met Leu Arg Pro
130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val His Ser Leu Lys Asp Glu Glu Ile Gly
            195                 200                 205

Tyr Asp Thr Lys Asp Met Ser Glu Glu Arg Arg Phe Ala Asp Ala
210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Val Gln Lys Ala Leu Asp Ala Thr
            260                 265                 270

Pro Glu Glu Leu Glu Lys Gln Gly Gly Tyr Val Phe Leu Tyr Glu Leu
            275                 280                 285

Val Lys Gln Thr Arg Asp Pro Lys Val Leu Arg Asp Gln Ser Leu Asn
290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335

Glu Ile Glu Gln Gln Phe Gly Leu Gly Glu Asp Ser Arg Val Glu Glu
            340                 345                 350

Ile Thr Phe Glu Ser Leu Lys Arg Cys Glu Tyr Leu Lys Ala Val Leu
            355                 360                 365

Asn Glu Thr Leu Arg Leu His Pro Ser Val Pro Arg Asn Ala Arg Phe
370                 375                 380

Ala Ile Lys Asp Thr Thr Leu Pro Arg Gly Gly Pro Asn Gly Lys
385                 390                 395                 400

Asp Pro Ile Leu Ile Arg Lys Asp Glu Val Gln Tyr Ser Ile Ser
                405                 410                 415

Ala Thr Gln Thr Asn Pro Ala Tyr Tyr Gly Ala Asp Ala Ala Asp Phe
            420                 425                 430

Arg Pro Glu Arg Trp Phe Glu Pro Ser Thr Arg Asn Leu Gly Trp Ala
            435                 440                 445

Phe Leu Pro Phe Asn Gly Gly Pro Arg Ile Cys Leu Gly Gln Gln Phe
450                 455                 460

Ala Leu Thr Glu Ala Gly Tyr Val Leu Val Arg Leu Val Gln Glu Phe
465                 470                 475                 480

Pro Asn Leu Ser Gln Asp Pro Glu Thr Lys Tyr Pro Pro Arg Leu
                485                 490                 495

Ala His Leu Thr Met Cys Leu Phe Asp Gly Ala His Val Lys Met Ser
            500                 505                 510
```

<210> SEQ ID NO 45
<211> LENGTH: 524
<212> TYPE: PRT
<213> ORGANISM: Lodderomyces elongisporus

<400> SEQUENCE: 45

```
Met Ser Asp Leu Leu Pro Pro Ile Ile Gln Glu Tyr Ala Thr Lys Trp
1               5                   10                  15

Tyr Ile Leu Leu Pro Ala Ile Val Leu Val Tyr Leu Thr Phe Ser Phe
            20                  25                  30

Leu Phe Glu Ile Tyr Leu Lys Arg Lys Leu Gly Ala Lys Gly Phe Thr
        35                  40                  45

Asn Thr Glu Arg Asp Gly Tyr Phe Gly Phe Tyr Thr Pro Phe Leu Leu
    50                  55                  60

Leu Arg Leu Lys Lys Glu Gly Asn Leu Val Asp Phe Gly Thr Glu Arg
65                  70                  75                  80

Tyr Gln Phe Leu Gln Asn Pro Asp Val Pro Thr Phe Lys Leu Arg Met
                85                  90                  95

Phe Gly Ile Pro Ile Val Thr Thr Lys Asp Pro Glu Asn Ile Lys Ala
            100                 105                 110

Ile Leu Ala Thr Gln Phe Ser Asp Phe Leu Leu Gly Leu Arg His Ala
        115                 120                 125

Gln Phe Met Pro Leu Leu Gly Asp Gly Ile Phe Thr Leu Asp Gly Gln
    130                 135                 140

Gly Trp Lys Asp Ser Arg Gln Met Leu Arg Pro Gln Phe Ala Arg Glu
145                 150                 155                 160

Gln Ile Ser His Val Lys Leu Leu Glu Pro His Met Gln Val Phe Phe
                165                 170                 175

Lys His Val Arg Lys His Lys Gly Met Thr Phe Asp Ile Gln Glu Leu
            180                 185                 190

Phe Phe Lys Leu Thr Val Asp Ser Ala Thr Glu Phe Leu Phe Gly Asn
        195                 200                 205

Ser Val Glu Cys Leu Lys Asp Ser Ser Ile Gly Met Arg Pro Asn Ser
    210                 215                 220

Ala Asp Phe Glu Gly Lys Glu Gln Phe Ala Asp Ala Phe Asn Tyr Ser
225                 230                 235                 240

Gln Thr Tyr Leu Ser Thr Arg Val Val Phe Gln Lys Phe Tyr Trp Leu
                245                 250                 255

Leu Asn Gly Lys Lys Phe Lys Glu Cys Asn Lys Ile Val His Ser Phe
            260                 265                 270

Ala Gln Tyr Tyr Val Asn Lys Ala Leu Gln Leu Thr Pro Asp Asp Leu
        275                 280                 285

Gln Lys Gln Glu Asn Tyr Val Phe Leu Tyr Glu Leu Ala Lys Asn Thr
    290                 295                 300

Arg Asp Pro Gln Val Leu Gln Asp Gln Leu Leu Asn Ile Met Val Ala
305                 310                 315                 320

Gly Arg Asp Thr Thr Ala Gly Leu Leu Ser Phe Val Phe Glu Leu
                325                 330                 335

Ala Arg Asn Gln Asp Val Leu Ala Lys Leu Lys Glu Glu Ile Tyr Gly
            340                 345                 350

Lys Phe Gly Phe Gly Ala Asp Ala Arg Val Asp Glu Ile Thr Phe Glu
        355                 360                 365

Ser Leu Lys Gly Cys Glu Tyr Leu Lys Ala Val Leu Asn Glu Cys Leu
    370                 375                 380
```

Arg Leu Tyr Pro Ser Val Pro Asn Asn Phe Arg Thr Ala Leu Arg Asp
385                 390                 395                 400

Thr Thr Leu Pro Arg Gly Gly Gly Lys Asp Gly Met Ser Pro Ile Leu
                405                 410                 415

Ile Arg Lys Gly Gln Asn Val Ile Tyr Ser Val Tyr Ala Leu His Arg
            420                 425                 430

Glu Glu Lys Phe Tyr Gly Lys Asp Ala Ala Glu Phe Arg Pro Glu Arg
        435                 440                 445

Trp Phe Glu Pro Glu Thr Arg Lys Leu Gly Trp Ala Phe Val Pro Phe
    450                 455                 460

Asn Gly Gly Pro Arg Ile Cys Leu Gly Gln Gln Phe Ala Leu Thr Glu
465                 470                 475                 480

Ala Ser Tyr Val Thr Thr Arg Leu Ile Gln Glu Phe Glu His Leu Thr
                485                 490                 495

Met Asp Pro Asp Thr Glu Tyr Pro Phe Lys Lys Met Ser His Leu Thr
            500                 505                 510

Met Ser Val Tyr Gly Gly Val Asn Val Gln Met Tyr
        515                 520

<210> SEQ ID NO 46
<211> LENGTH: 486
<212> TYPE: PRT
<213> ORGANISM: Candida maltosa

<400> SEQUENCE: 46

Met Arg Lys His His Ala Glu Pro Ile Leu Asp Val Val Asp Asp Gly
1               5                   10                  15

Ala Phe Gly Phe Lys Phe Gly Phe Gln Ser Leu Lys Ala Lys Lys Ile
            20                  25                  30

Gly Lys Gln Ile Asp Leu Ile Phe Ser Lys Phe Asn Glu Ala Lys His
        35                  40                  45

Pro Ser Ile Gly Thr Phe Met Thr Arg Asn Phe Gly Met Lys Leu Ile
    50                  55                  60

Leu Thr Lys Asp Pro Glu Asn Ile Lys Ala Met Leu Ala Thr Gln Phe
65                  70                  75                  80

Asn Glu Tyr Thr Leu Gly Gln Arg Leu Asn Phe Leu Ala Pro Leu Leu
                85                  90                  95

Gly Lys Gly Ile Phe Thr Leu Asp Gly Asn Gly Trp Lys His Ser Arg
            100                 105                 110

Ala Met Leu Arg Pro Gln Phe Ser Arg Asp Gln Ile Gly His Val Lys
        115                 120                 125

Met Leu Glu Pro His Phe Gln Leu Leu Lys Lys His Val Leu Lys Asn
130                 135                 140

Lys Gly Ser Phe Phe Asp Ile Gln Glu Leu Phe Phe Arg Phe Thr Val
145                 150                 155                 160

Asp Ser Ala Thr Glu Phe Leu Phe Gly Glu Ser Val Ser Ser Leu Lys
                165                 170                 175

Asp Glu Ser Ile Gly Tyr Asp Gln Glu Gly Ile Asp Phe Ala Gly Arg
            180                 185                 190

Lys Asp Phe Ala Glu Ala Phe Asn Lys Ser Gln Val Tyr Leu Ser Thr
        195                 200                 205

Arg Thr Leu Leu Gln Ser Leu Tyr Trp Leu Val Asn Ser Ser Asp Phe
210                 215                 220

Lys Arg Cys Asn Asn Ile Val His Lys Phe Ser Asp Tyr Tyr Ile Lys

```
                225                 230                 235                 240
Lys Ala Leu Thr Gly Thr Pro Glu Glu Leu Glu Lys His Ser Ser Tyr
                245                 250                 255

Ile Phe Leu Tyr Glu Leu Ala Lys Gln Thr Arg Asp Pro Ile Val Leu
                260                 265                 270

Arg Asp Gln Ser Leu Asn Ile Leu Ala Gly Arg Asp Thr Thr Ala
                275                 280                 285

Gly Leu Leu Ser Phe Ala Val Phe Glu Leu Gly Arg Asn Pro Glu Val
                290                 295                 300

Trp Ser Lys Leu Arg Gln Glu Ile Gly His Lys Phe Gly Leu Asp Ser
305                 310                 315                 320

Tyr Ser Arg Val Glu Asp Ile Ser Phe Glu Leu Lys Ser Cys Glu
                325                 330                 335

Tyr Leu Lys Ala Val Leu Asn Glu Thr Leu Arg Leu Tyr Pro Ser Val
                340                 345                 350

Pro Arg Asn Ala Arg Phe Ala Ala Lys Asn Thr Thr Leu Pro His Gly
                355                 360                 365

Gly Gly Lys Asp Gly Met Ser Pro Ile Leu Val Lys Lys Gly Gln Thr
                370                 375                 380

Val Met Tyr Ser Val Tyr Ala Leu Gln Arg Asp Glu Lys Tyr Tyr Gly
385                 390                 395                 400

Lys Asp Ala Asn Glu Phe Arg Pro Glu Arg Trp Phe Glu Pro Glu Val
                405                 410                 415

Arg Lys Leu Gly Trp Ala Phe Leu Pro Phe Asn Gly Gly Pro Arg Ile
                420                 425                 430

Cys Leu Gly Gln Gln Phe Ala Leu Thr Glu Ala Ser Tyr Val Leu Ala
                435                 440                 445

Arg Leu Val Gln Ser Phe Glu Thr Leu Glu Leu Ser Pro Asp Ala Glu
                450                 455                 460

Tyr Pro Pro Ala Lys Leu Ser His Leu Thr Met Cys Leu Phe Asp Gly
465                 470                 475                 480

Thr Pro Val Arg Phe Glu
                485

<210> SEQ ID NO 47
<211> LENGTH: 515
<212> TYPE: PRT
<213> ORGANISM: Scheffersomyces stipitis

<400> SEQUENCE: 47

Met Tyr Glu Lys Thr Ile Ile Ala Leu Ser Tyr Leu Ser Lys Trp Tyr
1               5                   10                  15

Val Leu Leu Gly Ser Ala Val Ala Val Leu Ala Leu Tyr Arg Tyr Ile
                20                  25                  30

Thr Val Gln Leu Ile Ile Arg Lys His Gly Cys Lys Asp Pro Ile Lys
                35                  40                  45

Phe Thr Gln Gly Gly Phe Leu Cys Ile Pro Ile Ile Leu Glu Leu Leu
                50                  55                  60

Arg Arg Met Lys Thr Gly Glu Met Ile Asp Glu Gly Phe Arg Leu Phe
65                  70                  75                  80

Asn Glu Tyr Pro Asp Thr Thr Gln Tyr Val Asn Leu Phe Gly Val Arg
                85                  90                  95

Val Leu Leu Thr Gly Glu Pro Glu Val Tyr Lys Ala Val Leu Ala Thr
                100                 105                 110
```

```
Gln Phe Asn Asn Phe Ala Leu Gly Phe Arg His Ser His Phe Ala Pro
            115                 120                 125

Leu Leu Gly Asp Gly Ile Phe Thr Leu Asp Gly Glu Gly Trp Lys Asn
130                 135                 140

Ser Arg Ala Met Leu Arg Pro Gln Phe Ala Arg Gln Gln Val Ser His
145                 150                 155                 160

Val Gln Met Leu Glu Pro His Ile Gln Thr Leu Ala Lys His Ile Lys
                165                 170                 175

Ala Arg Lys Gly Thr Thr Phe Asp Leu Gln Glu Leu Phe Phe Arg Leu
            180                 185                 190

Thr Met Asp Ser Ala Thr Glu Phe Leu Phe Gly Glu Ser Val Arg Ser
        195                 200                 205

Leu His Asp Glu Val Ile Gly Met Gln Arg Pro Asp Ile Glu Gly Ile
    210                 215                 220

Ser Asn Phe Ser Glu Ala Phe Asn Thr Ser Gln Arg Tyr Leu Ala Val
225                 230                 235                 240

Arg Ala Tyr Ser Gln Val Leu Tyr Trp Leu Thr Asn Pro Lys Glu Phe
                245                 250                 255

Arg Asp Cys Asn Ala Lys Val Gln Lys Val Ala Gln Tyr Phe Val Asn
            260                 265                 270

Lys Ala Leu Ser Phe Ser Asp Ser Glu Leu Glu Lys Ser Lys Lys
        275                 280                 285

Gly Tyr Ile Phe Leu Tyr Glu Leu Thr Lys Gln Thr Arg Asp Pro Lys
    290                 295                 300

Val Leu Gln Asp Gln Leu Leu Asn Ile Leu Ile Ala Gly Arg Asp Thr
305                 310                 315                 320

Thr Ala Gly Leu Leu Ser Phe Thr Phe Tyr Glu Leu Ala Arg Asn Pro
                325                 330                 335

Ala Ile Phe Glu Lys Leu Lys Ala Ala Ile Tyr Ala Asp Phe Gly Arg
            340                 345                 350

Gly Asp Val Ser Glu Ile Ser Phe Glu Ser Leu Lys Lys Cys Glu Tyr
        355                 360                 365

Leu Lys Phe Val Leu Asn Glu Ala Leu Arg Leu Tyr Pro Ser Val Pro
    370                 375                 380

Val Asn Phe Arg Val Ala Thr Lys Asp Thr Val Leu Pro Thr Gly Gly
385                 390                 395                 400

Gly Pro Asp Gly Gln Ser Pro Met Phe Val Arg Lys Tyr Thr Thr Val
                405                 410                 415

Ala Tyr Gly Val Tyr Phe Thr His Arg Met Lys Gln Phe Tyr Gly Glu
            420                 425                 430

Asp Ala Glu Val Phe Lys Pro Glu Arg Trp Ala Glu Asn Arg Lys Leu
        435                 440                 445

Gly Trp Ala Tyr Leu Pro Phe Asn Gly Gly Pro Arg Ile Cys Leu Gly
    450                 455                 460

Gln Gln Phe Ala Leu Thr Glu Ala Ser Tyr Val Val Arg Leu Ile
465                 470                 475                 480

Gln Met Phe Pro Asn Ile Val Ser Lys Asp Asp Gly Pro Tyr Pro Pro
                485                 490                 495

Arg Lys Ser Val Gln Leu Thr Met Cys Leu Gln Asp Gly Val Lys Ile
            500                 505                 510

Gln Met Ser
        515
```

<210> SEQ ID NO 48
<211> LENGTH: 517
<212> TYPE: PRT
<213> ORGANISM: Candida tropicalis

<400> SEQUENCE: 48

```
Met Ile Glu Gln Val Val Glu Tyr Trp Tyr Val Val Leu Pro Leu Val
1               5                   10                  15

Phe Ile Leu His Lys Val Phe Asp Met Trp His Thr Arg Arg Leu Met
            20                  25                  30

Lys Gln Leu Gly Ala Ala Pro Val Thr Asn Gln Leu His Asp Asn Phe
        35                  40                  45

Phe Gly Ile Ile Asn Gly Trp Lys Ala Leu Lys Phe Lys Lys Glu Gly
    50                  55                  60

Arg Ala Gln Glu Tyr Asn Asp Tyr Lys Phe Ala Asn Ser Lys Ile Pro
65                  70                  75                  80

Ser Val Gly Thr Tyr Val Ser Thr Ile Phe Gly Thr Lys Leu Leu Val
                85                  90                  95

Thr Lys Asp Pro Glu Asn Ile Lys Ala Leu Leu Ala Thr Gln Phe Ser
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys Asn Lys
                165                 170                 175

Gly Gly Phe Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Thr Ile Gly Tyr Asn Gln Asp Asp Ile Asp Phe Val Gly Arg Lys
    210                 215                 220

Asp Phe Ala Glu Ser Phe Asn Lys Ala Gln Glu Tyr Leu Ala Ile Arg
225                 230                 235                 240

Thr Leu Val Gln Asp Phe Tyr Tyr Leu Val Asn Asn Gln Glu Phe Arg
                245                 250                 255

Asp Cys Asn Lys Ser Val His Lys Phe Thr Asn Tyr Tyr Val Gln Arg
            260                 265                 270

Ala Leu Asp Ala Thr Pro Glu Glu Leu Glu Lys Gln Ser Gly Tyr Val
        275                 280                 285

Phe Leu Tyr Glu Leu Val Lys Gln Thr Arg Asp Pro Asn Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg Asn Pro His Ile Trp
                325                 330                 335

Ala Lys Leu Arg Glu Asp Val Glu Ser Gln Phe Gly Leu Gly Glu Glu
            340                 345                 350

Ser Arg Ile Glu Glu Ile Thr Phe Glu Ser Leu Lys Arg Cys Glu Tyr
        355                 360                 365

Leu Lys Ala Phe Leu Asn Glu Thr Leu Arg Val Tyr Pro Ser Val Pro
    370                 375                 380
```

```
Arg Asn Phe Arg Ile Ala Thr Lys Asn Thr Thr Leu Pro Arg Gly Gly
385                 390                 395                 400

Gly Ser Asp Gly Asn Ser Pro Val Leu Val Lys Lys Gly Glu Ala Val
            405                 410                 415

Ser Tyr Gly Ile Asn Ser Thr His Leu Asp Pro Val Tyr Tyr Gly Asp
            420                 425                 430

Asp Ala Ala Glu Phe Arg Pro Glu Arg Trp Asn Glu Pro Ser Thr Arg
            435                 440                 445

Lys Leu Gly Trp Ala Tyr Leu Pro Phe Asn Gly Pro Arg Ile Cys
            450                 455                 460

Leu Gly Gln Gln Phe Ala Leu Thr Glu Ala Gly Tyr Val Leu Val Arg
465                 470                 475                 480

Leu Ala Gln Ser Phe Asp Thr Leu Glu Leu Lys Pro Pro Val Val Tyr
            485                 490                 495

Pro Pro Lys Arg Leu Thr Asn Leu Thr Met Ser Leu Gln Asp Gly Thr
            500                 505                 510

Ile Val Lys Ile Asp
            515

<210> SEQ ID NO 49
<211> LENGTH: 520
<212> TYPE: PRT
<213> ORGANISM: Candida parapsilosis

<400> SEQUENCE: 49

Met Ile Glu Thr Val Ser Ile Ala Asn Ile Val Ala Tyr Trp Tyr Ile
1               5                   10                  15

Thr Ile Pro Ala Val Leu Leu Gly His Phe Val Ile Gly Tyr Ile His
                20                  25                  30

Glu Gln Val Leu Ile Arg Lys Leu Gly Ala Lys Pro Phe Ala Asn Asn
            35                  40                  45

Val Asn Gly Gly Phe Phe Gly Ser Ala Leu Gly Val Lys Ser Ile Val
        50                  55                  60

Ala Lys Gly Lys Gly Arg Ala Val Glu Phe Tyr Gln Asn Leu Tyr His
65                  70                  75                  80

Val Ser Pro His Thr Glu Val Pro Thr Ile Lys Thr Tyr Ile Phe Gly
                85                  90                  95

Thr Pro Ile Val Phe Thr Lys Asp Pro Glu Asn Ile Lys Ala Ile Leu
            100                 105                 110

Ala Thr Gln Phe Gln Asp Phe Cys Leu Gly Asn Arg Tyr His Phe Leu
        115                 120                 125

Lys Pro Leu Leu Gly Lys Gly Ile Phe Thr Leu Asp His Glu Gly Trp
130                 135                 140

Lys Asp Ser Arg Ala Ile Leu Arg Pro Gln Phe Ala Arg Asp Gln Ile
145                 150                 155                 160

Ala His Val Lys Ala Leu Glu Pro His Phe Gln Phe Leu Leu Arg His
                165                 170                 175

Ile Glu Lys Asn Asn Gly Gln Phe Phe Asp Ile Gln Glu Leu Phe Phe
            180                 185                 190

Arg Phe Thr Val Asp Ser Ala Thr Glu Phe Leu Phe Gly Ser Ser Val
        195                 200                 205

Ser Ser Leu Gln Asp Glu Ser Ile Gly Cys Asp Thr Ser Ala Leu Asp
    210                 215                 220

Phe Ser Gly Arg Leu Glu Phe Ala Glu Ala Phe Asn Val Ser Gln Val
225                 230                 235                 240
```

Tyr Leu Ser Thr Arg Ala Leu Leu Gln Arg Ile Tyr Trp Leu Cys Asn
            245                 250                 255

Asn Gln Glu Phe Lys Lys Cys Asn Lys Ile Val His Gln Phe Ser Asp
        260                 265                 270

Tyr Tyr Ile Asn Lys Val Leu Asn Cys Thr Pro Glu Glu Ile Glu Lys
            275                 280                 285

Gln Ser Gly Tyr Val Phe Leu Tyr Glu Leu Val Lys Gln Thr Arg Asp
        290                 295                 300

Pro Ile Val Leu Arg Asp Gln Ala Leu Asn Ile Leu Leu Thr Gly Arg
305                 310                 315                 320

Asp Thr Thr Ala Gly Leu Leu Ser Phe Val Leu Phe Glu Leu Ala Arg
                325                 330                 335

Asn Pro Glu Met Tyr Ala Lys Leu Arg His Glu Ile Leu Asp Lys Phe
            340                 345                 350

Gly Thr Ser Asn Leu Glu Asp Ile Thr Phe Glu Asn Leu Lys Lys Cys
        355                 360                 365

Glu Tyr Leu Lys Ala Ile Leu Asn Glu Thr Leu Arg Met Tyr Pro Ser
    370                 375                 380

Val Pro Arg Asn Ala Arg Val Ala Thr Arg Asn Thr Thr Leu Pro Arg
385                 390                 395                 400

Gly Gly Gly Ser Asp Gly Thr Ser Pro Val Phe Ile Pro Lys Gly Lys
                405                 410                 415

Ala Val Ile Tyr Asn Ile Ala Ala Thr His Met Asp Pro Arg Tyr Tyr
            420                 425                 430

Gly Lys Asp Val Glu Glu Phe Arg Pro Glu Arg Trp Phe Glu Glu Ser
        435                 440                 445

Thr Lys Lys Leu Gly Trp Ala Tyr Leu Pro Phe Asn Gly Gly Pro Arg
    450                 455                 460

Ile Cys Leu Gly Gln Gln Phe Ala Leu Thr Glu Ala Ser Tyr Val Val
465                 470                 475                 480

Ala Arg Leu Ala Gln Thr Ile Ser Lys Leu Glu Leu Lys Glu Gly Tyr
                485                 490                 495

Glu Tyr Pro Pro Lys Lys Met Thr His Leu Thr Met Ser Met Phe Asp
        500                 505                 510

Gly Val Tyr Val Lys Met Glu Leu
        515                 520

<210> SEQ ID NO 50
<211> LENGTH: 522
<212> TYPE: PRT
<213> ORGANISM: Candida tropicalis

<400> SEQUENCE: 50

Met Ser Ile Gln Asp Ile Val Glu Thr Tyr Ser Thr Lys Trp Tyr Val
1               5                   10                  15

Val Val Ser Val Ala Leu Ile Val Tyr Lys Val Phe Asp Phe Phe Tyr
            20                  25                  30

Ala Arg Tyr Leu Met Tyr Lys Leu Gly Ala Lys Pro Phe Leu Gln Ser
        35                  40                  45

Gln Thr Asp Gly Tyr Leu Gly Phe Arg Val Pro Phe Glu Leu Met Gly
    50                  55                  60

Lys Lys Ser Glu Gly Thr Leu Ile Asp Phe Thr Tyr Gln Arg Thr Leu
65                  70                  75                  80

Glu Leu Asp Asn Pro Asp Ile Pro Thr Phe Thr Phe Pro Ile Phe Ser

```
              85                  90                  95
Val Ser Ile Ile Ser Thr Leu Glu Pro Asp Asn Ile Lys Ala Ile Leu
            100                 105                 110

Ala Thr Gln Phe Asn Asp Phe Ser Leu Gly Thr Arg His Ser His Phe
            115                 120                 125

Ala Pro Leu Leu Gly Asp Gly Ile Phe Thr Leu Asp Gly Ala Gly Trp
130                 135                 140

Lys His Ser Arg Ser Met Leu Arg Pro Gln Phe Ala Arg Glu Gln Val
145                 150                 155                 160

Ser His Val Lys Leu Leu Glu Pro His Met Gln Val Phe Phe Lys His
                165                 170                 175

Ile Arg Lys His His Gly Gln Thr Phe Asp Ile Gln Glu Leu Phe Phe
                180                 185                 190

Arg Leu Thr Val Asp Ser Ala Thr Glu Phe Leu Phe Gly Glu Ser Val
                195                 200                 205

Glu Ser Leu Arg Asp Glu Ser Ile Gly Met Leu Asn Asp Ala Leu Asp
            210                 215                 220

Phe Asp Gly Lys Ala Gly Phe Ala Asp Ala Phe Asn Tyr Ser Gln Asn
225                 230                 235                 240

Tyr Leu Ala Ser Arg Ala Leu Met Gln Gln Met Tyr Trp Ile Leu Asn
                245                 250                 255

Gly Lys Lys Phe Lys Glu Cys Asn Ala Lys Val His Lys Phe Ala Asp
                260                 265                 270

Tyr Tyr Val Glu Lys Ala Leu Glu Leu Thr Pro Asp Gln Leu Glu Lys
                275                 280                 285

Gln Asp Gly Tyr Val Phe Leu Tyr Glu Leu Val Lys Gln Thr Arg Asp
            290                 295                 300

Arg Gln Val Leu Arg Asp Gln Leu Leu Asn Ile Leu Val Ala Gly Arg
305                 310                 315                 320

Asp Thr Thr Ala Gly Leu Leu Ser Phe Val Phe Phe Glu Leu Ala Arg
                325                 330                 335

Thr Pro Arg Val Ala Asn Lys Leu Arg Glu Glu Ile Glu Asp Lys Phe
                340                 345                 350

Gly Leu Gly Gln Asp Ala Arg Val Glu Glu Ile Ser Phe Glu Ser Leu
            355                 360                 365

Lys Ser Cys Glu Tyr Leu Lys Ala Val Leu Asn Glu Cys Leu Arg Leu
            370                 375                 380

Tyr Pro Ser Val Pro Gln Asn Phe Arg Val Ala Thr Arg Asn Thr Thr
385                 390                 395                 400

Leu Pro Arg Gly Gly Gly Lys Asp Gly Leu Ser Pro Val Leu Val Arg
                405                 410                 415

Lys Gly Gln Thr Val Met Tyr Ser Val Tyr Ala Ala His Arg Asn Lys
                420                 425                 430

Gln Ile Tyr Gly Glu Asp Ala Leu Glu Phe Arg Pro Glu Arg Trp Phe
            435                 440                 445

Glu Pro Glu Thr Lys Lys Leu Gly Trp Ala Phe Leu Pro Phe Asn Gly
            450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ser His Leu Thr Met Asp
                485                 490                 495

Pro Asn Thr Glu Tyr Pro Pro Lys Lys Met Ser His Leu Thr Met Ser
            500                 505                 510
```

Leu Phe Asp Gly Ala Asn Ile Gln Met Tyr
         515                 520

<210> SEQ ID NO 51
<211> LENGTH: 522
<212> TYPE: PRT
<213> ORGANISM: Candida tropicalis

<400> SEQUENCE: 51

Met Ser Ile Gln Asp Ile Val Glu Thr Tyr Ser Thr Lys Trp Tyr Val
1               5                   10                  15

Val Val Leu Val Ala Leu Ile Val Tyr Lys Val Phe Asp Phe Phe Tyr
            20                  25                  30

Ala Arg Tyr Leu Met Tyr Lys Leu Gly Ala Lys Pro Phe Leu Gln Ser
        35                  40                  45

Gln Thr Asp Gly Tyr Leu Gly Phe Arg Val Pro Phe Glu Leu Met Gly
    50                  55                  60

Lys Lys Ser Glu Gly Thr Leu Ile Asp Phe Thr Tyr Gln Arg Thr Leu
65                  70                  75                  80

Glu Leu Asp Asn Pro Asp Ile Pro Thr Phe Thr Phe Pro Ile Phe Ser
                85                  90                  95

Val Leu Ile Ile Ser Thr Leu Glu Pro Asp Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Val
145                 150                 155                 160

Ser His Val Lys Leu Leu Glu Pro His Met Gln Val Phe Phe Lys His
                165                 170                 175

Ile Arg Lys His His His Gly Gln Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Leu Asn Asp Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Leu Met Gln Gln Met Tyr Trp Ile Leu Asn
                245                 250                 255

Gly Lys Lys Phe Lys Glu Cys Asn Ala Lys Val His Lys Phe Ala Asp
            260                 265                 270

Tyr Tyr Val Glu Lys Ala Leu Glu Leu Thr Pro Asp Gln Leu Glu Lys
        275                 280                 285

Gln Asp Gly Tyr Val Phe Leu Tyr Glu Leu Val Lys Gln Thr Arg Asp
    290                 295                 300

Arg Gln Val Leu Arg Asp Gln Leu Leu Asn Ile Leu Val Ala Gly Arg
305                 310                 315                 320

Asp Thr Thr Ala Gly Leu Leu Ser Phe Val Phe Phe Glu Leu Ala Arg
                325                 330                 335

Thr Pro Arg Val Ala Asn Lys Leu Arg Glu Glu Ile Glu Asp Lys Phe
            340                 345                 350

Gly Leu Gly Gln Asp Ala Arg Val Glu Glu Ile Ser Phe Glu Ser Leu

```
                355                 360                 365
Lys Ser Cys Glu Tyr Leu Lys Ala Val Leu Asn Glu Cys Leu Arg Leu
    370                 375                 380

Tyr Pro Ser Val Pro Gln Asn Phe Arg Val Ala Thr Arg Asn Thr Thr
385                 390                 395                 400

Leu Pro Arg Gly Gly Lys Asp Gly Leu Ser Pro Val Leu Val Arg
                405                 410                 415

Lys Gly Gln Thr Val Met Tyr Ser Val Tyr Ala Ala His Arg Asn Lys
                420                 425                 430

Gln Ile Tyr Gly Glu Asp Ala Leu Glu Phe Arg Pro Glu Arg Trp Phe
                435                 440                 445

Glu Pro Glu Thr Lys Lys Leu Gly Trp Ala Phe Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ser His Leu Thr Met Asp
                485                 490                 495

Pro Asn Thr Glu Tyr Ser Pro Lys Lys Met Ser His Leu Thr Met Ser
                500                 505                 510

Leu Phe Asp Gly Ala Asn Ile Gln Met Tyr
                515                 520

<210> SEQ ID NO 52
<211> LENGTH: 522
<212> TYPE: PRT
<213> ORGANISM: Scheffersomyces stipitis

<400> SEQUENCE: 52

Met Thr Val Glu Thr Ile Val Gln Tyr Leu Ser Cys Trp Gln Val Tyr
1               5                   10                  15

Val Leu Ala Val Leu Val Tyr His Ile Phe Asn Trp Ile His Glu Gln
                20                  25                  30

Ile Leu Tyr Lys Lys Phe Gly Ala Ser Pro Cys Ile Asn Asn Glu Arg
            35                  40                  45

Gly Gly Phe Leu Gly Ile Arg Leu Leu Arg Thr Leu Leu Lys Ala Lys
        50                  55                  60

Ser Asp Gly Thr Leu Ser Asp Val Val Lys Asn Arg Tyr Tyr Glu Met
65                  70                  75                  80

Glu His Pro Glu Ile Glu Thr Phe Thr Ser Arg Val Phe Ser Gln Thr
                85                  90                  95

Val Ile Ala Thr Arg Asp Pro Ala Asn Leu Lys Ala Ile Leu Ala Thr
                100                 105                 110

Gln Phe Asn Asp Phe Ser Leu Gly Ile Arg His Ala Gln Leu Tyr Pro
            115                 120                 125

Leu Leu Gly Asp Gly Ile Phe Thr Leu Asp Gly Glu Gly Trp Lys His
        130                 135                 140

Ser Arg Ala Met Leu Arg Pro Gln Phe Ala Lys Glu Gln Ile Ala His
145                 150                 155                 160

Val Gln Ser Leu Glu Pro His Ile Gln Val Leu Ala Lys His Ile Arg
                165                 170                 175

Lys Ser Glu Gly Lys Ser Phe Glu Met Gln Glu Leu Phe Phe Arg Leu
                180                 185                 190

Thr Leu Asp Cys Ala Thr Glu Phe Leu Phe Gly Glu Ser Val Glu Ser
            195                 200                 205
```

```
Leu Arg Asp Ala Ser Ile Gly Met Ala Arg Ala Asp Val Glu Val Glu
    210                 215                 220

Gly Lys Asp Arg Phe Ala Glu Ala Phe Asn Leu Ala Gln Thr Gln Ile
225                 230                 235                 240

Ala Thr Arg Ser Met Met Asn Lys Met Tyr Phe Leu Tyr Asn Thr Glu
                245                 250                 255

Glu Leu Arg Asn Ser Cys Asp Val Val His Arg Phe Thr Asp Tyr Tyr
            260                 265                 270

Val Asn Leu Ala Leu Arg Thr Ser Thr Ala Glu Leu Asp Lys Lys Ser
        275                 280                 285

Lys Ser Gly Tyr Thr Phe Leu Tyr Glu Leu Val Lys Gln Thr Arg Asn
    290                 295                 300

Pro Gln Ile Leu Arg Asp Gln Leu Leu Asn Ile Leu Leu Ala Gly Arg
305                 310                 315                 320

Asp Thr Thr Ala Gly Leu Leu Ser Phe Ala Phe Phe Glu Leu Ala Arg
                325                 330                 335

Gln Pro His Ile Trp Ala Lys Leu Lys Asp Glu Ile Tyr Ser Ala Phe
            340                 345                 350

Gly Ser Gly Glu Asn Ser Arg Ile Asp Glu Ile Thr Phe Glu Ser Leu
        355                 360                 365

Lys Arg Cys Glu Tyr Leu Lys Ala Val Leu Asn Glu Thr Leu Arg Met
    370                 375                 380

Tyr Pro Ser Val Pro Asn Asn Gly Arg Ile Ala Val Arg Asn Thr Thr
385                 390                 395                 400

Leu Pro Arg Gly Gly Gly Pro Thr Gly Thr Glu Pro Met Leu Val Arg
                405                 410                 415

Lys Gly Gln Lys Val Val Tyr Ser Val Tyr Thr Thr His Arg Ser Lys
            420                 425                 430

Thr His Tyr Gly Glu Asp Ala Glu Val Phe Arg Pro Glu Arg Trp Phe
        435                 440                 445

Glu Pro Ser Ser Arg Lys Leu Gly Trp Ala Tyr Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Val Thr Arg Leu Ile Gln Met Phe Pro Asn Ile Ser Ser Asp
                485                 490                 495

Pro Thr Ile Glu Tyr Pro Pro Arg Lys Ala Ser Gln Leu Thr Met Cys
            500                 505                 510

Leu Gln Asp Gly Leu Leu Ile Ser Leu Tyr
        515                 520

<210> SEQ ID NO 53
<211> LENGTH: 543
<212> TYPE: PRT
<213> ORGANISM: Candida tropicalis

<400> SEQUENCE: 53

Met Ser Ser Ser Pro Ser Ile Ala Gln Glu Phe Leu Ala Thr Ile Thr
1               5                   10                  15

Pro Tyr Val Glu Tyr Cys Gln Glu Asn Tyr Thr Lys Trp Tyr Tyr Phe
                20                  25                  30

Ile Pro Leu Val Ile Leu Ser Leu Asn Leu Ile Ser Met Leu His Thr
            35                  40                  45

Lys Tyr Leu Glu Arg Lys Phe Lys Ala Lys Pro Leu Ala Val Tyr Val
        50                  55                  60
```

-continued

```
Gln Asp Tyr Thr Phe Cys Leu Ile Thr Pro Leu Val Leu Ile Tyr Tyr
 65                  70                  75                  80

Lys Ser Lys Gly Thr Val Met Gln Phe Ala Cys Asp Leu Trp Asp Lys
                 85                  90                  95

Asn Leu Ile Val Ser Asp Pro Lys Ala Lys Thr Ile Gly Leu Lys Ile
            100                 105                 110

Leu Gly Ile Pro Leu Ile Glu Thr Lys Asp Pro Glu Asn Val Lys Ala
        115                 120                 125

Ile Leu Ala Thr Gln Phe Asn Asp Phe Ser Leu Gly Thr Arg His Asp
130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Met Gln Val Leu Phe
            180                 185                 190

Lys His Ile Arg Lys His His Gly Gln Thr Phe Asp Ile Gln Glu Leu
        195                 200                 205

Phe Phe Arg Leu Thr Val Asp Ser Ala Thr Glu Phe Leu Leu Gly Glu
210                 215                 220

Ser Ala Glu Ser Leu Arg Asp Glu Ser Val Gly Leu Thr Pro Thr Thr
225                 230                 235                 240

Lys Asp Phe Asp Gly Arg Asn Glu Phe Ala Asp Ala Phe Asn Tyr Ser
                245                 250                 255

Gln Thr Asn Gln Ala Tyr Arg Phe Leu Gln Gln Met Tyr Trp Ile
            260                 265                 270

Leu Asn Gly Ser Glu Phe Arg Lys Ser Ile Ala Ile Val His Lys Phe
        275                 280                 285

Ala Asp His Tyr Val Gln Lys Ala Leu Glu Leu Thr Asp Glu Asp Leu
290                 295                 300

Glu Lys Lys Glu Gly Tyr Val Phe Leu Phe Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Leu Phe Glu Leu
            340                 345                 350

Ser Arg Asn Pro Glu Ile Phe Ala Lys Leu Arg Glu Glu Ile Glu Asn
        355                 360                 365

Lys Phe Gly Leu Gly Gln Asp Ala Arg Val Glu Glu Ile Ser Phe Glu
370                 375                 380

Thr Leu Lys Ser Cys Glu Tyr Leu Lys Ala Val Ile Asn Glu Thr Leu
385                 390                 395                 400

Arg Ile Tyr Pro Ser Val Pro His Asn Phe Arg Val Ala Thr Arg Asn
                405                 410                 415

Thr Thr Leu Pro Arg Gly Gly Gly Gly Leu Ser Pro Ile Ala
            420                 425                 430

Ile Lys Lys Gly Gln Val Val Met Tyr Thr Ile Leu Ala Thr His Arg
        435                 440                 445

Asp Lys Asp Ile Tyr Gly Glu Asp Ala Tyr Val Phe Arg Pro Glu Arg
450                 455                 460

Trp Phe Glu Pro Glu Thr Arg Lys Leu Gly Trp Ala Tyr Val Pro Phe
465                 470                 475                 480
```

```
Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Gly Asn Leu Lys
            500                 505                 510

Gln Asp Pro Asn Thr Glu Tyr Pro Pro Lys Leu Gln Asn Thr Leu Thr
        515                 520                 525

Leu Ser Leu Phe Glu Gly Ala Glu Val Gln Met Tyr Leu Ile Leu
    530                 535                 540

<210> SEQ ID NO 54
<211> LENGTH: 424
<212> TYPE: PRT
<213> ORGANISM: Scheffersomyces stipitis

<400> SEQUENCE: 54

Met Phe Met Thr Thr Asp Pro Glu Asn Phe Lys Ala Met Leu Ala Thr
1               5                   10                  15

Gln Phe Asn Asp Phe Ser Ile Gly Arg Arg Tyr Gln Ile Leu Ser Pro
            20                  25                  30

Val Ile Gly Asp Ser Ile Phe Thr Leu Asp Gly Glu Gly Trp Lys His
        35                  40                  45

Ser Arg Ala Met Leu Arg Pro Gln Phe Val Arg Glu Gln Val Gly His
    50                  55                  60

Val Gln Ala Leu Glu Pro His Leu Gln Leu Leu Ala Lys His Ile Arg
65                  70                  75                  80

Ser Tyr Lys Gly Glu Thr Val Asp Leu Gln Gln Leu Phe Thr Lys Phe
                85                  90                  95

Thr Leu Asp Thr Ala Thr Glu Phe Leu Phe Gly Gln Ser Val His Thr
            100                 105                 110

Leu Tyr Asp Glu Arg Ile Gly Met Lys Thr Pro Asp Asp Val Pro Tyr
        115                 120                 125

Ala Lys Asp Phe Thr Asp Gly Leu Phe Ile Thr Gln Lys Tyr Thr Ser
    130                 135                 140

Glu Arg Gly Tyr Ala Gln Gln Phe Tyr Trp Leu Ile Asp Gly Lys Glu
145                 150                 155                 160

Phe Arg Thr Ala Ile Ala Asn Val His Lys Phe Ala Arg Phe Tyr Val
                165                 170                 175

Asp Arg Ala Leu Asn Phe Ser Gln Ala Glu Leu Glu Lys Lys Ser Gln
            180                 185                 190

Glu Ser Tyr Thr Phe Leu Tyr Glu Leu Val Gln Gln Thr Arg Asp Pro
        195                 200                 205

Lys Val Leu Gln Asp Gln Leu Leu Ala Ile Met Leu Ala Gly Arg Asp
    210                 215                 220

Thr Thr Ser Ser Leu Leu Ser Phe Ile Phe Tyr Glu Leu Ser Arg Asn
225                 230                 235                 240

Pro Gly Ile Trp Glu Lys Leu Lys Lys Glu Val Tyr Glu Asn Phe Gly
                245                 250                 255

Ser Gly Thr Glu Lys Asp Ile Ala Lys Ile Thr Phe Glu Ser Leu Lys
            260                 265                 270

Lys Cys Asn Tyr Val Lys Trp Val Ile Asn Glu Thr Leu Arg Met Tyr
        275                 280                 285

Pro Thr Val Pro Val Asn Leu Arg Val Ser Asn Lys Asp Thr Ser Leu
    290                 295                 300

Pro Lys Gly Gly Gly Glu Asp Gly Lys Ser Pro Ile Phe Ile Pro Arg
305                 310                 315                 320
```

```
Gly Thr Thr Val Gly Phe Arg Val Tyr Ser Thr Gln Arg Asn Lys Glu
                325                 330                 335

Tyr Tyr Gly Glu Asp Pro Asp Val Phe Arg Pro Glu Arg Trp Ala Asp
                340                 345                 350

Ile Gly Lys Leu Gly Trp Ala Tyr Leu Pro Phe Leu Gly Gly Pro Arg
                355                 360                 365

Thr Cys Ile Gly Gln Gln Phe Ala Leu Thr Glu Ala Gly Tyr Ile Leu
                370                 375                 380

Val Arg Ile Ala Gln Leu Phe Pro Asn Leu Lys Ser Lys Asn Ser Val
385                 390                 395                 400

His Tyr Pro Pro Lys Lys Thr Leu Asn Val Ile Phe Asn Leu Phe Glu
                405                 410                 415

Gly Cys Leu Val Glu Met Gly Glu
                420

<210> SEQ ID NO 55
<211> LENGTH: 530
<212> TYPE: PRT
<213> ORGANISM: Candida tenuis

<400> SEQUENCE: 55

Met Ala Leu Asn Ser Tyr Gln Pro Asn Ser Leu Gln Ile Ile Asn Met
1               5                   10                  15

Ser Phe Lys Glu His Phe Ser Glu His Ser Ser Lys Trp Tyr Val Ala
                20                  25                  30

Ile Pro Ala Val Leu Val Leu Tyr Leu Val Leu Ser Ser Ile Gln Ala
                35                  40                  45

Arg Ile Phe Ala Tyr Lys Arg Gly Cys Lys Ala Pro Ala Tyr Ala Lys
            50                  55                  60

Gly Gly Arg Phe Gly Leu Val Leu Leu Lys Asn Ala Ile Lys Ala Lys
65                  70                  75                  80

Asn Glu Gly Thr Leu Asp Arg Phe Ser Glu Val Ser Leu Gly Ala Thr
                85                  90                  95

Met Thr Ser Lys Ile Ser Leu Gly Gly Val Pro Val Ile Leu Thr
                100                 105                 110

Arg Asp Pro Glu Asn Ile Lys Ala Leu Leu Gly Thr Gln Phe Asn Asp
            115                 120                 125

Phe Ala Leu Gly Thr Arg His Ala His Phe Lys Pro Leu Leu Gly Asp
130                 135                 140

Gly Ile Phe Thr Leu Asp Gly Gln Gly Trp Lys Asp Ser Arg Ser Met
145                 150                 155                 160

Leu Arg Pro Gln Phe Ser Arg Glu Gln Val Ala His Val Arg Ser Leu
                165                 170                 175

Glu Pro His Ile Gln Leu Leu Arg Lys His Ile Gln Lys Phe Gly Gly
            180                 185                 190

Lys Glu Phe Asp Ile Gln Glu Tyr Phe Phe Lys Phe Thr Ile Asp Thr
                195                 200                 205

Ala Thr Glu Phe Leu Phe Gly Glu Ser Val Asp Thr Leu Lys Asp Ala
            210                 215                 220

Ser Ile Gly Glu Val Pro Asp Ile Glu Phe Ala Ala Lys His Gln Phe
225                 230                 235                 240

Ala Asp Ser Phe Asn Val Ser Gln Val Tyr Leu Ser Thr Arg Ala Tyr
                245                 250                 255

Ser Gln Ile Phe Tyr Phe Leu Ile Asn Asn Lys Glu Phe Arg Glu Ser
```

```
            260                 265                 270
Asn Ser Arg Val His Asp Phe Thr Asn Tyr Phe Val Asp Lys Val Leu
        275                 280                 285

Glu Ser Asp Pro Glu Lys Leu Ser Glu Met Ser Lys Gly Gly Tyr Thr
        290                 295                 300

Phe Leu Tyr Glu Leu Ala Lys Gln Thr Arg Asp Arg Thr Val Leu Arg
305                 310                 315                 320

Asp Gln Ala Leu Asn Ile Leu Leu Ala Gly Arg Asp Thr Thr Ala Gly
                325                 330                 335

Leu Leu Ser Phe Thr Phe Tyr Glu Leu Ser Arg Asn Pro Val Val Trp
            340                 345                 350

Glu Thr Leu Arg Thr Ala Val Leu Gln Glu Phe Gly Ser Gly Thr Glu
        355                 360                 365

Glu Asp Ile Ser Asn Ile Ser Phe Glu Thr Leu Lys Lys Cys Glu Tyr
        370                 375                 380

Leu Lys Trp Val Leu Asn Glu Ala Leu Arg Leu Tyr Pro Ser Val Pro
385                 390                 395                 400

Asn Asn Phe Arg Val Ala Thr Lys Asn Thr Thr Leu Pro Lys Gly Gly
                405                 410                 415

Gly Lys Asp Glu Ser Ala Pro Ile Tyr Val Gly Lys Gly Thr Thr Val
            420                 425                 430

Ala Tyr Ser Ile Ile Ala Thr His Gln Met Glu Ala Tyr Tyr Gly Arg
        435                 440                 445

Asp Ala Lys Val Phe Lys Pro Glu Arg Trp Ala Thr Gln Asn Lys Leu
    450                 455                 460

Gly Trp Ala Tyr Leu Pro Phe Asn Gly Gly Pro Arg Ile Cys Leu Gly
465                 470                 475                 480

Gln Gln Phe Ala Leu Thr Glu Ala Ser Tyr Val Val Arg Leu Cys
                485                 490                 495

Gln Met Phe Ser Gln Ile Ser Thr Thr Asp Thr Val Tyr Pro Pro Lys
            500                 505                 510

Lys Asn Ile Gln Leu Thr Met Cys Leu Gln Asp Gly Ala His Ile Ser
        515                 520                 525

Leu Ser
    530

<210> SEQ ID NO 56
<211> LENGTH: 541
<212> TYPE: PRT
<213> ORGANISM: Lodderomyces elongisporus

<400> SEQUENCE: 56

Met Leu Leu Asp Glu Phe Ile Thr Tyr Leu Asn His Trp Tyr Val Ile
1               5                   10                  15

Ile Pro Leu Ala Phe Thr Thr Tyr His Val Phe His Tyr Ile Tyr Leu
            20                  25                  30

Asn Gln Leu Ala Lys Lys Phe Gly Ala Lys Pro Ile Thr Asn Val Leu
        35                  40                  45

Ser Asp Gly Trp Phe Gly Phe Lys Asn Gly Thr Gln Ala Ile Ala Leu
    50                  55                  60

Lys Asn Lys Gly Gln Ala Val Glu Trp Ala Gln Glu Lys Tyr Tyr Glu
65                  70                  75                  80

Thr Lys His Pro Glu Ile Pro Thr Phe Lys Glu Arg Ile Phe Gly Leu
                85                  90                  95
```

-continued

```
Tyr Leu Val Phe Thr Lys Asp Pro Glu Asn Ile Lys Ala Met Leu Ala
            100                 105                 110

Thr Gln Phe Ser Asp Phe Ser Leu Gly His Arg Leu Ala Tyr Phe Asp
        115                 120                 125

Pro Leu Leu Gly Lys Gly Ile Phe Thr Leu Asp His Glu Gly Trp Lys
        130                 135                 140

Asp Ser Arg Ala Met Leu Arg Pro Gln Phe Ala Arg Glu Gln Ile Ala
145                 150                 155                 160

His Val Lys Ser Leu Glu Pro His Ile Gln Tyr Leu Phe Lys His Ile
                165                 170                 175

Asp Lys Asn Gln Asn Ile Gln Ser Lys Asn Lys Ile Glu Asn Ala Asp
            180                 185                 190

Tyr Glu Thr Ser Ile Ser Ala Ser Tyr Phe Asp Ile Gln Glu Leu Phe
        195                 200                 205

Phe Arg Phe Thr Val Asp Ser Ala Thr Glu Phe Leu Phe Gly Gly Ser
        210                 215                 220

Val Ser Ser Leu Gln Asp Glu Thr Ile Gly Cys Asp Thr Arg Asp Ile
225                 230                 235                 240

Asp Phe Ala Gly Arg Arg Gln Phe Ala Asp Cys Phe Asn Lys Ala Gln
                245                 250                 255

Asn Tyr Leu Ala Thr Arg Asn Leu Leu Gln Lys Leu Tyr Trp Leu Val
            260                 265                 270

Asn Pro Lys Glu Phe Arg Glu Cys Asn Lys Val Val His Glu Phe Thr
        275                 280                 285

Asn Tyr Tyr Val Asn Lys Val Leu Ser Tyr Ser Pro Glu Glu Leu Glu
        290                 295                 300

Lys Ile Ser Asp Gly Tyr Val Phe Leu Tyr Glu Leu Ala Lys Gln Thr
305                 310                 315                 320

Arg Asp Pro Asn Val Leu Arg Asp Gln Ser Leu Asn Ile Leu Leu Ala
                325                 330                 335

Gly Arg Asp Thr Thr Ala Gly Leu Leu Ser Phe Val Ile Phe Glu Met
            340                 345                 350

Ala Lys Asn Pro Gln Met Trp Thr Lys Leu Arg Asn Glu Ile Leu Glu
        355                 360                 365

Arg Phe Gly Thr Thr Asn Leu Glu Asp Ile Thr Phe Glu Asn Leu Lys
        370                 375                 380

Lys Cys Glu Tyr Leu Lys Ala Val Leu Asn Glu Thr Leu Arg Leu Tyr
385                 390                 395                 400

Pro Ser Val Pro Arg Asn Ala Arg Val Ala Thr Arg Asn Thr Thr Leu
                405                 410                 415

Pro Arg Gly Gly Gly Pro Asp Gly Leu Ser Pro Ile Phe Ile Ala Lys
            420                 425                 430

Gly Ser Thr Val Gly Tyr Asn Ile Ser Ala Cys Gln Arg Asp Glu Thr
        435                 440                 445

His Tyr Gly Lys Asp Val Asp Glu Phe Arg Pro Glu Arg Trp Phe Glu
        450                 455                 460

Glu Ser Thr Arg Lys Leu Gly Trp Ala Tyr Leu Pro Phe Asn Gly Gly
465                 470                 475                 480

Pro Arg Ile Cys Leu Gly Gln Gln Phe Ala Leu Thr Glu Ala Ser Tyr
                485                 490                 495

Val Ile Thr Arg Ile Ala Gln Thr Tyr Ser Lys Leu Glu Leu Lys Pro
            500                 505                 510

Gly Tyr Gly Tyr Pro Pro Lys Arg Met Thr His Leu Thr Met Cys Leu
```

```
                515                 520                 525
Phe Asp Gly Cys Trp Val Lys Met Glu Arg Ala Gln Val
    530                 535                 540

<210> SEQ ID NO 57
<211> LENGTH: 540
<212> TYPE: PRT
<213> ORGANISM: Candida tropicalis

<400> SEQUENCE: 57

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
                20                  25                  30

Ile Pro Leu Val Leu Leu Ser Leu Asn Phe Ile Ser Leu Leu His Thr
            35                  40                  45

Arg Tyr Leu Glu Arg Arg Phe His Ala Lys Pro Leu Gly Asn Phe Val
        50                  55                  60

Arg Asp Pro Thr Phe Gly Ile Ala Thr Pro Leu Leu Ile Tyr Leu
65                  70                  75                  80

Lys Ser Lys Gly Thr Val Met Lys Phe Ala Trp Gly Leu Trp Asn Asn
                85                  90                  95

Lys Tyr Ile Val Arg Asp Pro Lys Tyr Lys Thr Thr Gly Leu Arg Ile
            100                 105                 110

Val Gly Leu Pro Leu Ile Glu Thr Met Asp Pro Glu Asn Ile Lys Ala
        115                 120                 125

Val Leu Ala Thr Gln Phe Asn Asp Phe Ser Leu Gly Thr Arg His Asp
130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Glu Ser Ile Gly Leu Thr Pro Thr Thr
225                 230                 235                 240

Lys Asp Phe Asp Gly Arg Arg Asp Phe Ala Asp Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ser Glu Phe Arg Lys Ser Ile Ala Val His Lys Phe
        275                 280                 285

Ala Asp His Tyr Val Gln Lys Ala Leu Glu Leu Thr Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Tyr Glu Leu
            340                 345                 350
```

```
Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
370                 375                 380

Ser Leu Lys Ser Cys Glu Tyr Leu Lys Ala Val Ile Asn Glu Thr Leu
385                 390                 395                 400

Arg Leu Tyr Pro Ser Val Pro His Asn Phe Arg Val Ala Thr Arg Asn
                405                 410                 415

Thr Thr Leu Pro Arg Gly Gly Glu Asp Gly Tyr Ser Pro Ile Val
                420                 425                 430

Val Lys Lys Gly Gln Val Val Met Tyr Thr Val Ile Ala Thr His Arg
            435                 440                 445

Asp Pro Ser Ile Tyr Gly Ala Asp Ala Asp Val Phe Arg Pro Glu Arg
        450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Ala His Leu Ser
            500                 505                 510

Met Asp Pro Asp Thr Glu Tyr Pro Pro Lys Leu Gln Asn Thr Leu Thr
        515                 520                 525

Leu Ser Leu Phe Asp Gly Ala Asp Val Arg Met Tyr
            530                 535                 540

<210> SEQ ID NO 58
<211> LENGTH: 538
<212> TYPE: PRT
<213> ORGANISM: Candida maltosa

<400> SEQUENCE: 58

Met Pro Val Ser Phe Val His Asn Val Leu Glu Val Val Thr Pro Tyr
1               5                   10                  15

Val Glu Tyr Tyr Gln Glu Asn Leu Thr Lys Trp Tyr Ile Leu Ile Pro
            20                  25                  30

Thr Ile Leu Leu Thr Leu Asn Phe Leu Ser Ile Leu His Thr Lys Tyr
        35                  40                  45

Leu Glu Tyr Lys Phe Asn Ala Lys Pro Leu Thr Asn Phe Ala Gln Asp
    50                  55                  60

Tyr Ser Phe Gly Val Ile Thr Pro Leu Met Leu Met Tyr Phe Lys Trp
65                  70                  75                  80

His Gly Thr Val Met Glu Phe Ala Cys Asn Val Trp Asn Asn Lys Phe
                85                  90                  95

Leu Val Leu Asn Gly Asn Val Arg Thr Val Gly Leu Arg Ile Met Gly
            100                 105                 110

Leu Asn Ile Ile Glu Thr Thr Asp Pro Glu Asn Val Lys Ala Ile Leu
        115                 120                 125

Ala Thr Gln Phe Asn Asp Phe Ser Leu Gly Thr Arg His Asp Phe Leu
    130                 135                 140

Tyr Ser Leu Leu Gly Asp Gly Ile Phe Thr Leu Asp Gly Ala Gly Trp
145                 150                 155                 160

Lys His Ser Arg Ala Met Leu Arg Pro Gln Phe Ala Arg Glu Gln Val
                165                 170                 175

Ala His Val Lys Leu Leu Glu Pro His Val Gln Val Leu Phe Lys His
            180                 185                 190
```

```
Val Arg Lys Ser Gln Gly Lys Thr Phe Asp Ile Gln Glu Leu Phe Phe
            195                 200                 205

Arg Leu Thr Val Asp Ser Ser Thr Glu Phe Leu Phe Gly Gly Ser Val
    210                 215                 220

Glu Ser Leu Arg Asp Ala Ser Ile Gly Met Thr Pro Ser Thr Lys Asn
225                 230                 235                 240

Ile Ala Gly Arg Glu Glu Phe Ala Asp Ala Phe Asn Tyr Ser Gln Thr
                245                 250                 255

Tyr Asn Ala Tyr Arg Phe Leu Leu Gln Gln Phe Tyr Trp Ile Leu Asn
            260                 265                 270

Gly Ser Lys Phe Asn Lys Ser Ile Lys Thr Val His Lys Phe Ala Asp
        275                 280                 285

Phe Tyr Val Gln Lys Ala Leu Ser Leu Thr Glu Ala Asp Leu Glu Lys
    290                 295                 300

Gln Glu Gly Tyr Val Phe Leu Tyr Glu Leu Ala Lys Gln Thr Arg Asp
305                 310                 315                 320

Pro Lys Val Leu Arg Asp Gln Leu Leu Asn Ile Leu Val Ala Gly Arg
                325                 330                 335

Asp Thr Thr Ala Gly Leu Leu Ser Phe Leu Phe Phe Glu Leu Ser Arg
            340                 345                 350

Asn Pro Thr Val Phe Glu Lys Leu Lys Glu Glu Ile His Asn Arg Phe
        355                 360                 365

Gly Ala Lys Glu Asp Ala Arg Val Glu Glu Ile Thr Phe Glu Ser Leu
    370                 375                 380

Lys Leu Cys Glu Tyr Leu Lys Ala Cys Val Asn Glu Ala Leu Arg Val
385                 390                 395                 400

Tyr Pro Ser Val Pro His Asn Phe Arg Val Ala Thr Arg Asn Thr Thr
                405                 410                 415

Leu Pro Arg Gly Gly Lys Asp Gly Met Ser Pro Ile Ala Ile Lys
            420                 425                 430

Lys Gly Gln Asn Val Met Tyr Thr Ile Leu Ala Thr His Arg Asp Pro
        435                 440                 445

Asn Ile Tyr Gly Glu Asp Ala Asn Val Phe Arg Pro Glu Arg Trp Phe
    450                 455                 460

Glu Pro Glu Thr Arg Lys Leu Gly Trp Ala Tyr Val Pro Phe Asn Gly
465                 470                 475                 480

Gly Pro Arg Ile Cys Leu Gly Gln Gln Phe Ala Leu Thr Glu Ala Ser
                485                 490                 495

Tyr Val Thr Val Arg Leu Leu Gln Glu Phe His Thr Leu Thr Gln Asp
            500                 505                 510

Ala Asp Thr Arg Tyr Pro Pro Arg Leu Gln Asn Ser Leu Thr Leu Ser
        515                 520                 525

Leu Cys Asp Gly Ala Asn Ile Gln Met Tyr
    530                 535

<210> SEQ ID NO 59
<211> LENGTH: 523
<212> TYPE: PRT
<213> ORGANISM: Candida tenuis

<400> SEQUENCE: 59

Met Leu Ser Asp Asn Phe Lys Ser Arg Val Ser Gln Leu Thr Trp Glu
1               5                   10                  15

Gly Val Leu Leu Tyr Ala Ile Gly Val Leu Thr Leu Tyr Phe Thr Tyr
```

```
                20                  25                  30
Arg Phe Ile Arg Lys Thr Thr Leu Lys Tyr Lys Phe Gly Val Thr Glu
             35                  40                  45

Ala Arg Leu Leu Pro Lys Ser Tyr Pro Phe Ser Arg Asn Pro Tyr
 50                  55                  60

Thr Phe Leu Cys Leu Lys Arg Asp Gly Leu Val Leu Ala Glu Val Leu
 65                  70                  75                  80

Lys Phe Met Arg Leu Tyr Gly His Thr Trp Lys Ala Asn Leu Gly His
                 85                  90                  95

Gln Ile Val Val Thr Ala Asp Pro Glu Asn Ile Lys Ser Ile Leu Ala
                100                 105                 110

Thr Gln Phe Asn Asp Phe Val Met Gly Leu Arg Leu Ser Gln Phe Arg
                115                 120                 125

Pro Leu Leu Gly Glu Gly Val Phe Thr Leu Asp Gly His Gly Trp Lys
                130                 135                 140

Gln Ser Arg Ala Met Leu Arg Pro Asn Phe Ser Arg Glu Lys Val Ala
145                 150                 155                 160

His Thr Gln Ser Leu Glu Phe His Val Gln Asn Leu Ser Lys His Ile
                165                 170                 175

Arg Lys His Asn Gly Gln Pro Phe Asp Ile Gln Glu Tyr Phe Phe Arg
                180                 185                 190

Tyr Thr Val Asp Thr Ser Thr Glu Phe Leu Phe Gly His Ser Leu Tyr
                195                 200                 205

Gly Leu Met Asp Glu Thr Ile Gly Glu Thr Pro Pro Glu Gly Ser Phe
                210                 215                 220

Arg Gly Ser Gly Asn Phe Tyr Glu Ser Phe Asn Ile Ser Gln Glu Ile
225                 230                 235                 240

Cys Ala Ser Arg Ala Trp Ala Gln Asn Leu Tyr Tyr Phe Val Asn Pro
                245                 250                 255

Arg Asn Phe Lys Ala Asn Asn Lys Ile Val His Glu Phe Ala Asp Phe
                260                 265                 270

Tyr Ile Ser Lys Ala Leu Gln Tyr Asp Asp Asn Val Leu Gln Asp Lys
                275                 280                 285

Ser Lys Glu Gly Tyr Ile Phe Leu Tyr Glu Leu Val Lys Glu Thr Arg
                290                 295                 300

Asn Pro Thr Val Leu Arg Asp Gln Leu Leu Asn Ile Met Ile Ala Gly
305                 310                 315                 320

Arg Asp Thr Thr Ala Gly Leu Leu Ser Met Phe Phe Phe Glu Met Ser
                325                 330                 335

Arg Asn Pro Asp Ile Phe Ala Lys Leu Lys Glu Glu Ile Tyr Arg Glu
                340                 345                 350

Phe Gly Thr Tyr Asp Met Cys Asp Pro Glu Asp Ile Thr Phe Glu Ser
                355                 360                 365

Leu Lys Lys Ser Glu Tyr Leu Lys Trp Cys Ile Asn Glu Thr Leu Arg
                370                 375                 380

Met Tyr Pro Asn Val Pro Leu Asn Phe Arg Cys Ala Lys Arg Asp Thr
385                 390                 395                 400

Thr Leu Pro Arg Gly Gly Gly Lys Asp Leu Gln Gln Pro Ile Leu Ile
                405                 410                 415

Glu Lys Gly Thr Val Val Ala Tyr Ile Ile Ser Ala Thr His Arg Asp
                420                 425                 430

Pro Gln Tyr Tyr Gly Lys Asp Ser Glu Val Phe Arg Pro Glu Arg Trp
                435                 440                 445
```

```
Gly Asp Lys Asp Leu Lys Pro Gly Trp Ala Phe Leu Pro Phe Asn Gly
        450                 455                 460

Gly Pro Arg Ile Cys Leu Gly Gln Gln Phe Ala Leu Thr Glu Ala Ser
465                 470                 475                 480

Tyr Thr Ile Val Arg Leu Leu Gln Met Phe Pro Asn Leu Val Asn Glu
                    485                 490                 495

Asp Lys Ser Lys Gln Tyr Pro Pro Arg Ile His Ala Gln Leu Thr Leu
            500                 505                 510

Ser Leu Thr Asp Gly Ala His Val Arg Met Phe
        515                 520

<210> SEQ ID NO 60
<211> LENGTH: 524
<212> TYPE: PRT
<213> ORGANISM: Candida tenuis

<400> SEQUENCE: 60

Met Pro Thr Thr Glu Glu Val Gln Ala Lys Ile Ser Ala Phe Ser Thr
1               5                   10                  15

Ser Trp Val Gly Leu Leu Ile Ala Val Leu Val Tyr Lys Ile Ala
            20                  25                  30

Tyr Thr Val Gln Asn Met Ile Leu Ala Lys Lys Met Gly Cys Lys Ala
            35                  40                  45

Pro Thr Thr Phe Leu Gln Asp Tyr Ala Leu Gly Phe Arg Asn Val Gly
        50                  55                  60

Glu Met Leu Lys Asn Lys Lys Ser Gly Phe Leu Asn Asn Phe Thr Leu
65                  70                  75                  80

Gln Arg Phe Asn Gln Phe Gly Asp Thr Ile Ser Leu Arg Val Ala Gly
            85                  90                  95

Asn Val Met Phe Ile Thr Arg Glu Pro Glu Asn Ile Lys Ala Ile Leu
            100                 105                 110

Gly Thr Gln Phe Asn Asp Phe Asp Leu Gly Ile Arg Tyr Lys Gln Phe
            115                 120                 125

Leu Pro Leu Leu Gly Asp Gly Ile Phe Thr Leu Asp His Lys Gly Trp
        130                 135                 140

Lys Asn Ser Arg Ala Met Leu Arg Pro Gln Phe Ala Arg Glu Gln Val
145                 150                 155                 160

Ala His Val Lys Met Leu Glu Pro His Val Gln Asn Leu Phe Ala His
                165                 170                 175

Ile Arg Lys Tyr Gln Gly Gln Val Phe Asp Ile Gln Thr Tyr Phe Phe
            180                 185                 190

Lys Leu Thr Met Asp Ser Ala Thr Glu Phe Leu Phe Gly Glu Ser Val
            195                 200                 205

Glu Ser Leu Arg Asp Glu Ser Ile Asn Met Val Pro Thr Gly Glu Cys
        210                 215                 220

Asp Val Gly Leu Lys Thr Arg Phe Ala Asp Ser Phe Asn Asp Ala Gln
225                 230                 235                 240

Thr Val Leu Ala Thr Arg Ala Met Leu Gln Gln Leu Tyr Phe Leu Val
            245                 250                 255

Asn Thr Thr Arg Phe Lys Glu Ala Cys Lys Asp Val His Gly Leu Thr
            260                 265                 270

Asp Phe Phe Val His Gln Ala Leu Asn Thr Ser Pro Asp Glu Leu Glu
        275                 280                 285

Lys Lys Ser Lys Gly Gly Tyr Ile Phe Leu Phe Glu Leu Val Lys Gln
```

```
            290                 295                 300
Thr Arg Asp Pro Lys Ile Leu Arg Asp Gln Ala Leu Asn Ile Leu Leu
305                 310                 315                 320

Ala Gly Arg Asp Thr Thr Ala Gly Leu Leu Ser Phe Thr Phe Phe Glu
                325                 330                 335

Leu Ala Arg Asn Pro Gln Met Phe Asp Lys Leu Lys Glu Glu Ile His
                340                 345                 350

Ala Thr Phe Gly Ala Gly Ala Glu Ser Arg Ile Asp Asp Ile Thr Phe
                355                 360                 365

Glu Ser Leu Lys Lys Cys Glu Tyr Leu Lys Ala Val Ile Asn Glu Ala
                370                 375                 380

Leu Arg Met Tyr Pro Ser Val Pro Gln Asn Phe Arg Ile Thr Asn Lys
385                 390                 395                 400

Asn Thr Thr Leu Pro Arg Gly Gly Gly Pro Asp Gly Leu Ser Pro Ile
                405                 410                 415

Phe Ile Pro Arg His Ser Thr Val Ala Tyr Ser Val Tyr Ala Thr His
                420                 425                 430

Arg His Glu Arg Phe Tyr Gly Lys Asp Ala Glu Val Phe Arg Pro Glu
                435                 440                 445

Arg Trp Phe Asp Glu Gly Thr Lys Lys Leu Gly Trp Ala Phe Leu Pro
                450                 455                 460

Phe Asn Gly Gly Pro Arg Ile Cys Leu Gly Gln Gln Phe Ala Leu Thr
465                 470                 475                 480

Glu Ala Ser Tyr Val Val Ala Arg Ile Val Gln Glu Phe Ser Ser Leu
                485                 490                 495

Lys Ser Phe Asp Glu Gln Tyr Pro Pro Lys Leu Asn Ser Gln Leu Thr
                500                 505                 510

Val Asn Leu Glu Asp Gly Cys His Ile Thr Leu Thr
                515                 520

<210> SEQ ID NO 61
<211> LENGTH: 499
<212> TYPE: PRT
<213> ORGANISM: Candida tropicalis

<400> SEQUENCE: 61

Met Ala Ile Ser Ser Leu Leu Ser Trp Asp Val Ile Cys Val Val Phe
1               5                   10                  15

Ile Cys Val Cys Val Tyr Phe Gly Tyr Glu Tyr Cys Tyr Thr Lys Tyr
                20                  25                  30

Leu Met His Lys His Gly Ala Arg Glu Ile Glu Asn Val Ile Asn Asp
                35                  40                  45

Gly Phe Phe Gly Phe Arg Leu Pro Leu Leu Met Arg Ala Ser Asn
50                  55                  60

Glu Gly Arg Leu Ile Glu Phe Ser Val Lys Arg Phe Glu Ser Ala Pro
65                  70                  75                  80

His Pro Gln Asn Lys Thr Leu Val Asn Arg Ala Leu Ser Val Pro Val
                85                  90                  95

Ile Leu Thr Lys Asp Pro Val Asn Ile Lys Ala Met Leu Ser Thr Gln
                100                 105                 110

Phe Asp Asp Phe Ser Leu Gly Leu Arg Leu His Gln Phe Ala Pro Leu
                115                 120                 125

Leu Gly Lys Gly Ile Phe Thr Leu Asp Gly Pro Glu Trp Lys Gln Ser
                130                 135                 140
```

```
Arg Ser Met Leu Arg Pro Gln Phe Ala Lys Asp Arg Val Ser His Ile
145                 150                 155                 160

Ser Asp Leu Glu Pro His Phe Val Leu Arg Lys His Ile Asp Gly
            165                 170                 175

His Asn Gly Asp Tyr Phe Asp Ile Gln Glu Leu Tyr Phe Arg Phe Ser
        180                 185                 190

Met Asp Val Ala Thr Gly Phe Leu Phe Gly Glu Ser Val Gly Ser Leu
        195                 200                 205

Lys Asp Glu Asp Ala Arg Phe Ser Glu Ala Phe Asn Glu Ser Gln Lys
    210                 215                 220

Tyr Leu Ala Thr Arg Ala Thr Leu His Glu Leu Tyr Phe Leu Cys Asp
225                 230                 235                 240

Gly Phe Arg Phe Arg Gln Tyr Asn Lys Val Val Arg Lys Phe Cys Ser
                245                 250                 255

Gln Cys Val His Lys Ala Leu Asp Val Ala Pro Glu Asp Thr Ser Glu
            260                 265                 270

Tyr Val Phe Leu Arg Glu Leu Val Lys His Thr Arg Asp Pro Val Val
        275                 280                 285

Leu Gln Asp Gln Ala Leu Asn Val Leu Ala Gly Arg Asp Thr Thr
290                 295                 300

Ala Ser Leu Leu Ser Phe Ala Thr Phe Glu Leu Ala Arg Asn Asp His
305                 310                 315                 320

Met Trp Arg Lys Leu Arg Glu Glu Val Ile Ser Thr Met Gly Pro Ser
                325                 330                 335

Ser Asp Glu Ile Thr Val Ala Gly Leu Lys Ser Cys Arg Tyr Leu Lys
            340                 345                 350

Ala Ile Leu Asn Glu Thr Leu Arg Leu Tyr Pro Ser Val Pro Arg Asn
        355                 360                 365

Ala Arg Phe Ala Thr Arg Asn Thr Thr Leu Pro Arg Gly Gly Pro
    370                 375                 380

Asp Gly Ser Phe Pro Ile Leu Ile Arg Lys Gly Gln Pro Val Gly Tyr
385                 390                 395                 400

Phe Ile Cys Ala Thr His Leu Asn Glu Lys Val Tyr Gly Asn Asp Ser
                405                 410                 415

His Val Phe Arg Pro Glu Arg Trp Ala Ala Leu Glu Gly Lys Ser Leu
            420                 425                 430

Gly Trp Ser Tyr Leu Pro Phe Asn Gly Gly Pro Arg Ser Cys Leu Gly
        435                 440                 445

Gln Gln Phe Ala Ile Leu Glu Ala Ser Tyr Val Leu Ala Arg Leu Thr
    450                 455                 460

Gln Cys Tyr Thr Thr Ile Gln Leu Arg Thr Thr Glu Tyr Pro Pro Lys
465                 470                 475                 480

Lys Leu Val His Leu Thr Met Ser Leu Leu Asn Gly Val Tyr Ile Arg
                485                 490                 495

Thr Arg Thr

<210> SEQ ID NO 62
<211> LENGTH: 523
<212> TYPE: PRT
<213> ORGANISM: Yarrowia lipolytica

<400> SEQUENCE: 62

Met Ser Asn Ala Leu Asn Leu Ser Leu Ala Leu Gly Val Phe Leu Leu
1               5                   10                  15
```

-continued

```
Ala Tyr Tyr Gly Phe Ser Val Ile Gln Tyr Arg Ile Lys Thr Arg Lys
                20                  25                  30

Leu Glu Lys Lys Trp Lys Cys Gly Lys Pro Lys Asp Ile Ser Arg Phe
         35                  40                  45

Pro Phe Ser Ala Ser Phe Phe Ile Pro Phe Leu Val Glu Ser Lys Lys
 50                  55                  60

Asn Arg Leu Leu Glu Phe Val Gln Trp Met Phe Glu Ser Gln Val Tyr
 65                  70                  75                  80

Pro Gly Tyr Thr Cys Lys Thr Thr Val Phe Gly Val Asp Met Tyr His
                 85                  90                  95

Thr Val Asp Pro Glu Asn Leu Lys Ala Val Leu Ala Thr Gln Phe Lys
             100                 105                 110

Asp Phe Cys Leu Gly Glu Arg His Ala Gln Phe Leu Pro Val Leu Gly
         115                 120                 125

Asn Gly Ile Phe Thr Leu Asp Gly Gln Gly Trp Gln His Ser Arg Ala
 130                 135                 140

Met Leu Arg Pro Gln Phe Ala Arg Asp Gln Val Ser Asp Val Glu Met
145                 150                 155                 160

Ile Glu Glu His Ile Gln Tyr Met Thr Ser Arg Ile Pro Lys Asp Gly
                 165                 170                 175

Ser Ala Phe Asp Ala Gln Glu Leu Phe Phe Asn Leu Thr Leu Asp Thr
             180                 185                 190

Ala Thr Glu Phe Leu Phe Gly Gln Ser Val Gly Ser Gln Thr Val Glu
         195                 200                 205

Thr Asn Pro Thr Ala Val Pro Thr Asp Met Pro Val His Leu Arg Lys
 210                 215                 220

Ser Phe Gln Glu Asp Phe Asn Thr Ala Gln Glu His Leu Gly Gln Arg
225                 230                 235                 240

Ala Arg Leu Gln Met Phe Tyr Trp Ala Trp Arg Pro Arg Glu Leu Tyr
                 245                 250                 255

Ser Ser Gly Glu Arg Val His Ala Phe Val Asp His Tyr Val Lys Lys
             260                 265                 270

Ala Leu Glu Glu Ser Glu Lys His Val Asp Asp Gly Lys Tyr Val Phe
         275                 280                 285

Leu Arg Glu Leu Ala Lys Glu Thr Lys Asp Pro Ile Val Leu Arg Asp
 290                 295                 300

Gln Ala Leu Asn Ile Leu Leu Ala Gly Arg Asp Thr Thr Ala Ser Leu
305                 310                 315                 320

Leu Ser Trp Cys Leu Tyr Leu Met Ala Arg Arg Pro Glu Val Tyr Ala
                 325                 330                 335

Lys Leu Arg Glu Glu Val Ile Glu Asn Leu Gly Asp Gly Glu Asp Leu
             340                 345                 350

Ser Thr Ile Thr Phe Glu Ser Leu Lys Arg Cys Asp Tyr Leu Arg Tyr
         355                 360                 365

Val Leu Asn Glu Val Leu Arg Leu Tyr Pro Ser Val Pro Ala Asn Met
 370                 375                 380

Arg Tyr Ala Thr Arg Asp Thr Thr Leu Pro Arg Gly Gly Gly Pro Asp
385                 390                 395                 400

Gly Met Gln Pro Ile Val Val Arg Lys Gly Asn Leu Val Ser Tyr His
                 405                 410                 415

Val Phe Thr Thr His Arg Leu Lys Glu Phe Trp Gly Glu Asp Ala Glu
             420                 425                 430

Glu Phe Arg Pro Glu Arg Trp Tyr Glu Asp Gly Ala Ser Gln Ala Lys
```

```
                       435                 440                 445
Gly Trp Glu Tyr Leu Pro Phe Asn Gly Gly Pro Arg Ile Cys Leu Gly
    450                 455                 460

Gln Gln Tyr Ala Leu Thr Glu Ala Gly Tyr Ala Leu Ala Arg Ile Ala
465                 470                 475                 480

Gln Leu Tyr Asp Thr Ile Glu Asn Ala Asp Lys Pro Glu Pro Pro
                    485                 490                 495

Val Lys Phe His Ala Leu Thr Met Cys His His Thr Gly Val Leu Val
                500                 505                 510

Lys Leu Tyr Asn Ser Lys Thr Thr Lys Ala Gln
            515                 520

<210> SEQ ID NO 63
<211> LENGTH: 523
<212> TYPE: PRT
<213> ORGANISM: Yarrowia lipolytica

<400> SEQUENCE: 63

Met Ile Ile Leu Tyr Val Leu Ala Val Ala Val Ser Phe Leu Ile Phe
1               5                   10                  15

Lys Arg Val Thr Tyr Thr Met Arg Ser Arg Glu Leu Ala Lys Lys Trp
            20                  25                  30

His Cys Glu Glu Pro His Asn Leu Asn Glu Phe Pro Leu Asn Leu Pro
        35                  40                  45

Leu Phe Phe Leu Ile Ile Asn Ala Ser Arg Arg His Glu Leu Leu Asp
    50                  55                  60

Thr Leu Leu Gly Leu Phe Arg Ser Phe Ala Pro Thr Lys Thr Val Lys
65                  70                  75                  80

Gln Val Leu Leu Gly Ser Phe Thr Ile Ile Pro Thr Asn Asp Pro Glu
                85                  90                  95

Asn Ile Lys Ala Val Leu Ala Thr Gln Phe Lys Asp Phe Cys Leu Gly
            100                 105                 110

Gln Arg His Gly Gln Leu Ala Pro Val Leu Gly Asp Gly Ile Phe Thr
        115                 120                 125

Leu Asp Gly Gln Gly Trp Gln His Ser Arg Ala Met Leu Arg Pro Gln
    130                 135                 140

Phe Ala Arg Asp Gln Val Ser Asp Val Glu Met Ile Glu Arg His Val
145                 150                 155                 160

Gln Met Met Leu Leu Arg Ile Pro Asn Asn Lys Lys Phe Asp Ile Gln
                165                 170                 175

Glu Leu Phe Phe Asn Leu Thr Leu Asp Thr Ala Thr Glu Phe Leu Phe
            180                 185                 190

Gly Gln Thr Val Gly Ser Gln Thr Val Glu Met Pro Asn Glu Asp Lys
        195                 200                 205

Ser Thr Val Ser Asp Met Pro Lys Asp Met Arg Lys Ser Phe Gln Glu
    210                 215                 220

Asp Phe Asn Val Ala Gln His His Gly Gly Ile Arg Thr Arg Phe Gln
225                 230                 235                 240

Met Phe Tyr Trp Leu Trp Arg Pro Thr Glu Leu Phe Ser Ser Ser Lys
                245                 250                 255

Arg Val His Ala Phe Val Asp His Tyr Val Glu Lys Ala Leu Ala Asn
            260                 265                 270

Ser Asp Glu Glu Lys Ser Asp Asp Lys Tyr Ile Phe Leu Arg Glu Leu
        275                 280                 285
```

Ala Arg Glu Val Lys Asp Pro Arg Val Leu Arg Asp Gln Ala Leu Asn
    290             295                 300

Ile Leu Leu Ala Gly Arg Asp Thr Thr Ala Gly Val Leu Ser Trp Ile
305             310                 315                 320

Val Tyr Glu Leu Ala Arg His Pro Gly Val Trp Lys Lys Leu Arg Ala
                325             330                 335

Glu Ile His Gln Asp Phe Gly Asp Gly Ser Asp Leu Ser Gln Ile Thr
            340                 345                 350

Phe Glu Gly Leu Lys Arg Cys Glu Tyr Leu Arg Phe Val Ile Asn Glu
                355                 360                 365

Thr Leu Arg Leu Tyr Pro Ser Val Pro Leu Asn Val Arg Tyr Ala Ser
370                 375                 380

Arg Asp Thr Thr Leu Pro Arg Gly Gly Pro Asp Glu Ser Lys Pro
385             390                 395                 400

Ile Leu Val Arg Lys Gly Asp Thr Ile Val Tyr Asn Val Phe Ser Met
                405                 410                 415

His Arg Thr Glu Glu Phe Trp Gly Lys Asp Cys Asp Glu Phe Arg Pro
            420                 425                 430

Glu Arg Trp Ala Glu Lys Gly Ser Arg Gly Trp Glu Tyr Leu Pro Phe
                435                 440                 445

Asn Gly Gly Pro Arg Ile Cys Leu Gly Gln Gln Tyr Ala Leu Thr Glu
450                 455                 460

Thr Ser Tyr Val Ile Thr Arg Ile Cys Gln Leu Phe Thr Asn Ile Glu
465                 470                 475                 480

Asn Ala Asp Thr Ala Val Glu Pro Pro Gln Lys Leu His Ala Leu Thr
                485                 490                 495

Leu Cys His Leu Asn Gly Val Phe Val Lys Met Thr Arg Asp Glu Ala
                500                 505                 510

Ala Phe Ala Glu Thr Glu Lys Leu Ile Asn Ala
                515                 520

<210> SEQ ID NO 64
<211> LENGTH: 519
<212> TYPE: PRT
<213> ORGANISM: Yarrowia lipolytica

<400> SEQUENCE: 64

Met Leu Thr Asn Leu Thr Ile Val Leu Ile Thr Leu Leu Val Thr Tyr
1               5                   10                  15

Thr Val Leu Thr Arg Thr Ala Leu Arg Ile Gln Arg Ala Arg Lys Ala
                20                  25                  30

Lys Gln Met Gly Ala Thr Leu Pro Pro Arg Val Asn Asn Gly Ile Leu
            35                  40                  45

Gly Trp Tyr Gly Leu Trp Leu Val Ile Gln Asn Ala Arg Ser Met Lys
50                  55                  60

Leu Pro His Thr Leu Gly Lys Arg Phe Ala Asn Gly Pro Thr Trp Leu
65                  70                  75                  80

Thr Pro Val Ala Gly Asn Glu Pro Ile Asn Thr Ile Asp Pro Glu Asn
                85                  90                  95

Val Lys Ala Ile Leu Ala Thr Gln Phe Lys Asp Phe Cys Leu Gly Ile
            100                 105                 110

Arg His Arg Ala Leu Ser Pro Ser Ile Gly Asp Gly Ile Phe Thr Leu
        115                 120                 125

Asp Gly Glu Gly Trp Thr His Ser Arg Ala Leu Leu Arg Pro Gln Phe
130                 135                 140

Ser Arg Gln Gln Ile Ser Arg Val His Ser Leu Glu Arg Leu Met Gln
145                 150                 155                 160

Ile Leu Phe Lys Leu Ile Arg Lys Glu Asn Gly Glu Tyr Phe Asp Leu
            165                 170                 175

Gln Asn Leu Phe Phe Met Phe Thr Leu Asp Ser Ala Thr Glu Phe Leu
        180                 185                 190

Tyr Gly Ala Ser Val Asp Thr Leu Ala Asp Leu Leu Gly Glu Pro Val
                195                 200                 205

Glu Gly Asp His Gly Gly Val Gly Glu Glu Val Arg Lys Ala Tyr Gln
210                 215                 220

Gln Ser Ile Asn Asn Ala Gln Asp Ile Ser Ala Ile Arg Thr Arg Leu
225                 230                 235                 240

Gln Gly Leu Tyr Trp Ile Ala Gly Asn Ile Tyr Gln Arg Asn Leu Tyr
                245                 250                 255

Gln Lys Ser Asn Lys Gly Val Lys Asp Phe Ser Gln Phe Phe Val Asp
            260                 265                 270

Lys Ala Leu Asn Thr Ser Lys Glu Lys Leu Lys Glu Met Glu Asp Ser
        275                 280                 285

Asp Asn Tyr Val Phe Leu Tyr Glu Leu Val Lys Ser Thr Arg Asn Pro
                295                 300
290

Val Val Ile Arg Asp Gln Leu Ile Asn Ile Leu Val Ala Gly Arg Asp
305                 310                 315                 320

Thr Thr Ala Ser Leu Leu Ser Phe Thr Phe Tyr Thr Leu Gly Arg Arg
                325                 330                 335

Pro Asp Val Leu Lys Lys Leu Arg Ala Ala Ile Leu Glu Asp Phe Gly
            340                 345                 350

Thr Ser Pro Asp Glu Ile Thr Phe Glu Ser Leu Lys Arg Cys Asp Tyr
        355                 360                 365

Leu Arg Tyr Val Leu Asn Glu Val Leu Arg Leu Tyr Pro Ser Val Pro
                375                 380
370

Ile Asn Ala Arg Ser Ala Thr Arg Asp Thr Thr Leu Pro Arg Gly Gly
385                 390                 395                 400

Gly Pro Asp Gly Lys Gln Pro Val Phe Val Tyr Lys Gly Gln Met Val
                405                 410                 415

Ala Tyr Cys Val Tyr Trp Met His Arg Asp Lys Lys Tyr Trp Gly Glu
            420                 425                 430

Asp Ala Leu Glu Phe Asn Pro Asp Arg Trp Asp Pro Lys Val Gln Pro
        435                 440                 445

Gln Asn Lys Gly Trp Glu Tyr Leu Pro Phe Asn Gly Gly Pro Arg Ile
450                 455                 460

Cys Leu Gly Gln Gln Phe Ala Leu Thr Glu Ala Gly Tyr Val Val Thr
465                 470                 475                 480

Arg Met Leu Gln Glu Phe Asp Thr Val His Cys Lys Asn Gln Lys Glu
                485                 490                 495

Glu Glu His Pro Pro Tyr Ala Leu Asp Leu Thr Met Arg His Gly Glu
            500                 505                 510

Gly Val Trp Val Ser Met Lys
            515

<210> SEQ ID NO 65
<211> LENGTH: 512
<212> TYPE: PRT
<213> ORGANISM: Aspergillus niger

```
<400> SEQUENCE: 65

Met Leu Ala Ala Ala Ile Val Phe Leu Gly Ala Ile Tyr Leu Thr Phe
  1               5                  10                  15

Arg Ile Leu Ser Ser Leu His Gln Ala Tyr His His Arg Lys Lys Ala
             20                  25                  30

Lys Ala Leu Gly Cys Gln Pro Pro Asn Ser Val Asp Thr Gly Phe Leu
         35                  40                  45

Gly Ile Thr Gly Phe Tyr Arg Ile Ala Lys Ala Ala Arg Glu Lys Arg
 50                  55                  60

Trp Val Glu Tyr Ile Ala Glu His Tyr Gln Thr Ser Gly Pro Thr Phe
 65                  70                  75                  80

Arg Gln Gln Ala Leu Gly Gly Leu Met Val Thr Asn Thr Val Glu Pro
                 85                  90                  95

Glu Asn Ile Lys Ala Leu Leu Ala Thr Gln Phe Gln Asp Phe Gly Leu
            100                 105                 110

Gly Thr Arg His Arg Glu Phe Tyr Pro Leu Leu Gly Asn Gly Ile Phe
        115                 120                 125

Thr Leu Asp Gly Ala Gly Trp Ser His Ala Arg Gly Met Leu Arg Pro
130                 135                 140

Gln Phe Thr Arg Asp Gln Val Ala Asp Leu Asp Leu Met Asp Gly His
145                 150                 155                 160

Val Thr Lys Met Met Asp Leu Ile Pro Lys Asp Gly Ser Thr Phe Asp
                165                 170                 175

Ile Gln Arg Leu Phe Phe Leu Leu Thr Ile Asp Ser Ala Thr His Phe
            180                 185                 190

Leu Phe Gly Glu Ser Val Gly Ser Met Arg Thr Ser Ala Glu Ser Ser
        195                 200                 205

Leu Leu Glu Lys Ser Thr Val Gly Asn Ala Gln Gly Phe Ala Glu Ala
    210                 215                 220

Phe Asn Arg Ala Gln Glu Tyr Leu Ala Ala Arg Ser Arg Ala Met Ala
225                 230                 235                 240

Phe Tyr Trp Leu Val Asn Pro Lys Glu Phe Arg Glu Ala Asn Gln Leu
                245                 250                 255

Val His Glu Val Val Asp His Tyr Val Arg Leu Ala Leu Glu Ala Lys
            260                 265                 270

Arg His Pro Glu Lys Lys Glu Pro Gly Arg Tyr Ile Phe Ala Glu Ala
        275                 280                 285

Leu Ala Gly Asp Thr Asp Pro Arg Val Ile Arg Asp Asn Met Leu
290                 295                 300

Asn Ile Leu Leu Ala Gly Arg Asp Thr Thr Ala Ser Leu Leu Ser Ser
305                 310                 315                 320

Ala Phe Phe Tyr Leu Ala Arg His Pro Asn Val Trp Thr Arg Leu Arg
                325                 330                 335

Gln Thr Ile Val Asp Glu Phe Gly Asp Ala Gln His Pro Asn Gly Lys
            340                 345                 350

Ile Thr His Ala Arg Leu Lys Asp Thr Pro Tyr Leu Arg Tyr Phe Leu
        355                 360                 365

Asn Glu Val Leu Arg Leu Leu Pro Pro Val Pro Leu Asn Phe Arg Val
    370                 375                 380

Ala Ala Lys Asp Thr Ser Leu Pro Leu Gly Gly Gly Pro Asp Gly Lys
385                 390                 395                 400

Ala Pro Ile Tyr Val Arg Lys Gly Glu Leu Val Ser Tyr Ser Val Tyr
                405                 410                 415
```

```
Ala Met His Arg Arg Thr Asp Leu Tyr Gly Pro Asp Ala His Ala Phe
            420                 425                 430

Arg Pro Glu Arg Trp Glu Glu Asn Ser Lys Arg Gly Trp Glu Tyr Leu
        435                 440                 445

Pro Phe Asn Gly Gly Pro Arg Ile Cys Leu Gly Gln Gln Tyr Ala Leu
    450                 455                 460

Thr Glu Ala Ser Tyr Thr Met Val Lys Leu Leu Gln Arg Tyr Asn Arg
465                 470                 475                 480

Ile Glu Asn Ala Asp Pro Asp Met Met Glu Pro Ile Ile Asn Ser Ser
                485                 490                 495

Leu Thr Leu Ser His Asp Arg Gly Val His Ile Arg Leu Phe Ser Ala
            500                 505                 510

<210> SEQ ID NO 66
<211> LENGTH: 526
<212> TYPE: PRT
<213> ORGANISM: Yarrowia lipolytica

<400> SEQUENCE: 66

Met Phe Gln Leu Phe Ser Ile Leu Val Leu Ala Phe Thr Thr Ala Leu
1               5                   10                  15

Val Ala Gln Leu Ala Tyr Asn Gln Tyr Asp Tyr Gln Arg Lys Val Lys
            20                  25                  30

Lys Phe Gly Cys Gly Gln Leu Arg Val Ala Glu Asn Gly Leu Phe Gly
        35                  40                  45

Trp Lys Gly Leu Arg Glu Val Leu Arg Ile Asn Lys Tyr Lys Leu Gly
    50                  55                  60

Pro Ala Leu Lys Asp Arg Phe Glu Lys Tyr Gly Lys Thr His Val
65                  70                  75                  80

Phe His Val Gly Pro Ser Pro Leu Ile Thr Thr Met Asp Pro Glu Asn
                85                  90                  95

Ile Lys Ala Met Leu Ala Thr Gln Phe Lys Asp Phe Cys Leu Ile Ala
            100                 105                 110

Arg Tyr Lys Ala Leu Gly Pro Met Leu Gly Asp Gly Ile Phe Thr Leu
        115                 120                 125

Asp Gly His Gly Trp Thr His Ser Arg Ala Leu Leu Arg Pro Gln Phe
    130                 135                 140

Ala Arg Glu Gln Val Ser Arg Leu Asp Ser Ile Glu His His Phe Gln
145                 150                 155                 160

Ile Leu Lys Lys Cys Ile Ser Lys Glu Met Ser Asp Lys Arg Asp Thr
                165                 170                 175

Gln Arg Gly Phe Asp Ile Gln Asn Leu Phe Phe Leu Met Thr Leu Asp
            180                 185                 190

Thr Ala Thr Glu Phe Leu Phe Gly Ser Ser Val Asp Ser Leu Val Asp
        195                 200                 205

Phe Leu Asp Asp Pro Ser Ile Gln Thr Gly Asp His Gly Gly Ile Asp
    210                 215                 220

Glu Ala Ala Arg Lys Gly Phe Ser Asn Ala Phe Asn Arg Ala Gln Glu
225                 230                 235                 240

Leu Ser Ser Leu Arg Thr Arg Leu His Lys Leu Tyr Trp Val Ile Gly
                245                 250                 255

Thr Leu Ala Val Arg Glu Pro Tyr His Arg Tyr Asn Arg Glu Val Lys
            260                 265                 270

Thr Phe Val Asp His Tyr Ala Ala Lys Ala Ile Lys Ala Arg Asn Glu
```

```
                275                 280                 285
Lys Asn Thr Asp Leu Leu Asp Asn Asp Lys Tyr Ile Phe Met Tyr Glu
    290                 295                 300

Leu Val Lys Glu Thr Ser Asn Pro Ile Thr Leu Arg Asp Gln Met Leu
305                 310                 315                 320

Asn Ile Leu Leu Ala Gly Arg Asp Thr Thr Ala Ser Met Leu Ser Trp
                325                 330                 335

Ile Tyr Phe Arg Leu Ala Arg Asp Pro Lys Arg Tyr Ala Lys Leu Arg
                340                 345                 350

Ala Ala Val Leu Ala Asp Phe Gly Pro Gly Pro Glu Asn Ile Thr Phe
                355                 360                 365

Glu Ser Leu Lys Lys Cys Asp Tyr Leu Arg Tyr Val Leu Asn Glu Ser
                370                 375                 380

Leu Arg Val Tyr Pro Val Val Pro Ile Asn Ala Arg Thr Ala Ser Arg
385                 390                 395                 400

Asp Thr Thr Leu Pro Arg Gly Gly Pro Asp Gly Ser Gln Pro Ile
                405                 410                 415

Phe Val Pro Lys Gly Gln Thr Val Ser Tyr Ser Val Trp Trp Thr His
                420                 425                 430

Arg Asp Pro Glu Phe Trp Gly Gln Asp Ala Glu Phe Ile Pro Glu
                435                 440                 445

Arg Trp Asp Thr Lys Asn Gly Ser Ile Gly Arg Gly Trp Glu Tyr Leu
                450                 455                 460

Pro Phe Asn Gly Gly Pro Arg Ile Cys Leu Gly Gln Gln Phe Ala Leu
465                 470                 475                 480

Thr Glu Val Gly Tyr Val Leu Ser Arg Met Val Gln Thr Tyr Glu Thr
                485                 490                 495

Leu Glu Ser Gly Asp Thr Lys Pro Leu Pro Pro Leu Tyr Asn His Ala
                500                 505                 510

Leu Thr Leu Cys His Gln Glu Gly Val Trp Ile Lys Thr Glu
                515                 520                 525

<210> SEQ ID NO 67
<211> LENGTH: 454
<212> TYPE: PRT
<213> ORGANISM: Candida tenuis

<400> SEQUENCE: 67

Met Phe Phe Phe Ile Ser Leu Leu Leu Lys Tyr Ser Lys Gln Gly
1               5                   10                  15

Phe Leu Leu Glu Lys Gln Leu Gln Asp Phe Arg Thr Ala Gly Thr His
                20                  25                  30

Thr Leu Ala Ala Lys Val Phe Leu Arg Asn Val Ile Ile Thr Cys Asn
                35                  40                  45

Gly Glu Asn Ile Lys Ser Ser Ile Ala Thr Gln Phe Asn Asn Tyr Ser
                50                  55                  60

Ile Gly Phe Arg Met His Ala Leu Glu Pro Leu Ile Gly Asn Gly Ile
65              70                  75                  80

Phe Ala Ser Glu Gly Glu Arg Trp Lys Ala Ser Arg Glu Met Leu Arg
                85                  90                  95

Pro Gln Phe Ser Arg Glu Gln Val Ser His Val Gln Thr Leu Glu Pro
                100                 105                 110

His Phe Lys Asn Phe Ala Arg Glu Ile Arg Lys Leu Asn Gly Lys Glu
                115                 120                 125
```

```
Phe Asn Ile Gln Asp Tyr Phe His Lys Ile Thr Ile Asp Thr Ser Ser
        130                 135                 140

Glu Phe Leu Phe Gly Glu Ser Thr Asn Thr Leu Thr Ser Ala Ser Asn
145                 150                 155                 160

Asp Lys Phe Gln Phe Ala Asp Ala Phe Asn Lys Val Gln Asp Thr Leu
                165                 170                 175

Thr Glu Lys Phe Met Leu Gly Pro Leu His Trp Val Ser Asn Ser Lys
            180                 185                 190

Glu Phe Gln Gly His Ile Lys Glu Ile His Asp Ala Val Lys Phe Tyr
        195                 200                 205

Val Asp Lys Ala Leu Glu Thr Gln Glu Glu Lys Leu Gln Glu Arg Ser
210                 215                 220

Gln Asp Asn Tyr Ile Phe Leu Tyr Glu Leu Val Lys Lys Thr Arg Asp
225                 230                 235                 240

Pro Lys Val Leu Gln Asp Glu Leu Leu Ser Ile Leu Leu Ala Gly Arg
                245                 250                 255

Asn Thr Thr Ala Gly Leu Leu Ser Phe Leu Phe Leu Glu Leu Ser Arg
            260                 265                 270

Asn Pro Arg Val Trp Ser Lys Leu Lys Glu Asp Ile Tyr Glu Ser Phe
        275                 280                 285

Gly Gln Gly Ser Ser Asp Glu Leu Glu Lys Ile Thr Phe Glu Ser Met
290                 295                 300

Lys Arg Cys Thr Tyr Leu Lys Tyr Cys Ile Asn Glu Ala Leu Arg Leu
305                 310                 315                 320

Tyr Pro Pro Ile Ser Arg Asn Val Arg Val Ser Lys Lys Asn Thr Thr
                325                 330                 335

Leu Pro Arg Gly Gly Lys Tyr Gly Asp Ser Ala Ile Phe Val Pro
            340                 345                 350

Lys Gly Thr Ile Val Met Met His Ile Tyr Ser Asn His Arg Gln Lys
        355                 360                 365

Asp Val Tyr Gly Glu Asp Ala Asp Glu Phe Asn Pro Glu Arg Trp Glu
370                 375                 380

Asn Leu Lys Pro Gly Trp Ala Phe Met Pro Phe Gly Ser Gly Pro Arg
385                 390                 395                 400

Ile Cys Leu Gly Gln Gln Phe Ala Leu Thr Glu Ala Ser Tyr Ile Thr
                405                 410                 415

Ile Arg Ile Leu Gln Thr Phe Pro His Ile Thr Gly Asn Asn Pro Gln
            420                 425                 430

Tyr Pro Pro Arg Lys Val Ser Asn Ala Thr Met Arg Leu Met Asp Gly
        435                 440                 445

Cys Ile Val Thr Leu Lys
    450

<210> SEQ ID NO 68
<211> LENGTH: 519
<212> TYPE: PRT
<213> ORGANISM: Starmerella bombicola

<400> SEQUENCE: 68

Met Asn Ile Asn Phe Ser Asp Val Leu Val Leu Gly Gly Ile Ser Val
1               5                   10                  15

Ser Phe Leu Leu Ala Tyr Gln Ala Ile Tyr Phe Tyr Phe Ile Tyr Ser
            20                  25                  30

Pro Arg Ala Lys Lys Leu Gly Cys Ala Leu Pro Pro Val Phe Phe Ser
        35                  40                  45
```

```
Phe Pro Leu Gly Ile Pro Glu Val Ile Arg Leu Val Asn Ala Trp Phe
    50                  55                  60
Asn Asp Asp Leu Leu Glu Tyr Phe Thr Phe Lys Phe Glu Glu Phe Gln
65                  70                  75                  80
Arg Lys Thr Gly Phe Gln Ser Val Ala Gly Gln Leu Trp Ile Gly Thr
                85                  90                  95
Ile Glu Pro Glu Asn Ile Lys Thr Met Leu Ala Thr Ser Phe Lys Asp
            100                 105                 110
Tyr Ser Leu Gly Phe Arg Tyr Glu Ala Met Tyr Gly Leu Leu Gly Asn
        115                 120                 125
Gly Ile Phe Thr Leu Ser Gly Glu Gly Trp Lys His Ser Arg Ala Leu
    130                 135                 140
Leu Arg Pro Gln Phe Ser Arg Glu Gln Val Ser His Leu Glu Ser Met
145                 150                 155                 160
Arg Thr His Ile Asn Met Leu Ile Asn Asn His Phe Lys Gly Gly Lys
                165                 170                 175
Val Val Asp Ala Gln Val Leu Phe His Asn Leu Thr Ile Asp Thr Ala
            180                 185                 190
Thr Glu Phe Leu Phe Gly Glu Ser Thr Asn Thr Leu Asp Pro Ala Leu
        195                 200                 205
Ala Gln His Gly Phe Pro Gly Pro Lys Gly Leu Val Thr Gly Glu Gln
    210                 215                 220
Phe Ala Glu Ala Phe Thr Ser Ala Leu Glu Leu Leu Ser Val Arg Val
225                 230                 235                 240
Met Ala Gly Ala Ala Trp Phe Leu Val Trp Thr Pro Lys Phe Trp Arg
                245                 250                 255
Ser Cys Lys Val Cys His Asn Phe Ile Asp Tyr Phe Val Phe Lys Ala
            260                 265                 270
Leu Ala Thr Pro Met Glu Lys Asp Gln Glu Ala Asp Arg Tyr Val Phe
        275                 280                 285
Ile Arg Glu Leu Thr Lys Glu Thr Ser Asp Pro Arg Val Ile Arg Asp
    290                 295                 300
Gln Ala Leu Asn Ile Leu Leu Ala Gly Arg Asp Thr Thr Ala Ala Leu
305                 310                 315                 320
Leu Ser Phe Thr Thr Tyr Tyr Leu Gly Ala Tyr Pro Glu Val Tyr Asp
                325                 330                 335
Glu Leu Arg Glu Ala Val Ile Ala Asp Phe Gly Lys Glu Asp Ala Glu
            340                 345                 350
Pro Pro Thr Phe Glu Gln Leu Lys Gln Cys Lys Val Leu Gln Asn Val
        355                 360                 365
Ile Arg Glu Val Leu Arg Leu His Pro Asn Val Pro Leu Asn Phe Arg
    370                 375                 380
Glu Ala Ile Thr Asp Thr Lys Phe Pro Thr Gly Gly Pro Asn Gly
385                 390                 395                 400
Asp Gln Pro Val Phe Val Pro Lys Gly Gln Lys Val Phe Tyr Ala Thr
                405                 410                 415
Tyr Val Met Gln Arg Asn Glu Gly Leu Trp Gly Pro Asp Ser Thr Thr
            420                 425                 430
Phe Arg Pro Asp Arg Trp Asn Glu Ser Arg Glu Ala Ile Ala Ser Gly
        435                 440                 445
Trp Asp Tyr Ile Pro Phe Asn Gly Gly Pro Arg Ile Cys Leu Gly Gln
    450                 455                 460
```

```
Gln Phe Ala Leu Thr Glu Ala Ser Tyr Thr Leu Val Arg Ile Cys Gln
465                 470                 475                 480

Glu Phe Ser Arg Ile Glu Val Leu His Pro Asp Val Ile Thr Ser Arg
            485                 490                 495

Asn Val Met Lys Gln Arg Met Arg Leu Thr Asn Ser Ser Ser Gly Gly
        500                 505                 510

Val Ile Ala Lys Phe Ile Arg
        515

<210> SEQ ID NO 69
<211> LENGTH: 531
<212> TYPE: PRT
<213> ORGANISM: Yarrowia lipolytica

<400> SEQUENCE: 69

Met Leu Gln Leu Phe Gly Val Leu Val Leu Ala Leu Thr Thr Ala Leu
1               5                   10                  15

Leu Ala Gln Leu Ala Tyr Asn Lys Tyr Glu Tyr Asn Arg Lys Val Lys
            20                  25                  30

Gln Phe Gly Cys Gly Glu Leu Thr Val Ala Lys Asn Gly Phe Leu Gly
        35                  40                  45

Trp Lys Gly Ile Arg Ala Val Leu His Val Leu Lys Thr Lys Lys Gly
50                  55                  60

Pro Ala Leu Lys Glu Arg Ile Asp Ala Tyr Gly Arg Thr Tyr Val
65                  70                  75                  80

Phe His Ile Gly Pro Ala Pro Val Ile Ser Thr Met Glu Pro Glu Asn
                85                  90                  95

Ile Lys Ala Met Leu Ala Thr Gln Phe Lys Asp Phe Ser Leu Gly Thr
            100                 105                 110

Arg Tyr Arg Ser Leu Ala Pro Thr Leu Gly Asp Gly Ile Phe Thr Leu
        115                 120                 125

Asp Gly His Gly Trp Thr His Ser Arg Ala Leu Leu Arg Pro Gln Phe
130                 135                 140

Ala Arg Glu Gln Val Ser Arg Leu Asp Ser Leu Glu Ala His Phe Gln
145                 150                 155                 160

Ile Leu Lys Met Cys Val Asp Lys Glu Met Arg Glu Lys Gly Asn Asp
                165                 170                 175

Pro Arg Gly Phe Asp Ile Gln Asn Leu Phe Phe Leu Thr Leu Asp
            180                 185                 190

Ser Ala Thr Glu Phe Leu Phe Gly Ser Ser Val Asp Ser Leu Val Asp
        195                 200                 205

Phe Leu Asp Asp Pro Ser Val Arg Thr Gly Asp His Gly Gly Val Asp
210                 215                 220

Glu Ala Ala Arg Lys Gly Phe Asn Asn Ser Asn His Ala Gln Glu
225                 230                 235                 240

Leu Cys Ala Leu Arg Ser Arg Leu His Thr Leu Tyr Trp Ile Val Gly
                245                 250                 255

Ser Val Val Lys Lys Glu Pro Phe Glu Arg Tyr Asn Lys Glu Ile Lys
            260                 265                 270

Thr Phe Val Asp Phe Ala Ala Lys Ala Leu Lys Ala Arg Lys Glu
        275                 280                 285

Lys Asp Met Ser Leu Met Asp Asn Asp Gln Tyr Ile Phe Met Tyr Glu
290                 295                 300

Leu Val Lys Glu Thr Thr Asn Pro Val Thr Leu Arg Asp Gln Met Leu
305                 310                 315                 320
```

```
Asn Ile Leu Leu Ala Gly Arg Asp Thr Thr Ala Ser Met Leu Ser Trp
                325                 330                 335

Ile Tyr Phe Arg Leu Ala Arg Asp Pro Lys Leu Tyr Ala Lys Leu Arg
            340                 345                 350

Ser Ala Ile Leu Glu Asp Phe Gly Thr Thr Pro Glu Ala Ile Thr Phe
            355                 360                 365

Glu Ser Leu Lys Gln Cys Asp Tyr Leu Arg Tyr Val Leu Asn Glu Ala
        370                 375                 380

Leu Arg Leu Tyr Pro Val Val Pro Ile Asn Gly Arg Thr Ala Thr Arg
385                 390                 395                 400

Asp Thr Thr Leu Pro Arg Gly Gly Pro Asp Gln Ser Gln Pro Ile
                405                 410                 415

Phe Ile Pro Lys Gly Gln Thr Val Ser Tyr Ser Val Tyr Trp Thr His
                420                 425                 430

Arg Asp Pro Arg Phe Trp Gly Glu Asp Ala Glu Phe Ile Pro Glu
            435                 440                 445

Arg Trp Asp Pro Arg Asn Gly Asn Ile Gly Arg Gly Trp Glu Tyr Leu
        450                 455                 460

Pro Phe Asn Gly Gly Pro Arg Ile Cys Leu Gly Gln Gln Phe Ala Leu
465                 470                 475                 480

Thr Glu Val Gly Tyr Val Leu Ser Arg Leu Val Gln Thr Tyr Glu Thr
                485                 490                 495

Leu Glu Thr Cys Asp His Lys Pro Leu Pro Pro Leu Tyr Asn His Ala
            500                 505                 510

Leu Thr Met Cys His Glu Glu Gly Val Trp Val Lys Met Tyr Lys Gly
                515                 520                 525

Glu Lys Ala
    530

<210> SEQ ID NO 70
<211> LENGTH: 497
<212> TYPE: PRT
<213> ORGANISM: Candida tenuis

<400> SEQUENCE: 70

Met Phe Asp Ser Ile Leu Leu Gln Leu Thr Ala Val Leu Ala Val Val
1               5                   10                  15

Leu Ile Ala Gln Gln Leu Tyr His Arg Tyr Leu Ala Arg Lys Trp Ala
            20                  25                  30

Cys Gly Asp Ile Leu Lys Val Asp Gln Asp Tyr Phe Gly Ile Trp Gln
        35                  40                  45

Ala Arg Lys Leu Phe Ala Asp Arg Asn Asp Gly Val Asp Leu Gln Glu
    50                  55                  60

Gln Arg Asn Arg Phe Asn Arg Tyr His Thr Glu Thr Phe Arg Glu Thr
65                  70                  75                  80

Leu Ile Gly Arg Glu Leu Tyr Tyr Thr Ser Asn Leu Glu Asn Ile Lys
                85                  90                  95

Ala Ile Val Asn Phe Gln Phe Asn Asp Phe Ser Ile Gly Tyr Arg Tyr
            100                 105                 110

Pro Ala Phe Lys Pro Leu Leu Gly Asp Gly Ile Phe Ala Thr Glu Gly
        115                 120                 125

His Lys Trp Lys Val Ala Lys Glu Val Leu Arg Pro Gln Phe Val Arg
    130                 135                 140

Glu Gln Ile Arg Asp Leu Asp His Leu Glu Val His Ile Lys Asn Met
```

```
                145                 150                 155                 160
Ala Ala Ile Ile Asn Asn Thr His Gly Gln Val Phe Asp Ile Gln Asp
                    165                 170                 175

Leu Phe Leu Arg Leu Thr Leu Asp Ala Ser Thr Asp Phe Leu Phe Gly
                    180                 185                 190

Glu Ser Val Ser Ser Leu Thr Lys Ser Glu Tyr Glu Met Gly Lys Tyr
                    195                 200                 205

Thr Phe Glu Ser Ala Phe Asn Lys Val Gln Lys Tyr Ile Phe Ala Arg
            210                 215                 220

Ser Ile Leu Gln Ser Leu Tyr Trp Thr Tyr Asn Pro Lys Asp Phe Arg
225                 230                 235                 240

Glu Cys Leu Asn Val Ile His Thr Phe Thr Asp Thr Phe Val Gln Lys
                    245                 250                 255

Ala Leu Ser Leu Thr Pro Glu Glu Leu Asp Ala Lys Ser Lys Lys Asn
                    260                 265                 270

Tyr Thr Phe Leu Tyr Glu Leu Val Lys Ile Thr Arg His Arg Lys Thr
                    275                 280                 285

Val His Asp His Leu Leu Asn Ile Met Leu Ala Gly Arg Asn Thr Thr
            290                 295                 300

Ser Ala Leu Ile Ser Ser Leu Met Leu Glu Leu Ala Arg Asn Pro Glu
305                 310                 315                 320

Cys Tyr Glu Lys Leu Lys Lys Asp Val Phe Glu Asn Phe Gly Asp Gly
                    325                 330                 335

Ser Asp Leu Ser Cys Val Thr Val Glu Ser Met Lys Lys Cys Asn Tyr
                    340                 345                 350

Leu Arg Tyr Cys Ile Asn Glu Ala Leu Arg Met Tyr Pro Ser Val Pro
                    355                 360                 365

Gln Asn Phe Arg Cys Ala Lys Thr Ala Thr Thr Leu Pro Arg Gly Gly
            370                 375                 380

Gly Pro Asp Gly Gln Asp Lys Ile Phe Leu Lys Lys Gly Gln Ala Val
385                 390                 395                 400

Phe Met Ser Phe Tyr Thr Leu Gln Arg Ser Glu Leu Tyr Tyr Gly Lys
                    405                 410                 415

Asp Ala Asn Glu Phe Asn Pro Asp Arg Trp Ala Thr Ile Lys Asn Pro
                    420                 425                 430

Gly Ala Phe Met Pro Phe Leu Ser Gly Pro Arg Ile Cys Leu Gly Gln
                    435                 440                 445

Gln Phe Ala Ile Ala Glu Ala Ser Tyr Thr Ile Leu Arg Ile Ala Gln
            450                 455                 460

Met Phe Pro Asn Ile Lys Ser Phe Glu Thr Glu Tyr Pro Pro Arg Ile
465                 470                 475                 480

Ser Ala Asn Ala Thr Met Lys Leu Arg Asp Gly Val Met Val Ser Leu
                    485                 490                 495

Ser

<210> SEQ ID NO 71
<211> LENGTH: 519
<212> TYPE: PRT
<213> ORGANISM: Candida apicola

<400> SEQUENCE: 71

Met Ile Ile Gly Leu Ser Asp Ala Phe Ala Leu Gly Gly Ile Ala Leu
1               5                   10                  15

Ser Phe Leu Val Ala Tyr Gln Phe Ile Tyr Phe Tyr Phe Ile Tyr Ser
```

```
            20                  25                  30
Pro Arg Ala Lys Lys Leu Gly Cys Ala Pro Val Ile Val Phe Ser
        35                  40                  45
Phe Pro Leu Gly Leu Pro Ala Leu Tyr Lys Phe Ala Thr Ala Met Leu
    50                  55                  60
His Asp Asn Leu Leu Glu Tyr Ile Ser Ile Arg Ile Ala Asp Met Lys
65                  70                  75                  80
Val Arg Thr Gly Phe Gln Thr Leu Ala Gly Gln Arg Trp Leu Val Thr
                85                  90                  95
Leu Glu Pro Glu Asn Ile Lys Thr Val Leu Ala Thr Ser Phe Lys Asp
            100                 105                 110
Tyr Ser Leu Gly Phe Arg Tyr Asp Ile Met Tyr Gly Leu Leu Gly Asn
            115                 120                 125
Gly Ile Phe Thr Leu Ser Gly Asp Gly Trp Lys His Ser Arg Ala Leu
        130                 135                 140
Leu Arg Pro Gln Phe Ser Arg Glu Gln Val Ser His Leu Glu Ser Met
145                 150                 155                 160
Arg Thr His Ile Asn Leu Met Ile Asn Asn His Phe Lys Gly Gly Gln
                165                 170                 175
Val Val Asp Ala Gln Ala Leu Tyr His Asn Leu Thr Ile Asp Thr Ala
            180                 185                 190
Thr Glu Phe Leu Phe Gly Glu Ser Thr Asn Thr Leu Asp Pro Asp Leu
            195                 200                 205
Ala Gln Gln Gly Leu Pro Gly Pro Lys Gly Leu Val Thr Gly Glu Gln
        210                 215                 220
Phe Ala Glu Ala Phe Thr Ser Ala Leu Glu Ile Leu Ser Val Arg Val
225                 230                 235                 240
Ile Val Gly Ala Ala Trp Phe Leu Ile Trp Thr Pro Lys Phe Trp Arg
                245                 250                 255
Ser Cys Lys Val Cys His Asn Phe Ile Asp Tyr Phe Val Tyr Lys Ala
            260                 265                 270
Leu Ala Thr Pro Met Glu Lys Asp Gln Glu Ala Asp Arg Tyr Val Phe
            275                 280                 285
Ile Arg Glu Leu Thr Lys Glu Thr Ser Asp Pro Arg Val Ile Arg Asp
        290                 295                 300
Gln Ala Leu Asn Ile Leu Leu Ala Gly Arg Asp Thr Thr Ala Gly Leu
305                 310                 315                 320
Leu Ser Phe Ile Thr Tyr Tyr Leu Gly Ala Tyr Pro Glu Val Tyr Ala
                325                 330                 335
Glu Leu Arg Glu Ala Val Leu Ser Phe Gly Ser Thr Asp Val Glu
            340                 345                 350
Thr Pro Thr Phe Glu Gln Leu Lys Gln Cys Lys Val Leu Gln Asn Val
            355                 360                 365
Ile Arg Glu Val Leu Arg Leu His Pro Asn Val Pro Leu Asn Phe Arg
        370                 375                 380
Gln Ala Ile Val Asp Thr Lys Leu Pro Thr Gly Gly Pro Asn Gly
385                 390                 395                 400
Asp Gln Pro Val Phe Val Pro Lys Gly Gln Asn Val Phe Tyr Ser Thr
                405                 410                 415
Tyr Ser Met Gln Arg Arg Thr Asp Ile Trp Gly Pro Asp Ala Thr Thr
            420                 425                 430
Phe Arg Pro Asp Arg Trp Asn Glu Pro Arg Glu Ala Leu Ala Ser Gly
        435                 440                 445
```

-continued

Trp Asp Tyr Ile Pro Phe Asn Gly Gly Pro Arg Ile Cys Leu Gly Gln
450                 455                 460

Gln Phe Ala Leu Thr Glu Ala Ser Tyr Thr Ile Val Arg Ile Cys Gln
465                 470                 475                 480

Glu Phe Ser Arg Ile Glu Val Leu His Pro Asp Val Ile Thr Ser Lys
            485                 490                 495

Asn Ser Met Lys Gln Arg Met Arg Leu Thr Gln Thr Ala Ser Gly Gly
            500                 505                 510

Val Ile Thr Arg Phe Ile Arg
        515

<210> SEQ ID NO 72
<211> LENGTH: 510
<212> TYPE: PRT
<213> ORGANISM: Candida maltosa

<400> SEQUENCE: 72

Met Ile Asp Ala Leu Tyr Ile Leu Ile Val Ala Leu Val Ile Tyr Lys
1               5                   10                  15

Thr Ala Gln Phe Val His Arg Lys Ser Leu Glu Lys Lys His His Cys
                20                  25                  30

Gln Pro Val Lys Gln Ile Pro Leu Val Ser Ile Leu Ser Gly Leu Gly
            35                  40                  45

Phe Asp Met Phe Phe Lys Asp Thr Ala Glu Met Thr Lys Asn Gly Gly
        50                  55                  60

Leu His Lys Lys Leu Gln Gln Met Leu Glu Ser Leu Gln Thr Thr Thr
65                  70                  75                  80

Phe Arg Ser Arg Met Leu Thr Gly Ser Gln Ile Val Thr Met Glu Pro
                85                  90                  95

Glu Asn Glu Arg Thr Met Cys Ser Ser Ala His Met Lys Asp Trp Thr
            100                 105                 110

Ile Gly Tyr Arg Pro Phe Ala Leu Lys Pro Leu Leu Gly Asp Gly Ile
        115                 120                 125

Phe Ser Ser Glu Gly Glu Ser Trp Lys His Ser Arg Ile Met Leu Arg
130                 135                 140

Pro Ile Phe Ala Lys Glu His Ile Lys Gln Ile Thr Ala Met Glu Pro
145                 150                 155                 160

Tyr Met Leu Leu Leu Ile Glu Ile Ile Lys Ser Ser Ser Ala Asn Glu
                165                 170                 175

Gly Pro Val Asp Leu Gln Pro Leu Phe His Ala Phe Thr Ile Asp Tyr
            180                 185                 190

Ala Ser Asp Phe Leu Phe Gly Glu Ser Cys Asp Val Leu Lys Glu Asn
        195                 200                 205

Leu Gly Gly Lys Ser Thr Ser Gly Met Asp Ala Gln Val Lys Arg Asp
210                 215                 220

Phe Ala Ser Val Phe Asn Asp Val Gln Asn Tyr Leu Thr Lys Arg Met
225                 230                 235                 240

Met Leu Gly Pro Leu Ala Phe Leu Val Ser Ser Lys Asp Phe His Asp
                245                 250                 255

Gly Ile Lys Lys Gln His Glu Phe Val Ser Tyr Phe Val Gln Lys Ala
            260                 265                 270

Ile Ser Met Ser Asp Glu Glu Leu Asn Asp Glu Ser Lys Asn Tyr Val
        275                 280                 285

Phe Leu Tyr Gln Leu Ala Lys Gln Thr Lys Asp Ala Lys Val Leu Gln

```
                290                 295                 300
Asp Glu Leu Leu Ser Ile Leu Leu Ala Gly Arg Asn Thr Thr Ala Ser
305                 310                 315                 320

Leu Leu Ser Phe Leu Phe Phe Glu Leu Ser His His Glu Asn Val Trp
                325                 330                 335

Thr Thr Leu Lys Glu Val Val Asp Gln Ser Phe Pro Asp Val Glu Ser
                340                 345                 350

Ile Thr Phe Glu Thr Ile Gln Asn Cys Asp Tyr Leu Arg Trp Cys Leu
                355                 360                 365

Phe Glu Ser Leu Arg Val Asn Pro Ser Val Pro Phe Asn Ser Arg Thr
                370                 375                 380

Ala Asn Lys Asp Thr Ile Leu Pro Arg Gly Gly Gly Glu Asp Cys Ser
385                 390                 395                 400

His Pro Ile Leu Val Lys Lys Gly Asp Gln Val Leu Phe Pro Leu Tyr
                405                 410                 415

Ala Ser Asn Arg Gln Glu Lys Tyr Phe Gly Arg Lys Pro Glu Glu Phe
                420                 425                 430

Ile Pro Glu Arg Trp Arg Asp Leu Pro Lys Thr Gly Gly Pro Ala Phe
                435                 440                 445

Met Pro Phe Ser Thr Gly Pro Arg Met Cys Leu Gly Gln Gln Phe Ala
                450                 455                 460

Leu Ile Glu Ala Ser Tyr Val Thr Ile Arg Leu Val Gln Thr Phe Ser
465                 470                 475                 480

Lys Leu Lys Ser His Ser Leu Glu Tyr Ala Pro Lys Arg Leu Val Ala
                485                 490                 495

Ala Thr Ile Arg Leu Ile Asp Gly Cys Phe Val Ser Phe Glu
                500                 505                 510

<210> SEQ ID NO 73
<211> LENGTH: 513
<212> TYPE: PRT
<213> ORGANISM: Yarrowia lipolytica

<400> SEQUENCE: 73

Met Ile Ile Ile Glu Thr Leu Ile Gly Ala Val Val Phe Val Ala Val
1               5                   10                  15

Tyr Val Ala Phe Val Lys Leu Asp Tyr Arg Arg Lys Ala Lys Phe
                20                  25                  30

Glu Thr Ser Asp Met Pro Val Ala Tyr Asn Gly Leu Leu Gly Trp Lys
                35                  40                  45

Gly Leu Arg His Met Leu Thr Val Phe Asn Asn Asp Ile Gly Pro Val
        50                  55                  60

Gly Trp Arg Glu Val Phe Ala Thr Tyr Gly Lys Thr Leu Lys Tyr Tyr
65                  70                  75                  80

Ala Phe Pro Ser Asn Thr Ile Leu Thr Tyr Asp Pro Asp Asn Ile Lys
                85                  90                  95

Ala Met Leu Ala Thr Gln Phe Lys Asp Phe Ser Leu Gly Leu Arg Lys
                100                 105                 110

Glu Ala Leu Ala Pro Ser Leu Gly Tyr Gly Ile Phe Thr Leu Asp Gly
                115                 120                 125

Ser Ser Trp Ser His Ser Arg Ala Leu Leu Arg Pro Gln Phe Ser Arg
        130                 135                 140

Glu Gln Ile Ser Arg Leu Glu Ser Val Glu Thr His Val Gln Glu Met
145                 150                 155                 160
```

Met Ser Cys Ile Asp Arg Asn Gln Gly Ala Tyr Phe Asp Ile Gln Arg
            165                 170                 175

Leu Phe Phe Ser Leu Ala Met Asp Thr Ala Thr Asp Phe Leu Leu Gly
        180                 185                 190

Glu Ala Val Gly Asn Leu Gln Glu Ile Leu His Pro Glu Met Pro Arg
        195                 200                 205

Thr Gly Thr Thr Phe Gln Val Ala Phe Asp Arg Ala Gln Arg Leu Gly
        210                 215                 220

Ser Leu Arg Ile Ile Cys Gln Glu Ala Phe Trp Val Val Gly Ser Leu
225                 230                 235                 240

Phe Trp Arg Arg Asp Phe Asn Asn Thr Asn Gln His Ile His Asp Tyr
                245                 250                 255

Val Asp Arg Tyr Val Asp Lys Ala Leu Leu Ala Arg Lys Glu Lys Ser
                260                 265                 270

Glu Ile Tyr Thr Asn Pro Asp Lys Tyr Ile Phe Leu Tyr Glu Leu Ala
            275                 280                 285

Arg Glu Thr Thr Asn Lys Ile Thr Leu Arg Asp Gln Val Leu Asn Ile
        290                 295                 300

Leu Ile Ala Gly Arg Asp Thr Thr Ala Ser Thr Leu Ser Trp Ile Phe
305                 310                 315                 320

Met Glu Leu Ala Lys Lys Pro Asp Ile Phe His Lys Leu Arg Glu Ala
                325                 330                 335

Ile Leu Asn Asp Phe Gly Thr Ser Cys Glu Ser Ile Ser Phe Glu Ser
                340                 345                 350

Leu Lys Lys Cys Asp Tyr Leu Arg Gln Val Leu Asn Glu Gly Leu Arg
            355                 360                 365

Leu His Pro Val Val Pro Val Asn Leu Arg Val Ala Val Arg Asp Thr
        370                 375                 380

Thr Leu Pro Arg Gly Gly Pro Gln Gly Asp Lys Pro Ile Phe Val
385                 390                 395                 400

Ala Lys Gly Gln Lys Ile Asn Tyr Ala Ile Phe Trp Thr His Arg Asp
                405                 410                 415

Lys Glu Tyr Trp Gly Glu Asp Ala Glu Glu Phe Arg Pro Glu Arg Trp
            420                 425                 430

Glu Thr Thr Ser Gly Gly Ala Leu Gly Lys Gly Trp Glu Phe Leu Pro
        435                 440                 445

Phe Asn Gly Gly Pro Arg Ile Cys Leu Gly Gln Gln Phe Ala Leu Thr
450                 455                 460

Glu Met Gly Tyr Val Ile Thr Arg Leu Leu Gln Glu Tyr Ser Asp Ile
465                 470                 475                 480

Ser Ile Gln Pro Ser Asp Ala Ala Val Lys Val Arg His Ser Leu Thr
                485                 490                 495

Met Cys Ser Ala Gln Gly Ile Asn Ile Ser Leu Thr Arg Ala Lys Glu
            500                 505                 510

Glu

<210> SEQ ID NO 74
<211> LENGTH: 515
<212> TYPE: PRT
<213> ORGANISM: Aspergillus niger

<400> SEQUENCE: 74

Met Ser Thr Leu Leu Phe Val Ala Thr Ala Ser Pro Ile Leu Tyr Leu
1               5                   10                  15

```
Leu Tyr Val Leu Leu Ser Arg Trp Gln His Ala Gln Asn Ala Arg Lys
             20                  25                  30

Trp Asn Cys Gly Ser Val Pro Ser Tyr Pro Gly Asp Leu Leu Gly Ile
         35                  40                  45

Asn Thr Leu Lys Glu Ala Leu Ala Met Asp Lys Ala Arg Gln Val Pro
     50                  55                  60

Thr Val Thr Arg Arg Val Glu Thr Met Ser Ala Arg Glu Asn Arg
65                  70                  75                  80

Tyr Thr Thr Thr Phe Gln Phe Arg Gln Leu Gly Thr Asp Val Ile Ser
                 85                  90                  95

Thr Cys Asp Pro Lys Asn Val Gln Ala Leu Leu Ala Thr Gln Phe Lys
             100                 105                 110

Asp Phe Glu Leu Gly Gln Ser Arg Arg Asn Ala Leu His Trp Leu Leu
         115                 120                 125

Gly Arg Gly Ile Phe Thr Ala Asp Gly Asp His Trp Ser Arg Ser Arg
     130                 135                 140

Ala Leu Leu Arg Pro Gln Phe Thr Arg Asp Gln Ile Ser Asp Leu Asp
145                 150                 155                 160

Leu Glu Glu Arg His Val Gln Val Ala Met Lys Ala Met Pro Val Asp
                 165                 170                 175

Ala Thr Gly Trp Thr Pro Ala Thr Asp Ile Gln Thr Ile Phe Phe Arg
             180                 185                 190

Leu Thr Met Asp Thr Ala Thr Glu Phe Leu Phe Gly Glu Ser Val Gln
         195                 200                 205

Ser Gln Ala Ala Leu Ser Asn Gly Ala Ile Pro Gln Asp Asp Phe
     210                 215                 220

Pro Ala Gln Phe Asp Arg Gly Gln Trp Tyr Ser Ala Gln Arg Ala Arg
225                 230                 235                 240

Phe Glu Lys Leu Tyr Trp Ile Ile Asn Asn Lys Glu Ser Arg Ala Ile
                 245                 250                 255

Asn Lys Ala Val His Ala Tyr Val Asp Arg Phe Val Thr Ala Ala Leu
             260                 265                 270

Asn Ser Asp Pro Glu Lys Lys Pro Thr Gly His Tyr Val Phe Leu His
         275                 280                 285

Gly Leu Ala Glu Ala Thr Arg Asp Pro Val Glu Leu Arg Ser Gln Leu
     290                 295                 300

Leu Asn Ile Leu Leu Ala Gly Arg Asp Thr Thr Ala Ser Leu Leu Ser
305                 310                 315                 320

Trp Cys Val Leu Phe Leu Ala Arg His Pro Ala Tyr Phe Ser Ser Leu
                 325                 330                 335

Arg Ala Thr Ile Leu Ala Glu Phe Gly Ser Tyr Ser Ser Pro Arg Asp
             340                 345                 350

Ile Thr Phe Ala Asn Leu Lys Ser Cys Arg Pro Leu Gln Asn Phe Leu
         355                 360                 365

Asn Glu Val Leu Arg Leu Tyr Pro Ile Val Pro Gly Asn Arg Arg Thr
     370                 375                 380

Ala Val Arg Asn Thr Thr Leu Pro Thr Gly Gly Pro Ala Gly Thr
385                 390                 395                 400

Asp Pro Val Tyr Val Lys Lys Gly Gln Pro Val Phe Tyr Ser Thr Tyr
                 405                 410                 415

Val Met His Arg Arg Pro Asp Leu Trp Gly Ala Asp Ala Asp Glu Phe
             420                 425                 430

Arg Pro Asp Arg Trp Asn Glu Arg Lys Ala Gly Trp Glu Tyr Leu Pro
```

```
        435                 440                 445

Phe Asn Gly Gly Pro Arg Ile Cys Ile Gly Gln Gln Phe Ala Leu Thr
    450                 455                 460

Glu Thr Gly Tyr Val Leu Val Arg Leu Leu Gln Arg Phe Asp Val Ile
465                 470                 475                 480

Glu Gly Val Gly Lys Thr Lys Glu Gly Glu Ile Asn Met Gln Met Ser
                485                 490                 495

Leu Thr Asn Ala Pro Gly Asp Asn Val Thr Val Arg Leu His Glu Asp
            500                 505                 510

Ala Ser Asn
        515

<210> SEQ ID NO 75
<211> LENGTH: 536
<212> TYPE: PRT
<213> ORGANISM: Beauveria bassiana

<400> SEQUENCE: 75

Met Pro Thr Leu Leu Ala Tyr Trp Pro Ile Ala Ala Gly Ile Val Thr
1               5                   10                  15

Leu Tyr Ile Leu Gln Gln Leu Trp Ile Glu Tyr Ser His Arg Gln Arg
            20                  25                  30

Ala Arg Ala Leu Gly Cys Lys Ala Pro Tyr Leu Arg Gln Gly Lys Leu
        35                  40                  45

Pro Leu Ser Val Asp His Leu Tyr Arg Ala Leu Thr Ala Leu Lys Glu
    50                  55                  60

Asp Glu Phe Leu Asn Leu Glu Val Arg Thr His Ala Glu Ile Pro Gly
65                  70                  75                  80

Gly Leu Ser Thr Phe His Gln Ala Ser Leu Gly Arg Lys Ile Leu Met
                85                  90                  95

Thr Thr Asp Pro Glu Asn Ile Lys Ala Met Leu Ala Thr Gln Phe Lys
            100                 105                 110

Asp Phe Gly Leu Gly Pro Ile Arg Tyr Asn Val Leu Glu Pro Leu Leu
        115                 120                 125

Gly Arg Gly Ile Phe Thr Ser Asp Gly Lys Asp Trp Gln His Ser Arg
    130                 135                 140

Ala Ile Leu Arg Pro Gln Phe Ser Arg Thr Gln Ile Ser Asn Leu His
145                 150                 155                 160

Val Glu Glu Ile His Val Gln His Leu Leu Asn Arg Leu Glu Gln Asp
                165                 170                 175

Ala Gly Gly Trp Thr Lys Glu Val Asn Leu Ala Pro Leu Phe Phe Asn
            180                 185                 190

Leu Thr Leu Asp Ser Ala Thr Glu Phe Leu Phe Gly Lys Ser Val Asn
        195                 200                 205

Thr Gln Val Leu Leu Gly Pro Asn Ala Lys Ala Arg Val Gly Gly Gly
    210                 215                 220

Gly Gly Gly Gly Gly Ser Glu Lys Ala Gly Asp Glu Ala Met Glu Asp
225                 230                 235                 240

Trp Ser Ser Phe Gly Gln Ala Phe Asp Ser Ala Asn Arg Ser Met Thr
                245                 250                 255

Arg Arg Phe Leu Leu Met Ser Phe Tyr Tyr Leu His Asn Pro Ser Ser
            260                 265                 270

Met His Arg Asp Cys Ala Glu Val Arg Arg Phe Ala Asp Tyr Tyr Val
        275                 280                 285
```

```
Gln Arg Ala Leu Ala Arg Ser Pro Ala Arg Ala Ala Glu Glu Asp Gly
    290                 295                 300

Thr Glu Tyr Val Phe Leu Asn Glu Leu Ala Lys Glu Thr Arg Asp Pro
305                 310                 315                 320

Asp Val Leu Arg Asn Gln Leu Leu Asn Ile Leu Leu Ala Gly Arg Asp
                325                 330                 335

Thr Thr Ala Gly Leu Leu Gly Trp Ala Thr Leu Arg Leu Ala Arg Gln
                340                 345                 350

Pro Ala Ala Tyr Ala Lys Leu Arg Ala Val Val Ala Asp Phe Gly
                355                 360                 365

Pro Tyr Ser Ala Thr Asp Thr Ser Arg Ile Thr Phe Glu Thr Leu Lys
    370                 375                 380

Ala Cys Thr His Leu Gln His Val Leu Ser Glu Thr Leu Arg Leu His
385                 390                 395                 400

Pro Ser Val Pro Ala Asn Phe Arg Arg Ala Leu Arg Asp Thr Thr Leu
                405                 410                 415

Pro Arg Gly Gly Gly Pro Asp Gly Gln Ser Pro Ile Tyr Val Arg Ala
                420                 425                 430

Gly Ser Glu Ile Ala Tyr Ser Thr Asn Val Met His Arg Arg Pro Asp
    435                 440                 445

Leu Trp Gly Pro Asp Ala Ala Glu Phe Arg Pro Glu Arg Trp Glu Gly
    450                 455                 460

Lys Lys Val Gly Trp Glu Tyr Leu Pro Phe Asn Gly Gly Pro Arg Ile
465                 470                 475                 480

Cys Leu Gly Gln Gln Phe Ala Leu Thr Glu Ala Ala Tyr Val Leu Val
                485                 490                 495

Arg Leu Val Gln Lys Tyr Asp Leu Met Glu Asn Leu Asp Pro Ser Pro
                500                 505                 510

Val Ile Lys Ser Asn Leu Thr Leu Thr Ser Ser Pro Val Gln Thr Leu
                515                 520                 525

Val Arg Leu His Glu Ala Ala Ala
                530                 535

<210> SEQ ID NO 76
<211> LENGTH: 523
<212> TYPE: PRT
<213> ORGANISM: Starmerella bombicola

<400> SEQUENCE: 76

Met Ile Leu Tyr Ala Val Leu Gly Ala Phe Ala Ala Phe Leu Leu Tyr
1               5                   10                  15

Met Asp Val Leu Tyr Pro Phe Val Ile Tyr Pro Leu Arg Ala Arg Trp
                20                  25                  30

His Lys Cys Gly Tyr Ile Pro Arg Asp Leu Ser Trp Pro Leu Gly Ile
            35                  40                  45

Pro Leu Thr Leu Val Val Leu Ser Lys Leu Arg Lys Asp Met Leu Leu
        50                  55                  60

Gln Phe Met Ala Ala Gln Asp Leu Ser Arg Pro Tyr Lys Thr Ser Leu
65              70                  75                  80

Arg Gln Phe Leu Gly Lys Trp Val Ile Ala Thr Arg Asp Pro Glu Asn
                85                  90                  95

Ile Lys Ala Val Leu Ser Thr Lys Phe Asn Asp Phe Ser Leu Lys Glu
            100                 105                 110

Arg Gly Asn Arg Met Arg His Val Ile Gly Asp Gly Ile Phe Thr Gln
        115                 120                 125
```

```
Asp Gly Ala Pro Trp Lys His Ser Arg Asp Met Leu Arg Pro Gln Phe
130                 135                 140

Thr Lys Asp Gln Ile Ser Arg Val Glu Leu Leu Ser His His Ile Asp
145                 150                 155                 160

Val Leu Ile Arg Glu Ile Arg Lys Ser Gly Gly Asn Val Glu Leu Gln
                165                 170                 175

Arg Leu Phe His Leu Met Thr Met Asp Thr Ala Thr His Phe Leu Phe
                180                 185                 190

Gly Glu Ser Val Gly Ser Leu Glu Val Ser Gly Glu Ser Lys Gly Ile
            195                 200                 205

Glu Ile Thr Asp Pro Lys Thr Gly Glu Ile Val Asn Thr Val Asp Phe
210                 215                 220

Val Glu Ser Tyr Thr Phe Ala Asn Lys Phe Ala Leu Lys Lys Ile Ile
225                 230                 235                 240

Leu Asn Asp Leu Glu Phe Leu Ala Asp Leu Thr Glu Pro Ser Tyr Lys
                245                 250                 255

Trp His Leu Arg Arg Val His Thr Val Met Asp His Tyr Val Gln Leu
                260                 265                 270

Ala Leu Lys Ala Thr Glu Lys Tyr Asp Pro Asp Asp Ser Glu Lys
            275                 280                 285

Gly Glu Tyr Tyr Phe Ser His Glu Leu Ala Lys Leu Thr Arg Asp Pro
290                 295                 300

Leu Ser Leu Arg Asp Gln Leu Phe Asn Ile Leu Ile Ala Gly Arg Asp
305                 310                 315                 320

Thr Thr Ala Ala Thr Leu Ser Tyr Ala Phe His Tyr Leu Thr Lys Asn
                325                 330                 335

Pro Ala Ile Tyr Ala Lys Val Arg Glu Asp Val Leu Thr Val Phe Pro
                340                 345                 350

Asn Gly Asp Ala Ser Leu Ala Thr Tyr Glu Asp Leu Arg Lys Ala Lys
                355                 360                 365

Tyr Leu Gln Met Val Ile Lys Glu Val Leu Arg Leu Ala Pro Ala Val
                370                 375                 380

Pro Leu Asn Thr Arg Ala Ala Val Arg Asp Thr Tyr Leu Pro Arg Gly
385                 390                 395                 400

Gly Gly Pro Ala Gly Asn Leu Pro Val Phe Val Pro Lys Gly Thr Ala
                405                 410                 415

Val Asn Tyr Pro Thr Tyr Ile Leu His Arg Asp Pro Asp Ile Tyr Gly
                420                 425                 430

Ala Asp Ala Tyr Glu Phe Asn Pro Glu Arg Trp Arg Pro Glu Asn Lys
                435                 440                 445

Leu Pro Asn Ser Pro Met Tyr Ser Trp Gly Tyr Ile Pro Phe Asn Gly
                450                 455                 460

Gly Pro Arg Ile Cys Ile Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Gln Asp Lys Ser Ser Leu Thr Val Met
                500                 505                 510

Val Gly Gly Ser Gly Val Arg Val Lys Leu Ser
            515                 520

<210> SEQ ID NO 77
<211> LENGTH: 528
```

<212> TYPE: PRT
<213> ORGANISM: Beauveria bassiana

<400> SEQUENCE: 77

Met Ala Val Leu Ser Val Ile Ser Leu Pro Ala Leu Leu Val Ser Leu
1 5 10 15

Thr Val Ala Phe Ile Leu Leu Gln Val Ile Glu Tyr Val Arg Phe Arg
20 25 30

Ser Lys Ala Ala Arg Leu Gly Cys Lys Ser Ala Pro Ser Gly Ile Ser
35 40 45

Ser Asp Trp Ser Gly Ile Ser Leu Met Arg Lys Gly Leu Lys Ala Gln
50 55 60

Arg Glu Lys Asn Val Pro Asn Trp Met Arg His Glu Phe Ala Arg Leu
65 70 75 80

Ser Ala Arg Glu Gly Arg Pro Val Gly Thr Phe Glu Met Ser Ala Pro
85 90 95

Leu Phe Arg Arg Val Leu Phe Thr Ser Glu Pro Glu Asn Ile Lys Thr
100 105 110

Ile Leu Ala Thr Ser Phe Lys Asp Phe Ser Leu Gly Asp Asn Arg Arg
115 120 125

Gly Asn Phe Lys Pro Leu Leu Gly Glu Gly Ile Phe Ala Ser Asp Gly
130 135 140

Lys Lys Trp Glu His Ser Arg Ala Met Leu Arg Pro Gln Phe Val Arg
145 150 155 160

Ser Gln Val Ser Asp Ile Ser Leu Glu Glu Thr His Val Gln Asn Leu
165 170 175

Met Thr Val Leu Asp Ser His Leu Asp Lys Thr Thr Gly Trp Ser Gly
180 185 190

Ala Val Asp Leu Gln Pro Leu Phe Phe Arg Leu Thr Leu Asp Ser Ala
195 200 205

Thr Glu Phe Leu Phe Gly Glu Ser Val Asn Ser Gln Leu Arg Arg Glu
210 215 220

Gly Asp Ala Asp Asn Asp Ala His Ala Phe Ala Thr Ser Phe Asp Ala
225 230 235 240

Ser Gln Asn Gln Leu Ala Val Ala Gly Arg Tyr Gly Ser Asn Tyr Trp
245 250 255

Ile Gly His Thr Lys Ala Phe Arg Glu Asp Val Arg Ile Cys His Glu
260 265 270

Phe Ile Asp Tyr Phe Val Gln Lys Ala Leu Asn Gly Gln Arg Asp Thr
275 280 285

Ser Glu Lys Ala Asp Ala Asp Lys Glu Glu Arg Tyr Val Phe Leu Glu
290 295 300

Ala Ile Ala Arg Glu Thr Ser Asp Pro Val Glu Leu Arg Ser Gln Leu
305 310 315 320

Ile Asn Ile Leu Leu Ala Gly Arg Asp Thr Thr Ala Ser Thr Leu Gly
325 330 335

Trp Phe Phe His Ile Met Gly Gln Ala Arg Asn Ala His Ile Tyr Lys
340 345 350

Arg Leu Arg Gln Ala Ile Leu Asp Glu Phe Gly Thr Tyr Arg Asn Pro
355 360 365

Lys Pro Ile Thr Phe Glu Gly Leu Lys Asn Leu Thr Tyr Leu Gln Trp
370 375 380

Cys Ile Asn Glu Thr Leu Arg Leu Tyr Pro Ile Val Pro Met Asn Gly
385 390 395 400

```
Arg Ala Ala Val Lys Asp Thr Val Leu Pro Leu Gly Gly Pro Asp
                405                 410                 415

Gly Arg Ser Pro Ile Leu Val Lys Lys Gly Gln Asp Ile Gly Tyr Ser
            420                 425                 430

Val His Val Met His His Arg Thr Asp Leu Trp Gly Ala Asp Ala Asp
        435                 440                 445

Asp Phe Arg Pro Glu Arg Trp Glu Lys Arg Lys Pro Gly Trp Asp Tyr
    450                 455                 460

Leu Pro Phe Asn Gly Gly Pro Arg Ile Cys Ile Gly Gln Gln Phe Ala
465                 470                 475                 480

Leu Thr Glu Ile Ala Tyr Val Val Ala Arg Met Leu Gln Arg Phe Asp
                485                 490                 495

Glu Leu Asp Gly Ser Thr Leu Ser Ala Glu Ser His Gly Leu Gly Leu
            500                 505                 510

Thr Asn Cys Pro Gly Glu Gly Val Thr Leu Lys Val His Phe Asp Glu
        515                 520                 525

<210> SEQ ID NO 78
<211> LENGTH: 420
<212> TYPE: PRT
<213> ORGANISM: Mycobacterium sp.

<400> SEQUENCE: 78

Met Thr Glu Met Thr Val Ala Ala Ser Asp Ala Thr Asn Ala Ala Tyr
1               5                   10                  15

Gly Met Ala Leu Glu Asp Ile Asp Val Ser Asn Pro Val Leu Phe Arg
            20                  25                  30

Asp Asn Thr Trp His Pro Tyr Phe Lys Arg Leu Arg Glu Glu Asp Pro
        35                  40                  45

Val His Tyr Cys Lys Ser Ser Met Phe Gly Pro Tyr Trp Ser Val Thr
    50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
                85                  90                  95

Ala Ser Leu Pro Met Phe Ile Ala Met Asp Pro Pro Lys His Asp Val
            100                 105                 110

Gln Arg Lys Thr Val Ser Pro Ile Val Ala Pro Glu Asn Leu Ala Thr
        115                 120                 125

Met Glu Ser Val Ile Arg Gln Arg Thr Ala Asp Leu Leu Asp Gly Leu
    130                 135                 140

Pro Ile Asn Glu Glu Phe Asp Trp Val His Arg Val Ser Ile Glu Leu
145                 150                 155                 160

Thr Thr Lys Met Leu Ala Thr Leu Phe Asp Phe Pro Trp Asp Asp Arg
                165                 170                 175

Ala Lys Leu Thr Arg Trp Ser Asp Val Thr Thr Ala Leu Pro Gly Gly
            180                 185                 190

Gly Ile Ile Asp Ser Glu Glu Gln Arg Met Ala Glu Leu Met Glu Cys
        195                 200                 205

Ala Thr Tyr Phe Thr Glu Leu Trp Asn Gln Arg Val Asn Ala Glu Pro
    210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Leu Ile Val Gly
```

```
            245                 250                 255
Gly Asn Asp Thr Thr Arg Asn Ser Met Thr Gly Gly Val Leu Ala Leu
            260                 265                 270

Asn Glu Phe Pro Asp Glu Tyr Arg Lys Leu Ser Ala Asn Pro Ala Leu
            275                 280                 285

Ile Ser Ser Met Val Ser Glu Ile Ile Arg Trp Gln Thr Pro Leu Ser
            290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
            325                 330                 335

Asp Pro Glu Ala Ile Asp Asn Pro Thr Phe Ile Ile Asp Arg Ala
            340                 345                 350

Lys Pro Arg Gln His Leu Ser Phe Gly Phe Gly Ile His Arg Cys Val
            355                 360                 365

Gly Asn Arg Leu Ala Glu Leu Gln Leu Asn Ile Leu Trp Glu Glu Ile
            370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
            405                 410                 415

Arg Ile Asn Ala
            420

<210> SEQ ID NO 79
<211> LENGTH: 418
<212> TYPE: PRT
<213> ORGANISM: Polaromonas sp.

<400> SEQUENCE: 79

Met Ser Glu Ala Ile Val Val Asn Asn Gln Asn Asp Gln Ser Arg Ala
1               5                   10                  15

Tyr Ala Ile Pro Leu Glu Asp Ile Asp Val Ser Asn Pro Glu Leu Phe
                20                  25                  30

Arg Asp Asn Thr Met Trp Gly Tyr Phe Glu Arg Leu Arg Arg Glu Asp
            35                  40                  45

Pro Val His Tyr Cys Lys Asp Ser Leu Phe Gly Pro Tyr Trp Ser Val
        50                  55                  60

Thr Lys Phe Lys Asp Ile Met Gln Val Glu Thr His Pro Glu Ile Phe
65                  70                  75                  80

Ser Ser Glu Gly Asn Ile Thr Ile Met Glu Ser Asn Ala Ala Val Thr
                85                  90                  95

Leu Pro Met Phe Ile Ala Met Asp Pro Pro Lys His Asp Val Gln Arg
            100                 105                 110

Met Ala Val Ser Pro Ile Val Ala Pro Glu Asn Leu Ala Lys Leu Glu
        115                 120                 125

Gly Leu Ile Arg Glu Arg Thr Gly Arg Ala Leu Asp Gly Leu Pro Ile
    130                 135                 140

Asn Glu Thr Phe Asp Trp Val Lys Leu Val Ser Ile Asn Leu Thr Thr
145                 150                 155                 160

Gln Met Leu Ala Thr Leu Phe Asp Phe Pro Trp Glu Asp Arg Ala Lys
                165                 170                 175

Leu Thr Arg Trp Ser Asp Val Ala Thr Ala Leu Val Gly Thr Gly Ile
            180                 185                 190
```

-continued

```
Ile Asp Ser Glu Glu Gln Arg Met Glu Glu Leu Lys Gly Cys Val Gln
            195                 200                 205

Tyr Met Thr Arg Leu Trp Asn Glu Arg Val Asn Val Pro Pro Gly Asn
    210                 215                 220

Asp Leu Ile Ser Met Met Ala His Thr Glu Ser Met Arg Asn Met Thr
225                 230                 235                 240

Pro Glu Glu Phe Leu Gly Asn Leu Ile Leu Leu Ile Val Gly Gly Asn
                245                 250                 255

Asp Thr Thr Arg Asn Ser Met Thr Gly Gly Val Leu Ala Leu Asn Glu
                260                 265                 270

Asn Pro Asp Glu Tyr Arg Lys Leu Cys Ala Asn Pro Ala Leu Ile Ala
            275                 280                 285

Ser Met Val Pro Glu Ile Val Arg Trp Gln Thr Pro Leu Ala His Met
    290                 295                 300

Arg Arg Thr Ala Leu Gln Asp Thr Glu Leu Gly Gly Lys Ser Ile Arg
305                 310                 315                 320

Lys Gly Asp Lys Val Ile Met Trp Tyr Val Ser Gly Asn Arg Asp Pro
                325                 330                 335

Glu Ala Ile Glu Asn Pro Asp Ala Phe Ile Ile Asp Arg Ala Lys Pro
            340                 345                 350

Arg His His Leu Ser Phe Gly Phe Gly Ile His Arg Cys Val Gly Asn
    355                 360                 365

Arg Leu Ala Glu Leu Gln Leu Arg Ile Val Trp Glu Glu Leu Leu Lys
370                 375                 380

Arg Trp Pro Asn Pro Gly Gln Ile Glu Val Val Gly Ala Pro Glu Arg
385                 390                 395                 400

Val Leu Ser Pro Phe Val Lys Gly Tyr Glu Ser Leu Pro Val Arg Ile
                405                 410                 415

Asn Ala

<210> SEQ ID NO 80
<211> LENGTH: 422
<212> TYPE: PRT
<213> ORGANISM: Caulobacter sp.

<400> SEQUENCE: 80

Met Ser Asp Gly Ser Ile Asp Phe Gly Asp Asp Ala Arg Ala Lys Ala
1               5                   10                  15

Trp Ser Ile Pro Leu Glu Asp Tyr His Val Ala Asp Pro Ala Leu Phe
            20                  25                  30

Gln Ala Asp Ala Met Trp Pro Tyr Phe Glu Arg Leu Arg Lys Glu Asp
        35                  40                  45

Pro Val His Trp Ser Arg Gly Ile Glu Glu Thr Gly Pro Tyr Trp Ser
    50                  55                  60

Ile Thr Lys Tyr Asn Asp Ile Met Ala Val Asp Thr Asn His Gln Val
65                  70                  75                  80

Phe Ser Ser Asp Ala His Leu Gly Gly Ile Thr Ile Arg Asp Phe Asp
                85                  90                  95

Glu Asp Phe Val Leu Pro Met Phe Ile Ala Met Asp Pro Pro Lys His
            100                 105                 110

Asp Ile Gln Arg Lys Thr Val Ser Pro Ile Val Ser Pro Gln Asn Leu
        115                 120                 125

Ala Arg Leu Glu Gly Ile Ile Arg Glu Arg Val Cys Thr Ile Leu Asp
    130                 135                 140
```

Gly Leu Pro Ile Gly Glu Thr Phe Asp Trp Val Asp Lys Val Ser Ile
145                 150                 155                 160

Glu Leu Thr Thr Gln Met Leu Ala Thr Leu Phe Asp Phe Pro Trp Glu
            165                 170                 175

Glu Arg Arg Lys Leu Thr Arg Trp Ser Asp Val Ala Thr Ala Ser Pro
        180                 185                 190

Glu Ser Gly Ile Ile Glu Ser Glu Ala Arg Arg Ala Glu Leu Leu
        195                 200                 205

Glu Cys Leu Ala Tyr Phe Thr Asn Leu Trp Asn Glu Arg Val Asn Ala
    210                 215                 220

Thr Glu Pro Gly Asp Asp Leu Ile Ser Met Leu Ala His Gly Glu Ala
225                 230                 235                 240

Thr Arg Asp Met Pro Pro Met Glu Tyr Leu Gly Asn Ile Ile Leu Leu
                245                 250                 255

Ile Val Gly Gly Asn Asp Thr Thr Arg Asn Ser Leu Thr Gly Gly Leu
            260                 265                 270

Tyr Ala Leu Ser Lys Asn Pro Glu Gln Glu Ala Lys Leu Arg Ala Asp
        275                 280                 285

Pro Glu Leu Ile Pro Ser Met Val Ser Glu Ile Arg Trp Gln Thr
    290                 295                 300

Pro Leu Ala His Met Arg Arg Thr Ala Leu Ala Asp Ile Glu Leu Gly
305                 310                 315                 320

Gly Lys Gln Ile Arg Lys Gly Asp Lys Val Met Trp Tyr Val Ser
                325                 330                 335

Gly Asn Arg Asp Asp Thr Val Ile Glu Asn Pro Asp Ala Phe Ile Ile
            340                 345                 350

Asp Arg Glu Asn Pro Arg Arg His Leu Ser Phe Gly Phe Gly Ile His
        355                 360                 365

Arg Cys Val Gly Asn Arg Leu Ala Glu Met Gln Leu Lys Ile Val Trp
    370                 375                 380

Glu Glu Ile Leu Lys Arg Phe Pro Lys Ile Glu Val Leu Gly Glu Pro
385                 390                 395                 400

Lys Arg Val Tyr Ser Ser Phe Val Lys Gly Tyr Glu Ser Leu Pro Val
                405                 410                 415

Arg Ile Pro Thr Arg Leu
                420

<210> SEQ ID NO 81
<211> LENGTH: 421
<212> TYPE: PRT
<213> ORGANISM: Parvibaculum lavamentivorans

<400> SEQUENCE: 81

Met Ser Glu Thr Leu Val Ala Ala Arg Asp Lys Ser Ile Ala Asp Ala
1               5                   10                  15

Tyr Ala Ile Pro Leu Glu Lys Ile Asp Val Ser Asn Pro Glu Leu Phe
            20                  25                  30

Arg Ala Asn Ala Ile Trp Pro Tyr Phe Glu Arg Leu Arg Arg Glu Asp
        35                  40                  45

Pro Val His Tyr Cys Lys Glu Ser Glu Tyr Gly Ser Phe Trp Ser Val
    50                  55                  60

Thr Lys Tyr Lys Asp Ile Met His Val Asp Thr Asn His Gly Ile Tyr
65                  70                  75                  80

Ser Ser Glu Ala Thr Leu Gly Gly Val Ala Leu Arg Asn Gln Glu Glu
                85                  90                  95

Gly Phe Phe Leu Pro Met Phe Ile Met Met Asp Pro Lys His Asp
                100                 105                 110

Ala Gln Arg Lys Val Val Ser Pro Ile Val Ala Pro Gly Asn Leu Ala
            115                 120                 125

Lys Leu Glu Gly Thr Ile Arg Glu Arg Ala Gly Asn Ile Leu Asp Ser
130                 135                 140

Leu Pro Val Asn Glu Thr Phe Asp Trp Val Asp Arg Val Ser Ile Glu
145                 150                 155                 160

Leu Thr Thr Gln Met Leu Ala Thr Leu Phe Asp Phe Pro Trp Glu Glu
                165                 170                 175

Arg Arg Lys Leu Thr Arg Trp Ser Asp Val Ala Ala Gly Thr Ala
            180                 185                 190

Phe Gly Asp Glu Glu Thr Glu Lys Ala Arg Arg Asn Glu Leu Arg Asp
        195                 200                 205

Cys Ala Ala Tyr Phe Thr Glu Leu Trp Asn Gln Arg Val Asn Ala Thr
    210                 215                 220

Glu Pro Gly Asn Asp Leu Ile Thr Met Leu Ala Gln Gly Glu Ala Thr
225                 230                 235                 240

Lys Asn Met Gly Pro Met Glu Tyr Leu Gly Asn Val Leu Leu Leu Ile
                245                 250                 255

Val Gly Gly Asn Asp Thr Thr Arg Asn Ser Ile Thr Gly Gly Leu Leu
            260                 265                 270

Ala Leu Asn Glu Asn Pro Val Gln Tyr Lys Lys Leu Arg Asp Asn Pro
        275                 280                 285

Ser Leu Val Glu Ser Met Val Pro Glu Ile Ile Arg Trp Gln Thr Pro
    290                 295                 300

Leu Ser His Met Arg Arg Thr Ala Leu Gln Asp Thr Glu Leu Gly Gly
305                 310                 315                 320

Lys Gln Ile Lys Lys Gly Asp Lys Val Val Met Trp Tyr Val Ser Gly
                325                 330                 335

Asn Arg Asp Glu Glu Ala Ile Glu Asn Ala Asn Ser Phe Ile Ile Asp
            340                 345                 350

Arg Lys His Pro Arg Gln His Leu Ser Phe Gly Phe Gly Ile His Arg
        355                 360                 365

Cys Val Gly Asn Arg Leu Ala Glu Met Gln Leu Arg Val Val Trp Glu
    370                 375                 380

Glu Ile Leu Lys Arg Trp Pro Asp Lys Pro Ile Glu Val Val Gly Glu
385                 390                 395                 400

Pro Thr Arg Val Phe Ser Asn Leu Ile Lys Gly Tyr Ser Ser Met Pro
                405                 410                 415

Val Arg Ile Pro Gly
            420

<210> SEQ ID NO 82
<211> LENGTH: 416
<212> TYPE: PRT
<213> ORGANISM: Sphingopyxis macrogoltabida

<400> SEQUENCE: 82

Met Glu His Thr Gly Gln Ser Ala Ala Ala Thr Met Pro Leu Asp Ser
1               5                   10                  15

Ile Asp Val Ser Ile Pro Glu Leu Phe Tyr Asn Asp Ser Val Gly Glu
            20                  25                  30

Tyr Phe Lys Arg Leu Arg Lys Asp Asp Pro Val His Tyr Cys Ala Asp

```
            35                  40                  45
Ser Ala Phe Gly Pro Tyr Trp Ser Ile Thr Lys Tyr Asn Asp Ile Met
 50                  55                  60

His Val Asp Thr Asn His Asp Ile Phe Ser Ser Asp Ala Gly Tyr Gly
 65                  70                  75                  80

Gly Ile Ile Ile Asp Gly Ile Gln Lys Gly Asp Gly Gly Leu
                 85                  90                  95

Asp Leu Pro Asn Phe Ile Ala Met Asp Arg Pro Arg His Asp Glu Gln
                100                 105                 110

Arg Lys Ala Val Ser Pro Ile Val Ala Pro Ala Asn Leu Ala Ala Leu
            115                 120                 125

Glu Gly Thr Ile Arg Glu Arg Val Ser Lys Thr Leu Asp Gly Leu Pro
            130                 135                 140

Val Gly Glu Glu Phe Asp Trp Val Asp Arg Val Ser Ile Glu Ile Thr
145                 150                 155                 160

Thr Gln Met Leu Ala Thr Leu Phe Asp Phe Pro Phe Glu Glu Arg Arg
                165                 170                 175

Lys Leu Thr Arg Trp Ser Asp Val Thr Thr Ala Pro Gly Gly Gly
            180                 185                 190

Val Val Glu Ser Trp Asp Gln Arg Lys Thr Glu Leu Leu Glu Cys Ala
            195                 200                 205

Ala Tyr Phe Gln Val Leu Trp Asn Glu Arg Val Asn Lys Asp Pro Gly
210                 215                 220

Asn Asp Leu Ile Ser Met Leu Ala His Ser Pro Ala Thr Arg Asn Met
225                 230                 235                 240

Thr Pro Glu Glu Tyr Leu Gly Asn Val Leu Leu Ile Val Gly Gly
                245                 250                 255

Asn Asp Thr Thr Arg Asn Ser Met Thr Gly Gly Val Leu Ala Leu His
            260                 265                 270

Lys Asn Pro Asp Gln Phe Ala Lys Leu Lys Ala Asn Pro Ala Leu Val
            275                 280                 285

Glu Thr Met Val Pro Glu Ile Ile Arg Trp Gln Thr Pro Leu Ala His
            290                 295                 300

Met Arg Arg Thr Ala Ile Ala Asp Ser Glu Leu Gly Lys Thr Ile
305                 310                 315                 320

Arg Lys Gly Asp Lys Val Val Met Trp Tyr Tyr Ser Gly Asn Arg Asp
                325                 330                 335

Asp Glu Val Ile Asp Arg Pro Glu Glu Phe Ile Ile Asp Arg Pro Arg
            340                 345                 350

Pro Arg Gln His Leu Ser Phe Gly Phe Gly Ile His Arg Cys Val Gly
            355                 360                 365

Asn Arg Leu Ala Glu Met Gln Leu Arg Ile Leu Trp Glu Glu Ile Leu
            370                 375                 380

Thr Arg Phe Ser Arg Ile Glu Val Met Ala Glu Pro Glu Arg Val Arg
385                 390                 395                 400

Ser Asn Phe Val Arg Gly Tyr Ala Lys Met Met Val Arg Val His Ala
                405                 410                 415
```

<210> SEQ ID NO 83
<211> LENGTH: 425
<212> TYPE: PRT
<213> ORGANISM: Sphingopyxis macrogoltabida

<400> SEQUENCE: 83

```
Met Ala Thr Arg Ser Met Gln Ser Gly Pro Asp Arg Glu Glu Pro Asp
1               5                   10                  15

Arg Pro Ile Ala Glu Ile Pro Leu Ala Glu Ile Asp Val Ser Arg Pro
            20                  25                  30

Ser Leu Phe Gln Ser Asp Lys Val Gly Ala Phe Phe Glu Arg Leu Arg
            35                  40                  45

Arg Glu Asp Pro Val His Tyr Cys Ser Glu Ser Ala Phe Gly Pro Tyr
            50                  55                  60

Trp Ser Ile Thr Arg Tyr Asn Asp Ile Met Ala Val Asp Thr Asn His
65                  70                  75                  80

Lys Leu Phe Ser Ser Glu Ala Lys Leu Gly Gly Ile Ala Ile Gln Asp
            85                  90                  95

Met His Asn Asp Ala Thr Asn Leu Glu Leu Glu Met Phe Ile Ala Met
            100                 105                 110

Asp Gln Pro Lys His Asp Ala Gln Arg Lys Ala Val Thr Pro Ala Val
            115                 120                 125

Ala Pro Ser Asn Leu Leu Leu Glu Pro Val Ile Arg Glu Arg Ala
            130                 135                 140

Gly Ala Ile Leu Asp Ser Leu Pro Val Gly Glu Glu Ile Asp Trp Val
145                 150                 155                 160

Lys Ser Val Ser Val Glu Leu Thr Thr Met Thr Leu Ala Thr Leu Phe
            165                 170                 175

Asp Phe Pro Trp Asp Glu Arg Ala Lys Leu Thr Arg Trp Ser Asp Val
            180                 185                 190

Thr Thr Ala Ile Pro Gly Ser Gly Ile Val Glu Ser Asn Glu Gln Arg
            195                 200                 205

Arg Gln Glu Leu Ile Glu Cys Ala Met Tyr Phe Lys Gly Leu Trp Asp
            210                 215                 220

Gln Arg Ile Asp Arg Ser Glu Gly Ser Asp Leu Ile Thr Met Met Ala
225                 230                 235                 240

Asn Ser Pro Ala Thr Arg Glu Met Pro Phe Leu Glu Phe Leu Gly Asn
            245                 250                 255

Leu Leu Leu Leu Ile Val Gly Gly Asn Asp Thr Thr Arg Asn Ser Ile
            260                 265                 270

Ser Gly Gly Val Ile Ala Leu Asn Gln Asn Pro Asp Gln Tyr Glu Lys
            275                 280                 285

Leu Arg Gln His Pro Ser Leu Ile Gly Ser Met Val Pro Glu Ile Ile
            290                 295                 300

Arg Trp Gln Thr Pro Leu Thr His Met Arg Arg Thr Ala Leu Ala Asp
305                 310                 315                 320

Ser Glu Ile Gly Gly Lys Arg Ile Ala Lys Gly Asp Lys Val Val Met
            325                 330                 335

Trp Tyr Leu Ser Gly Asn Arg Asp Glu Thr Val Ile Glu Arg Pro Glu
            340                 345                 350

Glu Phe Ile Ile Asp Arg Lys Asn Pro Arg Gln His Leu Ser Phe Gly
            355                 360                 365

Tyr Gly Ile His Arg Cys Met Gly Asn Arg Leu Ala Glu Leu Gln Leu
            370                 375                 380

Arg Ile Ile Trp Glu Glu Ile His Lys Arg Phe Arg Leu Val Glu Met
385                 390                 395                 400

Val Gly Glu Pro Glu Arg Leu Leu Ser Asn Leu Val Arg Gly Ile Thr
            405                 410                 415

Arg Leu Pro Val Lys Leu His Ala His
```

<210> SEQ ID NO 84
<211> LENGTH: 420
<212> TYPE: PRT
<213> ORGANISM: Erythrobacter litoralis

<400> SEQUENCE: 84

```
Met Asp Ser Gln Ile Ala Glu Pro Asp Ala Ala Arg Ile Ala Ser
1               5                   10                  15

Ile Pro Ile Glu Glu Ile Asp Val Ala Arg Pro Ser Leu Phe Gln Asn
            20                  25                  30

Asp Thr Ile Gly Leu Phe Phe Asp Arg Leu Arg Ala Glu Pro Val
            35                  40                  45

His Tyr Cys Arg Glu Ser Tyr Val Gly Pro Tyr Trp Ser Ile Thr Lys
    50                  55                  60

Phe Asp Asp Ile Met Ala Val Asp Thr Asn His Lys Val Phe Ser Ser
65                  70                  75                  80

Glu Ala Lys Leu Gly Gly Ile Ala Ile Gln Asp Met His Ser Val Glu
                85                  90                  95

Gly Ala Leu Glu Leu Glu Met Phe Ile Ala Met Asp Pro Pro Lys His
            100                 105                 110

Asp Gln Gln Arg Lys Ala Val Thr Pro Ala Val Ala Pro Ser Asn Leu
        115                 120                 125

Gln Leu Leu Glu Pro Ile Ile Arg Lys Arg Ala Gly Glu Ile Leu Asp
    130                 135                 140

Glu Leu Pro Ile Gly Glu Asp Phe Asp Trp Val Asp Lys Val Ala Ile
145                 150                 155                 160

Glu Leu Thr Thr Met Thr Leu Ala Thr Leu Phe Asp Phe Pro Trp Glu
                165                 170                 175

Glu Arg Arg Lys Leu Thr Arg Trp Ser Asp Val Ala Thr Ala Ala Pro
            180                 185                 190

Glu Thr Gly Ile Val Glu Ser Tyr Glu Ala Arg Arg Glu Glu Leu Ile
        195                 200                 205

Gly Cys Ala Met Tyr Phe Lys Thr Leu Trp Asp Glu Arg Ile Asn Glu
    210                 215                 220

Glu Pro Lys Asn Asp Leu Ile Ser Met Met Ala His Ser Pro Ala Thr
225                 230                 235                 240

Arg Asp Met Pro Phe Leu Glu Phe Leu Gly Asn Leu Met Leu Leu Ile
                245                 250                 255

Val Gly Gly Asn Asp Thr Thr Arg Asn Ser Ile Ser Gly Gly Val Leu
            260                 265                 270

Ala Leu Asn Gln Ser Pro Asp Glu Tyr Ala Lys Leu Asp Ala Asp Pro
        275                 280                 285

Ser Leu Ile Ser Lys Met Val Pro Glu Ile Ile Arg Trp Gln Thr Pro
    290                 295                 300

Leu Thr His Met Arg Arg Thr Ala Leu Glu Asp Trp Glu Ile Gly Gly
305                 310                 315                 320

Lys Gln Ile Lys Lys Gly Asp Lys Val Val Met Trp Tyr Leu Ser Gly
                325                 330                 335

Asn Arg Asp Glu Ser Ala Ile Glu Arg Ala Asp Gln Phe Ile Ile Asp
            340                 345                 350

Arg Lys Asn Pro Arg His Leu Ser Phe Gly Tyr Gly Ile His Arg
        355                 360                 365
```

```
Cys Met Gly Asn Arg Leu Ala Glu Leu Gln Leu Arg Ile Ile Trp Glu
    370                 375                 380
Glu Ile His Lys Arg Phe Ser Arg Val Glu Val Thr Gly Glu Pro Glu
385                 390                 395                 400
Arg Leu Phe Ser Asn Leu Val Arg Gly Ile Thr Arg Leu Pro Val Arg
                405                 410                 415
Leu Arg Ala Arg
            420

<210> SEQ ID NO 85
<211> LENGTH: 470
<212> TYPE: PRT
<213> ORGANISM: Marinobacter hydrocarbonoclasticus

<400> SEQUENCE: 85

Met Pro Thr Leu Pro Arg Thr Phe Asp Asp Ile Gln Ser Arg Leu Ile
1               5                   10                  15
Asn Ala Thr Ser Arg Val Val Pro Met Gln Arg Gln Ile Gln Gly Leu
                20                  25                  30
Lys Phe Leu Met Ser Ala Lys Arg Lys Thr Phe Gly Pro Arg Arg Pro
            35                  40                  45
Met Pro Glu Phe Val Glu Thr Pro Ile Pro Asp Val Asn Thr Leu Ala
    50                  55                  60
Leu Glu Asp Ile Asp Val Ser Asn Pro Phe Leu Tyr Arg Gln Gly Gln
65                  70                  75                  80
Trp Arg Ala Tyr Phe Lys Arg Leu Arg Asp Glu Ala Pro Val His Tyr
                85                  90                  95
Gln Lys Asn Ser Pro Phe Gly Pro Phe Trp Ser Val Thr Arg Phe Glu
            100                 105                 110
Asp Ile Leu Phe Val Asp Lys Ser His Asp Leu Phe Ser Ala Glu Pro
    115                 120                 125
Gln Ile Ile Leu Gly Asp Pro Pro Glu Gly Leu Ser Val Glu Met Phe
130                 135                 140
Ile Ala Met Asp Pro Pro Lys His Asp Val Gln Arg Ser Ser Val Gln
145                 150                 155                 160
Gly Val Val Ala Pro Lys Asn Leu Lys Glu Met Glu Gly Leu Ile Arg
                165                 170                 175
Ser Arg Thr Gly Asp Val Leu Asp Ser Leu Pro Thr Asp Lys Pro Phe
            180                 185                 190
Asn Trp Val Pro Ala Val Ser Lys Glu Leu Thr Gly Arg Met Leu Ala
    195                 200                 205
Thr Leu Leu Asp Phe Pro Tyr Glu Glu Arg His Lys Leu Val Glu Trp
210                 215                 220
Ser Asp Arg Met Ala Gly Ala Ala Ser Ala Thr Gly Gly Glu Phe Ala
225                 230                 235                 240
Asp Glu Asn Ala Met Phe Asp Asp Ala Ala Asp Met Ala Arg Ser Phe
                245                 250                 255
Ser Arg Leu Trp Arg Asp Lys Glu Ala Arg Ala Ala Gly Glu Glu
            260                 265                 270
Pro Gly Phe Asp Leu Ile Ser Leu Leu Gln Ser Asn Lys Glu Thr Lys
    275                 280                 285
Asp Leu Ile Asn Arg Pro Met Glu Phe Ile Gly Asn Leu Thr Leu Leu
290                 295                 300
Ile Val Gly Gly Asn Asp Thr Thr Arg Asn Ser Met Ser Gly Gly Leu
305                 310                 315                 320
```

Val Ala Met Asn Glu Phe Pro Arg Glu Phe Glu Lys Leu Lys Ala Lys
            325                 330                 335

Pro Glu Leu Ile Pro Asn Met Val Ser Glu Ile Ile Arg Trp Gln Thr
        340                 345                 350

Pro Leu Ala Tyr Met Arg Arg Ile Ala Lys Gln Asp Val Glu Leu Gly
            355                 360                 365

Gly Gln Thr Ile Lys Lys Gly Asp Arg Val Val Met Trp Tyr Ala Ser
    370                 375                 380

Gly Asn Arg Asp Glu Arg Lys Phe Asp Asn Pro Asp Gln Phe Ile Ile
385                 390                 395                 400

Asp Arg Lys Asp Ala Arg Asn His Met Ser Phe Gly Tyr Gly Val His
                405                 410                 415

Arg Cys Met Gly Asn Arg Leu Ala Glu Leu Gln Leu Arg Ile Leu Trp
            420                 425                 430

Glu Glu Ile Leu Lys Arg Phe Asp Asn Ile Glu Val Val Glu Glu Pro
            435                 440                 445

Glu Arg Val Gln Ser Asn Phe Val Arg Gly Tyr Ser Arg Leu Met Val
        450                 455                 460

Lys Leu Thr Pro Asn Ser
465                 470

<210> SEQ ID NO 86
<211> LENGTH: 463
<212> TYPE: PRT
<213> ORGANISM: Mycobacterium marinum

<400> SEQUENCE: 86

Met Ser Asn Ile Arg Glu Ala Val Thr Ala Lys Ala Gln Ala Thr Ile
1               5                   10                  15

Pro Met Asp Arg Ile Ile Gln Gly Ala His Leu Tyr Asp Arg Thr Arg
            20                  25                  30

Arg Trp Val Thr Gly Thr Asn Gly Glu Lys Ile Phe Ile Glu Arg Pro
        35                  40                  45

Ile Pro Pro Ala Asp Glu Val Glu Leu Thr Asp Ile Asp Leu Ser Asn
    50                  55                  60

Pro Phe Leu Tyr Arg Gln Gly Arg Trp Lys Ser Tyr Tyr Glu Arg Leu
65                  70                  75                  80

Arg Asn Glu Ala Pro Val His Tyr Gln Ala His Ser Ala Phe Gly Pro
                85                  90                  95

Phe Trp Ser Val Thr Arg His Ala Asp Ile Val Ala Val Asp Lys Asn
            100                 105                 110

His Glu Val Phe Ser Ser Glu Pro Phe Ile Val Ile Gly Ser Pro Pro
        115                 120                 125

Arg Phe Leu Asp Ile Ala Met Phe Ile Ala Met Asp Pro Pro Lys His
    130                 135                 140

Asp Arg Gln Arg Gln Ala Val Gln Gly Val Val Ala Pro Lys Asn Leu
145                 150                 155                 160

Arg Glu Met Glu Gly Leu Ile Arg Glu Arg Val Val Asp Val Leu Asp
                165                 170                 175

Ala Leu Pro Leu Gly Glu Pro Phe Asn Trp Val Gln His Val Ser Ile
            180                 185                 190

Glu Leu Thr Ala Arg Met Leu Ala Thr Leu Leu Asp Phe Pro Phe Glu
        195                 200                 205

Gln Arg Arg Lys Leu Val Gln Trp Ser Asp Leu Ala Thr Ser Met Glu

```
              210                 215                 220
Gln Ala Asn Gly Gly Pro Ser Asp Asn Asp Glu Ile Phe Arg Gly Met
225                 230                 235                 240

Val Asp Met Ala Arg Gly Leu Ser Ala His Trp Arg Asp Lys Ala Ala
                245                 250                 255

Arg Thr Ala Ala Gly Glu Leu Pro Gly Phe Asp Leu Ile Thr Met Leu
                260                 265                 270

Gln Ser Asp Glu Ser Thr Lys Asp Leu Ile Asp Arg Pro Met Glu Phe
            275                 280                 285

Leu Gly Asn Leu Val Leu Leu Ile Val Gly Gly Asn Asp Thr Thr Arg
        290                 295                 300

Asn Ser Met Ser Gly Gly Val Leu Ala Leu Asn Glu Phe Pro Asp Gln
305                 310                 315                 320

Phe Glu Lys Leu Lys Ala Asn Pro Glu Leu Ile Pro Asn Met Val Ser
                325                 330                 335

Glu Ile Ile Arg Trp Gln Thr Pro Leu Ala His Met Arg Arg Ile Ala
                340                 345                 350

Lys Ala Asp Thr Val Leu Asn Gly Gln Phe Ile Arg Lys Gly Asp Lys
            355                 360                 365

Val Leu Met Trp Tyr Ala Ser Gly Asn Arg Asp Glu Arg Val Phe Asp
        370                 375                 380

Arg Pro Asp Asp Leu Ile Ile Asp Arg Ala Asn Ala Arg Asn His Ile
385                 390                 395                 400

Ser Phe Gly Phe Gly Val His Arg Cys Met Gly Asn Arg Leu Ala Glu
                405                 410                 415

Met Gln Leu Arg Ile Leu Trp Glu Glu Leu Leu Pro Arg Phe Glu Asn
                420                 425                 430

Ile Glu Val Val Gly Glu Pro Glu Tyr Val Gln Ser Asn Phe Val Arg
            435                 440                 445

Gly Ile Ser Lys Leu Met Val Arg Leu Thr Pro Lys Gly Gly Ala
        450                 455                 460

<210> SEQ ID NO 87
<211> LENGTH: 497
<212> TYPE: PRT
<213> ORGANISM: Acinetobacter sp.

<400> SEQUENCE: 87

Met Asn Ser Val Ala Glu Ile Phe Glu Lys Ile Thr Gln Thr Val Thr
1               5                   10                  15

Ser Thr Ala Ala Asp Val Ala Thr Thr Val Thr Asp Lys Val Lys Ser
                20                  25                  30

Asn Glu Gln Phe Gln Thr Gly Lys Gln Phe Leu His Gly Gln Val Thr
            35                  40                  45

Arg Phe Val Pro Leu His Thr Gln Val Arg Gly Ile Gln Trp Met Gln
        50                  55                  60

Lys Ala Lys Phe Arg Val Phe Asn Val Gln Glu Phe Pro Ala Phe Ile
65                  70                  75                  80

Glu Gln Pro Ile Pro Glu Val Ala Thr Leu Ala Leu Ala Glu Ile Asp
                85                  90                  95

Val Ser Asn Pro Phe Leu Tyr Lys Gln Lys Trp Gln Ser Tyr Phe
            100                 105                 110

Lys Arg Leu Arg Asp Glu Ala Pro Val His Tyr Gln Ala Asn Ser Pro
        115                 120                 125
```

-continued

```
Phe Gly Ala Phe Trp Ser Val Thr Arg Tyr Asp Asp Ile Val Tyr Val
    130                 135                 140
Asp Lys Asn His Glu Ile Phe Ser Ala Glu Pro Val Ile Ala Ile Gly
145                 150                 155                 160
Asn Thr Pro Pro Gly Leu Gly Ala Glu Met Phe Ile Ala Met Asp Pro
                165                 170                 175
Pro Lys His Asp Val Gln Arg Gln Ala Val Gln Asp Val Val Ala Pro
            180                 185                 190
Lys Asn Leu Lys Glu Leu Glu Gly Leu Ile Arg Leu Arg Val Gln Glu
        195                 200                 205
Val Leu Asp Gln Leu Pro Thr Asp Gln Pro Phe Asp Trp Val Gln Asn
    210                 215                 220
Val Ser Ile Glu Leu Thr Ala Arg Met Leu Ala Thr Leu Phe Asp Phe
225                 230                 235                 240
Pro Tyr Glu Lys Arg His Lys Leu Val Glu Trp Ser Asp Leu Met Ala
                245                 250                 255
Gly Thr Ala Glu Ala Thr Gly Gly Thr Val Thr Asn Leu Asp Glu Ile
            260                 265                 270
Phe Asp Ala Ala Val Asp Ala Ala Lys His Phe Ala Glu Leu Trp His
        275                 280                 285
Arg Lys Ala Ala Gln Lys Ser Ala Gly Ala Glu Met Gly Tyr Asp Leu
    290                 295                 300
Ile Ser Leu Met Gln Ser Asn Glu Ala Thr Lys Asp Leu Ile Tyr Arg
305                 310                 315                 320
Pro Met Glu Phe Met Gly Asn Leu Val Leu Leu Ile Val Gly Gly Asn
                325                 330                 335
Asp Thr Thr Arg Asn Ser Met Thr Gly Gly Val Tyr Ala Leu Asn Leu
            340                 345                 350
Phe Pro Asn Glu Phe Val Lys Leu Lys Asn Asn Pro Ser Leu Ile Pro
        355                 360                 365
Asn Met Val Ser Glu Ile Ile Arg Trp Gln Thr Pro Leu Ala Tyr Met
    370                 375                 380
Arg Arg Ile Ala Lys Gln Asp Val Glu Leu Asn Gly Gln Thr Ile Lys
385                 390                 395                 400
Lys Gly Asp Lys Val Val Met Trp Tyr Val Ser Gly Asn Arg Asp Glu
                405                 410                 415
Arg Val Ile Glu Arg Pro Asp Glu Leu Ile Ile Asp Arg Lys Gly Ala
            420                 425                 430
Arg Asn His Leu Ser Phe Gly Phe Gly Val His Arg Cys Met Gly Asn
        435                 440                 445
Arg Leu Ala Glu Met Gln Leu Arg Ile Leu Trp Glu Glu Leu Leu Gln
    450                 455                 460
Arg Phe Glu Asn Ile Glu Val Leu Gly Glu Pro Glu Ile Val Gln Ser
465                 470                 475                 480
Asn Phe Val Arg Gly Tyr Ala Lys Met Met Val Lys Leu Thr Ala Lys
                485                 490                 495
Ala
```

<210> SEQ ID NO 88
<211> LENGTH: 462
<212> TYPE: PRT
<213> ORGANISM: Rhodococcus erythropolis

<400> SEQUENCE: 88

```
Met Lys Val Ser Glu Val Ile Thr Asp Lys Val Gln Ser Ala Ile Pro
1               5                   10                  15

Ile Asp Leu Gln Ile Arg Gly Ala His Leu Tyr Asp Arg Thr Arg Arg
            20                  25                  30

Trp Val Thr Gly Ser Asn Gly Lys Lys Leu Phe Val Glu Ser Pro Ile
        35                  40                  45

Pro Pro Val Glu Asp Val Glu Leu Ala Asp Ile Asp Leu Ser Asn Pro
    50                  55                  60

Phe Leu Tyr Arg Gln Gly Arg Trp Gln Ser Tyr Tyr Glu Arg Leu Arg
65                  70                  75                  80

Asn Glu Ala Pro Val His Tyr Leu Pro Asp Ser Pro Phe Gly Pro Phe
                85                  90                  95

Trp Ser Val Thr Arg His Ala Asp Ile Met Ala Val Asp Lys Asp His
            100                 105                 110

Glu Ser Phe Ser Ala Glu Pro Leu Ile Val Ile Gly Val Pro Pro Arg
        115                 120                 125

Phe Leu Asp Ile Thr Met Phe Ile Ala Met Asp Pro Pro Arg His Asp
    130                 135                 140

Arg Gln Arg Ala Ala Val Gln Gly Val Val Ala Pro Lys Asn Leu Arg
145                 150                 155                 160

Glu Met Glu Gly Leu Ile Arg Ser Arg Val Gln Glu Val Leu Asp Asp
                165                 170                 175

Leu Pro Arg Asn Glu Pro Phe Asp Trp Val Gln Asn Val Ser Ile Glu
            180                 185                 190

Leu Thr Ala Arg Met Leu Ala Thr Leu Leu Asp Phe Pro Tyr Glu Gln
        195                 200                 205

Arg His Lys Leu Val Glu Trp Ser Asp Leu Ala Thr Ser Met Glu Gln
    210                 215                 220

Thr Asn Gly Gly Pro Ser Asp Leu Asp Asp Thr Phe Val Gly Met Arg
225                 230                 235                 240

Glu Met Ala Gln Gly Leu Ser Glu His Trp His Asp Lys Ala Ala Arg
                245                 250                 255

Thr Ala Ala Gly Glu Glu Pro Gly Phe Asp Leu Ile Thr Met Leu Gln
            260                 265                 270

Ser Asn Ala Asp Thr Lys Asp Leu Ile Ser Arg Pro Met Glu Phe Leu
        275                 280                 285

Gly Asn Leu Val Leu Leu Ile Val Gly Gly Asn Asp Thr Thr Arg Asn
    290                 295                 300

Ser Met Ser Gly Gly Val Leu Ala Leu Asn Arg Phe Pro Asp Gln Phe
305                 310                 315                 320

Glu Lys Leu Lys Ala Asn Pro Asp Leu Ile Ser Asn Met Asn Ser Glu
                325                 330                 335

Ile Ile Arg Trp Gln Thr Pro Leu Ala Tyr Met Arg Arg Ile Ala Lys
            340                 345                 350

Val Asp Thr Val Leu Asn Gly Gln Phe Ile Arg Lys Gly Asp Lys Val
        355                 360                 365

Val Met Trp Tyr Ala Ser Gly Asn Arg Asp Glu Arg Val Phe Asp Arg
370                 375                 380

Pro Asp Asp Phe Ile Ile Asp Arg Ala Asn Ala Arg Asn His Ile Ser
385                 390                 395                 400

Phe Gly Phe Gly Val His Arg Cys Met Gly Asn Arg Leu Ala Glu Leu
                405                 410                 415

Gln Leu Arg Ile Leu Trp Glu Glu Leu Leu Ala Arg Phe Glu Asn Ile
```

```
                420                 425                 430
Asp Val Ile Gly Glu Pro Glu Tyr Val Gln Ser Asn Phe Val Arg Gly
            435                 440                 445

Ile Ser Lys Met Thr Val Arg Leu Thr Pro Lys Ser Asp Ala
        450                 455                 460

<210> SEQ ID NO 89
<211> LENGTH: 470
<212> TYPE: PRT
<213> ORGANISM: Alcanivorax borkumensis

<400> SEQUENCE: 89

Met Ser Thr Ser Ser Thr Ser Asn Asp Ile Gln Ala Lys Ile Ile
1               5                   10                  15

Asn Ala Thr Ser Lys Val Val Pro Met His Leu Gln Ile Lys Ala Leu
                20                  25                  30

Lys Asn Leu Met Lys Val Lys Arg Lys Thr Ile Gly Thr Ser Arg Pro
            35                  40                  45

Gln Val His Phe Val Glu Thr Asp Leu Pro Asp Val Asn Asp Leu Ala
        50                  55                  60

Ile Glu Asp Ile Asp Thr Ser Asn Pro Phe Leu Tyr Arg Gln Gly Lys
65                  70                  75                  80

Ala Asn Ala Tyr Phe Lys Arg Leu Arg Asp Glu Ala Pro Val His Tyr
                85                  90                  95

Gln Lys Asn Ser Ala Phe Gly Pro Phe Trp Ser Val Thr Arg Tyr Glu
            100                 105                 110

Asp Ile Val Phe Val Asp Lys Ser His Asp Leu Phe Ser Ala Glu Pro
        115                 120                 125

Gln Ile Ile Leu Gly Asp Pro Pro Glu Gly Leu Ser Val Glu Met Phe
    130                 135                 140

Ile Ala Met Asp Pro Pro Lys His Asp Val Gln Arg Arg Ala Val Gln
145                 150                 155                 160

Gly Val Val Ala Pro Lys Asn Leu Lys Glu Met Glu Gly Leu Ile Arg
                165                 170                 175

Lys Arg Thr Gly Asp Val Leu Asp Ser Leu Pro Leu Asp Thr Pro Phe
            180                 185                 190

Asn Trp Val Pro Val Val Ser Lys Glu Leu Thr Gly Arg Met Leu Ala
        195                 200                 205

Ser Leu Leu Asp Phe Pro Tyr Asp Glu Arg Glu Lys Leu Val Gly Trp
    210                 215                 220

Ser Asp Arg Leu Ser Gly Ala Ser Ser Ala Thr Gly Gly Glu Phe Thr
225                 230                 235                 240

Asn Glu Asp Val Phe Phe Asp Asp Ala Ala Asp Met Ala Trp Ala Phe
                245                 250                 255

Ser Lys Leu Trp Arg Asp Lys Glu Ala Arg Gln Lys Ala Gly Glu Glu
            260                 265                 270

Pro Gly Phe Asp Leu Ile Ser Met Leu Gln Ser Asn Glu Asp Thr Lys
        275                 280                 285

Asp Leu Ile Asn Arg Pro Leu Glu Phe Ile Gly Asn Leu Ala Leu Leu
    290                 295                 300

Ile Val Gly Gly Asn Asp Thr Thr Arg Asn Ser Met Ser Gly Gly Val
305                 310                 315                 320

Leu Ala Leu Asn Gln Phe Pro Glu Gln Phe Glu Lys Leu Lys Ala Asn
                325                 330                 335
```

-continued

```
Pro Lys Leu Ile Pro Asn Met Val Ser Glu Ile Ile Arg Trp Gln Thr
            340                 345                 350
Pro Leu Ala Tyr Met Arg Arg Val Ala Lys Gln Asp Val Glu Leu Asn
        355                 360                 365
Gly Gln Thr Ile Lys Lys Gly Asp Arg Val Leu Met Trp Tyr Ala Ser
    370                 375                 380
Gly Asn Gln Asp Glu Arg Lys Phe Glu Asn Pro Gln Phe Ile Ile
385                 390                 395                 400
Asp Arg Lys Asp Thr Arg Asn His Val Ser Phe Gly Tyr Gly Val His
                405                 410                 415
Arg Cys Met Gly Asn Arg Leu Ala Glu Leu Gln Leu Arg Ile Leu Trp
            420                 425                 430
Glu Glu Leu Leu Pro Arg Phe Glu Asn Ile Glu Val Ile Gly Glu Pro
        435                 440                 445
Glu Arg Val Gln Ser Asn Phe Val Arg Gly Tyr Ser Lys Met Met Val
    450                 455                 460
Lys Leu Thr Ala Lys Lys
465                 470

<210> SEQ ID NO 90
<211> LENGTH: 416
<212> TYPE: PRT
<213> ORGANISM: Sphingopyxis macrogoltabida
<220> FEATURE:
<221> NAME/KEY: VARIANT
<222> LOCATION: (118)..(118)
<223> OTHER INFORMATION: Xaa = any amino acid
<220> FEATURE:
<221> NAME/KEY: VARIANT
<222> LOCATION: (315)..(315)
<223> OTHER INFORMATION: Xaa = any amino acid
<220> FEATURE:
<221> NAME/KEY: VARIANT
<222> LOCATION: (318)..(319)
<223> OTHER INFORMATION: Xaa = any amino acid

<400> SEQUENCE: 90

Met Ala Ser Thr Ala Thr Leu Val Arg Thr Ala Ser Pro Ile Ala Pro
1               5                   10                  15
Ile Asp Val Ser Leu Pro Glu Leu Tyr Ala Glu Asp Arg Trp Gln Glu
            20                  25                  30
Pro Phe Arg Thr Leu Arg Ala Gln Ala Pro Ile Gln Tyr Val Pro Asp
        35                  40                  45
Ser Lys Phe Gly Pro Tyr Trp Ser Val Thr Thr Tyr Lys Pro Ile Val
    50                  55                  60
Tyr Ile Glu Ala Leu Pro Lys Leu Phe Ser Ser Ser Trp Gln Tyr Gly
65              70                  75                  80
Gly Ile Ser Ile Ala Phe Asp Ser Asp Lys Leu Leu Glu His Glu Val
            85                  90                  95
Arg Gln Pro Met Phe Ile Ala Met Asp Pro Pro Gln His Thr Ala Gln
        100                 105                 110
Arg Arg Thr Val Ala Xaa Ser Phe Gly Pro Ser Glu Val Ala Ala Met
    115                 120                 125
Lys Ala Glu Val Gln Leu Arg Thr Gly Ala Leu Leu Asp Ser Leu Pro
130                 135                 140
Val Gly Asp Pro Phe Asp Trp Val Gln Lys Val Ser Ile Glu Leu Thr
145                 150                 155                 160
Thr Gly Met Leu Ala Arg Leu Phe Asp Phe Pro Trp Glu Glu Arg His
            165                 170                 175
```

```
Asn Leu Thr His Trp Ser Asp Ile Gly Gly Asp Val Glu Leu Ile Arg
            180                 185                 190

Ser Pro Glu Gly Leu Val Glu Arg Asn Thr Lys Leu Leu Gln Met Gly
        195                 200                 205

Met Ala Phe Ala Ala Leu Trp Gln Glu Lys Ala Gln Asn Pro Gly Lys
    210                 215                 220

Asp Leu Ile Ser Val Met Leu Lys Ser Asp Ala Met Asn His Met Ser
225                 230                 235                 240

Asn Glu Glu Phe Ile Gly Asn Leu Val Leu Leu Ile Val Gly Gly Asn
                245                 250                 255

Asp Thr Thr Arg Asn Ser Met Ser Ser Tyr Ala Tyr Gly Leu Ala Gln
                260                 265                 270

Phe Pro Glu Glu Arg Ala Lys Leu Glu Ala Asn Pro Ala Leu Ile Pro
            275                 280                 285

Asn Ala Val Gln Glu Leu Ile Arg Trp Gln Thr Pro Leu Ala His Met
        290                 295                 300

Arg Arg Thr Val Glu Glu Asp Thr Glu Ile Xaa Gly Gln Xaa Xaa Lys
305                 310                 315                 320

Lys Gly Asp Lys Val Val Leu Trp Tyr Leu Ser Ala Asn Arg Asp Glu
                325                 330                 335

Thr Val Phe Lys Asp Ala Asp Arg Ile Ile Val Gly Arg Glu Asn Ala
                340                 345                 350

Arg Arg His Leu Ser Phe Gly Tyr Gly Ile His Arg Cys Val Gly Ala
                355                 360                 365

Arg Val Ala Glu Leu Gln Leu Val Thr Leu Leu Glu Glu Met Ala Lys
            370                 375                 380

Arg Arg Leu Arg Ala Asn Val Leu Ala Glu Pro Val Arg Val Pro Ala
385                 390                 395                 400

Cys Phe Val His Gly Tyr Lys Ser Leu Gln Val Glu Leu Ser His Tyr
                405                 410                 415

<210> SEQ ID NO 91
<211> LENGTH: 429
<212> TYPE: PRT
<213> ORGANISM: Sphingopyxis macrogoltabida

<400> SEQUENCE: 91

Met Ala Thr Val Ile Arg Glu Thr Pro Ala Asp Leu His Pro Leu Asp
1               5                   10                  15

Leu Ser Arg Ala Asp Leu Trp Arg Glu Asp Gln Trp Gln Glu Pro Met
            20                  25                  30

Arg Gln Leu Arg Ala Glu Ser Pro Ile Tyr Tyr Cys Glu Asp Ser Lys
        35                  40                  45

Phe Gly Pro Tyr Trp Ser Val Thr Thr Tyr Lys Pro Ile Gln His Ile
    50                  55                  60

Glu Ala Leu Pro Lys Ile Phe Ser Ser Trp Glu Tyr Gly Gly Ile
65                  70                  75                  80

Thr Val Ala Gly Asp Gly Ile Glu His Leu Lys Glu Gly Glu Ile Pro
                85                  90                  95

Met Pro Met Phe Ile Ala Met Asp Pro Gln His Thr Ala Gln Arg
            100                 105                 110

Arg Thr Val Ala Pro Ala Phe Gly Pro Ser Glu Ile Glu Arg Met Arg
        115                 120                 125

Ala Asp Thr Gln Ala Arg Thr Ala Ala Leu Ile Asp Thr Leu Pro Val
```

```
                   130                 135                 140
Gly Glu Ala Phe Asp Trp Val Glu Arg Leu Ser Ile Glu Leu Thr Thr
145                 150                 155                 160

Asp Met Leu Ala Ile Leu Phe Asp Phe Pro Trp Glu Asn Arg His Asn
                165                 170                 175

Leu Thr Arg Trp Ser Asp Ala Leu Gly Asp Ile Glu Ser Phe Asn Thr
            180                 185                 190

Leu Glu Glu Arg Gln Gln Arg Leu Ala Thr Ala Phe Glu Met Gly Ala
        195                 200                 205

Ala Phe Lys Glu Leu Trp Asp His Lys Ala Lys Asn Pro Gly Lys His
    210                 215                 220

Asp Leu Ile Ser Ile Met Leu Gln Ser Asp Ala Met Asn His Met Ser
225                 230                 235                 240

His Glu Glu Phe Met Gly Asn Leu Ile Leu Leu Ile Val Gly Gly Asn
                245                 250                 255

Asp Thr Thr Arg Asn Ser Met Ser Ala Tyr Ala Tyr Gly Leu His Cys
            260                 265                 270

Phe Pro Glu Glu Arg Ala Lys Leu Glu Ala Asn His Asp Pro Asp Leu
        275                 280                 285

Ala Val Asn Ala Met His Glu Ile Ile Arg Trp Gln Thr Pro Leu Ala
    290                 295                 300

His Met Arg Arg Thr Ala Leu Glu Asp Thr Glu Leu Phe Gly His Gln
305                 310                 315                 320

Ile Arg Ala Arg Asp Lys Ile Ala Leu Trp Tyr Ala Ser Ala Asn Arg
                325                 330                 335

Asp Glu Ser Ile Phe Pro Asp Gly Asp Arg Ile Ile Val Asp Arg Glu
            340                 345                 350

Asn Ala Arg Arg His Leu Ala Phe Gly Tyr Gly Ile His Arg Cys Val
        355                 360                 365

Gly Ala Arg Val Ala Glu Leu Gln Leu Thr Thr Leu Ile Ser Glu Met
    370                 375                 380

Gln Lys Arg Arg Leu Arg Val Asn Val Leu Ala Glu Pro Glu Arg Val
385                 390                 395                 400

Asn Ala Ser Phe Val His Val Ser Pro His Ala Gly Arg Thr Arg Ala
                405                 410                 415

Leu Leu Thr Ala Val Thr Ala Gly Pro Ile Ser Ala Arg
            420                 425

<210> SEQ ID NO 92
<211> LENGTH: 505
<212> TYPE: PRT
<213> ORGANISM: Candida maltosa

<400> SEQUENCE: 92

Met Ala Ile Phe Thr Pro Glu Leu Trp Leu Ile Cys Phe Ala Val Thr
1               5                   10                  15

Val Tyr Ile Phe Asp Tyr Ile Tyr Thr Lys Tyr Leu Met Tyr Lys Leu
                20                  25                  30

Gly Ala Lys Pro Ile Thr His Val Ile Asp Asp Gly Phe Phe Gly Phe
            35                  40                  45

Arg Leu Pro Phe Leu Ile Thr Leu Ala Asn Asn Gln Gly Arg Leu Ile
        50                  55                  60

Glu Phe Ser Val Lys Arg Phe Leu Ser Ser Pro His Gln Thr Phe Met
65                  70                  75                  80
```

```
Asn Arg Ala Phe Gly Ile Pro Ile Ile Leu Thr Arg Asp Pro Val Asn
                85                  90                  95

Ile Lys Ala Met Leu Ala Val Gln Phe Asp Glu Phe Ser Leu Gly Leu
            100                 105                 110

Arg Tyr Asn Gln Phe Glu Pro Leu Leu Gly Asn Gly Ile Phe Thr Ser
        115                 120                 125

Asp Gly Glu Pro Trp Lys His Ser Arg Ile Met Leu Arg Pro Gln Phe
    130                 135                 140

Ile Lys Ser Gln Val Ser His Val Asn Arg Leu Glu Pro His Phe Asn
145                 150                 155                 160

Leu Leu Gln Lys Asn Ile Thr Ala Gln Thr Asp Asn Tyr Phe Asp Ile
                165                 170                 175

Gln Thr Leu Phe Phe Arg Phe Thr Leu Asp Thr Ala Thr Glu Phe Leu
            180                 185                 190

Phe Gly Gln Ser Val His Ser Leu Asn Asp Gly Glu Asn Ser Leu Gln
        195                 200                 205

Phe Leu Glu Ala Phe Thr Lys Ser Gln Ala Ile Leu Ala Thr Arg Ala
    210                 215                 220

Asn Leu His Glu Leu Tyr Phe Leu Ala Asp Gly Ile Lys Phe Arg Gln
225                 230                 235                 240

Tyr Asn Lys Met Val Gln Asp Phe Ser Gln Arg Cys Val Asp Lys Val
                245                 250                 255

Leu Asn Met Ser Asn Ser Glu Ile Asp Lys Leu Asp Arg Tyr Phe Phe
            260                 265                 270

Leu Tyr Glu Met Val Lys Ile Thr Arg Asn Pro Gln Val Leu Arg Asp
        275                 280                 285

Gln Cys Leu Asn Ile Leu Leu Ala Gly Arg Asp Thr Thr Ala Ser Leu
    290                 295                 300

Leu Ser Phe Ala Phe Phe Glu Leu Ala Leu Asn Glu Pro Ile Trp Ile
305                 310                 315                 320

Lys Leu Arg Thr Glu Val Leu His Val Phe Gln Thr Ser Leu Glu Leu
                325                 330                 335

Ile Thr Phe Asp Leu Leu Lys Thr Lys Cys Pro Tyr Leu Gln Ala Ile
            340                 345                 350

Leu His Glu Thr Leu Arg Leu Tyr Pro Ser Val Pro Arg Asn Ala Arg
        355                 360                 365

Phe Ser Lys Lys Asn Thr Thr Leu Pro His Gly Gly Gly Val Asp Gly
    370                 375                 380

Met Ser Pro Ile Leu Ile Lys Lys Gly Gln Pro Val Ala Tyr Phe Ile
385                 390                 395                 400

Cys Ala Thr His Val Asp Glu Lys Phe Tyr Thr Lys Asp Ala Leu Ile
                405                 410                 415

Phe Arg Pro Glu Arg Trp Cys Glu Glu Pro Leu Ile Lys Lys Asn Leu
            420                 425                 430

Ala Trp Ser Tyr Leu Pro Phe Asn Gly Gly Pro Arg Ile Cys Leu Gly
        435                 440                 445

Gln Gln Phe Ala Leu Thr Glu Ala Ser Tyr Val Leu Thr Arg Leu Ala
    450                 455                 460

Gln Cys Tyr Thr Lys Ile Ser Leu Gln Pro Asn Ser Phe Glu Tyr Pro
465                 470                 475                 480

Pro Lys Lys Gln Val His Leu Thr Met Ser Leu Leu Asp Gly Val His
                485                 490                 495

Val Lys Ile Ser Asn Leu Ser Ile Ser
```

<210> SEQ ID NO 93
<211> LENGTH: 526
<212> TYPE: PRT
<213> ORGANISM: Yarrowia lipolytica

<400> SEQUENCE: 93

```
Met Ile Gln Ser Val Phe Leu Ala Leu Ala Ile Leu Ala Tyr Leu
1               5                   10                  15

Gly Phe Ala Glu Trp Phe Ser Arg Phe Gln His Arg Ile Ser Lys
            20                  25                  30

Lys Lys Gly Cys Gly Met Pro Met Ala Asn Gly Gly Phe Leu Gly
            35                  40                  45

Trp Tyr Gly Leu Tyr Lys Thr Tyr Gln Ile Thr Ser Glu Arg Thr Tyr
    50                  55                  60

Pro His Ser Met Arg Met Gly Leu Glu Ala Phe Gly His Thr Phe Val
65                  70                  75                  80

Tyr Pro Val Pro Gly Thr Asp Met Leu Gln Thr Ile His Pro Asp Asn
                85                  90                  95

Ile Lys Ala Ile Leu Ala Thr Gln Phe Lys Asp Phe Ser Leu Gly Thr
            100                 105                 110

Arg His Lys Ile Met Leu Pro Thr Leu Gly Asp Gly Ile Phe Thr Leu
            115                 120                 125

Asp Gly Glu Gly Trp Thr His Ser Arg Ala Leu Leu Arg Pro Gln Phe
130                 135                 140

Ala Arg Asp Gln Val Ser His Val Ala Ser Leu Glu Arg His Ile Gln
145                 150                 155                 160

Val Leu Phe Lys Thr Ile Lys Lys Glu Asn Lys Glu Cys Asp Pro Ala
                165                 170                 175

Lys Gly Phe Asp Ile Gln Glu Leu Phe Phe Met Leu Thr Leu Asp Thr
            180                 185                 190

Ala Thr Glu Phe Leu Cys Gly Asp Ser Val Asp Ser Leu Thr Asp Tyr
            195                 200                 205

Leu Ala Asp Pro Thr Ala Pro Gln Leu Asp His Ser Gly Ile Asp Glu
            210                 215                 220

Asn Val Arg Arg Ala Phe Pro Glu Ala Phe Asn Thr Ala Gln Trp Phe
225                 230                 235                 240

Cys Ser Ile Arg Ala Lys Leu Met Lys Leu Tyr Phe Ala Gly Thr
                245                 250                 255

Val Phe Tyr Arg Lys Lys Tyr Ala Asp Ala Asn Lys Ile Val His Asp
                260                 265                 270

Phe Thr Asp Phe Tyr Val Ser Lys Ala Leu Ala Ala Arg Lys Glu Lys
            275                 280                 285

Phe Gln Glu Leu Asp Gln Glu Gly Lys Tyr Ile Phe Leu Tyr Glu Leu
290                 295                 300

Ala Lys Glu Thr Arg Asn Pro Lys Val Leu Arg Asp Gln Met Leu Asn
305                 310                 315                 320

Ile Leu Leu Ala Gly Arg Asp Thr Thr Ala Ser Leu Leu Ser Trp Val
                325                 330                 335

Met Phe Arg Met Ala Arg Gln Pro Glu Thr Trp Lys Lys Leu Arg Gln
            340                 345                 350

Ala Val Ile Asn Asp Phe Gly Asp Thr Pro Asp Glu Leu Ser Phe Glu
            355                 360                 365
```

-continued

| | | | | | | | | | | | |
|---|---|---|---|---|---|---|---|---|---|---|---|
| Ser | Leu 370 | Lys | Arg | Cys | Glu 375 | Tyr | Leu | Arg | Tyr | Val 380 | Leu Asn Glu Gly Leu |

Ser Leu Lys Arg Cys Glu Tyr Leu Arg Tyr Val Leu Asn Glu Gly Leu
    370             375                 380

Arg Leu Tyr Pro Ser Val Pro Met Asn Phe Arg Val Ala Thr Arg Asp
385             390             395                 400

Thr Thr Leu Pro Lys Gly Gly Pro Asp Leu Asp Gln Pro Ile Phe
            405             410             415

Ile Pro Lys Gly Gly Ile Val Val Tyr Ser Val Tyr His Thr His Arg
        420             425             430

Ala Glu Glu Tyr Trp Gly Lys Asp Thr Glu Glu Phe Ile Pro Glu Arg
        435             440             445

Trp Asp Pro Ala Glu Gly Tyr Gln Ile Ala Arg Gly Trp Glu Tyr Leu
    450             455             460

Pro Phe Asn Gly Gly Pro Arg Ile Cys Leu Gly Gln Gln Phe Ala Leu
465             470             475             480

Thr Glu Ala Gly Tyr Val Leu Ala Arg Leu Ala Gln Glu Phe Glu Thr
            485             490             495

Val Thr Ser Cys Asp Asp Lys Pro Leu Pro Pro Lys Tyr Asn Thr His
        500             505             510

Leu Thr Met Ser His Asp Asp Gly Val Trp Leu Lys Met Glu
    515             520             525

SYNTHESIS OF OLEFINIC ALCOHOLS VIA ENZYMATIC TERMINAL HYDROXYLATION

CROSS-REFERENCES TO RELATED APPLICATIONS

The present application is a continuation of PCT/US2015/031219, filed May 15, 2015, which application claims priority to U.S. Provisional Application No. 61/994,662, filed May 16, 2014; U.S. Provisional Application No. 62/060,469, filed Oct. 6, 2014; U.S. Provisional Application No. 62/062,758, filed Oct. 10, 2014; U.S. Provisional Application No. 62/082,555, filed Nov. 20, 2014; U.S. Provisional Application No. 62/096,417, filed Dec. 23, 2014; and U.S. Provisional Application No. 62/096,429, filed Dec. 23, 2014; which applications are incorporated herein by reference in their entirety for all purposes.

STATEMENT AS TO RIGHTS TO INVENTIONS MADE UNDER FEDERALLY SPONSORED RESEARCH AND DEVELOPMENT

Certain aspects of this invention were made with government support under award number IIP-1448692, awarded by the National Science Foundation. The government may have certain rights in the invention.

REFERENCE TO A SEQUENCE LISTING

The Substitute Sequence Listing written in file SecondSubstituteSequenceListing_095864-0957387.txt created on Nov. 14, 2017, 359,804 bytes, machine format IBM-PC, MS-Windows operating system, is hereby incorporated by reference in its entirety for all purposes.

BACKGROUND OF THE INVENTION

Insect pheromones can be used in a variety of insect control strategies that include mating disruption and attract-and-kill, as well as mass trapping. These strategies have proven to be effective, selective (e.g., they do not harm beneficial insects, such as bees and lady bugs), and safe (e.g., the compounds are generally biodegradable and do not accumulate in the food chain). Even the very stringent USDA Organic Program lists insect pheromones as one of the few synthetic organic compounds allowed in organic crop production, another important recognition of the high safety of these products. Accordingly, pheromones already form the basis of integrated pest management (IPM) practices in fruit production on the U.S. west coast, and their use in organic farming is growing worldwide.

Despite these advantages, pheromones are not widely used today because of the high cost of about $500 to $14,000 per kg of active ingredient (AI). Even though thousands of insect pheromones have been identified, less than about twenty insect pests worldwide are currently controlled using pheromone strategies, and only 0.05% of global agricultural land employs pheromones.

Lepidopteran pheromones, which are naturally occurring compounds, or identical or substantially similar synthetic compounds, are designated by an unbranched aliphatic chain (between 9 and 18 carbons) ending in an alcohol, aldehyde, or acetate functional group and containing up to 3 double bonds in the aliphatic backbone.

The present invention provides methods by which lepidopteran insect pheromones as well as structurally related compounds are prepared using synthetic strategies that are enabled by a biocatalytic step.

BRIEF SUMMARY OF THE INVENTION

In a first aspect, the invention provides a method for synthesizing an olefinic alcohol product that includes incubating an unsaturated hydrocarbon substrate with an enzyme capable of selectively hydroxylating one terminal carbon of the unsaturated hydrocarbon substrate to form an unsaturated hydrocarbon alcohol. In some embodiments, the unsaturated hydrocarbon alcohol is the olefinic alcohol product. In some embodiments, the method further includes converting the unsaturated hydrocarbon alcohol to the olefinic alcohol product.

In some embodiments, the unsaturated hydrocarbon substrate is an olefinic substrate. The olefinic substrate can be prepared via olefin metathesis and other routes including alkylation and reduction of alkynes, as well as Wittig-type reaction of aldehydes with phosphine reagents.

In some embodiments, the unsaturated hydrocarbon substrate is an alkyne. In some embodiments, the unsaturated hydrocarbon substrate is an alkenyl halide.

In a related aspect, the invention provides a method for synthesizing an olefinic alcohol product that includes incubating a saturated hydrocarbon substrate with an enzyme capable of selectively hydroxylating one terminal carbon of the saturated hydrocarbon substrate to form a saturated hydrocarbon alcohol, and converting the saturated hydrocarbon alcohol to the olefinic alcohol product.

In some embodiments, the saturated hydrocarbon substrate is an alkane substrate. In some embodiments, the method includes incubating the alkane substrate with an enzyme capable of selectively hydroxylating both terminal carbons of the alkane substrate to form a terminal diol. The terminal diol can be converted to the olefinic alcohol product in one or more subsequent steps.

In some embodiments, the saturated hydrocarbon substrate is an alkyl halide. In some embodiments, the method includes incubating the alkyl halide with an enzyme capable of selectively hydroxylating one terminal carbon of the alkyl halide to form a halogen-substituted alkanol. The halogen-substituted alkanol can be converted to the olefinic alcohol product in one or more subsequent steps.

In some embodiments, the saturated hydrocarbon substrate is a fatty acid. In some embodiments, the method includes incubating the fatty acid with an enzyme capable of selectively hydroxylating the terminal carbon of the fatty acid to form a terminal hydroxy fatty acid. The terminal hydroxy fatty acid can be converted to the olefinic alcohol product in one or more subsequent steps.

In some embodiments, the enzyme used in the methods of the invention is a non-heme diiron monooxygenase. In some embodiments, the enzyme is a long-chain alkane hydroxylase. In some embodiments, the enzyme is a cytochrome P450. In some embodiments, the cytochrome P450 is a member of the CYP52 or CYP153 family.

In certain embodiments, the olefinic alcohol product prepared according to the method of the invention is a pheromone. In particular embodiments, the pheromone is a lepidopteran insect pheromone.

In another aspect, the invention provides a whole cell catalyst comprising an enzyme capable of selectively hydroxylating one terminal carbon of an unsaturated or saturated hydrocarbon substrate. In some embodiments, the cell is a microbial cell. In some embodiments, the enzyme is selected from the group consisting of a non-heme diiron monooxygenase, a long-chain alkane hydroxylase, a cytochrome P450, and combinations thereof.

Other objects, features, and advantages of the present invention will be apparent to one of skill in the art from the following detailed description and figures.

DETAILED DESCRIPTION OF THE INVENTION

I. Introduction

Figure 1:
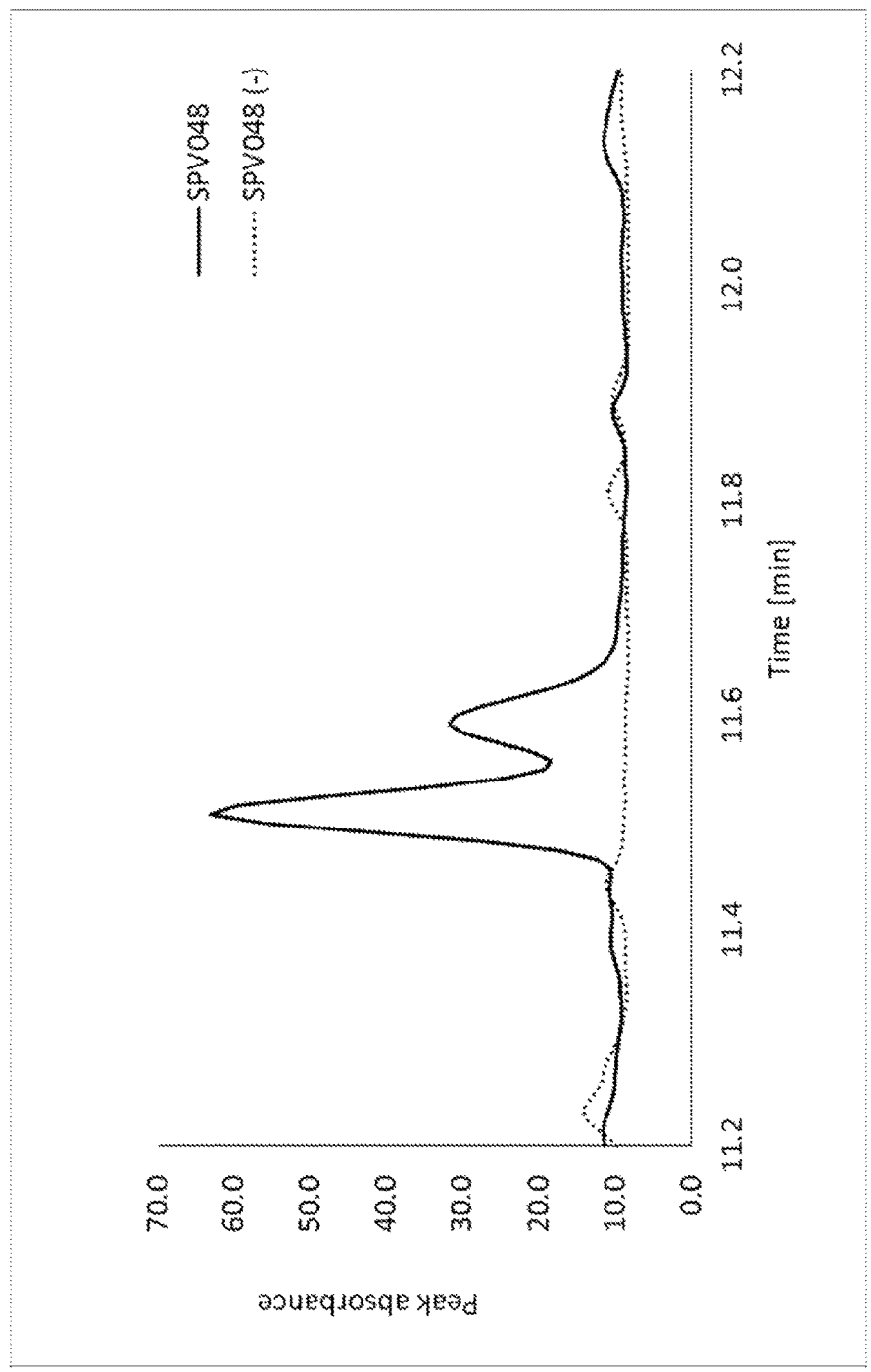
FIG. 1 shows the bioconversion reaction of (Z)-5-hexadecene using induced strain SPV048. (Z)-5-hexedecen-1-ol elutes at 11.5 min while (Z)-11-hexadecen-1-ol elutes at 11.6 min.
Figure 2:
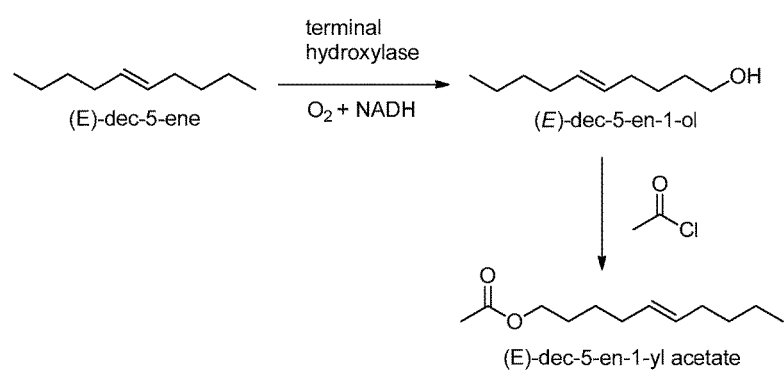
FIG. 2 shows a reaction scheme for hydroxylation of symmetric alkenes using the methods of the invention.

The present invention provides a method of producing terminally oxyfunctionalized alkenes and alkynes. In certain aspects, the method includes contacting an unsaturated or saturated hydrocarbon substrate with a hydroxylase enzyme in the presence of molecular oxygen, reducing equivalents, and optionally redox partners under conditions sufficient to provide a terminally hydroxylated alkene or alkyne. The unsaturated or saturated hydrocarbon substrates can be prepared using the methods described herein. Relevant terminal hydroxylases useful for carrying out this method exhibit strong selectivity towards the terminal carbon of an alkyl chain and include, but are not limited to, non-heme diiron alkane monooxygenases, cytochromes P450 (e.g., cytochromes P450 of the CYP52 and CYP153 family), as well as long chain alkane hydroxylases. In certain embodiments, the terminally hydroxylated alkene or alkyne is further converted to a terminal alkenal. The terminal alkenal can be obtained by chemically or enzymatically oxidizing the terminally hydroxylated alkene or alkyne. Alcohol oxidases, alcohol dehydrogenases, and alpha-dioxygenases can be used for the enzymatic oxidation. In certain embodiments, terminally hydroxylated alkenes and alkynes are useful as insect pheromones which modify insect behavior. In some embodiments, terminally hydroxylated alkenes and alkynes are useful intermediates for producing pheromones via acetylation or oxidation of the alcohol moiety.

II. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

The terms "engineered enzyme" and "enzyme variant" include any enzyme comprising at least one amino acid mutation with respect to wild-type and also include any chimeric protein comprising recombined sequences or blocks of amino acids from two, three, or more different enzymes.

The terms "engineered heme enzyme" and "heme enzyme variant" include any heme-containing enzyme comprising at least one amino acid mutation with respect to wild-type and also include any chimeric protein comprising recombined sequences or blocks of amino acids from two, three, or more different heme-containing enzymes.

The terms "engineered cytochrome P450" and "cytochrome P450 variant" include any cytochrome P450 enzyme comprising at least one amino acid mutation with respect to wild-type and also include any chimeric protein comprising recombined sequences or blocks of amino acids from two, three, or more different cytochrome P450 enzymes.

The term "whole cell catalyst" includes microbial cells expressing hydroxylase enzymes, wherein the whole cell catalyst displays hydroxylation activity.

As used herein, the term "metathesis reaction" refers to a catalytic reaction which involves the interchange of alkylidene units (i.e., $R_2C=$units) among compounds containing one or more carbon-carbon double bonds (e.g., olefinic compounds) via the formation and cleavage of the carbon-carbon double bonds. Metathesis can occur between two like molecules (often referred to as self-metathesis) and/or between two different molecules (often referred to as cross-metathesis).

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction.

As used herein, the term "metathesis product" refers to an olefin containing at least one double bond, the bond being formed via a metathesis reaction.

As used herein, the terms "microbial," "microbial organism," and "microorganism" include any organism that exists as a microscopic cell that is included within the domains of archaea, bacteria or eukarya. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As used herein, the term "non-naturally occurring", when used in reference to a microbial organism or enzyme activity of the invention, is intended to mean that the microbial organism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microbial organism or enzyme activity includes the hydroxylation activity described above.

As used herein, the term "exogenous" is intended to mean that the referenced molecule or the referenced activity is introduced into the host microbial organism. The term as it is used in reference to expression of an encoding nucleic acid refers to the introduction of the encoding nucleic acid in an expressible form into the microbial organism. When used in reference to a biosynthetic activity, the term refers to an activity that is introduced into the host reference organism.

The term "heterologous" as used herein with reference to molecules, and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the terms "native" and/or "endogenous" as used herein with reference to molecules, and in particular enzymes and polynucleotides, indicate molecules that are expressed in the organism in which they originated or are found in nature, independently of the level of expression that can be lower equal or higher than the level of expression of the molecule in the native microorganism. It is to be understood that expression of native enzymes or polynucleotides may be modified in recombinant microorganisms.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The terms "analog" and "analogous" include nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

As used herein, the term "alkane" refers to a straight or branched, saturated, aliphatic hydrocarbon having the number of carbon atoms indicated. The term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkanes and alkyl groups can be optionally substituted with one or more moieties selected from halo, alkenyl, and alkynyl.

As used herein, the term "alkene" refers to a straight chain or branched hydrocarbon having at least 2 carbon atoms and at least one double bond. A "terminal" alkene refers to an alkene wherein the double bond is between two carbon atoms at the end of the hydrocarbon chain (e.g., hex-1-ene). An "internal" alkene refers to an alkene wherein the double bond is between two carbon atoms that are not at the end of the hydrocarbon chain (e.g., (E)-hex-3-ene and (Z)-hex-3-ene). An "α,ω-alkenol" refers to a hydroxy-substituted terminal alkene having the formula $(CH_2=CH)(CH_2)_m OH$, wherein m is an integer ranging from 1-30, such as 2-18. The term "alkenyl" refers to a straight chain or branched hydrocarbon radical having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenes and alkenyl groups can be optionally substituted with one or more moieties selected from halo, alkyl, and alkynyl.

As used herein, the term "selective" refers to preferential reaction of one site on a chemical compound over another site on the compound. As a non-limiting example, selectively hydroxylating hept-3-ene (an asymmetric alkene) refers to preferentially hydroxylating one end of the hept-3-ene to form more hept-3-en-1-ol than hept-4-en-1-ol (or forming exclusively hept-3-en-1-ol without forming hept-4-en-1-ol). Selectively hydroxylating the other end of hept-3-ene would result in the formation of more hept-4-en-1-ol than hept-3-en-1-ol (or the exclusive formation of hept-4-en-1-ol without formation of hept-3-en-1-ol).

As used herein, the term "alkyne" refers to either a straight chain or branched hydrocarbon having at least 2 carbon atoms and at least one triple bond. A "terminal" alkyne refers to an alkyne wherein the triple bond is between two carbon atoms at the end of the hydrocarbon chain (e.g., hex-1-yne). An "internal" alkyne refers to an alkyne wherein the triple bond is between two carbon atoms that are not at the end of the hydrocarbon chain (e.g., hex-3-yne). The term "alkynyl" refers to either a straight chain or branched hydrocarbon radical having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynes and alkynyl groups can be optionally substituted with one or more moieties selected from halo, alkyl, and alkenyl.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be optionally substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "carboxy" refers to a moiety —C(O)OH. The carboxy moiety can be ionized to form the carboxylate anion.

As used herein, the term "hydroxy" refers to a moiety —OH.

As used herein, the term "amino" refers to a moiety —$NR_3$, wherein each R group is H or alkyl. An amino moiety can be ionized to form the corresponding ammonium cation.

As used herein, the term "amido" refers to a moiety —NRC(O)R or —C(O)$NR_2$, wherein each R group is H or alkyl.

As used herein, the term "nitro" refers to the moiety —$NO_2$.

As used herein, the term "oxo" refers to an oxygen atom that is double-bonded to a compound (i.e., O=).

As used herein, the term "cyano" refers to the moiety —CN.

III. Description of the Embodiments

Traditionally, straight chain monoene alcohols, acetates, and aldehydes are synthesized via multi-step syntheses. Scheme 1 represents an example of such synthesis.

Scheme 1. General synthesis strategy for straight chain monoene alcohols, acetates, and aldehydes.

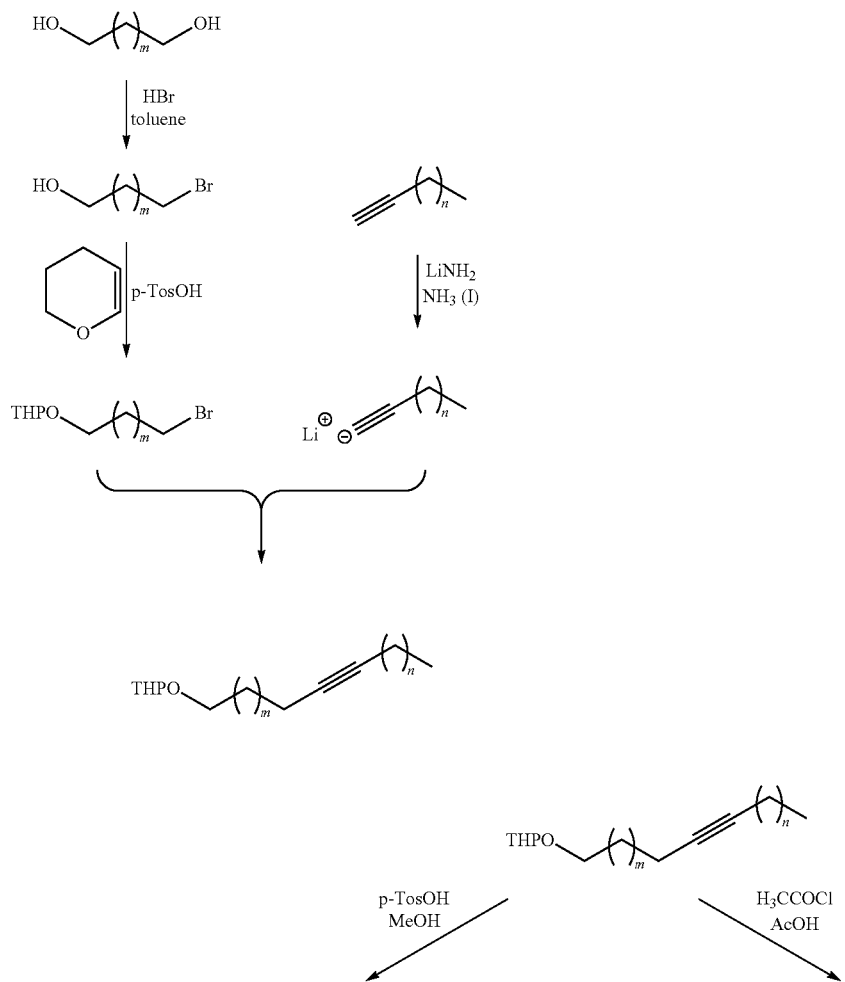

-continued

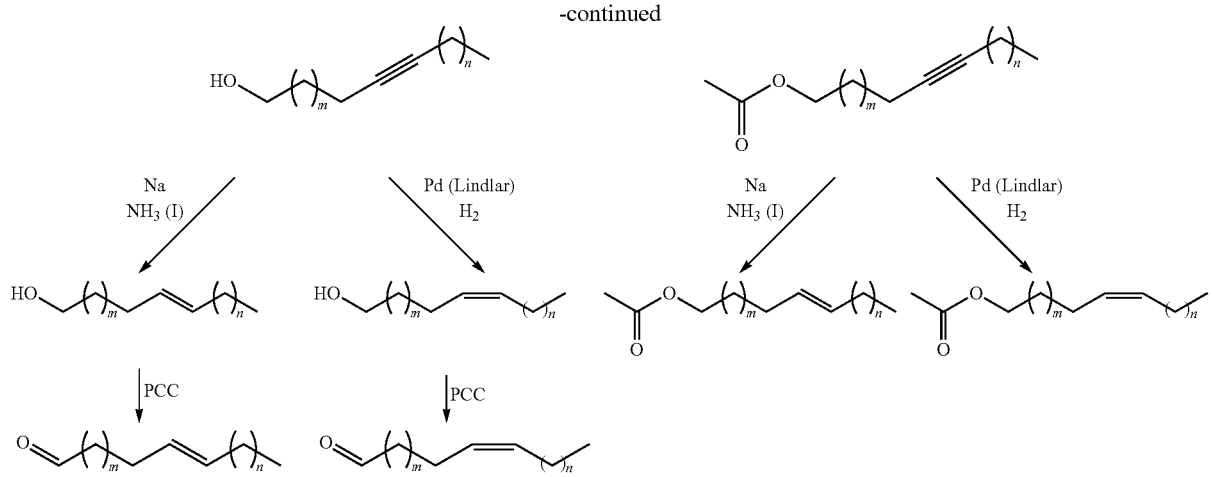

The present disclosure describes several methods for the synthesis of terminally oxyfunctionalized alkenes. Said methods are described in detail below and are generally applicable to the synthesis of various compounds, including but not limited to those shown in Table 1.

Some embodiments of the invention provide methods for synthesizing olefinic alcohol products wherein the olefinic alcohol product is a pheromone. In some embodiments, the olefinic alcohol product is selected from the alcohols in Table 1. Pheromones containing aldehyde functional groups can also be prepared using the olefinic alcohol products as intermediates. In such cases, the methods of the invention generally include oxidizing the olefinic alcohol product to form an olefinic aldehyde product. In some of these embodiments, the olefinic aldehyde product is selected from the aldehydes in Table 1.

Pheromones containing ester functional groups can also be prepared using the olefinic alcohol products as intermediates. In such cases, the methods of the invention generally include esterifying the olefinic alcohol product to form an olefinic ester product. In some embodiments, the olefinic ester product is an acetate ester. In some embodiments, the olefinic ester product is selected from the esters in Table 1.

TABLE 1

Exemplary compounds that can be synthesized using methods described in the present disclosure.

| Name | Structure | Example of Biological importance |
|---|---|---|
| (Z)-3-hexanol | 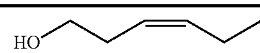 | See, Sugimoto et al. (2014) |
| (Z)-3-nonen-1-ol | 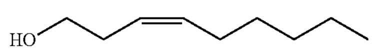 | West Indian Fruity Fly male sex pheromone |
| (Z)-5-decen-1-ol | 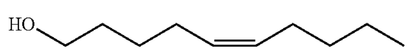 | |
| (Z)-5-decenyl acetate | 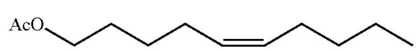 | *Agrotis segetum* sex pheromone component |
| (E)-5-decen-1-ol | 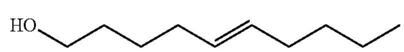 | *Anarsia lineatella* sex pheromone component |
| (E)-5-decenyl acetate | 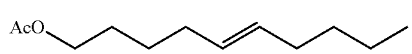 | *Anarsia lineatella* sex pheromone component |
| (Z)-7-dodecen-1-ol | 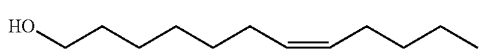 | |
| (Z)-7-dodecenyl acetate | 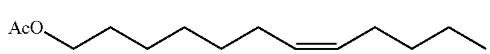 [SMILES: CCCC/C=C\CCCCCCOC(C)=O] | *Pseudoplusia includens* sex pheromone |
| | | *Agrotis segetum* sex pheromone component |
| (E)-8-dodecen-1-ol | 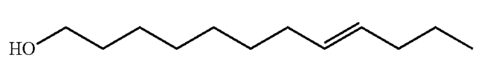 | Citrus Fruit Moth sex pheromone |
| (E)-8-dodecenyl acetate | 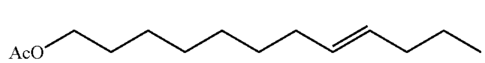 [SMILES: CCC/C=C/CCCCCCCOC(C)=O] | *Grapholitha molesta, Ecdytolopha aurantiana* sex pheromone component |

TABLE 1-continued

Exemplary compounds that can be synthesized using methods described in the present disclosure.

| Name | Structure | Example of Biological importance |
|---|---|---|
| (Z)-8-dodecen-1-ol | 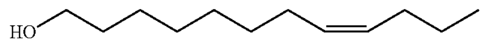 | *Grapholitha molesta, Ecdytolopha aurantiana* sex pheromone component |
| (Z)-8-dodecenyl acetate | 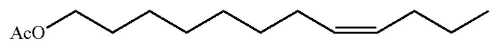 | *Grapholitha molesta* sex pheromone component |
| (Z)-9-dodecen-1-ol | 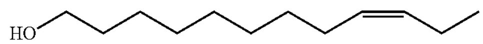 | |
| (Z)-9-dodecenyl acetate | 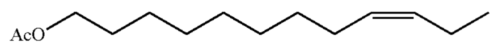 [SMILES: CC/C=C\CCCCCCCCOC(C)=O] | *Eupoecilia ambiguella* sex pheromone |
| (Z)-9-tetradecen-1-ol | 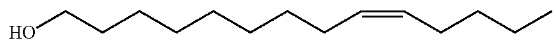 | |
| (Z)-9-tetradecenyl acetate | 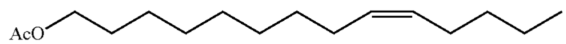 [SMILES: CCCC/C=C\CCCCCCCCOC(C)=O] | *Pandemis pyrusana, Naranga aenescens, Agrotis segetum* sex pheromone component |
| (Z)-11-tetraceden-1-ol | 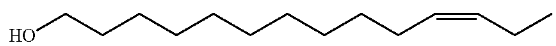 | |
| (Z)-11-tetracedenyl acetate | 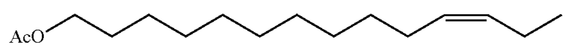 | *Pandemis pyrusana, Choristoneura roseceana* sex pheromone component |
| (E)-11-tetradecen-1-ol | 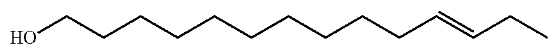 | |
| (E)-11-tetradecenyl acetate | 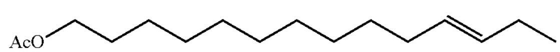 [SMILES: CC/C=C/CCCCCCCCCCOC(C)=O] | *Choristoneura roseceana, Crocidolomia pavonana* sex pheromone component |
| (Z)-7-hexadecen-1-ol | 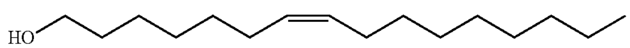 [SMILES: CCCCCCCC/C=C\CCCCCCO] | |
| (Z)-7-hexadecenal | 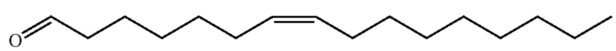 | *Diatraea considerata* sex pheromone component |
| (Z)-9-hexadecen-1-ol | 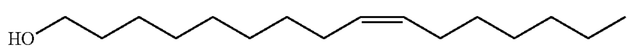 | |
| (Z)-9-hexadecenal | 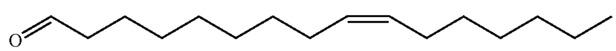 | *Helicoverpa zea, Helicoverpa armigera, Heliothis virescens* sex pheromone component |
| (Z)-9-hexadecenyl acetate | 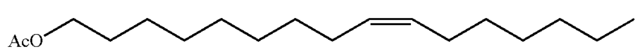 [SMILES: CCCCCC/C=C\CCCCCCCCOC(C)=O] | *Naranga aenescens* sex pheromone component |
| (Z)-11-hexadecen-1-ol | 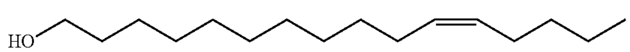 | |
| (Z)-11-hexadecenal | 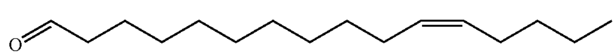 [SMILES: CCCC/C=C\CCCCCCCCCC=O] | *Platyptila carduidactyla, Heliothis virescens* sex pheromone<br>*Helicoverpa zea, Helicoverpa armigera, Plutella xylostella, Diatraea considerate, Diatraea grandiosella, Diatraea saccharalis, Acrolepiopsis assectella* sex pheromone component |
| (Z)-11-hexadecenyl acetate | 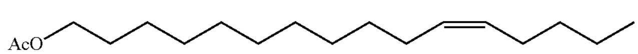 [SMILES: CCCC/C=C\CCCCCCCCCCOC(C)=O] | *Discestra trifolii* sex pheromone<br>*Heliothis virescens, Plutella xylostella, Acrolepiopsis assectella, Crocidolomia pavonana, Naranga aenescens* sex pheromone component |

TABLE 1-continued

Exemplary compounds that can be synthesized using methods described in the present disclosure.

| Name | Structure | Example of Biological importance |
|---|---|---|
| (Z)-13-octadecen-1-ol | HO~~~~~~~~~~~~~~~ | |
| (Z)-13-octadecenal | O=~~~~~~~~~~~~~~~ | *Diatraea considerata*, *Diatraea grandiosella* sex pheromone component |

Ac = —(CO)CH$_3$

Useful unsaturated fatty acids and related compounds can also be prepared using the olefinic alcohol products as intermediates. In such cases, the methods of the invention generally include oxidizing the olefinic alcohol product to form an olefinic acid product.

The synthetic strategies disclosed herein chiefly rely on the ability of hydroxylases to terminally hydroxylate hydrocarbon substrates such as linear alkenes. Linear alkenes and other hydrocarbon substrates can be synthesized via any route, including but not limited to olefin metathesis, Wittig olefination, or alkyne substitution followed by partial hydrogenation. The hydroxylation products can further be modified via any method, including—but not limited to—oxidation, esterification, and olefin metathesis, to produce the desired end products (Scheme 2). Deviations from this general scheme are also disclosed.

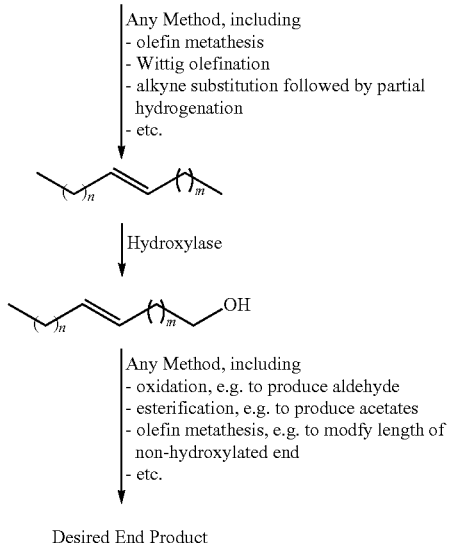

Synthesis of Terminal Alkenols Via Metathesis and Hydroxylation

In a first aspect, the invention provides a method for synthesizing an olefinic alcohol product that includes incubating an unsaturated hydrocarbon substrate with an enzyme capable of selectively hydroxylating one terminal carbon of the unsaturated hydrocarbon substrate to form an unsaturated hydrocarbon alcohol. In some embodiments, the unsaturated hydrocarbon alcohol is the olefinic alcohol product. In some embodiments, the method further includes converting the unsaturated hydrocarbon alcohol to the olefinic alcohol product. In some embodiments, the unsaturated hydrocarbon substrate is an olefinic substrate. In some embodiments, the olefinic substrate is a metathesis product.

Hydroxylation of Symmetric Alkenes

In some embodiments, the method for synthesizing an oxyfunctionalized alkene includes a combination of metathesis and terminal hydroxylation as shown in Scheme 3.

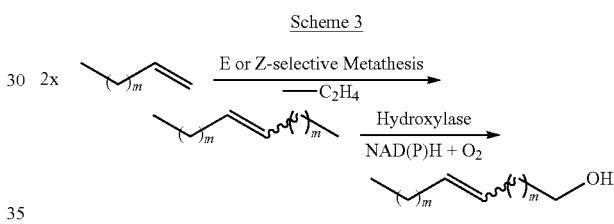

According to Scheme 3, an E-selective metathesis catalyst or a Z-selective metathesis catalyst is used to convert a linear, terminal alkene of chain length m to the respective linear symmetric alkene. Following the metathesis step, a terminal hydroxylation biocatalyst is used to convert the symmetric alkene to the terminal alkenol. Optionally, this scheme can be expanded by an additional metathesis step that replaces the non-hydroxylated end of the terminal alkenol with one of another chain length (Scheme 4a).

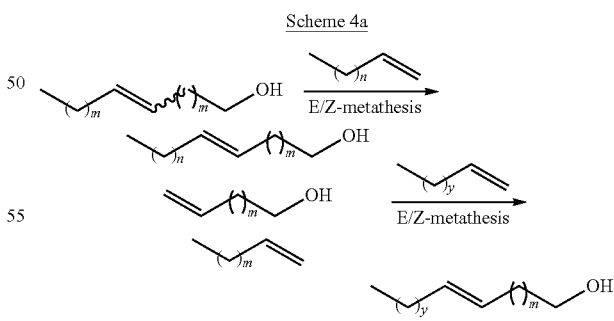

In some instances, Scheme 4a can be further modified to protect the alcohol prior to metathesis. For example, the alcohol can be esterified prior to the metathesis step (Scheme 4b). The esterification is typically performed with formate or acetate, resulting in R=H or CH$_3$, respectively. The ester intermediates or final products can be hydrolysed to yield alcohol products.

Scheme 4b

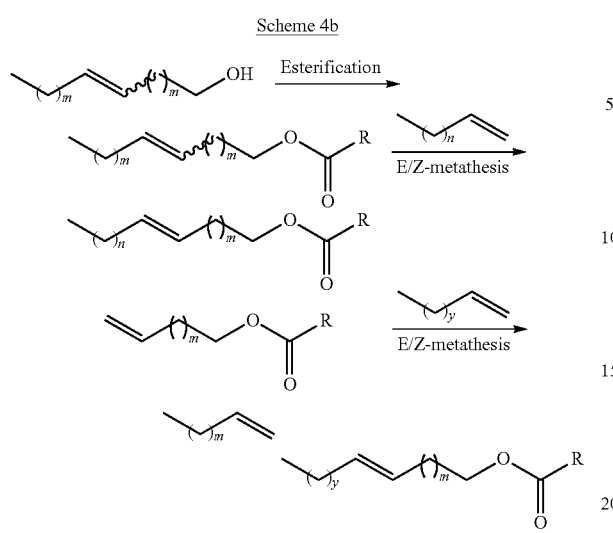

The methods can be conducted with alkenes of any suitable length, which will depend on factors such as the desired olefinic alcohol product and the enzyme used in the biohydroxylation step. In some embodiments, the olefinic alcohol product is a C4-C20 olefinic alcohol product. The olefinic alcohol can contain, for example, 4-20 carbon atoms, or 8-20 carbon atoms, or 12-20 carbon atoms, or 16-20 carbon atoms. In such embodiments, the sum of the subscripts m, n, and y shown in Scheme 3 and Scheme 4 will bring the total number of carbon atoms in a particular olefinic alcohol product to 4-20, when added to the number of the non-subscripted carbon atoms shown in the structure for the olefinic alcohol product. In such embodiments, for example, subscript m in Scheme 3 can be an integer from 0-8, bringing the total number of the carbons in the symmetric olefinic substrate to 4-20. When m is 3, the route depicted in Scheme 3 provides (E/Z)-5-decen-1-ol.

Accordingly, some embodiments of the invention provide methods for preparing an olefinic alcohol product as described above, wherein the olefinic substrate is a metathesis product, and wherein the method includes: a) self-metathesizing a terminal olefin in the presence of a metathesis catalyst to form the metathesis product; and b) incubating the metathesis product with an enzyme capable of selectively hydroxylating one terminal carbon of the metathesis product to form an olefinic alcohol product.

In some embodiments, the terminal olefin has the formula $(CH_2=CH)(CH_2)_mH$, the metathesis product has the formula $H(CH_2)_m(CH=CH)(CH_2)_mH$, the olefinic alcohol product has the formula $H(CH_2)_m(CH=CH)(CH_2)_mOH$, and m is selected from an integer between 1 and 17. In some embodiments, m is selected from an integer between 1 and 9. In some embodiments, for example, m is 1, 2, 3, 4, 5, 6, 7, or 8. It is to be understood that any range disclosed in the present specification and recited in the claims includes the endpoints the endpoints of the range, unless explicitly stated otherwise. As a non-limiting example, integers in the range "between 1 and 17" include 1, 2, 3, 4, 5, 6, 7, 8, 9, 10, 11, 12, 13, 14, 15, 16, and 17.

Hydroxylation of Asymmetric Alkenes

In some embodiments, the method for synthesizing an oxyfunctionalized alkene includes a combination of metathesis and terminal hydroxylation as shown in Scheme 5. In this process, terminal alkenes of different lengths are combined to generate asymmetric alkenes, which are then subjected to biohydroxylation conditions to afford the desired alkenol products.

Scheme 5

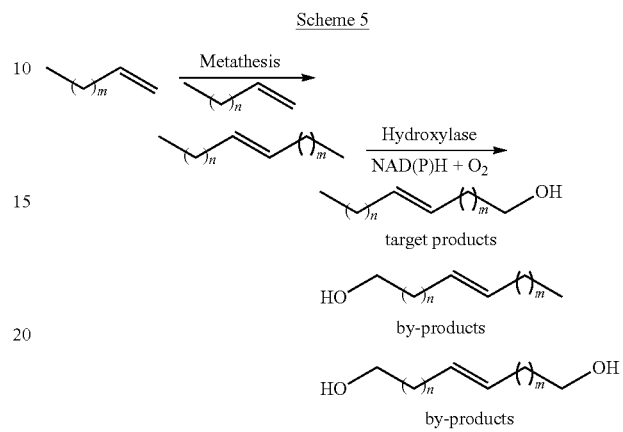

Methods including hydroxylation of asymmetric alkenes can be conducted with alkenes of any suitable length. In some embodiments, the asymmetric olefinic alcohol product is a C4-C30 olefinic alcohol product. In such embodiments, the sum of the subscripts m and n shown in Scheme 5 will bring the total number of carbon atoms in a particular asymmetric olefinic alcohol product to 4-30, when added to the number of the non-subscripted carbon atoms shown in the structure for the asymmetric olefinic alcohol product. In such embodiments, for example, subscript m in Scheme 5 can be an integer from 8-18 and subscript n in Scheme 5 can be a different integer from 0-8, bringing the total number of the carbons in the asymmetric olefinic substrate to 4-30. When m is 9 and n is 3, the route depicted in Scheme 5 provides (E/Z)-hexadec-11-en-1-ol as the target product. In some embodiments, the asymmetric olefinic alcohol product is a C4-C20 olefinic alcohol product. The asymmetric olefinic alcohol can contain, for example, 4-20 carbon atoms, or 8-20 carbon atoms, or 12-20 carbon atoms, or 16-20 carbon atoms.

In some embodiments, for example, m is 0 and n is 4; or m is 1 and n is 3; or m is 3 and n is 1; or m is 4 and n is 0; or m is 0 and n is 5; or m is 1 and n is 4; or m is 2 and n is 3; or m is 3 and n is 2; or m is 4 and n is 1; or m is 5 and n is 0; or m is 0 and n is 6; or m is 1 and n is 5; or m is 2 and n is 4; or m is 4 and n is 2; or m is 5 and n is 1; or m is 6 and n is 0; or m is 0 and n is 7; or m is 1 and n is 6; or m is 2 and n is 5; or m is 3 and n is 4; or m is 4 and n is 3; or m is 5 and n is 2; or m is 6 and n is 1; or m is 7 and n is 0; or m is 0 and n is 8; or m is 1 and n is 7; or m is 2 and n is 6; or m is 3 and n is 5; or m is 5 and n is 3; or m is 6 and n is 2; or m is 7 and n is 1; or m is 8 and n is 0; or m is 0 and n is 9; or m is 1 and n is 8; or m is 2 and n is 7; or m is 3 and n is 6; or m is 4 and n is 5; or m is 5 and n is 4; or m is 6 and n is 3; or m is 7 and n is 2; or m is 8 and n is 1; or m is 9 and n is 0; or m is 0 and n is 10; or m is 1 and n is 9; or m is 2 and n is 8; or m is 3 and n is 7; or m is 4 and n is 6; or m is 6 and n is 4; or m is 7 and n is 3; or m is 8 and n is 2; or m is 9 and n is 1; or m is 10 and n is 0; or m is 0 and n is 11; or m is 1 and n is 10; or m is 2 and n is 9; or m is 3 and n is 8; or m is 4 and n is 7; or m is 5 and n is 6; or m is 6 and n is 5; or m is 7 and n is 4; or m is 8 and n is 3; or m is 9 and n is 2; or m is 10 and n is 1; or m is 11 and n is 0; or m is 0 and n is 12; or m is 1 and n is 11; or m is 2 and n is 10; or m is 3 and n is 9; or m is 4 and n is 8; or m is 5 and n is 7; or m is 7 and n is 5; or m is 8 and n is 4; or m is 9 and n is 3; or m is 10 and n is 2; or m is 11 and n is 1; or m is 12 and n is 0; or m is 0 and n is 13; or m is 1 and n is 12; or m is 2 and n is 11; or m is 3 and n is 10; or m is 4 and n is 9; or m is 5 and n is 8; or m is 6 and n is 7; or m is 7 and n is 6; or m is 8 and n is 5; or m is 9 and n is 4; or m is 10 and n is 3; or m is 11 and n is 2; or m is 12 and n is 1; or m is 13 and n is 0; or m is 0 and n is 14; or m is 1 and n is 13; or m is 2 and n is 12; or m is 3 and n is 11; or m is 4 and n is 10; or m is 5 and n is 9; or m is 6 and n is 8; or m is 8 and n is 6; or m is 9 and n is 5; or m is 10 and n is 4; or m is 11 and n is 3; or m is 12 and n is 2; or m is 13 and n is 1; or m is 14 and n is 0; or m is 0 and n is 15; or m is 1 and n is 14; or m is 2 and n is 13; or m is 3 and n is 12; or m is 4 and n is 11; or m is 5 and n is 10; or m is 6 and n is 9; or m is 7 and n is 8; or m is 8 and n is 7; or m is 9 and n is 6; or m is 10 and n is 5; or m is 11 and n is 4; or m is 12 and n is 3; or m is 13 and n is 2; or m is 14 and n is 1; or m is 15 and n is 0; or m is 0 and n is 16; or m is 1 and n is 15; or m is 2 and n is 14; or m is 3 and n is 13; or m is 4 and n is 12; or m is 5 and n is 11; or m is 6 and n is 10; or m is 7 and n is 9; or m is 9 and n is 7; or m is 10 and n is 6; or m is 11 and n is 5; or m is 12 and n is 4; or m is 13 and n is 3; or m is 14 and n is 2; or m is 15 and n is 1; or m is 16 and n is 0; or m is 1 and n is 16; or m is 2 and n is 15; or m is 3 and n is 14; or m is 4 and n is 13; or m is 5 and n is 12; or m is 6 and n is 11; or m is 7 and n is 10; or m is 8 and n is 9; or m is 9 and n is 8; or m is 10 and n is 7; or m is 11 and n is 6; or m is 12 and n is 5; or m is 13 and n is 4; or m is 14 and n is 3; or m is 15 and n is 2; or m is 16 and n is 1; or m is 17 and n is 0; or m is 0 and n is 17; or m is 1 and n is 17; or m is 2 and n is 16; or m is 3 and n is 15; or m is 4 and n is 14; or m is 5 and n is 13; or m is 6 and n is 12; or m is 7 and n is 11; or m is 8 and n is 10; or m is 10 and n is 8; or m is 11 and n is 7; or m is 12 and n is 6; or m is 13 and n is 5; or m is 14 and n is 4; or m is 15 and n is 3; or m is 16 and n is 2; or m is 17 and n is 1; or m is 18 and n is 0.

Accordingly, some embodiments of the invention provide methods for preparing an olefinic alcohol product as described above, wherein the olefinic substrate is a metathesis product, and wherein the method includes: a) cross-metathesizing a first terminal olefin and a second different terminal olefin in the presence of a metathesis catalyst to form the metathesis product; and b) incubating the metathesis product with an enzyme capable of selectively hydroxylating one terminal carbon of the metathesis product to form an olefinic alcohol product.

In some embodiments, the first terminal olefin has the formula $(CH_2=CH)(CH_2)_mH$, the second different terminal olefin has the formula $(CH_2=CH)(CH_2)_nH$, the metathesis product has the formula $H(CH_2)_m(CH=CH)(CH_2)_nH$, the olefinic alcohol product has the formula $H(CH_2)_m(CH=CH)(CH_2)_nOH$, and m and n are different integers between 1 and 17. In some embodiments, m and n are different integers between 1 and 9.

The methods of the invention can also be conducted such that the biohydroxylation step is conducted prior to the metathesis step and/or other synthetic transformation steps. Accordingly, some embodiments of the invention provide methods wherein the olefinic substrate is a first terminal olefin, and wherein the method includes: a) incubating the first terminal olefin with an enzyme capable of selectively hydroxylating the terminal carbon of the terminal olefin to form an α,ω-alkenol; and b) metathesizing the α,ω-alkenol and a second terminal olefin in the presence of a metathesis catalyst to form the olefinic alcohol product.

The alcohol can be protected with a suitable protecting group if necessary. In some embodiments, the methods of the invention include: a) incubating the first terminal olefin with an enzyme capable of selectively hydroxylating the terminal carbon of the terminal olefin to form an α,ω-alkenol; b) protecting the α,ω-alkenol to form a protected α,ω-alkenol; c) metathesizing the protected α,ω-alkenol and a second terminal olefin in the presence of a metathesis catalyst to form a protected olefinic alcohol product; and d) deprotecting the protected olefinic alcohol product to form the olefinic alcohol product.

Any suitable alcohol protecting group can be used in the methods of the invention. Such protecting groups are well known to one of ordinary skill in the art, including those that are disclosed in *Protective Groups in Organic Synthesis,* 4th edition, T. W. Greene and P. G. M. Wuts, John Wiley & Sons, New York, 2006, which is incorporated herein by reference in its entirety. In some embodiments, the α,ω-alkenol is protected via esterification and the protected olefinic alcohol product is deprotected via hydrolysis. In some embodiments, the α,ω-alkenol is protected via esterification with an acid selected from the group consisting of formate and acetate.

Any suitable olefinic substrate can be used in methods where the biohydroxylation step is conducted prior to the metathesis step and/or other synthetic transformation steps. In some embodiments, the first terminal olefin has the formula $(CH_2=CH)(CH_2)_mH$, the α,ω-alkenol has the formula $(CH_2=CH)(CH_2)_mOH$, the second terminal olefin has the formula $(CH_2=CH)(CH_2)_nH$, the olefinic alcohol product has the formula $H(CH_2)_n(CH=CH)(CH_2)_mOH$, and m and n are each independently selected from an integer between 1 and 17. In some embodiments, m and n are each independently selected from an integer between 1 and 9.

Hydroxylation of Alkanes to Terminal Diols Followed by Monodehydration and Metathesis Saturated hydrocarbon substrates can also be used in the methods of the invention. Accordingly, another aspect of the invention provides a method for synthesizing an olefinic alcohol product that includes: incubating a saturated hydrocarbon substrate with an enzyme capable of selectively hydroxylating one terminal carbon of the saturated hydrocarbon substrate to form a saturated hydrocarbon alcohol; and converting the saturated hydrocarbon alcohol to the olefinic alcohol product.

In some embodiments, terminal alkenols are synthesized according to Scheme 6a.

Scheme 6a

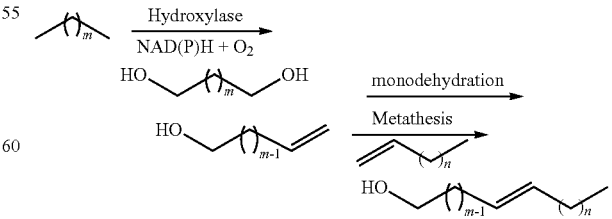

In this synthesis scheme, the terminal hydroxylation occurs on both ends of a linear alkane, resulting in a diol. The diol is then selectively monodehydrated through various chemical processes, including but not limited to those described in the literature (Sato et al., 2013) to generate a terminal alkenol. Coupling of the terminal alkenol with other alkenes via an olefin metathesis process allows for the synthesis of various pheromones.

In some instances, Scheme 6a can be further modified to protect the alcohol prior to metathesis. For example, the alcohol can be esterified prior to the metathesis step (Scheme 6b). The esterification is typically performed with formate or acetate, resulting in R=H or $CH_3$, respectively. The ester intermediates or final products can be hydrolysed to yield the alcohol products.

Scheme 6b

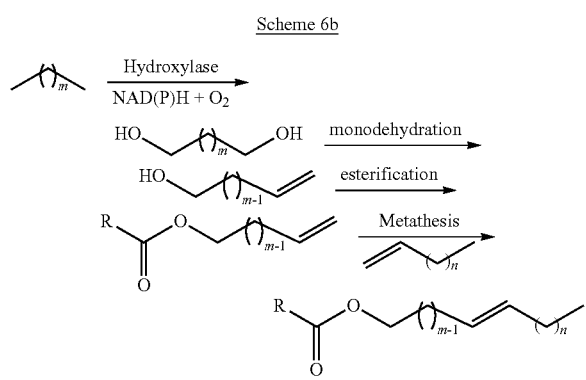

Accordingly, some embodiments of the invention provide a method wherein the saturated hydrocarbon substrate is an alkane substrate, and wherein the method includes:
 a) incubating an alkane substrate with an enzyme capable of selectively hydroxylating both terminal carbons of the alkane substrate to form a terminal diol;
 b) selectively dehydrating one of the terminal hydroxyl groups of the terminal diol to form an α,ω-alkenol; and
 c) metathesizing the α,ω-alkenol and a terminal olefin in the presence of a metathesis catalyst to form the olefinic alcohol product.

Accordingly, some embodiments of the invention provide a method wherein the saturated hydrocarbon substrate is an alkane substrate, and wherein the method includes:
 a) incubating an alkane substrate with an enzyme capable of selectively hydroxylating both terminal carbons of the alkane substrate to form a terminal diol;
 b) selectively dehydrating one of the terminal hydroxyl groups of the terminal diol to form an α,ω-alkenol;
 c) protecting the α,ω-alkenol to form a protected α,ω-alkenol;
 d) metathesizing the protected α,ω-alkenol and a terminal olefin in the presence of a metathesis catalyst to form a protected olefinic alcohol product; and
 e) deprotecting the protected olefinic alcohol product to form the olefinic alcohol product.

In some embodiments, the α,ω-alkenol is protected via esterification and the protected olefinic alcohol product is deprotected via hydrolysis. In some embodiments, the α,ω-alkenol is protected via esterification with an acid selected from the group consisting of formate and acetate.

In some embodiments, the alkane substrate has the formula $H(CH_2)_mH$, the terminal diol has the formula $HO(CH_2)_mOH$, the α,ω-alkenol has the formula $(CH_2=CH)(CH_2)_{m-2}OH$, the terminal olefin has the formula $(CH_2=CH)(CH_2)_nH$, the olefinic alcohol product has the formula $H(CH_2)_n(CH=CH)(CH_2)_{m-2}OH$, m is an integer between 3 and 17, and n is an integer between 1 and 17. The alkane substrate, the terminal diol, the α,ω-alkenol, the terminal olefin, and the olefinic alcohol product can have any suitable combination of subscripts m and n, as described above. In some embodiments, m and n are independently selected integers between 1 and 9. In some embodiments, m and n are different integers between 1 and 9.

Hydroxylation of Terminal Alkenes

In some embodiments, terminal alkenols are synthesized according to Scheme 7a.

Scheme 7a

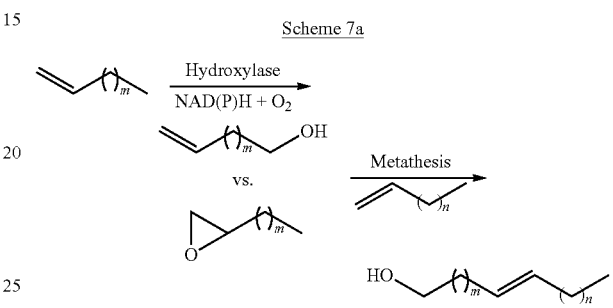

In a particular embodiment, the hydroxylase enzyme favors hydroxylation of the terminal $CH_3$ group over epoxidation of the C=C double bond.

In some instances, Scheme 7a can be further modified to protect the alcohol prior to metathesis. For example, the alcohol can be esterified prior to the metathesis step (Scheme 7b). The esterification is typically performed with formate or acetate, resulting in R=H or $CH_3$, respectively. The ester intermediates or final products can be hydrolysed to yield alcohol products.

Scheme 7b

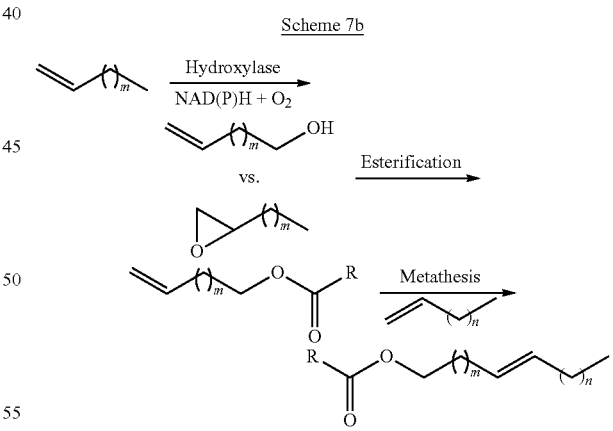

The alkenes and the olefinic alcohol product can have any suitable combination of subscripts m and n, as described above. In some embodiments, m and n are independently selected integers between 1 and 9. In some embodiments, m and n are different integers between 1 and 9.

Hydroxylation of Fatty Acids

In some embodiments, terminal alkenols are synthesized according to Scheme 8a. In this Scheme, a terminal olefin forming fatty acid decarboxylase is used to convert a ω-hydroxy fatty acid into a fatty alkene.

Scheme 8a

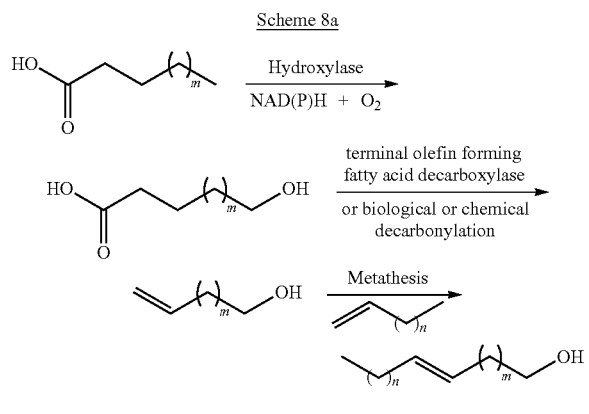

In some instances, Scheme 8a can be further modified to protect the alcohol prior to metathesis. For example, the alcohol can be esterified prior to the metathesis step (Scheme 8b). The esterification is typically performed with formate or acetate, resulting in R=H or CH$_3$, respectively. The ester intermediates or final products can be hydrolysed to yield alcohol products.

Scheme 8b

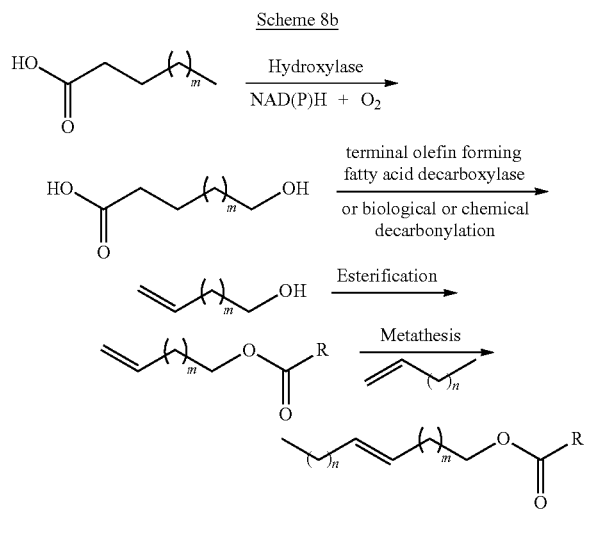

The fatty acid substrate, the terminal hydroxy fatty acid, the alkenes, and the olefinic alcohol product can have any suitable combination of subscripts m and n, as described above. In some embodiments, m and n are independently selected integers between 1 and 9. In some embodiments, m and n are different integers between 1 and 9.

Alternative Synthesis of Terminal Alkenols Via Hydroxylation

Hydroxylation of Symmetric or Asymmetric Alkenes

In some embodiments, symmetric or asymmetric alkenes are hydroxylated according to Schemes 3 and 4, respectively to produce symmetric or asymmetric alkenols. However, in this embodiment, the alkene is produced according to Scheme 9 (see, Oprean et al. (2006) for the acetylation step and Buck and Chong (2001) for the alkyne alkylation step), Scheme 10 (see, Buck and Chong (2001) regarding the alkyne alkylation step), Scheme 11a, or Scheme 11b. Scheme 11b shows Wittig reaction conditions that favor the formation of the Z-isomer according to Smith et al. (2000).

Scheme 9

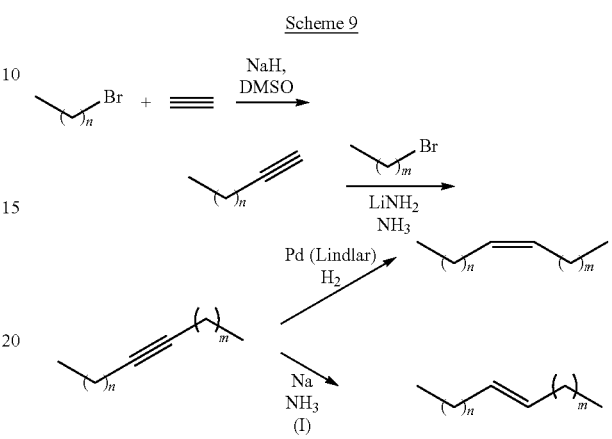

Scheme 10

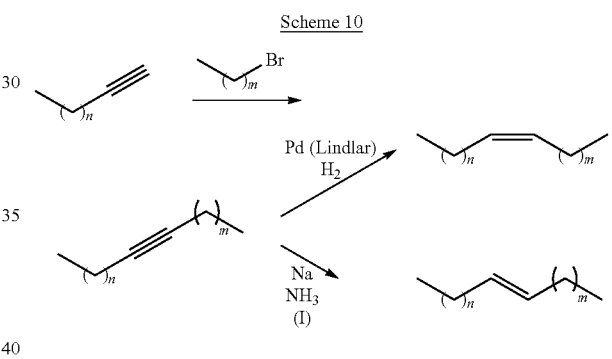

Scheme 11

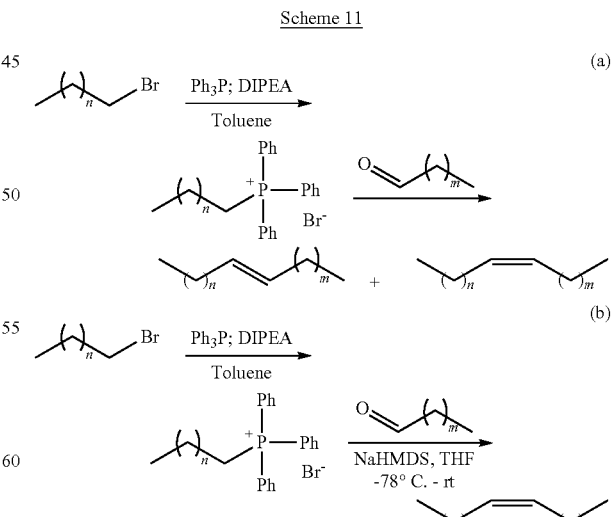

Accordingly, some embodiments of the invention provide a method for synthesizing an olefinic alcohol product wherein the method includes:

a) forming a reaction mixture comprising a terminal alkyne according to formula I

(I)

wherein n is an integer from 0 to 16, and an alkyl halide according to formula II

(II)

wherein X is a halogen and m is an integer from 0 to 16, under conditions sufficient to form a disubstituted alkyne according to formula III

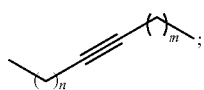
(III)

b) reducing the disubstituted alkyne to form an olefin according to formula IVa or IVb

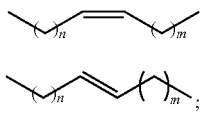
(IVa)
(IVb)

and c) incubating the olefin with an enzyme capable of selectively hydroxylating one terminal carbon of the olefin to form the olefinic alcohol product.

The terminal alkyne, the alkyl halide, the disubstituted alkyne, the olefin, and the olefinic alcohol product can have any suitable combination of subscripts m and n, as described above. In some embodiments, m and n are independently selected integers between 1 and 9. In some embodiments, m and n are different integers between 1 and 9.

In some embodiments, the invention includes:
a) forming a reaction mixture comprising a phosphonium salt according to formula XVI

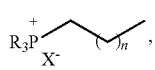
(XVI)

wherein
each R is independently selected from $C_{1-6}$ alkyl and $C_{6-10}$ aryl,
X is a halogen, and
n is an integer from 0 to 16, and an aldehyde according to formula XVII

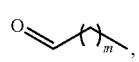
(XVII)

wherein m is an integer from 0 to 16, under conditions sufficient to form an olefin according to formula XVIIIa or formula XVIIIb

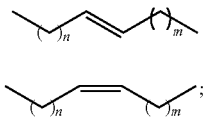
(XVIIIa)
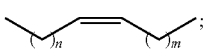
(XVIIIb)

and
b) incubating the olefin with an enzyme capable of selectively hydroxylating one terminal carbon of the olefin to form the olefinic alcohol product.

The phosphonium salt, the aldehyde, the olefin, and the olefinic alcohol product can have any suitable combination of subscripts m and n, as described above. In some embodiments, m and n are independently selected integers between 1 and 9. In some embodiments, m and n are different integers between 1 and 9.

Enzymatic or Other Oxidation of Diol to Aldehyde Followed by Wittig

In some embodiments, terminal alkenols are synthesized according to Scheme 12a. In certain embodiments, the Wittig reaction favors formation of the Z-olefin (Scheme 12b; see, Smith et al. 2000).

Scheme 12a

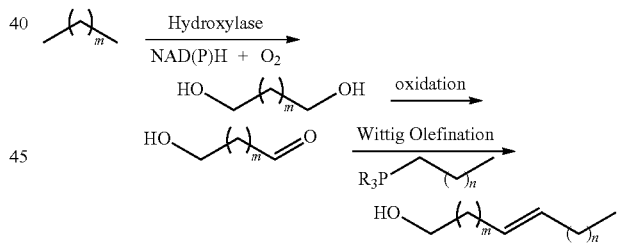

Scheme 12b

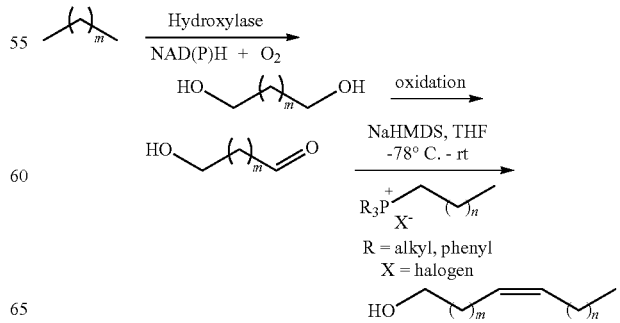

Accordingly, some embodiments of the invention provide methods that include:

a) incubating an alkane according to formula XIX

  (XIX)

wherein m is an integer from 0 to 16,
with an enzyme capable of hydroxylating the terminal carbons of the alkane to form a diol according to formula XX

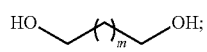  (XX)

b) oxidizing the diol to form an aldehyde according to formula XXI

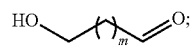  (XXI)

and c) forming a reaction mixture comprising the aldehyde and a phosphonium salt according to formula XXII

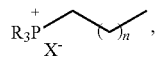  (XXII)

wherein
each R is independently selected from $C_{1-6}$ alkyl and $C_{6-10}$ aryl,
X is a halogen, and
n is an integer from 0 to 16,
under conditions sufficient to form an olefinic alcohol product according to formula XXIIIa or formula XXIIIb

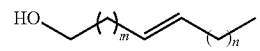  (XXIIIa)

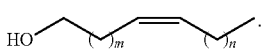  (XXIIIb)

The alkane, the diol, the aldehyde, the phosphonium salt, and the olefinic alcohol product can have any suitable combination of subscripts m and n, as described above. In some embodiments, m and n are independently selected integers between 1 and 9. In some embodiments, m and n are different integers between 1 and 9.

Hydroxylation of Terminal Alkynes

In some embodiments, terminal alkenols are synthesized by first hydroxylating terminal alkynes to their corresponding alkynols. Upon protection of the hydroxyl functional group, the alkynols can be further functionalized by alkylation with other haloalkanes to generate disubstituted alkynols and partial hydrogenation to afford the desired alkene products, as shown in Scheme 13.

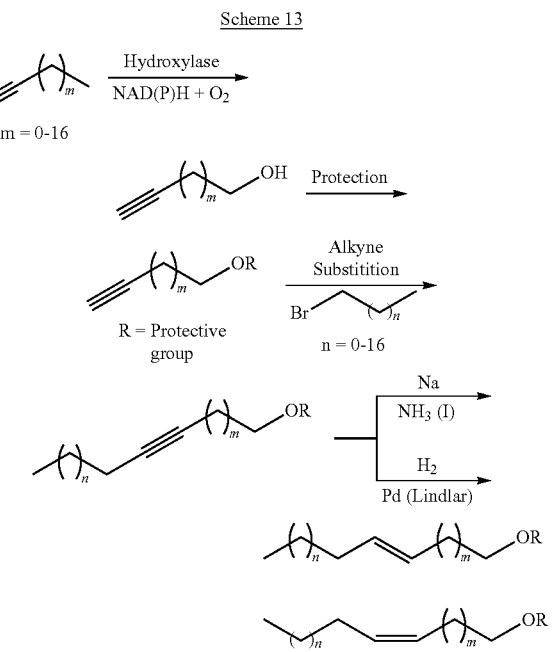

Accordingly, some embodiments of the invention provide a method wherein the hydrocarbon substrate is an alkyne and the method includes:

a) incubating a terminal alkyne according to formula V

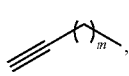  (V)

wherein m is an integer from 0 to 16,
with an enzyme capable of selectively hydroxylating one terminal carbon of the terminal alkyne to form an unsaturated hydrocarbon alcohol according to formula VI

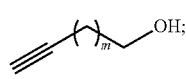  (VI)

b) forming a reaction mixture comprising the unsaturated hydrocarbon alcohol and an alkyl halide according to formula VII

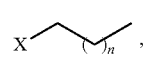  (VII)

wherein X is a halogen and n is an integer from 0 to 16,
under conditions sufficient to form a disubstituted alkyne according to formula VIII

 (VIII)

and c) reducing the disubstituted alkyne to form an olefinic alcohol product according to formula IXa or IXb

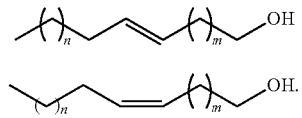 (IXa)

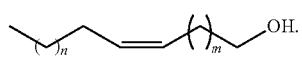 (IXb)

In some embodiments, the unsaturated hydrocarbon alcohol according to formula VI is protected, and then the resulting protected unsaturated hydrocarbon alcohol is combined with an alkyl halide according to formula VII under conditions sufficient to form a protected disubstituted alkyne. The protected disubstituted alkyne can be reduced and deprotected to provide an olefinic alcohol product according to formula IXa or IXb.

The terminal alkyne, the unsaturated hydrocarbon alcohol, the alkyl halide, the disubstituted alkyne, and the olefinic alcohol product can have any suitable combination of subscripts m and n, as described above. In some embodiments, m and n are independently selected integers between 1 and 9. In some embodiments, m and n are different integers between 1 and 9.

Hydroxylation of Halogenated Alkanes

In some embodiments, terminal halogenated alkanes can be biohydroxylated to generate α,ω-halogenated alcohols. Upon protection of the alcohol moiety, the substrate can be coupled with a terminal alkyne to afford an internal alkyne product, which can be partially reduced via known chemical processes to generate either the cis- or trans-alkenes that can be readily converted to insect pheromones, as illustrated in Scheme 14.

Scheme 14

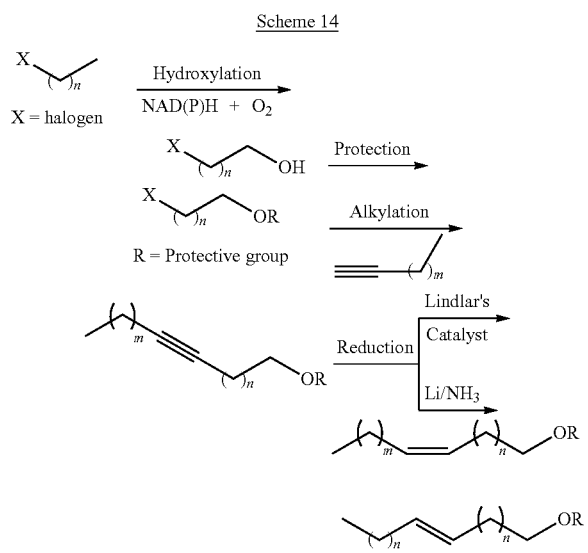

Accordingly, some embodiments of the invention provide a method wherein the saturated hydrocarbon substrate is an alkyl halide, and wherein the method includes:

a) incubating an alkyl halide according to formula X

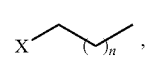 (X)

wherein X is a halogen and n is an integer from 0 to 16, with an enzyme capable of selectively hydroxylating one terminal carbon of the alkyl halide to form a halogen-substituted alkanol according to formula XI

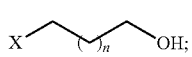 (XI)

b) converting the halogen-substituted alkanol to a protected halogen-substituted alkanol according to formula XII

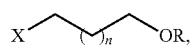 (XII)

wherein R is a protecting group;

c) forming a reaction mixture comprising the protected halogen-substituted alkanol and a terminal alkyne according to formula XIII

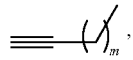 (XIII)

wherein m is an integer from 0 to 16,
under conditions sufficient to form a disubstituted alkyne according to formula XIV

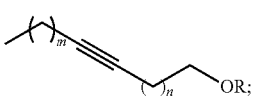 (XIV)

d) reducing the disubstituted alkyne to form a protected olefinic alcohol according to formula XVa or formula XVb

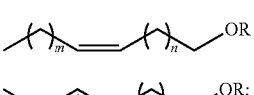 (XVa)

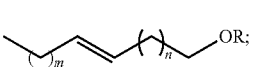 (XVb)

and e) converting the protected olefinic alcohol to the olefinic alcohol product.

The alkyl halide, the halogen-substituted alkanol, the protected halogen-substituted alkanol, the terminal alkyne, the disubstituted alkyne, and the olefinic alcohol product can have any suitable combination of subscripts m and n, as described above. In some embodiments, m and n are independently selected integers between 1 and 9. In some embodiments, m and n are different integers between 1 and 9.

Hydroxylation of Halogenated Alkenes

In some embodiments, halogenated alkenes can be biohydroxylated to generate corresponding alkenols. Upon protection of the alcohol moiety, the substrate is then coupled with haloalkanes, alkenes, or alkynes to provide suitable intermediates for synthesis of insect pheromones as illustrated in Scheme 15 below.

Scheme 15

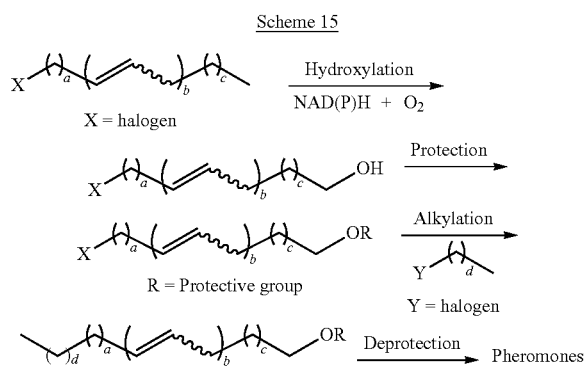

Accordingly, some embodiments of the invention provide a method wherein the unsaturated hydrocarbon substrate is an alkenyl halide, and wherein the method includes:
a) incubating an alkenyl halide according to formula X'

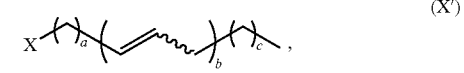 (X')

wherein X is a halogen,
a and c are independently integers from 1 to 15, and
b is an integer from 1 to 3,
with an enzyme capable of selectively hydroxylating one terminal carbon of the alkenyl halide to form a halogen-substituted unsaturated hydrocarbon alcohol according to formula XI'

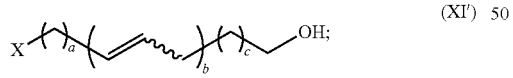 (XI');

b) converting the halogen-substituted unsaturated hydrocarbon alcohol to a protected halogen-substituted unsaturated hydrocarbon alcohol according to formula XII'

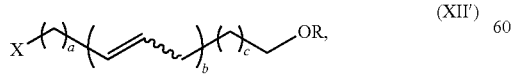 (XII')

wherein R is a protecting group;
c) forming a reaction mixture comprising the protected halogen-substituted unsaturated hydrocarbon alcohol and a reactant according to formula XIIa'

 (XIIa')

wherein Y is a halogen and
d is an interger from 0 to 15
under conditions sufficient to form an elongated protected unsaturated hydrocarbon alcohol according to formula XIIb'

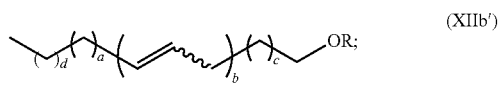 (XIIb');

and
d) converting the elongated protected unsaturated hydrocarbon alcohol to the olefinic alcohol product.

Dehydration of Diols to Alkyne Followed by Alkyne Substitution and Reduction

In some embodiments, terminal alkenols are synthesized according to Scheme 16.

Scheme 16

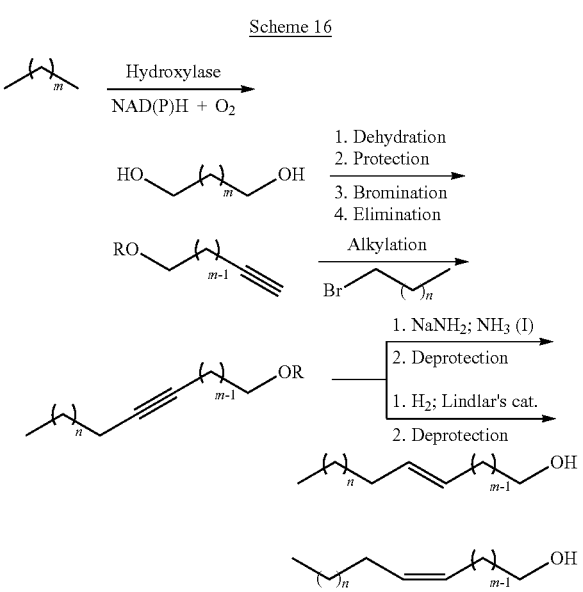

Accordingly, some embodiments of the invention provide a method which includes:
a) incubating an alkane according to formula XXIX

 (XXIX)

wherein m is an integer from 0 to 16,
with an enzyme capable of hydroxylating the terminal carbons of the alkane to form a diol according to formula XXX

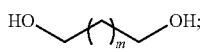 (XXX)

b) converting the diol to an alkyne according to formula XXXI

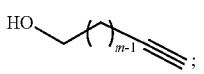 (XXXI)

c) forming a reaction mixture comprising the alkyne and an alkyl halide according to formula XXXII

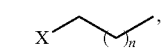 (XXXII)

wherein
X is a halogen and n is an integer from 0 to 15,
under conditions sufficient to form a disubstituted alkyne according to formula XXXIII

 (XXXIII)

and
d) reducing the disubstituted alkyne to form an olefinic alcohol product according to formula XXXIVa or formula XXXIVb

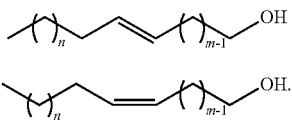

(XXXIVa)
(XXXIVb)

The alkane, the diol, the alkyne, the alkyl halide, the disubstituted alkyne, and the olefinic alcohol product can have any suitable combination of subscripts m and n, as described above. In some embodiments, m and n are independently selected integers between 1 and 9. In some embodiments, m and n are different integers between 1 and 9.

Hydroxylation of Fatty Acids Followed by a Reduction and Wittig Olefination

In some embodiments, terminal alkenols are synthesized according to Scheme 17a. Under certain conditions, the Wittig reaction favors the formation of the Z-isomer (Scheme 17b; see, Smith et al. 2000).

Scheme 17a

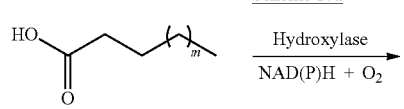

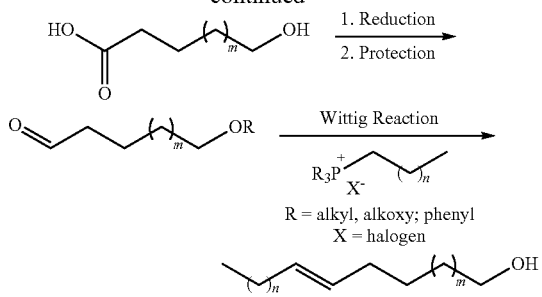

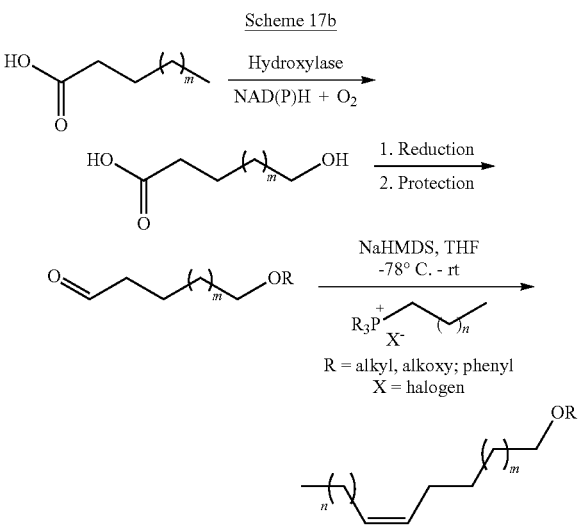

Accordingly, some embodiments of the invention provide a method wherein the saturated hydrocarbon substrate is a fatty acid, and wherein the method includes:
a) incubating a fatty acid with an enzyme capable of selectively hydroxylating the terminal carbon of the fatty acid to form a terminal hydroxy fatty acid;
b) selectively decarbonylating the carboxyl group of the terminal hydroxy fatty acid to form an α,ω-alkenol; and
c) metathesizing the α,ω-alkenol and a terminal olefin in the presence of a metathesis catalyst to form the olefinic alcohol product.

In some embodiments, the invention provides a method wherein the saturated hydrocarbon substrate is a fatty acid, and wherein the method includes:
a) incubating a fatty acid with an enzyme capable of selectively hydroxylating the terminal carbon of the fatty acid to form a terminal hydroxy fatty acid;
b) selectively decarbonylating the carboxyl group of the terminal hydroxy fatty acid to form an α,ω-alkenol;
c) protecting the α,ω-alkenol to form a protected α,ω-alkenol;
d) metathesizing the protected α,ω-alkenol and a terminal olefin in the presence of a metathesis catalyst to form a protected olefinic alcohol product; and
e) deprotecting the protected olefinic alcohol product to form the olefinic alcohol product.

In some embodiments, the α,ω-alkenol is protected via esterification and the protected olefinic alcohol product is deprotected via hydrolysis. In some embodiments, the α,ω- alkenol is protected via esterification with an acid selected from the group consisting of formate and acetate.

In some embodiments wherein the saturated hydrocarbon substrate is a fatty acid, the fatty acid has the formula $H(CH_2)_mCO_2H$, the terminal hydroxy fatty acid has the formula $HO(CH_2)_mCO_2H$, the α,ω-alkenol has the formula $(CH_2=CH)(CH_2)_{m-2}OH$, the terminal olefin has the formula $(CH_2=CH)(CH_2)_nH$, the olefinic alcohol product has the formula $H(CH_2)_n(CH=CH)(CH_2)_{m-2}OH$, and m and n are each independently selected from an integer between 3 and 17.

The fatty acid, the terminal hydroxy fatty acid, the α,ω-alkenol, the terminal olefin, and the olefinic alcohol product can have any suitable combination of subscripts m and n, as described above. In some embodiments, m and n are different integers between 1 and 9.

In some embodiments, the invention provides a method wherein the saturated hydrocarbon substrate is a fatty acid, and wherein the method includes:

a) incubating a fatty acid according to formula XXIV

(XXIV)

wherein m is an integer from 0 to 14, with an enzyme capable of hydroxylating the terminal carbon of the fatty acid to form a terminal hydroxy fatty acid according to formula XXV

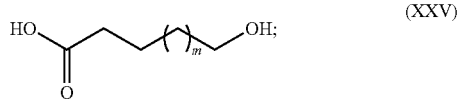

(XXV)

b) reducing the terminal hydroxy fatty acid to form an aldehyde according to formula XXVI

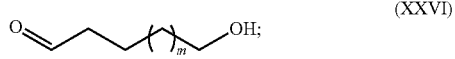

(XXVI)

and c) forming a reaction mixture comprising the aldehyde and a phosphonium salt according to formula XXVII

(XXVII)

wherein
each R is independently selected from $C_{1-6}$ alkyl and $C_{6-10}$ aryl,
X is a halogen, and
n is an integer from 0 to 14,
under conditions sufficient to form an olefinic alcohol product according to formula XXVIIIa or formula XXVIIIb

(XXVIIIa)

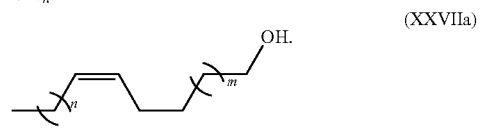

(XXVIIa)

The alkane, fatty acid, the terminal hydroxy fatty acid, the aldehyde, the phosponium salt, and the olefinic alcohol product can have any suitable combination of subscripts m and n, as described above. In some embodiments, m and n are independently selected integers between 1 and 9. In some embodiments, m and n are different integers between 1 and 9.

Synthesis of Oxyfunctionalized Olefins Comprising More than One C=C Double Bond

Hydroxylation of Conjugated and Unconjugated Alkenes

In some embodiments, conjugated and unconjugated alkenes can be biohydroxylated to generate corresponding conjugated and unconjugated alkenols. The resulting products are then coupled with haloalkanes, haloalkenes, or alkynes to provide suitable intermediates for synthesis of insect pheromones as illustrated in Scheme 18 below.

Scheme 18

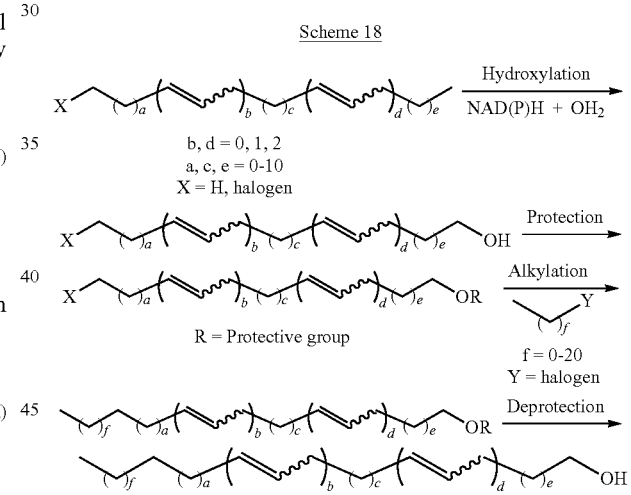

Accordingly, some embodiments of the invention provide a method wherein the unsaturated hydrocarbon substrate is an alkenyl halide, and wherein the method includes:

a) incubating an alkenyl halide according to formula X"

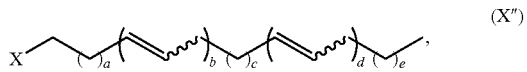

(X")

wherein X a halogen,
a, c, and e are independently integers from 0 to 15, and
b and d are independently integers from 0 to 2, provided that at least one of b and d is other than 0,
with an enzyme capable of selectively hydroxylating one terminal carbon of the alkene to form a halogen-substituted unsaturated hydrocarbon alcohol according to formula XI"

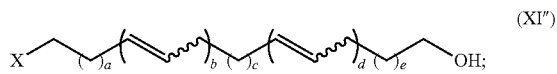

(XI")

b) converting the halogen-substituted unsaturated hydrocarbon alcohol to a protected halogen-substituted unsaturated hydrocarbon alcohol according to formula XII"

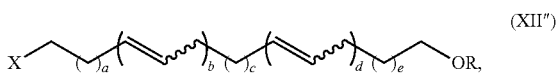

(XII")

wherein R is a protecting group;
c) forming a reaction mixture comprising the protected halogen-substituted unsaturated hydrocarbon alcohol and an alkyl halide according to formula XIIa"

XIIa"

wherein Y is a halogen and
f is an integer from 0 to 15
under conditions sufficient to form an elongated protected unsaturated hydrocarbon alcohol according to formula XIIb"

(XIIb")

and
d) converting the elongated protected unsaturated hydrocarbon alcohol to the olefinic alcohol product.

The alkenyl halide, the halogen-substituted unsaturated hydrocarbon alcohol, the protected halogen-substituted unsaturated hydrocarbon alcohol, the alkyl halide according to formula XIIa", the elongated protected unsaturated hydrocarbon alcohol, and the olefinic alcohol product can have any suitable combination of subscripts a, b, c, d, e, and f. In some embodiments, a, b, c, d, e, and f are integers independently selected from 1, 2, 3, 4, 5, 6, 7, 8 and 9. In some embodiments, the sum of a, b, c, d, e, and f is an integer from 1 to 14. In some embodiments, the sum of a, b, c, d, e, and f is an integer from 1 to 8.

Hydroxylation of Conjugated and Unconjugated Alkene-Alkynes

In some embodiments, conjugated and unconjugated alkene-alkyne bi-functional substrates can be biohydroxylated to generate alkene-alkynols. The resulting biohydroxylation products can then be used for coupling with haloalkanes, alkenes, or alkynes to provide suitable intermediates for synthesis of insect pheromones as illustrated in Scheme 19 below.

Scheme 19

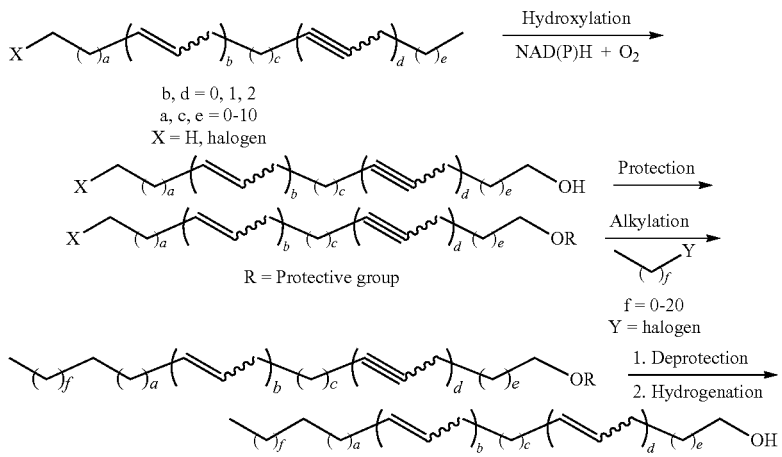

Accordingly, some embodiments of the invention provide a method which includes:
a) incubating an unsaturated halogen-substituted hydrocarbon according to formula X'''

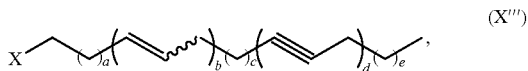

(X''')

wherein X is a halogen,
a, c, and e are independently integers from 0 to 30, and
b and d are independently integers from 1 to 2, provided that at least one of b and d is other than 0,
with an enzyme capable of selectively hydroxylating one terminal carbon of the halogen-substituted unsaturated hydrocarbon to form a halogen-substituted unsaturated hydrocarbon alcohol according to formula XI'''

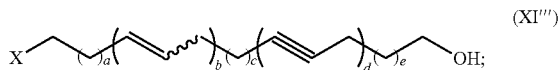

(XI''')

b) converting the halogen-substituted unsaturated hydrocarbon alcohol to a protected halogen-substituted unsaturated hydrocarbon alcohol according to formula XII'''

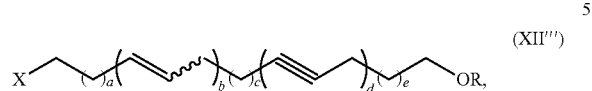

wherein R is a protecting group;
c) forming a reaction mixture comprising the protected halogen-substituted unsaturated hydrocarbon alcohol and an alkyl halide according to formula XIIa'''

wherein Y is a halogen and
f is an interger from 0 to 15
under conditions sufficient to form an elongated protected unsaturated hydrocarbon alcohol according to formula XIIb'''

and
d) converting the elongated protected unsaturated hydrocarbon alcohol to the olefinic alcohol product.

The unsaturated halogen-substituted hydrocarbon, the halogen-substituted unsaturated hydrocarbon alcohol, the protected halogen-substituted unsaturated hydrocarbon alcohol, the alkyl halide according to formula XIIa''', the elongated protected unsaturated hydrocarbon alcohol, and the olefinic alcohol product can have any suitable combination of subscripts a, b, c, d, e, and f. In some embodiments, a, b, c, d, e, and f are integers independently selected from 1, 2, 3, 4, 5, 6, 7, 8 and 9. In some embodiments, the sum of a, b, c, d, e, and f is an integer from 1 to 14. In some embodiments, the sum of a, b, c, d, e, and f is an integer from 1 to 8.

Metathesis Catalysts

In general, any metathesis catalyst stable under the reaction conditions and nonreactive with the functional groups present on the reactant shown in Schemes 3 through 8 may be used with the present invention. Such catalysts are, for example, those described by Grubbs (Grubbs, R. H.," Synthesis of large and small molecules using olefin metathesis catalysts." *PMSE Prepr.*, 2012), herein incorporated by reference in its entirety. Depending on the desired isomer of the olefin, as cis-selective metathesis catalyst may be used, for example one of those described by Shahane et al. (Shahane, S., et al. *Chem Cat Chem*, 2013. 5(12): p. 3436-3459), herein incorporated by reference in its entirety. Specific catalysts 1-5 exhibiting cis-selectivity are shown below (Scheme 19a) and have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5.; Rosebrugh, L. E., et al. *J. Am. Chem. Soc.*, 2013. 135(4): p. 1276-9.; Marx, V. M., et al. *J. Am. Chem. Soc.*, 2013. 135(1): p. 94-7.; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3.; Keitz, B. K., et al. *J. Am. Chem. Soc.*, 2012. 134(1): p. 693-9.; Endo, K. et al. *J. Am. Chem. Soc.*, 2011. 133(22): p. 8525-7).

Scheme 19a

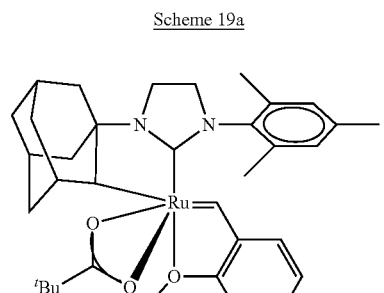

1

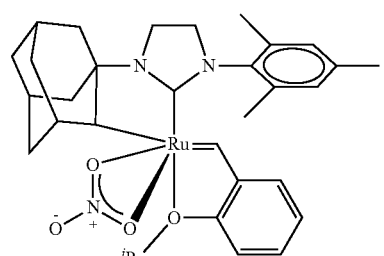

2

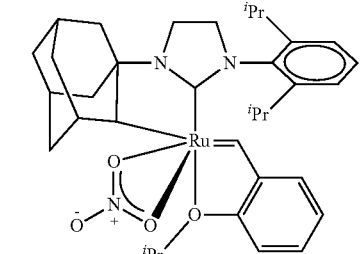

3

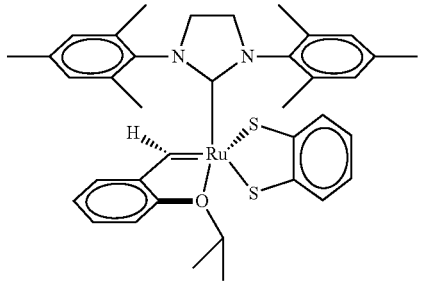

4

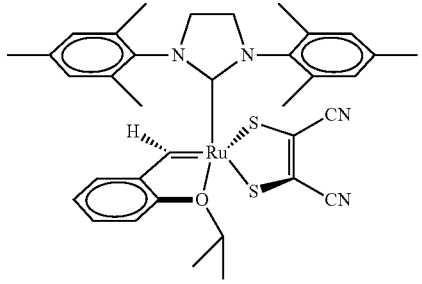

5

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Due to their excellent stability and functional group tolerance, preferred metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis (hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the invention also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.*, 2012, 134: 2788-2799; Halford. *Chem. Eng. News*, 2011, 89 (45): 11; Yu, et al. *Nature*, 2011, 479: 88-93; Lee. *Nature*, 2011, 471: 452-453; Meek, et al. *Nature*, 2011: 471: 461-466; Flook, et al. *J. Am. Chem. Soc.* 2011, 133: 1784-1786; Zhao, et al. *Org Lett.*, 2011, 13(4): 784-787; Ondi, et al. "High activity, stabilized formulations, efficient synthesis and industrial use of Mo- and W-based metathesis catalysts" *XiMo Technology Updates*, 2015: http://www.ximo-inc.com/files/ximo/uploads/download/Summary_3.11.15.pdf; Schrock, et al. *Macromolecules*, 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the invention also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the invention also include those described in U.S. Pat. No. 4,231,947; U.S. Pat. No. 4,245,131; U.S. Pat. No. 4,427,595; U.S. Pat. No. 4,681,956; U.S. Pat. No. 4,727,215; International Pub. No. WO 1991/009825; U.S. Pat. No. 5,087,710; U.S. Pat. No. 5,142,073; U.S. Pat. No. 5,146,033; International Pub. No. WO 1992/019631; U.S. Pat. No. 6,121,473; U.S. Pat. No. 6,346,652; U.S. Pat. No. 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the invention also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the invention also include those set forth in the following table:

| Structure | Name |
|---|---|
| (structure shown) | dichloro[1,3-bis(2,6-isopropylphenyl)-2-imidazolidinylidene](benzylidene)(tricyclohexylphosphine)ruthenium(II) |

-continued

| Structure | Name |
|---|---|
| 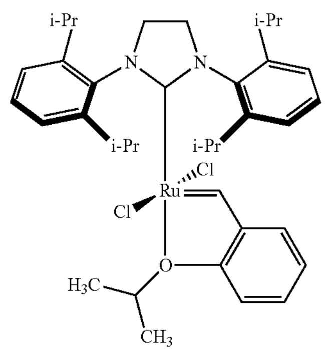 | dichloro[1,3-bis(2,6-isopropylphenyl)-2-imidazolidinylidene](2-isopropoxyphenylmethylene)ruthenium(II) |
|  | dichloro[1,3-Bis(2-methylphenyl)-2-imidazolidinylidene](benzylidene)(tricyclohexylphosphine)ruthenium(II) |
| 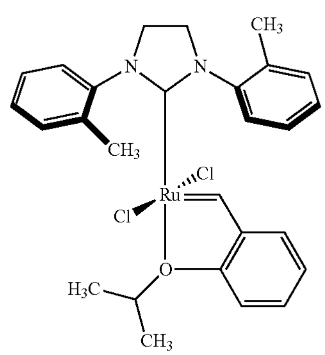 | dichloro[1,3-bis(2-methylphenyl)-2-imidazolidinylidene](2-isopropoxyphenylmethylene)ruthenium(II) |
| 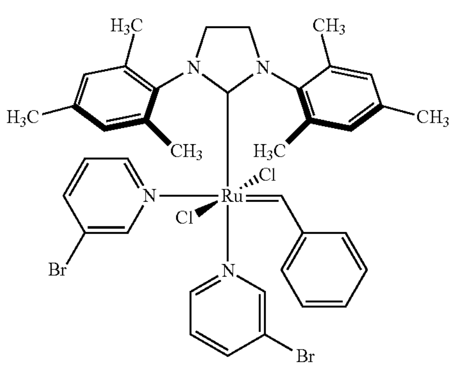 | dichloro[1,3-bis(2,4,6-trimethylphenyl)-2-imidazolidinylidene](benzylidene)bis(3-bromopyridine)ruthenium(II) |

-continued

| Structure | Name |
|---|---|
| 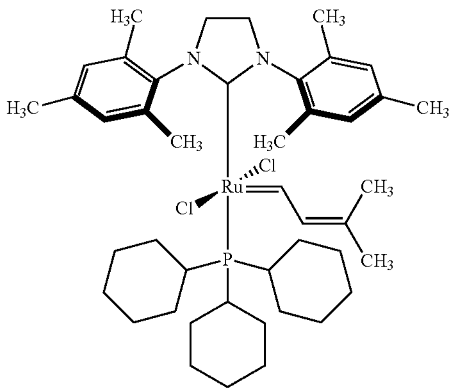 | dichloro[1,3-bis(2,4,6-trimethylphenyl)-2-imidazolidinylidene](3-methyl-2-butenylidene)(tricyclohexylphosphine)ruthenium(II) |
| 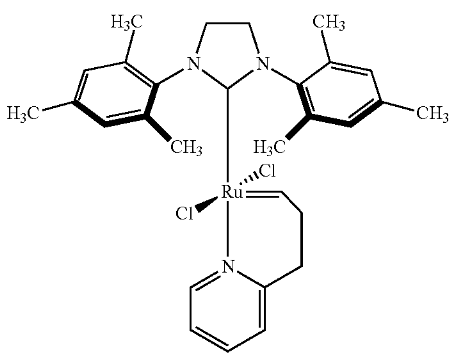 | dichloro[1,3-bis(2,4,6-trimethylphenyl)-2-imidazolidinylidene][3-(2-pyridinyl)propylidene]ruthenium(II) |
| 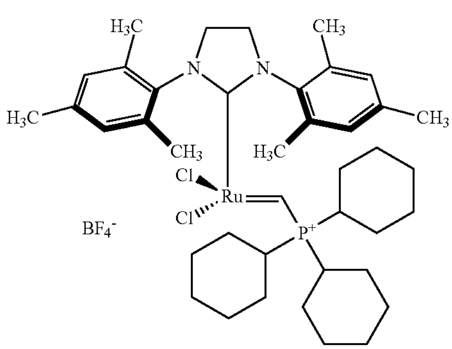 | dichloro[1,3-bis(2,4,6-trimethylphenyl)-2-imidazolidinylidene][(tricyclohexylphosphoranyl)methylidene]ruthenium(II) tetrafluoroborate |
| 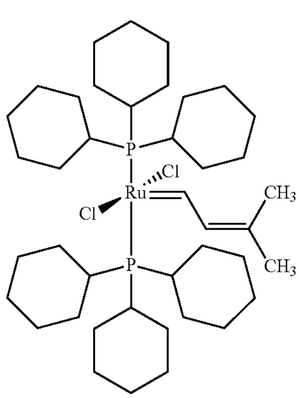 | dichloro(3-methyl-2-butenylidene)bis(tricyclohexylphosphine)ruthenium(II) |

| Structure | Name |
|---|---|
| 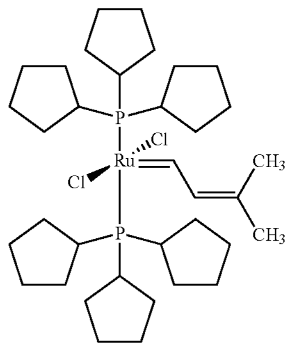 | dichloro(3-methyl-2-butenylidene)bis(tricyclopentylphosphine)ruthenium(II) |
| 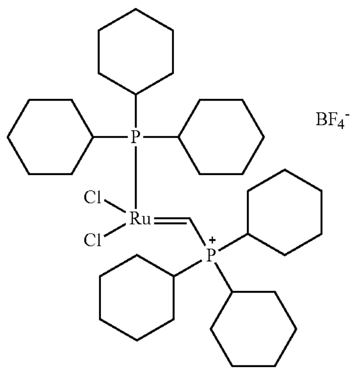 | dichloro(tricyclohexylphosphine)[(tricyclohexyl-phosphoranyl)methylidene]ruthenium(II) tetrafluoroborate |
| 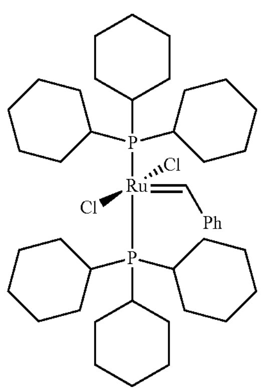 | bis(tricyclohexylphosphine) benzylidine ruthenium(IV) dichloride |
| 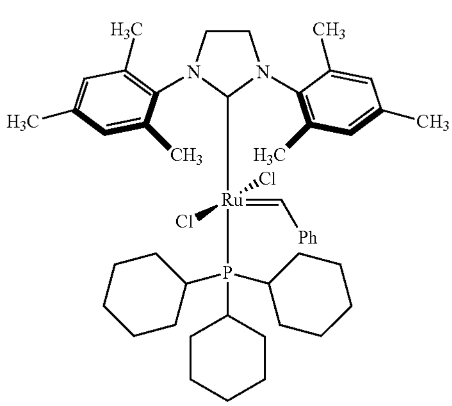 | [1,3-bis-(2,4,6-trimethylpheny)-2-imidazolidinylidene]dichloro(phenylmethylene)(tricyclohexylphosphine)ruthenium |

| Structure | Name |
|---|---|
| 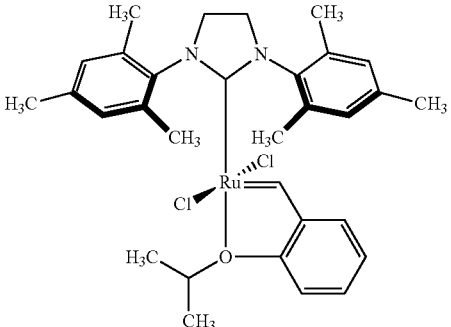 | (1,3-bis-(2,4,6-trimethylphenyl)-2-imidazolidinylidene)dichloro(o-isopropoxyphenylmethylene)ruthenium |
| 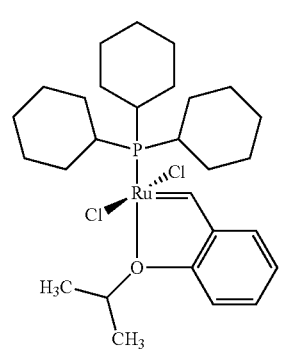 | dichloro(o-isopropoxyphenylmethylene)(tricyclohexylphosphine)ruthenium(II) |
| 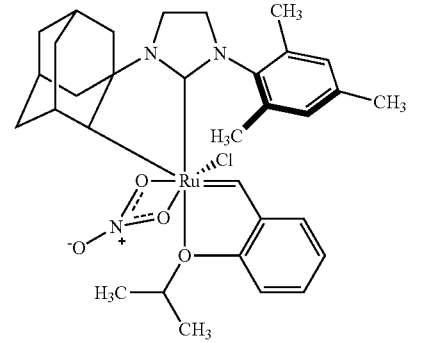 | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-y lidene]}ruthenium |

Catalysts useful in the methods of the invention also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the invention include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, preferably better than 50%, more preferably better than 75%, and most preferably better than 90%. In addition, the reactants and products are chosen to provide at least a 5° C. difference, preferably a greater than 20° C. difference, and most preferably a greater than 40° C. difference in boiling points. Additionally, the use of metathesis catalysts allows for much faster product formation than byproduct, it is desirable to run these reactions as quickly as practical. In particular, the reactions are performed in less than about 24 hours, preferably less than 12 hours, more preferably less than 8 hours, and most preferably less than 4 hours.

One of skill in the art will appreciate that the time, temperature and solvent can depend on each other, and that changing one can require changing the others to prepare the pyrethroid products and intermediates in the methods of the invention. The metathesis steps can proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

Hydroxylation Catalysts

Various enzymes and/or whole cells comprising enzymes can be used to catalyze hydroxylation reactions described above.

Known enzyme families with terminal hydroxylation activity for medium and long chain alkanes and fatty acids include AlkB, CYP52, CYP153, and LadA (Bordeaux et al., 2012, *Angew. Chem.-Int. Edit.* 51: 10712-10723; Ji et al., 2013, *Front. Microbiol.* 4). For example, Malca et al. describe terminal hydroxylation of mono-unsaturated fatty There are four families of enzymes with reported terminal alkane and fatty acid hydroxylation activity: (1) methane monoxxygenases; (2) integral membrane diiron non-heme alkane hydroxylases (AlkB); (3) Cytochrome P450s (P450s); and (4) long chain alkane monoxygenases (LadA) (Bordeaux et al., 2012, *Angew. Chem.-Int. Edit.* 51: 10712-10723; Ji et al., 2013, *Front. Microbiol.* 4). Methane monooxygenases are difficult to express in heterologous non-methanotrophic hosts and generally prefer small substrate (<C4). Of the remaining three families, the substrate specificity based on substrate chain length of representative members is summarized below in Table 2.

TABLE 2

Relative activities of terminal hydroxylases for alkanes and fatty acids with various chain lengths.

| Alkane/FA chain length | CYP153 A6 (Funhoff et al., 2006, *J. Bacteriol.* 188: 5220-5227) | CYP15 3A16 (Scheps et al., 2011, *Org. Biomol. Chem.* 9: 6727-6733) | CYP15 3A *P.* sp. (Scheps et al., 2011, *Org. Biomol. Chem.* 9: 6727-6733) | AlkB *P. putida* GPo1 (Vanbeilen et al., 1994, *Enzyme Microb. Technol.* 16: 904-911) | alkB2 *Gordonia* sp TF6* (Fujii et al., 2004, *Biosci. Biotechnol. Biochem.* 68: 2171-2177) | LadA (Feng et al., 2007, *Proc. Natl. Acad. Sci. U.S.A.* 104: 5602-5607) | CYP52 A3 (Scheller et al., 1996, *Arch. Biochem. Biophys.* 328: 245-254) | CYP52 A4 (Scheller et al., 1996, *Arch. Biochem. Biophys.* 328: 245-254) | CYP52 A21 (Kim et al., 2007, *Arch. Biochem. Biophys.* 464: 213-220) |
|---|---|---|---|---|---|---|---|---|---|
| C8 | 100 | 100 | 100 | 95 | 72 | | | | |
| C9 | 82 | 29 | 69 | 100 | 63 | | | | |
| C10 | 23 | 13 | 60 | 60 | 66 | | | | |
| C11 | 1 | <8 | <6 | 6 | 48 | | | | |
| C12 | | | | | 34 | | 41 | 37 | |
| C12 FA (lauric) | | | | | | | 20 | 100 | 100 |
| C14 | | | | | | | | | |
| C14 FA (Myristic) | | | | | | | | | 86 |
| C15 | | | | | | 83 | | | |
| C16 | | | | | | 100 | 100 | 33 | |
| C16 FA (Palmetic) | | | | | | | 35 | 18 | 29 |
| C18 | | | | | | 78 | 48 | 20 | |
| C18 FA (Stearic) | | | | | | | 30 | 1 | |
| C22 | | | | | | 74 | | | |
| C24 | | | | | | 65 | | | |

*100% relative activity obtained with hexane acid by cytochromes P450 of the CYP153 family (Malca et al., 2012, *Chemical Communications* 48: 5115-5117). Weissbart et al. describe the terminal hydroxylation of various cis and trans unsaturated lauric acid analogs (Weissbart et al., 1992, *Biochimica et Biophysica Acta, Lipids and Lipid Metabolism* 1124: 135-142). However, to date, none of these enzymes has been demonstrated to perform terminal hydroxylation of alkenes with internal olefins such as (E)-dec-5-ene. The presence of C=C bonds present competing sites of oxygen insertion and alters the 3-dimensional orientation of the molecule. The regioselectivity of these enzymes for the terminal C—H bond of alkanes and fatty acid substrate may not extend to alkenes with internal olefins for these reasons. For asymmetric substrates, obtaining hydroxylation at the desired terminal C—H bond presents additional challenges compared to symmetric substrates. Finally, controlling the reaction selectivity to produce a single terminal alcohol instead of α-ω diols, acids, or diacids is also a major concern.

In particular embodiments, the search for a terminal hydroxylase with activity for alkene with internal olefins starts with known terminal alkane and fatty acid hydroxylases.

In certain embodiments, depending on the chain length of the desired substrate, some members of these four enzyme families are better suited than others as candidates for evaluation. For C-10 substrates such as (E)-dec-5-ene, the substrate specificity of characterized CYP153 and AlkB enzymes makes them candidate enzymes. Likewise, for longer substrates such as (Z)-hexadec-11-ene, members of the LadA and CYP52 families appear to have the closest substrate profile.

The most widely characterized member of the AlkB family is obtained from the Alk system of *Pseudomonas putida* GPo1 (van Beilen and Funhoff, 2005, *Curr. Opin. Biotechnol.* 16: 308-314). In addition to the integral membrane diiron non-heme hydroxylase AlkB, a rubredoxin (AlkG) and a rubredoxin reductase (AlkT) are required for hydroxylation function. The entire Alk system of *P. putida* GPo1, alkBFGHJKL and alkST genes, which allows the strain to grown on alkanes as its sole carbon source, has been cloned into the broad host range vector pLAFR1 (pGEc47) and is available from DSMZ in the host *E. Coli* K12 Gec137 (Smits et al., 2001, *Plasmid* 46: 16-24). The other alk genes alkF, alkJ, alkH, alkK, alkL, and alkS encode an inactive rubredoxin, an alcohol dehydrogenase, an aldehyde dehydrogenase, an acyl-CoA synthase, an alkane transporter and a global pathway regulator, respectively (Smits et al., 2003, *Antonie Van Leeuwenhoek* 84: 193-200). These genes facilitate the use of the alcohol product from the AlkB reaction to generate the fatty acyl-CoA that is substrate for β-oxidation. To accumulate the alcohol product, a knockout strain of alkJ, *E. coli* GEC137 pGEc47ΔJ has been used in a whole-cell biotransformation to produce 1-dodecanol (Grant et al., 2011, *Enzyme Microb. Technol.* 48: 480-486). The presence of alkL appears to enhance substrate uptake and consequently improve the whole-cell activity for both *Pseudomonas* and *E. coli* (Cornelissen et al., 2013, *Biotechnology and Bioengineering* 110: 1282-1292; Julsing et al., 2012, *Appl. Environ. Microbiol.* 78: 5724-5733; Scheps et al., 2013, *Microb. Biotechnol.* 6: 694-707). A simplified version of pGEc47 containing only alkBFGST in the broad-host range vector pCOM10, pBT10, has also been used for the conversion of fatty-acid methyl esters to ω-hydroxy fatty acid methyl esters in *E. coli* W3110 (Schrewe et al., 2011, *Advanced Synthesis & Catalysis* 353: 3485-3495).

CYP52 family members are membrane bound cytochrome P450s that require electron delivery from a reductase for function. CYP52 members have mainly been identified from alkane-degrading *Candida* species (Scheller et al., 1996, *Arch. Biochem. Biophys.* 328: 245-254; Craft et al., 2003, Appl. Environ. Microbiol. 69: 5983-5991; Scheller et al., 1998, *J. Biol. Chem.* 273: 32528-32534; Seghezzi et al., 1992, *DNA Cell Biol.* 11: 767-780; Zimmer et al., 1996, *Biochem. Biophys. Res. Commun.* 224: 784-789). Thus far, expression and characterization of CYP52 enzymes have been performed in the native *Candida* host and other yeast hosts. Gene knockouts of (1) the β-oxidation pathways, (2) alcohol dehydrogenases and (3) select native CYP52s has resulted in strains that can accumulate ω-hydroxy fatty acids when fatty acids are fed to the culture (Lu et al., 2010, *J. Am. Chem. Soc.* 132: 15451-15455). Of particular interest, DP428, DP522 and DP526 are *C. tropicalis* strains expressing a single CYP52 with the appropriate knockouts for catalyzing terminal hydroxylation of fatty acids (Lu et al., 2010, *J. Am. Chem. Soc.* 132: 15451-15455).

CYP153 family members are soluble and membrane associated cytochrome P450s that also depend on electron transfer from ferredoxin and ferredoxin reductase for function (Funhoff et al., 2007, *Enzyme and Microbial Technology* 40: 806-812). CYP153 members have been isolated from a range of alkane-degrading microorganisms. There are currently 56 annotated CYP153 sequences available from the Nelson P450 database, a BLAST search of CYP153A6 resulted in 221 identified homologs with >70% sequence identity. The use of CYP153 enzymes for terminal hydroxylation of octane and dodecanoic acid has been demonstrated with heterologous expression in *E. coli*. For the conversion of octane to octanol, the CYP153 operon from *Mycobacterium* sp. HXN-1500 was cloned into pET28b(+) and the biotransformation was performed in *E. coli* BL21(DE3) (Gudiminchi et al., 2012, *Appl. Microbiol. Biotechnol.* 96: 1507-1516). For the conversion of dodecanoic acid, an *E. coli* HMS174 strain containing a fusion of a CYP153A$_{M.aq.}$ mutant with the CYP102A1 reductase domain in pCola-Duet-1 along with alkL was used for the transformation (Scheps et al., 2013, *Microb. Biotechnol.* 6: 694-707).

Long chain alkane monooxygenase, LadA, isolated from *G. thermodemtrificants* NG80-2 catalyzes the terminal hydroxylation of C15 to C36 alkanes with a metal-free flavoprotein mechanism that differs from AlkB and CYP enzymes (Dong et al., 2012, *Appl. Microbiol. Biotechnol.* 94: 1019-1029). The LadA reaction requires FMNH$_2$ or NADPH and the native reductase partner has yet to be identified. Expression of the LadA gene in *E. coli* BL21 (DE3) using the pET-28a(+) plasmid yielded cell extracts with terminal hydroxylation activity for hexadecane (Dong et al., 2012, *Appl. Microbial. Biotechnol.* 94: 1019-1029). Literature reports of LadA hydroxylation reactions have been performed using purified enzymes and examples of whole-cell biotransformation is lacking.

Coding sequences for enzymes that may be used herein may be derived from bacterial, fungal, or plant sources. Tables 3, 4, and 5 list enzymes for coding regions of representative non-heme diiron alkane monooxygenases, long-chain alkane hydroxylases, and cytochromes P450, respectively. Additional enzymes and their coding sequences may be identified by BLAST searching of public databases. Typically, BLAST searching of publicly available databases with known non-heme diiron alkane monooxygenases, cytochromes P450, and long-chain alkane hydroxylase sequences, such as those provided herein, is used to identify enzymes and their encoding sequences that may be used in the present invention. For example, enzymes having amino acid sequence identities of at least about 80-85%, 85%-90%, 90%-95%, or about 90%, 91%, 92%, 93%, 94%, 95%, 96%, 97%, 98%, or 99% sequence identity to any of the enzymes listed in Tables 3, 4, and 5 may be used. Hydroxylase enzymes can be codon-optimized for expression in certain desirable host organisms, such as yeast and *E. coli*.

In other embodiments, the sequences of the enzymes provided herein may be used to identify other homologs in nature. For example, each of the encoding nucleic acid fragments described herein may be used to isolate genes encoding homologous proteins. Isolation of homologous genes using sequence-dependent protocols is well known in the art. Examples of sequence-dependent protocols include, but are not limited to, (1) methods of nucleic acid hybridization, (2) methods of DNA and RNA amplification, as exemplified by various uses of nucleic acid amplification technologies (e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker et al., *Proc. Natl. Acad. Sci. USA*, 89:392 (1992)), and (3) methods of library construction and screening by complementation.

Hydroxylase enzymes or whole cells expressing hydroxylase enzymes can be further engineered for use in the methods of the invention. Enzymes can be engineered for improved hydroxylation activity, improved Z:E selectivity, improved regioselectivity, improved selectivity for hydroxylation over epoxidation and/or improved selectivity for hydroxylation over dehalogenation. The term "improved hydroxylation activity" as used herein with respect to a particular enzymatic activity refers to a higher level of enzymatic activity than that measured in a comparable non-engineered hydroxylase enzyme of whole cells comprising a hydroxylase enzyme. For example, overexpression of a specific enzyme can lead to an increased level of activity in the cells for that enzyme. Mutations can be introduced into a hydroxylase enzyme resulting in engineered enzymes with improved hydroxylation activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the KM for the substrate, or by directed evolution. See, e.g., *Methods in Molecular Biology* (vol. 231), ed. Arnold and Georgiou, Humana Press (2003).

Accordingly, some embodiments of the invention provide methods for synthesizing olefinic alcohol products as described above, wherein the enzyme is a non-heme diiron monooxygenase. In some embodiments, the non-heme diiron monooxygenase is selected from Table 3 or a variant thereof having at least 90% identity thereto.

TABLE 3

Non-heme diiron monooxygenase enzymes capable of catalyzing selective terminal alkene hydroxylation.

| Species Origin | Gene Name | Accession No |
|---|---|---|
| *Pseudomonas oleovorans* | alkB | P12691 (SEQ ID NO: 25) |
| *Pseudomonas mendocina* (strain ymp) | Pmen_0443 | A4XPE8 |
| *Pseudomonas aeruginosa* | alkB | Q932R7 |
| Enterobacteriaceae bacterium 58 | alkB | B5TVB4 |
| *Bacillus* sp. BTRH40 | alkB | B5TVB3 |
| uncultured bacterium | alkB | B6Z2G6 |
| *Pseudomonas aeruginosa* | alk | B7U6M1 |
| uncultured bacterium | alkB | U3PXQ1 |
| uncultured bacterium | alkB | U3Q1X4 |
| *Pseudomonas stutzeri* (*Pseudomonas perfectomarina*) | alkB | Q7X4G8 |
| uncultured organism | alkB | G3EBX4 |
| uncultured bacterium | alkB | U3PXQ7 |
| *Pseudomonas aeruginosa* | alk | B7U6M0 |
| *Pseudomonas chlororaphis* subsp. *aureofaciens* | alkB | Q9RLI5 |
| *Arthrobacter* sp. ITRH48 | alkB | B5TVB7 |
| *Streptomyces* sp. ITRH51 | alkB | B5TVB6 |
| *Arthrobacter* sp. ITRH49 | alkB | B5TVC0 |
| *Dietzia* sp. ITRH56 | alkB | B5TVB8 |
| *Microbacterium* sp. ITRH47 | alkB | B5TVB5 |
| *Pantoea* sp. BTRH11 | alkB | B5TVB2 |
| *Pseudomonas* sp. ITRI53 | alkB | B5TVB1 |
| *Pseudomonas* sp. ITRI73 | alkB | B5TVB0 |
| *Pseudomonas* sp. ITRH25 | alkB | B5TVA9 |
| *Pseudomonas* sp. MIXRI75 | alkB | B5TVA8 |
| *Pseudomonas* sp. MIXRI74 | alkB | B5TVA7 |
| *Rhodococcus* sp. ITRH43 | alkB | B5TVA4 |
| *Ochrobactrum* sp. ITRH1 | alkB | B5TVA3 |
| Alcaligenaceae bacterium BTRH5 | alkB | B5TVA6 |
| *Pseudomonas* sp. ITRH76 | alkB | B5TVA5 |
| *Pseudomonas* sp. 7/156 | alkB | Q93LR8 |
| uncultured Rhizobiales bacterium | alkB | D6NSH3 |
| uncultured soil bacterium | | S5DSW0 |
| uncultured bacterium | alkB | U3PYH2 |
| uncultured prokaryote | alkB | C7EAT4 |
| uncultured Rhizobiales bacterium | alkB | D6NSL1 |
| uncultured Rhizobiales bacterium | alkB | D6NSJ4 |
| uncultured prokaryote | alkB | C7EAZ5 |
| uncultured Rhizobiales bacterium | alkB | D6NSK5 |
| uncultured Rhizobiales bacterium | alkB | D6NSK3 |
| uncultured Rhizobiales bacterium | alkB | D6NSJ7 |
| uncultured Rhizobiales bacterium | alkB | D6NSK1 |
| uncultured Rhizobiales bacterium | alkB | D6NSH4 |
| uncultured Rhizobiales bacterium | alkB | D6NSJ2 |
| uncultured Rhizobiales bacterium | alkB | D6NSI2 |
| uncultured Rhizobiales bacterium | alkB | D6NSJ3 |
| uncultured Rhizobiales bacterium | alkB | D6NSJ6 |
| *Pseudomonas* sp. ITRI22 | alkB | B5TVB9 |
| uncultured Rhizobiales bacterium | alkB | D6NSK7 |
| uncultured soil bacterium | | S5DTG4 |
| *Pseudomonas putida* (*Arthrobacter siderocapsulatus*) | alkB | Q9WWW6 (SEQ ID NO: 26) |
| uncultured Rhizobiales bacterium | alkB | D6NSI6 |
| uncultured bacterium | alkB | B6Z2E6 |
| uncultured bacterium | alkB | B1P6K4 |
| *Pseudomonas* sp. G5(2012) | PG5_40690 | S2EW96 |
| *Alcanivorax dieselolei* | alkB | B6Z2B7 |
| *Alcanivorax borkumensis* | alkB | B6Z284 |
| uncultured bacterium | alkB | B6Z2G9 |
| *Marinobacter* sp. S17-4 | alkB | C7DLJ8 |
| uncultured bacterium | alkB | B6Z2H0 |
| *Alcanivorax* sp. S17-16 | alkB | B6Z2D8 |
| uncultured organism | alkB | G3EBX7 |
| uncultured bacterium | alkB | H9NJ23 |
| uncultured bacterium | alkB | C8AYB7 |
| uncultured bacterium | alkB | W0UB63 |
| uncultured bacterium | alkB | U3Q1V0 |

TABLE 3-continued

Non-heme diiron monooxygenase enzymes capable of catalyzing selective terminal alkene hydroxylation.

| Species Origin | Gene Name | Accession No |
|---|---|---|
| *Alcanivorax borkumensis* | alkB | T1WPB9 |
| uncultured organism | alkB | G3EBX5 |
| uncultured Rhizobiales bacterium | alkB | D6NSK6 |
| uncultured bacterium | alkB | U3Q5C8 |
| uncultured bacterium | alkB | Q3HXE5 |
| *Xanthobacter flavus* | alkane-1-monooxygenase | Q934J9 |
| uncultured bacterium | alkB | Q3HXD6 |
| *Acidisphaera* sp. C197 | alkB | Q5RLH8 |
| uncultured bacterium | alkB | M9T624 |
| uncultured bacterium | alkB | M9T8D1 |
| uncultured bacterium | alkB | H9B8U8 |
| *Kordiimonas gwangyangensis* | alkB | B6Z2E4 |
| uncultured soil bacterium | | S5DPL2 |
| uncultured bacterium | alkB | F0X332 |
| uncultured bacterium | alkB | F0X324 |
| uncultured bacterium | alkB | F0X334 |
| uncultured organism | alkB | G3EBX2 |
| uncultured bacterium | alkB | F0X328 |
| uncultured soil bacterium | | S5DTI7 |
| uncultured bacterium | alkB | Q3HXF7 |
| uncultured bacterium | alkB | F0X327 |
| uncultured bacterium | alkB | F0X335 |
| uncultured bacterium | alkB | F0X329 |
| uncultured bacterium | alkB | F0X342 |
| uncultured bacterium | alkB | F0X300 |
| uncultured bacterium | alkB | Q3HXE8 |
| uncultured bacterium | alkB | U3Q1X0 |
| uncultured bacterium | alkB | Q3HXD7 |
| *Ralstonia* sp. PT11 | alkB | Q3HXC9 |
| uncultured bacterium | alkB | Q3HXE6 |
| uncultured bacterium | alkB | F0X305 |
| uncultured bacterium | alkB | U3Q5A0 |
| uncultured bacterium | alkB | F0X306 |
| *Marinobacter* sp. P1-14D | alkB1 | C6KEH4 |
| uncultured Rhizobiales bacterium | alkB | D6NSI7 |
| uncultured bacterium | alkB | F0X346 |
| uncultured bacterium | alkB | F0X346 |
| uncultured bacterium | alkB | F0X343 |
| uncultured bacterium | alkB | F0X339 |
| uncultured bacterium | alkB | F0X309 |
| uncultured bacterium | alkB | F0X333 |
| uncultured bacterium | alkB | F0X321 |
| uncultured bacterium | alkB | Q3HXF0 |
| uncultured bacterium | alkB | F0X312 |
| uncultured bacterium | alkB | F0X303 |
| uncultured bacterium | alkB | F0X331 |
| uncultured bacterium | alkB | F0X302 |
| uncultured bacterium | alkB | Q3HXE9 |
| uncultured bacterium | alkB | F0X313 |
| uncultured bacterium | alkB | F0X316 |
| uncultured bacterium | alkB | M9TDK6 |
| uncultured bacterium | alkB | H9B8V5 |
| uncultured Rhizobiales bacterium | alkB | D6NSF4 |
| uncultured Rhizobiales bacterium | alkB | D6NSF2 |
| uncultured bacterium | alkB | B6Z2G8 |
| uncultured Rhizobiales bacterium | alkB | D6NSF1 |
| uncultured Rhizobiales bacterium | alkB | D6NSG4 |
| uncultured Rhizobiales bacterium | alkB | D6NSG3 |
| uncultured Rhizobiales bacterium | alkB | D6NSF3 |
| uncultured Rhizobiales bacterium | alkB | D6NSI4 |
| uncultured Rhizobiales bacterium | alkB | D6NSH9 |
| uncultured Rhizobiales bacterium | alkB | D6NSG1 |
| uncultured Rhizobiales bacterium | alkB | D6NSJ9 |
| uncultured Rhizobiales bacterium | alkB | D6NSG6 |
| uncultured soil bacterium | | S5DP42 |
| uncultured bacterium | alkB | F0X323 |
| uncultured bacterium | alkB | F0X318 |
| uncultured bacterium | alkB | F0X317 |
| uncultured bacterium | alkB | F0X325 |
| uncultured bacterium | alkB | F0X308 |
| uncultured bacterium | alkB | F0X336 |
| uncultured soil bacterium | | S5E0W0 |
| uncultured bacterium | alkB | F0X304 |
| *Bradyrhizobium* sp. DFCI-1 | C207_00091 | U1HQ84 |
| uncultured Rhizobiales bacterium | alkB | D6NSF9 |
| uncultured Rhizobiales bacterium | alkB | D6NSH2 |

TABLE 3-continued

Non-heme diiron monooxygenase enzymes capable of catalyzing selective terminal alkene hydroxylation.

| Species Origin | Gene Name | Accession No |
| --- | --- | --- |
| uncultured Rhizobiales bacterium | alkB | D6NSF6 |
| uncultured Rhizobiales bacterium | alkB | D6NSG2 |
| uncultured Rhizobiales bacterium | alkB | D6NSH7 |
| uncultured bacterium | alkB | F0X322 |
| uncultured soil bacterium | | S5DPY4 |
| uncultured bacterium | alkB | F0X349 |
| uncultured bacterium | alkB | F0X310 |
| uncultured bacterium | alkB | F0X315 |
| uncultured bacterium | alkB | F0X344 |
| uncultured bacterium | alkB | F0X326 |
| uncultured bacterium | alkB | W0UB94 |
| uncultured bacterium | alkB | W0UAL7 |
| uncultured soil bacterium | | S5DP84 |
| uncultured soil bacterium | | S5E064 |
| uncultured soil bacterium | | S5E0M5 |
| uncultured bacterium | alkB | M9T7Y4 |
| uncultured prokaryote | alkB | C7EAZ7 |
| *Thalassolituus oleivorans* | alkB | Q8RSS6 |
| uncultured prokaryote | alkB | C7EAZ8 |
| *Marinobacter* sp. EVN1 | Q672_13115 | U7NVU4 |
| uncultured Rhizobiales bacterium | alkB | D6NSF8 |
| *Marinobacter aquaeolei* (strain ATCC 700491/DSM 11845/VT8) (*Marinobacter hydrocarbonoclasticus* (strain DSM 11845)) | Maqu_0610 | A1TY92 |
| *Marinobacter hydrocarbonoclasticus* ATCC 49840 | alkB MARHY2847 | H8WCU7 |
| uncultured Rhizobiales bacterium | alkB | D6NSG8 |
| *Alcanivorax borkumensis* | alkB1 | Q93UQ1 |
| *Alcanivorax borkumensis* (strain SK2/ATCC 700651/DSM 11573) | alkB1 ABO_2707 | Q0VKZ3 (SEQ ID NO: 27) |
| *Marinobacter aquaeolei* (strain ATCC 700491/DSM 11845/VT8) (*Marinobacter hydrocarbonoclasticus* (strain DSM 11845)) | Maqu_0440 | A1TXS2 |
| *Alcanivorax* sp. 97CO-5 | Y017_07510 | W7AC06 |
| *Marinobacter* sp. C1S70 | Q667_13505 | U7P171 |
| *Marinobacter* sp. EVN1 | Q672_13130 | U7NYF9 |
| *Pseudoxanthomonas spadix* (strain BD-a59) | DSC_08960 | G7UVX3 |
| *Marinobacter* sp. EN3 | Q673_04890 | U7H9M7 |
| *Marinobacter* sp. ES-1 | Q666_09550 | U7G9A6 |
| *Oceanicaulis* sp. HTCC2633 | OA2633_08724 | A3UHL2 |
| *Citreicella* sp. 357 | C357_19621 | I1AS33 |
| *Caulobacter* sp. (strain K31) | Caul_5439 | B0TA04 |
| *Thalassolituus oleivorans* MIL-1 | TOL_1423 | M5DQR5 |
| uncultured bacterium | alkB | W0UAQ4 |
| uncultured bacterium | alkB | W0UAL9 |
| uncultured bacterium | alkB | W0UAQ9 |
| gamma proteobacterium NOR5-3 | NOR53_3428 | B8KLY6 |
| uncultured marine microorganism | 21G8-5 | A5CFX9 |
| uncultured marine microorganism | 9E7-8 | A5CFU5 |
| *Alcanivorax pacificus* W11-5 | S7S_02132 | K2GLA3 |
| *Alcanivorax dieselolei* | | C3W4W7 (SEQ ID NO: 28) |
| *Alcanivorax* sp. PN-3 | Q668_06955 | U7I1M1 |
| *Alcanivorax dieselolei* (strain DSM 16502/CGMCC 1.3690/B-5) | B5T_00721 | K0C8Z6 |
| *Alcanivorax dieselolei* | alkB2 | D2JNY2 |
| bacterium enrichment culture clone US3-MTBE | mdpA | L7T214 |
| bacterium enrichment culture clone US2-MTBE | mdpA | L7SZY0 |
| *Marinobacter* sp. ELB17 | MELB17_10558 | A3JHB9 |
| *Marinobacter* sp. BSs20148 | alkB1 MRBBS_1602 | M1FBW8 |
| *Pseudomonas alcaligenes* NBRC 14159 | alkB PA6_005_01830 | U3AUD1 |
| *Simiduia agarivorans* (strain DSM 21679/JCM 13881/BCRC 17597/SA1) | M5M_18065 | K4KP06 |
| gamma proteobacterium HTCC2207 | GB2207_03060 | Q1YPC4 |
| *Limnobacter* sp. MED105 | LMED105_14555 | A6GTF8 |
| *Alcanivorax* sp. R8-12 | alkB2 | R9R6I2 |
| Gammaproteobacteria bacterium MOLA455 | alkB1 U062_00014 | W2UFM4 |
| *Alcanivorax hongdengensis* A-11-3 | A11A3_01150 | L0WGR7 |
| *Acidovorax* sp. KKS102 | C380_12125 | K0IAD8 |
| *Moritella* sp. PE36 | PE36_11657 | A6FHH9 |
| *Moritella* sp. PE36 | PE36_11657 | A6FHH9 |
| *Ahrensia* sp. R2A130 | alkB R2A130_3229 | E0MP68 |
| *Hoeflea phototrophica* DFL-43 | HPDFL43_04645 | A9D3P4 |
| *Curvibacter* putative symbiont of *Hydra magnipapillata* | alkB Csp_A02180 | C9Y7W7 |

TABLE 3-continued

Non-heme diiron monooxygenase enzymes capable of catalyzing selective terminal alkene hydroxylation.

| Species Origin | Gene Name | Accession No |
|---|---|---|
| *Pseudovibrio* sp. JE062 | PJE062_1512 | B6QXF8 |
| Oxalobacteraceae bacterium IMCC9480 | IMCC9480_2292 | F1W4Y4 |
| *Methylibium petroleiphilum* (strain PM1) | alkB Mpe_B0606 | A2SP81 |
| *Ralstonia* sp. AU12-08 | C404_01360 | S9TME3 |
| *Burkholderia phytofirmans* (strain DSM 17436/PsJN) | Bphyt_5401 | B2TBV7 |
| gamma proteobacterium BDW918 | DOK_05250 | I2JMD3 |
| *Pseudovibrio* sp. (strain FO-BEG1) | alkB PSE_3490 | G8PKM2 |
| *Bradyrhizobium* sp. DFCI-1 | C207_06028 | U1H8I8 |
| *Alcanivorax dieselolei* (strain DSM 16502/CGMCC 1.3690/B-5) | B5T_04393 | K0CLJ4 |
| *Alcanivorax* sp. PN-3 | Q668_04650 | U7HLN0 |
| *Alcanivorax dieselolei* | alkB1 | Q6B431 |
| *Burkholderia thailandensis* E444 | BTJ_212 | W6C501 |
| *Burkholderia thailandensis* 2002721723 | BTQ_2100 | W6BLA1 |
| *Burkholderia thailandensis* H0587 | BTL_1506 | W6BA85 |
| *Burkholderia thailandensis* (strain E264/ATCC 700388/DSM 13276/CIP 106301) | BTH_I1814 | Q2SXK3 |
| *Burkholderia pseudomallei* 1026b | BP1026B_I0975 | I1WH83 |
| *Burkholderia pseudomallei* 1026a | BP1026A_4019 | I2KNJ5 |
| *Burkholderia pseudomallei* MSHR305 | BDL_3139 | S5P5X7 |
| *Burkholderia pseudomallei* 305 | alkB BURPS305_7408 | A4LDP5 |
| *Burkholderia pseudomallei* Pasteur 52237 | alkB BURPSPAST_R0133 | A8KVJ2 |
| *Burkholderia pseudomallei* (strain K96243) | BPSL2350 | Q63SH1 |
| *Burkholderia pseudomallei* (strain 1710b) | BURPS1710b_2801 | Q3JQG8 |
| *Burkholderia pseudomallei* BPC006 | BPC006_I2776 | K7Q7Y2 |
| *Burkholderia pseudomallei* 1710a | alkB BURPS1710A_3234 | C6TUD4 |
| *Burkholderia pseudomallei* 1106b | alkB_2BURPS1106B_A1957 | C5ZKC8 |
| *Burkholderia pseudomallei* (strain 1106a) | alkB BURPS1106A_2735 | A3NXB5 |
| *Burkholderia pseudomallei* (strain 668) | BURPS668_2678 | A3NBI1 |
| *Burkholderia pseudomallei* NCTC 13178 | BBJ_481 | V9Y591 |
| *Burkholderia pseudomallei* MSHR1043 | D512_14116 | M7EHA3 |
| *Burkholderia pseudomallei* 354a | BP354A_0895 | I2MQ94 |
| *Burkholderia pseudomallei* 354e | BP354E_0708 | I2MD23 |
| *Burkholderia pseudomallei* 1258b | BP1258B_0905 | I2LQQ4 |
| *Burkholderia pseudomallei* 1258a | BP1258A_0812 | I2LKD3 |
| *Burkholderia pseudomallei* 576 | alkB BUC_2998 | B7CM79 |
| *Burkholderia pseudomallei* 1655 | alkB BURPS1655_H0133 | B2HAC8 |
| *Burkholderia pseudomallei* S13 | alkB BURPSS13_V0139 | B1HDJ2 |
| *Burkholderia pseudomallei* 406e | alkB BURPS406E_H0229 | A8EBS1 |
| *Burkholderia pseudomallei* MSHR146 | BBN_1088 | W0PXC8 |
| *Burkholderia pseudomallei* MSHR511 | BBQ_961 | W0MCN0 |
| *Burkholderia pseudomallei* NAU20B-16 | BBS_2570 | V9YGA1 |
| *Burkholderia pseudomallei* MSHR346 | GBP346_A2857 | C4KQU6 |
| *Burkholderia pseudomallei* MSHR338 | M218_13015 | W1M8G5 |
| *Burkholderia xenovorans* (strain LB400) | Bxe_B1208 | Q13ME1 |
| *Burkholderia thailandensis* MSMB43 | A33K_14899 | I6AHY8 |
| *Burkholderia* sp. Ch1-1 | BCh1lDRAFT_02054 | I2IU52 |
| *Alcanivorax* sp. R8-12 | alkB3 | R9R6Q8 |
| gamma proteobacterium HTCC5015 | GP5015_636 | B5JV27 |
| *Alcanivorax pacificus* W11-5 | S7S_03034 | K2GFU4 |
| *Actinoplanes* sp. (strain ATCC 31044/CBS 674.73/SE50/110) | alkB ACPL_4910 | G8SLX8 |
| *Alcanivorax* sp. DG881 | ADG881_1174 | B4X426 |
| *Methylibium* sp. T29-B | alkB1 Y694_03823 | W7WAG2 |
| *Methylibium* sp. T29 | mdpA X551_03232 | W7VT91 |
| *Burkholderia thailandensis* MSMB121 | BTI_1284 | N0AI18 |
| *Burkholderia* sp. TJI49 | B1M_44170 | F0GKQ0 |
| *Burkholderia mallei* (strain ATCC 23344) | alkB BMA0635 | Q62LK2 |
| *Burkholderia mallei* (strain NCTC 10247) | alkB BMA10247_1692 | A3MLU7 |
| *Burkholderia mallei* (strain NCTC 10229) | alkB BMA10229_A2910 | A2SA87 |
| *Burkholderia mallei* (strain SAVP1) | alkB BMASAVP1_A2377 | A1V630 |
| *Burkholderia mallei* PRL-20 | alkB BMAPRL20_A0647 | C5NLY3 |
| *Burkholderia mallei* GB8 horse 4 | BMAGB8_0674 | C4AYJ3 |
| *Burkholderia mallei* ATCC 10399 | alkB BMA10399_E0136 | A9KA35 |
| *Burkholderia mallei* JHU | alkB BMAJHU_C0140 | A5XN41 |
| *Burkholderia mallei* FMH | alkB BMAFMH_C0136 | A5XJ42 |
| *Burkholderia mallei* 2002721280 | alkB BMA721280_A1345 | A5TJ65 |
| *Burkholderia pseudomallei* Pakistan 9 | alkB BUH_2787 | C0YFB6 |
| *Burkholderia* sp. (strain 383) (*Burkholderia cepacia* (strain ATCC 17760/NCIB 9086/R18194)) | Bcep18194_A4085 | Q39IN4 |
| *Ralstonia* sp. 5_2_56FAA | HMPREF0989_00681 | U3G9A8 |
| *Ralstonia* sp. 5_7_47FAA | HMPREF1004_00261 | E2ST40 |
| *Burkholderia cenocepacia* (strain AU 1054) | Bcen_0501 | Q1BY92 |
| *Burkholderia cenocepacia* (strain HI2424) | Bcen2424_0980 | A0K5F6 |

TABLE 3-continued

Non-heme diiron monooxygenase enzymes capable of catalyzing selective terminal alkene hydroxylation.

| Species Origin | Gene Name | Accession No |
|---|---|---|
| *Burkholderia* sp. KJ006 | MYA_0870 | I2DKR1 |
| *Burkholderia vietnamiensis* (strain G4/LMG 22486) (*Burkholderia cepacia* (strain R1808)) | Bcep1808_0897 | A4JCA5 |
| *Burkholderia cenocepacia* KC-01 | P355_2107 | V5A0K9 |
| *Ralstonia pickettii* (strain 12D) | Rpic12D_4221 | C6BN09 |
| *Ralstonia pickettii* (strain 12J) | Rpic_4109 | B2UI09 |
| *Ralstonia pickettii* OR214 | OR214_00862 | R0CSD0 |
| *Mycobacterium thermoresistibile* ATCC 19527 | KEK_22639 | G7CND0 |
| *Burkholderia cenocepacia* PC184 | BCPG_00786 | A2VS55 |
| *Parvularcula bermudensis* (strain ATCC BAA-594/HTCC2503/KCTC 12087) | PB2503_09204 | E0TD71 |
| *Rhodococcus triatomae* BKS 15-14 | G419_20650 | M2WXQ1 |
| *Alcanivorax hongdengensis* A-11-3 | A11A3_01155 | L0WH65 |
| *Alcanivorax hongdengensis* | | G1C7G7 |
| *Micromonospora* sp. ATCC 39149 | MCAG_04553 | C4REI2 |
| *Micromonospora lupini* str. Lupac 08 | alkB MILUP08_41795 | I0KZ81 |
| *Patulibacter medicamentivorans* | PAI11_23570 | H0E6A7 |
| *Burkholderia cenocepacia* (strain ATCC BAA-245/DSM 16553/LMG 16656/NCTC 13227/J2315/CF5610) (*Burkholderia cepacia* (strain J2315)) | BCAL3029 | B4EBR3 |
| *Burkholderia cenocepacia* BC7 | BURCENBC7_AP5666 | U1ZCU6 |
| *Burkholderia cenocepacia* K56-2Valvano | BURCENK562V_C5856 | T0E860 |
| *Burkholderia cenocepacia* H111 | I35_3695 | G7HIJ0 |
| *Burkholderia cepacia* GG4 | GEM_2548 | J7J4L5 |
| *Burkholderia ambifaria* IOP40-10 | BamIOP4010DRAFT_1629 | B1FC70 |
| *Burkholderia vietnamiensis* AU4i | L810_3738 | U2H0D0 |
| *Burkholderia ambifaria* MEX-5 | BamMEX5DRAFT_0109 | B1SX43 |
| *Burkholderia cenocepacia* (strain MC0-3) | Bcenmc03_0941 | B1JX99 |
| *Burkholderia cepacia* (*Pseudomonas cepacia*) | alkB | Q9AEN3 |
| *Burkholderia multivorans* CGD1 | BURMUCGD1_2488 | B9BAK1 |
| *Burkholderia multivorans* (strain ATCC 17616/249) | alkB BMULJ_00816 | B3CYB3 |
| *Burkholderia multivorans* (strain ATCC 17616/249) | alkB BMULJ_00816 | B3CYB3 |
| *Burkholderia multivorans* CGD2M | BURMUCGD2M_2894 | B9CFY2 |
| *Burkholderia multivorans* CGD2 | BURMUCGD2_2807 | B9BSN6 |
| *Burkholderia glumae* (strain BGR1) | bglu_1g25240 | C5AA12 |
| *Burkholderia multivorans* CF2 | BURMUCF2_0698 | J5AST2 |
| *Burkholderia multivorans* ATCC BAA-247 | BURMUCF1_0763 | J4JJJ2 |
| *Mycobacterium xenopi* RIVM700367 | MXEN_06581 | I0RWI2 |
| *Alcanivorax* sp. P2S70 | Q670_07625 | U7G3V1 |
| *Rhodococcus* sp. p52 | alkB | U5S015 |
| *Rhodococcus pyridinivorans* AK37 | AK37_15478 | H0JTS8 |
| *Micromonospora* sp. M42 | MCBG_00051 | W7V9N0 |
| *Nocardia nova* SH22a | NONO_c63170 | W5TPA6 |
| *Actinoplanes missouriensis* (strain ATCC 14538/DSM 43046/CBS 188.64/JCM 3121/NCIMB 12654/NBRC 102363/431) | AMIS_28610 | I0H4Z4 |
| *Mycobacterium thermoresistibile* ATCC 19527 | KEK_04707 | G7CD93 |
| *Streptomyces collinus* Tu 365 | B446_00650 B446_34640 | S5VEV9 |
| *Mycobacterium smegmatis* MKD8 | alkB D806_1894 | L8FH78 |
| *Mycobacterium smegmatis* (strain ATCC 700084/mc(2)155) | alkB MSMEG_1839 MSMEI_1797 | A0QTH1 |
| *Burkholderia gladioli* (strain BSR3) | bgla_1g28520 | F2LCU4 |
| *Nocardia cyriacigeorgica* (strain GUH-2) | alkB NOCYR_2725 | H6R6Y1 |
| *Mycobacterium* sp. (strain Spyr1) | Mspyr1_40540 | E6TPD9 |
| *Mycobacterium gilvum* (strain PYR-GCK) (*Mycobacterium flavescens* (strain ATCC 700033/PYR-GCK)) | Mflv_4721 | A4TF88 |
| *Mycobacterium hassiacum* DSM 44199 | C731_1322 | K5BKD8 |
| *Mycobacterium phlei* RIVM601174 | MPHLEI_02293 | I0S2Q3 |
| *Burkholderia ambifaria* (strain MC40-6) | BamMC406_0853 | B1YUL7 |
| *Conexibacter woesei* (strain DSM 14684/JCM 11494/NBRC 100937/ID131577) | Cwoe_5739 | D3F1V9 |
| *Burkholderia ambifaria* (strain ATCC BAA-244/AMMD) (*Burkholderia cepacia* (strain AMMD)) | Bamb_0841 | Q0BHH3 |
| *Mycobacterium vaccae* ATCC 25954 | MVAC_06502 | K0V939 |
| *Streptomyces* sp. AA4 | SSMG_06597 | D9UYP9 |
| *Nocardia asteroides* NBRC 15531 | alkB NCAST_33_00580 | U5EK43 |
| *Hydrocarboniphaga effusa* AP103 | WQQ_35830 | I8T3V4 |
| *Mycobacterium* sp. (strain Spyr1) | Mspyr1_27000 | E6TM45 |
| *Rhodococcus* sp. EsD8 | EBESD8_14280 | N1M251 |
| *Rhodococcus pyridinivorans* SB3094 | Y013_10875 Y013_14995 | V9XCI1 |
| uncultured bacterium | alk | A7XY59 |
| *Dietzia* sp. D5 | | W0C8S6 |
| *Gordonia amarae* NBRC 15530 | alkB GOAMR_34_00200 | G7GP29 |
| gamma proteobacterium BDW918 | DOK_15269 | I2JH75 |
| *Marinobacter* sp. EVN1 | Q672_03155 | U7NQ32 |

TABLE 3-continued

Non-heme diiron monooxygenase enzymes capable of catalyzing selective terminal alkene hydroxylation.

| Species Origin | Gene Name | Accession No |
|---|---|---|
| *Marinobacter santoriniensis* NKSG1 | MSNKSG1_09613 | M7CV98 |
| *Marinobacter* sp. ES-1 | Q666_05770 | U7GFG6 |
| gamma proteobacterium HdN1 | alkM HDN1F_04190 | E1VGR0 |
| *Nocardia farcinica* (strain IFM 10152) | NFA_33210 | Q5YUH3 |
| *Mycobacterium chubuense* (strain NBB4) | Mycch_2783 | I4BJT7 |
| *Acinetobacter towneri* DSM 14962 = CIP 107472 | F947_01315 | N9CH84 |
| *Rhodococcus erythropolis* CCM2595 | O5Y_10330 | T1VNI2 |
| *Rhodococcus erythropolis* (strain PR4/NBRC 100887) | alkB RER_21620 | C0ZWY5 |
| *Rhodococcus* sp. P27 | N806_20680 | U0E9X4 |
| *Rhodococcus erythropolis* DN1 | N601_09550 | T5IBP7 |
| *Rhodococcus erythropolis* (*Arthrobacter picolinophilus*) | alkB | A4ZZL2 |
| *Mycobacterium fortuitum* subsp. *fortuitum* DSM 46621 | MFORT_07571 | K0VIS2 |
| *Rhodococcus qingshengii* BKS 20-40 | G418_14624 | M2XAS5 |
| *Rhodococcus erythropolis* (*Arthrobacter picolinophilus*) | alkB2 | Q9AE68 |
| *Rhodococcus* sp. (strain RHA1) | alkB RHA1_ro02534 | Q0SDP7 |
| *Rhodococcus* sp. JVH1 | JVH1_3134 | J1RMD5 |
| *Rhodococcus wratislaviensis* IFP 2016 | Rwratislav_18854 | L2TK91 |
| *Rhodococcus wratislaviensis* | alkB1 | K7WI49 |
| *Rhodococcus* sp. (strain Q15) | alkB2 | Q93DM7 |
| *Rhodococcus opacus* M213 | WSS_A20069 | K8XV97 |
| *Rhodococcus erythropolis* (*Arthrobacter picolinophilus*) | alkB | V5LET8 |
| *Streptomyces* sp. AA4 | SSMG_06805 | D9V1L5 |
| *Geobacillus* sp. MH-1 | alkB-geo6 | C5J0F7 |
| *Mycobacterium neoaurum* VKM Ac-1815D | D174_08465 | V5X9E7 |
| *Rhodococcus imtechensis* RKJ300 = JCM 13270 | W59_13161 | I0WSJ7 |
| *Prauserella rugosa* | alkB | Q9XBM1 |
| *Rhodococcus erythropolis* SK121 | RHOER0001_4201 | C3JG64 |
| *Amycolatopsis azurea* DSM 43854 | C791_5134 | M2PZK0 |
| *Mycobacterium rhodesiae* (strain NBB3) | MycrhN_0412 | G8RK27 |
| *Rhodococcus ruber* | alkB7 | D3U111 |
| *Rhodococcus ruber* BKS 20-38 | G352_25762 | M2XQQ3 |
| *Mycobacterium chubuense* (strain NBB4) | | D2JYT1 |
| *Mycobacterium chubuense* (strain NBB4) | Mycch_1351 | I4BFU6 |
| *Mycobacterium smegmatis* JS623 | Mycsm_01384 | L0IUF4 |
| *Nocardia nova* SH22a | alkB NONO_c46180 | W5TJL9 |
| *Rhodococcus* sp. BCP1 | alkB | E5G6V9 |
| *Saccharomonospora marina* XMU15 | SacmaDRAFT_4417 | H5X9W5 |
| *Mycobacterium* sp. (strain JLS) | Mjls_1369 | A3PW94 |
| *Rhodococcus ruber* | alkB7 | D3U119 |
| *Mycobacterium tuberculosis* BT1 | alkB HKBT1_3428 | W6HJ76 |
| *Mycobacterium tuberculosis* BT2 | alkB HKBT2_3435 | W6H3Z6 |
| *Mycobacterium tuberculosis* HKBS1 | alkB HKBS1_3438 | W6GVB7 |
| *Mycobacterium tuberculosis* EAI5 | M943_16800 | S5F023 |
| *Mycobacterium tuberculosis* EAI5/NITR206 | J114_17435 | R4MLW1 |
| *Mycobacterium tuberculosis* CAS/NITR204 | J113_22685 | R4MIF7 |
| *Mycobacterium bovis* (strain ATCC BAA-935/AF2122/97) | alkB Mb3280c | Q7TWW3 |
| *Mycobacterium tuberculosis* (strain ATCC 25618/H37Rv) | alkB Rv3252c RVBD_3252c | O05895 |
| *Mycobacterium tuberculosis* str. Beijing/NITR203 | J112_17475 | M9UX97 |
| *Mycobacterium bovis* BCG str. Korea 1168P | K60_033810 | M1IQ04 |
| *Mycobacterium liflandii* (strain 128FXT) | alkB MULP_01451 | L7V4G7 |
| *Mycobacterium tuberculosis* (strain CDC 1551/Oshkosh) | alkB MT3350 | L7N540 |
| *Mycobacterium canettii* CIPT 140070017 | alkB BN45_60281 | L0QZH1 |
| *Mycobacterium canettii* CIPT 140070008 | alkB BN43_60261 | L0QC77 |
| *Mycobacterium canettii* CIPT 140060008 | alkB BN44_70036 | L0Q026 |
| *Mycobacterium tuberculosis* 7199-99 | MT7199_3294 | L0NZI4 |
| *Mycobacterium tuberculosis* KZN 605 | TBXG_003280 | I6RJV1 |
| *Mycobacterium tuberculosis* KZN 4207 | TBSG_03323 | I1SDS8 |
| *Mycobacterium tuberculosis* RGTB327 | MRGA327_20020 | H8HLB9 |
| *Mycobacterium tuberculosis* (strain ATCC 35801/TMC 107/Erdman) | alkB ERDMAN_3566 | H8EY95 |
| *Mycobacterium tuberculosis* UT205 | alkB UDA_3252c | H6S7Q5 |
| *Mycobacterium bovis* BCG str. Mexico | alkB BCGMEX_3279c | G7QY42 |
| *Mycobacterium tuberculosis* CTRI-2 | alkB MTCTRI2_3319 | G2N7Q9 |
| *Mycobacterium canettii* (strain CIPT 140010059) | alkB MCAN_32711 | G0THM9 |
| *Mycobacterium canettii* (strain CIPT 140010059) | alkB MCAN_32711 | G0THM9 |
| *Mycobacterium africanum* (strain GM041182) | alkB MAF_32630 | F8M6G6 |
| *Mycobacterium tuberculosis* (strain CCDC5180) | alkB CCDC5180_2963 CFBR_3446 | F7WQM1 |
| *Mycobacterium tuberculosis* (strain CCDC5079) | alkB CCDC5079_3000 CFBS_3441 | F7WLN9 |
| *Mycobacterium tuberculosis* (strain KZN 1435/MDR) | TBMG_03300 | C6DXJ8 |
| *Mycobacterium bovis* (strain BCG/Tokyo 172/ATCC 35737/TMC 1019) | alkB JTY_3277 | C1AH26 |

TABLE 3-continued

Non-heme diiron monooxygenase enzymes capable of catalyzing selective terminal alkene hydroxylation.

| Species Origin | Gene Name | Accession No |
|---|---|---|
| Mycobacterium marinum (strain ATCC BAA-535/M) | alkB MMAR_1291 | B2HEP2 |
| Mycobacterium tuberculosis (strain F11) | TBFG_13281 | A5WSG7 |
| Mycobacterium tuberculosis (strain ATCC 25177/H37Ra) | alkB MRA_3293 | A5U7S6 |
| Mycobacterium tuberculosis str. Haarlem | TBHG_03188 | A4KLE9 |
| Mycobacterium bovis (strain BCG/Pasteur 1173P2) | alkB BCG_3281c | A1KNQ4 |
| Mycobacterium bovis 04-303 | O216_17560 | V2W1E0 |
| Mycobacterium bovis AN5 | O217_17270 | V2VQT4 |
| Mycobacterium tuberculosis GuangZ0019 | alkB GuangZ0019_1145 | T5HDB1 |
| Mycobacterium tuberculosis FJ05194 | alkB FJ05194_2026 | T5H4I2 |
| Mycobacterium tuberculosis '98-R604 INH-RIF-EM' | TBKG_02259 | T0EL87 |
| Mycobacterium marinum str. Europe | MMEU_4939 | S7S303 |
| Mycobacterium marinum MB2 | MMMB2_4134 | S7QZY6 |
| Mycobacterium orygis 112400015 | MORY_17288 | M8DBT2 |
| Mycobacterium tuberculosis NCGM2209 | alkB NCGM2209_3538 | G2UTS8 |
| Mycobacterium bovis BCG str. Moreau RDJ | alkB BCGM_3265c | F9UZB9 |
| Mycobacterium tuberculosis W-148 | TBPG_00365 | F2VCH4 |
| Mycobacterium tuberculosis CDC1551A | TMMG_02400 | E9ZP16 |
| Mycobacterium tuberculosis SUMu012 | TMLG_02024 | E2WM40 |
| Mycobacterium tuberculosis SUMu011 | TMKG_02511 | E2WA16 |
| Mycobacterium tuberculosis SUMu010 | TMJG_03436 | E2VYW3 |
| Mycobacterium tuberculosis SUMu009 | TMIG_02769 | E2VMD7 |
| Mycobacterium tuberculosis SUMu006 | TMFG_00461 | E2UQS7 |
| Mycobacterium tuberculosis SUMu005 | TMEG_03649 | E2UEQ4 |
| Mycobacterium tuberculosis SUMu004 | TMDG_02087 | E2U2V2 |
| Mycobacterium tuberculosis SUMu003 | TMCG_01675 | E2TRB4 |
| Mycobacterium tuberculosis SUMu002 | TMBG_01947 | E2TG69 |
| Mycobacterium tuberculosis SUMu001 | TMAG_02705 | E1HE07 |
| Mycobacterium africanum K85 | TBOG_03815 | D6FRF3 |
| Mycobacterium tuberculosis CPHL_A | TBNG_02887 | D6FLF8 |
| Mycobacterium tuberculosis T46 | TBLG_03890 | D6F9Q1 |
| Mycobacterium tuberculosis T17 | TBJG_02010 | D5ZLD1 |
| Mycobacterium tuberculosis GM 1503 | TBIG_02964 | D5Z897 |
| Mycobacterium tuberculosis 02_1987 | TBBG_01719 | D5YWK4 |
| Mycobacterium tuberculosis EAS054 | TBGG_02463 | D5YJM0 |
| Mycobacterium tuberculosis T85 | TBEG_02389 | D5Y8I4 |
| Mycobacterium tuberculosis T92 | TBDG_02114 | D5XYS2 |
| Mycobacterium tuberculosis C | TBCG_03191 | A2VP49 |
| Rhodococcus sp. EsD8 | EBESD8_35530 | N1M6K3 |
| Amycolatopsis orientalis HCCB10007 | AORI_4274 | R4SU00 |
| Mycobacterium tuberculosis SUMu008 | TMHG_02473 | E2VD73 |
| Mycobacterium tuberculosis SUMu007 | TMGG_02800 | E2V1Z1 |
| Mycobacterium tuberculosis 94_M4241A | TBAG_02148 | D7EUC2 |
| Gordonia amarae NBRC 15530 | alkB GOAMR_02_00080 | G7GIN7 |
| Rhodococcus rhodochrous ATCC 21198 | RR21198_2302 | W4A7D8 |
| Amycolatopsis decaplanina DSM 44594 | H074_07696 | M2XNH0 |
| Mycobacterium sp. 012931 | MMSP_4721 | S7R3L1 |
| Rhodococcus erythropolis (strain PR4/NBRC 100887) | alkB RER_07460 | C0ZPX6 |
| Rhodococcus sp. (strain Q15) | alkB1 | Q93DN3 |
| Rhodococcus erythropolis CCM2595 | O5Y_03630 | T1VI31 |
| Rhodococcus sp. P27 | N806_28900 | U0EPX3 |
| Rhodococcus erythropolis (Arthrobacter picolinophilus) | alkB1 | Q9XAU0 |
| Rhodococcus qingshengii BKS 20-40 | G418_23516 | M2V230 |
| Rhodococcus erythropolis SK121 | RHOER0001_0742 | C3JUT8 |
| Rhodococcus erythropolis DN1 | N601_07180 | T5HYU5 |
| Nocardia farcinica (strain IFM 10152) | NFA_46180 | Q5YQS2 |
| Rhodococcus equi NBRC 101255 = C 7 | H849_17115 | U5DRE7 |
| Shewanella sp. NJ49 | alkB1 | E3VRS8 |
| Mycobacterium canettii CIPT 140070010 | alkB BN42_41302 | L0QPN9 |
| Nocardia nova SH22a | NONO_c63220 | W5TPB1 |
| Rhodococcus equi (strain 103S) (Corynebacterium equi) | alkB REQ_33430 | E4WK80 |
| Gordonia terrae C-6 | GTC6_09699 | R7YA99 |
| Nocardioides sp. (strain BAA-499/JS614) | Noca_0122 | A1SCY2 |
| Gordonia sp. TF6 | alkB2 | Q5WA49 |
| Hydrocarboniphaga effusa AP103 | WQQ_18760 | I7ZII6 |
| Gordonia terrae NBRC 100016 | alkB GOTRE_037_00320 | H5UBE8 |
| Nocardia brasiliensis ATCC 700358 | O3I_035145 | K0FBU4 |
| Amycolatopsis mediterranei RB | B737_6308 | T1V895 |
| Amycolatopsis mediterranei (strain S699) (Nocardia mediterranei) | AMES_6308 RAM_32810 | G0FN68 |
| Amycolatopsis mediterranei (strain U-32) | AMED_6400 | D8HXC8 |
| Rhodococcus sp. p52 | alkB | U5S065 |
| Rhodococcus pyridinivorans AK37 | AK37_01067 | H0JKW2 |
| Rhodococcus pyridinivorans SB3094 | Y013_07620 | V9XAS5 |
| Janibacter sp. HTCC2649 | JNB_17248 | A3TPZ2 |
| Gordonia sp. KTR9 | KTR9_2914 | J9SIP3 |

TABLE 3-continued

Non-heme diiron monooxygenase enzymes capable of catalyzing selective terminal alkene hydroxylation.

| Species Origin | Gene Name | Accession No |
| --- | --- | --- |
| *Aeromicrobium marinum* DSM 15272 | HMPREF0063_10220 | E2S863 |
| *Dietzia cinnamea* P4 | ES5_02159 | E6J5E4 |
| *Micromonospora aurantiaca* (strain ATCC 27029/DSM 43813/JCM 10878/NBRC 16125/INA 9442) | Micau_3940 | D9T1D7 |
| *Dietzia* sp. E1 | alkB/rub fusion | C0LMW6 |
| *Rhodococcus ruber* BKS 20-38 | G352_24171 | M2YYB5 |
| *Mycobacterium gilvum* (strain PYR-GCK) (*Mycobacterium flavescens* (strain ATCC 700033/PYR-GCK)) | Mflv_3369 | A4TAB7 |
| *Nocardioidaceae bacterium* Broad-1 | NBCG_03866 | E9UYJ8 |
| *Rhodococcus rhodochrous* ATCC 21198 | RR21198_2485 | W4A610 |
| *Salinisphaera shabanensis* E1L3A | SSPSH_001855 | U2E637 |
| *Rhodococcus erythropolis* (strain PR4/NBRC 100887) | alkB RER_54580 | C0ZSH4 |
| *Corynebacterium falsenii* DSM 44353 | CFAL_02965 | W5WPK1 |
| *Rhodococcus erythropolis* CCM2595 | O5Y_25995 | T1VVR3 |
| gamma proteobacterium BDW918 | DOK_04793 | I2JMI2 |
| *Rhodococcus* sp. P27 | N806_02390 | U0DZR9 |
| *Rhodococcus erythropolis* DN1 | N601_00885 | T5IAL6 |
| *Rhodococcus erythropolis* SK121 | RHOER0001_2104 | C3JNE0 |
| *Rhodococcus qingshengii* BKS 20-40 | G418_13569 | M2WBK9 |

In some embodiments, the invention provides methods for synthesizing olefinic alcohol products as described above, wherein the enzyme is a long-chain alkane hydroxylase. In some embodiments, the long-chain alkane hydroxylase is selected from Table 4 or a variant thereof having at least 90% identity thereto.

TABLE 4

Long chain alkane hydroxylase enzymes capable of catalyzing selective terminal alkene hydroxylation.

| Species Origin | Gene names | Accession No |
| --- | --- | --- |
| *Geobacillus thermodenitrificans* (strain NG80-2) | ladA GTNG_3499 | A4IU28 (SEQ ID NO: 29) |
| *Geobacillus stearothermophilus* (*Bacillus stearothermophilus*) | | A8DC15 (SEQ ID NO: 30) |
| *Paenibacillus* sp. JCM 10914 | JCM10914_4324 | V9GEW8 |
| *Bacillus methanolicus* MGA3 | MGA3_06970 | I3E8X7 (SEQ ID NO: 31) |
| *Geobacillus* sp. (strain Y4.1MC1) | GY4MC1_0235 | E3IA76 |
| *Geobacillus thermoglucosidans* TNO-09.020 | GT20_0226 | I0U377 |
| *Geobacillus thermoglucosidasius* (strain C56-YS93) | Geoth_0249 | F8CWH6 |
| *Bacillus methanolicus* PB1 | PB1_11994 | I3DVL0 |
| *Alicyclobacillus acidoterrestris* ATCC 49025 | N007_16655 | T0BMR6 |
| *Bhargavaea cecembensis* DSE10 | ntaA_1 C772_00943 | M7P9Z6 |
| *Bacillus* sp. 1NLA3E | B1NLA3E_02955 | N0AV94 |
| *Burkholderia graminis* C4D1M | BgramDRAFT_6080 | B1G9N8 |
| *Burkholderia thailandensis* H0587 | BTL_4503 | W6BDT9 |
| *Planomicrobium glaciei* CHR43 | G159_18855 | W3A818 |
| *Burkholderia thailandensis* E444 | BTJ_3656 | W6C8D0 |
| *Burkholderia thailandensis* 2002721723 | BTQ_5029 | W6BNA4 |
| *Burkholderia pseudomallei* (strain K96243) | BPSS0686 | Q63MH2 |
| *Burkholderia mallei* (strain ATCC 23344) | BMAA1146 | Q62BX8 |
| *Burkholderia thailandensis* (strain E264/ATCC 700388/DSM 13276/CIP 106301) | BTH_II1741 | Q2T4G4 |
| *Burkholderia pseudomallei* BPC006 | BPC006_II0968 | K7QBE8 |
| *Burkholderia pseudomallei* 1106b | BURPS1106B_1056 | C5ZS78 |
| *Burkholderia pseudomallei* MSHR346 | GBP346_B0209 | C4I1H5 |
| *Burkholderia pseudomallei* (strain 1106a) | BURPS1106A_A0931 | A3P3Q7 |
| *Burkholderia mallei* (strain NCTC 10247) | BMA10247_A1520 | A3MEL8 |
| *Burkholderia mallei* (strain NCTC 10229) | BMA10229_0093 | A2RW50 |
| *Burkholderia pseudomallei* MSHR338 | M218_32405 | W1LX20 |
| *Burkholderia mallei* PRL-20 | BMAPRL20_0872 | C5N9G7 |
| *Burkholderia mallei* GB8 horse 4 | BMAGB8_A1284 | C4B2F1 |
| *Burkholderia mallei* Pakistan 9 | BUH_5241 | C0Y1N2 |
| *Burkholderia pseudomallei* 576 | BUC_5105 | B7CGH3 |
| *Burkholderia pseudomallei* S13 | BURPSS13_T0065 | B1H503 |
| *Burkholderia mallei* ATCC 10399 | BMA10399_L0048 | A9LC22 |
| *Burkholderia pseudomallei* Pasteur 52237 | BURPSPAST_J0304 | A8KQQ8 |
| *Burkholderia pseudomallei* 406e | BURPS406E_G0092 | A8EKE5 |
| *Burkholderia mallei* JHU | BMAJHU_I0303 | A5XK99 |

TABLE 4-continued

Long chain alkane hydroxylase enzymes capable of catalyzing selective terminal alkene hydroxylation.

| Species Origin | Gene names | Accession No |
| --- | --- | --- |
| *Burkholderia mallei* 2002721280 | BMA721280_L0585 | A5TFQ0 |
| *Alicyclobacillus acidoterrestris* ATCC 49025 | N007_09450 | T0BMI0 |
| *Burkholderia pseudomallei* MSHR305 | BDL_3916 | S5NPF6 |
| *Burkholderia pseudomallei* MSHR146 | BBN_4086 | W0Q1C4 |
| *Burkholderia pseudomallei* MSHR511 | BBQ_5508 | W0MJC7 |
| *Burkholderia pseudomallei* NAU20B-16 | BBS_5466 | V9YUR9 |
| *Burkholderia pseudomallei* NCTC 13178 | BBJ_4354 | V9YFT0 |
| *Burkholderia pseudomallei* NCTC 13179 | BBK_3804 | U5V4E4 |
| *Burkholderia pseudomallei* MSHR1043 | D512_19607 | M7EBY4 |
| *Burkholderia pseudomallei* 1655 | BURPS1655_I0183 | B2H6F2 |
| *Burkholderia pseudomallei* 305 | BURPS305_5546 | A4LI20 |
| *Segniliparus rugosus* ATCC BAA-974 | HMPREF9336_02889 | E5XTR7 |
| *Burkholderia pseudomallei* 1026b | BP1026B_II0759 | I1WRX2 |
| *Burkholderia pseudomallei* 354a | BP354A_4019 | I2MG65 |
| *Burkholderia pseudomallei* 354e | BP354E_3240 | I2M2Q7 |
| *Burkholderia pseudomallei* 1026a | BP1026A_2436 | I2L127 |
| *Burkholderia pseudomallei* 1258b | BP1258B_3899 | I2KY00 |
| *Burkholderia pseudomallei* 1258a | BP1258A_3523 | I2KWT0 |
| *Pseudomonas putida* (strain DOT-T1E) | T1E_2746 | I7B0Q5 |
| *Pseudomonas putida* ND6 | YSA_09788 | I3V2W3 |
| *Pseudomonas putida* TRO1 | C206_18269 | N9VYA0 |
| *Pseudomonas putida* LS46 | PPUTLS46_018911 | M7RI48 |
| *Burkholderia graminis* C4D1M | BgramDRAFT_6182 | B1G9Y6 |
| *Burkholderia phytofirmans* (strain DSM 17436/PsJN) | Bphyt_4538 | B2TDZ4 |
| *Bhargavaea cecembensis* DSE10 | moxC_3 C772_02411 | M7NEH3 |
| *Burkholderia thailandensis* MSMB121 | BTI_5494 | N0APC1 |
| *Burkholderia pseudomallei* (strain 668) | BURPS668_A1016 | A3NI44 |
| *Burkholderia pseudomallei* (strain 1710b) | BURPS1710b_A2257 | Q3JG95 |
| *Burkholderia pseudomallei* 1710a | BURPS1710A_A0072 | C6U1I8 |
| *Planomicrobium glaciei* CHR43 | G159_14295 | W3AA87 |
| *Burkholderia thailandensis* MSMB43 | A33K_16732 | I6AD68 |
| *Pseudomonas* sp. GM50 | PMI30_04278 | J3GFD6 |
| *Pseudomonas fluorescens* BBc6R8 | MHB_001910 | V7EA47 |
| *Pseudomonas* sp. Ag1 | A462_06954 | J0YEG1 |
| *Pseudomonas* sp. GM102 | PMI18_00569 | J2VSE5 |
| *Pseudomonas fluorescens* (strain SBW25) | PFLU_3858 | C3JYC1 |
| *Pseudomonas* sp. (strain M1) | PM1_0212365 | W5IVB1 |
| *Pseudomonas* sp. TKP | U771_20325 | V9R055 |
| *Pseudomonas putida* (strain F1/ATCC 700007) | Pput_3007 | A5W4S5 |
| *Pseudomonas putida* (strain GB-1) | PputGB1_1120 | B0KS73 |
| *Azotobacter vinelandii* CA6 | seuA AvCA6_43810 | M9YDA5 |
| *Azotobacter vinelandii* CA | seuA AvCA_43810 | M9Y6B1 |
| *Azotobacter vinelandii* (strain DJ/ATCC BAA-1303) | seuA Avin_43810 | C1DGK6 |
| *Pseudomonas brassicacearum* (strain NFM421) | PSEBR_a2282 | F2KFH4 |
| *Pseudomonas fluorescens* Q8r1-96 | PflQ8_2313 | I4KKG5 |
| *Klebsiella oxytoca* E718 | A225_4709 | I6X485 |
| *Pseudomonas putida* (strain KT2440) | PP_2746 | Q88JA3 |
| *Pseudomonas fluorescens* BBc6R8 | MHB_002244 | V7E7E4 |
| *Pseudomonas fluorescens* Q2-87 | PflQ2_2259 | J2EFB8 |
| *Pseudomonas* sp. Ag1 | A462_04671 | J0PSS9 |
| *Klebsiella oxytoca* MGH 42 | L388_04093 | V3KYZ2 |
| *Klebsiella oxytoca* 10-5245 | HMPREF9689_03721 | H3M9T3 |
| *Klebsiella oxytoca* 10-5243 | HMPREF9687_03258 | H3LSS6 |
| *Klebsiella oxytoca* (strain ATCC 8724/DSM 4798/JCM 20051/NBRC 3318/NRRL B-199/KCTC 1686) | KOX_01240 | G8WD25 |
| *Streptomyces himastatinicus* ATCC 53653 | SSOG_01846 | D9WSJ3 |
| *Klebsiella oxytoca* MGH 28 | L374_04760 | V3PRZ9 |
| *Klebsiella oxytoca* 10-5250 | HMPREF9694_02187 | H3N1Z4 |
| *Klebsiella* sp. OBRC7 | HMPREF1144_4230 | J8VYP0 |
| *Klebsiella oxytoca* 10-5242 | HMPREF9686_03185 | H3LCA0 |
| *Pantoea ananatis* LMG 5342 | soxA PANA5342_1855 | G9ARF4 |
| *Pantoea ananatis* PA13 | PAGR_g1792 | G7UD55 |
| *Pantoea ananatis* (strain AJ13355) | soxA PAJ_1557 | F2EW92 |
| *Pantoea ananatis* (strain LMG 20103) | soxA PANA_2246 | D4GGW6 |
| *Pantoea ananatis* BRT175 | L585_00145 | U4W7P0 |
| *Segniliparus rotundus* (strain ATCC BAA-972/CDC 1076/CIP 108378/DSM 44985/JCM 13578) | Srot_2598 | D6ZC64 |
| *Pantoea stewartii* subsp. *stewartii* DC283 | CKS_1871 | H3RFH9 |
| *Pantoea stewartii* subsp. *stewartii* DC283 | CKS_1871 | H3RFH9 |
| *Rhodococcus opacus* M213 | WSS_A14179 | K8XV73 |
| *Klebsiella pneumoniae* DMC0799 | H217_2899 | S7AJY1 |
| *Klebsiella pneumoniae* 700603 | KP700603_18582 | M7P910 |
| *Klebsiella* sp. MS 92-3 | HMPREF9538_02211 | F3Q553 |
| *Klebsiella pneumoniae* CG43 | D364_16040 | U5MF64 |
| *Klebsiella pneumoniae* subsp. *pneumoniae* 1084 | A79E_0950 | K4HBM3 |

TABLE 4-continued

Long chain alkane hydroxylase enzymes capable of catalyzing
selective terminal alkene hydroxylation.

| Species Origin | Gene names | Accession No |
|---|---|---|
| *Klebsiella pneumoniae* subsp. *pneumoniae* (strain HS11286) | KPHS_42240 | G8VT84 |
| *Klebsiella pneumoniae* KCTC 2242 | KPN2242_18760 | G0GTG2 |
| *Klebsiella pneumoniae* NB60 | X657_3893 | W7K535 |
| *Klebsiella pneumoniae* EGD-HP19-C | N035_09715 | W1LTN4 |
| *Escherichia coli* ISC56 | | W1HC22 |
| *Klebsiella pneumoniae* IS33 | | W1CX87 |
| *Klebsiella pneumoniae* subsp. *pneumoniae* BJ1-GA | KPST380_90022 | W0YH64 |
| *Klebsiella pneumoniae* subsp. *pneumoniae* SA1 | KPST86_100232 | W0XPM0 |
| *Klebsiella pneumoniae* subsp. *pneumoniae* T69 | SB4536_310004 | W0XIP7 |
| *Klebsiella pneumoniae* MGH 18 | L364_01157 | V3UHS5 |
| *Klebsiella pneumoniae* MGH 17 | L363_03338 | V3SPP7 |
| *Klebsiella pneumoniae* MGH 21 | L367_03372 | V3RJW0 |
| *Klebsiella pneumoniae* MGH 19 | L365_03262 | V3RDD9 |
| *Klebsiella pneumoniae* MGH 32 | L378_01018 | V3P5E6 |
| *Klebsiella pneumoniae* MGH 30 | L376_01094 | V3NNG8 |
| *Klebsiella pneumoniae* MGH 40 | L386_03550 | V3MB44 |
| *Klebsiella pneumoniae* MGH 36 | L382_03249 | V3M7N6 |
| *Klebsiella pneumoniae* BWH 28 | L399_01071 | V3JYS4 |
| *Klebsiella pneumoniae* BWH 30 | L401_03358 | V3IHX3 |
| *Klebsiella pneumoniae* UCICRE 2 | L413_01241 | V3H9M1 |
| *Klebsiella pneumoniae* UCICRE 7 | L418_00976 | V3FW02 |
| *Klebsiella pneumoniae* UCICRE 6 | L417_03180 | V3FI89 |
| *Klebsiella pneumoniae* BIDMC 21 | L457_03247 | V3DWM2 |
| *Klebsiella pneumoniae* BIDMC 22 | L458_03227 | V3DGZ8 |
| *Klebsiella pneumoniae* BIDMC 24 | L460_03188 | V3BDU6 |
| *Klebsiella pneumoniae* BIDMC 25 | L461_03214 | V3B499 |
| *Klebsiella pneumoniae* BIDMC 40 | L477_03188 | V3A962 |
| *Klebsiella pneumoniae* BIDMC 36 | L473_03258 | V3A6I8 |
| *Klebsiella pneumoniae* BIDMC 41 | L478_00374 | V2Z7W2 |
| *Klebsiella pneumoniae* BIDMC 12C | L441_03468 | U7BFN1 |
| *Klebsiella pneumoniae* BIDMC 18C | L450_03424 | U7AVL5 |
| *Klebsiella pneumoniae* BIDMC 16 | L445_03710 | U7AGB1 |
| *Enterococcus gallinarum* EGD-AAK12 | N036_14515 | U1CX13 |
| *Klebsiella pneumoniae* subsp. *pneumoniae* MP14 | KKPNMP14_39700 | S8A752 |
| *Klebsiella pneumoniae* subsp. *pneumoniae* UKKV901664 | UKKV901664_39580 | S7YC36 |
| *Klebsiella pneumoniae* 120_1020 | J048_0227 | S7I734 |
| *Klebsiella pneumoniae* 140_1040 | J046_0551 | S7HZ61 |
| *Klebsiella pneumoniae* 280_1220 | J049_0615 | S7H6G5 |
| *Klebsiella pneumoniae* 160_1080 | J047_06104 | S7FI27 |
| *Klebsiella pneumoniae* UHKPC06 | H228_0695 | S7F6A3 |
| *Klebsiella pneumoniae* UHKPC67 | H212_0084 | S7EIH5 |
| *Klebsiella pneumoniae* UHKPC02 | H229_0083 | S7EFH7 |
| *Klebsiella pneumoniae* UHKPC17 | H225_0083 | S7E3F9 |
| *Klebsiella pneumoniae* UHKPC31 | H227_0223 | S7E0F6 |
| *Klebsiella pneumoniae* UHKPC59 | H223_2084 | S7DJY5 |
| *Klebsiella pneumoniae* UHKPC18 | H226_0627 | S7CZN2 |
| *Klebsiella pneumoniae* UHKPC61 | H220_0228 | S7CKP4 |
| *Klebsiella pneumoniae* UHKPC07 | H224_0554 | S7C1T8 |
| *Klebsiella pneumoniae* DMC1316 | H219_1515 | S7C0U0 |
| *Klebsiella pneumoniae* UHKPC33 | H222_0227 | S7BH54 |
| *Klebsiella pneumoniae* DMC1097 | H218_2245 | S7A1J0 |
| *Klebsiella pneumoniae* UHKPC96 | H215_0710 | S6YYA8 |
| *Klebsiella pneumoniae* UHKPC77 | H214_0083 | S6YU31 |
| *Klebsiella pneumoniae* UHKPC28 | H209_0679 | S6YQS7 |
| *Klebsiella pneumoniae* UHKPC69 | H213_0083 | S6YBZ0 |
| *Klebsiella pneumoniae* UHKPC47 | H211_0128 | S6XBP3 |
| *Klebsiella pneumoniae* UHKPC32 | H242_0078 | S2J6Y7 |
| *Klebsiella pneumoniae* UHKPC48 | H221_0076 | S2I2J3 |
| *Klebsiella pneumoniae* DMC0526 | H216_2445 | S2I0S2 |
| *Klebsiella pneumoniae* VAKPC278 | H247_0907 | S2H7F7 |
| *Klebsiella pneumoniae* UHKPC29 | H241_0227 | S2GQ63 |
| *Klebsiella pneumoniae* UHKPC05 | H210_0554 | S2G118 |
| *Klebsiella pneumoniae* UHKPC45 | H239_0077 | S2FVN7 |
| *Klebsiella pneumoniae* UHKPC 52 | H234_0218 | S2FQ55 |
| *Klebsiella pneumoniae* 646_1568 | J054_0227 | S2E5R5 |
| *Klebsiella pneumoniae* 540_1460 | J053_0083 | S2E2M9 |
| *Klebsiella pneumoniae* 440_1540 | J051_2140 | S2CWI6 |
| *Klebsiella pneumoniae* 500_1420 | J052_0542 | S2CKG8 |
| *Klebsiella pneumoniae* VAKPC309 | H252_1202 | S2C6A5 |
| *Klebsiella pneumoniae* KP-11 | H254_0775 | S2BTB1 |
| *Klebsiella pneumoniae* 361_1301 | J050_2658 | S2B565 |
| *Klebsiella pneumoniae* VAKPC297 | H251_0083 | S2ACA5 |
| *Klebsiella pneumoniae* VAKPC270 | H249_0897 | S1ZBB5 |

TABLE 4-continued

Long chain alkane hydroxylase enzymes capable of catalyzing selective terminal alkene hydroxylation.

| Species Origin | Gene names | Accession No |
| --- | --- | --- |
| *Klebsiella pneumoniae* VAKPC280 | H248_0984 | S1Z9L1 |
| *Klebsiella pneumoniae* VAKPC276 | H250_1158 | S1Z4C6 |
| *Klebsiella pneumoniae* VAKPC269 | H246_1198 | S1YJN2 |
| *Klebsiella pneumoniae* VAKPC254 | H245_0083 | S1XZP2 |
| *Klebsiella pneumoniae* UHKPC22 | H240_0083 | S1XYX9 |
| *Klebsiella pneumoniae* UHKPC04 | H243_0549 | S1X5H6 |
| *Klebsiella pneumoniae* VAKPC252 | H244_3523 | S1WWW4 |
| *Klebsiella pneumoniae* UHKPC26 | H236_0227 | S1W5H8 |
| *Klebsiella pneumoniae* UHKPC27 | H233_0552 | S1VUY3 |
| *Klebsiella pneumoniae* UHKPC24 | H235_0228 | S1V9Y4 |
| *Klebsiella pneumoniae* UHKPC01 | H231_1154 | S1V1B9 |
| *Klebsiella pneumoniae* UHKPC81 | H232_2378 | S1TWU9 |
| *Klebsiella pneumoniae* UHKPC40 | H207_0083 | S1TR15 |
| *Klebsiella pneumoniae* UHKPC09 | H230_0227 | S1TQU1 |
| *Klebsiella pneumoniae* KP-7 | H253_1042 | S1T453 |
| *Klebsiella pneumoniae* UHKPC23 | H208_0755 | R9BIA6 |
| *Klebsiella pneumoniae* subsp. *pneumoniae* KpMDU1 | C210_21528 | N9SXP2 |
| *Klebsiella pneumoniae* ATCC BAA-1705 | KPBAA1705_02256 | M7QWX8 |
| *Klebsiella pneumoniae* ATCC BAA-2146 | G000_17665 Kpn2146_4394 | M7PZV3 |
| *Klebsiella pneumoniae* VA360 | MTE2_213 | M5T2W9 |
| *Klebsiella pneumoniae* RYC492 | KPRYC492_05065 | M5Q5H7 |
| *Klebsiella pneumoniae* RYC492 | KPRYC492_05065 | M5Q5H7 |
| *Klebsiella pneumoniae* subsp. *pneumoniae* KpQ3 | B819_29014 | M5GIZ6 |
| *Klebsiella pneumoniae* subsp. *pneumoniae* Ecl8 | BN373_37921 | K4UK89 |
| *Klebsiella pneumoniae* subsp. *pneumoniae* WGLW5 | HMPREF1308_03340 | K1NXD5 |
| *Klebsiella pneumoniae* subsp. *pneumoniae* WGLW3 | HMPREF1307_01233 | K1NCK1 |
| *Klebsiella pneumoniae* subsp. *pneumoniae* WGLW1 | HMPREF1305_01058 | K1MMN7 |
| *Klebsiella pneumoniae* subsp. *pneumoniae* KPNIH23 | KPNIH23_01714 | J2W4N5 |
| *Klebsiella pneumoniae* subsp. *pneumoniae* KPNIH21 | KPNIH21_18909 | J2UUP0 |
| *Klebsiella pneumoniae* subsp. *pneumoniae* KPNIH18 | KPNIH18_04648 | J2TP42 |
| *Klebsiella pneumoniae* subsp. *pneumoniae* KPNIH17 | KPNIH17_07852 | J2SZ94 |
| *Klebsiella pneumoniae* subsp. *pneumoniae* KPNIH9 | KPNIH9_07912 | J2PY88 |
| *Klebsiella pneumoniae* subsp. *pneumoniae* KPNIH6 | KPNIH6_12977 | J2NIU0 |
| *Klebsiella pneumoniae* subsp. *pneumoniae* KPNIH1 | KPNIH1_04615 | J2MHH3 |
| *Klebsiella pneumoniae* subsp. *pneumoniae* KPNIH22 | KPNIH22_01396 | J2KA06 |
| *Klebsiella pneumoniae* subsp. *pneumoniae* KPNIH19 | KPNIH19_02887 | J2JA47 |
| *Klebsiella pneumoniae* subsp. *pneumoniae* KPNIH16 | KPNIH16_07898 | J2HIQ1 |
| *Klebsiella pneumoniae* subsp. *pneumoniae* KPNIH14 | KPNIH14_01932 | J2GTK1 |
| *Klebsiella pneumoniae* subsp. *pneumoniae* KPNIH11 | KPNIH11_05794 | J2G1J7 |
| *Klebsiella pneumoniae* subsp. *pneumoniae* KPNIH2 | KPNIH2_14379 | J2BUC4 |
| *Klebsiella pneumoniae* subsp. *pneumoniae* KPNIH20 | KPNIH20_08348 | J2BFJ4 |
| *Klebsiella pneumoniae* subsp. *pneumoniae* KPNIH12 | KPNIH12_01874 | J1YXJ0 |
| *Klebsiella pneumoniae* subsp. *pneumoniae* KPNIH10 | KPNIH10_07382 | J1X9E8 |
| *Klebsiella pneumoniae* subsp. *pneumoniae* KPNIH8 | KPNIH8_09376 | J1WTX7 |
| *Klebsiella pneumoniae* subsp. *pneumoniae* KPNIH7 | KPNIH7_03054 | J1WDZ3 |
| *Klebsiella pneumoniae* subsp. *pneumoniae* KPNIH5 | KPNIH5_11286 | J1V7M9 |
| *Klebsiella pneumoniae* subsp. *pneumoniae* KPNIH4 | KPNIH4_01334 | J1UFY7 |
| *Klebsiella* sp. 4_1_44FAA | HMPREF1024_02306 | G9REB7 |
| *Klebsiella pneumoniae* JM45 | N559_1083 | S5YDY6 |
| *Klebsiella pneumoniae* subsp. *pneumoniae* Kp13 | KP13_02362 | V9ZFM9 |
| *Klebsiella pneumoniae* subsp. *rhinoscleromatis* ATCC 13884 | HMPREF0484_1763 | C8T2C2 |
| *Klebsiella pneumoniae* subsp. *pneumoniae* ST258-K26BO | BN426_1797 | K4RX40 |
| *Klebsiella variicola* (strain At-22) | Kvar_0908 | D3RIP8 |
| *Klebsiella pneumoniae* (strain 342) | KPK_0975 | B5XUZ5 |
| *Klebsiella pneumoniae* MGH 20 | L366_04030 | V3R3V0 |
| *Klebsiella pneumoniae* UCICRE 10 | L421_04096 | V3DSZ3 |
| *Klebsiella* sp. KTE92 | A1WC_04002 | R8X357 |
| *Klebsiella pneumoniae* hvKP1 | G057_03698 | M2A8M6 |
| *Mycobacterium hassiacum* DSM 44199 | C731_0966 | K5B980 |
| *Klebsiella pneumoniae* MGH 48 | L394_03318 | V3J564 |
| *Pantoea vagans* (strain C9-1) (*Pantoea agglomerans* (strain C9-1)) | Pvag_pPag10056 | E1PKF9 |
| *Klebsiella pneumoniae* IS22 | | W1BJB8 |
| *Klebsiella pneumoniae* subsp. *pneumoniae* NTUH-K2044 | KP1_4424 | C4XCS7 |
| *Burkholderia* sp. CCGE1001 | BC1001_4137 | E8YTA8 |
| *Microvirga lotononidis* | MicloDRAFT_00046760 | I4YVV6 |
| *Burkholderia phenoliruptrix* BR3459a | BUPH_00719 | K0DVZ1 |
| *Pseudomonas cichorii* JBC1 | PCH70_03420 | W0H3V5 (SEQ ID NO: 32) |
| *Burkholderia* sp. (strain CCGE1003) | BC1003_5279 | E1TDZ6 |
| *Pseudomonas protegens* CHA0 | soxA1 PFLCHA0_c02440 | R4QZ42 |
| *Herbaspirillum* sp. CF444 | PMI16_04881 | J2L7C4 |
| *Pseudomonas fluorescens* (strain Pf-5/ATCC BAA-477) | PFL_0243 | Q4KK44 |

TABLE 4-continued

Long chain alkane hydroxylase enzymes capable of catalyzing selective terminal alkene hydroxylation.

| Species Origin | Gene names | Accession No |
|---|---|---|
| *Bacillus megaterium* WSH-002 | BMWSH_4371 | G2RTT4 |
| *Pseudomonas* sp. GM30 | PMI25_001642 | W6W1D9 |
| *Pseudomonas* sp. GM78 | PMI35_05139 | J3D9L9 |
| *Pseudomonas* sp. GM60 | PMI32_02771 | J2U6I1 |
| *Pseudomonas* sp. FH1 | H096_21398 | W2DLN3 |
| *Pseudomonas* sp. GM41(2012) | PMI27_000125 | W6VAV2 |
| *Pseudomonas* sp. GM67 | PMI33_04861 | J2TPB1 |
| *Pseudomonas fluorescens* EGD-AQ6 | O204_08695 | U1U9U7 |
| *Pseudomonas* sp. CF161 | CF161_31485 | S6JVW1 |
| *Pseudomonas fluorescens* BRIP34879 | A986_05371 | L7HKJ7 |
| *Pseudomonas* sp. Lz4W | B195_18896 | M5QDB7 |
| *Collimonas fungivorans* (strain Ter331) | CFU_2748 | G0A9F2 |
| *Pseudomonas poae* RE*1-1-14 | H045_11420 | M4K052 |
| *Pseudomonas fluorescens* BBc6R8 | MHB_005864 | V7DXC0 |
| *Pseudomonas* sp. Lz4W | B195_14957 | M5QFC1 |
| *Pseudomonas* sp. GM24 | PMI23_03232 | J2QII9 |
| *Pseudomonas* sp. GM16 | PMI19_05169 | J2MFI6 |
| *Rhizobium* sp. CF080 | PMI07_000401 | W6W3M6 |
| *Pseudomonas* sp. FH1 | H096_13584 | W2DVJ0 |
| *Pseudomonas* sp. GM25 | PMI24_00141 | J2Q9Q8 |
| *Rhizobium leguminosarum* bv. *trifolii* (strain WSM2304) | Rleg2_6510 | B6A4D5 |
| *Pseudomonas* sp. G5(2012) | PG5_63250 | S2FDS8 |
| *Pseudomonas chlororaphis* O6 | PchlO6_2640 | I4XU61 |
| *Pseudomonas protegens* CHA0 | soxA3 PFLCHA0_c26840 | R4R5M1 |
| *Pseudomonas fluorescens* (strain Pf-5/ATCC BAA-477) | PFL_2617 | Q4KDF9 |
| *Rhizobium leguminosarum* bv. *trifolii* WSM597 | Rleg9DRAFT_0832 | I9N5T8 |
| *Bacillus megaterium* (strain DSM 319) | BMD_1582 | D5DC52 |
| *Pseudomonas fluorescens* WH6 | PFWH6_3643 | E2XUD7 |
| *Rhizobium* sp. Pop5 | RCCGEPOP_16608 | K0VYN0 |
| *Bacillus megaterium* (strain ATCC 12872/QMB1551) | BMQ_0870 | D5E197 |
| *Pseudomonas cichorii* JBC1 | PCH70_26220 | W0HAE8 |
| *Pseudomonas* sp. TKP | U771_03925 | V9QRK7 |
| *Pseudomonas aeruginosa* C41 | Q088_02376 | U8DE40 |
| *Pseudomonas aeruginosa* 62 | P997_00130 | U9DU73 |
| *Pseudomonas aeruginosa* BL19 | Q073_02117 | U8H8T3 |
| *Pseudomonas aeruginosa* YL84 | AI22_19865 | W5VAE7 |
| *Pseudomonas aeruginosa* SCV20265 | SCV20265_2995 | V9U1K6 |
| *Pseudomonas aeruginosa* LES431 | T223_15220 | V9T819 |
| *Pseudomonas aeruginosa* MTB-1 | U769_13585 | V5SWN7 |
| *Pseudomonas aeruginosa* PA1R | PA1R_gp0125 | U6AQA7 |
| *Pseudomonas aeruginosa* PA1 | PA1S_gp0125 | U6A6M8 |
| *Pseudomonas aeruginosa* PAO1-VE13 | N297_2400 | U5RPB5 |
| *Pseudomonas aeruginosa* PAO1-VE2 | N296_2400 | U5R2L8 |
| *Pseudomonas aeruginosa* c7447m | M802_2397 | T2EJL9 |
| *Pseudomonas aeruginosa* RP73 | M062_12135 | R9ZF43 |
| *Pseudomonas aeruginosa* (strain ATCC 15692/PAO1/1C/PRS 101/LMG 12228) | PA2326 | Q9I1F2 |
| *Pseudomonas aeruginosa* (strain UCBPP-PA14) | PA14_34540 | Q02MC3 |
| *Pseudomonas aeruginosa* B136-33 | G655_13420 | M9S636 |
| *Pseudomonas aeruginosa* DK2 | PADK2_13640 | I6SJ32 |
| *Pseudomonas aeruginosa* (strain LESB58) | PLES_29781 | B7V8Z7 |
| *Pseudomonas aeruginosa* (strain PA7) | PSPA7_2933 | A6V5F8 |
| *Pseudomonas aeruginosa* (strain PA7) | PSPA7_2933 | A6V5F8 |
| *Pseudomonas aeruginosa* DHS29 | V441_13990 | W1QXR3 |
| *Pseudomonas aeruginosa* MH38 | P38_3412 | W0WGT3 |
| *Pseudomonas aeruginosa* VRFPA06 | V527_13850 | V8HJN2 |
| *Pseudomonas aeruginosa* VRFPA08 | X922_29130 | V8DQV8 |
| *Pseudomonas aeruginosa* DHS01 | DPADHS01_13190 | V4WR77 |
| *Pseudomonas aeruginosa* VRFPA01 | G039_0203575 | V4QMQ4 |
| *Pseudomonas aeruginosa* HB15 | PA15_0330520 | V4MN40 |
| *Pseudomonas aeruginosa* M8A.3 | Q082_00075 | U9SHI5 |
| *Pseudomonas aeruginosa* CF27 | Q003_00104 | U9RU06 |
| *Pseudomonas aeruginosa* MSH10 | Q000_02112 | U9RT23 |
| *Pseudomonas aeruginosa* CF127 | Q001_02232 | U9RQB8 |
| *Pseudomonas aeruginosa* CF5 | Q004_02036 | U9R042 |
| *Pseudomonas aeruginosa* S54485 | Q007_00776 | U9QQE4 |
| *Pseudomonas aeruginosa* BWHPSA007 | Q020_00157 | U9PK67 |
| *Pseudomonas aeruginosa* BWHPSA009 | Q022_02698 | U9NGB4 |
| *Pseudomonas aeruginosa* BWHPSA008 | Q021_00149 | U9NF67 |
| *Pseudomonas aeruginosa* BWHPSA010 | Q023_01638 | U9MXZ6 |
| *Pseudomonas aeruginosa* BWHPSA015 | Q028_00447 | U9MBW2 |
| *Pseudomonas aeruginosa* BWHPSA016 | Q029_01714 | U9LQK4 |
| *Pseudomonas aeruginosa* BL03 | Q057_00105 | U9LB58 |
| *Pseudomonas aeruginosa* BL01 | Q055_02736 | U9KLQ0 |
| *Pseudomonas aeruginosa* BL02 | Q056_06394 | U9JUP8 |

TABLE 4-continued

Long chain alkane hydroxylase enzymes capable of catalyzing
selective terminal alkene hydroxylation.

| Species Origin | Gene names | Accession No |
|---|---|---|
| *Pseudomonas aeruginosa* BL05 | Q059_02100 | U9JF28 |
| *Pseudomonas aeruginosa* BL06 | Q060_06378 | U9IJ92 |
| *Pseudomonas aeruginosa* BL21 | Q075_03038 | U9GQQ1 |
| *Pseudomonas aeruginosa* BL23 | Q077_03073 | U9FQH5 |
| *Pseudomonas aeruginosa* BL24 | Q078_06288 | U9EQY5 |
| *Pseudomonas aeruginosa* M8A.4 | Q083_01720 | U9ECA2 |
| *Pseudomonas aeruginosa* MSH3 | P999_02290 | U9D2B6 |
| *Pseudomonas aeruginosa* X24509 | Q005_02076 | U9CCX5 |
| *Pseudomonas aeruginosa* UDL | Q006_01725 | U9C927 |
| *Pseudomonas aeruginosa* CF18 | Q002_02068 | U9BVH8 |
| *Pseudomonas aeruginosa* 19660 | Q010_02159 | U9AF43 |
| *Pseudomonas aeruginosa* X13273 | Q013_02044 | U8Z334 |
| *Pseudomonas aeruginosa* S35004 | Q012_06204 | U8YF61 |
| *Pseudomonas aeruginosa* BWHPSA001 | Q014_02765 | U8YAB2 |
| *Pseudomonas aeruginosa* BWHPSA003 | Q016_02194 | U8XR83 |
| *Pseudomonas aeruginosa* BWHPSA002 | Q015_02292 | U8XP62 |
| *Pseudomonas aeruginosa* BWHPSA004 | Q017_02030 | U8X7A0 |
| *Pseudomonas aeruginosa* BWHPSA005 | Q018_03069 | U8W6E8 |
| *Pseudomonas aeruginosa* BWHPSA011 | Q024_01957 | U8VA48 |
| *Pseudomonas aeruginosa* BWHPSA013 | Q026_03028 | U8URW4 |
| *Pseudomonas aeruginosa* BWHPSA012 | Q025_02769 | U8UQP2 |
| *Pseudomonas aeruginosa* BWHPSA014 | Q027_01719 | U8TK96 |
| *Pseudomonas aeruginosa* BWHPSA017 | Q030_05589 | U8SKH8 |
| *Pseudomonas aeruginosa* BWHPSA020 | Q033_02593 | U8S609 |
| *Pseudomonas aeruginosa* BWHPSA019 | Q032_03133 | U8RPR9 |
| *Pseudomonas aeruginosa* BWHPSA022 | Q035_01895 | U8R8U4 |
| *Pseudomonas aeruginosa* BWHPSA023 | Q036_00320 | U8R6B4 |
| *Pseudomonas aeruginosa* BWHPSA021 | Q034_02035 | U8R1N4 |
| *Pseudomonas aeruginosa* BWHPSA025 | Q038_01757 | U8PR31 |
| *Pseudomonas aeruginosa* BWHPSA024 | Q037_02761 | U8PP93 |
| *Pseudomonas aeruginosa* BWHPSA027 | Q040_02049 | U8N8N1 |
| *Pseudomonas aeruginosa* BL07 | Q061_01439 | U8LYS6 |
| *Pseudomonas aeruginosa* BL04 | Q058_06192 | U8LL05 |
| *Pseudomonas aeruginosa* BL11 | Q065_03099 | U8K8S5 |
| *Pseudomonas aeruginosa* BL10 | Q064_02801 | U8JQ84 |
| *Pseudomonas aeruginosa* BL15 | Q069_01997 | U8IMR3 |
| *Pseudomonas aeruginosa* BL16 | Q070_01957 | U8IID0 |
| *Pseudomonas aeruginosa* BL18 | Q072_02105 | U8H8J8 |
| *Pseudomonas aeruginosa* M8A.2 | Q081_01961 | U8FTG3 |
| *Pseudomonas aeruginosa* M8A.1 | Q080_04721 | U8FHJ8 |
| *Pseudomonas aeruginosa* M9A.1 | Q084_05530 | U8EPH5 |
| *Pseudomonas aeruginosa* C20 | Q085_03119 | U8EML6 |
| *Pseudomonas aeruginosa* C23 | Q086_03122 | U8EJ68 |
| *Pseudomonas aeruginosa* C40 | Q087_02201 | U8DKJ1 |
| *Pseudomonas aeruginosa* C48 | Q089_02700 | U8CPW7 |
| *Pseudomonas aeruginosa* C51 | Q090_05806 | U8BVH7 |
| *Pseudomonas aeruginosa* CF77 | Q092_01904 | U8BA80 |
| *Pseudomonas aeruginosa* C52 | Q091_05688 | U8AZD2 |
| *Pseudomonas aeruginosa* CF614 | Q093_06204 | U8ACM4 |
| *Pseudomonas aeruginosa* VRFPA04 | P797_30195 | U5AHY5 |
| *Pseudomonas aeruginosa* HB13 | PA13_1029315 | U1E3A4 |
| *Pseudomonas aeruginosa* MSH-10 | L346_02111 | S0IJJ1 |
| *Pseudomonas aeruginosa* PA14 | CIA_02266 | S0I9C6 |
| *Pseudomonas aeruginosa* PAK | PAK_02986 | S0I695 |
| *Pseudomonas* sp. P179 | HMPREF1224_05539 | N2DDM6 |
| *Pseudomonas aeruginosa* str. Stone 130 | HMPREF1223_07114 | N2D7D2 |
| *Pseudomonas aeruginosa* PA21_ST175 | H123_24636 | M3AW72 |
| *Pseudomonas aeruginosa* E2 | P998_02032 PAE2_2544 | K1DHT6 |
| *Pseudomonas aeruginosa* ATCC 25324 | PABE173_3188 | K1DD82 |
| *Pseudomonas aeruginosa* CI27 | PACI27_2786 | K1CTB3 |
| *Pseudomonas aeruginosa* ATCC 700888 | PABE177_2660 | K1CGR7 |
| *Pseudomonas aeruginosa* ATCC 14886 | PABE171_3115 | K1BXJ5 |
| *Pseudomonas aeruginosa* PADK2_CF510 | CF510_22344 | I1ACS3 |
| *Pseudomonas aeruginosa* MPAO1/P2 | O1Q_15090 | H3TFC3 |
| *Pseudomonas aeruginosa* MPAO1/P1 | O1O_28545 | H3T6G4 |
| *Pseudomonas* sp. 2_1_26 | HMPREF1030_05556 | G5G1F3 |
| *Pseudomonas aeruginosa* 2192 | PA2G_01431 | A3LB74 |
| *Pseudomonas aeruginosa* C3719 | PACG_01235 | A3KU95 |
| *Erwinia billingiae* (strain Eb661) | EbC_20720 | D8MRZ6 |
| *Xanthomonas axonopodis* pv. *citri* (strain 306) | XAC0855 | Q8PP33 |
| *Xanthomonas citri* subsp. *citri* Aw12879 | XCAW_03724 | M4W2T5 |
| *Xanthomonas axonopodis* Xac29-1 | XAC29_04355 | M4U7K3 |
| *Xanthomonas citri* pv. *mangiferaeindicae* LMG 941 | ladA XMIN_2789 | H8FHG1 |
| *Xanthomonas axonopodis* pv. *punicae* str. LMG 859 | ladA XAPC_728 | H1XCV7 |
| *Leifsonia aquatica* ATCC 14665 | N136_01626 | U2TBF7 |

TABLE 4-continued

Long chain alkane hydroxylase enzymes capable of catalyzing selective terminal alkene hydroxylation.

| Species Origin | Gene names | Accession No |
|---|---|---|
| *Serratia marcescens* subsp. *marcescens* Db11 | SMDB11_2421 | V6A0D9 |
| *Pseudomonas aeruginosa* VRFPA05 | T266_33830 | V4WJP9 |
| *Pseudomonas aeruginosa* BL22 | Q076_01761 | U9GCW5 |
| *Pseudomonas aeruginosa* BL22 | Q076_01761 | U9GCW5 |
| *Xanthomonas axonopodis* pv. *malvacearum* str. GSPB1386 | MOU_00060 | K8GBN4 |
| *Pseudomonas aeruginosa* VRFPA07 | X778_28580 | V8E3G0 |
| *Pseudomonas aeruginosa* BL20 | Q074_02826 | U9HSV9 |
| *Pseudomonas aeruginosa* BL25 | Q079_01143 | U9F0W8 |
| *Pseudomonas aeruginosa* BL09 | Q063_00187 | U8L2Y0 |
| *Serratia marcescens* WW4 | SMWW4_v1c31920 | L7ZQQ5 |
| *Serratia marcescens* VGH107 | F518_24469 | M3BTM0 |
| *Pseudomonas aeruginosa* BWHPSA018 | Q031_00379 | U8TSK3 |
| *Pseudomonas aeruginosa* M18 | PAM18_2715 | G2L1H6 |
| *Pseudomonas aeruginosa* BL12 | Q066_03852 | U9I855 |
| *Pseudomonas aeruginosa* BWHPSA028 | Q041_02218 | U8NES6 |
| *Pseudomonas aeruginosa* WC55 | L683_26830 | T5KSU5 |
| *Pseudomonas aeruginosa* NCMG1179 | NCGM1179_2739 | G2U5R3 |
| *Rhodococcus erythropolis* SK121 | RHOER0001_2299 | C3JDL9 |
| *Pseudomonas aeruginosa* VRFPA03 | M770_16185 | W1MK34 |
| *Pseudomonas aeruginosa* BL13 | Q067_03184 | U9I925 |
| *Serratia marcescens* EGD-HP20 | N040_11055 | U1TLQ0 |
| *Pseudomonas aeruginosa* NCGM2.S1 | NCGM2_3338 | G4LI50 |
| *Pseudomonas aeruginosa* 39016 | PA39016_002700003 | E3A2U8 |
| *Pseudomonas aeruginosa* MH27 | PAMH27_2887 | V6AFD9 |
| *Pseudomonas aeruginosa* JJ692 | Q008_02805 | U9PMT7 |
| *Pseudomonas aeruginosa* 6077 | Q011_02150 | U9ATK4 |
| *Pseudomonas aeruginosa* U2504 | Q009_02593 | U9AAM5 |
| *Pseudomonas aeruginosa* BWHPSA006 | Q019_02936 | U8VL16 |
| *Pseudomonas aeruginosa* BL08 | Q062_04340 | U8KSZ8 |
| *Pseudomonas aeruginosa* BL14 | Q068_02182 | U8JUF2 |
| *Pseudomonas aeruginosa* BL17 | Q071_02971 | U8H8J5 |
| *Pseudomonas aeruginosa* PA45 | H734_07342 | N4W202 |
| *Rhodococcus erythropolis* CCM2595 | O5Y_21155 | T1VSG7 |
| *Rhodococcus* sp. P27 | N806_09240 | U0ED84 |
| *Kosakonia radicincitans* DSM 16656 | Y71_0158 | J1QW00 |
| *Rhodococcus erythropolis* (strain PR4/NBRC 100887) | RER_45000 | C0ZMF0 |
| *Klebsiella pneumoniae* MGH 46 | L392_03264 | V3LZ98 |
| *Klebsiella pneumoniae* MGH 44 | L390_02205 | V3JUR2 |
| *Klebsiella pneumoniae* UCICRE 4 | L415_03363 | V3FXF6 |
| *Klebsiella pneumoniae* 303K | N598_24365 | U6T101 |
| *Klebsiella pneumoniae* UHKPC179 | H238_2267 | S7F9A7 |
| *Klebsiella pneumoniae* UHKPC57 | H237_2247 | S2EDB5 |
| *Klebsiella pneumoniae* JHCK1 | MTE1_213 | M3U9Q5 |
| *Klebsiella pneumoniae* subsp. *pneumoniae* WGLW2 | HMPREF1306_03733 | K1NBI6 |
| *Klebsiella pneumoniae* UCICRE 14 | L425_03054 | V3CJD9 |
| *Rhodococcus qingshengii* BKS 20-40 | G418_04858 | M2XMT9 |
| *Pantoea* sp. Sc1 | S7A_19914 | H8DUB8 |
| *Klebsiella* sp. 1_1_55 | HMPREF0485_02899 | D6GIG4 |
| *Pantoea agglomerans* Tx10 | L584_13665 | U4VW62 |
| *Escherichia coli* 909957 | HMPREF1619_02817 | V0B421 |
| *Klebsiella pneumoniae* KP-1 | KLP1_1662 | U2ABR1 |
| *Rhodococcus erythropolis* DN1 | N601_05680 | T5I9L8 |
| *Klebsiella pneumoniae* UCICRE 8 | L419_03300 | V3F3T1 |
| *Brenneria* sp. EniD312 | BrE312_1717 | G7LVX2 |
| *Klebsiella pneumoniae* BIDMC 23 | L459_03205 | V3BAE8 |
| *Raoultella ornithinolytica* B6 | RORB6_23555 | M9W8P0 |
| *Klebsiella oxytoca* 10-5246 | HMPREF9690_03902 | H3MRJ7 |
| *Pantoea agglomerans* 299R | F385_1445 | L7BV82 |
| *Pantoea* sp. aB | PanABDRAFT_3926 | E0M3F8 |
| *Pseudomonas* sp. CFII64 | CFII64_23274 | S6GXI3 |
| *Pseudomonas synxantha* BG33R | PseBG33_0275 | I4KV50 |
| *Pseudomonas syringae* pv. *actinidiae* ICMP 18801 | A221_07756 | S6XYV3 |
| *Pseudomonas syringae* pv. *actinidiae* ICMP 19072 | A3SO_07400 | S6PNP2 |
| *Pseudomonas syringae* pv. *actinidiae* ICMP 19073 | A262_20054 | S6MLA8 |
| *Pseudomonas syringae* pv. *actinidiae* ICMP 19071 | A264_07551 | S6M2E1 |
| *Pseudomonas syringae* pv. *actinidiae* ICMP 19104 | A258_19792 | S6QSB5 |
| *Pseudomonas syringae* pv. *actinidiae* ICMP 9855 | A252_19596 | S6QRN6 |
| *Pseudomonas syringae* pv. *actinidiae* ICMP 19102 | A253_19857 | S6Q6B9 |
| *Pseudomonas syringae* pv. *actinidiae* ICMP 19068 | A260_20086 | S6Q126 |
| *Pseudomonas syringae* pv. *theae* ICMP 3923 | A584_21008 | S6MKD2 |
| *Pseudomonas syringae* pv. *actinidiae* ICMP 19103 | A256_19800 | S6M4P1 |
| *Rhizobium leguminosarum* bv. *viciae* (strain 3841) | pRL90300 | Q1M8E2 |
| *Pseudomonas* sp. GM25 | PMI24_01694 | J2PHH1 |
| *Herbaspirillum* sp. YR522 | PMI40_00700 | J3HY53 |

TABLE 4-continued

Long chain alkane hydroxylase enzymes capable of catalyzing selective terminal alkene hydroxylation.

| Species Origin | Gene names | Accession No |
|---|---|---|
| *Pseudomonas syringae* pv. *morsprunorum* str. M302280 | PSYMP_05599 | F3DS65 |
| *Pseudomonas fluorescens* (strain Pf0-1) | Pfl01_0238 | Q3KJS4 |
| *Pseudomonas avellanae* BPIC 631 | Pav631_4731 | K2RRZ8 |
| *Pseudomonas fluorescens* R124 | I1A_000262 | K0W8U4 |
| *Pseudomonas syringae* pv. *syringae* (strain B728a) | Psyr_2869 | Q4ZSG7 |
| *Pseudomonas syringae* CC1557 | N018_12850 | W0MW63 |
| *Pseudomonas* sp. GM80 | PMI37_03766 | J3DKC5 |
| *Pseudomonas syringae* pv. *syringae* SM | PssSM_2902 | S3MKC4 |
| *Pseudomonas syringae* pv. *avellanae* str. ISPaVe037 | Pav037_2494 | K2T3F9 |
| *Pseudomonas syringae* pv. *aceris* str. M302273 | PSYAR_06142 | F3JE47 |
| *Pseudomonas syringae* pv. *maculicola* str. ES4326 | PMA4326_07981 | F3HHE2 |
| *Pseudomonas syringae* BRIP39023 | A988_19986 | L7GSY0 |
| *Pseudomonas syringae* pv. *aptata* str. DSM 50252 | PSYAP_18083 | F3J2D2 |
| *Pseudomonas savastanoi* pv. *savastanoi* NCPPB 3335 | PSA3335_0550 | D7HUP0 |
| *Pseudomonas syringae* pv. *aesculi* str. 0893_23 | PSYAE_00125 | F3D7S6 |
| *Pseudomonas syringae* BRIP34881 | A987_17762 | L7G2P2 |
| *Pseudomonas syringae* BRIP34876 | A979_21556 | L7FTL3 |
| *Rhizobium leguminosarum* bv. *viciae* WSM1455 | Rleg5DRAFT_0033 | J0URT9 |
| *Pseudomonas syringae* Cit 7 | PSYCIT7_07619 | F3GWQ5 |
| *Acinetobacter baumannii* NIPH 410 | F910_02332 | S3TEC4 |
| *Acinetobacter baumannii* OIFC110 | ACIN5110_2029 | K5S1X4 |
| *Acinetobacter baumannii* WC-692 | ACINWC692_1619 | K1ER91 |
| *Pseudomonas* sp. TKP | U771_01460 | V9QPN2 |
| *Pseudomonas syringae* pv. *syringae* B64 | PssB64_3039 | L8NFP3 |
| *Pseudomonas syringae* pv. *actinidiae* ICMP 19094 | A241_11585 | S6VCM5 |
| *Pseudomonas syringae* pv. *actinidiae* ICMP 18883 | A243_23241 | S6TZP7 |
| *Pseudomonas syringae* pv. *actinidiae* ICMP 19095 | A242_23680 | S6TDL4 |
| *Pseudomonas syringae* pv. *actinidiae* ICMP 19099 | A247_15969 | S6S3V9 |
| *Pseudomonas syringae* pv. *actinidiae* ICMP 19100 | A248_23237 | S6R962 |
| *Pseudomonas syringae* pv. *actinidiae* ICMP 19098 | A246_16023 | S6LVQ8 |

In some embodiments, the invention provides methods for synthesizing olefinic alcohol products as described above, wherein the enzyme is a cytochrome P450. In some embodiments, the cytochrome P450 is selected from Table 5 or a variant thereof having at least 90% identity thereto. In some embodiments, the cytochrome P450 is a member of the CYP52 or CYP153 family.

TABLE 5

Cytochrome P450 enzymes capable of catalyzing selective terminal alkene hydroxylation.

| Species Origin | Gene names | Accession No |
|---|---|---|
| *Candida tropicalis* (Yeast) | CYP52A12 | Q874J5 (SEQ ID NO: 33) |
| *Candida tropicalis* (strain ATCC MYA-3404/T1) (Yeast) | CTRG_02725 | C5M8K3 (SEQ ID NO: 34) |
| *Candida tropicalis* (Yeast) | CYP52A6 | P30608 |
| *Candida albicans* (Yeast) | | Q9C2X5 |
| *Candida maltosa* (Yeast) | CYP52A3-B | P24458 (SEQ ID NO: 35) |
| *Candida dubliniensis* (strain CD36/ATCC MYA-646/CBS 7987/NCPF 3949/NRRL Y-17841) (Yeast) | CYP52A5 CD36_64140 | B9WJ64 |
| *Candida albicans* (strain SC5314/ATCC MYA-2876) (Yeast) | ALK1 CaO19.13150 orf19.13150 | Q5A8M1 |
| *Candida albicans* (strain SC5314/ATCC MYA-2876) (Yeast) | ALK1 CaO19.5728 orf19.5728 | Q5A8U5 |
| *Candida maltosa* (strain Xu316) (Yeast) | G210_4862 | M3HRI7 |
| *Candida maltosa* (Yeast) | CYP52A3-A | P16496 |
| *Candida orthopsilosis* (strain 90-125) (Yeast) | CORT_0F01930 | H8X8E5 |
| *Candida parapsilosis* (strain CDC 317/ATCC MYA-4646) (Yeast) (*Monilia parapsilosis*) | CPAR2_600870 | G8B4X9 (SEQ ID NO: 36) |
| *Lodderomyces elongisporus* (strain ATCC 11503/CBS 2605/JCM 1781/NBRC 1676/NRRL YB-4239) (Yeast) (*Saccharomyces elongisporus*) | LELG_04957 | A5E5R8 (SEQ ID NO: 37) |

TABLE 5-continued

Cytochrome P450 enzymes capable of catalyzing selective terminal alkene hydroxylation.

| Species Origin | Gene names | Accession No |
| --- | --- | --- |
| *Candida maltosa* (Yeast) | ALK3-B (CYP52A4) | B0VX53 |
| *Candida maltosa* (Yeast) | ALK8-B | Q12584 |
| *Candida tropicalis* (Yeast) | CYP52A8 | P30610 |
| *Debaryomyces hansenii* (strain ATCC 36239/CBS 767/ JCM 1990/NBRC 0083/IGC 2968) (Yeast) (*Torulaspora hansenii*) | DEHA2E18634g | Q6BNV8 (SEQ ID NO: 38) |
| *Candida tropicalis* (Yeast) | CYP52A17 | Q874I9 |
| *Candida maltosa* (strain Xu316) (Yeast) | G210_3820 | M3II00 |
| *Spathaspora passalidarum* (strain NRRL Y-27907/11-Y1) | SPAPADRAFT_59378 | G3AJR6 |
| *Scheffersomyces stipitis* (strain ATCC 58785/CBS 6054/ NBRC 10063/NRRL Y-11545) (Yeast) (*Pichia stipitis*) | CP52M PICST_58031 | A3LRT5 |
| *Candida parapsilosis* (strain CDC 317/ATCC MYA-4646) (Yeast) (*Monilia parapsilosis*) | CPAR2_503950 | G8BH23 (SEQ ID NO: 39) |
| *Candida parapsilosis* (strain CDC 317/ATCC MYA-4646) (Yeast) (*Monilia parapsilosis*) | CPAR2_800510 | G8BBI4 (SEQ ID NO: 40) |
| *Candida tropicalis* (Yeast) | CYP52A18 | Q874I8 |
| *Candida maltosa* (strain Xu316) (Yeast) | G210_4812 | M3K5V3 |
| *Debaryomyces hansenii* (Yeast) (*Torulaspora hansenii*) | CYP52A13 ALK2 | Q9Y758 |
| *Meyerozyma guilliermondii* (strain ATCC 6260/CBS 566/ DSM 6381/JCM 1539/NBRC 10279/NRRL Y-324) (Yeast) (*Candida guilliermondii*) | PGUG_05855 | A5DRF4 |
| *Debaryomyces hansenii* (strain ATCC 36239/CBS 767/ JCM 1990/NBRC 0083/IGC 2968) (Yeast) (*Torulaspora hansenii*) | DEHA2C02596g | Q6BVH7 |
| *Candida maltosa* (Yeast) | CYP52A5 | Q12581 (SEQ ID NO: 41) |
| *Meyerozyma guilliermondii* (strain ATCC 6260/CBS 566/ DSM 6381/JCM 1539/NBRC 10279/NRRL Y-324) (Yeast) (*Candida guilliermondii*) | PGUG_01238 | A5DD87 |
| *Debaryomyces hansenii* (Yeast) (*Torulaspora hansenii*) | CYP52A12 ALK1 | Q9Y757 |
| *Candida dubliniensis* (strain CD36/ATCC MYA-646/ CBS 7987/NCPF 3949/NRRL Y-17841) (Yeast) | CYP52A14 CD36_25250 | B9WKL6 |
| *Meyerozyma guilliermondii* (strain ATCC 6260/CBS 566/ DSM 6381/JCM 1539/NBRC 10279/NRRL Y-324) (Yeast) (*Candida guilliermondii*) | PGUG_05670 | A5DQW9 |
| *Candida albicans* (strain SC5314/ATCC MYA-2876) (Yeast) | ALK2 CaO19.7513 orf19.7513 | Q5AAH6 |
| *Candida albicans* (strain WO-1) (Yeast) | CAWG_01382 | C4YNC3 |
| *Candida tropicalis* (Yeast) | CYP52A14 CYP14 | Q874J3 |
| *Candida tropicalis* (Yeast) | CYP52A13 | Q874J4 (SEQ ID NO: 42) |
| *Pichia sorbitophila* (strain ATCC MYA-4447/BCRC 22081/CBS 7064/NBRC 10061/NRRL Y-12695) (Hybrid yeast) | Piso0_002820 GNLVRS01_PISO0I18532g | G8YG24 |
| *Candida parapsilosis* (strain CDC 317/ATCC MYA-4646) (Yeast) (*Monilia parapsilosis*) | CPAR2_204220 | G8BFZ5 (SEQ ID NO: 43) |
| *Candida tropicalis* (Yeast) | CYP52A20 | Q874I6 |
| *Candida tropicalis* (Yeast) | CYP52A19 | Q874I7 (SEQ ID NO: 44) |
| *Lodderomyces elongisporus* (strain ATCC 11503/CBS 2605/JCM 1781/NBRC 1676/NRRL YB-4239) (Yeast) (*Saccharomyces elongisporus*) | LELG_00044 | A5DRQ8 (SEQ ID NO: 45) |
| *Candida albicans* (strain WO-1) (Yeast) | CAWG_02011 | C4YMD2 |
| *Candida albicans* (strain SC5314/ATCC MYA-2876) (Yeast) | ALK8 CaO19.10 CaO19.7683 | Q59K96 |
| *Candida albicans* (Yeast) | alk8 | O74626 |
| *Candida maltosa* (strain Xu316) (Yeast) | G210_4811 | M3JDC1 (SEQ ID NO: 46) |
| *Scheffersomyces stipitis* (strain ATCC 58785/CBS 6054/ NBRC 10063/NRRL Y-11545) (Yeast) (*Pichia stipitis*) | CP52C PICST_56580 | A3LR60 (SEQ ID NO: 47) |
| *Lodderomyces elongisporus* (strain ATCC 11503/CBS 2605/JCM 1781/NBRC 1676/NRRL YB-4239) (Yeast) (*Saccharomyces elongisporus*) | LELG_03506 | A5E1L9 |
| *Candida tropicalis* (strain ATCC MYA-3404/T1) (Yeast) | CTRG_03115 | C5MAM3 (SEQ ID NO: 48) |

TABLE 5-continued

Cytochrome P450 enzymes capable of catalyzing selective terminal alkene hydroxylation.

| Species Origin | Gene names | Accession No |
| --- | --- | --- |
| *Pichia sorbitophila* (strain ATCC MYA-4447/BCRC 22081/CBS 7064/NBRC 10061/NRRL Y-12695) (Hybrid yeast) | Piso0_002820 GNLVRS01_PISO0J20293g | G8YDL5 |
| *Candida parapsilosis* (strain CDC 317/ATCC MYA-4646) (Yeast) (*Monilia parapsilosis*) | CPAR2_204210 | G8BFZ4 (SEQ ID NO: 49) |
| *Spathaspora passalidarum* (strain NRRL Y-27907/11-Y1) | SPAPADRAFT_134963 | G3AJD3 |
| *Candida tropicalis* (strain ATCC MYA-3404/T1) (Yeast) | CTRG_01061 | C5M4S1 (SEQ ID NO: 50) |
| *Candida tropicalis* (Yeast) | CYP52A2 | P30607 (SEQ ID NO: 51) |
| *Candida parapsilosis* (strain CDC 317/ATCC MYA-4646) (Yeast) (*Monilia parapsilosis*) | CPAR2_800520 | G8BBI5 |
| *Scheffersomyces stipitis* (strain ATCC 58785/CBS 6054/ NBRC 10063/NRRL Y-11545) (Yeast) (*Pichia stipitis*) | CP52L PICST_56638 | A3LSP0 (SEQ ID NO: 52) |
| *Candida parapsilosis* (strain CDC 317/ATCC MYA-4646) (Yeast) (*Monilia parapsilosis*) | CPAR2_203780 | G8BFV1 |
| *Candida maltosa* (strain Xu316) (Yeast) | G210_4902 | M3IU34 |
| *Candida orthopsilosis* (strain 90-125) (Yeast) | CORT_0D03890 | H8X5Y1 |
| *Candida dubliniensis* (strain CD36/ATCC MYA-646/ CBS 7987/NCPF 3949/NRRL Y-17841) (Yeast) | CD36_32710 | B9WMB3 |
| *Pichia sorbitophila* (strain ATCC MYA-4447/BCRC 22081/CBS 7064/NBRC 10061/NRRL Y-12695) (Hybrid yeast) | | G8YJP0 |
| *Debaryomyces hansenii* (strain ATCC 36239/CBS 767/ JCM 1990/NBRC 0083/IGC 2968) (Yeast) (*Torulaspora hansenii*) | DEHA2E18590g | Q6BNW0 |
| *Candida maltosa* (Yeast) | CYP52A9 | Q12586 |
| *Scheffersomyces stipitis* (strain ATCC 58785/CBS 6054/ NBRC 10063/NRRL Y-11545) (Yeast) (*Pichia stipitis*) | ALK2 PICST_35590 | A3LS01 |
| *Spathaspora passalidarum* (strain NRRL Y-27907/11-Y1) | SPAPADRAFT_67265 | G3APG2 |
| *Candida tropicalis* (strain ATCC MYA-3404/T1) (Yeast) | CTRG_03120 | C5MAM8 |
| *Candida maltosa* (Yeast) | CYP52A11 | Q12589 |
| *Candida albicans* (strain WO-1) (Yeast) | CAWG_01383 | C4YNC4 |
| *Candida tropicalis* (strain ATCC MYA-3404/T1) (Yeast) | CTRG_01060 | C5M4S0 |
| *Candida albicans* (strain SC5314/ATCC MYA-2876) (Yeast) | ALK3 CaO19.7512 orf19.7512 | Q5AAH7 |
| *Candida tropicalis* (Yeast) | CYP52A1 | P10615 (SEQ ID NO: 53) |
| *Scheffersomyces stipitis* (strain ATCC 58785/CBS 6054/ NBRC 10063/NRRL Y-11545) (Yeast) (*Pichia stipitis*) | CYP52 PICST_37142 | A3LZV9 (SEQ ID NO: 54) |
| *Debaryomyces hansenii* (strain ATCC 36239/CBS 767/ JCM 1990/NBRC 0083/IGC 2968) (Yeast) (*Torulaspora hansenii*) | DEHA2E18612g | Q6BNV9 |
| *Candida tenuis* (strain ATCC 10573/BCRC 21748/CBS 615/JCM 9827/NBRC 10315/NRRL Y-1498/VKM Y-70) (Yeast) | CANTEDRAFT_115474 | G3BA51 (SEQ ID NO: 55) |
| *Lodderomyces elongisporus* (strain ATCC 11503/CBS 2605/JCM 1781/NBRC 1676/NRRL YB-4239) (Yeast) (*Saccharomyces elongisporus*) | LELG_03309 | A5E122 (SEQ ID NO: 56) |
| *Lodderomyces elongisporus* (strain ATCC 11503/CBS 2605/JCM 1781/NBRC 1676/NRRL YB-4239) (Yeast) (*Saccharomyces elongisporus*) | LELG_03505 | A5E1L8 |
| *Candida tropicalis* (Yeast) | CYP52A16 CYP16 | Q874J1 |
| *Candida tropicalis* (Yeast) | CYP52A15 | Q874J2 (SEQ ID NO: 57) |
| *Candida maltosa* (Yeast) | CYP52A10 | Q12588 |
| *Candida dubliniensis* (strain CD36/ATCC MYA-646/ CBS 7987/NCPF 3949/NRRL Y-17841) (Yeast) | ALK3-A CD36_25260 | B9WKL7 |
| *Candida maltosa* (Yeast) | CYP52A4 | P16141 (SEQ ID NO: 58) |
| *Candida tenuis* (strain ATCC 10573/BCRC 21748/CBS 615/JCM 9827/NBRC 10315/NRRL Y-1498/VKM Y-70) (Yeast) | CANTEDRAFT_113909 | G3B3X3 (SEQ ID NO: 59) |
| *Meyerozyma guilliermondii* (Yeast) (*Candida guilliermondii*) | CYP52 | I6UGD5 |

TABLE 5-continued

Cytochrome P450 enzymes capable of catalyzing selective terminal alkene hydroxylation.

| Species Origin | Gene names | Accession No |
|---|---|---|
| *Spathaspora passalidarum* (strain NRRL Y-27907/11-Y1) | SPAPADRAFT_153278 | G3AMY8 |
| *Candida tenuis* (strain ATCC 10573/BCRC 21748/CBS 615/JCM 9827/NBRC 10315/NRRL Y-1498/VKM Y-70) (Yeast) | CANTEDRAFT_116673 | G3BEU9 (SEQ ID NO: 60) |
| *Candida maltosa* (strain Xu316) (Yeast) | G210_3821 | M3J257 |
| *Candida tropicalis* (Yeast) | CYP52A7 | P30609 |
| *Clavispora lusitaniae* (strain ATCC 42720) (Yeast) (*Candida lusitaniae*) | CLUG_03984 | C4Y750 |
| *Debaryomyces hansenii* (strain ATCC 36239/CBS 767/JCM 1990/NBRC 0083/IGC 2968) (Yeast) (*Torulaspora hansenii*) | DEHA2C01100g | Q6BVP2 |
| *Candida tropicalis* (Yeast) | CYP52D2 | Q874J0 (SEQ ID NO: 61) |
| *Clavispora lusitaniae* (strain ATCC 42720) (Yeast) (*Candida lusitaniae*) | CLUG_04851 | C4Y9G1 |
| *Meyerozyma guilliermondii* (strain ATCC 6260/CBS 566/DSM 6381/JCM 1539/NBRC 10279/NRRL Y-324) (Yeast) (*Candida guilliermondii*) | PGUG_04005 | A5DL54 |
| *Yarrowia lipolytica* (*Candida lipolytica*) | ALK6 | O74132 (SEQ ID NO: 93) |
| *Yarrowia lipolytica* (strain CLIB 122/E 150) (Yeast) (*Candida lipolytica*) | YALI0_B01848g | F2Z623 |
| *Yarrowia lipolytica* (strain CLIB 122/E 150) (Yeast) (*Candida lipolytica*) | YALI0_E25982g | Q6C4K6 |
| *Yarrowia lipolytica* (*Candida lipolytica*) | ALK1 | O74127 (SEQ ID NO: 62) |
| *Yarrowia lipolytica* (*Candida lipolytica*) | ALK2 | O74128 (SEQ ID NO: 63) |
| *Yarrowia lipolytica* (strain CLIB 122/E 150) (Yeast) (*Candida lipolytica*) | YALI0_F01320g | F2Z6J3 |
| *Candida maltosa* (Yeast) | CYP52D1 | Q12585 (SEQ ID NO: 92) |
| *Yarrowia lipolytica* (strain CLIB 122/E 150) (Yeast) (*Candida lipolytica*) | YALI0_B20702g | Q6CDW4 |
| *Byssochlamys spectabilis* (strain No. 5/NBRC 109023) (*Paecilomyces variotii*) | PVAR5_4403 | V5G4E7 |
| *Byssochlamys spectabilis* (strain No. 5/NBRC 109023) (*Paecilomyces variotii*) | PVAR5_4403 | V5G4E7 |
| *Aspergillus terreus* (strain NIH 2624/FGSC A1156) | ATEG_02198 | Q0CVT6 |
| *Neosartorya fischeri* (strain ATCC 1020/DSM 3700/FGSC A1164/NRRL 181) (*Aspergillus fischerianus*) | NFIA_029600 | A1D9P7 |
| *Yarrowia lipolytica* (*Candida lipolytica*) | ALK4 | O74130 (SEQ ID NO: 64) |
| *Yarrowia lipolytica* (strain CLIB 122/E 150) (Yeast) (*Candida lipolytica*) | YALI0_B13816g | F2Z6H3 |
| *Penicillium digitatum* (strain PHI26/CECT 20796) (Green mold) | PDIG_58170 | K9G9Y0 |
| *Penicillium digitatum* (strain Pd1/CECT 20795) (Green mold) | PDIP_67660 | K9FGZ9 |
| *Aspergillus niger* (strain ATCC 1015/CBS 113.46/FGSC A1144/LSHB Ac4/NCTC 3858a/NRRL 328/USDA 3528.7) | ASPNIDRAFT_210944 | G3XNK4 |
| *Aspergillus niger* (strain CBS 513.88/FGSC A1513) | An14g01110 | A2R2K9 (SEQ ID NO: 65) |
| *Tuber melanosporum* (strain Mel28) (Perigord black truffle) | GSTUM_00009186001 | D5GJT6 |
| *Yarrowia lipolytica* (*Candida lipolytica*) | ALK7 | O74133 (SEQ ID NO: 66) |
| *Yarrowia lipolytica* (strain CLIB 122/E 150) (Yeast) (*Candida lipolytica*) | YALI0_A15488g | F2Z6A4 |
| *Arthrobotrys oligospora* (strain ATCC 24927/CBS 115.81/DSM 1491) (Nematode-trapping fungus) (*Didymozoophaga oligospora*) | AOL_s00109g132 | G1XKA3 |
| *Dactylellina haptotyla* (strain CBS 200.50) (Nematode-trapping fungus) (*Monacrosporium haptotylum*) | H072_6900 | S8ADY3 |
| *Yarrowia lipolytica* (strain CLIB 122/E 150) (Yeast) (*Candida lipolytica*) | YALI0_B06248g | Q6CFK2 |

TABLE 5-continued

Cytochrome P450 enzymes capable of catalyzing selective terminal alkene hydroxylation.

| Species Origin | Gene names | Accession No |
|---|---|---|
| *Aspergillus clavatus* (strain ATCC 1007/CBS 513.65/DSM 816/NCTC 3887/NRRL 1) | ACLA_054640 | A1C993 |
| *Byssochlamys spectabilis* (strain No. 5/NBRC 109023) (*Paecilomyces variotii*) | PVAR5_0196 | V5FIS1 |
| *Aspergillus kawachii* (strain NBRC 4308) (White koji mold) (*Aspergillus awamori* var. *kawachi*) | AKAW_05280 | G7XJE1 |
| *Aspergillus oryzae* (strain 3.042) (Yellow koji mold) | Ao3042_00039 | I8AC74 |
| *Aspergillus flavus* (strain ATCC 200026/FGSC A1120/NRRL 3357/JCM 12722/SRRC 167) | AFLA_041790 | B8NCU4 |
| *Aspergillus oryzae* (strain ATCC 42149/RIB 40) (Yellow koji mold) | AO090011000346 | Q2U0Q3 |
| *Aspergillus oryzae* (Yellow koji mold) | CYP52H3 | D4QC14 |
| *Candida tenuis* (strain ATCC 10573/BCRC 21748/CBS 615/JCM 9827/NBRC 10315/NRRL Y-1498/VKM Y-70) (Yeast) | CANTEDRAFT_130130 | G3B1J0 (SEQ ID NO: 67) |
| *Emericella nidulans* (strain FGSC A4/ATCC 38163/CBS 112.46/NRRL 194/M139) (*Aspergillus nidulans*) | AN7131.2 ANIA_07131 | Q5AX49 |
| *Talaromyces stipitatus* (strain ATCC 10500/CBS 375.48/QM 6759/NRRL 1006) (*Penicillium stipitatum*) | TSTA_012000 | B8ME14 |
| *Starmerella bombicola* | | B8QHP3 (SEQ ID NO: 68) |
| *Hordeum vulgare* var. *distichum* (Two-rowed barley) | | F2E8C2 |
| *Mycosphaerella graminicola* (strain CBS 115943/IPO323) (Speckled leaf blotch fungus) (*Septoria tritici*) | CYP-27 MYCGRDRAFT_70822 | F9X9F0 |
| *Neosartorya fumigata* (strain ATCC MYA-4609/Af293/CBS 101355/FGSC A1100) (*Aspergillus fumigatus*) | AFUA_4G03800 | Q4W9T4 |
| *Neosartorya fumigata* (strain CEA10/CBS 144.89/FGSC A1163) (*Aspergillus fumigatus*) | AFUB_099220 | B0YEH7 |
| *Penicillium chrysogenum* (strain ATCC 28089/DSM 1075/Wisconsin 54-1255) (*Penicillium notatum*) | Pc14g00320 PCH_Pc14g00320 | B6H5K4 |
| *Clavispora lusitaniae* (strain ATCC 42720) (Yeast) (*Candida lusitaniae*) | CLUG_04098 | C4Y4W0 |
| *Penicillium roqueforti* | CYP52A12PROQFM164_S03g001613 | W6QFZ4 |
| *Yarrowia lipolytica* (*Candida lipolytica*) | ALK5 | O74131 (SEQ ID NO: 69) |
| *Yarrowia lipolytica* (strain CLIB 122/E 150) (Yeast) (*Candida lipolytica*) | YALI0_B13838g | F2Z5W7 |
| *Candida tenuis* (strain ATCC 10573/BCRC 21748/CBS 615/JCM 9827/NBRC 10315/NRRL Y-1498/VKM Y-70) (Yeast) | CANTEDRAFT_107892 | G3B8A7 (SEQ ID NO: 70) |
| *Penicillium marneffei* (strain ATCC 18224/CBS 334.59/QM 7333) | PMAA_059650 | B6QM59 |
| *Yarrowia lipolytica* (strain CLIB 122/E 150) (Yeast) (*Candida lipolytica*) | YALI0_A20130g | Q6CGD9 |
| *Candida apicola* (Yeast) | CYP52E2 | Q12573 |
| *Macrophomina phaseolina* (strain MS6) (Charcoal rot fungus) | MPH_10814 | K2RGW0 |
| *Cyphellophora europaea* CBS 101466 | HMPREF1541 06043 | W2RTP6 |
| *Cochliobolus sativus* (strain ND90Pr/ATCC 201652) (Common root rot and spot blotch fungus) (*Bipolaris sorokiniana*) | COCSADRAFT_40532 | M2STM3 |
| *Cochliobolus sativus* (strain ND90Pr/ATCC 201652) (Common root rot and spot blotch fungus) (*Bipolaris sorokiniana*) | COCSADRAFT_148934 | M2SE93 |
| *Bipolaris victoriae* FI3 | COCVIDRAFT_89176 | W7ES92 |
| *Bipolaris zeicola* 26-R-13 | COCCADRAFT_102357 | W6Y6Y4 |
| *Cochliobolus heterostrophus* (strain C5/ATCC 48332/race O) (Southern corn leaf blight fungus) (*Bipolaris maydis*) | COCHEDRAFT_1085873 | M2TJW9 |
| *Cochliobolus heterostrophus* (strain C4/ATCC 48331/race T) (Southern corn leaf blight fungus) (*Bipolaris maydis*) | COCC4DRAFT_201005 | N4WTS2 |
| *Pseudogymnoascus destructans* (strain ATCC MYA-4855/20631-21) (Bat white-nose syndrome fungus) (*Geomyces destructans*) | GMDG_04968 | L8GCB9 |
| *Aspergillus terreus* (strain NIH 2624/FGSC A1156) | ATEG_03903 | Q0CQY1 |
| *Marssonina brunnea* f. sp. *multigermtubi* (strain MB_m1) (*Marssonina* leaf spot fungus) | MBM_06876 | K1WCN3 |
| *Penicillium marneffei* (strain ATCC 18224/CBS 334.59/QM 7333) | PMAA_093890 | B6QHD0 |

TABLE 5-continued

Cytochrome P450 enzymes capable of catalyzing selective terminal alkene hydroxylation.

| Species Origin | Gene names | Accession No |
|---|---|---|
| *Neosartorya fumigata* (strain CEA10/CBS 144.89/ FGSC A1163) (*Aspergillus fumigatus*) | AFUB_025410 | B0XRZ8 |
| *Candida apicola* (Yeast) | CYP52E1 | P43083 (SEQ ID NO: 71) |
| *Neosartorya fumigata* (strain ATCC MYA-4609/Af293/ CBS 101355/FGSC A1100) (*Aspergillus fumigatus*) | AFUA_2G09540 | Q4X1L5 |
| *Neosartorya fischeri* (strain ATCC 1020/DSM 3700/ FGSC A1164/NRRL 181) (*Aspergillus fischerianus*) | NFIA_085030 | A1DGP3 |
| *Cordyceps militaris* (strain CM01) (Caterpillar fungus) | CCM_07376 | G3JQU8 |
| *Coniosporium apollinis* (strain CBS 100218) (Rock-inhabiting black yeast) | W97_02755 | R7YNR2 |
| *Penicillium chrysogenum* (strain ATCC 28089/DSM 1075/Wisconsin 54-1255) (*Penicillium notatum*) | Pc22g19240 PCH_Pc22g19240 | B6HVQ7 |
| *Penicillium digitatum* (strain Pd1/CECT 20795) (Green mold) | PDIP_65200 | K9G3N2 |
| *Penicillium digitatum* (strain PHI26/CECT 20796) (Green mold) | PDIG_30820 | K9FYP6 |
| *Penicillium roqueforti* | PROQFM164_S01g001598 | W6QDZ0 |
| *Marssonina brunnea* f. sp. *multigermtubi* (strain MB_m1) (Marssonina leaf spot fungus) | MBM_06372 | K1WQC3 |
| *Botryotinia fuckeliana* (strain BcDW1) (Noble rot fungus) (*Botrytis cinerea*) | BcDW1_3993 | M7U1E8 |
| *Botryotinia fuckeliana* (strain T4) (Noble rot fungus) (*Botrytis cinerea*) | BofuT4P27000003001 | G2Y6G5 |
| *Emericella nidulans* (strain FGSC A4/ATCC 38163/ CBS 112.46/NRRL 194/M139) (*Aspergillus nidulans*) | AN9384.2 ANIA_09384 | Q5AQP6 |
| *Candida maltosa* (Yeast) | CYP52C2 | Q12587 (SEQ ID NO: 72) |
| *Phaeosphaeria nodorum* (strain SN15/ATCC MYA-4574/ FGSC 10173) (Glume blotch fungus) (*Septoria nodorum*) | SNOG_02153 | Q0V1G1 |
| *Pyrenophora tritici-repentis* (strain Pt-1C-BFP) (Wheat tan spot fungus) (*Drechslera tritici-repentis*) | PTRG_08257 | B2WF96 |
| *Pyrenophora teres* f. *teres* (strain 0-1) (Barley net blotch fungus) (*Drechslera teres* f. *teres*) | PTT_00451 | E3RCI0 |
| *Aspergillus niger* (strain ATCC 1015/CBS 113.46/ FGSC A1144/LSHB Ac4/NCTC 3858a/NRRL 328/ USDA 3528.7) | ASPNIDRAFT_140405 | G3YCS1 |
| *Bipolaris oryzae* ATCC 44560 | COCMIDRAFT_998 | W7A2Q6 |
| *Cochliobolus heterostrophus* (strain C4/ATCC 48331/ race T) (Southern corn leaf blight fungus) (*Bipolaris maydis*) | COCC4DRAFT_169587 | N4X0M1 |
| *Cochliobolus heterostrophus* (strain C5/ATCC 48332/ race O) (Southern corn leaf blight fungus) (*Bipolaris maydis*) | COCHEDRAFT_1140715 | M2U5K5 |
| *Botryosphaeria parva* (strain UCR-NP2) (Grapevine canker fungus) (*Neofusicoccum parvum*) | UCRNP2_24 | R1GXQ4 |
| *Ajellomyces capsulatus* (strain H88) (Darling's disease fungus) (*Histoplasma capsulatum*) | HCEG_07709 | F0URG7 |
| *Bipolaris oryzae* ATCC 44560 | COCMIDRAFT_1291 | W7A267 |
| *Dactylellina haptotyla* (strain CBS 200.50) (Nematode-trapping fungus) (*Monacrosporium haptotylum*) | H072_402 | S8ARJ7 |
| *Cladophialophora carrionii* CBS 160.54 | G647_04218 | V9DES7 |
| *Exophiala dermatitidis* (strain ATCC 34100/CBS 525.76/ NIH/UT8656) (Black yeast) (*Wangiella dermatitidis*) | HMPREF1120_06284 | H6C3Q7 |
| *Yarrowia lipolytica* (*Candida lipolytica*) | ALK3 | O74129 (SEQ ID NO: 73) |
| *Yarrowia lipolytica* (strain CLIB 122/E 150) (Yeast) (*Candida lipolytica*) | YALI0_E23474g | F2Z6D5 |
| *Blumeria graminis* f. sp. *hordei* (strain DH14) (Barley powdery mildew) (*Oidium monilioides* f. sp. *hordei*) | BGHDH14_bgh01926 | N1JHB2 |
| *Neosartorya fischeri* (strain ATCC 1020/DSM 3700/ FGSC A1164/NRRL 181) (*Aspergillus fischerianus*) | NFIA_063580 | A1D653 |
| *Dactylellina haptotyla* (strain CBS 200.50) (Nematode-trapping fungus) (*Monacrosporium haptotylum*) | H072_3894 | S8C337 |
| *Aspergillus kawachii* (strain NBRC 4308) (White koji mold) (*Aspergillus awamori* var. *kawachi*) | AKAW_03269 | G7XDZ6 |
| *Aspergillus niger* (strain ATCC 1015/CBS 113.46/ FGSC A1144/LSHB Ac4/NCTC 3858a/NRRL 3287 USDA 3528.7) | ASPNIDRAFT_183349 | G3Y6F0 (SEQ ID NO: 74) |
| *Aspergillus oryzae* (strain 3.042) (Yellow koji mold) | Ao3042_02280 | I8IPH3 |
| *Aspergillus flavus* (strain ATCC 200026/FGSC A1120/ NRRL 3357/JCM 12722/SRRC 167) | AFLA_089870 | B8NKB3 |

TABLE 5-continued

Cytochrome P450 enzymes capable of catalyzing selective terminal alkene hydroxylation.

| Species Origin | Gene names | Accession No |
| --- | --- | --- |
| *Arthroderma gypseum* (strain ATCC MYA-4604/CBS 118893) (*Microsporum gypseum*) | MGYG_08468 | E4V5T0 |
| *Arthroderma otae* (strain ATCC MYA-4605/CBS 113480) (*Microsporum canis*) | MCYG_06305 | C5FUA2 |
| *Bipolaris victoriae* FI3 | COCVIDRAFT_33397 | W7EVM0 |
| *Bipolaris oryzae* ATCC 44560 | COCMIDRAFT_22726 | W6ZD79 |
| *Byssochlamys spectabilis* (strain No. 5/NBRC 109023) (*Paecilomyces variotii*) | PVAR5_0072 | V5HQF9 |
| *Bipolaris zeicola* 26-R-13 | COCCADRAFT_21391 | W6YP58 |
| *Mycosphaerella fijiensis* (strain CIRAD86) (Black leaf streak disease fungus) (*Pseudocercospora fijiensis*) | MYCFIDRAFT_153745 | M3AEP8 |
| *Aspergillus terreus* (strain NIH 2624/FGSC A1156) | ATEG_01150 | Q0CYT4 |
| *Setosphaeria turcica* (strain 28A) (Northern leaf blight fungus) (*Exserohilum turcicum*) | SETTUDRAFT_96298 | R0JZR2 |
| *Colletotrichum graminicola* (strain M1.001/M2/FGSC 10212) (Maize anthracnose fungus) (*Glomerella graminicola*) | GLRG_01676 | E3Q5P1 |
| *Aspergillus clavatus* (strain ATCC 1007/CBS 513.65/DSM 816/NCTC 3887/NRRL 1) | ACLA_055810 | A1C9K9 |
| *Ajellomyces capsulatus* (strain G186AR/H82/ATCC MYA-2454/RMSCC 2432) (Darling's disease fungus) (*Histoplasma capsulatum*) | HCBG_07070 | C0NV90 |
| *Aspergillus oryzae* (strain ATCC 42149/RIB 40) (Yellow koji mold) | AO090124000014 | Q2U799 |
| *Aspergillus oryzae* (strain ATCC 42149/RIB 40) (Yellow koji mold) | AO090124000014 | Q2U799 |
| *Aspergillus niger* (strain CBS 513.88/FGSC A1513) | An11g04220 | A2QW84 |
| *Penicillium marneffei* (strain ATCC 18224/CBS 334.59/QM 7333) | PMAA_050330 | B6QKF3 |
| *Tuber melanosporum* (strain Mel28) (Perigord black truffle) | GSTUM_00004620001 | D5G7M1 |
| *Colletotrichum higginsianum* (strain IMI 349063) (Crucifer anthracnose fungus) | CH063_01685 | H1VAW5 |
| *Beauveria bassiana* (strain ARSEF 2860) (White muscardine disease fungus) (*Tritirachium shiotae*) | BBA_08136 | J5JHI3 (SEQ ID NO: 75) |
| *Yarrowia lipolytica* (strain CLIB 122/E 150) (Yeast) (*Candida lipolytica*) | YALI0_C10054g | Q6CCE5 |
| *Botryosphaeria parva* (strain UCR-NP2) (Grapevine canker fungus) (*Neofusicoccum parvum*) | UCRNP2_3112 | R1ERB7 |
| *Setosphaeria turcica* (strain 28A) (Northern leaf blight fungus) (*Exserohilum turcicum*) | SETTUDRAFT_104406 | R0IY48 |
| *Aspergillus clavatus* (strain ATCC 1007/CBS 513.65/DSM 816/NCTC 3887/NRRL 1) | ACLA_081330 | A1CT08 |
| *Mycosphaerella fijiensis* (strain CIRAD86) (Black leaf streak disease fungus) (*Pseudocercospora fijiensis*) | MYCFIDRAFT_65755 | M3A1E6 |
| *Aspergillus oryzae* (strain ATCC 42149/RIB 40) (Yellow koji mold) | AO090026000094 | Q2UFS5 |
| *Aspergillus oryzae* (strain 3.042) (Yellow koji mold) | Ao3042_06896 | I7ZXQ6 |
| *Aspergillus oryzae* (Yellow koji mold) | CYP584G1 | D4QC67 |
| *Aspergillus flavus* (strain ATCC 200026/FGSC A1120/NRRL 3357/JCM 12722/SRRC 167) | AFLA_138460 | B8NGX8 |
| *Candida tenuis* (strain ATCC 10573/BCRC 21748/CBS 615/JCM 9827/NBRC 10315/NRRL Y-1498/VKM Y-70) (Yeast) | CANTEDRAFT_120218 | G3B2O1 |
| *Aspergillus niger* (strain ATCC 1015/CBS 113.46/FGSC A1144/LSHB Ac4/NCTC 3858a/NRRL 3287 USDA 3528.7) | ASPNIDRAFT_51356 | G3Y8H5 |
| *Aspergillus niger* (strain CBS 513.88/FGSC A1513) | An03g02570 | A2QGB4 |
| *Pseudogymnoascus destructans* (strain ATCC MYA-4855/20631-21) (Bat white-nose syndrome fungus) (*Geomyces destructans*) | GMDG_01087 | L8FNT2 |
| *Cladophialophora carrionii* CBS 160.54 | G647_06237 | V9D5I6 |
| *Candida albicans* (strain WO-1) (Yeast) | CAWG_05505 | C4YTL0 |
| *Coccidioides posadasii* (strain RMSCC 757/Silveira) (Valley fever fungus) | CPSG_05074 | E9D644 |
| *Coccidioides posadasii* (strain C735) (Valley fever fungus) | CPC735_058630 | C5PIZ0 |
| *Candida maltosa* (strain Xu316) (Yeast) | G210_3874 | M3J212 |
| *Metarhizium acridum* (strain CQMa 102) | MAC_00168 | E9DQZ9 |
| *Bipolaris zeicola* 26-R-13 | COCCADRAFT_112912 | W6XW09 |
| *Pyronema omphalodes* (strain CBS 100304) (*Pyronema confluens*) | PCON_11087 | U4LQK1 |
| *Bipolaris victoriae* FI3 | COCVIDRAFT_39745 | W7E2W7 |
| *Botryotinia fuckeliana* (strain T4) (Noble rot fungus) (*Botrytis cinerea*) | BofuT4_P153970.1 | G2YW37 |
| *Fusarium heterosporum* | fsdH | S0ARX1 |

TABLE 5-continued

Cytochrome P450 enzymes capable of catalyzing selective terminal alkene hydroxylation.

| Species Origin | Gene names | Accession No |
|---|---|---|
| *Cyphellophora europaea* CBS 101466 | HMPREF1541_04435 | W2RWT0 |
| *Metarhizium acridum* (strain CQMa 102) | MAC_07120 | E9EB72 |
| *Macrophomina phaseolina* (strain MS6) (Charcoal rot fungus) | MPH_05063 | K2R5H7 |
| *Colletotrichum graminicola* (strain M1.001/M2/FGSC 10212) (Maize anthracnose fungus) (*Glomerella graminicola*) | GLRG_01883 | E3Q8M4 |
| *Bipolaris zeicola* 26-R-13 | COCCADRAFT_111835 | W6Y8G6 |
| *Cochliobolus heterostrophus* (strain C5/ATCC 48332/race O) (Southern corn leaf blight fungus) (*Bipolaris maydis*) | COCHEDRAFT_1160314 | M2SMR0 |
| *Bipolaris zeicola* 26-R-13 | COCCADRAFT_101405 | W6YJB0 |
| *Cochliobolus heterostrophus* (strain C4/ATCC 48331/race T) (Southern corn leaf blight fungus) (*Bipolaris maydis*) | COCC4DRAFT_62846 | N4XCY6 |
| *Colletotrichum gloeosporioides* (strain Cg-14) (Anthracnose fungus) (*Glomerella cingulata*) | CGLO_16193 | T0L9W5 |
| *Botryotinia fuckeliana* (strain BcDW1) (Noble rot fungus) (*Botrytis cinerea*) | BcDW1_1090 | M7U9F3 |
| *Botryotinia fuckeliana* (strain T4) (Noble rot fungus) (*Botrytis cinerea*) | BofuT4P90000010001 | G2YMJ6 |
| *Sclerotinia sclerotiorum* (strain ATCC 18683/1980/Ss-1) (White mold) (*Whetzelinia sclerotiorum*) | SS1G_10037 | A7EXH2 |
| *Penicillium digitatum* (strain PHI26/CECT 20796) (Green mold) | PDIG_44570 | K9FT94 |
| *Penicillium digitatum* (strain Pd1/CECT 20795) (Green mold) | PDIP_16560 | K9GHJ2 |
| *Metarhizium anisopliae* (strain ARSEF 23/ATCC MYA-3075) | MAA_06634 | E9F2Y5 |
| *Starmerella bombicola* | | B8QHP1 |
| *Penicillium marneffei* (strain ATCC 18224/CBS 334.59/QM 7333) | PMAA_088180 | B6QDT4 |
| *Metarhizium acridum* (strain CQMa 102) | MAC_09276 | E9EHC8 |
| *Mycosphaerella pini* (strain NZE10/CBS 128990) (Red band needle blight fungus) (*Dothistroma septosporum*) | DOTSEDRAFT_74860 | N1PCY6 |
| *Aspergillus kawachii* (strain NBRC 4308) (White koji mold) (*Aspergillus awamori* var. *kawachi*) | AKAW_10068 | G7XYF8 |
| *Aspergillus niger* (strain CBS 513.88/FGSC A1513) | An13g03000 | A2R1Z6 |
| *Aspergillus niger* (strain ATCC 1015/CBS 113.46/FGSC A1144/LSHB Ac4/NCTC 3858a/NRRL 328/USDA 3528.7) | ASPNIDRAFT_44878 | G3XQ89 |
| *Beauveria bassiana* (strain ARSEF 2860) (White muscardine disease fungus) (*Tritirachium shiotae*) | BBA_05173 | J4UM22 |
| *Beauveria bassiana* (White muscardine disease fungus) (*Tritirachium shiotae*) | | E2EAF8 |
| *Aspergillus oryzae* (strain 3.042) (Yellow koji mold) | Ao3042_05622 | I8IHV7 |
| *Aspergillus flavus* (strain ATCC 200026/FGSC A1120/NRRL 3357/JCM 12722/SRRC 167) | AFLA_045270 | B8NBF2 |
| *Aspergillus oryzae* (strain ATCC 42149/RIB 40) (Yellow koji mold) | AO090011000712 | Q2TZU9 |
| *Aspergillus oryzae* (Yellow koji mold) | CYP52G3 | D4QC12 |
| *Endocarpon pusillum* (strain Z07020/HMAS-L-300199) (Lichen-forming fungus) | EPUS_05482 | U1GCZ9 |
| *Sclerotinia sclerotiorum* (strain ATCC 18683/1980/Ss-1) (White mold) (*Whetzelinia sclerotiorum*) | SS1G_05980 | A7EKY3 |
| *Pyrenophora tritici-repentis* (strain Pt-1C-BFP) (Wheat tan spot fungus) (*Drechslera tritici-repentis*) | PTRG_06344 | B2W8N6 |
| *Candida albicans* (strain SC5314/ATCC MYA-2876) (Yeast) | ALK6 CaO19.13927 CaO19.6574 | Q5AGW4 |
| *Candida albicans* (Yeast) | ALK6 CaJ7.0170 CaO19.6574 | G1U9Z0 |
| *Trichophyton verrucosum* (strain HKI 0517) | TRV_06353 | D4DGP8 |
| *Coccidioides immitis* (strain RS) (Valley fever fungus) | CIMG_00331 | J3KGS4 |
| *Ajellomyces dermatitidis* ATCC 26199 | BDFG_02901 | T5C2N4 |
| *Ajellomyces dermatitidis* (strain ATCC 18188/CBS 674.68) (*Blastomyces dermatitidis*) | BDDG_01558 | F2T5V8 |
| *Ajellomyces dermatitidis* (strain SLH14081) (*Blastomyces dermatitidis*) | BDBG_07037 | C5JWU3 |
| *Ajellomyces dermatitidis* (strain ER-3/ATCC MYA-2586) (*Blastomyces dermatitidis*) | BDCG_07223 | C5GSH0 |
| *Coccidioides posadasii* (strain C735) (Valley fever fungus) | CPC735_073410 | C5P014 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_02045 | N4V6W7 |
| *Coccidioides immitis* (strain RS) (Valley fever fungus) | CIMG_11305 | J3KDU2 |
| *Talaromyces stipitatus* (strain ATCC 10500/CBS 375.48/QM 6759/NRRL 1006) (*Penicillium stipitatum*) | TSTA_056150 | B8MRH9 |

TABLE 5-continued

Cytochrome P450 enzymes capable of catalyzing selective terminal alkene hydroxylation.

| Species Origin | Gene names | Accession No |
|---|---|---|
| *Coccidioides posadasii* (strain RMSCC 757/Silveira) (Valley fever fungus) | CPSG_06231 | E9D8S9 |
| *Uncinocarpus reesii* (strain UAMH 1704) | UREG_01634 | C4JJ27 |
| *Starmerella bombicola* | | B8QHP5 (SEQ ID NO: 76) |
| *Pyrenophora tritici-repentis* (strain Pt-1C-BFP) (Wheat tan spot fungus) (*Drechslera tritici-repentis*) | PTRG_04241 | B2W1A6 |
| *Marssonina brunnea* f. sp. *multigermtubi* (strain MB_m1) (*Marssonina* leaf spot fungus) | MBM_07629 | K1XPF9 |
| *Metarhizium anisopliae* (strain ARSEF 23/ATCC MYA-3075) | MAA_00167 | E9EKL9 |
| *Macrophomina phaseolina* (strain MS6) (Charcoal rot fungus) | MPH_02135 | K2S0W5 |
| *Glarea lozoyensis* (strain ATCC 20868/MF5171) | GLAREA_00730 | S3CV81 |
| *Arthroderma otae* (strain ATCC MYA-4605/CBS 113480) (*Microsporum canis*) | MCYG_02969 | C5FKC8 |
| *Trichophyton verrucosum* (strain HKI 0517) | TRV_03431 | D4D8J5 |
| *Hypocrea atroviridis* (strain ATCC 20476/IMI 206040) (*Trichoderma atroviride*) | TRIATDRAFT_130690 | G9P640 |
| *Glarea lozoyensis* (strain ATCC 74030/MF5533) | M7I_0305 | H0ED06 |
| *Ajellomyces capsulatus* (strain NAm1/WU24) (Darling's disease fungus) (*Histoplasma capsulatum*) | HCAG_08121 | A6REQ6 |
| *Pyronema omphalodes* (strain CBS 100304) (*Pyronema confluens*) | PCON_14046 | U4LA29 |
| *Endocarpon pusillum* (strain Z07020/HMAS-L-300199) (Lichen-forming fungus) | EPUS_04540 | U1GA45 |
| *Penicillium marneffei* (strain ATCC 18224/CBS 334.59/QM 7333) | PMAA_048940 | B6QS70 |
| *Emericella nidulans* (strain FGSC A4/ATCC 38163/CBS 112.46/NRRL 194/M139) (*Aspergillus nidulans*) | AN6057.2 ANIA_06057 | Q5B073 |
| *Botryotinia fuckeliana* (strain T4) (Noble rot fungus) (*Botrytis cinerea*) | BofuT4_P148640.1 | G2YX16 |
| *Aspergillus terreus* (strain NIH 2624/FGSC A1156) | ATEG_02893 | Q0CTU1 |
| *Aspergillus niger* (strain ATCC 1015/CBS 113.46/FGSC A1144/LSHB Ac4/NCTC 3858a/NRRL 3287 USDA 3528.7) | ASPNIDRAFT_55501 | G3XTI8 |
| *Aspergillus kawachii* (strain NBRC 4308) (White koji mold) (*Aspergillus awamori* var. *kawachi*) | AKAW_10154 | G7XYN1 |
| *Beauveria bassiana* (strain ARSEF 2860) (White muscardine disease fungus) (*Tritirachium shiotae*) | BBA_02382 | J4WEG4 |
| *Sclerotinia sclerotiorum* (strain ATCC 18683/1980/Ss-1) (White mold) (*Whetzelinia sclerotiorum*) | SS1G_13470 | A7F790 |
| *Beauveria bassiana* (strain ARSEF 2860) (White muscardine disease fungus) (*Tritirachium shiotae*) | BBA_02428 | J5K2V9 |
| *Beauveria bassiana* (White muscardine disease fungus) (*Tritirachium shiotae*) | | E2EAF6 (SEQ ID NO: 77) |
| *Cordyceps militaris* (strain CM01) (Caterpillar fungus) | CCM_04719 | G3JD19 |
| *Penicillium chrysogenum* (strain ATCC 28089/DSM 1075/Wisconsin 54-1255) (*Penicillium notatum*) | Pc21g14130 PCH Pc21g14130 | B6HHN6 |
| *Mycosphaerella pini* (strain NZE10/CBS 128990) (Red band needle blight fungus) (*Dothistroma septosporum*) | DOTSEDRAFT_70063 | N1PRA2 |
| *Mycosphaerella pini* (strain NZE10/CBS 128990) (Red band needle blight fungus) (*Dothistroma septosporum*) | DOTSEDRAFT_70063 | N1PRA2 |
| *Aspergillus terreus* (strain NIH 2624/FGSC A1156) | ATEG_07540 | Q0CFJ4 |
| *Arthroderma benhamiae* (strain ATCC MYA-4681/CBS 112371) (*Trichophyton mentagrophytes*) | ARB_05989 | D4AP22 |
| *Baudoinia compniacensis* (strain UAMH 10762) (Angels' share fungus) | BAUCODRAFT_63612 | M2NKX8 |
| *Candida tropicalis* (strain ATCC MYA-3404/T1) (Yeast) | CTRG_04959 | C5MFW6 |
| *Candida tropicalis* (Yeast) | CYP52C1 | P30612 |
| *Metarhizium anisopliae* (strain ARSEF 23/ATCC MYA-3075) | MAA_07989 | E9F6U0 |
| *Mycosphaerella graminicola* (strain CBS 115943/IPO323) (Speckled leaf blotch fungus) (*Septoria tritici*) | CYP-29MYCGRDRAFT_76681 | F9XML6 |
| *Cladophialophora carrionii* CBS 160.54 | G647_07950 | V9D5N0 |
| *Glarea lozoyensis* (strain ATCC 20868/MF5171) | GLAREA_09137 | S3DII6 |
| *Hypocrea virens* (strain Gv29-8/FGSC 10586) (*Gliocladium virens*) (*Trichoderma virens*) | TRIVIDRAFT_50878 | G9N4V4 |
| *Marssonina brunnea* f. sp. *multigermtubi* (strain MB_m1) (*Marssonina* leaf spot fungus) | MBM_02308 | K1X1G5 |
| *Talaromyces stipitatus* (strain ATCC 10500/CBS 375.48/QM 6759/NRRL 1006) (*Penicillium stipitatum*) | TSTA_125560 | B8MCM6 |
| *Arthroderma benhamiae* (strain ATCC MYA-4681/CBS 112371) (*Trichophyton mentagrophytes*) | ARB_01737 | D4AZW7 |
| *Colletotrichum higginsianum* (strain IMI 349063) (Crucifer anthracnose fungus) | CH063_01286 | H1V527 |

TABLE 5-continued

Cytochrome P450 enzymes capable of catalyzing selective terminal alkene hydroxylation.

| Species Origin | Gene names | Accession No |
|---|---|---|
| *Trichophyton tonsurans* (strain CBS 112818) (Scalp ringworm fungus) | TESG_03185 | F2RW94 |
| *Marssonina brunnea* f. sp. *multigermtubi* (strain MB_m1) (*Marssonina* leaf spot fungus) | MBM_09278 | K1WJW9 |
| *Aspergillus terreus* (strain NIH 2624/FGSC A1156) | ATEG_06678 | Q0CI06 |
| *Claviceps purpurea* (strain 20.1) (Ergot fungus) (*Sphacelia segetum*) | CPUR_01906 | M1VZT8 |
| *Trichophyton rubrum* (strain ATCC MYA-4607/CBS 118892) (Athlete's foot fungus) | TERG_01394 | F2SCB2 |
| *Setosphaeria turcica* (strain 28A) (Northern leaf blight fungus) (*Exserohilum turcicum*) | SETTUDRAFT_39981 | R0ILM4 |
| *Paracoccidioides brasiliensis* (strain Pb03) | PABG_02000 | C0S2T6 |
| *Arthroderma gypseum* (strain ATCC MYA-4604/CBS 118893) (*Microsporum gypseum*) | MGYG_08184 | E4V596 |
| *Trichophyton equinum* (strain ATCC MYA-4606/CBS 127.97) (Horse ringworm fungus) | TEQG_06653 | F2Q0K1 |
| *Talaromyces stipitatus* (strain ATCC 10500/CBS 375.48/QM 6759/NRRL 1006) (*Penicillium stipitatum*) | TSTA_036210 | B8M882 |
| *Leptosphaeria maculans* (strain JN3/isolate v23.1.37 race Av1-4-5-6-7-8) (Blackleg fungus) (Phoma lingam) | LEMA_P030820.1 | E4ZWF4 |
| *Bipolaris victoriae* FI3 | COCVIDRAFT_43025 | W7E4E8 |
| *Magnaporthe oryzae* (strain Y34) (Rice blast fungus) (*Pyricularia oryzae*) | OOU_Y34scaffold00740g4 | L7HW63 |
| *Fusarium oxysporum* f. sp. *cubense* (strain race 1) (Panama disease fungus) | FOC1_g10015382 | N4TN76 |
| *Fusarium oxysporum* f. sp. *lycopersici* (strain 4287/CBS 123668/FGSC 9935/NRRL 34936) (*Fusarium* vascular wilt of tomato) | FOXG_00101 | J9MB56 |
| *Endocarpon pusillum* (strain Z07020/HMAS-L-300199) (Lichen-forming fungus) | EPUS_06065 | U1GKM5 |
| *Sphaerulina musiva* (strain SO2202) (Poplar stem canker fungus) (*Septoria musiva*) | SEPMUDRAFT_55938 | N1QLI3 |
| *Mycosphaerella graminicola* (strain CBS 115943/IPO323) (Speckled leaf blotch fungus) (*Septoria tritici*) | CYP-31.1MYCGRDRAFT_47046 | F9XH30 |
| *Penicillium oxalicum* (strain 114-2/CGMCC 5302) (*Penicillium decumbens*) | PDE_08994 | S8BFY9 |
| *Mycosphaerella graminicola* (strain CBS 115943/IPO323) (Speckled leaf blotch fungus) (*Septoria tritici*) | CYP-30MYCGRDRAFT_73230 | F9XDL6 |
| *Cladophialophora carrionii* CBS 160.54 | G647_01266 | V9DPI5 |
| *Togninia minima* (strain UCR-PA7) (Esca disease fungus) (*Phaeoacremonium aleophilum*) | UCRPA7_6516 | R8BF53 |
| *Fusarium oxysporum* (strain Fo5176) (*Fusarium* vascular wilt) | FOXB_00215 | F9F1C9 |
| *Gaeumannomyces graminis* var. *tritici* (strain R3-111a-1) (Wheat and barley take-all root rot fungus) | GGTG_11345 | J3PCX6 |
| *Cochliobolus sativus* (strain ND90Pr/ATCC 201652) (Common root rot and spot blotch fungus) (*Bipolaris sorokiniana*) | COCSADRAFT_143540 | M2R997 |
| *Neosartorya fumigata* (strain CEA10/CBS 144.89/FGSC A1163) (*Aspergillus fumigatus*) | AFUB_002090 | B0XRD5 |
| *Neosartorya fumigata* (strain ATCC MYA-4609/Af293/CBS 101355/FGSC A1100) (*Aspergillus fumigatus*) | AFUA_1G01690 | Q4WKQ1 |
| *Neosartorya fischeri* (strain ATCC 1020/DSM 3700/FGSC A1164/NRRL 181) (*Aspergillus fischerianus*) | NFIA_022940 | A1D590 |
| *Hypocrea atroviridis* (strain ATCC 20476/IMI 206040) (*Trichoderma atroviride*) | TRIATDRAFT_239723 | G9NQ55 |
| *Candida orthopsilosis* (strain 90-125) (Yeast) | CORT_0A06350 | H8WY74 |
| *Cyphellophora europaea* CBS 101466 | HMPREF1541_09254 | W2SBP3 |
| *Penicillium oxalicum* (strain 114-2/CGMCC 5302) (*Penicillium decumbens*) | PDE_02656 | S8B080 |
| *Penicillium chrysogenum* (strain ATCC 28089/DSM 1075/Wisconsin 54-1255) (*Penicillium notatum*) | Pc20g13950 PCH_Pc20g13950 | B6HH32 |
| *Arthroderma gypseum* (strain ATCC MYA-4604/CBS 118893) (*Microsporum gypseum*) | MGYG_07586 | E4V3K6 |
| *Hypocrea virens* (strain Gv29-8/FGSC 10586) (Gliocladium virens) (*Trichoderma virens*) | TRIVIDRAFT_91340 | G9MUE6 |
| *Botryotinia fuckeliana* (strain BcDW1) (Noble rot fungus) (*Botrytis cinerea*) | BcDW1_3132 | M7U3N6 |
| *Botryosphaeria parva* (strain UCR-NP2) (Grapevine canker fungus) (*Neofusicoccum parvum*) | UCRNP2_9778 | R1E711 |
| *Cochliobolus sativus* (strain ND90Pr/ATCC 201652) (Common root rot and spot blotch fungus) (*Bipolaris sorokiniana*) | COCSADRAFT_79461 | M2SNB8 |
| *Aspergillus niger* (strain CBS 513.88/FGSC A1513) | An01g00510 | A2Q7F5 |
| *Candida dubliniensis* (strain CD36/ATCC MYA-646/CBS 7987/NCPF 3949/NRRL Y-17841) (Yeast) | CD36_71370 | B9WK39 |

TABLE 5-continued

Cytochrome P450 enzymes capable of catalyzing selective terminal alkene hydroxylation.

| Species Origin | Gene names | Accession No |
|---|---|---|
| *Cochliobolus heterostrophus* (strain C4/ATCC 48331/race T) (Southern corn leaf blight fungus) (*Bipolaris maydis*) | COCC4DRAFT_41710 | N4XB06 |
| *Cochliobolus heterostrophus* (strain C5/ATCC 48332/race O) (Southern corn leaf blight fungus) (*Bipolaris maydis*) | COCHEDRAFT_1208754 | M2VA93 |
| *Aspergillus clavatus* (strain ATCC 1007/CBS 513.65/DSM 816/NCTC 3887/NRRL 1) | ACLA_032820 | A1CSC5 |
| *Hypocrea jecorina* (strain QM6a) (*Trichoderma reesei*) | TRIREDRAFT_103147 | G0R9K0 |
| *Trichophyton tonsurans* (strain CBS 112818) (Scalp ringworm fungus) | TESG_02758 | F2RVB9 |
| *Glarea lozoyensis* (strain ATCC 20868/MF5171) | GLAREA_12102 | S3D2G7 |
| *Trichophyton rubrum* (strain ATCC MYA-4607/CBS 118892) (Athlete's foot fungus) | TERG_03231 | F2SJM4 |
| *Leptosphaeria maculans* (strain JN3/isolate v23.1.37 race Av1-4-5-6-7-8) (Blackleg fungus) (*Phoma lingam*) | LEMA_P073070.1 | E5A7X3 |
| *Cyphellophora europaea* CBS 101466 | HMPREF1541_04444 | W2RWL1 |
| *Hypocrea jecorina* (strain QM6a) (*Trichoderma reesei*) | TRIREDRAFT_65036 | G0RNX6 |
| *Beauveria bassiana* (strain ARSEF 2860) (White muscardine disease fungus) (*Tritirachium shiotae*) | BBA_09022 | J5J6F5 |
| *Cordyceps militaris* (strain CM01) (Caterpillar fungus) | CCM_02084 | G3JCK3 |
| *Trichophyton rubrum* (strain ATCC MYA-4607/CBS 118892) (Athlete's foot fungus) | TERG_05441 | F2SSI7 |
| *Botryotinia fuckeliana* (strain BcDW1) (Noble rot fungus) (*Botrytis cinerea*) | BcDW1_9224 | M7U6H3 |
| *Magnaporthe oryzae* (strain P131) (Rice blast fungus) (*Pyricularia oryzae*) | OOW_P131scaffold01201g5 | L7J0M9 |
| *Magnaporthe oryzae* (strain Y34) (Rice blast fungus) (*Pyricularia oryzae*) | OOU_Y34scaffold00145g13 | L7IJZ9 |
| *Magnaporthe oryzae* (strain 70-15/ATCC MYA-4617/FGSC 8958) (Rice blast fungus) (*Pyricularia oryzae*) | MGG_09920 | G4MR75 |
| *Paracoccidioides lutzii* (strain ATCC MYA-826/Pb01) (*Paracoccidioides brasiliensis*) | PAAG_01378 | C1GS83 |
| *Bipolaris zeicola* 26-R-13 | COCCADRAFT_9928 | W6Y8S8 |
| *Verticillium dahliae* (strain VdLs.17/ATCC MYA-4575/FGSC 10137) (*Verticillium wilt*) | VDAG_04483 | G2X2F9 |
| *Trichophyton verrucosum* (strain HKI 0517) | TRV_02251 | D4D581 |
| *Arthroderma benhamiae* (strain ATCC MYA-4681/CBS 112371) (*Trichophyton mentagrophytes*) | ARB_01131 | D4AY62 |
| *Chaetomium globosum* (strain ATCC 6205/CBS 148.51/DSM 1962/NBRC 6347/NRRL 1970) (Soil fungus) | CHGG_01610 | Q2HDU4 |
| *Magnaporthe poae* (strain ATCC 64411/73-15) (Kentucky bluegrass fungus) | | M4G6C3 |
| *Hypocrea atroviridis* (strain ATCC 20476/IMI 206040) (*Trichoderma atroviride*) | TRIATDRAFT_45536 | G9NQR1 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_03064 | N4W651 |
| *Penicillium chrysogenum* (strain ATCC 28089/DSM 1075/Wisconsin 54-1255) (*Penicillium notatum*) | Pc20g11290 PCH_Pc20g11290 | B6HG66 |
| *Ophiocordyceps sinensis* (strain Co18/CGMCC 3.14243) (Yarsagumba caterpillar fungus) (*Hirsutella sinensis*) | OCS_02874 | T5AG58 |
| *Pyrenophora teres* f. *teres* (strain 0-1) (Barley net blotch fungus) (*Drechslera teres* f. *teres*) | PTT_07245 | E3RH76 |
| *Baudoinia compniacensis* (strain UAMH 10762) (Angels' share fungus) | BAUCODRAFT_71913 | M2MX22 |
| *Podospora anserina* (strain S/ATCC MYA-4624/DSM 980/FGSC 10383) (*Pleurage anserina*) | PODANS_0_160 | B2AFV1 |
| *Aspergillus terreus* (strain NIH 2624/FGSC A1156) | ATEG_05807 | Q0CKH7 |
| *Hypocrea jecorina* (strain QM6a) (*Trichoderma reesei*) | TRIREDRAFT_75713 | G0RDE9 |
| *Claviceps purpurea* (strain 20.1) (Ergot fungus) (*Sphacelia segetum*) | CPUR_06997 | M1WHP2 |
| *Aspergillus flavus* (strain ATCC 200026/FGSC A1120/NRRL 3357/JCM 12722/SRRC 167) | AFLA_128090 | B8NNJ8 |
| *Mycosphaerella fijiensis* (strain CIRAD86) (Black leaf streak disease fungus) (*Pseudocercospora fijiensis*) | MYCFIDRAFT_49209 | M3AV82 |
| *Grosmannia clavigera* (strain kw1407/UAMH 11150) (Blue stain fungus) (*Graphiocladiella clavigera*) | CMQ_2882 | F0XHG6 |
| *Lodderomyces elongisporus* (strain ATCC 11503/CBS 2605/JCM 1781/NBRC 1676/NRRL YB-4239) (Yeast) (*Saccharomyces elongisporus*) | LELG_05768 | A5H2Q3 |
| *Candida tropicalis* (strain ATCC MYA-3404/T1) (Yeast) | CTRG_03114 | C5MAM2 |
| *Coniosporium apollinis* (strain CBS 100218) (Rock-inhabiting black yeast) | W97_03898 | R7YRY7 |
| *Candida parapsilosis* (strain CDC 317/ATCC MYA-4646) (Yeast) (*Monilia parapsilosis*) | CPAR2_206990 | G8BCR1 |

TABLE 5-continued

Cytochrome P450 enzymes capable of catalyzing selective terminal alkene hydroxylation.

| Species Origin | Gene names | Accession No |
|---|---|---|
| *Aspergillus niger* (strain CBS 513.88/FGSC A1513) | An02g_10700 | A5AAH7 |
| *Baudoinia compniacensis* (strain UAMH 10762) (Angels' share fungus) | BAUCODRAFT_187941 | M2MV99 |
| *Candida tropicalis* (Yeast) | CYP52B1 | P30611 |
| *Aspergillus kawachii* (strain NBRC 4308) (White koji mold) (*Aspergillus awamori* var. *kawachi*) | AKAW_04070 | G7XG31 |
| *Colletotrichum gloeosporioides* (strain Cg-14) (Anthracnose fungus) (*Glomerella cingulata*) | CGLO_15455 | T0JYY2 |
| *Colletotrichum gloeosporioides* (strain Cg-14) (Anthracnose fungus) (*Glomerella cingulata*) | CGLO_15455 | T0JYY2 |
| *Endocarpon pusillum* (strain Z07020/HMAS-L-300199) (Lichen-forming fungus) | EPUS_09448 | U1HSE1 |
| *Arthroderma gypseum* (strain ATCC MYA-4604/CBS 118893) (*Microsporum gypseum*) | MGYG_00140 | E5R368 |
| *Botryotinia fuckeliana* (strain T4) (Noble rot fungus) (*Botrytis cinerea*) | BofuT4_P052870.1 | G2XWR8 |
| *Exophiala dermatitidis* (strain ATCC 34100/CBS 525.76/NIH/UT8656) (Black yeast) (*Wangiella dermatitidis*) | HMPREF1120_00302 | H6BMQ6 |
| *Aspergillus oryzae* (Yellow koji mold) | CYP52K1 | D4QC15 |
| *Aspergillus oryzae* (strain ATCC 42149/RIB 40) (Yellow koji mold) | AO090010000548 | Q2TWI0 |
| *Neurospora tetrasperma* (strain FGSC 2508/ATCC MYA-4615/P0657) | NEUTE1DRAFT_150004 | F8N2K8 |
| *Sordaria macrospora* (strain ATCC MYA-333/DSM 997/K(L3346)/K-hell) | SMAC_04611 | F7W1Z0 |
| *Neurospora crassa* (strain ATCC 24698/74-OR23-1A/CBS 708.71/DSM 1257/FGSC 987) | NCU09115 | Q7S0G0 |
| *Eutypa lata* (strain UCR-EL1) (Grapevine dieback disease fungus) (*Eutypa armeniacae*) | UCREL1_11542 | M7T4H1 |
| *Neurospora tetrasperma* (strain FGSC 2509/P0656) | NEUTE2DRAFT_153986 | G4U5S9 |
| *Setosphaeria turcica* (strain 28A) (Northern leaf blight fungus) (*Exserohilum turcicum*) | SETTUDRAFT_164879 | R0JQZ4 |
| *Pyrenophora tritici-repentis* (strain Pt-1C-BFP) (Wheat tan spot fungus) (*Drechslera tritici-repentis*) | PTRG_11480 | B2WN31 |
| *Paracoccidioides lutzii* (strain ATCC MYA-826/Pb01) (*Paracoccidioides brasiliensis*) | PAAG_01137 | C1GRJ2 |
| *Neosartorya fischeri* (strain ATCC 1020/DSM 3700/FGSC A1164/NRRL 181) (*Aspergillus fischerianus*) | NFIA_054110 | A1DMP4 |
| *Sphaerulina musiva* (strain SO2202) (Poplar stem canker fungus) (*Septoria musiva*) | SEPMUDRAFT_149283 | M3D461 |
| *Emericella nidulans* (strain FGSC A4/ATCC 38163/CBS 112.46/NRRL 194/M139) (*Aspergillus nidulans*) | AN3917.2 ANIA_03917 | Q5B6B3 |
| *Candida orthopsilosis* (strain 90-125) (Yeast) | CORT_0H01020 | H8XAX0 |
| *Aspergillus oryzae* (strain 3.042) (Yellow koji mold) | Ao3042_10143 | I8I9N9 |
| *Aspergillus flavus* (strain ATCC 200026/FGSC A1120/NRRL 3357/JCM 12722/SRRC 167) | AFLA_074560 | B8MWJ8 |
| *Candida parapsilosis* (strain CDC 317/ATCC MYA-4646) (Yeast) (*Monilia parapsilosis*) | CPAR2_301000 | G8B912 |
| *Aspergillus oryzae* (strain ATCC 42149/RIB 40) (Yellow koji mold) | AO090005000220 | Q2UT03 |
| *Aspergillus oryzae* (Yellow koji mold) | CYP52G4 | D4QC13 |
| *Neosartorya fumigata* (strain ATCC MYA-4609/Af293/CBS 101355/FGSC A1100) (*Aspergillus fumigatus*) | AFUA_6G03090 | Q4WD09 |
| *Botryotinia fuckeliana* (strain T4) (Noble rot fungus) (*Botrytis cinerea*) | BofuT4_P109530.1 | G2Y7G7 |
| *Sclerotinia sclerotiorum* (strain ATCC 18683/1980/Ss-1) (White mold) (*Whetzelinia sclerotiorum*) | SS1G_11430 | A7F1G0 |
| *Pyronema omphalodes* (strain CBS 100304) (*Pyronema confluens*) | PCON_02181 | U4LWN1 |
| *Thielavia heterothallica* (strain ATCC 42464/BCRC 31852/DSM 1799) (*Myceliophthora thermophila*) | MYCTH_2294752 | G2Q2L5 |
| *Pestalotiopsis fici* W106-1 | PFICI_00042 | W3XJN2 |
| *Eutypa lata* (strain UCR-EL1) (Grapevine dieback disease fungus) (*Eutypa armeniacae*) | UCREL1_5311 | M7TLT9 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_03446 | N4W590 |
| *Colletotrichum graminicola* (strain M1.001/M2/FGSC 10212) (Maize anthracnose fungus) (*Glomerella graminicola*) | GLRG_09839 | E3QV05 |
| *Trichophyton verrucosum* (strain HKI 0517) | TRV_06704 | D4DHP8 |
| *Sphaerulina musiva* (strain SO2202) (Poplar stem canker fungus) (*Septoria musiva*) | SEPMUDRAFT_39329 | M3B7G5 |

TABLE 5-continued

Cytochrome P450 enzymes capable of catalyzing selective terminal alkene hydroxylation.

| Species Origin | Gene names | Accession No |
|---|---|---|
| *Nectria haematococca* (strain 77-13-4/ATCC MYA-4622/FGSC 9596/MPVI) (*Fusarium solani* subsp. *pisi*) | NECHADRAFT_31103 | C7YK50 |
| *Coniosporium apollinis* (strain CBS 100218) (Rock-inhabiting black yeast) | W97_03080 | R7YPM4 |
| *Gaeumannomyces graminis* var. *tritici* (strain R3-111a-1) (Wheat and barley take-all root rot fungus) | GGTG_12245 | J3PFH0 |
| *Fusarium pseudograminearum* (strain CS3096) (Wheat and barley crown-rot fungus) | FPSE_11595 | K3V5M1 |
| *Magnaporthe oryzae* (strain P131) (Rice blast fungus) (*Pyricularia oryzae*) | OOW_P131scaffold00556g2 | L7J9P9 |
| *Magnaporthe oryzae* (strain Y34) (Rice blast fungus) (*Pyricularia oryzae*) | OOU_Y34scaffold00501g3 | L7I9Z3 |
| *Magnaporthe oryzae* (strain 70-15/ATCC MYA-4617/FGSC 8958) (Rice blast fungus) (*Pyricularia oryzae*) | MGG_08956 | G4MW35 |
| *Thielavia terrestris* (strain ATCC 38088/NRRL 8126) (*Acremonium alabamense*) | THITE_2057357 | G2RF28 |
| *Gibberella fujikuroi* (strain CBS 195.34/IMI 58289/NRRL A-6831) (Bakanae and foot rot disease fungus) (*Fusarium fujikuroi*) | FFUJ_01480 | S0DIN1 |
| *Pyronema omphalodes* (strain CBS 100304) (*Pyronema confluens*) | PCON_09796 | U4L3P6 |
| *Gibberella moniliformis* (strain M3125/FGSC 7600) (Maize ear and stalk rot fungus) (*Fusarium verticillioides*) | FVEG_01415 | W7LF29 |
| *Magnaporthe oryzae* (strain P131) (Rice blast fungus) (*Pyricularia oryzae*) | OOW_P131scaffold01216g6 | L7IZ69 |
| *Magnaporthe oryzae* (strain 70-15/ATCC MYA-4617/FGSC 8958) (Rice blast fungus) (*Pyricularia oryzae*) | MGG_08494 | G4NAN9 |
| *Fusarium oxysporum* f. sp. *cubense* (strain race 4) (Panama disease fungus) | FOC4_g10003027 | N1RRF1 |
| *Chaetomium thermophilum* (strain DSM 1495/CBS 144.50/IMI 039719) | CTHT_0057700 | G0SCL9 |
| *Botryotinia fuckeliana* (strain BcDW1) (Noble rot fungus) (*Botrytis cinerea*) | BcDW1_5818 | M7UFT7 |
| *Verticillium alfalfae* (strain VaMs.102/ATCC MYA-4576/FGSC 10136) (Verticillium wilt of alfalfa) (*Verticillium albo-atrum*) | VDBG_04942 | C9SIR0 |
| *Arthroderma gypseum* (strain ATCC MYA-4604/CBS 118893) (*Microsporum gypseum*) | MGYG_09210 | E4V712 |
| *Uncinocarpus reesii* (strain UAMH 1704) | UREG_00942 | C4JF41 |
| *Bipolaris oryzae* ATCC 44560 | COCMIDRAFT_34506 | W6ZKE3 |
| *Paracoccidioides brasiliensis* (strain Pb03) | PABG_01712 | C0S297 |
| *Paracoccidioides brasiliensis* (strain Pb18) | PADG_03693 | C1G8V7 |
| *Neosartorya fumigata* (strain ATCC MYA-4609/Af293/CBS 101355/FGSC A1100) (*Aspergillus fumigatus*) | AFUA_6G08460 | Q4WMW7 |
| *Neosartorya fumigata* (strain CEA10/CBS 144.89/FGSC A1163) (*Aspergillus fumigatus*) | AFUB_074420 | B0Y7N4 |
| *Aspergillus niger* (strain ATCC 1015/CBS 113.46/FGSC A1144/LSHB Ac4/NCTC 3858a/NRRL 328/USDA 3528.7) | ASPNIDRAFT_189129 | G3XM79 |
| *Coniosporium apollinis* (strain CBS 100218) (Rock-inhabiting black yeast) | W97_05529 | R7YX00 |
| *Aspergillus niger* (strain CBS 513.88/FGSC A1513) | An11g07010 | A2QWZ5 |
| *Aspergillus niger* (strain ATCC 1015/CBS 113.46/FGSC A1144/LSHB Ac4/NCTC 3858a/NRRL 328/USDA 3528.7) | ASPNIDRAFT_56022 | G3YAT8 |
| *Neosartorya fischeri* (strain ATCC 1020/DSM 3700/FGSC A1164/NRRL 181) (*Aspergillus fischerianus*) | NFIA_049440 | A1DLD3 |
| *Aspergillus oryzae* (strain ATCC 42149/RIB 40) (Yellow koji mold) | AO090010000075 | Q2TXN5 |
| *Aspergillus oryzae* (strain 3.042) (Yellow koji mold) | Ao3042_00404 | I8ABC4 |
| *Aspergillus oryzae* (Yellow koji mold) | CYP584E5 | D4QC66 |
| *Magnaporthe poae* (strain ATCC 64411/73-15) (Kentucky bluegrass fungus) | | M4GA78 |
| *Cladophialophora carrionii* CBS 160.54 | G647_04914 | V9DAX0 |
| *Podospora anserina* (strain S/ATCC MYA-4624/DSM 980/FGSC 10383) (*Pleurage anserina*) | PODANS_1_9520 | B2AY12 |
| *Gibberella zeae* (strain PH-1/ATCC MYA-4620/FGSC 9075/NRRL 31084) (Wheat head blight fungus) (*Fusarium graminearum*) | FG01284.1 FGSG_01284 | I1RCH0 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_05738 | N4VDA5 |
| *Neosartorya fischeri* (strain ATCC 1020/DSM 3700/FGSC A1164/NRRL 181) (*Aspergillus fischerianus*) | NFIA_113870 | A1D8Z5 |

TABLE 5-continued

Cytochrome P450 enzymes capable of catalyzing selective terminal alkene hydroxylation.

| Species Origin | Gene names | Accession No |
|---|---|---|
| *Trichophyton verrucosum* (strain HKI 0517) | TRV_00955 | D4D1K4 |
| *Botryotinia fuckeliana* (strain T4) (Noble rot fungus) (*Botrytis cinerea*) | BofuT4_P140470.1 | G2YYT7 |
| *Trichophyton rubrum* (strain ATCC MYA-4607/CBS 118892) (Athlete's foot fungus) | TERG_02747 | F2SKM8 |
| *Botryotinia fuckeliana* (strain T4) (Noble rot fungus) (*Botrytis cinerea*) | BofuT4_P075800.1 | G2XNP1 |
| *Setosphaeria turcica* (strain 28A) (Northern leaf blight fungus) (*Exserohilum turcicum*) | SETTUDRAFT_159435 | R0IYM1 |
| *Bipolaris victoriae* FI3 | COCVIDRAFT_96117 | W7ECV3 |
| *Bipolaris zeicola* 26-R-13 | COCCADRAFT_86052 | W6YCN0 |
| *Podospora anserina* (strain S/ATCC MYA-4624/DSM 980/FGSC 10383) (*Pleurage anserina*) | PODANS_3_1920 | B2AZX1 |
| *Sporothrix schenckii* (strain ATCC 58251/de Perez 2211183) (Rose-picker's disease fungus) | HMPREF1624_01101 | U7Q4H5 |
| *Exophiala dermatitidis* (strain ATCC 34100/CBS 525.76/NIH/UT8656) (Black yeast) (*Wangiella dermatitidis*) | HMPREF1120_04188 | H6BWM7 |
| *Colletotrichum gloeosporioides* (strain Cg-14) (Anthracnose fungus) (*Glomerella cingulata*) | CGLO_16096 | T0JPF3 |
| *Arthroderma benhamiae* (strain ATCC MYA-4681/CBS 112371) (*Trichophyton mentagrophytes*) | ARB_05099 | D4ALA2 |
| *Macrophomina phaseolina* (strain MS6) (Charcoal rot fungus) | MPH_10488 | K2QR42 |
| *Trichophyton tonsurans* (strain CBS 112818) (Scalp ringworm fungus) | TESG_05856 | F2S4I4 |
| *Trichophyton equinum* (strain ATCC MYA-4606/CBS 127.97) (Horse ringworm fungus) | TEQG_04559 | F2PUI2 |
| *Arthroderma benhamiae* (strain ATCC MYA-4681/CBS 112371) (*Trichophyton mentagrophytes*) | ARB_07892 | D4AUH5 |
| *Arthroderma otae* (strain ATCC MYA-4605/CBS 113480) (*Microsporum canis*) | MCYG_08648 | C5G126 |
| *Aspergillus flavus* (strain ATCC 200026/FGSC A1120/NRRL 3357/JCM 12722/SRRC 167) | AFLA_116530 | B8NVG6 |
| *Mycosphaerella graminicola* (strain CBS 115943/IPO323) (Speckled leaf blotch fungus) (*Septoria tritici*) | CYP-28MYCGRDRAFT_111399 | F9XPH9 |
| *Penicillium chrysogenum* (strain ATCC 28089/DSM 1075/Wisconsin 54-1255) (*Penicillium notatum*) | Pc18g04990 PCH_Pc18g04990 | B6HBW9 |
| *Alternaria solani* | alt2 | Q5KTN2 |
| *Colletotrichum higginsianum* (strain IMI 349063) (Crucifer anthracnose fungus) | CH063_05380 | H1UYS7 |
| *Thielavia heterothallica* (strain ATCC 42464/BCRC 31852/DSM 1799) (*Myceliophthora thermophila*) | MYCTH_2060315 | G2QDC4 |
| *Togninia minima* (strain UCR-PA7) (Esca disease fungus) (*Phaeoacremonium aleophilum*) | UCRPA7_1480 | R8BUP2 |
| *Ophiostoma piceae* (strain UAMH 11346) (Sap stain fungus) | F503_00556 | S3C2T4 |
| *Cladophialophora carrionii* CBS 160.54 | G647_02236 | V9DGM2 |
| *Botryotinia fuckeliana* (strain BcDW1) (Noble rot fungus) (*Botrytis cinerea*) | BcDW1_141 | M7UBZ7 |
| *Mycobacterium* sp. HXN-1500 | cyp153 | Q65A64 (SEQ ID NO: 78) |
| *Gordonia amicalis* NBRC 100051 = JCM 11271 | GOAMI_64_00090 | L7L6P4 |
| *Mycobacterium austroafricanum* | | B6UKY3 |
| *Mycobacterium* sp. ENV421 | ahpG | I7CD96 |
| uncultured bacterium | cyp153 | W0UDE1 |
| uncultured bacterium | P450 | Q33DR8 |
| uncultured bacterium | P450 | Q33DR9 |
| uncultured bacterium | cyp153 | W0UDG2 |
| uncultured bacterium | cyp153 | W0UDM1 |
| uncultured bacterium | cyp153 | W0UCX8 |
| uncultured bacterium | cyp153 | W0UAP1 |
| uncultured bacterium | cyp153 | W0UCW9 |
| *Polaromonas* sp. (strain JS666/ATCC BAA-500) | Bpro_5301 | Q11ZY2 (SEQ ID NO: 79) |
| uncultured bacterium | cyp153 | W0UDK1 |
| uncultured bacterium | cyp153 | W0UD29 |
| uncultured bacterium | cyp153 | W0UD32 |
| uncultured bacterium | cyp153 | W0UD27 |
| uncultured bacterium | cyp153 | W0UAW2 |
| uncultured bacterium | cyp153 | W0UAW6 |
| *Parvibaculum* sp. S13-6 | CYP153A | C7A8P8 |
| uncultured bacterium | cyp153 | W0UDM5 |
| uncultured bacterium | cyp153 | W0UD31 |
| uncultured bacterium | cyp153 | W0UDB6 |

TABLE 5-continued

Cytochrome P450 enzymes capable of catalyzing selective terminal alkene hydroxylation.

| Species Origin | Gene names | Accession No |
| --- | --- | --- |
| *Parvibaculum* sp. S13-5 | CYP153A | C7A8P2 |
| uncultured bacterium | P450 | Q33DS1 |
| uncultured bacterium | cyp153 | W0UDK5 |
| uncultured bacterium | cyp153 | W0UDU1 |
| *Tistrella mobilis* | CYP153A | C7A8Q6 |
| uncultured bacterium | cyp153 | W0UDS7 |
| *Parvibaculum* sp. S13-6 | CYP153A | C7A8P9 |
| uncultured bacterium | cyp153 | W0UB47 |
| *Parvibaculum* sp. S13-6 | CYP153A | C7A8P7 |
| gamma proteobacterium S10-1 | CYP153A | C7A8N2 |
| uncultured bacterium | cyp153 | W0UDS4 |
| uncultured bacterium | cyp153 | W0UAY8 |
| uncultured bacterium | cyp153 | W0UDB2 |
| uncultured bacterium | cyp153 | W0UB02 |
| uncultured bacterium | cyp153 | W0UDV5 |
| uncultured bacterium | cyp153 | W0UDM7 |
| uncultured bacterium | cyp153 | W0UD83 |
| uncultured bacterium | cyp153 | W0UD50 |
| *Parvibaculum* sp. S13-5 | CYP153A | C7A8P4 |
| *Parvibaculum* sp. S18-4 | CYP153A | C7A8S8 |
| *Parvibaculum* sp. S18-4 | CYP153A | C7A8S9 |
| uncultured bacterium | cyp153 | W0UB69 |
| *Parvibaculum* sp. S13-5 | CYP153A | C7A8P5 |
| uncultured bacterium | cyp153 | W0UDU6 |
| uncultured bacterium | cyp153 | W0UDD0 |
| uncultured bacterium | cyp153 | W0UDA8 |
| uncultured bacterium | cyp153 | W0UDC3 |
| uncultured bacterium | cyp153 | W0UDF5 |
| uncultured bacterium | cyp153 | W0UDD2 |
| uncultured bacterium | cyp153 | W0UD99 |
| uncultured bacterium | cyp153 | W0UB78 |
| uncultured bacterium | cyp153 | W0UDU2 |
| uncultured bacterium | cyp153 | W0UD95 |
| uncultured bacterium | cyp153 | W0UDT1 |
| uncultured bacterium | cyp153 | W0UD70 |
| uncultured bacterium | cyp153 | W0UAV3 |
| uncultured bacterium | cyp153 | W0UDJ0 |
| *Parvibaculum* sp. S18-4 | CYP153A | C7A8S7 |
| uncultured bacterium | cyp153 | W0UD49 |
| uncultured bacterium | cyp153 | W0UB74 |
| uncultured bacterium | cyp153 | W0UDG4 |
| uncultured bacterium | cyp153 | W0UDJ4 |
| uncultured bacterium | cyp153 | W0UDL1 |
| uncultured bacterium | cyp153 | W0UD80 |
| uncultured bacterium | cyp153 | W0UDP8 |
| uncultured bacterium | cyp153 | W0UDS6 |
| uncultured bacterium | cyp153 | W0UDC9 |
| uncultured bacterium | cyp153 | W0UDE6 |
| uncultured bacterium | cyp153 | W0UDU9 |
| uncultured bacterium | cyp153 | W0UDC0 |
| uncultured bacterium | cyp153 | W0UDW1 |
| uncultured bacterium | cyp153 | W0UDT4 |
| uncultured bacterium | cyp153 | W0UDB5 |
| uncultured bacterium | cyp153 | W0UB64 |
| uncultured bacterium | cyp153 | W0UDA3 |
| uncultured bacterium | cyp153 | W0UDR7 |
| uncultured bacterium | cyp153 | W0UB52 |
| uncultured bacterium | cyp153 | W0UDA5 |
| uncultured bacterium | cyp153 | W0UDT6 |
| *Caulobacter* sp. (strain K31) | Caul_0020 | B0T154 (SEQ ID NO: 80) |
| uncultured bacterium | cyp153 | W0UCV6 |
| uncultured bacterium | cyp153 | W0UCU1 |
| uncultured bacterium | cyp153 | W0UDK0 |
| uncultured bacterium | cyp153 | W0UDI6 |
| uncultured bacterium | cyp153 | W0UAU9 |
| uncultured bacterium | cyp153 | W0UAZ2 |
| uncultured bacterium | cyp153 | W0UD75 |
| uncultured bacterium | cyp153 | W0UD14 |
| uncultured bacterium | cyp153 | W0UB97 |
| uncultured bacterium | cyp153 | W0UD23 |
| uncultured bacterium | cyp153 | W0UD18 |
| uncultured bacterium | cyp153 | W0UDQ2 |
| uncultured bacterium | cyp153 | W0UDH4 |
| uncultured bacterium | cyp153 | W0UAT6 |

TABLE 5-continued

Cytochrome P450 enzymes capable of catalyzing selective terminal alkene hydroxylation.

| Species Origin | Gene names | Accession No |
| --- | --- | --- |
| uncultured bacterium | cyp153 | W0UD79 |
| uncultured bacterium | cyp153 | W0UAN4 |
| uncultured bacterium | cyp153 | W0UDW9 |
| uncultured bacterium | cyp153 | W0UCZ3 |
| uncultured bacterium | cyp153 | W0UCZ3 |
| Erythrobacter sp. S11-13 | CYP153A | C7A8R4 |
| uncultured bacterium | cyp153 | W0UDK7 |
| Parvibaculum sp. S13-5 | CYP153A | C7A8P3 |
| uncultured bacterium | cyp153 | W0UDS2 |
| uncultured bacterium | cyp153 | W0UD84 |
| uncultured bacterium | cyp153 | W0UD90 |
| uncultured bacterium | cyp153 | W0UB38 |
| uncultured bacterium | cyp153 | W0UCW4 |
| uncultured bacterium | cyp153 | W0UB22 |
| uncultured bacterium | cyp153 | W0UDQ8 |
| uncultured Rhizobiales bacterium HF4000_48A13 | | E0XZ55 |
| uncultured Rhizobiales bacterium HF4000_48A13 | | E0XZ44 |
| uncultured bacterium | P450 | Q33DS2 |
| uncultured bacterium | P450 | Q33DS0 |
| uncultured bacterium | cyp153 | W0UDB4 |
| Erythrobacter flavus | | C5MKK1 |
| uncultured bacterium | cyp153 | W0UD08 |
| uncultured bacterium | cyp153 | W0UCW2 |
| Sphingobium sp. S13-2 | CYP153A | C7A8P1 |
| Sphingopyxis sp. S16-14 | CYP153A | C7A8R8 |
| uncultured bacterium | cyp153 | W0UD46 |
| Parvibaculum sp. S13-6 | CYP153A | C7A8P6 |
| uncultured bacterium | cyp153 | W0UDQ1 |
| uncultured bacterium | cyp153 | W0UB27 |
| uncultured bacterium | cyp153 | W0UD73 |
| uncultured bacterium | cyp153 | W0UDE2 |
| uncultured bacterium | cyp153 | W0UD17 |
| Erythrobacter sp. S17-1 | CYP153A | C7A8R9 |
| uncultured bacterium | cyp153 | W0UD15 |
| uncultured bacterium | cyp153 | W0UAU6 |
| Erythrobacter flavus | CYP153A | C7A8N4 |
| uncultured bacterium | cyp153 | W0UDD6 |
| uncultured bacterium | cyp153 | W0UDP1 |
| uncultured bacterium | cyp153 | W0UDF8 |
| uncultured bacterium | cyp153 | W0UDN8 |
| uncultured bacterium | cyp153 | W0UDD3 |
| uncultured bacterium | cyp153 | W0UDN1 |
| uncultured bacterium | cyp153 | W0UDK3 |
| uncultured bacterium | cyp153 | W0UD11 |
| uncultured bacterium | cyp153 | W0UB85 |
| uncultured bacterium | cyp153 | W0UDI2 |
| Bradyrhizobium sp. CCGE-LA001 | BCCGELA001_36078 | W1JJD5 |
| uncultured bacterium | cyp153 | W0UDP5 |
| uncultured bacterium | cyp153 | W0UB19 |
| uncultured bacterium | cyp153 | W0UAL6 |
| uncultured bacterium | cyp153 | W0UDN3 |
| uncultured bacterium | cyp153 | W0UD72 |
| uncultured bacterium | cyp153 | W0UCX1 |
| uncultured bacterium | cyp153 | W0UDF6 |
| uncultured bacterium | cyp153 | W0UD00 |
| uncultured bacterium | cyp153 | W0UD65 |
| Caulobacter sp. AP07 | PMI01_00728 | J2H335 |
| Parvibaculum lavamentivorans (strain DS-1/DSM 13023/NCIMB 13966) | Plav_1765 | A7HU01 (SEQ ID NO: 81) |
| uncultured bacterium | P450 | Q33DS3 |
| uncultured bacterium | cyp153 | W0UDH8 |
| Erythrobacter flavus | CYP153A | C7A8R2 |
| Erythrobacter sp. S2-1 | CYP153A | C7A8K9 |
| Erythrobacter citreus | CYP153A | C7A8R1 |
| Erythrobacter citreus | CYP153A | C7A8R3 |
| Erythrobacter flavus | CYP153A | C7A8N5 |
| uncultured bacterium | cyp153 | W0UD37 |
| Erythrobacter sp. S14-1 | CYP153A | C7A8Q4 |
| uncultured bacterium | cyp153 | W0UDF2 |
| uncultured bacterium | cyp153 | W0UDR6 |
| uncultured bacterium | cyp153 | W0UAN1 |
| uncultured bacterium | cyp153 | W0UCX5 |
| uncultured bacterium | cyp153 | W0UD38 |
| uncultured bacterium | cyp153 | W0UDM9 |
| uncultured bacterium | cyp153 | W0UCW7 |

TABLE 5-continued

Cytochrome P450 enzymes capable of catalyzing selective terminal alkene hydroxylation.

| Species Origin | Gene names | Accession No |
|---|---|---|
| uncultured bacterium | cyp153 | W0UB12 |
| uncultured bacterium | cyp153 | W0UD04 |
| uncultured bacterium | cyp153 | W0UDQ6 |
| Sphingopyxis macrogoltabida (Sphingomonas macrogoltabidus) | ahpG1 | Q5F4D9 (SEQ ID NO: 82) |
| Afipia broomeae ATCC 49717 | HMPREF9695_03199 | K8P5Q2 |
| uncultured bacterium | cyp153 | W0UD96 |
| Parvibaculum sp. S18-4 | CYP153A | C7A8S5 |
| uncultured bacterium | cyp153 | W0UAN7 |
| uncultured bacterium | cyp153 | W0UCS9 |
| uncultured bacterium | cyp153 | W0UDX6 |
| uncultured bacterium | cyp153 | W0UDB7 |
| uncultured bacterium | cyp153 | W0UD56 |
| uncultured bacterium | cyp153 | W0UD44 |
| Parvibaculum lavamentivorans (strain DS-1/DSM 13023/NCIMB 13966) | Plav_2128 | A7HV09 |
| Caulobacter crescentus (strain NA1000/CB15N) | CCNA_00061 | B8GXF2 |
| Caulobacter crescentus (strain ATCC 19089/CB15) | CC_0063 | Q9AC06 |
| Parvibaculum lavamentivorans (strain DS-1/DSM 13023/NCIMB 13966) | Plav_0025 | A7HP15 |
| Caulobacter segnis (strain ATCC 21756/DSM 7131/JCM 7823/NBRC 15250/LMG 17158/TK0059) (Mycoplana segnis) | Cseg_0011 | D5VDJ3 |
| Novosphingobium sp. PP1Y | PP1Y_AT31178 | F6IH26 |
| uncultured bacterium | cyp153 | W0UDC7 |
| uncultured bacterium | cyp153 | W0UDA2 |
| uncultured bacterium | cyp153 | W0UDP7 |
| Parvibaculum sp. S18-4 | CYP153A | C7A8S6 |
| uncultured bacterium | cyp153 | W0UAK6 |
| uncultured bacterium | cyp153 | W0UD52 |
| uncultured bacterium | cyp153 | W0UCU6 |
| uncultured bacterium | cyp153 | W0UCR4 |
| uncultured bacterium | cyp153 | W0UCS6 |
| uncultured bacterium | cyp153 | W0UDV6 |
| uncultured bacterium | cyp153 | W0UDY0 |
| uncultured bacterium | cyp153 | W0UDF0 |
| uncultured bacterium | cyp153 | W0UDF0 |
| uncultured bacterium | cyp153 | W0UAV7 |
| uncultured bacterium | cyp153 | W0UDL7 |
| Bradyrhizobium sp. STM 3843 | BRAS3843_1530026 | H0THQ7 |
| Bradyrhizobium sp. (strain ORS278) | BRADO1446 | A4YN62 |
| Bradyrhizobium sp. (strain BTAi1/ATCC BAA-1182) | BBta_6659 | A5EQW5 |
| Caulobacter crescentus OR37 | OR37_01714 | R0EKG8 |
| Afipia broomeae ATCC 49717 | HMPREF9695_03200 | K8P2K6 |
| Afipia clevelandensis ATCC 49720 | HMPREF9696_02236 | K8P5K9 |
| Bradyrhizobiaceae bacterium SG-6C | CSIRO_4275 | F7QRQ2 |
| Novosphingobium pentaromativorans US6-1 | ahpG3 NSU_pLA1167 | G6EL94 |
| marine gamma proteobacterium HTCC2143 | GP2143_12206 | A0YHG8 |
| Sphingopyxis macrogoltabida (Sphingomonas macrogoltabidus) | ahpG2 | Q5F4D6 |
| uncultured bacterium | cyp153 | W0UD98 |
| uncultured bacterium | cyp153 | W0UAZ7 |
| uncultured bacterium | cyp153 | W0UCU0 |
| uncultured bacterium | cyp153 | W0UCW6 |
| Bradyrhizobium sp. ORS 375 | BRAO375_960079 | H0SSR8 |
| Bradyrhizobium sp. ORS 285 | BRAO285_1310010 | H0RSU1 |
| Bradyrhizobium sp. STM 3809 | BRAS3809_1790009 | H0SVY3 |
| Rhodopseudomonas palustris (strain BisA53) | RPE_4309 | Q07IK1 |
| Bradyrhizobium sp. YR681 | PMI42_06128 | J3CQJ7 |
| Bradyrhizobium sp. STM 3843 | BRAS3843_1530027 | H0THQ8 |
| Rhodopseudomonas palustris (strain BisB18) | RPC_4264 | Q20YJ8 |
| Caulobacter sp. (strain K31) | Caul_5296 | B0T9L7 |
| Sphingopyxis macrogoltabida (Sphingomonas macrogoltabidus) | ahpG3 | Q5F4D3 (SEQ ID NO: 83) |
| Bradyrhizobium oligotrophicum S58 | S58_15720 | M4ZMZ3 |
| Bradyrhizobium diazoefficiens (strain JCM 10833/IAM 13628/NBRC 14792/USDA 110) | blr7242 | Q89E45 |
| uncultured bacterium | cyp153 | W0UAK0 |
| uncultured bacterium | cyp153 | W0UD34 |
| Bradyrhizobium oligotrophicum S58 | S58_15730 | M4Z3Y5 |
| Erythrobacter litoralis (strain HTCC2594) | ELI_14945 | Q2N5G0 (SEQ ID NO: 84) |
| Erythrobacter sp. SD-21 | ED21_32074 | A5PDG4 |

TABLE 5-continued

Cytochrome P450 enzymes capable of catalyzing selective terminal alkene hydroxylation.

| Species Origin | Gene names | Accession No |
| --- | --- | --- |
| *Bradyrhizobium* sp. DFCI-1 | C207_05440 | U1GV14 |
| *Bradyrhizobium* sp. DFCI-1 | C207_05439 | U1HA94 |
| *Bradyrhizobium diazoefficiens* (strain JCM 10833/IAM 13628/NBRC 14792/USDA 110) | blr7243 | Q89E44 |
| *Rhodopseudomonas palustris* (strain TIE-1) | Rpa1_1803 | B3Q8D0 |
| *Bradyrhizobium* sp. CCGE-LA001 | BCCGELA001_36088 | W1JKM5 |
| *Parvibaculum lavamentivorans* (strain DS-1/DSM 13023/NCIMB 13966) | Plav_1782 | A7HU17 |
| *Rhodopseudomonas palustris* (strain ATCC BAA-98/CGA009) | RPA1613 | Q6N9D6 |
| *Bradyrhizobium* sp. S23321 | S23_58660 | I0GE69 |
| *Bradyrhizobium* sp. ORS 285 | BRAO285_1310011 | H0RSU2 |
| *Bradyrhizobium* sp. ORS 375 | BRAO375_960081 | H0SSR9 |
| *Bradyrhizobium* sp. (strain BTAi1/ATCC BAA-1182) | BBta_6660 | A5EQW6 |
| *Bradyrhizobium japonicum* USDA 6 | BJ6T_79720 | G7DEP2 |
| uncultured bacterium | cyp153 | W0UDA7 |
| uncultured bacterium | cyp153 | W0UDB9 |
| *Afipia* sp. P52-10 | X566_03415 | W3RJ54 |
| *Afipia* sp. P52-10 | X566_20970 | W3RG92 |
| marine gamma proteobacterium HTCC2143 | GP2143_06774 | A0YGV8 |
| *Afipia* sp. P52-10 | X566_16815 | W3RJ04 |
| *Bradyrhizobium japonicum* USDA 6 | BJ6T_21500 | G7D7D2 |
| *Bradyrhizobium* sp. WSM471 | Bra471DRAFT_06475 | H5YKH9 |
| *Bradyrhizobium* sp. S23321 | S23_58670 | I0GE70 |
| *Rhodopseudomonas palustris* (strain DX-1) | Rpdx1_3910 | E6VIP2 |
| *Bradyrhizobium* sp. STM 3809 | BRAS3809_1790008 | H0SVY2 |
| *Bradyrhizobium* sp. (strain ORS278) | BRADO1445 | A4YN61 |
| *Rhodopseudomonas palustris* (strain HaA2) | RPB_3934 | Q2IT33 |
| *Rhodopseudomonas palustris* (strain BisB5) | RPD_3694 | Q13284 |
| *Phenylobacterium zucineum* (strain HLK1) | p450_PHZ_c0813 | B4RGA3 |
| *Bradyrhizobium* sp. WSM1253 | Bra1253DRAFT_03743 | I2QGW7 |
| *Bradyrhizobium* sp. WSM471 | Bra471DRAFT_06476 | H5YKI0 |
| *Bradyrhizobium* sp. WSM1253 | Bra1253DRAFT_03744 | I2QGW8 |
| *Bradyrhizobium japonicum* USDA 6 | BJ6T_21490 | G7D7D1 |
| *Bradyrhizobium* sp. YR681 | PMI42_06129 | J2WD32 |
| *Afipia* sp. P52-10 | X566_20975 | W3RG20 |
| gamma proteobacterium NOR5-3 | NOR53_2355 | B8KH72 |
| *Bradyrhizobium* sp. CCGE-LA001 | BCCGELA001_12206 | W1JZ89 |
| marine gamma proteobacterium HTCC2148 | GPB2148_2599 | B7RZN8 |
| gamma proteobacterium BDW918 | DOK_00120 | I2JQ45 |
| *Congregibacter litoralis* KT71 | KT71_14444 | A4A7Y2 |
| *Bradyrhizobium diazoefficiens* (strain JCM 10833/IAM 13628/NBRC 14792/USDA 110) | blr1853 | H7C6Q5 |
| *Bradyrhizobium japonicum* | id311 | Q9AND6 |
| uncultured bacterium | cyp153 | W0UCV0 |
| uncultured bacterium | cyp153 | W0UAD7 |
| *Pseudomonas* sp. 19-rlim | | G3LGZ6 |
| *Bradyrhizobium* sp. WSM1253 | Bra1253DRAFT_06024 | I2QN59 |
| *Bradyrhizobium* sp. WSM471 | Bra471DRAFT_01541 | H5Y7S1 |
| uncultured gamma proteobacterium EB000_65A11 | | E0XZZ2 |
| marine gamma proteobacterium HTCC2148 | GPB2148_1452 | B7RXX8 |
| marine gamma proteobacterium HTCC2143 | GP2143_15156 | A0Y901 |
| *Afipia* sp. P52-10 | X566_17435 | W3RGW1 |
| gamma proteobacterium NOR5-3 | NOR53_537 | B8KPR5 |
| *Glaciecola psychrophila* 170 | C427_3047 GPSY_3092 | K7ADG3 |
| *Marinobacter lipolyticus* SM19 | MARLIPOL_15764 | R8AWZ8 |
| gamma proteobacterium IMCC3088 | IMCC3088_2432 | F3L451 |
| uncultured bacterium | P450 | Q33DT3 |
| uncultured bacterium | P450 | Q33DS9 |
| uncultured bacterium | P450 | Q33DS8 |
| uncultured bacterium | cyp153 | W0UD71 |
| *Congregibacter litoralis* KT71 | KT71_02837 | A4A779 |
| marine gamma proteobacterium HTCC2080 | MGP2080_14441 | A0Z7J1 |
| *Marinobacter santoriniensis* NKSG1 | MSNKSG1_10343 | M7CRK4 |
| *Alcanivorax hongdengensis* | | G1C7P2 |
| *Alcanivorax* sp. DG881 | ADG881_2620 | B4WXL2 |
| uncultured bacterium | P450 | Q33DS6 |
| uncultured bacterium | cyp153 | W0UCP6 |
| uncultured bacterium | cyp153 | W0UCQ6 |
| *Ochrobactrum anthropi* | CYP153A | C7A8M0 |
| uncultured bacterium | cyp153 | W0UCN8 |
| uncultured bacterium | cyp153 | W0UCT1 |
| uncultured bacterium | cyp153 | W0UCT1 |
| uncultured bacterium | cyp153 | W0UAI3 |
| gamma proteobacterium HIMB55 | OMB55_00002070 | H3NWG4 |
| *Bradyrhizobium* sp. DFCI-1 | C207_06143 | U1H776 |

TABLE 5-continued

Cytochrome P450 enzymes capable of catalyzing selective terminal alkene hydroxylation.

| Species Origin | Gene names | Accession No |
| --- | --- | --- |
| gamma proteobacterium HIMB55 | OMB55_00014510 | H3NWP3 |
| marine gamma proteobacterium HTCC2080 | MGP2080_06587 | A0Z166 |
| *Burkholderia xenovorans* (strain LB400) | Bx_A3593 | Q143U3 |
| *Alcanivorax* sp. P2S70 | Q670_08165 | U7G5C1 |
| *Marinobacter hydrocarbonoclasticus* ATCC 49840 | MARHY3773 | H8WA08 |
| *Marinobacter* sp. EVN1 | Q672_10645 | U7NYR4 |
| uncultured bacterium | P450 | Q33DS4 |
| uncultured bacterium | cyp153 | W0UDA1 |
| uncultured bacterium | cyp153 | W0UCR5 |
| uncultured bacterium | cyp153 | W0UD97 |
| uncultured bacterium | cyp153 | W0UD81 |
| uncultured bacterium | cyp153 | W0UCN3 |
| uncultured bacterium | cyp153 | W0UCN5 |
| uncultured bacterium | cyp153 | W0UCT3 |
| gamma proteobacterium HdN1 | ahpG HDN1F_17560 | E1VKJ7 |
| *Marinobacter adhaerens* (strain HP15) | HP15_p187g148 | E4PSB0 |
| uncultured bacterium | P450 | Q33DT0 |
| uncultured bacterium | P450 | Q33DS5 |
| uncultured bacterium | cyp153 | W0UD61 |
| uncultured bacterium | P450 | Q33DT1 |
| *Alcanivorax hongdengensis* | | B3U002 |
| uncultured bacterium | P450 | Q33DT2 |
| uncultured bacterium | P450 | Q33DS7 |
| uncultured bacterium | cyp153 | W0UCL9 |
| uncultured bacterium | cyp153 | W0UDB3 |
| *Hyphomonas neptunium* (strain ATCC 15444) | HNE_2042 | Q0C0K3 |
| *Alcanivorax dieselolei* (strain DSM 16502/CGMCC 1.3690/B-5) | ahpG B5T_02075 | K0C9X8 |
| *Alcanivorax hongdengensis* A-11-3 | A11A3_15327 | L0WAH6 |
| *Alcanivorax dieselolei* | p450 | D0Q1H3 |
| *Alcanivorax pacificus* W11-5 | S7S_02138 | K2GI89 |
| *Marinobacter* sp. ES-1 | Q666_09590 | U7G612 |
| *Limnobacter* sp. MED105 | LMED105_04587 | A6GLB5 |
| *Marinobacter aquaeolei* (strain ATCC 700491/DSM 11845/VT8) (*Marinobacter hydrocarbonoclasticus* (strain DSM 11845)) | Maqu_0600 | A1TY82 (SEQ ID NO: 85) |
| *Marinobacter* sp. EVN1 | Q672_13925 | U7NUC4 |
| *Marinobacter* sp. EN3 | Q673_05250 | U7H5S5 |
| *Marinobacter manganoxydans* MnI7-9 | KYE_03215 | G6YPH4 |
| *Marinobacter hydrocarbonoclasticus* ATCC 49840 | ahpG2 MARHY2838 | H8WCT8 |
| *Marinobacter hydrocarbonoclasticus* (*Pseudomonas nautica*) | ahpG2 MARHY2838 | D9UAS2 |
| *Patulibacter medicamentivorans* | PAI11_40170 | H0EAZ2 |
| *Acinetobacter baumannii* WC-141 | ACINWC141_2468 | K8ZRD3 |
| *Saccharomonospora marina* XMU15 | SacmaDRAFT_5365 | H5X733 |
| *Mycobacterium marinum* (strain ATCC BAA-535/M) | cyp153A16 MMAR_3154 | B2HGN5 (SEQ ID NO: 86) |
| *Mycobacterium abscessus* 3A-0930-R | p450 MA3A0930R_2169 | I9I3J4 |
| *Mycobacterium abscessus* 3A-0930-S | p450 MA3A0930S_1729 | I9I1F6 |
| *Mycobacterium abscessus* 3A-0731 | p450 MA3A0731_2042 | I9GVU0 |
| *Mycobacterium abscessus* 3A-0119-R | p450 MA3A0119R_2080 | I9FPY3 |
| *Mycobacterium abscessus* 6G-0728-R | p450 MA6G0728R_2104 | I9DR77 |
| *Mycobacterium abscessus* subsp. *bolletii* 1S-154-0310 | p450 MM1S1540310_1492 | I9CBZ2 |
| *Mycobacterium abscessus* 6G-0728-S | p450 MA6G0728S_5133 | I9A485 |
| *Mycobacterium abscessus* 3A-0810-R | p450 MM3A0810R_2169 | I8Q799 |
| *Mycobacterium abscessus* 3A-0122-S | p450 MA3A0122S_1691 | I8LTR4 |
| *Mycobacterium abscessus* 3A-0122-R | p450 MA3A0122R_2136 | I8L4A4 |
| *Mycobacterium abscessus* 6G-0212 | p450 MA6G0212_2171 | I8I9K7 |
| *Mycobacterium abscessus* subsp. *bolletii* 1S-153-0915 | p450 MM1S1530915_1484 | I8H4G3 |
| *Mycobacterium abscessus* subsp. *bolletii* 1S-152-0914 | p450 MM1S1520914_2142 | I8GFC6 |
| *Mycobacterium abscessus* subsp. *bolletii* 1S-151-0930 | p450 MM1S1510930_1936 | I8G1R8 |
| *Mycobacterium abscessus* 6G-1108 | p450 MA6G1108_2106 | I8G1I8 |
| *Mycobacterium abscessus* 6G-0125-S | p450 MA6G0125S_2116 | I8F2E6 |
| *Mycobacterium abscessus* 6G-0125-R | p450 MA6G0125R_1143 | I8EZ93 |
| *Mycobacterium abscessus* subsp. *bolletii* 2B-0307 | p450 MM2B0307_1166 | I9EQ97 |
| *Mycobacterium abscessus* subsp. *bolletii* 2B-0107 | p450 MM2B0107_1179 | I8Q7R9 |
| *Mycobacterium abscessus* subsp. *bolletii* 2B-1231 | p450 MM2B1231_1908 | I8PT86 |
| *Mycobacterium abscessus* subsp. *bolletii* 2B-0912-S | p450 MM2B0912S_1850 | I8KHB7 |
| *Mycobacterium abscessus* subsp. *bolletii* 2B-0912-R | p450 MM2B0912R_2246 | I8JU18 |
| *Mycobacterium abscessus* subsp. *bolletii* 2B-0626 | p450 MM2B0626_1842 | I8HVB7 |
| uncultured bacterium | cyp153 | W0UAF0 |
| *Parvibaculum lavamentivorans* (strain DS-1/DSM 13023/NCIMB 13966) | Plav_1951 | A7HUI3 |
| *Alcanivorax hongdengensis* | | G1C7L3 |
| *Alcanivorax* sp. DG881 | ADG881_2119 | B4X0H6 |

TABLE 5-continued

Cytochrome P450 enzymes capable of catalyzing selective terminal alkene hydroxylation.

| Species Origin | Gene names | Accession No |
|---|---|---|
| *Marinobacter* sp. C1S70 | Q667_02605 | U7NVJ0 |
| marine gamma proteobacterium HTCC2143 | GP2143_06784 | A0YGW0 |
| *Alcanivorax* sp. P2S70 | Q670_00635 | U7G5B3 |
| *Marinobacter goseongensis* | p450 | T1WMH0 |
| gamma proteobacterium BDW918 | DOK_13444 | I2JHG9 |
| *Hirschia baltica* (strain ATCC 49814/DSM 5838/IFAM 1418) | Hba1_0836 | C6XQ13 |
| *Acinetobacter indicus* CIP 110367 | P253_02820 | V2UD76 |
| *Acinetobacter indicus* ANC 4215 | F956_01111 | S3N495 |
| *Acinetobacter* sp. OC4 | cyp | Q2MHE2 (SEQ ID NO: 87) |
| *Acinetobacter baumannii* NIPH 527 | F921_03852 | N9HTE2 |
| *Acinetobacter* sp. CIP 102129 | F973_00680 | N8UI43 |
| *Acinetobacter* sp. NIPH 809 | F993_03507 | N8P4U1 |
| *Acinetobacter baumannii* OIFC0162 | ACIN5162_A0021 | K5DS46 |
| *Acinetobacter* sp. EB104 | nonM | Q93SX3 |
| *Dietzia cinnamea* P4 | ES5_05410 | E6J787 |
| *Acinetobacter* sp. WC-743 | ACINWC743_A0288 | L9LSK8 |
| *Acinetobacter baumannii* WC-348 | ACINWC348_A0080 | K9B8A0 |
| *Acinetobacter baumannii* WC-141 | ACINWC141_A0026 | K8ZRU7 |
| *Acinetobacter baumannii* WC-323 | ACINWC323_A0095 | K9AWS1 |
| *Gordonia malaquae* NBRC 108250 | GM1_050_00120 | M3VCF1 |
| *Rhodococcus erythropolis* SK121 | RHOER0001_0266 | C3JL15 |
| *Acinetobacter* sp. COS3 | Q674_03885 | U7GP11 |
| *Acinetobacter guillouiae* MSP4-18 | L291_2817 | S3YTQ7 |
| *Acinetobacter gyllenbergii* MTCC 11365 | L293_2966 | S3YIH4 |
| *Acinetobacter gyllenbergii* CIP 110306 | F957_03919 | S3MT86 |
| *Acinetobacter* sp. CIP 110321 | F896_03869 | R9AJ00 |
| *Acinetobacter pittii* ANC 3678 | F930_03216 | N9FYL9 |
| *Acinetobacter beijerinckii* CIP 110307 | F933_03106 | N9FFM7 |
| *Acinetobacter beijerinckii* CIP 110307 | F933_03106 | N9FFM7 |
| *Acinetobacter guillouiae* CIP 63.46 | F981_00071 | N8TRF0 |
| *Acinetobacter* sp. NIPH 236 | F992_00196 | N8PQM8 |
| *Acinetobacter radioresistens* DSM 6976 = NBRC 102413 = CIP 103788 | ACRAD_64_00110 | K6W366 |
| | F939_02890 | |
| *Acinetobacter* sp. NBRC 100985 | ACT4_067_00170 | G7GIJ8 |
| *Williamsia* sp. D3 | W823_14840 | V8CZP3 |
| *Rhodococcus ruber* BKS 20-38 | G352_16177 | M2XNX0 |
| *Gordonia neofelifaecis* NRRL B-59395 | SCNU_19987 | F1YPY6 |
| *Nocardioidaceae bacterium* Broad-1 | NBCG_04744 | E9V105 |
| *Rhodococcus erythropolis* DN1 | N601_30795 | T5HW62 |
| *Rhodococcus erythropolis* (strain PR4/NBRC 100887) | RER_pREL1-02600 | Q3L9B0 |
| *Rhodococcus erythropolis* DN1 | N601_30930 | T5HZQ2 (SEQ ID NO: 88) |
| *Alcanivorax dieselolei* | | B0LCZ6 |
| uncultured bacterium | cyp153 | W0UD28 |
| uncultured bacterium | cyp153 | W0UD53 |
| uncultured bacterium | cyp153 | W0UCL1 |
| *Alcanivorax borkumensis* | ahpG1 | Q5K134 |
| *Alcanivorax* sp. 97CO-5 | Y017_09710 | W6ZMW5 |
| *Alcanivorax borkumensis* (strain SK2/ATCC 700651/DSM 11573) | p450 ABO_0201 ABO_2288 | Q0VM62 (SEQ ID NO: 89) |
| *Alcanivorax borkumensis* | ahpG2 | Q5K133 |
| gamma proteobacterium HIMB55 | OMB55_00008700 | H3NSZ4 |
| *Amycolicicoccus subflavus* (strain DSM 45089/DQS3-9A1) | AS9A_4287 | F6EL57 |
| *Dietzia cinnamea* P4 | ES5_17094 | E6JDU2 |
| *Rhodococcus* sp. R04 | | G0YY52 |
| *Dietzia* sp. DQ12-45-1b | | L7QFU8 |
| *Gordonia terrae* C-6 | GTC6_22847 | R7Y2Z3 |
| *Gordonia rubripertincta* NBRC 101908 | GORBP_030_00030 | L7K246 |
| *Gordonia polyisoprenivorans* NBRC 16320 | GOPIP_035_00030 | H0RD32 |
| *Gordonia amicalis* NBRC 100051 = JCM 11271 | GOAMI_32_00650 | L7L3E0 |
| *Nocardia cyriacigeorgica* (strain GUH-2) | NOCYR_1539 | H6R8V9 |
| *Mycobacterium gilvum* (strain PYR-GCK) (*Mycobacterium flavescens* (strain ATCC 700033/PYR-GCK)) | Mflv_4592 | A4TFM0 |
| *Acinetobacter* sp. ANC 3862 | F900_00467 | N9M6H3 |
| *Rhodococcus erythropolis* (strain PR4/NBRC 100887) | RER_pREL1-02830 | Q3L987 |
| *Mycobacterium rhodesiae* (strain NBB3) | MycrhN_5185 | G8RXP7 |
| *Rhodococcus wratislaviensis* IFP 2016 | Rwratislav_02222 | L2TWM7 |
| *Nocardioides* sp. CF8 | CF8_1774 | R7XZ06 |
| *Rhodococcus* sp. AW25M09 | RHODMAR_4781 | L8DQ69 |
| *Mycobacterium* sp. (strain MCS) | Mmcs_3218 | Q1B709 |
| *Mycobacterium* sp. (strain JLS) | Mjls_3229 | A3Q1I0 |

TABLE 5-continued

Cytochrome P450 enzymes capable of catalyzing selective terminal alkene hydroxylation.

| Species Origin | Gene names | Accession No |
|---|---|---|
| *Mycobacterium* sp. (strain KMS) | Mkms_3280 | A1UI16 |
| *Mycobacterium intracellulare* MOTT-02 | OCO_23030 | H8J7G3 |
| *Mycobacterium abscessus* subsp. *bolletii* str. GO 06 | linC MYCMA_1074 | I6ZDN8 |
| *Mycobacterium abscessus* (strain ATCC 19977/DSM 44196) | MAB_2048c | B1MP79 |
| *Mycobacterium abscessus* V06705 | M879_18655 | T0B128 |
| *Mycobacterium abscessus* M94 | S7W_02670 | I0PWL5 |
| *Mycobacterium avium* subsp. *hominissuis* 10-4249 | O971_10910 | V7M646 |
| *Mycobacterium parascrofulaceum* ATCC BAA-614 | HMPREF0591_1257 | D5P513 |
| *Rhodococcus* sp. AW25M09 | RHODMAR_0629 | L8DBR6 |
| *Nocardia asteroides* NBRC 15531 | NCAST_16_00270 | U5E995 |
| *Aeromicrobium marinum* DSM 15272 | HMPREF0063_10876 | E2SA86 |
| *Mycobacterium abscessus* MAB_091912_2446 | L833_0535 | V6ZS84 |
| *Mycobacterium abscessus* MAB_082312_2258 | L830_0536 | V6ZGT1 |
| *Mycobacterium abscessus* 47J26 | MAB47J26_13072 | G6X6X6 |
| *Nocardioides* sp. CF8 | CF8_1685 | R7XZ92 |
| *Gordonia polyisoprenivorans* NBRC 16320 | GOPIP_007_00470 | H0R8L5 |
| *Gordonia araii* NBRC 100433 | GOARA_078_00570 | G7H6Y3 |
| marine gamma proteobacterium HTCC2080 | MGP2080_13483 | A0Z5X9 |
| *Gordonia paraffinivorans* NBRC 108238 | GP2_063_00030 | M3V7L0 |
| *Planctomyces maris* DSM 8797 | PM8797T_18726 | A6CH25 |
| *Amycolicicoccus subflavus* (strain DSM 45089/DQS3-9A1) | AS9A_2813 | F6EJ28 |
| *Candidatus Microthrix parvicella* RN1 | BN381_420018 | R4Z0X4 |
| *Gordonia paraffinivorans* NBRC 108238 | GP2_036_00650 | M3TVA1 |
| *Nocardioides* sp. CF8 | CF8_2601 | R7XVN2 |
| *Mycobacterium chubuense* (strain NBB4) | Mycch_5830 | D2K2F1 |
| *Gordonia polyisoprenivorans* (strain DSM 44266/VH2) | GPOL_c44990 | H6MXH6 |
| *Aeromicrobium marinum* DSM 15272 | HMPREF0063_10264 | E2S8A7 |
| *Gordonia rubripertincta* NBRC 101908 | GORBP_109_00410 | L7KEM4 |
| *Gordonia namibiensis* NBRC 108229 | GONAM_02_01570 | K6XIG5 |
| *Gordonia* sp. KTR9 | KTR9_5380 | J9STN3 |
| *Gordonia terrae* NBRC 100016 | GOTRE_050_00060 | H5UDF7 |
| *Gordonia alkanivorans* NBRC 16433 | GOALK_030_00300 | F9VS44 |
| *Gordonia alkanivorans* | goaBAC | B3IX64 |
| *Gordonia* sp. TF6 | aoxA | A9CMS7 |
| *Alcanivorax borkumensis* (strain SK2/ATCC 700651/DSM 11573) | | Q6RCE3 |
| *Gordonia malaquae* NBRC 108250 | GM1_011_00750 | M3UVQ9 |
| alpha proteobacterium JLT2015 | C725_0051 | M2TQQ4 |
| *Oceanicola batsensis* HTCC2597 | OB2597_05915 | A3TT18 |
| *Sphingobium baderi* LL03 | L485_17855 | T0HGM2 |
| *Erythrobacter litoralis* (strain HTCC2594) | ELI_12445 | Q2N6W0 |
| *Erythrobacter* sp. SD-21 | ED21_18817 | A5P986 |
| *Novosphingobium nitrogenifigens* DSM 19370 | Y88_2850 | F1Z4F0 |
| *Sphingopyxis macrogoltabida* (*Sphingomonas macrogoltabidus*) | ahpG5 | Q5F4D8 (SEQ ID NO: 90) |
| *Sphingopyxis alaskensis* (strain DSM 13593/LMG 18877/RB2256) (*Sphingomonas alaskensis*) | Sala_2865 | Q1GP52 |
| *Sphingopyxis macrogoltabida* (*Sphingomonas macrogoltabidus*) | ahpG4 | Q5F4D1 (SEQ ID NO: 91) |
| *Novosphingobium aromaticivorans* (strain DSM 12444) | Saro_0220 | Q2GBV5 |
| *Dickeya dadantii* (strain Ech586) | Dd586_1369 | D2BW78 |
| *Sphingopyxis* sp. MC1 | EBMC1_05939 | N9UVB0 |
| *Dietzia* sp. D5 | | W0C650 |
| *Sphingobium indicum* B90A | SIDU_06697 | I5BFE4 |
| *Sphingobium chinhatense* IP26 | M527_09955 | W1KG42 |
| *Sphingobium* sp. HDIP04 | L286_21540 | T0G3B9 |
| *Erythrobacter* sp. NAP1 | NAP1_13673 | A3WFL2 |
| *Dickeya dadantii* (strain 3937) (*Erwinia chrysanthemi* (strain 3937)) | Dda3937_03358 | E0SIQ2 |
| *Sphingomonas sanxanigenens* DSM 19645 = NX02 | NX02_10200 | W0AB84 |
| *Sphingopyxis* sp. MC1 | EBMC1_03994 | N9WE44 |
| *Dickeya* sp. D s0432-1 | A544_2711 | U6Z9W7 |
| *Novosphingobium aromaticivorans* (strain DSM 12444) | Saro_1821 | Q2G7B2 |
| *Erythrobacter litoralis* (strain HTCC2594) | ELI_09815 | Q2N8D6 |
| *Parvibaculum lavamentivorans* (strain DS-1/DSM 13023/NCIMB 13966) | Plav_0029 | A7HP19 |
| *Novosphingobium pentaromativorans* US6-1 | NSU_3817 | G6EHJ6 |

In some embodiments, the invention provide methods for synthesizing olefinic alcohol products as described above, wherein the enzyme is selected from AlkB, AlkB P1, and AlkB1 AB. In some embodiments, the enzyme is selected from CYP153 M. sp.; CYP153A M. aq.; CYP153A M. aq. (G307A); Cyp153A M. aq. (G307A)-CPR$_{BM3}$; Cyp153A P.sp.-CPR$_{BM3}$; CYP153A13N2; CYP153A13N3; CYP153A13P2; and CYP153A7. In some embodiments, the enzyme is selected from CYP52A13 and CYP52A3.

In a related aspect, the invention provides a whole cell catalyst comprising an enzyme capable of selectively hydroxylating one terminal carbon of an unsaturated or saturated hydrocarbon substrate. In some embodiments, the cell is a microbial cell. In some embodiments, the enzyme is selected from the group consisting of a non-heme diiron monooxygenase, a long-chain alkane hydroxylase, a cytochrome P450, and combinations thereof. In some embodiments, the enzyme is selected from Table 3, Table 4, Table 5, or a variant thereof having at least 90% identity thereto.

In certain instances, a hydroxylase enzyme will exhibit catalytic efficiency with one isomer of an internal alkene (e.g., the cis or Z isomer of an internal alkene) that is greater than the catalytic efficiency exhibited with the other isomer of the same internal alkene (e.g., the trans or E isomer of an internal alkene). In some embodiments, the invention provides methods wherein the catalytic efficiency of the hydroxylase enzyme is at least about 2-fold greater with one isomer of an internal alkene than with the other isomer of the internal alkene. The catalytic efficiency exhibited by a hydroxylase with one isomer of an internal alkene can be, for example, at least about 4-fold, at least about 5-fold, at least about 6-fold, at least about 7-fold, at least about 8-fold, at least about 9-fold, at least about 10-fold, at least about 25-fold, at least about 50-fold, at least about 100-fold, or at least about 500-fold greater than the catalytic efficiency exhibited by the hydroxylase with the other isomer of the internal alkene.

A particular enzyme can therefore produce Z product over E product from a mixture of Z and E isomeric substrates or

TABLE 6

Exemplary strains suitable for the present invention.

| Species | Plasmid Genotype (or relevant gene deletions) | Reference |
| --- | --- | --- |
| E. coli K12 GEc137 | pGEc47J contains alkBFGKL alkST | Grant et al. Enzyme Microb. Technol. 2011 |
| E. coli W3110 | pBT10 contains alkBFG alkST | Schrewe et al. Adv. Synth. Cat. 2011 |
| E. coli W3110 | pBTL10 contains alkBFGL alkST | Julsing et al. Adv. Synth. Cat. 2011 |
| E. coli BL21(DE3) | pET-28a(+)-LadA contains LadA | Dong el al. Appl. Microbiol. Biotechnol. 2012 |
| E. coli BL21(DE3) | pET-28a(+)-CYP153A6 operon | Gudimichi et al. Appl. Microbiol. Biotechnol. 2012 |
| E. coli JM109 | pJOE-CYP153A$_{M.\ aq.}$(G307A)-CPR$_{BM3}$ | Scheps et al. Microb. Biotechnol. 2013 |
| E. coli HMS174 | pET-28(+)-CYP153A$_{M.\ aq.}$(G307A)-CPR$_{BM3}$ | |
| E. coli HMS174 | pColaDuet-1-CYP153A$_{M.\ aq.}$(G307A)-CPR$_{BM3}$, alkL | |
| E. coli HMS174 | pET-28(+)-CYP153A$_{P.\ sp.}$-CPR$_{BM3}$ | Malca et al. Chem. Comm. 2012 |
| C. tropicalis DP522 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A13 | Lu et al. J. Am. Chem. Soc. 2010 |
| C. tropicalis DP526 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A12 | |
| C. tropicalis DP428 | DP1 Δcyp52a17/Δ cyp52a18 Δ cyp52a13/Δcyp52a14 Δ fao1/Δ fao1b Δ fao2a/Δ fao2b Δcyp52a12/Δcyp52a12b Δadh-a4/Δadh-a4b Δadhb4/Δadh-b4b Δadh-a10 Δ adh-b11 pXICL::CYP52A17 | |

The methods of the invention allow for the production of terminal alcohols with controlled regioselectivity, while disfavoring the formation of unwanted species such as epoxides or elimination products. The stereochemistry of an olefinic alcohol product will depend on factors including the structure of the particular olefinic substrate used in a particular reaction, as well as the identity of the enzyme. The methods of the invention can be conducted with enzymes that are selective for particular substrates (e.g., cis or Z alkenes vs. trans or E alkenes), as well as with enzymes that demonstrate terminal selectivity (e.g., hydroxylation of one end of an asymmetric alkene vs. the other end of the asymmetric alkene).

enrich the Z product over the E product. In certain embodiments, the invention provides methods for preparing olefinic alcohol products wherein the Z:E (cis:trans) isomeric ratio of the olefinic alcohol product is different from the Z:E (cis:trans) isomeric ratio of the olefinic substrate. The Z:E isomeric ratio of the olefinic alcohol product can be, for example, around 2 times greater than the Z:E isomeric ratio of the olefinic substrate. The Z:E isomeric ratio of the olefinic alcohol product can be, for example, around 1.25 times, 1.5 times, 2 times, 2.5 times, 3 times, 4 times, 5 times, 10 times, 20 times, 30 times, or 40 times greater than the Z:E isomeric ratio of the olefinic substrate.

In some embodiments, the invention provides methods for preparing olefinic alcohol products wherein the E:Z (trans:cis) isomeric ratio of the olefinic alcohol product is different from the E:Z (trans:cis) isomeric ratio of the olefinic substrate. The E:Z isomeric ratio of the olefinic alcohol product can be, for example, around 2 times greater than the E:Z isomeric ratio of the olefinic substrate. The E:Z isomeric ratio of the olefinic alcohol product can be, for example, around 1.25 times, 1.5 times, 2 times, 2.5 times, 3 times, 4 times, 5 times, 10 times, 20 times, 30 times, or 40 times greater than the E:Z isomeric ratio of the olefinic substrate.

In some embodiments, the Z:E isomeric ratio of the olefinic alcohol is about 1.25 times greater than the Z:E isomeric ratio of the olefinic substrate. In some embodiments, the E:Z isomeric ratio of the olefinic alcohol is about 1.25 times greater than the E:Z isomeric ratio of the olefinic substrate.

In certain instances, the biohydroxylation reactions in the methods of the invention have the potential to form a mixture of two or more products from the same substrate. When an olefinic substrate is asymmetric, for example, hydroxylation of one end/terminus of the substrate leads to one product while hydroxylation of the other end/terminus of the substrate leads to a different product. A reaction could therefore result in a mixture of two olefinic alcohol products. The terminal isomer ratio of an asymmetric olefinic alcohol product can range from about 1:99 to about 99:1. The terminal isomer ratio can be, for example, from about 1:99 to about 1:75, or from about 1:75 to about 1:50, or from about 1:50 to about 1:25, or from about 99:1 to about 75:1, or from about 75:1 to about 50:1, or from about 50:1 to about 25:1. The terminal isomer ratio can be from about 1:80 to about 1:20, or from about 1:60 to about 1:40, or from about 80:1 to about 20:1 or from about 60:1 to about 40:1. The terminal isomer ratio can be about 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, or about 1:95. The terminal isomer ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

Figure 3:
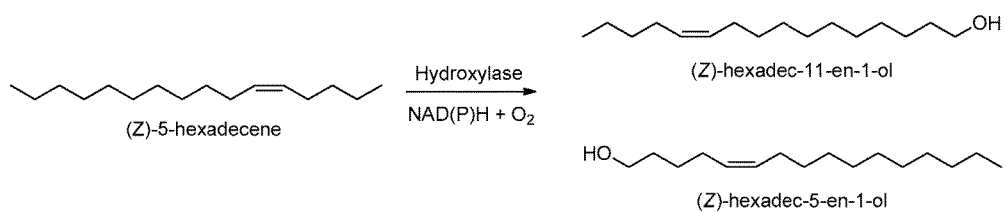
FIG. 3 shows a reaction scheme for hydroxylation of asymmetric alkenes using the methods of the invention.

The distribution of a product mixture can be expressed as a regioselectivity percentage ("regioselectivity %"). Taking the reaction in FIG. 3 as a non-limiting example, for instance, the regioselectivity of (Z)-5-hexadecene hydroxylation can be calculated using the formula: regioselectivity %=$[(\chi_{11})/(\chi_{11}+\chi_5)] \times 100\%$, wherein $\omega_{11}$ is the mole fraction for (Z)-11-hexadecen-1-ol and wherein $\chi_5$ is the mole fraction for (Z)-5-hexadecen-1-ol. In general, the regioselectivity % with respect to terminal alcohol isomers ranges from about 1% to about 99%. The regioselectivity % can be from about 1% to about 99%, or from about 20% to about 80%, or from about 40% to about 60%, or from about 1% to about 25%, or from about 25% to about 50%, or from about 50% to about 75%. The regioselectivity % can be at least about 5% 10%, 15%, 20%, 25%, 30%, 35%, 40%, 45%, 50%, 55%, 60%, 65%, 70%, 75%, 80%, 85%, 90%, or 95%.

In some embodiments, the regioselectivity % is at least about 60%. In some embodiments, the regioselectivity % is at least about 60% and the Z:E isomeric ratio of the olefinic alcohol is about 1.25 times greater than the Z:E isomeric ratio of the olefinic substrate.

In certain instances, varying levels of olefin epoxidation will occur during the biohydroxylation reactions used in the methods of the invention. See, e.g., Scheme 7. Epoxidation of terminal alkenes, in particular, can occur when certain hydroxylase enzymes are used. It is often desirable to minimize such epoxidation or avoid the formation of epoxides altogether. Typically, methods of the invention are conducted with hydroxylase enzymes that produce product mixtures with alcohol product:epoxide ratios of at least 1:1. The alcohol product:epoxide ratio can range from about 1:1 to about 99:1. The alcohol:epoxide ratio can be, for example, from about 99:1 to about 75:1, or from about 75:1 to about 50:1, or from about 50:1 to about 25:1. The alcohol:epoxide ratio can be from about 80:1 to about 20:1 or from about 60:1 to about 40:1. The alcohol:epoxide ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

In some embodiments, methods are conducted using an enzyme that produces an olefinic alcohol product:epoxide product ratio of greater than 1:1. In some embodiments, the enzyme produces an olefinic alcohol product:epoxide product ratio of greater than 2:1.

The distribution of a product mixture can be expressed as a percent selectivity for hydroxylation vs. epoxidation. Taking the reaction in Scheme 7a as a non-limiting example, the percent selectivity for hydroxylation vs. epoxidation of a terminal alkene can be calculated using the formula: selectivity %=$[(\chi_H)/(\chi_H+\chi_E)] \times 100\%$, wherein $\chi_H$ is the mole fraction for the hydroxylation product (i.e., the terminal olefinic alcohol) and wherein $\chi_E$ is the mole fraction for the epoxidation product (i.e., the terminal epoxide). In general, the percent selectivity for hydroxylation vs. epoxidation ranges from about 1% to about 99%. The percent selectivity for hydroxylation vs. epoxidation can be from about 1% to about 99%, or from about 20% to about 80%, or from about 40% to about 60%, or from about 1% to about 25%, or from about 25% to about 50%, or from about 50% to about 75%. The percent selectivity for hydroxylation vs. epoxidation can be about 5% 10%, 15%, 20%, 25%, 30%, 35%, 40%, 45%, 50%, 55%, 60%, 65%, 70%, 75%, 80%, 85%, 90%, or 95%.

When halogen-substituted substrates are used in the methods of the invention, varying levels of dehalogenation can occur during hydroxylation. Dehalogenation typically results in the formation of aldehyde byproduct. Preferably, dehalogenation is minimized or avoided during the hydroxylation reactions. Typically, methods of the invention are conducted with hydroxylase enzymes that produce product mixtures with alcohol:aldehyde ratios of at least 1:1. The alcohol:aldehyde ratio of the product can range from about 1:1 to about 99:1. The alcohol:aldehyde ratio can be, for example, from about 99:1 to about 75:1, or from about 75:1 to about 50:1, or from about 50:1 to about 25:1. The alcohol:aldehyde ratio can be from about 80:1 to about 20:1 or from about 60:1 to about 40:1. The alcohol:aldehyde ratio can be about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, or about 95:1.

The distribution of a product mixture can be expressed as a percent selectivity for hydroxylation vs. dehalogenation. The percent selectivity for hydroxylation vs. dehalogenation of a halogen-substituted substrate can be calculated using the formula: selectivity %=$[(\chi_H)/(\chi_H+\chi_A)] \times 100\%$, wherein $\chi_H$ is the mole fraction for the hydroxylation product and wherein $\chi_A$ is the mole fraction for the aldehyde product. In general, the percent selectivity for hydroxylation vs. dehalogenation ranges from about 1% to about 99%. The percent selectivity for hydroxylation vs. dehalogenation can be from about 1% to about 99%, or from about 20% to about 80%, or from about 40% to about 60%, or from about 1% to about 25%, or from about 25% to about 50%, or from about 50% to about 75%. The percent selectivity for hydroxylation vs.

dehalogenation can be about 5% 10%, 15%, 20%, 25%, 30%, 35%, 40%, 45%, 50%, 55%, 60%, 65%, 70%, 75%, 80%, 85%, 90%, or 95%.

Synthesis of Terminal Alkenals

As indicated above, the alcohol moiety generated via hydroxylation can be further modified to generate alkenals or acetate esters.

Oxidation of Fatty Alcohols

Oxidation of fatty alcohols is often achieved via selective oxidation via pyridinium chlorocrhomate (PCC) (Scheme 20).

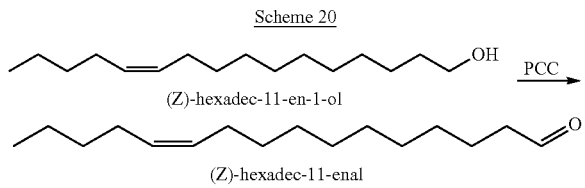

Scheme 20

Alternatively, TEMPO (TEMPO=2,2,6,6-tetramethylpiperidinyl-N-oxyl) and related catalyst systems can be used to selectively oxidize alcohols to aldehydes. These methods are described in Ryland and Stahl (2014), herein incorporated by reference in its entirety.

Bio-Oxidation of Terminal Alcohols

Many insect pheromones are fatty aldehydes or comprise a fatty aldehyde component. As such, the conversion of the fatty alcohol produced via terminal hydroxylation to the fatty aldehyde is required to produce certain pheromones. The conversion of a fatty alcohol to a fatty aldehyde is known to be catalyzed by alcohol dehydrogenases (ADH) and alcohol oxidases (AOX). Additionally, the conversion of a length $C_n$ fatty acid to a $C_{n-1}$ fatty aldehyde is catalyzed by plant α-dioxygenases (α-DOX) (Scheme 21).

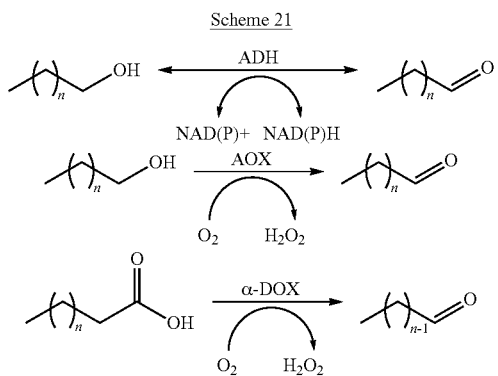

Scheme 21

The present invention describes enzymes that oxidize fatty alcohols to fatty aldehydes.

In some embodiments, an alcohol oxidase (AOX) is used to catalyze the conversion of a fatty alcohol to a fatty aldehyde. Alcohol oxidases catalyze the conversion of alcohols into corresponding aldehydes (or ketones) with electron transfer via the use of molecular oxygen to form hydrogen peroxide as a by-product. AOX enzymes utilize flavin adenine dinucleotide (FAD) as an essential cofactor and regenerate with the help of oxygen in the reaction medium. Catalase enzymes may be coupled with the AOX to avoid accumulation of the hydrogen peroxide via catalytic conversion into water and oxygen.

Based on the substrate specificities, AOXs may be categorized into four groups: (a) short chain alcohol oxidase, (b) long chain alcohol oxidase, (c) aromatic alcohol oxidase, and (d) secondary alcohol oxidase (Goswami et al. 2013). Depending on the chain length of the desired substrate, some member of these four groups are better suited than others as candidates for evaluation.

Short chain alcohol oxidases (including but not limited to those currently classified as EC 1.1.3.13, Table 7) catalyze the oxidation of lower chain length alcohol substrates in the range of C1-C8 carbons (van der Klei et al. 1991) (Ozimek et al. 2005). Aliphatic alcohol oxidases from methylotrophic yeasts such as *Candida boidinii* and *Komagataella pastoris* (formerly *Pichia pastoris*) catalyze the oxidation of primary alkanols to the corresponding aldehydes with a preference for unbranched short-chain aliphatic alcohols. The most broad substrate specificity is found for alcohol oxidase from the *Pichia pastoris* including propargyl alcohol, 2-chloroethanol, 2-cyanoethanol (Dienys et al. 2003). The major challenge encountered in alcohol oxidation is the high reactivity of the aldehyde product. Utilization of a two liquid phase system (water/solvent) can provide in-situ removal of the aldehyde product from the reaction phase before it is further converted to the acid. For example, hexanal production from hexanol using *Pichia pastoris* alcohol oxidase coupled with bovine liver catalase was achieved in a biphasic system by taking advantage of the presence of a stable alcohol oxidase in aqueous phase (Karra-Chaabouni et al. 2003). For example, alcohol oxidase from *Pichia pastoris* was able to oxidize aliphatic alcohols of C6 to C11 when used biphasic organic reaction system (Murray and Duff 1990). Methods for using alcohol oxidases in a biphasic system according to (Karra-Chaabouni et al. 2003) and (Murray and Duff 1990) are incorporated by reference in their entirety.

Long chain alcohol oxidases (including but not limited to those currently classified as EC 1.1.3.20; Table 8) include fatty alcohol oxidases, long chain fatty acid oxidases, and long chain fatty alcohol oxidases that oxidize alcohol substrates with carbon chain length of greater than six (Goswami et al. 2013). Banthorpe et al. reported a long chain alcohol oxidase purified from the leaves of *Tanacetum vulgare* that was able to oxidize saturated and unsaturated long chain alcohol substrates including hex-trans-2-en-1-ol and octan-1-ol (Banthorpe 1976) (Cardemil 1978). Other plant species, including *Simmondsia chinensis* (Moreau, R. A., Huang 1979), *Arabidopsis thaliana* (Cheng et al. 2004), and *Lotus japonicas* (Zhao et al. 2008) have also been reported as sources of long chain alcohol oxidases. Fatty alcohol oxidases are mostly reported from yeast species (Hommel and Ratledge 1990) (Vanhanen et al. 2000) (Hommel et al. 1994) (Kemp et al. 1990) and these enzymes play an important role in long chain fatty acid metabolism (Cheng et al. 2005). Fatty alcohol oxidases from yeast species that degrade and grow on long chain alkanes and fatty acid catalyze the oxidation of fatty alcohols. Fatty alcohol oxidase from *Candida tropicalis* has been isolated as microsomal cell fractions and characterized for a range of substrates (Eirich et al. 2004) (Kemp et al. 1988) (Kemp et al. 1991) (Mauersberger et al. 1992). Significant activity is observed for primary alcohols of length $C_8$ to $C_{16}$ with reported KM in the 10-50 μM range (Eirich et al. 2004). Alcohol oxidases described may be used for the conversion of medium chain aliphatic alcohols to aldehydes as described, for example, for whole-cells *Candida boidinii* (Gabelman and Luzio 1997), and *Pichia pastoris* (Duff and Murray 1988) (Murray and Duff 1990). Long chain alcohol oxidases from filamentous fungi were produced during growth on hydrocarbon substrates (Kumar and Goswami 2006) (Savitha and Ratledge 1991). The long chain fatty alcohol oxidase (LjFAO1) from *Lotus japonicas* has been heterologously expressed in *E. coli* and exhibited broad substrate specificity for alcohol oxidation including 1-dodecanol and 1-hexadecanol (Zhao et al. 2008).

TABLE 7

Alcohol oxidase enzymes capable of oxidizing short chain alcohols (EC 1.1.3.13)

| Organism | Gene names | Accession No. |
|---|---|---|
| *Komagataella pastoris* (strain ATCC 76273/CBS 7435/CECT 11047/NRRL Y-11430/Wegner 21-1) (Yeast) (*Pichia pastoris*) | AOX1 PP7435_Chr4-0130 | F2QY27 |
| *Komagataella pastoris* (strain GS115/ATCC 20864) (Yeast) (*Pichia pastoris*) | AOX1 PAS_chr4_0821 | P04842 |
| *Komagataella pastoris* (strain ATCC 76273/CBS 7435/CECT 11047/NRRL Y-11430/Wegner 21-1) (Yeast) (*Pichia pastoris*) | AOX2 PP7435_Chr4-0863 | F2R038 |
| *Komagataella pastoris* (strain GS115/ATCC 20864) (Yeast) (*Pichia pastoris*) | AOX2 PAS_chr4_0152 | C4R702 |
| *Candida boidinii* (Yeast) | AOD1 | Q00922 |
| *Pichia angusta* (Yeast) (*Hansenula polymorpha*) | MOX | P04841 |
| *Thanatephorus cucumeris* (strain AG1-IB/isolate 7/3/14) (Lettuce bottom rot fungus) (*Rhizoctonia solani*) | AOD1 BN14_10802 | M5CC52 |
| *Thanatephorus cucumeris* (strain AG1-IB/isolate 7/3/14) (Lettuce bottom rot fungus) (*Rhizoctonia solani*) | MOX BN14_12214 | M5CF32 |
| *Thanatephorus cucumeris* (strain AG1-IB/isolate 7/3/14) (Lettuce bottom rot fungus) (*Rhizoctonia solani*) | AOD1 BN14_10691 | M5CAV1 |
| *Thanatephorus cucumeris* (strain AG1-IB/isolate 7/3/14) (Lettuce bottom rot fungus) (*Rhizoctonia solani*) | AOD1 BN14_09479 | M5C7F4 |
| *Thanatephorus cucumeris* (strain AG1-IB/isolate 7/3/14) (Lettuce bottom rot fungus) (*Rhizoctonia solani*) | AOD1 BN14_10803 | M5CB66 |
| *Thanatephorus cucumeris* (strain AG1-IB/isolate 7/3/14) (Lettuce bottom rot fungus) (*Rhizoctonia solani*) | AOD1 BN14_09900 | M5C9N9 |
| *Thanatephorus cucumeris* (strain AG1-IB/isolate 7/3/14) (Lettuce bottom rot fungus) (*Rhizoctonia solani*) | AOD1 BN14_08302 | M5C2L8 |
| *Thanatephorus cucumeris* (strain AG1-IB/isolate 7/3/14) (Lettuce bottom rot fungus) (*Rhizoctonia solani*) | MOX BN14_09408 | M5C784 |
| *Thanatephorus cucumeris* (strain AG1-IB/isolate 7/3/14) (Lettuce bottom rot fungus) (*Rhizoctonia solani*) | MOX BN14_09478 | M5C8F8 |
| *Thanatephorus cucumeris* (strain AG1-IB/isolate 7/3/14) (Lettuce bottom rot fungus) (*Rhizoctonia solani*) | AOD1 BN14_11356 | M5CH40 |
| *Ogataea henricii* | AOD1 | A5LGF0 |
| *Candida methanosorbosa* | AOD1 | A5LGE5 |
| *Candida methanolovescens* | AOD1 | A5LGE4 |
| *Candida succiphila* | AOD1 | A5LGE6 |
| *Aspergillus niger* (strain CBS 513.88/FGSC A1513) | An15g02200 | A2R501 |
| *Aspergillus niger* (strain CBS 513.88/FGSC A1513) | An18g05480 | A2RB46 |
| *Moniliophthora perniciosa* (Witches'-broom disease fungus) (*Marasmius perniciosus*) | | I7CMK2 |
| *Candida cariosilignicola* | AOD1 | A5LGE3 |
| *Candida pignaliae* | AOD1 | A5LGE1 |
| *Candida pignaliae* | AOD2 | A5LGE2 |
| *Candida sonorensis* | AOD1 | A5LGD9 |
| *Candida sonorensis* | AOD2 | A5LGE0 |
| *Pichia naganishii* | AOD1 | A5LGF2 |
| *Ogataea minuta* | AOD1 | A5LGF1 |
| *Ogataea philodendri* | AOD1 | A5LGF3 |
| *Ogataea wickerhamii* | AOD1 | A5LGE8 |
| *Kuraishia capsulata* | AOD1 | A5LGE7 |
| *Talaromyces stipitatus* (strain ATCC 10500/CBS 375.48/QM 6759/NRRL 1006) (*Penicillium stipitatum*) | TSTA_021940 | B8MHF8 |
| *Talaromyces stipitatus* (strain ATCC 10500/CBS 375.48/QM 6759/NRRL 1006) (*Penicillium stipitatum*) | TSTA_065150 | B8LTH7 |
| *Talaromyces stipitatus* (strain ATCC 10500/CBS 375.48/QM 6759/NRRL 1006) (*Penicillium stipitatum*) | TSTA_065150 | B8LTH8 |
| *Talaromyces stipitatus* (strain ATCC 10500/CBS 375.48/QM 6759/NRRL 1006) (*Penicillium stipitatum*) | TSTA_000410 | B8MSB1 |
| *Ogataea glucozyma* | AOD1 | A5LGE9 |
| *Ogataea parapolymorpha* (strain DL-1/ATCC 26012/NRRL Y-7560) (Yeast) (*Hansenula polymorpha*) | HPODL_03886 | W1QCJ3 |
| *Gloeophyllum trabeum* (Brown rot fungus) | AOX | A8DPS4 |
| *Pichia angusta* (Yeast) (*Hansenula polymorpha*) | mox1 | A6PZG8 |
| *Pichia trehalophila* | AOD1 | A5LGF4 |

TABLE 7-continued

Alcohol oxidase enzymes capable of oxidizing short chain alcohols (EC 1.1.3.13)

| Organism | Gene names | Accession No. |
|---|---|---|
| *Pichia angusta* (Yeast) (*Hansenula polymorpha*) | mox1 | A6PZG9 |
| *Pichia angusta* (Yeast) (*Hansenula polymorpha*) | mox1 | A6PZG7 |
| *Ixodes scapularis* (Black-legged tick) (Deer tick) | IscW_ISCW017898 | B7PIZ7 |

TABLE 8

Alcohol oxidase enzymes capable of oxidizing long chain alcohols including fatty alcohols (EC 1.1.3.20)

| Organism | Gene names | Accession No. |
|---|---|---|
| *Lotus japonicus* (*Lotus corniculatus* var. *japonicus*) | FAO1 | B5WWZ8 |
| *Arabidopsis thaliana* (Mouse-ear cress) | FAO1 At1g03990 F21M11.7 | Q9ZWB9 |
| *Lotus japonicus* (*Lotus corniculatus* var. *japonicus*) | FAO2 | B5WWZ9 |
| *Arabidopsis thaliana* (Mouse-ear cress) | FAO3 At3g23410 MLM24.14 MLM24.23 | Q9LW56 |
| *Arabidopsis thaliana* (Mouse-ear cress) | FAO4A At4g19380 T5K18.160 | O65709 |
| *Arabidopsis thaliana* (Mouse-ear cress) | FAO4B At4g28570 T5F17.20 | Q94BP3 |
| *Microbotryum violaceum* (strain p1A1 Lamole) (Anther smut fungus) (*Ustilago violacea*) | MVLG_06864 | U5HIL4 |
| *Ajellomyces dermatitidis* ATCC 26199 | BDFG_03507 | T5BNQ0 |
| *Gibberella zeae* (strain PH-1/ATCC MYA-4620/FGSC 9075/NRRL 31084) (Wheat head blight fungus) (*Fusarium graminearum*) | FG06918.1 FGSG_06918 | I1RS14 |
| *Pichia sorbitophila* (strain ATCC MYA-4447/BCRC 22081/CBS 7064/NBRC 10061/NRRL Y-12695) (Hybrid yeast) | Piso0_004410 GNLVRS01_PISO0K16268g GNLVRS01_PISO0L16269g | G8Y5E1 |
| *Emericella nidulans* (strain FGSC A4/ATCC 38163/CBS 112.46/NRRL 194/M139) (*Aspergillus nidulans*) | AN0623.2 ANIA_00623 | Q5BFQ7 |
| *Pyrenophora tritici-repentis* (strain Pt-1C-BFP) (Wheat tan spot fungus) (*Drechslera tritici-repentis*) | PTRG_10154 | B2WJW5 |
| *Paracoccidioides lutzii* (strain ATCC MYA-826/Pb01) (*Paracoccidioides brasiliensis*) | PAAG_09117 | C1HEC6 |
| *Candida parapsilosis* (strain CDC 317/ATCC MYA-4646) (Yeast) (*Monilia parapsilosis*) | CPAR2_204420 | G8BG15 |
| *Pseudozyma brasiliensis* (strain GHG001) (Yeast) | PSEUBRA_SCAF2g03010 | V5GPS6 |
| *Candida parapsilosis* (strain CDC 317/ATCC MYA-4646) (Yeast) (*Monilia parapsilosis*) | CPAR2_204430 | G8BG16 |
| *Sclerotinia borealis* F-4157 | SBOR_5750 | W9CDE2 |
| *Sordaria macrospora* (strain ATCC MYA-333/DSM 997/K(L3346)/K-hell) | SMAC_06361 | F7W6K4 |
| *Sordaria macrospora* (strain ATCC MYA-333/DSM 997/K(L3346)/K-hell) | SMAC_01933 | F7VSA1 |
| *Meyerozyma guilliermondii* (strain ATCC 6260/CBS 566/DSM 6381/JCM 1539/NBRC 10279/NRRL Y-324) (Yeast) (*Candida guilliermondii*) | PGUG_03467 | A5DJL6 |
| *Trichophyton rubrum* CBS 202.88 | H107_00669 | A0A023ATC5 |
| *Arthrobotrys oligospora* (strain ATCC 24927/CBS 115.81/DSM 1491) (Nematode-trapping fungus) (*Didymozoophaga oligospora*) | AOL_s00097g516 | G1XJI9 |
| *Scheffersomyces stipitis* (strain ATCC 58785/CBS 6054/NBRC 10063/NRRL Y-11545) (Yeast) (*Pichia stipitis*) | FAO1 PICST_90828 | A3LYX9 |
| *Scheffersomyces stipitis* (strain ATCC 58785/CBS 6054/NBRC 10063/NRRL Y-11545) (Yeast) (*Pichia stipitis*) | FAO2 PICST_32359 | A3LW61 |
| *Aspergillus oryzae* (strain 3.042) (Yellow koji mold) | Ao3042_09114 | I8TL25 |
| *Fusarium oxysporum* (strain Fo5176) (*Fusarium* vascular wilt) | FOXB_17532 | F9GFU8 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_08271 | I1C536 |
| *Rhizopus delemar* (strain RA 99-880/ATCC MYA-4621/FGSC 9543/NRRL 43880) (Mucormycosis agent) (*Rhizopus arrhizus* var. *delemar*) | RO3G_00154 | I1BGX0 |
| *Fusarium oxysporum* (strain Fo5176) (*Fusarium* vascular wilt) | FOXB_07532 | F9FMA2 |
| *Penicillium roqueforti* | PROQFM164_S02g001772 | W6QPY1 |
| *Aspergillus clavatus* (strain ATCC 1007/CBS 513.65/DSM 816/NCTC 3887/NRRL 1) | ACLA_018400 | A1CNB5 |
| *Arthroderma otae* (strain ATCC MYA-4605/CBS 113480) (*Microsporum canis*) | MCYG_08732 | C5G1B0 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Trichophyton tonsurans* (strain CBS 112818) (Scalp ringworm fungus) | TESG_07214 | F2S8I2 |
| *Colletotrichum higginsianum* (strain IMI 349063) (Crucifer anthracnose fungus) | CH063_13441 | H1VUE7 |
| *Ajellomyces capsulatus* (strain H143) (Darling's disease fungus) (*Histoplasma capsulatum*) | HCDG_07658 | C6HN77 |
| *Trichophyton rubrum* (strain ATCC MYA-4607/ CBS 118892) (Athlete's foot fungus) | TERG_08235 | F2TO96 |
| *Cochliobolus heterostrophus* (strain C5/ATCC 48332/race O) (Southern corn leaf blight fungus) (*Bipolaris maydis*) | COCHEDRAFT_1201414 | M2UMT9 |
| *Candida orthopsilosis* (strain 90-125) (Yeast) | CORT_0D04510 | H8X643 |
| *Candida orthopsilosis* (strain 90-125) (Yeast) | CORT_0D04520 | H8X644 |
| *Candida orthopsilosis* (strain 90-125) (Yeast) | CORT_0D04530 | H8X645 |
| *Pseudozyma aphidis* DSM 70725 | PaG_03027 | W3VP49 |
| *Coccidioides posadasii* (strain C735) (Valley fever fungus) | CPC735_000380 | C5P005 |
| *Magnaporthe oryzae* (strain P131) (Rice blast fungus) (*Pyricularia oryzae*) | OOW_P131scaffold01214g15 | L7IZ92 |
| *Neurospora tetrasperma* (strain FGSC 2508/ATCC MYA-4615/P0657) | NEUTE1DRAFT_82541 | F8MKD1 |
| *Hypocrea virens* (strain Gv29-8/FGSC 10586) (*Gliocladium virens*) (*Trichoderma virens*) | TRIVIDRAFT_54537 | G9MMY7 |
| *Hypocrea virens* (strain Gv29-8/FGSC 10586) (*Gliocladium virens*) (*Trichoderma virens*) | TRIVIDRAFT_53801 | G9MT89 |
| *Aspergillus niger* (strain CBS 513.88/FGSC A1513) | An01g09620 | A2Q9Z3 |
| *Verticillium dahliae* (strain VdLs.17/ATCC MYA-4575/ FGSC 10137) (*Verticillium* wilt) | VDAG_05780 | G2X6J8 |
| *Ustilago maydis* (strain 521/FGSC 9021) (Corn smut fungus) | UM02023.1 | Q4PCZ0 |
| *Fusarium oxysporum* f. sp. *lycopersici* MN25 | FOWG_13006 | W9LNI9 |
| *Fusarium oxysporum* f. sp. *lycopersici* MN25 | FOWG_02542 | W9N9Z1 |
| *Candida tropicalis* (Yeast) | FAO1 | Q6QIR6 |
| *Magnaporthe oryzae* (strain 70-15/ATCC MYA-4617/ FGSC 8958) (Rice blast fungus) (*Pyricularia oryzae*) | MGG_11317 | G4MVK1 |
| *Candida tropicalis* (Yeast) | faot | Q9P8D9 |
| *Candida tropicalis* (Yeast) | FAO2a | Q6QIR5 |
| *Phaeosphaeria nodorum* (strain SN15/ATCC MYA-4574/FGSC 10173) (Glume blotch fungus) (*Septoria nodorum*) | SNOG_02371 | Q0V0U3 |
| *Candida tropicalis* (Yeast) | FAO2b | Q6QIR4 |
| *Pestalotiopsis fici* W106-1 | PFICI_11209 | W3WU04 |
| *Magnaporthe oryzae* (strain Y34) (Rice blast fungus) (*Pyricularia oryzae*) | OOU_Y34scaffold00240g57 | L7IFT5 |
| *Pseudogymnoascus destructans* (strain ATCC MYA-4855/20631-21) (Bat white-nose syndrome fungus) (*Geomyces destructans*) | GMDG_01756 | L8G0G6 |
| *Pseudogymnoascus destructans* (strain ATCC MYA-4855/20631-21) (Bat white-nose syndrome fungus) (*Geomyces destructans*) | GMDG_04950 | L8GCY2 |
| *Mycosphaerella fijiensis* (strain CIRAD86) (Black leaf streak disease fungus) (*Pseudocercospora fijiensis*) | MYCFIDRAFT_52380 | M2Z831 |
| *Bipolaris oryzae* ATCC 44560 | COCMIDRAFT_84580 | W7A0I8 |
| *Cladophialophora psammophila* CBS 110553 | A1O5_08147 | W9WTM9 |
| *Fusarium oxysporum* f. sp. *melonis* 26406 | FOMG_05173 | X0AEE6 |
| *Fusarium oxysporum* f. sp. *melonis* 26406 | FOMG_17829 | W9ZBB7 |
| *Cyphellophora europaea* CBS 101466 | HMPREF1541_02174 | W2S2S5 |
| *Aspergillus kawachii* (strain NBRC 4308) (White koji mold) (*Aspergillus awamori* var. *kawachi*) | AKAW_00147 | G7X626 |
| *Aspergillus terreus* (strain NIH 2624/FGSC A1156) | ATEG_05086 | Q0CMJ8 |
| *Coccidioides immitis* (strain RS) (Valley fever fungus) | CIMG_02987 | J3KAI8 |
| *Ajellomyces dermatitidis* (strain ER-3/ATCC MYA-2586) (*Blastomyces dermatitidis*) | BDCG_04701 | C5GLS5 |
| *Fusarium oxysporum* f. sp. *cubense* (strain race 1) (Panama disease fungus) | FOC1_g10013865 | N4U732 |
| *Rhodotorula glutinis* (strain ATCC 204091/IIP 30/ MTCC 1151) (Yeast) | RTG_00643 | G0SVU8 |
| *Aspergillus niger* (strain ATCC 1015/CBS 113.46/ FGSC A1144/LSHB Ac4/NCTC 3858a/NRRL 328/USDA 3528.7) | ASPNIDRAFT_35778 | G3XTM6 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Candida cloacae* | fao1 | Q9P8D8 |
| *Candida cloacae* | fao2 | Q9P8D7 |
| *Fusarium oxysporum* f. sp. *cubense* (strain race 1) (Panama disease fungus) | FOC1_g10006358 | N4TUH3 |
| *Candida albicans* (strain SC5314/ATCC MYA-2876) (Yeast) | FAO1 CaO19.13562 orf19.13562 | Q59RS8 |
| *Candida albicans* (strain SC5314/ATCC MYA-2876) (Yeast) | FAO1 CaO19.6143 orf19.6143 | Q59RP0 |
| *Chaetomium thermophilum* (strain DSM 1495/CBS 144.50/IMI 039719) | CTHT_0018560 | G0S2U9 |
| *Mucor circinelloides* f. *circinelloides* (strain 1006PhL) (Mucormycosis agent) (*Calyptromyces circinelloides*) | HMPREF1544_05296 | S2JDN0 |
| *Mucor circinelloides* f. *circinelloides* (strain 1006PhL) (Mucormycosis agent) (*Calyptromyces circinelloides*) | HMPREF1544_05295 | S2JYP5 |
| *Mucor circinelloides* f. *circinelloides* (strain 1006PhL) (Mucormycosis agent) (*Calyptromyces circinelloides*) | HMPREF1544_06348 | S2JVK9 |
| *Botryotinia fuckeliana* (strain BcDW1) (Noble rot fungus) (*Botrytis cinerea*) | BcDW1_6807 | M7UD26 |
| *Podospora anserina* (strain S/ATCC MYA-4624/DSM 980/FGSC 10383) (*Pleurage anserina*) | PODANS_5_13040 | B2AFD8 |
| *Neosartorya fumigata* (strain ATCC MYA-4609/Af293/CBS 101355/FGSC A1100) (*Aspergillus fumigatus*) | AFUA_1G17110 | Q4WR91 |
| *Fusarium oxysporum* f. sp. *vasinfectum* 25433 | FOTG_00686 | X0MEE6 |
| *Fusarium oxysporum* f. sp. *vasinfectum* 25433 | FOTG_12485 | X0LE98 |
| *Trichophyton interdigitale* H6 | H101_06625 | A0A022U717 |
| *Beauveria bassiana* (strain ARSEF 2860) (White muscardine disease fungus) (*Tritirachium shiotae*) | BBA_04100 | J4UNY3 |
| *Fusarium oxysporum* f. sp. *radicis-lycopersici* 26381 | FOCG_00843 | X0GQ62 |
| *Fusarium oxysporum* f. sp. *radicis-lycopersici* 26381 | FOCG_15170 | X0F4T1 |
| *Neurospora tetrasperma* (strain FGSC 2509/P0656) | NEUTE2DRAFT_88670 | G4UNN6 |
| *Pseudozyma hubeiensis* (strain SY62) (Yeast) | PHSY_000086 | R9NVU1 |
| *Lodderomyces elongisporus* (strain ATCC 11503/CBS 2605/JCM 1781/NBRC 1676/NRRL YB-4239) (Yeast) (*Saccharomyces elongisporus*) | LELG_03289 | A5E102 |
| *Malassezia globosa* (strain ATCC MYA-4612/CBS 7966) (Dandruff-associated fungus) | MGL_3855 | A8QAY8 |
| *Byssochlamys spectabilis* (strain No. 5/NBRC 109023) (*Paecilomyces variotii*) | PVAR5_7014 | V5GBL6 |
| *Ajellomyces capsulatus* (strain H88) (Darling's disease fungus) (*Histoplasma capsulatum*) | HCEG_03274 | F0UF47 |
| *Trichosporon asahii* var. *asahii* (strain ATCC 90039/CBS 2479/JCM 2466/KCTC 7840/NCYC 2677/UAMH 7654) (Yeast) | A1Q1_03669 | J6FBP4 |
| *Penicillium oxalicum* (strain 114-2/CGMCC 5302) (*Penicillium decumbens*) | PDE_00027 | S7Z8U8 |
| *Fusarium oxysporum* f. sp. *conglutinans* race 2 54008 | FOPG_02304 | X0IBE3 |
| *Fusarium oxysporum* f. sp. *conglutinans* race 2 54008 | FOPG_13066 | X0H540 |
| *Fusarium oxysporum* f. sp. *raphani* 54005 | FOQG_00704 | X0D1G8 |
| *Fusarium oxysporum* f. sp. *raphani* 54005 | FOQG_10402 | X0C482 |
| *Metarhizium acridum* (strain CQMa 102) | MAC_03115 | E9DZR7 |
| *Arthroderma benhamiae* (strain ATCC MYA-4681/CBS 112371) (*Trichophyton mentagrophytes*) | ARB_02250 | D4B1C1 |
| *Fusarium oxysporum* f. sp. *cubense* tropical race 4 54006 | FOIG_12161 | X0JFI6 |
| *Fusarium oxysporum* f. sp. *cubense* tropical race 4 54006 | FOIG_12751 | X0JDU5 |
| *Cochliobolus heterostrophus* (strain C4/ATCC 48331/race T) (Southern corn leaf blight fungus) (*Bipolaris maydis*) | COCC4DRAFT_52836 | N4WZZ0 |
| *Trichosporon asahii* var. *asahii* (strain CBS 8904) (Yeast) | A1Q2_00631 | K1VZW1 |
| *Mycosphaerella graminicola* (strain CBS 115943/IPO323) (Speckled leaf blotch fungus) (*Septoria tritici*) | MYCGRDRAFT_37086 | F9X375 |
| *Botryotinia fuckeliana* (strain T4) (Noble rot fungus) (*Botrytis cinerea*) | BofuT4_P072020.1 | G2XQ18 |
| *Metarhizium anisopliae* (strain ARSEF 23/ATCC MYA-3075) | MAA_05783 | E9F0I4 |
| *Cladophialophora carrionii* CBS 160.54 | G647_05801 | V9DAR1 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Coccidioides posadasii* (strain RMSCC 757/Silveira) (Valley fever fungus) | CPSG_09174 | E9DH75 |
| *Rhodosporidium toruloides* (strain NP11) (Yeast) (*Rhodotorula gracilis*) | RHTO_06879 | M7X159 |
| *Puccinia graminis* f. sp. *tritici* (strain CRL 75-36-700-3/race SCCL) (Black stem rust fungus) | PGTG_10521 | E3KIL8 |
| *Trichophyton rubrum* CBS 288.86 | H103_00624 | A0A022WG28 |
| *Colletotrichum fioriniae* PJ7 | CFIO01_08202 | A0A010RKZ4 |
| *Trichophyton rubrum* CBS 289.86 | H104_00611 | A0A022XB46 |
| *Cladophialophora yegresii* CBS 114405 | A1O7_02579 | W9WC55 |
| *Colletotrichum orbiculare* (strain 104-T/ATCC 96160/CBS 514.97/LARS 414/MAFF 240422) (Cucumber anthracnose fungus) (*Colletotrichum lagenarium*) | Cob_10151 | N4VFP3 |
| *Drechslerella stenobrocha* 248 | DRE_03459 | W7IDL6 |
| *Neosartorya fumigata* (strain CEA10/CBS 144.89/FGSC A1163) (*Aspergillus fumigatus*) | AFUB_016500 | B0XP90 |
| *Thielavia terrestris* (strain ATCC 38088/NRRL 8126) (*Acremonium alabamense*) | THITE_2117674 | G2R8H9 |
| *Gibberella fujikuroi* (strain CBS 195.34/IMI 58289/NRRL A-6831) (Bakanae and foot rot disease fungus) (*Fusarium fujikuroi*) | FFUJ_02948 | S0DZP7 |
| *Gibberella fujikuroi* (strain CBS 195.34/IMI 58289/NRRL A-6831) (Bakanae and foot rot disease fungus) (*Fusarium fujikuroi*) | FFUJ_12030 | S0EMC6 |
| *Aspergillus flavus* (strain ATCC 200026/FGSC A1120/NRRL 3357/JCM 12722/SRRC 167) | AFLA_109870 | B8N941 |
| *Togninia minima* (strain UCR-PA7) (Esca disease fungus) (*Phaeoacremonium aleophilum*) | UCRPA7_1719 | R8BTZ6 |
| *Ajellomyces dermatitidis* (strain ATCC 18188/CBS 674.68) (*Blastomyces dermatitidis*) | BDDG_09783 | F2TUC0 |
| *Macrophomina phaseolina* (strain MS6) (Charcoal rot fungus) | MPH_10582 | K2RHA5 |
| *Neurospora crassa* (strain ATCC 24698/74-OR23-1A/CBS 708.71/DSM 1257/FGSC 987) | NCU08977 | Q7S2Z2 |
| *Neosartorya fischeri* (strain ATCC 1020/DSM 3700/FGSC A1164/NRRL 181) (*Aspergillus fischerianus*) | NFIA_008260 | A1D156 |
| *Fusarium pseudograminearum* (strain CS3096) (Wheat and barley crown-rot fungus) | FPSE_11742 | K3U9J5 |
| *Spathaspora passalidarum* (strain NRRL Y-27907/11-Y1) | SPAPADRAFT_54193 | G3AJP0 |
| *Spathaspora passalidarum* (strain NRRL Y-27907/11-Y1) | SPAPADRAFT_67198 | G3ANX7 |
| *Trichophyton verrucosum* (strain HKI 0517) | TRV_07960 | D4DL86 |
| *Arthroderma gypseum* (strain ATCC MYA-4604/CBS 118893) (*Microsporum gypseum*) | MGYG_07264 | E4V2J0 |
| *Hypocrea jecorina* (strain QM6a) (*Trichoderma reesei*) | TRIREDRAFT_43893 | G0R7P8 |
| *Trichophyton rubrum* MR1448 | H110_00629 | A0A022Z1G4 |
| *Aspergillus ruber* CBS 135680 | EURHEDRAFT_512125 | A0A017SPR0 |
| *Glarea lozoyensis* (strain ATCC 20868/MF5171) | GLAREA_04397 | S3D6C1 |
| *Setosphaeria turcica* (strain 28A) (Northern leaf blight fungus) (*Exserohilum turcicum*) | SETTUDRAFT_20639 | R0K6H8 |
| *Paracoccidioides brasiliensis* (strain Pb18) | PADG_06552 | C1GH16 |
| *Fusarium oxysporum* Fo47 | FOZG_13577 | W9JPG9 |
| *Fusarium oxysporum* Fo47 | FOZG_05344 | W9KPH3 |
| *Trichophyton rubrum* MR1459 | H113_00628 | A0A022ZY09 |
| *Penicillium marneffei* (strain ATCC 18224/CBS 334.59/QM 7333) | PMAA_075740 | B6QBY3 |
| *Sphaerulina musiva* (strain SO2202) (Poplar stem canker fungus) (*Septoria musiva*) | SEPMUDRAFT_154026 | M3DAK6 |
| *Gibberella moniliformis* (strain M3125/FGSC 7600) (Maize ear and stalk rot fungus) (*Fusarium verticillioides*) | FVEG_10526 | W7N4P8 |
| *Gibberella moniliformis* (strain M3125/FGSC 7600) (Maize ear and stalk rot fungus) (*Fusarium verticillioides*) | FVEG_08281 | W7MVR9 |
| *Pseudozyma antarctica* (strain T-34) (Yeast) (*Candida antarctica*) | PANT_22d00298 | M9MGF2 |
| *Paracoccidioides brasiliensis* (strain Pb03) | PABG_07795 | C0SJD4 |
| *Rhizophagus irregularis* (strain DAOM 181602/DAOM 197198/MUCL 43194) (Arbuscular mycorrhizal fungus) (*Glomus intraradices*) | GLOINDRAFT_82554 | U9TF61 |
| *Penicillium chrysogenum* (strain ATCC 28089/ | Pc21g23700 | B6HJ58 |

TABLE 8-continued

Alcohol oxidase enzymes capable of oxidizing long chain
alcohols including fatty alcohols (EC 1.1.3.20)

| Organism | Gene names | Accession No. |
|---|---|---|
| DSM 1075/Wisconsin 54-1255) (*Penicillium notatum*) | PCH_Pc21g23700 | |
| *Baudoinia compniacensis* (strain UAMH 10762) (Angels' share fungus) | BAUCODRAFT_274597 | M2M6Z5 |
| *Hypocrea atroviridis* (strain ATCC 20476/IMI 206040) (*Trichoderma atroviride*) | TRIATDRAFT_280929 | G9NJ32 |
| *Colletotrichum gloeosporioides* (strain Cg-14) (Anthracnose fungus) (*Glomerella cingulata*) | CGLO_06642 | T0LPH0 |
| *Cordyceps militaris* (strain CM01) (Caterpillar fungus) | CCM_02665 | G3JB34 |
| *Pyronema omphalodes* (strain CBS 100304) (*Pyronema confluens*) | PCON_13062 | U4LKE9 |
| *Colletotrichum graminicola* (strain M1.001/M2/FGSC 10212) (Maize anthracnose fungus) (*Glomerella graminicola*) | GLRG_08499 | E3QR67 |
| *Glarea lozoyensis* (strain ATCC 74030/MF5533) | M7I_2117 | H0EHX4 |
| *Fusarium oxysporum* f. sp. *cubense* (strain race 4) (Panama disease fungus) | FOC4_g10002493 | N1S969 |
| *Fusarium oxysporum* f. sp. *cubense* (strain race 4) (Panama disease fungus) | FOC4_g10011461 | N1RT80 |
| *Cochliobolus sativus* (strain ND90Pr/ATCC 201652) (Common root rot and spot blotch fungus) (*Bipolaris sorokiniana*) | COCSADRAFT_295770 | M2TBE4 |
| *Mixia osmundae* (strain CBS 9802/IAM 14324/JCM 22182/KY 12970) | Mo05571 E5Q_05571 | G7E7S3 |
| *Mycosphaerella pini* (strain NZE10/CBS 128990) (Red band needle blight fungus) (*Dothistroma septosporum*) | DOTSEDRAFT_69651 | N1PXR0 |
| *Grosmannia clavigera* (strain kw1407/UAMH 11150) (Blue stain fungus) (*Graphiocladiella clavigera*) | CMQ_1113 | F0XC64 |
| *Fusarium oxysporum* FOSC 3-a | FOYG_03004 | W9IUE5 |
| *Fusarium oxysporum* FOSC 3-a | FOYG_16040 | W9HNP0 |
| *Fusarium oxysporum* FOSC 3-a | FOYG_17058 | W9HB31 |
| *Nectria haematococca* (strain 77-13-4/ATCC MYA-4622/FGSC 9596/MPVI) (*Fusarium solani* subsp. *pisi*) | NECHADRAFT_37686 | C7YQL1 |
| *Nectria haematococca* (strain 77-13-4/ATCC MYA-4622/FGSC 9596/MPVI) (*Fusarium solani* subsp. *pisi*) | NECHADRAFT_77262 | C7ZJI0 |
| *Tuber melanosporum* (strain Mel28) (Perigord black truffle) | GSTUM_00010376001 | D5GLS0 |
| *Ajellomyces dermatitidis* (strain SLH14081) (*Blastomyces dermatitidis*) | BDBG_07633 | C5JYI9 |
| *Chaetomium globosum* (strain ATCC 6205/CBS 148.51/DSM 1962/NBRC 6347/NRRL 1970) (Soil fungus) | CHGG_09885 | Q2GQ69 |
| *Candida tenuis* (strain ATCC 10573/BCRC 21748/CBS 615/JCM 9827/NBRC 10315/NRRL Y-1498/VKM Y-70) (Yeast) | CANTEDRAFT_108652 | G3B9Z1 |
| *Trichophyton rubrum* CBS 100081 | H102_00622 | A0A022VKY4 |
| *Pyrenophora teres* f. *teres* (strain 0-1) (Barley net blotch fungus) (*Drechslera teres* f. *teres*) | PTT_09421 | E3RLZ3 |
| *Colletotrichum gloeosporioides* (strain Nara gc5) (Anthracnose fungus) (*Glomerella cingulata*) | CGGC5_4608 | L2GB29 |
| *Gibberella zeae* (Wheat head blight fungus) (*Fusarium graminearum*) | FG05_06918 | A0A016PCS4 |
| *Trichophyton soudanense* CBS 452.61 | H105_00612 | A0A022Y6A6 |
| *Sclerotinia sclerotiorum* (strain ATCC 18683/1980/Ss-1) (White mold) (*Whetzelinia sclerotiorum*) | SS1G_07437 | A7EQ37 |
| *Fusarium oxysporum* f. sp. *pisi* HDV247 | FOVG_14401 | W9NWU8 |
| *Fusarium oxysporum* f. sp. *pisi* HDV247 | FOVG_02874 | W9Q5V3 |
| *Ustilago hordei* (strain Uh4875-4) (Barley covered smut fungus) | UHOR_03009 | I2G1Z4 |
| *Sporisorium reilianum* (strain SRZ2) (Maize head smut fungus) | sr12985 | E6ZYF7 |
| *Bipolaris zeicola* 26-R-13 | COCCADRAFT_81154 | W6YIP8 |
| *Melampsora larici-populina* (strain 98AG31/pathotype 3-4-7) (Poplar leaf rust fungus) | MELLADRAFT_78490 | F4RUZ8 |
| *Fusarium oxysporum* f. sp. *lycopersici* (strain 4287/CBS 123668/FGSC 9935/NRRL 34936) (*Fusarium* vascular wilt of tomato) | FOXG_01901 | J9MG95 |
| *Fusarium oxysporum* f. sp. *lycopersici* (strain 4287/CBS 123668/FGSC 9935/NRRL 34936) (*Fusarium* vascular wilt of tomato) | FOXG_11941 | J9N9S4 |

TABLE 8-continued

Alcohol oxidase enzymes capable of oxidizing long chain
alcohols including fatty alcohols (EC 1.1.3.20)

| Organism | Gene names | Accession No. |
|---|---|---|
| *Bipolaris victoriae* FI3 | COCVIDRAFT_39053 | W7EMJ8 |
| *Debaryomyces hansenii* (strain ATCC 36239/CBS 767/JCM 1990/NBRC 0083/IGC 2968) (Yeast) (*Torulaspora hansenii*) | DEHA2E04268g | Q6BQL4 |
| *Clavispora lusitaniae* (strain ATCC 42720) (Yeast) (*Candida lusitaniae*) | CLUG_01505 | C4XZX3 |
| *Candida albicans* (strain WO-1) (Yeast) | CAWG_02023 | C4YME4 |
| *Trichophyton rubrum* MR850 | H100_00625 | A0A022U0Q2 |
| *Candida dubliniensis* (strain CD36/ATCC MYA-646/CBS 7987/NCPF 3949/NRRL Y-17841) (Yeast) | CD36_32890 | B9WMC7 |
| *Starmerella bombicola* | AOX1 | A0A024FB95 |
| *Thielavia heterothallica* (strain ATCC 42464/BCRC 31852/DSM 1799) (*Myceliophthora thermophila*) | MYCTH_103590 | G2QJL7 |
| *Claviceps purpurea* (strain 20.1) (Ergot fungus) (*Sphacelia segetum*) | CPUR_07614 | M1WFI4 |
| *Aspergillus oryzae* (strain ATCC 42149/RIB 40) (Yellow koji mold) | AO090023000571 | Q2UH61 |
| *Dictyostelium discoideum* (Slime mold) | DDB_0184181 DDB_G0292042 | Q54DT6 |
| *Triticum urartu* (Red wild einkorn) (*Crithodium urartu*) | TRIUR3_22733 | M7YME5 |
| *Solanum tuberosum* (Potato) | PGSC0003DMG400017211 | M1BG07 |
| *Oryza sativa* subsp. *japonica* (Rice) | OSJNBb0044B19.5 LOC_Os10g33540 | Q8W5P8 |
| *Oryza sativa* subsp. *japonica* (Rice) | OJ1234_B11.20 Os02g0621800 | Q6K9N5 |
| *Oryza sativa* subsp. *japonica* (Rice) | OSJNBa0001K12.5 LOC_Os10g33520 | Q8W5P3 |
| *Zea mays* (Maize) | ZEAMMB73_809149 | C0P3J6 |
| *Citrus clementina* | CICLE_v10011111mg | V4S9P4 |
| *Citrus clementina* | CICLE_v10018992mg | V4U4C9 |
| *Citrus clementina* | CICLE_v10004405mg | V4S9D3 |
| *Citrus clementina* | CICLE_v10004403mg | V4RZZ6 |
| *Morus notabilis* | L484_011703 | W9RIK0 |
| *Morus notabilis* | L484_005930 | W9RET7 |
| *Medicago truncatula* (Barrel medic) (*Medicago tribuloides*) | MTR_1g075650 | G7I4U3 |
| *Arabidopsis thaliana* (Mouse-ear cress) | | Q8LDP0 |
| *Medicago truncatula* (Barrel medic) (*Medicago tribuloides*) | MTR_4g081080 | G7JF07 |
| *Simmondsia chinensis* (Jojoba) (*Buxus chinensis*) | | L7VFV2 |
| *Prunus persica* (Peach) (*Amygdalus persica*) | PRUPE_ppa018458mg | M5VXL1 |
| *Aphanomyces astaci* | H257_07411 | W4GI89 |
| *Aphanomyces astaci* | H257_07412 | W4GI44 |
| *Aphanomyces astaci* | H257_07411 | W4GKE3 |
| *Aphanomyces astaci* | H257_07411 | W4GK29 |
| *Aphanomyces astaci* | H257_07411 | W4GJ79 |
| *Aphanomyces astaci* | H257_07411 | W4GI38 |
| *Phaeodactylum tricornutum* (strain CCAP 1055/1) | PHATRDRAFT_48204 | B7G6C1 |
| *Hordeum vulgare* var. *distichum* (Two-rowed barley) | | F2E4R4 |
| *Hordeum vulgare* var. *distichum* (Two-rowed barley) | | F2DZG1 |
| *Hordeum vulgare* var. *distichum* (Two-rowed barley) | | M0YPG7 |
| *Hordeum vulgare* var. *distichum* (Two-rowed barley) | | M0YPG6 |
| *Hordeum vulgare* var. *distichum* (Two-rowed barley) | | F2CUY4 |
| *Ricinus communis* (Castor bean) | RCOM_0867830 | B9S1S3 |
| *Brassica rapa* subsp. *pekinensis* (Chinese cabbage) (*Brassica pekinensis*) | BRA014947 | M4DEM5 |
| *Ricinus communis* (Castor bean) | RCOM_0258730 | B9SV13 |
| *Brassica rapa* subsp. *pekinensis* (Chinese cabbage) (*Brassica pekinensis*) | BRA001912 | M4CCI2 |
| *Brassica rapa* subsp. *pekinensis* (Chinese cabbage) (*Brassica pekinensis*) | BRA012548 | M4D7T8 |
| *Brassica rapa* subsp. *pekinensis* (Chinese cabbage) (*Brassica pekinensis*) | BRA024190 | M4E5Y6 |
| *Brassica rapa* subsp. *pekinensis* (Chinese cabbage) (*Brassica pekinensis*) | BRA015283 | M4DFL0 |

TABLE 8-continued

Alcohol oxidase enzymes capable of oxidizing long chain alcohols including fatty alcohols (EC 1.1.3.20)

| Organism | Gene names | Accession No. |
|---|---|---|
| *Ricinus communis* (Castor bean) | RCOM_1168730 | B9SS54 |
| *Zea mays* (Maize) | | C4J691 |
| *Oryza glaberrima* (African rice) | | I1P2B7 |
| *Zea mays* (Maize) | | B6SXM3 |
| *Zea mays* (Maize) | | C0HFU4 |
| *Aegilops tauschii* (Tausch's goatgrass) (*Aegilops squarrosa*) | F775_19577 | R7W4J3 |
| *Solanum habrochaites* (Wild tomato) (*Lycopersicon hirsutum*) | | R9R6T0 |
| *Physcomitrella patens* subsp. *patens* (Moss) | PHYPADRAFT_124285 | A9S535 |
| *Physcomitrella patens* subsp. *patens* (Moss) | PHYPADRAFT_113581 | A9RG13 |
| *Physcomitrella patens* subsp. *patens* (Moss) | PHYPADRAFT_182504 | A9S9A5 |
| *Solanum pennellii* (Tomato) (*Lycopersicon pennellii*) | | R9R6Q1 |
| *Vitis vinifera* (Grape) | VIT_02s0087g00630 | F6HJ27 |
| *Vitis vinifera* (Grape) | VIT_07s0005g03780 | F6HZM3 |
| *Vitis vinifera* (Grape) | VIT_05s0049g01400 | F6H8T4 |
| *Vitis vinifera* (Grape) | VITISV_019349 | A5AH38 |
| *Capsella rubella* | CARUB_v10013046mg | R0HIT3 |
| *Capsella rubella* | CARUB_v10004212mg | R0GUX4 |
| *Capsella rubella* | CARUB_v10004208mg | R0F3X6 |
| *Capsella rubella* | CARUB_v10012453mg | R0ILD0 |
| *Capsella rubella* | CARUB_v10004208mg | R0GUX1 |
| *Eutrema salsugineum* (Saltwater cress) (*Sisymbrium salsugineum*) | EUTSA_v10024496mg | V4MD54 |
| *Eutrema salsugineum* (Saltwater cress) (*Sisymbrium salsugineum*) | EUTSA_v10020141mg | V4NM59 |
| *Eutrema salsugineum* (Saltwater cress) (*Sisymbrium salsugineum*) | EUTSA_v10024496mg | V4LUR9 |
| *Eutrema salsugineum* (Saltwater cress) (*Sisymbrium salsugineum*) | EUTSA_v10024528mg | V4P767 |
| *Eutrema salsugineum* (Saltwater cress) (*Sisymbrium salsugineum*) | EUTSA_v10006882mg | V4L2P6 |
| *Selaginella moellendorffii* (Spikemoss) | SELMODRAFT_87684 | D8R6Z6 |
| *Selaginella moellendorffii* (Spikemoss) | SELMODRAFT_87621 | D8R6Z5 |
| *Selaginella moellendorffii* (Spikemoss) | SELMODRAFT_74601 | D8QN81 |
| *Selaginella moellendorffii* (Spikemoss) | SELMODRAFT_73531 | D8QN82 |
| *Sorghum bicolor* (Sorghum) (*Sorghum vulgare*) | Sb04g026390 SORBIDRAFT_04g026390 | C5XXS4 |
| *Sorghum bicolor* (Sorghum) (*Sorghum vulgare*) | Sb04g026370 SORBIDRAFT_04g026370 | C5XXS1 |
| *Sorghum bicolor* (Sorghum) (*Sorghum vulgare*) | Sb01g019470 SORBIDRAFT_01g019470 | C5WYH6 |
| *Sorghum bicolor* (Sorghum) (*Sorghum vulgare*) | Sb01g019480 SORBIDRAFT_01g019480 | C5WYH7 |
| *Sorghum bicolor* (Sorghum) (*Sorghum vulgare*) | Sb01g019460 SORBIDRAFT_01g019460 | C5WYH5 |
| *Solanum pimpinellifolium* (Currant tomato) (*Lycopersicon pimpinellifolium*) | | R9R6J2 |
| *Phaseolus vulgaris* (Kidney bean) (French bean) | PHAVU_007G124200g | V7BGM7 |
| *Phaseolus vulgaris* (Kidney bean) (French bean) | PHAVU_011G136600g | V7AI35 |
| *Phaseolus vulgaris* (Kidney bean) (French bean) | PHAVU_001G162800g | V7D063 |
| *Solanum tuberosum* (Potato) | PGSC0003DMG400024294 | M1C923 |
| *Solanum tuberosum* (Potato) | PGSC0003DMG400018458 | M1BKV4 |
| *Solanum tuberosum* (Potato) | PGSC0003DMG400018458 | M1BKV3 |
| *Glycine max* (Soybean) (*Glycine hispida*) | | K7LK61 |
| *Glycine max* (Soybean) (*Glycine hispida*) | | K7KXQ9 |
| *Populus trichocarpa* (Western balsam poplar) (*Populus balsamifera* subsp. *trichocarpa*) | POPTR_0008s16920g | B9HKS3 |
| *Picea sitchensis* (Sitka spruce) (*Pinus sitchensis*) | | B8LQ84 |
| *Populus trichocarpa* (Western balsam poplar) (*Populus balsamifera* subsp. *trichocarpa*) | POPTR_0004s24310g | U5GKQ5 |
| *Populus trichocarpa* (Western balsam poplar) (*Populus balsamifera* subsp. *trichocarpa*) | POPTR_0010s07980g | B9HSG9 |
| *Glycine max* (Soybean) (*Glycine hispida*) | | I1N9S7 |
| *Glycine max* (Soybean) (*Glycine hispida*) | | I1LSK5 |
| *Setaria italica* (Foxtail millet) (*Panicum italicum*) | Si034362m.g | K4A658 |
| *Solanum lycopersicum* (Tomato) (*Lycopersicon esculentum*) | Solyc09g072610.2 | K4CUT7 |
| *Setaria italica* (Foxtail millet) (*Panicum italicum*) | Si016380m.g | K3YQ38 |
| *Solanum lycopersicum* (Tomato) (*Lycopersicon esculentum*) | | R9R6I9 |

TABLE 8-continued

Alcohol oxidase enzymes capable of oxidizing long chain alcohols including fatty alcohols (EC 1.1.3.20)

| Organism | Gene names | Accession No. |
|---|---|---|
| Solanum lycopersicum (Tomato) (Lycopersicon esculentum) | Solyc09g090350.2 | K4CW61 |
| Solanum lycopersicum (Tomato) (Lycopersicon esculentum) | Solyc08g005630.2 | K4CI54 |
| Solanum lycopersicum (Tomato) (Lycopersicon esculentum) | Solyc08g075240.2 | K4CMP1 |
| Setaria italica (Foxtail millet) (Panicum italicum) | Si034359m.g | K4A655 |
| Setaria italica (Foxtail millet) (Panicum italicum) | Si034354m.g | K4A650 |
| Mimulus guttatus (Spotted monkey flower) (Yellow monkey flower) | MIMGU_mgv1a001896mg | A0A022PU07 |
| Mimulus guttatus (Spotted monkey flower) (Yellow monkey flower) | MIMGU_mgv1a022390mg | A0A022RAV4 |
| Mimulus guttatus (Spotted monkey flower) (Yellow monkey flower) | MIMGU_mgv1a001868mg | A0A022S2E6 |
| Mimulus guttatus (Spotted monkey flower) (Yellow monkey flower) | MIMGU_mgv1a001883mg | A0A022S275 |
| Mimulus guttatus (Spotted monkey flower) (Yellow monkey flower) | MIMGU_mgv1a001761mg | A0A022QNF0 |
| Musa acuminata subsp. malaccensis (Wild banana) (Musa malaccensis) | | M0SNA8 |
| Musa acuminata subsp. malaccensis (Wild banana) (Musa malaccensis) | | M0RUT7 |
| Musa acuminata subsp. malaccensis (Wild banana) (Musa malaccensis) | | M0RUK3 |
| Saprolegnia diclina VS20 | SDRG_10901 | T0RG89 |
| Brachypodium distachyon (Purple false brome) (Trachynia distachya) | BRADI3G49085 | I1IBP7 |
| Brachypodium distachyon (Purple false brome) (Trachynia distachya) | BRADI3G28677 | I1I4N2 |
| Brachypodium distachyon (Purple false brome) (Trachynia distachya) | BRADI3G28657 | I1I4N0 |
| Oryza sativa subsp. indica (Rice) | OsI_34012 | B8BHG0 |
| Oryza sativa subsp. indica (Rice) | OsI_08118 | B8AFT8 |
| Oryza sativa subsp. indica (Rice) | OsI_34008 | A2Z8H1 |
| Oryza sativa subsp. indica (Rice) | OsI_34014 | B8BHG1 |
| Oryza sativa subsp. japonica (Rice) | LOC_Os10g33460 | Q7XDG3 |
| Oryza sativa subsp. japonica (Rice) | Os10g0474800 | Q0IX12 |
| Oryza sativa subsp. japonica (Rice) | Os10g0474966 | C7J7R1 |
| Oryza sativa subsp. japonica (Rice) | OSJNBa0001K12.13 | Q8W5N7 |
| Oryza sativa subsp. japonica (Rice) | OsJ_31873 | B9G683 |
| Oryza sativa subsp. japonica (Rice) | OsJ_31875 | B9G684 |
| Oryza sativa subsp. japonica (Rice) | OSJNBa0001K12.3 | Q8W5P5 |
| Arabidopsis lyrata subsp. lyrata (Lyre-leaved rock-cress) | ARALYDRAFT_470376 | D7KDA3 |
| Arabidopsis lyrata subsp. lyrata (Lyre-leaved rock-cress) | ARALYDRAFT_479855 | D7L3B6 |
| Arabidopsis lyrata subsp. lyrata (Lyre-leaved rock-cress) | ARALYDRAFT_491906 | D7MDA9 |
| Arabidopsis lyrata subsp. lyrata (Lyre-leaved rock-cress) | ARALYDRAFT_914728 | D7MGS9 |

In some embodiments, an alcohol dehydrogenase (ADH, Table 9) is used to catalyze the conversion of a fatty alcohol to a fatty aldehyde. A number of ADHs identified from alkanotrophic organisms, Pseudomonas fluorescens NRRL B-1244 (Hou et al. 1983), Pseudomonas butanovora ATCC 43655 (Vangnai and Arp 2001), and Acinetobacter sp. strain M-1 (Tani et al. 2000), have shown to be active on short to medium-chain alkyl alcohols ($C_2$ to $C_{14}$). Additionally, commercially available ADHs from Sigma, Horse liver ADH and Baker's yeast ADH have detectable activity for substrates with length $C_{10}$ and greater. The reported activities for the longer fatty alcohols may be impacted by the difficulties in solubilizing the substrates. For the yeast ADH from Sigma, little to no activity is observed for $C_{12}$ to $C_{14}$ aldehydes by (Tani et al. 2000), however, activity for $C_{12}$ and $C_{16}$ hydroxy-ω-fatty acids has been observed (Lu et al. 2010). Recently, two ADHs were characterized from Geobacillus thermodenitrificans NG80-2, an organism that degrades $C_{15}$ to $C_{36}$ alkanes using the LadA hydroxylase. Activity was detected from methanol to 1-triacontanol ($C_{30}$) for both ADHs, with 1-octanol being the preferred substrate for ADH2 and ethanol for ADH1 (Liu et al. 2009).

The use of ADHs in whole-cell bioconversions has been mostly focused on the production of chiral alcohols from ketones (Ernst et al. 2005) (Schroer et al. 2007). Using the ADH from Lactobacillus brevis and coupled cofactor regeneration with isopropanol, Schroer et al. reported the production of 797 g of (R)-methyl-3 hydroxybutanoate from methyl acetoacetate, with a space time yield of 29 g/L/h (Schroer et al. 2007). Examples of aliphatic alcohol oxidation in whole-cell transformations have been reported with commercially obtained S. cerevisiae for the conversion of hexanol to hexanal (Presecki et al. 2012) and 2-heptanol to 2-heptanone (Cappaert and Larroche 2004).

TABLE 9

Exemplary alcohol dehydrogenase enzymes.

| Organisms | Gene Name | Accession No. |
|---|---|---|
| *Bactrocera oleae* (Olive fruit fly) (*Dacus oleae*) | ADH | Q9NAR7 |
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affinidisjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticornis* (Fruit fly) (*Idiomyia picticornis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyres malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus* sp. (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699/H16/DSM 428/Stanier 337) (*Ralstonia eutropha*) | adh, H16_A0757 | Q0KDL6 |
| *Mycobacterium tuberculosis* (strain CDC 1551/Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618/H37Rv) | adh, Rv1530 | P9WQC3 |
| *Staphylococcus aureus* (strain N315) | adh, SA0562 | Q7A742 |
| *Staphylococcus aureus* (strain bovine RF122/ET3-1) | adh, SAB0557 | Q2YSX0 |
| *Sulfolobus acidocaldarius* (strain ATCC 33909/DSM 639/JCM 8929/NBRC 15157/NCIMB 11770) | adh, Saci_2057 | Q4J781 |
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |
| *Staphylococcus aureus* (strain Mu50/ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984/RP62A) | adh, SERP0257 | Q5HRD6 |
| *Sulfolobus solfataricus* (strain ATCC 35092/DSM 1617/JCM 11322/P2) | adh, SSO2536 | P39462 |
| *Sulfolobus tokodaii* (strain DSM 16993/JCM 10545/NBRC 100140/7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |
| *Ceratitis cosyra* (Mango fruit fly) (*Trypeta cosyra*) | ADH1 | Q70UN9 |
| *Gallus gallus* (Chicken) | ADH1 | P23991 |

TABLE 9-continued

Exemplary alcohol dehydrogenase enzymes.

| Organisms | Gene Name | Accession No. |
|---|---|---|
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adh1 | P23236 |
| *Drosophila montana* (Fruit fly) | Adh1 | P48586 |
| *Drosophila mettleri* (Fruit fly) | Adh1 | P22246 |
| *Drosophila mulleri* (Fruit fly) | Adh1 | P07161 |
| *Drosophila navojoa* (Fruit fly) | Adh1 | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (Petunia) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508/S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972/ATCC 24843) (Fission yeast) | adh1, adh, SPCC13B11.01 | P00332 |
| *Drosophila lacicola* (Fruit fly) | Adh1, Adh-1 | Q27404 |
| *Mus musculus* (Mouse) | Adh1, Adh-1 | P00329 |
| *Peromyscus maniculatus* (North American deer mouse) | ADH1, ADH-1 | P41680 |
| *Rattus norvegicus* (Rat) | Adh1, Adh-1 | P06757 |
| *Drosophila virilis* (Fruit fly) | Adh1, Adh-1, GJ18208 | B4M8Y0 |
| *Scheffersomyces stipitis* (strain ATCC 58785/CBS 6054/NBRC 10063/NRRL Y-11545) (Yeast) (*Pichia stipitis*) | ADH1, ADH2, PICST_68558 | O00097 |
| *Aspergillus flavus* (strain ATCC 200026/FGSC A1120/NRRL 3357/JCM 12722/SRRC 167) | adh1, AFLA_048690 | P41747 |
| *Neurospora crassa* (strain ATCC 24698/74-OR23-1A/CBS 708.71/DSM 1257/FGSC 987) | adh-1, B17C10.210, NCU01754 | Q9P6C8 |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |
| *Drosophila mojavensis* (Fruit fly) | Adh1, GI17644 | P09370 |
| *Kluyveromyces lactis* (strain ATCC 8585/CBS 2359/DSM 70799/NBRC 1267/NRRL Y-1140/WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (Hamadryas baboon) | ADH1B | P14139 |
| *Homo sapiens* (Human) | ADH1B, ADH2 | P00325 |
| *Homo sapiens* (Human) | ADH1C, ADH3 | P00326 |
| *Papio hamadryas* (Hamadryas baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q70UP5 |
| *Ceratitis rosa* (Natal fruit fly) (*Pterandrus rosa*) | ADH2 | Q70UP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |

TABLE 9-continued

Exemplary alcohol dehydrogenase enzymes.

| Organisms | Gene Name | Accession No. |
|---|---|---|
| *Scheffersomyces stipitis* (strain ATCC 58785/CBS 6054/NBRC 10063/NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508/S288c) (Baker's yeast) | ADH2, ADR2, YMR303C, YM9952.05C | P00331 |
| *Candida albicans* (strain SC5314/ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC_Os11g10510 | Q0ITW7 |
| *Drosophila mojavensis* (Fruit fly) | Adh2, GI17643 | P09369 |
| *Kluyveromyces lactis* (strain ATCC 8585/CBS 2359/DSM 70799/NBRC 1267/NRRL Y-1140/WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585/CBS 2359/DSM 70799/NBRC 1267/NRRL Y-1140/WM37) (Yeast) (*Candida sphaerica*) | ADH3, KLLA0B09064g | P49384 |
| *Saccharomyces cerevisiae* (strain ATCC 204508/S288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585/CBS 2359/DSM 70799/NBRC 1267/NRRL Y-1140/WM37) (Yeast) (*Candida sphaerica*) | ADH4, KLLA0F13530g | P49385 |
| *Schizosaccharomyces pombe* (strain 972/ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508/S288c) (Baker's yeast) | ADH4, ZRG5, YGL256W, NRC465 | P10127 |
| *Saccharomyces pastorianus* (Lager yeast) (*Saccharomyces cerevisiae* x *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |
| *Mus musculus* (Mouse) | Adh5, Adh-2, Adh2 | P28474 |
| *Rattus norvegicus* (Rat) | Adh5, Adh-2, Adh2 | P12711 |
| *Oryctolagus cuniculus* (Rabbit) | ADH5, ADH3 | O19053 |
| *Homo sapiens* (Human) | ADH5, ADHX, FDH | P11766 |
| *Dictyostelium discoideum* (Slime mold) | adh5, DDB_G0281865 | Q54TC2 |
| *Saccharomyces cerevisiae* (strain ATCC 204508/S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551/Oshkosh) | adhA, MT1911 | P9WQC0 |
| *Rhizobium meliloti* (strain 1021) (*Ensifer meliloti*) (*Sinorhizobium meliloti*) | adhA, RA0704, SMa1296 | O31186 |
| *Mycobacterium tuberculosis* (strain ATCC 25618/H37Rv) | adhA, Rv1862 | P9WQC1 |
| *Zymomonas mobilis* subsp. *mobilis* (strain ATCC 31821/ZM4/CP4) | adhA ZMO1236 | P20368 |
| *Mycobacterium bovis* (strain ATCC BAA-935/AF2122/97) | adhB, Mb0784c | Q7U1B9 |
| *Mycobacterium tuberculosis* (strain CDC 1551/Oshkosh) | adhB, MT0786 | P9WQC6 |
| *Mycobacterium tuberculosis* (strain ATCC 25618/H37Rv) | adhB, Rv0761c, MTCY369.06c | P9WQC7 |
| *Zymomonas mobilis* subsp. *mobilis* (strain ATCC 31821/ZM4/CP4) | adhB, ZMO1596 | P0DJA2 |
| *Zymomonas mobilis* subsp. *mobilis* (strain ATCC 10988/DSM 424/LMG 404/NCIMB 8938/NRRL B-806/ZM1) | adhB, Zmob_1541 | F8DVL8 |
| *Mycobacterium tuberculosis* (strain CDC 1551/Oshkosh) | adhD, MT3171 | P9WQB8 |
| *Mycobacterium tuberculosis* (strain ATCC 25618/H37Rv) | adhD, Rv3086 | P9WQB9 |

TABLE 9-continued

Exemplary alcohol dehydrogenase enzymes.

| Organisms | Gene Name | Accession No. |
|---|---|---|
| *Clostridium acetobutylicum* (strain ATCC 824/DSM 792/JCM 1419/LMG 5710/VKM B-1787) | adhE, aad, CA_P0162 | P33744 |
| *Escherichia coli* (strain K12) | adhE, ana, b1241, JW1228 | P0A9Q7 |
| *Escherichia coli* O157:H7 | adhE, Z2016, ECs1741 | P0A9Q8 |
| *Rhodobacter sphaeroides* (strain ATCC 17023/2.4.1/NCIB 8253/DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (*Bacillus stearothermophilus*) | adhT | P12311 |
| *Emericella nidulans* (strain FGSC A4/ATCC 38163/CBS 112.46/NRRL 194/M139) (*Aspergillus nidulans*) | alcA, AN8979 | P08843 |
| *Emericella nidulans* (strain FGSC A4/ATCC 38163/CBS 112.46/NRRL 194/M139) (*Aspergillus nidulans*) | alc, AN3741 | P54202 |
| *Emericella nidulans* (strain FGSC A4/ATCC 38163/CBS 112.46/NRRL 194/M139) (*Aspergillus nidulans*) | alcC, adh3, AN2286 | P07754 |
| *Arabidopsis thaliana* (Mouse-ear cress) | At1g22430, F12K8.22 | Q9SK86 |
| *Arabidopsis thaliana* (Mouse-ear cress) | At1g22440, F12K8.21 | Q9SK87 |
| *Arabidopsis thaliana* (Mouse-ear cress) | At1g32780, F6N18.16 | A1L4Y2 |
| *Arabidopsis thaliana* (Mouse-ear cress) | At1g64710, F13O11.3 | Q8VZ49 |
| *Arabidopsis thaliana* (Mouse-ear cress) | At4g22110, F1N20.210 | Q0V7W6 |
| *Arabidopsis thaliana* (Mouse-ear cress) | At5g24760, T4C12_30 | Q8LEB2 |
| *Arabidopsis thaliana* (Mouse-ear cress) | At5g42250, K5J14.5 | Q9FH04 |
| *Zea mays* (Maize) | FDH | P93629 |
| *Drosophila melanogaster* (Fruit fly) | Fdh, gfd, ODH, CG6598 | P46415 |
| *Bacillus subtilis* (strain 168) | gbsB, BSU31050 | P71017 |
| *Caenorhabditis elegans* | H24K24.3 | Q17335 |
| *Oryza sativa* subsp. *japonica* (Rice) | Os02g0815500, LOC_Os02g57040, OsJ_008550, P0643F09.4 | Q0DWH1 |
| *Mycobacterium tuberculosis* (strain ATCC 25618/H37Rv) | Rv1895 | O07737 |
| *Caenorhabditis elegans* | sodh-1, K12G11.3 | Q17334 |
| *Caenorhabditis elegans* | sodh-2, K12G11.4 | O45687 |
| *Pseudomonas* sp. | terPD | P33010 |
| *Escherichia coli* (strain K12) | yiaY, b3589, JW5648 | P37686 |
| *Moraxella* sp. (strain TAE123) | | P81786 |
| *Alligator mississippiensis* (American alligator) | | P80222 |
| *Catharanthus roseus* (Madagascar periwinkle) (*Vinca rosea*) | | P85440 |
| *Gadus morhua* subsp. *callarias* (Baltic cod) (*Gadus callarias*) | | P26325 |
| *Naja naja* (Indian cobra) | | P80512 |
| *Pisum sativum* (Garden pea) | | P12886 |
| *Pelophylax perezi* (Perez's frog) (*Rana perezi*) | | P22797 |
| *Saara hardwickii* (Indian spiny-tailed lizard) (*Uromastyx hardwickii*) | | P25405 |
| *Saara hardwickii* (Indian spiny-tailed lizard) (*Uromastyx hardwickii*) | | P25406 |
| *Equus caballus* (Horse) | | P00327 |
| *Equus caballus* (Horse) | | P00328 |
| *Geobacillus stearothermophilus* (*Bacillus stearothermophilus*) | | P42328 |
| *Gadus morhua* (Atlantic cod) | | P81600 |
| *Gadus morhua* (Atlantic cod) | | P81601 |
| *Myxine glutinosa* (Atlantic hagfish) | | P80360 |
| *Octopus vulgaris* (Common octopus) | | P81431 |
| *Pisum sativum* (Garden pea) | | P80572 |
| *Saara hardwickii* (Indian spiny-tailed lizard) (*Uromastyx hardwickii*) | | P80467 |
| *Scyliorhinus canicula* (Small-spotted catshark) (*Squalus canicula*) | | P86884 |
| *Sparus aurata* (Gilthead sea bream) | | P79896 |

In some embodiments, an α-dioxygenase is used to catalyze the conversion of a fatty acid to a fatty aldehyde (Hamberg et al. 2005). Alpha-dioxygenases catalyze the conversion of a $C_n$ fatty acid to a $C_{n-1}$ aldehyde and may serve as an alternative to both ADH and AOX for fatty aldehyde production if a fatty acid is used as a biotransformation substrate. Due to the chain shortening of the dioxygenase reaction, this route requires a different synthesis pathway compared to the ADH and AOX routes. Biotransformations of *E. coli* cells expressing a rice α-dioxygenase exhibited conversion of C10, C12, C14 and C16 fatty acids to the corresponding $C_{n-1}$ aldehydes. With the addition of the detergent Triton X 100, 3.7 mM of pentadecanal (0.8 g/L) was obtained after 3 hours from hexadecanoic acid with 74% conversion (Kaehne et al. 2011). Exemplary α-dioxygenases are shown in Table 10.

TABLE 10

Exemplary alpha-dioxygenases

| Entry | Organism | Gene names |
|---|---|---|
| Q9SGH6 | *Arabidopsis thaliana* (Mouse-ear cress) | DOX1 DIOX1 PADOX-1 PIOX At3g01420 T13O15.6 |
| Q9C9U3 | *Arabidopsis thaliana* (Mouse-ear cress) | DOX2 DIOX2 At1g73680 F25P22.10 |
| P14550 | *Homo sapiens* (Human) | AKR1A1 ALDR1 ALR |
| Q69EZ9 | *Solanum lycopersicum* (Tomato) (*Lycopersicon esculentum*) | LOC543896 |
| Q5WM33 | *Solanum lycopersicum* (Tomato) (*Lycopersicon esculentum*) | alpha-DOX2 |
| Q69F00 | *Solanum lycopersicum* (Tomato) (*Lycopersicon esculentum*) | |
| D7LAG3 | *Arabidopsis lyrata* subsp. *lyrata* (Lyre-leaved rock-cress) | ALPHA-DOX1 ARALYDRAFT_317048 |
| D8LJL3 | *Ectocarpus siliculosus* (Brown alga) | DOX Esi_0026_0091 |
| E3U9P5 | *Nicotiana attenuata* (Coyote tobacco) | adox2 |

An enzyme's total turnover number (or TTN) refers to the maximum number of molecules of a substrate that the enzyme can convert before becoming inactivated. In general, the TTN for the hydroxylases and other enzymes used in the methods of the invention range from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more.

When whole cells expressing a hydroxylase are used to carry out a hydroxylation reaction, the turnover can be expressed as the amount of substrate that is converted to product by a given amount of cellular material. In general, in vivo hydroxylation reactions exhibit turnovers from at least about 0.01 to at least about 10 mmol·$g_{cdw}^{-1}$, wherein $g_{cdw}$ is the mass of cell dry weight in grams. When whole cells expressing a hydroxylase are used to carry out a hydroxylation reaction, the activity can further be expressed as a specific productivity, e.g., concentration of product formed by a given concentration of cellular material per unit time, e.g., in g/L of product per g/L of cellular material per hour (g $g_{cdw}^{-1} h^{-1}$). In general, in vivo hydroxylation reactions exhibit specific productivities from at least about 0.01 to at least about 0.5 g·$g_{cdw}^{-1} h^{-1}$, wherein $g_{cdw}$ is the mass of cell dry weight in grams.

The TTN for heme enzymes, in particular, typically ranges from about 1 to about 100,000 or higher. For example, the TTN can be from about 1 to about 1,000, or from about 1,000 to about 10,000, or from about 10,000 to about 100,000, or from about 50,000 to about 100,000, or at least about 100,000. In particular embodiments, the TTN can be from about 100 to about 10,000, or from about 10,000 to about 50,000, or from about 5,000 to about 10,000, or from about 1,000 to about 5,000, or from about 100 to about 1,000, or from about 250 to about 1,000, or from about 100 to about 500, or at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, or more. In certain embodiments, the variant or chimeric heme enzymes of the present invention have higher TTNs compared to the wild-type sequences. In some instances, the variant or chimeric heme enzymes have TTNs greater than about 100 (e.g., at least about 100, 150, 200, 250, 300, 325, 350, 400, 450, 500, or more) in carrying out in vitro hydroxylation reactions. In other instances, the variant or chimeric heme enzymes have TTNs greater than about 1000 (e.g., at least about 1000, 2500, 5000, 10,000, 25,000, 50,000, 75,000, 100,000, or more) in carrying out in vivo whole cell hydroxylation reactions.

When whole cells expressing a heme enzyme are used to carry out a hydroxylation reaction, the turnover can be expressed as the amount of substrate that is converted to product by a given amount of cellular material. In general, in vivo hydroxylation reactions exhibit turnovers from at least about 0.01 to at least about 10 mmol·$g_{cdw}^{-1}$, wherein $g_{cdw}$ is the mass of cell dry weight in grams. For example, the turnover can be from about 0.1 to about 10 mmol·$g_{cdw}^{-1}$, or from about 1 to about 10 mmol·$g_{cdw}^{-1}$, or from about 5 to about 10 mmol·$g_{cdw}^{-1}$, or from about 0.01 to about 1 mmol·$g_{cdw}^{-1}$, or from about 0.01 to about 0.1 mmol·$g_{cdw}^{-1}$, or from about 0.1 to about 1 mmol·$g_{cdw}^{-1}$, or greater than 1 mmol·$g_{cdw}^{-1}$. The turnover can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or about 10 mmol·$g_{cdw}^{-1}$.

When whole cells expressing a heme enzyme are used to carry out a hydroxylation reaction, the activity can further be expressed as a specific productivity, e.g., concentration of product formed by a given concentration of cellular material per unit time, e.g., in g/L of product per g/L of cellular material per hour (g·$g_{cdw}^{-1} h^{-1}$). In general, in vivo hydroxylation reactions exhibit specific productivities from at least about 0.01 to at least about 0.5 $g \cdot g_{cdw}^{-1} h^{-1}$, wherein $g_{cdw}$ is the mass of cell dry weight in grams. For example, the specific productivity can be from about 0.01 to about 0.1 $g \cdot g_{cdw}^{-1} h^{-1}$, or from about 0.1 to about 0.5 $g \cdot g_{cdw}^{-1} h^{-1}$, or greater than 0.5 $g \cdot g_{cdw}^{-1} h^{-1}$. The specific productivity can be about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, or about 0.5 $g \cdot g_{cdw}^{-1} h^{-1}$.

In certain embodiments, mutations can be introduced into the target gene using standard cloning techniques (e.g., site-directed mutagenesis) or by gene synthesis to produce the hydroxylases (e.g., cytochrome P450 variants) of the present invention. The mutated gene can be expressed in a host cell (e.g., bacterial cell) using an expression vector under the control of an inducible promoter or by means of chromosomal integration under the control of a constitutive promoter. Hydroxylation activity can be screened in vivo or in vitro by following product formation by GC or HPLC as described herein.

The expression vector comprising a nucleic acid sequence that encodes a heme enzyme of the invention can be a viral vector, a plasmid, a phage, a phagemid, a cosmid, a fosmid, a bacteriophage (e.g., a bacteriophage P1-derived vector (PAC)), a baculovirus vector, a yeast plasmid, or an artificial chromosome (e.g., bacterial artificial chromosome (BAC), a yeast artificial chromosome (YAC), a mammalian artificial chromosome (MAC), and human artificial chromosome (HAC)). Expression vectors can include chromosomal, non-chromosomal, and synthetic DNA sequences. Equivalent expression vectors to those described herein are known in the art and will be apparent to the ordinarily skilled artisan.

The expression vector can include a nucleic acid sequence encoding a heme enzyme that is operably linked to a promoter, wherein the promoter comprises a viral, bacterial, archaeal, fungal, insect, or mammalian promoter. In certain embodiments, the promoter is a constitutive promoter. In some embodiments, the promoter is an inducible promoter. In other embodiments, the promoter is a tissue-specific promoter or an environmentally regulated or a developmentally regulated promoter.

It is to be understood that affinity tags may be added to the N- and/or C-terminus of a heme enzyme expressed using an expression vector to facilitate protein purification. Non-limiting examples of affinity tags include metal binding tags such as His6-tags and other tags such as glutathione S-transferase (GST).

Non-limiting expression vectors for use in bacterial host cells include pCWori, pET vectors such as pET22 (EMD Millipore), pBR322 (ATCC37017), pQE™ vectors (Qiagen), pBluescript™ vectors (Stratagene), pNH vectors, lambda-ZAP vectors (Stratagene); ptrc99a, pKK223-3, pDR540, pRIT2T (Pharmacia), pRSET, pCR-TOPO vectors, pET vectors, pSyn_1 vectors, pChlamy_1 vectors (Life Technologies, Carlsbad, Calif.), pGEM1 (Promega, Madison, Wis.), and pMAL (New England Biolabs, Ipswich, Mass.). Non-limiting examples of expression vectors for use in eukaryotic host cells include pXT1, pSG5 (Stratagene), pSVK3, pBPV, pMSG, pSVLSV40 (Pharmacia), pcDNA3.3, pcDNA4/TO, pcDNA6/TR, pLenti6/TR, pMT vectors (Life Technologies), pKLAC1 vectors, pKLAC2 vectors (New England Biolabs), pQE™ vectors (Qiagen), BacPak baculoviral vectors, pAdeno-X™ adenoviral vectors (Clontech), and pBABE retroviral vectors. Any other vector may be used as long as it is replicable and viable in the host cell.

The host cell can be a bacterial cell, an archaeal cell, a fungal cell, a yeast cell, an insect cell, or a mammalian cell. Suitable bacterial host cells include, but are not limited to, BL21 *E. coli*, DE3 strain *E. coli*, *E. coli* M15, DH5α, DH10β, HB101, T7 Express Competent *E. coli* (NEB), *B. subtilis* cells, *Pseudomonas fluorescens* cells, and cyanobacterial cells such as *Chlamydomonas reinhardtii* cells and *Synechococcus elongates* cells. Non-limiting examples of archaeal host cells include *Pyrococcus furiosus*, *Metallosphera sedula*, *Thermococcus litoralis*, *Methanobacterium thermoautotrophicum*, *Methanococcus jannaschii*, *Pyrococcus abyssi*, *Sulfolobus solfataricus*, *Pyrococcus woesei*, *Sulfolobus shibatae*, and variants thereof. Fungal host cells include, but are not limited to, yeast cells from the genera *Saccharomyces* (e.g., *S. cerevisiae*), *Pichia* (*P. Pastoris*), *Kluyveromyces* (e.g., *K. lactis*), *Hansenula* and *Yarrowia*, and filamentous fungal cells from the genera *Aspergillus*, *Trichoderma*, and *Myceliophthora*. Suitable insect host cells include, but are not limited to, Sf9 cells from *Spodoptera frugiperda*, Sf21 cells from *Spodoptera frugiperda*, Hi-Five cells, BTI-TN-5B1-4 *Trichophusia ni* cells, and Schneider 2 (S2) cells and Schneider 3 (S3) cells from *Drosophila melanogaster*. Non-limiting examples of mammalian host cells include HEK293 cells, HeLa cells, CHO cells, COS cells, Jurkat cells, NS0 hybridoma cells, baby hamster kidney (BHK) cells, MDCK cells, NIH-3T3 fibroblast cells, and any other immortalized cell line derived from a mammalian cell.

In certain embodiments, the present invention provides heme enzymes such as the P450 variants described herein that are active hydroxylation catalysts inside living cells. As a non-limiting example, bacterial cells (e.g., *E. coli*) can be used as whole cell catalysts for the in vivo hydroxylation reactions of the present invention. In some embodiments, whole cell catalysts containing P450 enzymes with the equivalent C400X mutation are found to significantly enhance the total turnover number (TTN) compared to in vitro reactions using isolated P450 enzymes.

Biohydroxylation Reaction Conditions

The methods of the invention include forming reaction mixtures that contain the hydroxylases described herein. The hydroxylases can be, for example, purified prior to addition to a reaction mixture or secreted by a cell present in the reaction mixture. The reaction mixture can contain a cell lysate including the enzyme, as well as other proteins and other cellular materials. Alternatively, a hydroxylase can catalyze the reaction within a cell expressing the hydroxylase. Any suitable amount of hydroxylase can be used in the methods of the invention. In general, hydroxylation reaction mixtures contain from about 0.01 weight % (wt %) to about 100 wt % hydroxylase with respect to the hydrocarbon substrate. The reaction mixtures can contain, for example, from about 0.01 wt % to about 0.1 wt % hydroxylase, or from about 0.1 wt % to about 1 wt % hydroxylase, or from about 1 wt % to about 10 wt % hydroxylase, or from about 10 wt % to about 100 wt % hydroxylase. The reaction mixtures can contain from about 0.05 wt % to about 5 wt % hydroxylase, or from about 0.05 wt % to about 0.5 wt % hydroxylase. The reaction mixtures can contain about 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, or about 3 wt % hydroxylase. One of skill in the art will understand how to convert wt % values to mol % values with respect to the hydroxylase and/or substrate concentrations set forth herein.

If the hydroxylase catalyses the reaction within a cell expressing the hydroxylase then any suitable amount of cells can be used in the methods of the invention. In general, hydroxylation whole-cell reaction mixtures contain from about 1 weight % to about 10,000 wt % of cells on a cell dry weight basis with respect to the hydrocarbon substrate. The whole-cell reaction mixtures can contain, for example, from about 1 wt % to about 10 wt % cells, or from about 10 wt % to about 100 wt % cells, or from about 100 wt % to about 1000 wt % cells, or from about 1000 wt % cells to about 2500 wt % cells, or from about 2500 wt % cells to about 5000 wt % cells, or from about 5000 wt % cells to about 7500 wt % cells, or from about 7500 wt % cells to about 10000 wt % cells with respect to the hydrocarbon substrate. The whole-cell reaction mixtures can contain from about 2 wt % to about 1000 wt % cells, or from about 5 wt % to about 500 wt % cells with respect to the hydrocarbon substrate. The whole-cell reaction mixtures can contain about 5, 10, 20, 30, 40, 50, 60, 70, 80, 90, 100, 200, 300, 400, 500, 600, 700, 800, 900, or about 1000 wt % cells with respect to the hydrocarbon substrate.

The concentration of a saturated or unsaturated hydrocarbon substrate is typically in the range of from about 100 µM to about 1 M. The concentration can be, for example, from about 100 µM to about 1 mM, or about from 1 mM to about 100 mM, or from about 100 mM to about 500 mM, or from about 500 mM to 1 M. The concentration can be from about 500 µM to about 500 mM, 500 µM to about 50 mM, or from about 1 mM to about 50 mM, or from about 15 mM to about 45 mM, or from about 15 mM to about 30 mM. The concentration of the saturated or unsaturated hydrocarbon substrate can be, for example, about 100, 200, 300, 400, 500, 600, 700, 800, or 900 µM. The concentration of the saturated or unsaturated hydrocarbon substrate can be about 1, 5, 10, 15, 20, 25, 30, 35, 40, 45, 50, 55, 60, 65, 70, 75, 80, 85, 90, 95, 100, 150, 200, 250, 300, 350, 400, 450, or 500 mM.

Reaction mixtures can contain additional reagents. As non-limiting examples, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$), and salts of $Mn^{2+}$ and $Mg^{2+}$), denaturants (e.g., urea and guandinium hydrochloride), detergents (e.g., sodium dodecylsulfate and Triton-X 100), chelators (e.g., ethylene glycol-bis(2-aminoethylether)-N,N,N',N'-tetraacetic acid (EGTA), 2-({2-[Bis(carboxymethyl)amino]ethyl}(carboxymethyl)amino)acetic acid (EDTA), and 1,2-bis(o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v/v).

Reactions are conducted under conditions sufficient to catalyze the formation of a hydroxylation product. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 3 to about 10. The reactions can be conducted, for example, at a pH of from about 6.5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours, or about 96 hours, or about 120 hours, or about 144 hours, or about 168 hours, or about 192 hours. In general, reactions are conducted under aerobic conditions. In some embodiments, the solvent forms a second phase, and the hydroxylation occurs in the aqueous phase. In some embodiments, the hydroxylases is located in the aqueous layer whereas the substrates and/or products occur in an organic layer. Other reaction conditions may be employed in the methods of the invention, depending on the identity of a particular hydroxylase, or olefinic substrate.

Reactions can be conducted in vivo with intact cells expressing a hydroxylase of the invention. The in vivo reactions can be conducted with any of the host cells used for expression of the hydroxylases, as described herein. A suspension of cells can be formed in a suitable medium supplemented with nutrients (such as mineral micronutrients, glucose and other fuel sources, and the like). Hydroxylation yields from reactions in vivo can be controlled, in part, by controlling the cell density in the reaction mixtures. Cellular suspensions exhibiting optical densities ranging from about 0.1 to about 50 at 600 nm can be used for hydroxylation reactions. Other densities can be useful, depending on the cell type, specific hydroxylases, or other factors.

Pheromone Compositions and Uses Thereof

As described above, many of the olefinic alcohol products made via the methods described herein are pheromones. Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; and mixtures thereof. Baits or feeding stimulants can also be added to the carrier.

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices.

Pheromone compositions can contain other pheromones or attractants provided that the other compounds do not substantially interfere with the activity of the composition. The pheromone compositions can also include insecticides. Examples of suitable insecticides include, but are not limited to, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, and mixtures thereof.

Pheromone compositions can be used in conjuction with a dispenser for release of the composition in a particular environment. Any suitable dispenser known in the art can be used. Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

A variety of pheromones, including those set forth in Table 1 can be prepared according to the methods of the invention and formulated as described above. For example, the methods of the invention can be used to prepare peach twig borer (PTB) sex pheromone, which is a mixture of (E)-dec-5-en-1-ol (17%) and (E)-dec-5-en-1-yl acetate (83%). The PTB sex pheromone can be used in conjunction with a sustained pheromone release device having a polymer container containing a mixture of the PTB sex pheromone and a fatty acid ester (such as a sebacate, laurate, palmitate, stearate or arachidate ester) or a fatty alcohol (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol). The polymer container can be a tube, an ampul, or a bag made of a polyolefin or an olefin component-containing copolymer. Sex pheromones of other pest insects such the cotton bollworm (*Helicoverpa armigera*), fall army worm (*Spodoptera frugiperda*), oriental fruit moth (*Grapholita molesta*) and leaf roller (Tortricidae) can be used in this type of sustained pheromone release device. The sex pheromones typically include one or more aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like) and/or one or more aliphatic aldehyde compounds having from 10 to 16 carbon atoms (e.g., 7-hexadecenal, 11-hexadecenal, 13-octadecenal, and the like).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the invention can be colored brightly, to provide additional attraction for the insects.

The trap is positioned in an area infested (or potentially infested) with insects. Generally, the trap is placed on or close to a tree or large plant. The aroma of the pheromone attracts the insects to the trap. The insects can then be caught, immobilised and/or killed within the trap, for example, by the killing agent present in the trap.

Pheromones prepared according to the methods of the invention can also be used to disrupt mating. Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

Insect populations can be surveyed or monitored by counting the number of insects in a target area (e.g., the number of insects caught in a trap). Inspection by a horticulturist can provide information about the life stage of a population. Knowing where insects are, how many of them there are, and their life stage enables informed decisions to be made as to where and when insecticides or other treatments are warranted. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

General Methods.

*E. coli* heat shock transformation: Heat shock transformation of plasmids/Gibson assembly products/ligation products were performed with competent BL21 (DE3) cells from NEB (C2527H). Set a water bath to 42° C. and remove the SOC media from storage at 4° C. and incubate at 37° C. Remove chemically competent cells from the −80° C. freezer and thaw on ice for 5-10 minutes. Add the DNA solution to be transformed to the cells and tap the tube gently to mix, keep the mixture on ice for 5 more minutes. Submerge the tube containing the cell/DNA mixture in the 42° C. water bath for 10 seconds and quickly place the tubes back on ice for 2 minutes. After the two minute incubation on ice, add 500 µl of SOC recovery media and incubate at 37° C. with 210 rpm shaking for 60 minutes. After incubation, 50-200 µl of the recovered cells are plated on LB/agar plates supplemented with the appropriate antibiotics.

*E. coli* plasmid isolation: Plasmid isolation of 2.5 ml overnight culture were performed with the SpinSmart™ Plasmid Miniprep DNA Purification kit (Danville Scientific). The overnight culture is collected by centrifugation at 14,000 rpm for 10 minutes. Resuspend the pellet in 250 µl of P1 buffer and transfer the mixture to a 1.5 ml microcentrifuge tube. Add 250 µl of P2 buffer and mix by inverting the tube. Add 300 µl of P3 buffer and mix by inverting the tube. Centrifuge the mixture at 14,000 rpm for 5 minutes and transfer the supernatant containing DNA onto a fresh plasmid binding spin column. Bind DNA onto the column by centrifugation at 14,000 rpm for 30 seconds, followed by washes with 500 µl of P4 wash buffer and 650 µl of P5 wash buffer. Dry the column by centrifugation at 14,000 rpm for 2 minutes and then discard the collection tube. Place the plasmid binding spind column in a 1.5 ml microcentrifuge tube. Add 50 µl of warm DI water (50° C.) and centrifuge at 14000 rpm to elute the DNA.

*E. coli* DNA isolation: DNA fragment isolation from agarose gel was performed with the Zymoclean Gel DNA Recovery Kits (Zymo research). Excise the desired gel fragment using a razor blade and transfer it to a 1.5 ml microcentrifuge tube. Add 250 µl of ADB to the tube and incubate at 50° C. for 5 to 10 minutes until the gel slice is dissolved. Transfer the melted agarose solution to a Zymo-spin™ column in a collection tube, centrifuge for 30-60 seconds and discard the flow through. Wash the column with 200 µl of DNA wash buffer and centrifuge for 30 seconds. Repeat the wash step. Dry the column by centrifugation at 14,000 rpm for 2 minutes. Place the Zymo-spin™ column in a 1.5 ml microcentrifuge tube. Add 12 µl of warm DI water (50° C.) and centrifuge at 14000 rpm to elute DNA.

PCR: PCR reactions were performed using Phusion High-Fidelity PCR Master Mix with HF Buffer (NEB: M0531S). In a typical 25 µl PCR reaction, 0.5 µl of the template DNA (plasmid, PCR product, synthesized DNA, etc) is mixed with 1.25 µl of each of the forward and reverse primers (10 mM) along with 0.75 µl of DMSO, 12.5 µl of the Phusion master mix and 8.75 µl of DI water. A typical thermocycler program consists of the follow steps:

| Step | Temperature (° C.) | Time (s) | |
|---|---|---|---|
| 1 | 98 | 30 | |
| 2 | 98 | 10 | Repeat |
| 3 | 55 | 10 | 25X |
| 4 | 72 | 50 | |
| 5 | 72 | 600 | |
| 6 | 10 | ∞ | |

SOE-PCR: A typical 50 µl reaction contains (1) 0.5 to 3 µl of each isolated DNA fragment being spliced (2) 2.5 µl of each the forward and reverse primers (10 mM), (3) 1.5 µl of DMSO, (4) 25 µl of Phusion master mix and (5) enough DI water to reach a final total volume of 50 µl. The thermocycler program is modified from that of table # by extending the time of step 3 to 20 seconds.

*E. coli* biotransformations: Each *E. coli* strain expressing a terminal hydroxylase as well as the necessary redox partners was cultured in shake flasks to produce cell mass and induce protein expression. At the end of the protein expression phase, the cells were collected by centrifugation and washed with the bioconversion buffer. The washed cells were resuspended in bioconversion buffer to yield a cell density of ~100 g cell wet weight (g cww)/L. A volume of 1 ml of this cell mixture was transferred to a 20 ml amber vial. The bioconversion was initiated by the addition of 200 µl of a 50/50 (v/v) mixture of substrate and isopropyl alcohol. For E/Z-5-decene and 1-bromodecane, the reactions were quenched after 1 hour with the addition of 100 µl 3 M HCl and analyzed for product formation with GC/FID. For 1-dodecene, 1-dodecyne, and hexadecane, the reactions were quenched after 4 hours with HCl and analyzed with GC/FID.

Example 1. Synthesis of Peach Twig Borer (PTB) Sex Pheromone Using Biocatalytic Terminal Hydroxylation The PTB pheromone is a mixture of (E)-dec-5-en-1-ol (17%) and (E)-dec-5-en-1-yl acetate (83%). Using a terminal hydroxylase described in Table 3, 4, or 5, (E)-dec-5-ene can be readily converted into (E)-dec-5-en-1-ol, which can be acetylated to yield (E)-dec-5-en-1-yl acetate, as shown in Scheme 22. A suitable terminal hydroxylase enables this original synthesis route and reduces the synthesis cost of this pheromone.

Scheme 22. Exemplary synthesis route for (E)-dec-5-en-1-ol and (E)-dec-5-en-1-yl acetate

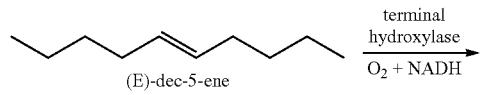

(E)-dec-5-ene  →[terminal hydroxylase, O₂ + NADH]

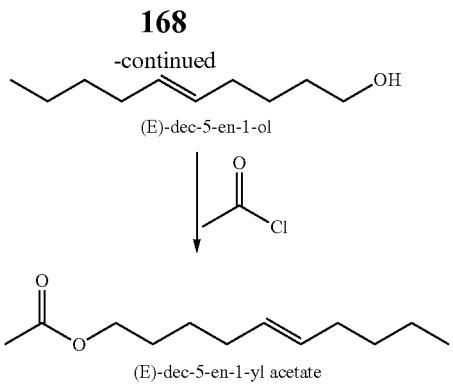

Example 2. Biocatalytic Hydroxylation of Asymmetric and Diolefin Substrates

Asymmetric substrates shown in Tables 11, 12, and 13, including (Z)-hexadec-11-ene and diolefin substrates such as (E,E)-8,10-dodecadiene, are terminally hydroxylated via the enzymes presented in Tables 3, 4, and 5.

TABLE 11

Production of representative alkenols enabled by a terminal hydroxylase with activity for alkenes with internal olefins.

| Substrate (alkene) | Product (alkenol) | Biological importance of Product |
| --- | --- | --- |
| (Z)-non-3-ene | (Z)-non-3-en-1-ol | West indian fruit fly sex pheromone |
| (E)-dec-5-ene | (E)-dec-5-en-1-ol | Peach twig borer sex pheromone |
| (Z)-dodec-8-ene | (Z)-dodec-8-en-12-ol | Oriental fruit moth sex pheromone |
| (E,E)-8,10-Dodecadiene | (E,E)-8,10-Dodecadien-1-ol | Codling moth sex pheromone |

TABLE 12

Production of representative alkenals and allylic acetates enabled by a terminal hydroxylase with activity for alkenes with internal olefins.

| Substrate (alkene) | Final product (alkenal or allylic acetate) | Biological importance of Product |
| --- | --- | --- |
| (Z)-hexadec-11-ene | (Z)-hexadec-11-en-1-yl acetate | *Pandemis* leafroller sex pheromone |

TABLE 12-continued

Production of representative alkenals and allylic acetates enabled by a terminal hydroxylase with activity for alkenes with internal olefins.

| Substrate (alkene) | Final product (alkenal or allylic acetate) | Biological importance of Product |
|---|---|---|
| (Z)-tetradec-9-ene | (Z)-hexadec-11-enal | |
| | (Z)-tetradec-9-en-1-yl acetate | |
| (Z)-hexadec-11-ene | (Z)-hexadec-9-enal | Cotton bollworm sex pheromone |
| (Z)-hexadec-9-ene | (Z)-hexadec-11-enal | |
| (Z)-tetradec-11-ene | (Z)-tetradec-11-en-1-yl acetate | Oblique banded leafroller sex pheromone |

TABLE 13

Production of representative alkenols enabled by a terminal hydroxylase with activity for alkenes with internal olefins. The products listed here are either pheromones in their own right, or are precursors to pheromones, e.g. via oxidation or acetylation.

| Substrate (alkene) | Product (alkenol) | Biological importance of Product |
|---|---|---|
| (Z)-3-nonene | (Z)-3-nonenol | West Indian Fruity Fly male sex pheromone |
| Z-5-decene | Z-5-decen-1-ol | |
| (E)-8-dodecene | (E)-8-dodecenol | Citrus Fruit Moth sex pheromone |
| (Z)-8-dodecene | (Z)-8-dodecenol | Oriental Fruit moth sex pheromone component |
| Z-7-dodecene | Z-7-dodecen-1-ol | |
| Z-9-tetradecene | Z-9-tetradecen-1-ol | |
| Z-11-tetradecene | Z-11-tetradecen-1-ol | |
| E-11-tetradecene | E-11-tetradecen-1-ol | |
| (Z,E)-9,11,13-Tetradecatriene | (Z,E)-9,11,13-Tetradecatrienol | |

TABLE 13-continued

Production of representative alkenols enabled by a terminal hydroxylase with activity for alkenes with internal olefins. The products listed here are either pheromones in their own right, or are precursors to pheromones, e.g., via oxidation or acetylation.

| Substrate (alkene) | Product (alkenol) | Biological importance of Product |
|---|---|---|
| Z-7-hexadecene | Z-7-hexadecen-1-ol | |
| Z-9-hexadecene | Z-9-hexadecenol | |
| Z-11-hexadecene | Z-11-hexadecenol | |
| (Z,E)-9,11-Hexadecadiene | (Z,E)-9,11-Hexadecadien-1-ol | Naval Orangeworm sex pheromone component |
| (Z,Z)-11,13-Hexadecadiene | (Z,Z)-11,13-Hexadecadien-1-ol | |
| (Z,E)-11,13-Hexadecadiene | (Z,E)-11,13-Hexadecadien-1-ol | Naval Orangeworm sex pheromone component |
| Z-13-octadecene | Z-13-octadecen-1-ol | |

Example 3: Biocatalyst Identity and/or Construction

The purpose of this example is to illustrate the construction and/or identity of the various biocatalysts described in the present disclosure.

Strains, plasmids, and oligonucleotides disclosed herein are listed in Tables 14-16.

TABLE 14

Genotypes of strains used in the examples.

| Strain No. | Strain host | Strain type | Plasmid No. |
|---|---|---|---|
| SPV001 | E. coli | BL21(DE3) | pPV001 |
| SPV027 | E. coli | BL21(DE3) | pPV024 |
| SPV014 | E. coli | BL21(DE3) | pPV009 |
| SPV015 | E. coli | BL21(DE3) | pPV010 |
| SPV016 | E. coli | BL21(DE3) | pPV011 |
| SPV017 | E. coli | BL21(DE3) | pPV012 |
| SPV028 | E. coli | BL21(DE3) | pPV025 |
| SPV018 | E. coli | BL21(DE3) | pPV013 |

TABLE 14-continued

Genotypes of strains used in the examples.

| Strain No. | Strain host | Strain type | Plasmid No. |
|---|---|---|---|
| SPV029 | E. coli | BL21(DE3) | pPV026 |
| SPV019 | E. coli | BL21(DE3) | pPV014 |
| SPV035 | E. coli | BL21(DE3) | pPV028 |
| SPV036 | E. coli | BL21(DE3) | pPV029 |
| SPV020 | E. coli | BL21(DE3) | pPV015 |
| SPV0021 | E. coli | BL21(DE3) | pPV016 |
| SPV0022 | E. coli | BL21(DE3) | pPV017 |
| SPV0025 | E. coli | BL21(DE3) | pPV003 |
| SPV0013 | E. coli | BL21(DE3) | pPV008 |
| SPV0026 | E. coli | BL21(DE3) | pPV004 |
| SPV0012 | E. coli | BL21(DE3) | pPV007 |
| SPV0023 | E. coli | BL21(DE3) | pPV018 |
| SPV0030 | E. coli | BL21(DE3) | pPV020 |
| SPV0031 | E. coli | BL21(DE3) | pPV021 |
| SPV032 | E. coli | BL21(DE3) | pPV022 |
| SPV037 | E. coli | BL21(DE3) | pPV030 |
| SPV033 | E. coli | BL21(DE3) | pPV023 |

TABLE 15

Plasmids used in the examples.

| Plasmid No. | Vector | Hydroxylase insert | Hydroxylase Accession No. (protein ID) | Other inserts (reductase components and transporter) | Flanking restriction sites |
|---|---|---|---|---|---|
| pPV001 | pET28a(+) | none | n/a | none | n/a |
| pPV002 | pCom10 | none | n/a | none | n/a |
| pPV024 | pET28a(+) | LadA | ABO68832 | none | BamHI, XhoI |
| pPV009 | pET28a(+) | LadA_GS | EU151491 | none | BamHI, XhoI |
| pPV010 | pET28a(+) | CYP153A7 | AJ850057 (SEQ ID NO: 15) | A6FDR, A6FDX | XbaI, HindIII |
| pPV011 | pET28a(+) | CYP153 M. sp. | AFO66437 (SEQ ID NO: 16) | aphH, aphI | XbaI, HindIII |
| pPV012 | pET28a(+) | CYP153A13N2 | AB206793 (SEQ ID NO: 17) | RhFred fused | XbaI, SacI |
| pPV025 | pET28a(+) | CYP153A13N3 | AB206799 | RhFred fused | XbaI, SacI |
| pPV013 | pET28a(+) | CYP153A13N5 | AB206801 | RhFred fused | XbaI, SacI |
| pPV026 | pET28a(+) | CYP153A13P2 | AB206795 (SEQ ID NO: 18) | RhFred fused | XbaI, SacI |
| pPV014 | pColaDuet-1 | CYP153RE | BAE46203 | CPR(BM3) fused, AlkL | NcoI, SacI |
| pPV028 | pColaDuet-1 | CYP153CspK31 | ABZ69158 | CPR(BM3) fused, AlkL | NcoI, SacI |
| pPV029 | pColaDuet-1 | CYP153Plav | ABS63384 | CPR(BM3) fused, AlkL | NcoI, SacI |
| pPV015 | pColaDuet-1 | CYP153A7 | AJ850057 (SEQ ID NO: 15) | CPR(BM3) fused, AlkL | NcoI, SacI |
| pPV016 | pColaDuet-1 | CYP153A11 | AJ850059 | CPR(BM3) fused, AlkL | NcoI, SacI |
| pPV017 | pColaDuet-1 | CYP153D2 | AJ850060 | CPR(BM3) fused, AlkL | NcoI, SacI |
| pPV003 | pColaDuet-1 | CYP153A M. aq. (G307A) | ABM17701 (SEQ ID NO: 19) | CPR(BM3) fused, AlkL | n/a |
| pPV008 | pET28a(+) | CYP153A M. aq. | ABM17701 (SEQ ID NO: 19) | RhFred fused | n/a |
| pPV004 | pET28a(+) | CYP153A M. aq. (G307A) | ABM17701 (SEQ ID NO: 19) | CPR(BM3) fused | n/a |
| pPV007 | pET28a(+) | CYP153A P.Sp | ABE47160 | CPR(BM3) fused | n/a |
| pPV018 | pCom10 | AlkB | YP_009076004 (SEQ ID NO: 20) | AlkF, AlkG | EcoRI/SalI |
| pPV019 | pCom10 | none | n/a | AlkT | XhoI/XbaI |
| pPV020 | pCom10 | AlkB | YP_009076004 (SEQ ID NO: 20) | AlkF, AlkG, AlkT | n/a |
| pPV021 | pCom10 | AlkB | YP_009076004 (SEQ ID NO: 20) | AlkF, AlkG, AlkT, AlkL | n/a |
| pPV022 | pCom10 | AlkB P1 | CAB51047 (SEQ ID NO: 21) | AlkF, AlkG, AlkT, AlkL | n/a |

TABLE 15-continued

Plasmids used in the examples.

| Plasmid No. | Vector | Hydroxylase insert | Hydroxylase Accession No. (protein ID) | Other inserts (reductase components and transporter) | Flanking restriction sites |
|---|---|---|---|---|---|
| pPV030 | pCom10 | AlkB1 AB | CAC38027 (SEQ ID NO: 22) | AlkF, AlkG, AlkT, AlkL | n/a |
| pPV023 | pCom10 | AlkB2 AB | CAB51047 (SEQ ID NO: 21) | AlkF, AlkG, AlkT, AlkL | n/a |

TABLE 16

Oligonucleotide sequences used in the examples.

| Oligo-nucleotide | Sequence | Description | SEQ ID NO. |
|---|---|---|---|
| 1406_provivi 023 | AGCCATCA TCATCATC ATCACAGC AGC | AlkB construct for DNA synthesis | 1 |
| 1406_provivi 024 | CACTATAG GGGAATTG TGAGCGGA TAACAATT CC | AlkB P1 construct for DNA synthesis | 2 |
| 1406_provivi 025 | CTATAGGG GAATTGTG AGCGGATA ACAATTCC C | AlkB1A.p. construct for DNA synthesis | 3 |
| 1406_provivi 026 | TGGTGGTG CTCGAGTG CGGCCGCA AGCTTCTA ATG | AlkB2A.p. construct for DNA synthesis | 4 |
| oPV001 | CTTAAATC TCGTAGCG ACTAATTT AATAAAAA TTG | Fwd primer for alkB constructs | 5 |
| oPV002 | AAACAGAA GCTTGGCT GCAGGTCG | Rev primer for alkB constructs | 6 |
| oPV003 | CTTATTCC TGAGGATT GGTGCTGC C | fwd primer from alkG | 7 |
| oPV004 | GGCAGCAC CAATCCTC AGGAATAA G | rev primer from alkG | 8 |
| oPV005 | GATGCCGC TGGATCTG GCCTAGA | fwd primer from SfiI | 9 |

All strains listed in Table 14 were obtained by transforming their corresponding plasmid into E. coli BL21(DE3) cells using standard heat shock protocol. Briefly, aliquots of competent E. coli BL21(DE3) were thawed on ice and mixed with 1 ng of isolated DNA plasmid. The mixture was immersed in a 42° C. water bath for 10 seconds, followed by incubation at 4° C. for 2 minutes and 37° C. for 30 minutes before plating on Luria-Bertani agar plates with the appropriate antibiotics.

Plasmid pPV001 was obtained directly from EMD Millipore. Plasmids pPV003, pPV004, pPV007, and pPV008 were directly obtained from the Institut fur Technische Biochemie (Stuttgart, Germany). Plasmid pPV002 was obtained from the California Institute of Technology (Pasadena, USA). Plasmids pPV001, pPV003 and pPV002 served as the vector backbone for pET28a(+), pColaDuet-1, and pCom10 based plasmids listed in Table 15. Gene inserts of pPV009, pPV010, pPV011, pPV012, pPV013, pPV014, pPV015, pPV016, pPV017, pPV018, pPV019, pPV020, pPV021, pPV022, pPV023, pPV024, pPV025, pPV026, pPV0028, pPV0029, and pPV030 designed for the expression of terminal hydroxylases and their redox partners were synthesized (Gen9, Inc. Cambridge, Mass.). The inserts of pPV009, pPV010, pPV011, pPV012, pPV013, pPV014, pPV015, pPV016, pPV017, pPV018, pPV019, pPV024, pPV025, pPV026, pPV0028 and pPV0029 were cloned into the vector by ligation of vector and insert DNA fragments generated by restriction digest at flanking sites indicated in Table 15. Plasmid pPV0020 was produced by ligation of DNA fragments obtained by restriction digest of pPV0018 (9195 bp fragment) and pPV0019 (2399 bp fragment) with XhoI and XbaI. Plasmid pPV021 was produced by Gibson assembly of DNA fragments obtained by (1) restriction digest of pPV0019 (9089 bp fragment) with EcoRI and SalI and (2) PCR product of 1406_provivi 023 with primers oPV001 and oPV002. The pPV022, pPV023 and pPV030 plasmids were produced by Gibson assembly of DNA fragments obtained by (1) restriction digest of pPV0019 (8550 bp fragment) with EcoRI and SfiI and (2) a splicing by overhang extension (SOE)-PCR product. For pPV022, the SOE-PCR was performed using primers oPV001 and oPV005 along with the PCR products from reactions containing (1) 1406_provivi024 with primers oPV001 and oPV004 and (2) pPV021 with primers oPV003 and oPV005. For pPV023, the SOE-PCR was similarly performed using primers oPV001 and oPV005 along with the PCR products from reactions containing (1) 1406_provivi026 with primers oPV001 and oPV004 and (2) pPV021 with primers oPV003 and oPV005. For pPV030, the SOE-PCR was similarly performed using primers oPV001 and oPV005 along with the PCR products from reactions containing (1) 1406_provivi025 with primers oPV001 and oPV004 and (2) pPV021 with primers oPV003 and oPV005.

Example 4. Identification of Candidate Enzymes/Strains with Known Terminal Alkane Hydroxylation Activity Enzymes with terminal hydroxylation activity reported in the literature have generally been characterized for their substrate specificity with linear alkanes and/or fatty acids of various lengths. In certain aspects, the present invention relies upon the observation that the presence of the alkene bonds does not affect the regioselectivity and substrate specificity of the hydroxylases. A subset of known terminal hydroxylases selected from Tables 3, 4, and 5 with preference for $C_8$-$C_{18}$ substrates is determined. These sequences are evaluated for terminal hydroxylation according to Scheme 23 with substrates shown in Tables 11, 12, and 13, including (E)-dec-5-ene, (Z)-hexadec-11-ene, and (E,E)-8,10-dodecadiene:

Scheme 23

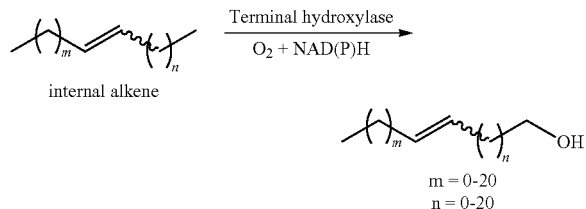

$m = 0\text{-}20$
$n = 0\text{-}20$

Strains containing these types of enzymes that have been previously used for whole-cell terminal hydroxylation of alkanes or fatty acids are shown in Table 6.

To evaluate the activity of candidate enzymes not already present in an expression strain, the appropriate DNA expression vectors are constructed and transformed in the desired hosts. The identified genes are synthesized as gene products or multiple DNA fragments and inserted into vectors that have been previously used for expression, e.g., pET28a(+) for CYP153 and pGEc47 for AlkB, using standard molecular biology techniques. The correct expression vectors are confirmed by DNA sequencing and then introduced into the desired host via transformation to obtain the desired expression strains.

The constructed expression strains are used to determine the in vivo terminal hydroxylation activity of each candidate enzyme for substrates shown in Tables 11, 12, and 13, including (E)-dec-5-ene, (Z)-hexadec-11-ene, and (E,E)-8,10-dodecadiene. Typically, each strain is cultured in a suitable medium, such as Terrific Broth, until a sufficient cell density to induce enzyme expression with Isopropyl β-D-1-thiogalactopyranoside or dicyclopropylketone. After a predetermined expression period, the cells are pelleted by centrifugation to remove the growth media. The biotransformation reaction is performed in nitrogen-free medium such as M9 or phosphate buffer to ensure the cells are in a resting state to maximize the supply of redox cofactors for the hydroxylation reaction. The alkene is present in the reaction as a neat organic overlay or part of the organic phase in a two-phase reaction. To evaluate strains with sufficient replicates, the initial reaction is performed on a 5-25 mL scale in a vial or flask. A carbon source such as glucose or glycerol can also be added to the reaction to support the regeneration of redox cofactors by the cells. The addition of a co-solvent such as bis(2-ethylhexyl) phthalate to improve the extraction of the product to the organic phase can be explored. In addition, reaction parameters such as reaction time, temperature, volume, ratio of organic and aqueous phases, aeration and cell density can be optimized.

The analysis of the whole-cell hydroxylation of substrates shown in Tables 11, 12, and 13, including (E)-dec-5-ene, (Z)-hexadec-11-ene, and (E,E)-8,10-dodecadiene reactions, requires the development of appropriate gas chromatography (GC) methods. The GC analysis of alkane and fatty acid terminal hydroxylation reactions has been performed with both mass spectrometry and flame ionization detectors. Authentic standards for (E)-dec-5-ene, (E)-dec-5-en-1-ol, and potential side-products, (E)-dec-5-ene-1,10-diol, (E)-dec-5-en-1-al, (E)-dec-5-enoic acid and 2,3-dibutyloxirane are obtained for method development and product quantification. Likewise, (Z)-hexadec-11-ene and (E,E)-8,10-dodecadiene and an assortment of likely hydroxylation or epoxidation products of these two molecules are used for method development and product quantification. A procedure for terminating the hydroxylation reaction and extracting the organic phase into a suitable GC solvent is used.

Demonstration of gram-scale production of (E)-dec-5-en-1-ol using biocatalytic terminal hydroxylation is performed in biotransformation reactions on a liter scale. To efficiently perform whole-cell hydroxylation on a liter scale, the reaction pH and aeration are controlled.

Evaluation of the most promising candidates from the 5-25 mL screening reactions in fermenters enables the identification and alleviation of reaction bottle-necks and inhibition effects of the product and by-products. Enzyme expression can also be further optimized in fermenters with enhanced control over culturing conditions.

Example 5: Hydroxylation of (E)-5-decene and (Z)-5-decene

The purpose of this example is to illustrate the biocatalytic hydroxylation of (E)-5-decene and (Z)-5-decene to (E)-5-decen-1-ol and (Z)-5-decen-1-ol, respectively, and the selectivity of the various enzymes towards either (E)-5-decene or (Z)-5-decene.

The 25 strains detailed in Example 3 were characterized for their ability to convert a mixture of (E)-5-decene and (Z)-5-decene to (E)-5-decen-1-ol and (Z)-5-decen-1-ol in whole cell bioconversion reactions.

Overnight cultures of these 25 strains were inoculated from single colonies grown on LB agar plates containing 30 μg/ml of kanamycin into 2.5 mL of LB medium containing 30 μg/ml of kanamycin and incubated for 24 hours at 37° C. and 210 rpm. The overnight culture was used to inoculate 50 or 100 ml of Terrific Broth with a starting $OD_{600}$ of 0.1. After incubation for approximately 2.5 hours at 37° C. and 210 rpm the cultures reached an OD600 of approximately 1.0-1.5, at which point they were induced with 0.5 mM IPTG and supplemented with 0.5 mM 5-aminolevulinic acid, 50 mg/L thiamine, 1.2 mM $MgSO_4$, and 25 mL of a solution of trace elements (190 mg $CaCl_2$*$2H_2O$, 90 mg $ZnSO_4$*$7H_2O$, 90 mg $CoCl_2$*$6H_2O$, 75 mg $CuSO_4$*$5H_2O$, 50 mg $MnSO_4$*$H_2O$, 11.1 mg $Na_2$-EDTA*$2H_2O$ and 8.35 mg $FeCl_3$*$6H_2O$ in 500 ml of dd$H_2O$). The culture was further incubated for 20 hours at 20° C. and 180 rpm. The cultures were then pelleted via centrifugation at 3900×g at 4° C. for 10 min, washed once with bioconversion buffer (100 mM phosphate buffer (pH7.2), 1% glycerol/0.4% glucose, 100 μg/ml FeSO4*$7H_2O$, and 30 μg/ml kanamycin), and pelleted again. Next, bioconversion buffer was added to the cell pellets targeting a cell wet weight of 100 g/L and the cell pellets were resuspended.

To carry out biotransformations, 1 mL of this mixture was transferred into sterile 40 mL amber screw cap vials and 1004 of an 84:16 mixture of (E)-5-decene:(Z)-5-decene was added along with 100 μL of isopropyl alcohol. This reaction mixture was incubated at 20° C. and 180 rpm for 1 hour before the reaction was quenched via addition of 100 μL of 3M HCL.

To extract the biotransformation products, 5 mL of n-hexane was added. The mixture was thoroughly mixed via shaking in an orbital shaker (20 min @ 250 rpm) and then allowed to settle undisturbed for 20 minutes. An aliquot (1 mL) of the organic layer was analyzed via gas chromatography (GC) using a J&W DB-23 column (30 m×25 mm×25 µm) coupled to an FID detector using the following temperature profile: 45° C. for 0.5 min; ramp 5° C./min to 50° C.; hold 0.5 min; ramp 30° C./min to 220° C.; hold 3.3 min. Retention for substrates and products were verified using authentic standards and were as follows: (E)-5-decene at 2.84 min, (Z)-5-decene at 2.91 min, (E)-5-decen-1-ol at 6.73 min, and (Z)-5-decen-1-ol at 6.79 min.

Results are shown in Table 17. These results demonstrate the capability of members of the CYP153 and AlkB family of enzymes to catalyze the hydroxylation of (E)-5-decene and (Z)-5-decene. Since the (E/Z)-5-decene substrate used in these bioconversion was an 84:16 mixture of the E:Z enantiomers, a product mixture with the same 84:16 ratio of (E)-5-decen-1-ol to (Z)-5-decen-1-ol would be obtained if the terminal hydroxylase exhibits no selectivity for either enantiomer. Our results demonstrate that the terminal hydroxylase does have a preference for one of the two substrate isomers, and isomeric enrichment for a particular alcohol product can be achieved by biohydroxylation.

and 210 rpm. The overnight culture was used to inoculate 50 or 100 ml of Terrific Broth with a starting $OD_{600}$ of 0.1. After incubation for approximately 2.5 hours at 37° C. and 210 rpm the cultures reached an OD600 of approximately 1.0-1.5, at which point they were induced with 0.5 mM IPTG and supplemented with 0.5 mM 5-aminolevulinic acid, 50 mg/L thiamine, 1.2 mM $MgSO_4$, and 25 mL of a solution of trace elements (190 mg $CaCl_2*2H_2O$, 90 mg $ZnSO_4*7H_2O$, 90 mg $CoCl_2*6H_2O$, 75 mg $CuSO_4*5H_2O$, 50 mg $MnSO_4*H_2O$, 11.1 mg $Na_2$-$EDTA*2H_2O$ and 8.35 mg $FeCl_3*6H_2O$ in 500 ml of $ddH_2O$). The culture was further incubated for 20 hours at 20° C. and 180 rpm. The cultures were then pelleted via centrifugation at 3900×g at 4° C. for 10 min, washed once with bioconversion buffer (100 mM phosphate buffer (pH7.2), 1% glycerol/0.4% glucose, 100 µg/ml FeSO4*7H2O, and 30 µg/ml kanamycin), and pelleted again. Next, bioconversion buffer was added to the cell pellets targeting a cell wet weight of 100 g/L and the cell pellets were resuspended.

To carry out biotransformations, 1 mL of this mixture was transferred into sterile 40 mL amber screw cap vials and 100 µL of 1-dodecene was added along with 100 µL of isopropyl alcohol. This reaction mixture was incubated at 20° C. and

TABLE 17

Biotransformation rate and selectivity of terminal hydroxylase expressing strains on E/Z-5-decene.

| Strain No. | Expressed terminal hydroxylase | Terminal hydroxylase Accession No. | (E)-5-decen-1-ol formation rate (mg/L/h) | Z/E selectivity |
|---|---|---|---|---|
| SPV001 | None | n/a | 0 | n.d. |
| SPV015 | CYP153A7 | AJ850057 (SEQ ID NO: 15) | 290 ± 63 | 85 ± 2:15 ± 2 |
| SPV016 | CYP153 M. sp. | AFO66437 (SEQ ID NO: 16) | 347 | 73:27 |
| SPV017 | CYP153A13N2 | AB206793 (SEQ ID NO: 17) | 41 | 80:20 |
| SPV029 | CYP153A13P2 | AB206795 (SEQ ID NO: 18) | 91 | 86:14 |
| SPV0025 | CYP153A M. aq. (G307A) | ABM17701 (SEQ ID NO: 19) | 88 | 80:20 |
| SPV0013 | CYP153A M. aq. | ABM17701 (SEQ ID NO: 19) | 52 | 77:23 |
| SPV0026 | CYP153A M. aq. (G307A) | ABM17701 (SEQ ID NO: 19) | 66 | 78:22 |
| SPV0023 | AlkB | YP_009076004 (SEQ ID NO: 20) | 244 | 78:22 |
| SPV0030 | AlkB | YP_009076004 (SEQ ID NO: 20) | 232 | 78:22 |
| SPV0031 | AlkB | YP_009076004 (SEQ ID NO: 20) | 304 | 79:21 |
| SPV032 | AlkB P1 | CAB51047 (SEQ ID NO: 21) | 321 | 77:23 |
| SPV037 | AlkB1 AB | CAC38027 (SEQ ID NO: 22) | 221 | 77:23 |

Example 6: Hydroxylation of 1-Dodecene

The purpose of this example is to illustrate the biocatalytic hydroxylation of 1-dodecene to 11-dodecen-1-ol, and the selectivity of the various enzymes towards the production of either 11-dodecen-1-ol or 1,2-epoxydodecane.

The 25 strains detailed in Example 3 were characterized for their ability to convert 1-dodecene to 11-dodecen-1-ol and 1,2-epoxydodecane in whole cell bioconversion reactions.

Overnight cultures of these 25 strains were inoculated from single colonies grown on LB agar plates containing 30 µg/ml of kanamycin into 2.5 mL of LB medium containing 30 µg/ml of kanamycin and incubated for 24 hours at 37° C.

180 rpm for 4 hour before the reaction was quenched via addition of 100 µL of 3M HCL.

To extract the biotransformation products, 5 mL of n-hexane was added. The mixture was thoroughly mixed via shaking in an orbital shaker (20 min @ 250 rpm) and then allowed to settle undisturbed for 20 minutes. An aliquot (1 mL) of the organic layer was analyzed via gas chromatography (GC) using a J&W DB-23 column (30 m×25 mm×25 µm) coupled to an FID detector using the following temperature profile: 45° C. for 0.5 min; ramp 5° C./min to 50° C.; hold 0.5 min; ramp 30° C./min to 220° C.; hold 3.3 min. Retention for substrates and products were verified using authentic standards and were as follows: 1-dodecene at 4.35 min, 11-dodecen-1-ol at 8.91 min, and 1,2-epoxydodecane at 7.86 min.

Results are shown in Table 18. These results demonstrate the capability of members of the CYP153 and AlkB family of enzymes to catalyze the hydroxylation of 1-dodecene to produce 11-dodecen-1-ol. Furthermore, some of these enzyme are able to selectively form 11-dodecen-1-ol over the energetically favored 1,2-epoxydodecane product.

Cultures of the strains listed in Table 19 are inoculated, cultured, and subjected to a biotransformation procedure as described in Example 5 with the exception that (Z)-5-hexadecene was used as the substrate instead of the 84:16 mixture of (E)-5-decene:(Z)-5-decene. The biotransformation products are extracted and then analyzed via gas chromatography as described in Example 5 to identify products including (Z)-11-hexadecene-1-ol and (Z)-5-hexadecene-1-ol.

TABLE 18

Biotransformation rate and selectivity of terminal hydroxylase expressing strains on 1-dodecene.

| Strain No. | Expressed terminal hydroxylase | Terminal hydroxylase Accession No. (protein ID) (SEQ ID NO:) | 11-dodecen-1-ol titer (mg/L) | 11-dodecen-1-ol:1,2-epoxydodecane selectivity |
|---|---|---|---|---|
| SPV001 | None | n/a | 0 | n.d. |
| SPV015 | CYP153A7 | AJ850057 (SEQ ID NO: 15) | 85 ± 33 | 86 ± 13:14 ± 13 |
| SPV016 | CYP153 M. sp. | AFO66437 (SEQ ID NO: 16) | 68 | 61:39 |
| SPV017 | CYP153A13N2 | AB206793 (SEQ ID NO: 17) | 25 | 54:46 |
| SPV028 | CYP153A13N3 | AB206799 | 64 | 55:45 |
| SPV029 | CYP153A13P2 | AB206795 (SEQ ID NO: 18) | 21 | 55:45 |
| SPV0025 | CYP153A M. aq. (G307A) | ABM17701 (SEQ ID NO: 19) | 52 | 65:35 |
| SPV0026 | CYP153A M. aq. (G307A) | ABM17701 (SEQ ID NO: 19) | 42 | 61:39 |
| SPV0023 | AlkB | YP_009076004 (SEQ ID NO: 20) | 26 | 67:33 |
| SPV0030 | AlkB | YP_009076004 (SEQ ID NO: 20) | 34 | 67:33 |
| SPV0031 | AlkB | YP_009076004 (SEQ ID NO: 20) | 71 | 68:32 |
| SPV032 | AlkB P1 | CAB51047 (SEQ ID NO: 21) | 86 | 69:31 |
| SPV037 | AlkB1 AB | CAC38027 (SEQ ID NO: 22) | 38 | 48:52 |

Example 7. Hydroxylation of (Z)-5-hexadecene by Cytochromes P450 of the CYP153 Family The purpose of this example is to illustrate the biocatalytic hydroxylation of (Z)-5-hexadecene by members of the CYP153 family.

The following strains are constructed by (1) restriction digest of a synthesized DNA fragment containing the target gene insert and the desired expression plasmid followed by (2) ligation of the digested fragment and (3) transformation of the ligation mixture into the desired *E. coli* strain (Table 19).

Example 8: Hydroxylation of (Z)-5-hexadecene by Cytochromes P450 of the CYP52 Family The purpose of this example is to illustrate the biocatalytic hydroxylation of (Z)-5-hexadecene by members of the CYP52 family.

Two P450 cytochromes of the CYP52 family were integrated into the *P. pastoris* CBS7435 Mut$^S$ genome along with their corresponding cytochrome P450 reductases (CPR). Biotransformations were performed with these strains to determine whether these P450s hydroxylate (Z)-

TABLE 19

Strains constructed.

| Strain No. | Plasmid | *E. coli* strain | Gene insert | Hydroxylase Accession No. |
|---|---|---|---|---|
| SPV0001 | pET28a(+) | *E. coli* BL21 (DE3) | None | n/a |
| SPV0012 | pET28a(+) | *E. coli* BL21 (DE3) | Cyp153A P.sp.-CPR$_{BM3}$ | Q11ZY2 |
| SPV0025 | pColaDuet-1 | *E. coli* BL21 (DE3) | Cyp153A M. aq. (G307A)-CPR$_{BM3}$ | A1TY82 |
| SPV0026 | pET28a(+) | *E. coli* BL21 (DE3) | Cyp153A M. aq. (G307A)-CPR$_{BM3}$ | A1TY82 |

5-hexadecene. Strains and oligonucleotides disclosed in this example are listed in Tables 20 and 21.

TABLE 20

Genotypes of strains used in Example 8.

| Strain No. | Genotype |
|---|---|
| SPV048 | *P. pastoris* CBS7435 mut$^S$ pPpT4_SmiI_cmRED_cmCYP52A3 |
| SPV051 | *P. pastoris* CBS7435 mut$^S$ pPpT4_SmiI_ctRED_ctCYP52A13 |

TABLE 21

Oligonucleotide sequences used in Example 8.

| Primer | Sequence | Description | SEQ ID NO. |
|---|---|---|---|
| OPV 0042 | ATGACGGT TCATGACA TCATCGC | CYP52A13 forward primer | 10 |
| OPV 0043 | CTGACATC CTCTTGAG CGGC | CYP52A13/A3 reverse primer | 11 |
| OPV 0044 | ATGGCTAT TGAGCAGA TTATCGAA G | CYP52A3 forward primer | 12 |

Gene sequences for *C. tropicalis* CYP52A13 (Accession No. AAO73953.1 (SEQ ID NO: 23)), *C. tropicalis* CPR (Accession No. P37201.1), *C. maltosa* CYP52A3 (Accession No. P24458.1 (SEQ ID NO: 24)), as well as the *C. maltosa* CPR (Accession No. P50126.1), were ordered as synthetic genes (DNA 2.0, Menlo Park, Calif., USA), and cloned into the pT4_S vector using EcoRI/NotI restriction sites for directional cloning. The plasmid containing the expression cassettes for CYP52A3/CPR and CYP52A13/CPR under the control of an AOX promoter and terminator were linearized using the restriction enzyme SmiI and purified. Next, 500 ng of the linearized DNA sequences for expressing CYP52A3/CPR (SEQ ID NO:13) and CYP52A13/CPR (SEQ ID NO:14) were used to transform *P. pastoris* CBS7435 Mut$^S$. The parent strain and the generation of the pT4 S plasmid used to generate the subsequent constructs are described by Gudiminchi et al. (*Biotechnology Journal*, 2013, 8(1), 146-52).

Colony PCR of the obtained *P. pastoris* strains was performed to verify the P450 enzymes CYP52A3 and CYP52A13 were present using the Failsafe™ PCR Kit (EPICENTRE® Biotechnologies, Madison, Wis.; Catalog #FS99060) using Premix D and primers shown in Table 21 according to the manufactures recommendations.

Shake flask cultivations of the strains SPV048 and SPV051 were started from single colonies derived from an YBD agar plate (10 g/L Bacto™ yeast extract, 20 g/L Bacto™ peptone, 20 g/L D (+) glucose, 15 g/L agar) containing 100 mg/L Zeocin™. A volume of 45 mL of BMD1 medium (BMD1(1 L): 10 g/L D (+) glucose autoclaved, 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500× buffer B (buffer B:10 mg/50 mL d-Biotin, filter sterilized), add autoclaved H$_2$O to 1 L) was inoculated with a single colony and incubated for approximately 63 h at 28° C. to 30° C. and 130 rpm in a 250 mL baffled Erlenmeyer flask. After the initial 63 h incubation 5 mL of BMM10 medium (BMM10 (1 L): 50 mL methanol, 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500× buffer B (buffer B:10 mg/50 mL d-Biotin, filter sterilized), add autoclaved H$_2$O to 1 L) was added. The cultivations were incubated for 12 h at 28° C. to 30° C., 130 rpm. After 12 hours incubation 0.4 mL of methanol was added to induce expression of the P450 enzymes and their corresponding CPR's and incubated for 12 h at 28° C. to 30° C., 130 rpm. Thereafter, 0.4 mL of methanol was added every 12 h and incubated at 28° C. to 30° C., 130 rpm. Cells were harvested after induction for approximately 72 h to 80 h and a total cultivation time of approximately 132 h to 143 h.

As control a volume of 45 mL of BMD1 medium (BMD1 (1 L): 10 g/L D (+) glucose autoclaved, 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500× buffer B (buffer B:10 mg/50 mL d-Biotin, filter sterilized), add autoclaved H$_2$O to 1 L) was inoculated with a single colony of strain SPV051 incubated for approximately 63 h at 28° C. to 30° C. and 130 rpm in a 250 mL baffled Erlenmeyer flask. After the initial 63 h incubation 5 mL of BMM10 medium without methanol (BMM10 without methanol (1 L): 200 mL 10×PPB (10×PPB: 30.0 g/L K$_2$HPO$_4$, 118 g/L KH$_2$PO$_4$, pH 6.0, autoclaved), 100 mL 10×YNB (10×YNB: 134 g/L Difco™ yeast nitrogen base without amino acids, autoclaved), 2 mL 500× buffer B (buffer B:10 mg/50 mL d-Biotin, filter sterilized), add autoclaved H$_2$O to 1 L) was added. The cultivations were incubated for additional 60 h to 68 h at 28° C. to 30° C., 130 rpm. Cells were harvested after a total cultivation time of approximately 132 h to 143 h.

Cultivations were harvested in 50 mL Falcon tubes via centrifugation at 3000×rcf for 5 min at 4° C. The supernatant was discarded. The pellet was resuspended in 5 mL 100 mM PPB (mix stock solutions: 80.2 mL of 1M K$_2$HPO$_4$ (174.18 g/L) with 19.8 mL of 1M KH$_2$PO$_4$ (136.09 g/L) autoclaved, add autoclaved H$_2$O to 1 L and adjust pH 7.4), containing 20% glycerol, pH 7.4 and centrifuged again at 3000×rcf for 5 min at 4° C. (washing step). The supernatant was discarded and the Falcon tube was carefully patted on a Kimwipe to remove excess buffer. Each pellet was weighed to determine the cell wet weight (cww) of the cultures. The washed pellet was resuspended in bioconversion buffer (100 mM PPB (mix stock solutions: 80.2 mL of 1M K$_2$HPO$_4$ (174.18 g/L) with 19.8 mL of 1M KH$_2$PO$_4$ (136.09 g/L) autoclaved, add autoclaved H$_2$O to 1 L and adjust to pH 7.4), 20% glycerol, 0.2% Emulgen 913 (Kao Chemicals, Japan), pH 7.4) targeting a final cell density of ~200 g cww/L.

1 ml of the resuspended cultivation (200 g cww/L) was dispensed in a 50 mL Falcon tube. 125 μL neat substrate was added to each culture to initiate the bioconversion reactions. The bioconversion reactions were incubated at 30° C. and 200 rpm for 40 h to 48 h. The samples were stored at −80° C. until extraction and analysis of the respective product formation.

250 μL of 3 M HCl was added to each of the frozen samples. After addition of HCl samples were extracted twice with 1×1 mL or 2×2 mL diethyl ether. 10 μL of 10 mg/mL 1-Heptanol or 10 μL of 10 mg/mL 1-Tetradecanol was added to the sample as internal standard. Upon addition of diethyl ether and internal standard the sample was vortexed for 5 min. The entire sample was transferred to new reaction tubes and centrifuged for 10 min/8000×rcf at room temperature. The organic upper phase was transferred to a glass vial and air dried. The sample was resuspended to a final volume of 100 μL to 150 μL using Methyl Tertiary Butyl Ether (MTBE) or resuspended to a final volume of 200 μL using Tetrahydrofuran (THF) and analyzed via gas chromatography (GC).

An Agilent 6890 equipped with an FID detector and a J&W DB-23 column (length: 30 m, I.D. 25 mm, film 25 μm) was used to analyze the samples using the following program: Split ratio of 1:10. 240° C. for the injector inlet: 240° C. for the detector, $H_2$ at 40.0 Air at 450 mL/min, Makeup flow (He) at 45 mL/min. Carrier He at 1.1 mL/min and 13 psi. 45° C. oven for 0.5 min; 5° C./min gradient to 50° C. then hold at 50° C. for 0.5 min; 30° C./min gradient to 220° C., then hold at 220° C. for 3.33 min. Analysis was performed in triplicate using authentic standards (obtained from Sigma-Aldrich or Bedoukian Research).

Results are shown in Table 22 and FIG. 1. Surprisingly, the CYP52 enzymes exhibit selectivity for one end of the (Z)-5-hexadecene substrate over the other: The SPV048 bioconversion produced 66.8% (Z)-5-hexadecen-1-ol and 33.2% (Z)-11-hexadecen-1-ol while the SPV051 bioconversion produced 27.6% (Z)-5-hexadecen-1-ol and 74.4% (Z)-11-hexadecen-1-ol.

TABLE 22

Results for bioconversions.

| Strain | Enzyme | Induced (Y/N) | Substrate | Products | Selectivity [%] |
|---|---|---|---|---|---|
| SPV048 | CYP52A3 | N | (Z)-5-hexadecene | n.d. | n/a |
| SPV048 | CYP52A3 | Y | (Z)-5-hexadecene | (Z)-5-hexadecen-1-ol | 66.8 ± 7.6 |
|  |  |  |  | (Z)-11-hexadecen-1-ol | 33.2 ± 1.0 |
| SPV051 | CYP52A13 | N | (Z)-5-hexadecene | n.d. | n/a |
| SPV051 | CYP52A13 | Y | (Z)-5-hexadecene | (Z)-5-hexadecen-1-ol, | 27.6 ± 4.3 |
|  |  |  |  | (Z)-11-hexadecen-1-ol | 74.4 ± 2.2 |

Example 9: Hydroxylation of 1-dodecyne

The purpose of this example is to illustrate the biocatalytic hydroxylation of 1-dodecyne to 11-dodecyn-1-ol.

The 25 strains detailed in Example 3 were characterized for their ability to convert 1-dodecyne to 11-dodecyn-1-ol in whole cell bioconversion reactions.

Overnight cultures of these 25 strains were inoculated from single colonies grown on LB agar plates containing 30 μg/ml of kanamycin into 2.5 mL of LB medium containing 30 μg/ml of kanamycin and incubated for 24 hours at 37° C. and 210 rpm. The overnight culture was used to inoculate 50 or 100 ml of Terrific Broth with a starting $OD_{600}$ of 0.1. After incubation for approximately 2.5 hours at 37° C. and 210 rpm the cultures reached an OD600 of approximately 1.0-1.5, at which point they were induced with 0.5 mM IPTG and supplemented with 0.5 mM 5-aminolevulinic acid, 50 mg/L thiamine, 1.2 mM $MgSO_4$, and 25 mL of a solution of trace elements (190 mg $CaCl_2*2H_2O$, 90 mg $ZnSO_4*7H_2O$, 90 mg $CoCl_2*6H_2O$, 75 mg $CuSO_4*5H_2O$, 50 mg $MnSO_4*H_2O$, 11.1 mg $Na_2$-EDTA*$2H_2O$ and 8.35 mg $FeCl_3*6H_2O$ in 500 ml of $ddH_2O$). The culture was further incubated for 20 hours at 20° C. and 180 rpm. The cultures were then pelleted via centrifugation at 3900×g at 4° C. for 10 min, washed once with bioconversion buffer (100 mM phosphate buffer (pH7.2), 1% glycerol/0.4% glucose, 100 μg/ml $FeSO_4*7H_2O$, and 30 μg/ml kanamycin), and pelleted again. Next, bioconversion buffer was added to the cell pellets targeting a cell wet weight of 100 g/L and the cell pellets were resuspended.

To carry out biotransformations, 1 mL of this mixture was transferred into sterile 40 mL amber screw cap vials and 100 μL of 1-dodecyne was added along with 100 μL of isopropyl alcohol. This reaction mixture was incubated at 20° C. and 180 rpm for 4 hour before the reaction was quenched via addition of 100 μL of 3M HCL.

To extract the biotransformation products, 5 mL of n-hexane was added. The mixture was thoroughly mixed via shaking in an orbital shaker (20 min @ 250 rpm) and then allowed to settle undisturbed for 20 minutes. An aliquot (1 mL) of the organic layer was analyzed via gas chromatography (GC) using a J&W DB-23 column (30 m×25 mm×25 um) coupled to an FID detector using the following temperature profile: 45° C. for 0.5 min; ramp 5° C./min to 50° C.; hold 0.5 min; ramp 30° C./min to 220° C.; hold 3.3 min. Retention for substrates and products were verified using authentic standards and were as follows: 1-dodecyne at 6.34 min and 11-dodecyn-1-ol at 9.71 min.

Results are shown in Table 23. These results demonstrate the capability of members of the CYP153 and AlkB family of enzymes to catalyze the hydroxylation of 1-dodecyne to produce 11-dodecyn-1-ol.

TABLE 23

Biotransformation rate and selectivity of terminal hydroxylase expressing strains on 1-dodecyne.

| Strain No. | Expressed terminal hydroxylase | Terminal hydroxylase Accession No. | 11-dodecyn-1-ol titer (mg/L) |
|---|---|---|---|
| SPV001 | None | n/a | 0 |
| SPV015 | CYP153A7 | AJ850057 (SEQ ID NO: 15) | 67 ± 21 |
| SPV016 | CYP153 M. sp. | AFO66437 (SEQ ID NO: 16) | 74 |
| SPV029 | CYP153A13P2 | AB206795 (SEQ ID NO: 18) | 10 |
| SPV0025 | CYP153A M. aq. (G307A) | ABM17701 (SEQ ID NO: 19) | 27 |
| SPV0013 | CYP153A M. aq. | ABM17701 (SEQ ID NO: 19) | 48 |
| SPV0026 | CYP153A M. aq. (G307A) | ABM17701 (SEQ ID NO: 19) | 49 |
| SPV0023 | AlkB | YP_009076004 (SEQ ID NO: 20) | 150 |
| SPV0030 | AlkB | YP_009076004 (SEQ ID NO: 20) | 166 |
| SPV0031 | AlkB | YP_009076004 (SEQ ID NO: 20) | 251 |
| SPV032 | AlkB P1 | CAB51047 (SEQ ID NO: 21) | 265 |

TABLE 23-continued

Biotransformation rate and selectivity of terminal hydroxylase expressing strains on 1-dodecyne.

| Strain No. | Expressed terminal hydroxylase | Terminal hydroxylase Accession No. | 11-dodecyn-1-ol titer (mg/L) |
|---|---|---|---|
| SPV037 | AlkB1 AB | CAC38027 (SEQ ID NO: 22) | 178 |

Example 10: Hydroxylation of 1-bromodecane

The purpose of this example is to illustrate the biocatalytic hydroxylation of 1-bromodecane to 10-bromodecan-1-ol, and the selectivity of the various enzymes towards 10-bromodecan-1-ol formation over 1-decanal formation as the result of dehalogenation.

The 25 strains detailed in Example 3 were characterized for their ability to convert 1-bromodecane to 10-bromodecan-1-ol in whole cell bioconversion reactions.

Overnight cultures of these 25 strains were inoculated from single colonies grown on LB agar plates containing 30 μg/ml of kanamycin into 2.5 mL of LB medium containing 30 μg/ml of kanamycin and incubated for 24 hours at 37° C. and 210 rpm. The overnight culture was used to inoculate 50 or 100 ml of Terrific Broth with a starting $OD_{600}$ of 0.1. After incubation for approximately 2.5 hours at 37° C. and 210 rpm the cultures reached an OD600 of approximately 1.0-1.5, at which point they were induced with 0.5 mM IPTG and supplemented with 0.5 mM 5-aminolevulinic acid, 50 mg/L thiamine, 1.2 mM $MgSO_4$, and 25 mL of a solution of trace elements (190 mg $CaCl_2*2H_2O$, 90 mg $ZnSO_4*7H_2O$, 90 mg $CoCl_2*6H_2O$, 75 mg $CuSO_4*5H_2O$, 50 mg $MnSO_4*H_2O$, 11.1 mg $Na_2$-EDTA$*2H_2O$ and 8.35 mg $FeCl_3*6H_2O$ in 500 ml of $ddH_2O$). The culture was further incubated for 20 hours at 20° C. and 180 rpm. The cultures were then pelleted via centrifugation at 3900×g at 4° C. for 10 min, washed once with bioconversion buffer (100 mM phosphate buffer (pH7.2), 1% glycerol/0.4% glucose, 100 μg/ml FeSO4*7H2O, and 30 μg/ml kanamycin), and pelleted again. Next, bioconversion buffer was added to the cell pellets targeting a cell wet weight of 100 g/L and the cell pellets were resuspended.

To carry out biotransformations, 1 mL of this mixture was transferred into sterile 40 mL amber screw cap vials and 100 μL, of 1-bromodecane was added along with 100 μL, of isopropyl alcohol. This reaction mixture was incubated at 20° C. and 180 rpm for 1 hour before the reaction was quenched via addition of 100 μL of 3M HCL.

To extract the biotransformation products, 5 mL of n-hexane was added. The mixture was thoroughly mixed via shaking in an orbital shaker (20 min @ 250 rpm) and then allowed to settle undisturbed for 20 minutes. An aliquot (1 mL) of the organic layer was analyzed via gas chromatography (GC) using a J&W DB-23 column (30 m×25 mm×25 μm) coupled to an FID detector using the following temperature profile: 45° C. for 0.5 min; ramp 5° C./min to 50° C.; hold 0.5 min; ramp 30° C./min to 220° C.; hold 3.3 min. Retention for substrates and products were verified using authentic standards and were as follows: 1-bromodecane at 7.42 min, 10-bromodecan-1-ol at 11.6 min and 1-decanal at 7.24 min.

Results are shown in Table 24. These results demonstrate the capability of members of the CYP153 and AlkB family of enzymes to catalyze the hydroxylation of 1-bromodecane to 10-bromodecan-1-ol. Furthermore, these results demonstrate selective hydroxylation to from 10-bromodecan-1-ol over the dehalogenated product 1-decanal.

TABLE 24

Biotransformation rate and selectivity of terminal hydroxylase expressing strains on 1-bromodecane.

| Strain No. | Expressed terminal hydroxylase | Terminal hydroxylase Accession No. | 10-bromodecan-1-ol formation rate (mg/L/h) | 10-bromodecan-1-ol:1-decanal selectivity |
|---|---|---|---|---|
| SPV001 | None | n/a | 0 | n.d. |
| SPV015 | CYP153A7 | AJ850057 (SEQ ID NO: 15) | 470 ± 125 | 93 ± 3:7 ± 3 |
| SPV016 | CYP153 M. sp. | AFO66437 (SEQ ID NO: 16) | 170 | 73:27 |
| SPV0025 | CYP153A M. aq. (G307A) | ABM17701 (SEQ ID NO: 19) | 80 | 82:8 |
| SPV0013 | CYP153A M. aq. | ABM17701 (SEQ ID NO: 19) | 131 | 93:7 |
| SPV0026 | CYP153A M. aq. (G307A) | ABM17701 (SEQ ID NO: 19) | 105 | 83:17 |
| SPV0030 | AlkB | YP_009076004 (SEQ ID NO: 20) | 92 | 71:29 |
| SPV0031 | AlkB | YP_009076004 (SEQ ID NO: 20) | 209 | 83:17 |

TABLE 24-continued

Biotransformation rate and selectivity of terminal hydroxylase expressing strains on 1-bromodecane.

| Strain No. | Expressed terminal hydroxylase | Terminal hydroxylase Accession No. | 10-bromodecan-1-ol formation rate (mg/L/h) | 10-bromodecan-1-ol:1-decanal selectivity |
|---|---|---|---|---|
| SPV032 | AlkB P1 | CAB51047 (SEQ ID NO: 21) | 197 | 86:14 |
| SPV037 | AlkB1 AB | CAC38027 (SEQ ID NO: 22) | 161 | 81:19 |

Example 11

Synthesis of (E)-5-decen-1-ol is carried out according to Scheme 24.

E-5-Decene:

The synthesis of E-5-decene is carried out according to the Example 6 disclosed in the US Patent Application No. 2013/0023665 A1. Briefly, into a 25 mL Schlenk flask, the catalyst (Richard Pederson et al. Adv. Synth. Catal. 2002, 344, 728) (0.0032 mmol) and then 0.4 mL of 1-hexene is added under argon atmosphere. The mixture is stirred at 40° C. for 2 hours. The reaction is quenched by filtration through a plug of silica gel (~2 cm) packed in a Pasteur pipette using pentane as eluent. The reaction solvent is removed under reduced pressured. The desired product, E-5-decene, is purified by distillation and characterized by GC and NMR.

E-5-decen-1-ol:

E-5-Decene is then subjected to biohydroxylation according to the process disclosed in Example 6 to generate E-5-decen-1-ol. The product is isolated by extraction of the fermentation broth with organic solvent and purified by distillation.

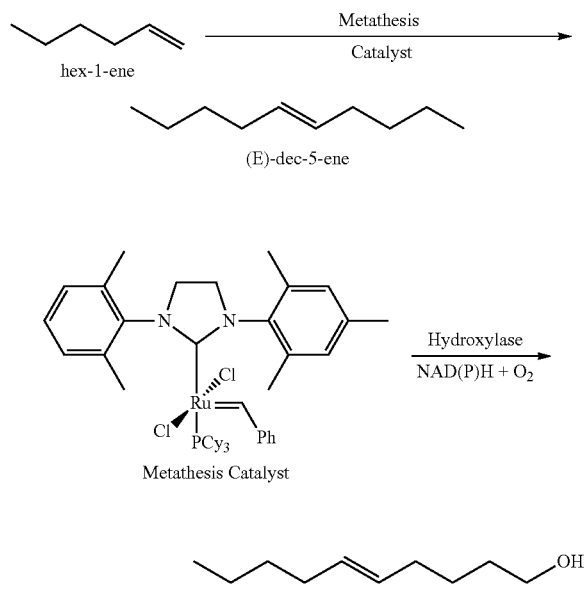

Example 12

Synthesis of (Z)-3-hexen-1-ol is carried out according to Scheme 25.

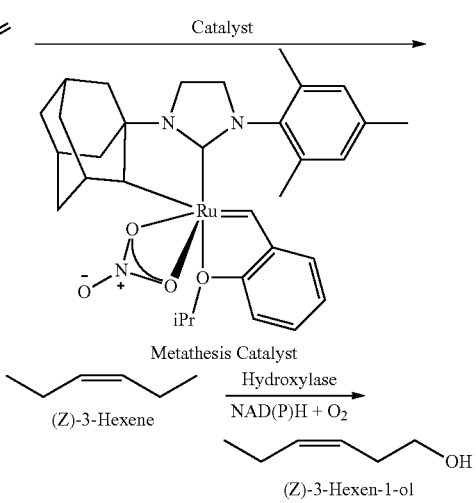

Z-3-Hexene:

A 5-L jacketed 3-necked flask is equipped with a magnetic stir bar, gas feeding tube and a packed bed column containing a dry ice condenser. Z-selective catalyst (see, Scheme 19a) 2.97 g, 0.0035 mol, 0.023 mol % based on 1-butene added) and toluene (240 g) are added. The flask is sparged with argon for 15 min, while being cooled to 15° C. 1-Butene (841 g, 15.0 mol) is added by bubbling into the toluene solution over 10.5 hours. The rate of addition is such that the reaction temperature remains above 10° C. After 10.5 hours, the packed bed column and the dry ice condenser are replaced with a Friedrich condenser. The Friedrich condenser is circulated with 0° C. coolant. The reaction flask is cooled to 10° C. An argon purge with a flow rate of 1 L/minute is maintained for 12 hours. The metathesis catalyst is removed by the in-situ generation of catalyst-tris(hydroxymethyl)phosphine (THP) complex. Tetrakis(hydroxymethyl)phosphonium chloride (TKC) (80% purity, 20.80 g, 25 equivalent to catalyst) and NaHCO$_3$ (7.35 g, 25 equivalent to catalyst) are added to the solution. The chiller/heater controlling the jacketed flask is set to 40° C. and stirred for 18 hours. The reaction is cooled to 10° C. and washed with water (500 mL) and brine (500 mL) and dried over anhydrous Na$_2$SO$_4$. Z-3-Hexene is isolated by distillation.

Z-3-Hexen-1-ol:

Z-3-Decene is subjected to biohydroxylation according to the process disclosed in Example 6 to generate Z-3-hexen-1-ol. The product is isolated by extraction of the fermentation broth with organic solvent and purified by distillation.

Example 13

Synthesis of (Z)-11-hexadecenol is carried out according to Scheme 26.

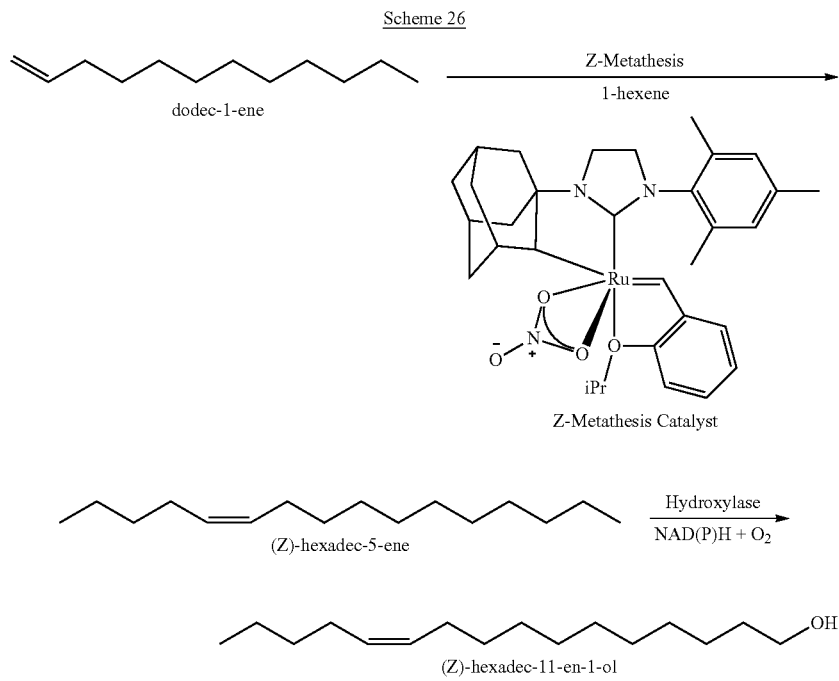

Scheme 26

Z-5-hexadecene:

The cross metathesis reactions of 1-hexene and dodec-1-ene is carried out in a 250 mL three-necked round-bottomed flask fitted with a condenser, thermometer and septum. The dodec-1-ene (20 mL) is transferred to the reaction flask along with 4 mole equivalent of 1-hexene and the mixture is heated to the desired reaction temperature (ranging from 30 to 100° C.) using an oil bath on a controlled hotplate magnetic stirrer. Thereafter 0.5 mol % of the catalyst (based on dodec-1-ene added; see Scheme 19a) is added to the flask and the reaction mixture is continuously stirred with a magnetic stirrer bar until the formation of the primary metathesis products is completed. The progress of the reaction is monitored by GC/FID. The sample is prepared for GC analysis by diluting an aliquot (0.3 mL) of the sample, taken at various reaction time intervals, with 0.3 mL toluene and quenched with 2 drops of tert-butyl hydrogen peroxide prior to analysis. Once dodec-1-ene is completely consumed, the reaction is quenched with tert-butyl hydrogen peroxide and filtered through a plug of silica using hexane as eluent. The hexane filtrate is concentrated and the Z-5-hexadecene is isolated by distillation.

Z-11-Hexadecen-1-ol:

Z-5-Hexadecene is subjected to biohydroxylation according to the process disclosed in Example 6 to generate Z-11-hexadecen-1-ol. The product is isolated by extraction of the fermentation broth with organic solvent, concentrate and silica-gel chromatography.

Example 14

Synthesis of (Z)-11-hexadecenol is carried out according to Scheme 27.

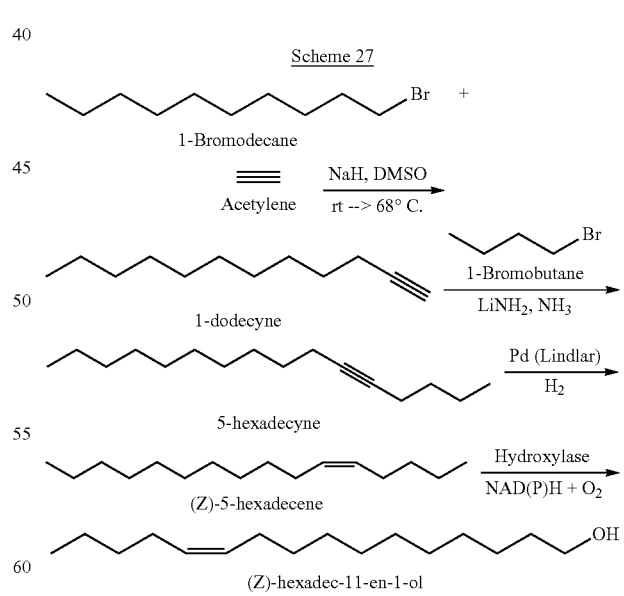

Scheme 27

1-Dodecyne:

The synthesis of 1-dodecyne is carried out according to the protocol described in Oprean, Joan et al. Studia Universitatis Babes-Bolyai, *Chemia*, 2006, 51, 33.

5-Hexadecyne:

To a −78° C. solution of 1-dodecyne (5 mmol) in THF (20 mL), 2.5 M n-BuLi (5 mmol) in hexane is added dropwise via a syringe. A solution of 1-bromobutane (5 mmol) and TBAI (0.2 mmol) dissolve in THF is then dropwise added to the reaction mixture. The reaction mixture is allowed to warm to room temperature and then heat at 70° C. for 24 hours. The reaction is quenched with 5 mL of 1M NH$_4$Cl and extract with hexanes (3×). The organic fractions are combined, dry with anhydrous MgSO$_4$ and concentrate under reduced pressure. The resulting residue is purified by silica gel flash chromatography using 60:1/hexane:ethyl acetate as mobile phase. Fractions containing the desired product are pulled and concentrate. 5-Hexadecyne is further purified by distillation.

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford the desired product, Z-5-hexadecene, which can be further purified by distillation.

Z-11-Hexadecen-1-ol:

Z-5-Hexadecene is then subjected to biohydroxylation according to the process disclosed in Example 6 to generate Z-11-hexadecen-1-ol. The product is isolated by extraction of the fermentation broth with ethyl acetate and further purified by distillation.

Example 15

Synthesis of (Z)-11-hexadecenol is carried out according to Scheme 28.

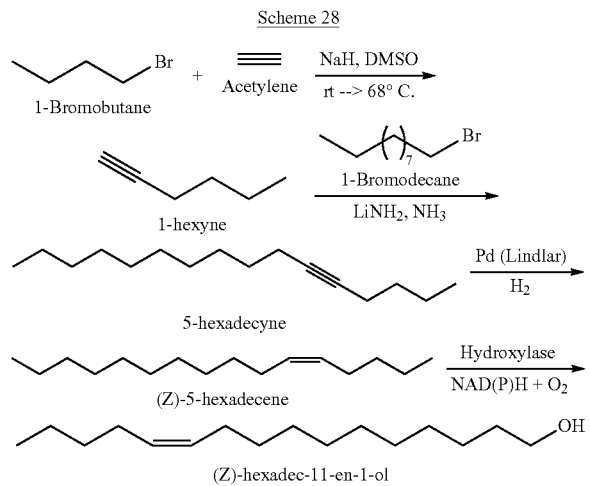

Scheme 28

1-Hexyne:

The synthesis of 1-hexyne is carried out according to the protocol described in Oprean, Joan et al. *Studia Universitatis Babes-Bolyai, Chemia*, 2006, 51, 33.

5-Hexadecyne:

To a −78° C. solution of 1-hexyne (5 mmol) in THF (20 mL), 2.5 M n-BuLi (5 mmol) in hexane is added dropwise via a syringe. A solution of 1-bromodecane (5 mmol) and n-Bu$_4$NI (TBAI) (0.2 mmol) dissolve in THF is then dropwise added to the reaction mixture. The reaction mixture is allowed to warm to room temperature and then heat at 70° C. for 24 hours. The reaction is quenched with 5 mL of 1M NH$_4$Cl and extract with hexanes (3×). The organic fractions are combined, dry with anhydrous MgSO$_4$ and concentrate under reduced pressure. The resulting residue is purified by silica gel flash chromatography using 60:1/hexane:ethyl acetate as mobile phase. Fractions containing the desired product are pulled and concentrate.

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford Z-5-hexadecene, which can be further purified by distillation.

Z-11-Hexadecen-1-ol:

Z-5-Hexadecene is then subjected to biohydroxylation according to the process disclosed in Example 6 to generate Z-11-hexadecen-1-ol. The product is isolated by extraction of the fermentation broth with organic solvent and further purified by distillation.

Example 16

Synthesis of (Z)-11-hexadecenol is carried out according to Scheme 29.

5-Hexadecyne:

To a −78° C. solution of 1-hexyne (0.383 g, 4.67 mmol) in THF (20 mL), 2.5 M n-BuLi (1.87 mL, 4.67 mmol) in hexane is added dropwise via a syringe. A solution of 1-bromodecane (4.67 mmol) and n-Bu$_4$NI (TBAI, 57 mg, 0.16 mmol) dissolved in THF is then dropwise added to the reaction mixture. The reaction mixture is allowed to warm to room temperature and then heat at 70° C. for 24 hours. The reaction is quenched with 5 mL of 1M NH$_4$Cl and extract with hexanes (3×). The organic fractions are combined, dried with anhydrous MgSO$_4$, and concentrated under reduced pressure. The resulting residue is purified by silica gel flash chromatography using 60:1 hexane:ethyl acetate as the mobile phase. Fractions containing the desired product, 5-hexadecyne, are pooled and concentrated.

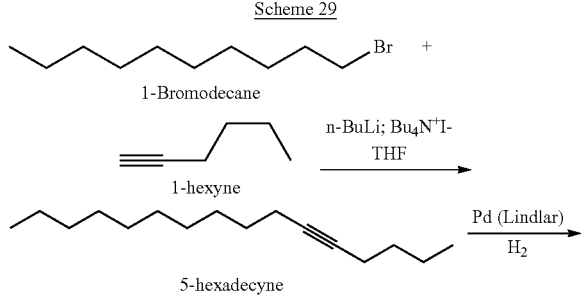

Scheme 29

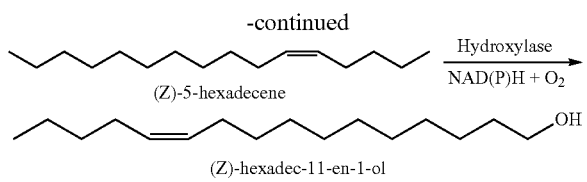

Z-5-Hexadecene:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of Z-5-hexadecene (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford the desired product, Z-5-hexadecene.

Z-11-Hexadecen-1-ol:

Z-5-Hexadecene is then subjected to biohydroxylation according to the process disclosed in Example 6 to generate Z-11-hexadecen-1-ol. The product is isolated by extraction of the fermentation broth with organic solvent and purified by distillation.

Example 17

Synthesis of (Z)-11-hexadecenol is carried out according to Scheme 30.

Scheme 30

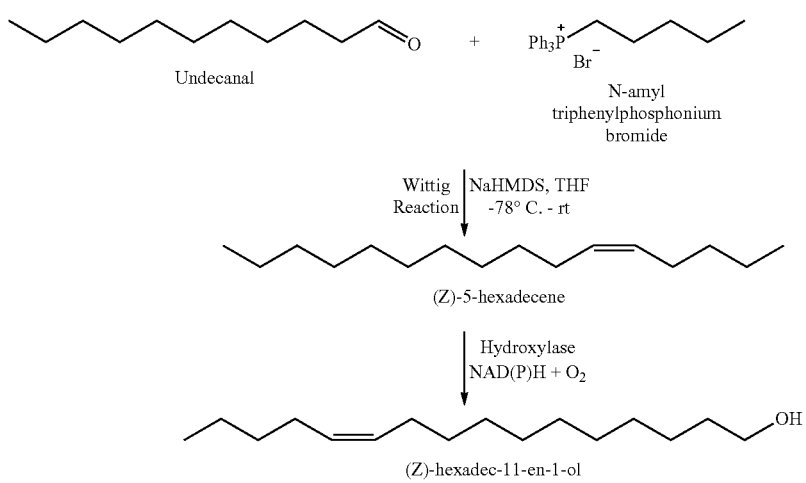

Z-5-Hexadecene:

Into an oven-dried three-neck RBF, N-amyl triphenylphosphnium bromide (13.98 g, 33.83 mmol) is dissolved in anhydrous toluene (30 mL). The mixture is allowed to stir via a magnetic stir bar at ambient temperature until complete dissolution of the alkyl phosphonium bromide salt is achieved. A solution of 6.57 g of potassium bis(trimethylsilyl)amide (KHMDS) in anhydrous toluene (30 mL) is then dropwise added to the reaction mixture. Upon complete addition of KHMDS solution to the reaction mixture, the reaction solution is allowed to stir for another 15 minutes, and is then cooled to −78° C. in an acetone and dry ice bath.

A solution of undecanal (4.59 mL, 22.28 mmol) in toluene (40 mL) is then dropwise added to the reaction mixture via an addition funnel. The reaction is stirred at −78° C. for 20 minutes, then allowed to warm at room temperature with stirring for another 30 minutes. The reaction is terminated by addition of methanol (40 mL) and then concentrated under reduced pressure. The resulting residue is triturated with hexanes and white precipitate, triphenyl phosphine oxide, is removed by filtration. The process is repeated until triphenyl phosphine oxide is no longer precipitated out of the solution. The remnant triphenyl phosphine oxide is removed by passing the crude reaction product through a short bed of silica using hexane as mobile phase. Z-5-hexadecene is obtained as a colorless oil.

Z-11-hexadecen-1-ol:

Z-5-Hexadecene is subjected to biohydroxylation according to the process disclosed in Example 6 to generate Z-11-hexadecen-1-ol. The product is isolated by extraction of the fermentation broth with organic solvent and purified by distillation.

Example 18

Synthesis of (Z)-11-hexadecenol is carried out according to Scheme 31.

Scheme 31

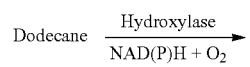

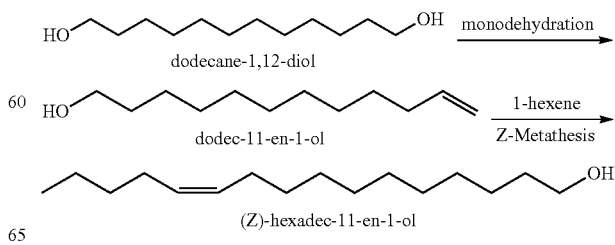

1,12-Dodecanediol:

Dodecane is subjected to biohydroxylation according to the process disclosed in Example 6 to generate dodecane-1,12-diol. The product is isolated by extraction of the fermentation broth with organic solvent and purified by distillation.

11-Dodecen-1-ol:

Monodehydration of 1,12-dodecanediol to 11-dodecen-1-ol is carried out according to a vapor-phase catalytic process as described in M. Segawa et al. Journal of Molecular Catalysis A: Chemical 2009, 310, 166. The catalytic reactions are performed in a fixed-bed down-flow reactor with the inside diameter of 17 mm. Prior to the reactions, an $In_2O_3$ sample (weight, W=0.50 g) is preheated in the reactor in $N_2$ flow at 500° C. for 1 h. The temperature of catalyst bed set at a prescribed temperature between 300 and 375° C., and 1,12-dodecanediol is then fed through the reactor top at a liquid feed rate of 2.67 mL per hour together with $N_2$ flow of 30 mL per min. The effluent is collected at −77° C., analyzed by GC. The 11-dodecen-1-ol product is purified by distillation.

Z-11-Hexadecen-1-ol:

The cross metathesis reactions of 1-hexene and 11-dodecen-1-ol is carried out in a 250 mL three-necked round-bottomed flask fitted with a condenser, thermometer and septum. The 11-dodecen-1-ol (20 mL) is transferred to the reaction flask along with 3 mole equivalents of 1-hexene and the mixture is heated to the desired reaction temperature (ranging from 30 to 100° C.) using an oil bath on a controlled hotplate magnetic stirrer. Thereafter 0.5 mol % of the catalyst (based on 11-dodecen-1-ol added) is added to the flask and the reaction mixture is continuously stirred with a magnetic stirrer bar until the formation of the primary metathesis products is completed. The progress of the reaction is monitored by GC/FID. The sample is prepared for GC analysis by diluting an aliquot (0.3 mL) of the sample, taken at various reaction time intervals, with 0.3 mL toluene and quenched with 2 drops of tert-butyl hydrogen peroxide prior to analysis. Once the limiting starting material, 11-dodecen-1-ol, is completely consumed, the reaction is quenched with tert-butyl hydrogen peroxide and filtered through a plug of silica using hexane as eluent. The hexane filtrate is concentrated and the Z-11-hexadecen-1-ol is obtained by distillation.

Example 19

Synthesis of (Z)-11-hexadecenol is carried out according to Scheme 32.

Scheme 32

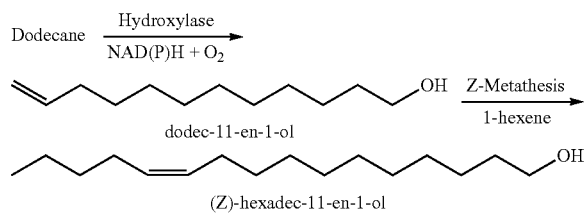

11-Dodecen-1-ol:

1-Dodecene is subjected to biohydroxylation according to the process disclosed in Example 6 to generate 11-dodecen-1-ol. The product is isolated by extraction of the fermentation broth with organic solvent and purified by distillation.

Z-11-Hexadecen-1-ol:

The synthesis of Z-11-hexadecen-1-ol is carried out the same way as described in Example 13.

Example 20

Synthesis of (Z)-11-hexadecenal via hydroxylation of 1-halodecane is carried out according to Scheme 33. In particular, Scheme 33 illustrates the synthesis of an important pheromone, (Z)-11-hexadecenal, utilizing biohydroxylation of 1-halodecane. In this process, biohydroxylation of 1-halodecane provides the desired α,ω-halodecanol. Upon protection of the hydroxyl moiety, the molecule can be alkylated with 1-hexyne to provide the C16 internal alkyne, which can be reduced to the cis-alkene via the use of the Lindlar's hydrogenation catalyst. Deprotection of the alcohol moiety, followed by oxidation of the free alcohol to aldehyde provides the desired product, (Z)-11-hexadecenal.

10-halodecanol:

1-Halodecane is subjected to biohydroxylation according to the process disclosed in Example 6 to generate 11-halodecanol. The product is isolated by extraction of the fermentation broth with organic solvent and purified by distillation.

THP-Protected 10-halodecanol:

Into an oven-dried 50 mL round-bottom flask, 10-halodecan-1-ol (1 mmol) and p-toluenesulfonic acid monohydrate (catalytic amount) were dissolved in 20 mL of dichloromethane. The mixture was allowed to mix at 0° C. for 10 min. With stirring, 3,4-Dihydro-2H-pyran (5 mmol) dissolved in 10 mL of dichloromethane was then dropwise added to the reaction mixture at 0° C. The progress of the reaction was monitored by TLC and the reaction was observed to be completed within 3 hours. The reaction mixture was concentrated under reduced pressure and the resulting residue was purified by silica gel chromatography. Fractions contain the desired product were pulled and the solvent was removed under reduced pressure to afford the desired product.

THP-Protected 11-hexadecyn-1-ol:

To a −78° C. solution of 1-hexyne (5 mmol) in THF (20 mL), 2.5 M n-BuLi (5 mmol) in hexane is added dropwise via a syringe. A solution of THP-protected 10-halodecanol (5 mmol) and n-Bu$_4$NI (TBAI) (0.16 mmol) dissolve in THF is then dropwise added to the reaction mixture. The reaction mixture is allowed to warm to room temperature and then heat at 70° C. for 24 hours. The reaction is quenched with 5 mL of 1M NH$_4$Cl and extract with hexanes (3×). The organic fractions are combined, dry with anhydrous MgSO$_4$ and concentrate under reduced pressure. The resulting residue is purified by silica gel flash chromatography using 60:1/hexane:ethyl acetate as mobile phase to obtain the desired product, THP-protected 11-hexadecyn-1-ol, as pure component.

Scheme 33

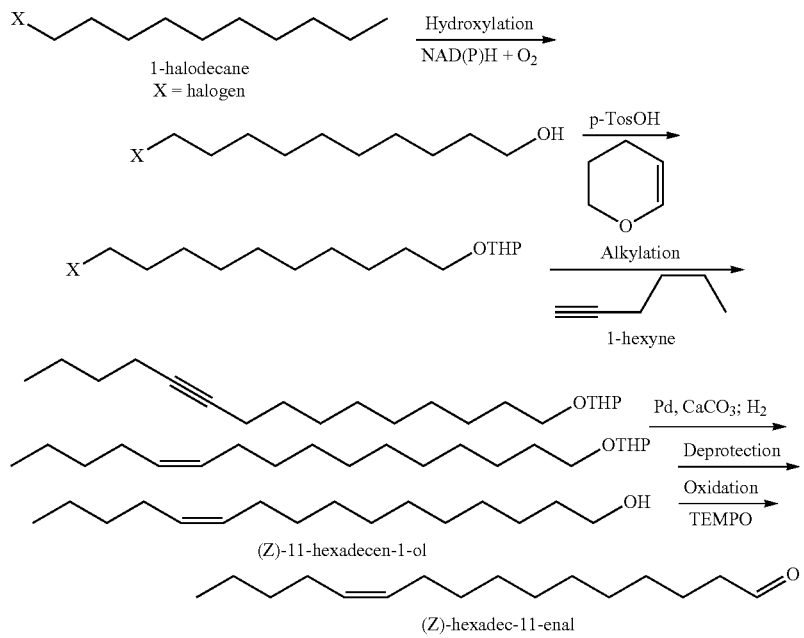

THP-Protected Z-11-Hexadecenol:

With stirring, a mixture of Lindlar's catalyst (40 mg) in pentane (10 mL) is put under a balloon of hydrogen for 90 min at 0° C. Quinoline (1 mg) is then added and the mixture is allowed to stir at 0° C. for another 30 min. A solution of THP-protected 11-hexadecyn-1-ol (55 mg) in 2 mL of pentane is then added to the reaction mixture via a syringe. The reaction is allowed to warm to room temperature and the progress of the reaction is monitored by GC. After 18 hours of reaction time, the reaction mixture is filtered through a No. 4 Whatman filter paper and the filtrate is concentrated under reduced pressure to afford the desired product.

Z-11-Hexadecenol:

THP-protected Z-11-hexadecenol (1 mmol) is dissolved in methanol (10 mL) with a catalytic amount of monohydrate p-TsOH. The mixture is heated to 70° C. for 30 min. The reaction solvent is removed under reduced pressure and the resulting residue is re-suspended in hexane and purified by silica gel flash chromatography using 9:1/hexane:ethyl acetate as mobile phase. Pure fractions containing the desired product is pulled and concentrated to dryness to provide the desired product, Z-11-hexadecenol.

Z-11-Hexadecenal:

To a 25 mL RBF, Pyridinium chlorochromate (PCC) (90 mg, 0.41 mmol) was dissolved in dichloromethane (15 mL) and the mixture was allowed to stir at ambient temperature for 10 min. A solution of Z-11-Hexadecen-1-ol (48 mg) in dichloromethane (15 ml) was then dropwise added to the reaction mixture. The progress of the oxidation was monitored by TLC and deemed to be finished within 2 hrs. The reaction mixture was filtered through a bed of silica and the filtrate was concentrated under reduced pressure. The resulting residue was purify by silica gel flash chromatography to provide 7 mg of Z-11-hexadecen-1-al, a yield of 14%.

Example 21

Synthesis of Codling Moth pheromone via hydroxylation of 1-bromohexane is carried out according to Scheme 34. Illustrated in Scheme 34 below are possible approaches to the synthesis of Codling Moth pheromone utilizing biohydroxylation of 1-bromohexane and (E,E)-2,4-hexadiene to generate 6-bromo-hexan-1-ol and (E,E)-2,4-hexadien-1-ol, respectively, as key and novel steps. Alternatively, (E,E)-2,4-hexadien-1-ol can be synthesized by reduction of sorbic acid with lithium aluminum hydride. In a similar fashion, 1-bromohexane was subjected to biohydroxylation to generate 1-bromohexanol. With appropriate chemical manipulation, the coupling of (E,E)-2,4-hexadien-1-ol derivative to 1-bromohexanol derivative can be carried out to obtain the desired Codling Moth pheromone as shown in Scheme 34 below.

(E,E)-2,4-Hexadien-1-ol:

(E,E)-2,4-hexadiene is subjected to biohydroxylation according to the process disclosed in Example 6 to generate (E,E)-2,4-hexadienol. The product is isolated by extraction of the fermentation broth with ethyl acetate and purified by distillation.

Alternatively, (E,E)-2,4-hexadienol can also be made by reduction of sorbic acid with one equivalent of lithium aluminium hydride in diethyl ether solvent according to known literature procedures.

Scheme 34

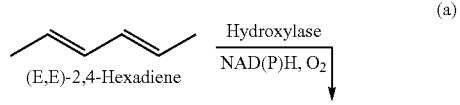

(a)

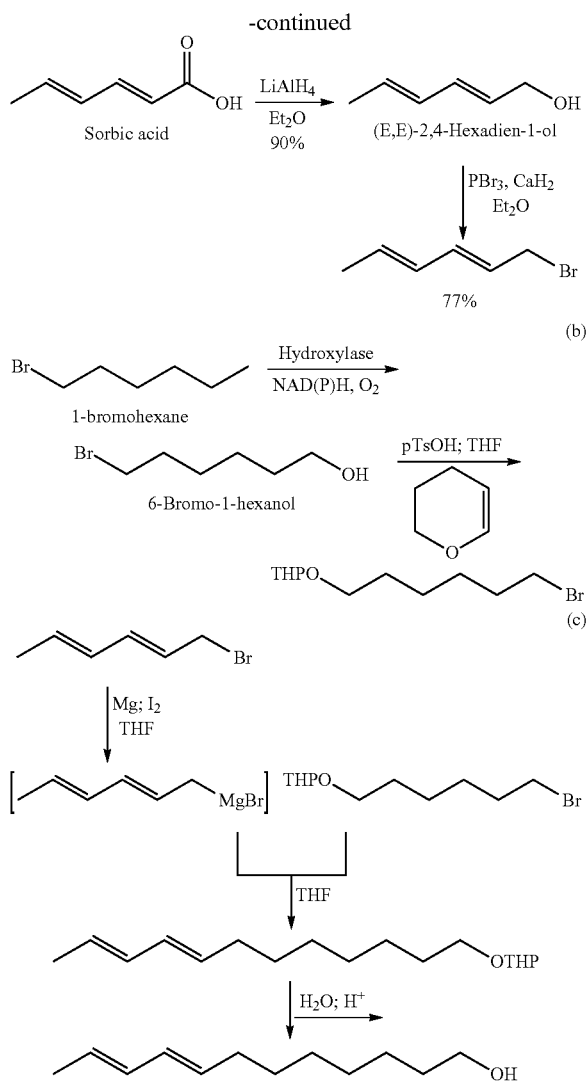

6-Bromo-1-hexanol:

1-Bromohexane is subjected to biohydroxylation according to the process disclosed in Example 6 to generate 6-bromo-1-hexanol. The product is isolated by extraction of the fermentation broth with ethyl acetate and purified by distillation.

THP-protected 6-bromo-1-hexanol:

Into an oven-dried 50 mL round-bottom flask, 6-Bromo-1-hexanol (1 mmol) and p-toluenesulfonic acid monohydrate (catalytic amount) are dissolved in 20 mL of dichloromethane. The mixture was allowed to mix at 0° C. for 10 min. With stirring, 3,4-Dihydro-2H-pyran (3 mmol) dissolved in 10 mL of dichloromethane was then dropwise added to the reaction mixture at 0° C. The progress of the reaction was monitored by TLC and the reaction was observed to be completed within 3 hours. The reaction mixture was concentrated under reduced pressure and the resulting residue was purified by silica gel chromatography. Fractions contain the desired product were pulled and the solvent was removed under reduced pressure to afford the desired product.

1-Bromo-2,3-Hexadiene:

Into an oven-dried 50 mL round-bottom flask, CaH$_2$ (1 mmol) is suspended in anhydrous THF (10 mL) at −78° C. and to this a solution of 2,4-hexadien-1-ol in 10 mL of THF is then dropwise added. The reaction solution is allowed to stir at −78° C. for 30 min. Phosphorus tribromide (1 mmol) dissolves in THF (10 mL) is then dropwise added to the reaction mixture via an addition funnel. The reaction mixture is allowed to warm to ambient temperature and allows to react until complete consumption of the starting material is achieved that can be monitored by TLC. The reaction mixture is quenched with 5 mL of 1 M NH4Cl and extracted three times with ethyl acetate. The organic fractions are combined, dry with anhydrous MgSO4, and concentrate to dryness. The resulting residue is purified by silica gel chromatography to obtain 1-bromo-2,3-hexadiene as pure compound.

THP-protected (8E,10E)-dodecadien-1-ol:

Into an oven-dried 50 mL round-bottom flask, freshly prepared magnesium strip (0.5 g) is added along with a few crystals of iodide and 10 mL of anhydrous THF. A solution of 1-bromo-2,3-hexadiene in THF (10 mL) is then dropwise added to the reaction vessel and a gentle reflux of the reaction mixture is maintained via a heating oil bath. A solution of THP-protected 6-bromo-1-hexanol (1 mmol) in THF (10 mL) is then dropwise added to the reaction mixture via an additional funnel. The reaction mixture is maintained at reflux and the progress of the reaction is monitored by TLC. Once the starting material, 1-bromo-2,3-hexadiene, is observed to have been consumed, the reaction is quenched with 10 mL of water. The reaction mixture is extracted with ethyl acetate (3×) and the organic fractions are combined, dry with anhydrous MgSO$_4$ and concentrate. THP-protected (8E,10E)-dodecadien-1-ol is further purified by silica gel chromatography.

(8E,10E)-dodecadien-1-ol:

THP-protected (8E,10E)-dodecadien-1-ol (1 mmol) is dissolved in methanol (10 mL) with a catalytic amount of monohydrate p-toluenesulphonic acid. The mixture is heated to 70° C. for 30 min. The reaction solvent is removed under reduced pressure and the resulting residue is re-suspended in hexane and purified by silica gel flash chromatography using 9:1/hexane:ethyl acetate as mobile phase. Pure fractions containing the desired product are combined and concentrated to dryness to provide the desired product, (8E,10E)-dodecadien-1-ol.

LIST OF REFERENCES

S. H. Malca, D. Scheps, L. Kuhnel, E. Venegas-Venegas, A. Seifert, B. M. Nestl, B. Hauer, Bacterial CYP153A monooxygenases for the synthesis of omega-hydroxylated fatty acids. *Chemical Communications* 48, 5115-5117 (2012)10.1039/c2cc18103g).

D. Weissbart, J. P. Salaun, F. Durst, P. Pflieger, C. Mioskowski, Regioselectivity of a plant lauric acid omega hydroxylase. Omega hydroxylation of cis and trans unsaturated lauric acid analogs and epoxygenation of the terminal olefin by plant cytochrome P-450. *Biochimica et Biophysica Acta, Lipids and Lipid Metabolism* 1124, 135-142 (1992); published online Epub//(10.1016/0005-2760(92)90089-E).

M. Bordeaux, A. Galarneau, J. Drone, Catalytic, Mild, and Selective Oxyfunctionalization of Linear Alkanes: Current Challenges. *Angew. Chem.-Int. Edit.* 51, 10712-10723 (2012)10.1002/anie.201203280).

Y. R. Ji, G. N. Mao, Y. Y. Wang, M. Bartlam, Structural insights into diversity and n-alkane biodegradation mechanisms of alkane hydroxylases. *Front. Microbiol.* 4, (2013); published online EpubMar (10.3389/fmicb.2013.00058).

E. G. Funhoff, U. Bauer, I. Garcia-Rubio, B. Witholt, J. B. van Beilen, CYP153A6, a soluble P450 oxygenase catalyzing terminal-alkane hydroxylation. *J. Bacteriol.* 188, 5220-5227 (2006); published online EpubJul (10.1128/jb.00286-06).

D. Scheps, S. H. Malca, H. Hoffmann, B. M. Nestl, B. Hauer, Regioselective omega-hydroxylation of medium-chain n-alkanes and primary alcohols by CYP153 enzymes from *Mycobacterium marinum* and *Polaromonas* sp strain J5666. *Org. Biomol. Chem.* 9, 6727-6733 (2011)10.1039/c1ob05565h).

J. B. Vanbeilen, J. Kingma, B. Witholt, Substrate-specificity of the alkane hydroxylase system of *Pseudomonas-oleovorans* GPO1. *Enzyme Microb. Technol.* 16, 904-911 (1994); published online EpubOct (10.1016/0141-0229 (94)90066-3).

T. Fujii, T. Narikawa, K. Takeda, J. Kato, Biotransformation of various alkanes using the *Escherichia coli* expressing an alkane hydroxylase system from *Gordonia* sp TF6. *Biosci. Biotechnol. Biochem.* 68, 2171-2177 (2004); published online EpubOct (10.1271/bbb.68.2171).

L. Feng, W. Wang, J. S. Cheng, Y. Ren, G. Zhao, C. X. Gao, Y. Tang, X. Q. Liu, W. Q. Han, X. Peng, R. L. Liu, L. Wang, Genome and proteome of long-chain alkane degrading *Geobacillus thermodenitrificans* NG80-2 isolated from a deep-subsurface oil reservoir. *Proc. Natl. Acad. Sci. U S A.* 104, 5602-5607 (2007); published online EpubMar (10.1073/pnas.0609650104).

U. Scheller, T. Zimmer, E. Kargel, W. H. Schunck, Characterization of the n-alkane and fatty acid hydroxylating cytochrome P450 forms 52A3 and 52A4. *Arch. Biochem. Biophys.* 328, 245-254 (1996); published online EpubApr (10.1006/abbi.1996.0170).

D. Kim, M. J. Cryle, J. J. De Voss, P. R. O. de Montellano, Functional expression and characterization of cytochrome P450 52A21 from *Candida albicans*. *Arch. Biochem. Biophys.* 464, 213-220 (2007); published online EpubAug (10.1016/j.abb.2007.02.032).

J. B. van Beilen, E. G. Funhoff, Expanding the alkane oxygenase toolbox: new enzymes and applications. *Curr. Opin. Biotechnol.* 16, 308-314 (2005); published online EpubJun (10.1016/j.copbio.2005.04.005).

T. H. M. Smits, M. A. Seeger, B. Witholt, J. B. van Beilen, New alkane-responsive expression vectors for *Escherichia coli* and *Pseudomonas*. *Plasmid* 46, 16-24 (2001); published online EpubJul (10.1006/plas.2001.1522).

T. H. M. Smits, B. Witholt, J. B. van Beilen, Functional characterization of genes involved in alkane oxidation by *Pseudomonas aeruginosa*. *Antonie Van Leeuwenhoek* 84, 193-200 (2003)10.1023/a:1026000622765).

C. Grant, J. M. Woodley, F. Baganz, Whole-cell bio-oxidation of n-dodecane using the alkane hydroxylase system of *P-putida* GPo1 expressed in *E-coil*. *Enzyme Microb. Technol.* 48, 480-486 (2011); published online EpubMay (10.1016/j.enzmictec.2011.01.008).

S. Cornelissen, M. K. Julsing, J. Volmer, O. Riechert, A. Schmid, B. Buhler, Whole-cell-based CYP153A6-catalyzed (S)-limonene hydroxylation efficiency depends on host background and profits from monoterpene uptake via AlkL. Biotechnology and Bioengineering 110, 1282-1292 (2013); published online EpubMay (10.1002/bit.24801).

M. K. Julsing, M. Schrewe, S. Cornelissen, I. Hermann, A. Schmid, B. Buhler, Outer Membrane Protein AlkL Boosts Biocatalytic Oxyfunctionalization of Hydrophobic Substrates in *Escherichia coli*. *Appl. Environ. Microbiol.* 78, 5724-5733 (2012); published online EpubAug (10.1128/aem.00949-12).

D. Scheps, S. H. Malca, S. M. Richter, K. Marisch, B. M. Nestl, B. Hauer, Synthesis of omega-hydroxy dodecanoic acid based on an engineered CYP153A fusion construct. *Microb. Biotechnol.* 6, 694-707 (2013); published online EpubNov (10.1111/1751-7915.12073).

M. Schrewe, A. O. Magnusson, C. Willrodt, B. Buhler, A. Schmid, Kinetic Analysis of Terminal and Unactivated C?H Bond Oxyfunctionalization in Fatty Acid Methyl Esters by Monooxygenase-Based Whole-Cell Biocatalysis. *Advanced Synthesis & Catalysis* 353, 3485-3495 (2011); published online EpubDec (10.1002/adsc.201100440).

D. L. Craft, K. M. Madduri, M. Eshoo, C. R. Wilson, Identification and characterization of the CYP52 family of *Candida tropicalis* ATCC 20336, important for the conversion of fatty acids and Alkanes to alpha,omega-dicarboxylic acids. *Appl. Environ. Microbiol.* 69, 5983-5991 (2003); published online EpubOct (10.1128/aem.69.10.5983-5991.2003).

U. Scheller, T. Zimmer, D. Becher, F. Schauer, W. H. Schunck, Oxygenation cascade in conversion of n-alkanes to alpha,omega-dioic acids catalyzed by cytochrome p450 52A3. *J. Biol. Chem.* 273, 32528-32534 (1998); published online EpubDec (10.1074/jbc.273.49.32528).

W. Seghezzi, C. Meili, R. Ruffiner, R. Kuenzi, D. Sanglard, A. Fiechter, Identification and characterization of additional members of the cytochrome-p450 multigene family CYP52 of *Candida-tropicalis*. *DNA Cell Biol.* 11, 767-780 (1992); published online EpubDec (10.1089/dna.1992.11.767).

T. Zimmer, M. Ohkuma, A. Ohta, M. Takagi, W. H. Schunck, The CYP52 multigene family of *Candida maltosa* encodes functionally diverse n-alkane-inducible cytochromes P450. *Biochem. Biophys. Res. Commun.* 224, 784-789 (1996); published online EpubJul (10.1006/bbrc.1996.1100).

W.-H. Lu, J. E. Ness, W.-C. Xie, X.-Y. Zhang, J. Minshull, R. A. Gross, Biosynthesis of Monomers for Plastics from Renewable Oils. *J. Am. Chem. Soc.* 132, 15451-15455 (2010)10.1021/ja107707v).

E. G. Funhoff, J. Salzmann, U. Bauer, B. Witholt, J. B. van Beilen, Hydroxylation and epoxidation reactions catalyzed by CYP153 enzymes. *Enzyme and Microbial Technology* 40, 806-812 (2007); published online EpubMar (10.1016/j.enzmictec.2006.06.014).

R. K. Gudiminchi, C. Randall, D. J. Opperman, O. A. Olaofe, S. T. L. Harrison, J. Albertyn, M. S. Smit, Whole-cell hydroxylation of n-octane by *Escherichia coli* strains expressing the CYP153A6 operon. *Appl. Microbiol. Biotechnol.* 96, 1507-1516 (2012); published online EpubDec (10.1007/s00253-012-3984-5).

Y. P. Dong, J. Yan, H. Q. Du, M. Chen, T. Ma, L. Feng, Engineering of LadA for enhanced hexadecane oxidation using random- and site-directed mutagenesis. *Appl. Microbiol. Biotechnol.* 94, 1019-1029 (2012); published online EpubMay (10.1007/s00253-012-4035-y).

Banthorpe D (1976) Purification and properties of alcohol oxidase from *Tanacetum vulgare*. Phytochemistry 15:391-394. doi: 10.1016/S0031-9422(00)86829-6

Bronner S M, Herbert M B, Patel P R, et al. (2014) Ru-based Z-selective metathesis catalysts with modified cyclometalated carbene ligands. Chem Sci 5:4091-4098. doi: 10.1039/C4SC01541J Buck M, Chong J M (2001) Alkylation of 1-alkynes in THF. Tetrahedron Lett 42:5825-5827. doi: http://dx.doi.org/10.1016/S0040-4039(01)01131-5

Cannon J S, Grubbs R H (2013) Alkene Chemoselectivity in Ruthenium-Catalyzed Z-Selective Olefin Metathesis. Angew Chemie, Int Ed 52:9001-9004. doi: 10.1002/anie.201302724

Cappaert L, Larroche C (2004) Oxidation of a mixture of 2-(R) and 2-(S)-heptanol to 2-heptanone by *Saccharomyces cerevisiae* in a biphasic system. Biocatal Biotransformation 22:291-296. doi: 10.1080/10242420400011992

Cardemil E (1978) Alcohol-oxidizing enzymes from various organisms. Comp Biochem Physiol B 60:1-7. doi: 10.1016/0305-0491(78)90019-6

Cheng Q, Liu H T, Bombelli P, et al. (2004) Functional identification of AtFao3, a membrane bound long chain alcohol oxidase in *Arabidopsis thaliana*. FEBS Lett 574: 62-68. doi: 10.1016/j.febslet.2004.07.086

Cheng Q, Sanglard D, Vanhanen S, et al. (2005) *Candida* yeast long chain fatty alcohol oxidase is a c-type haemoprotein and plays an important role in long chain fatty acid metabolism. Biochim Biophys Acta-Mol Cell Biol Lipids 1735:192-203. doi: 10.1016/j.bbalip.2005.06.006

Dienys G, Jarmalavičius B, Budriene S, et al. (2003) Alcohol oxidase from the yeast *Pichia pastoris*—A potential catalyst for organic synthesis. J. Mol. Catal. B Enzym. pp 47-49

Duff S J B, Murray W D (1988) Production and application of methylotrophic yeast *pichia-pastoris*. Biotechnol Bioeng 31:44-49. doi: 10.1002/bit.260310108

Eirich L D, Craft D L, Steinberg L, et al. (2004) Cloning and characterization of three fatty alcohol oxidase genes from *Candida tropicalis* strain ATCC 20336. Appl Environ Microbiol 70:4872-4879. doi: 10.1128/aem.70.8.4872-4879.2004

Endo K, Grubbs R H (2011) Chelated ruthenium catalysts for Z-selective olefin metathesis. J Am Chem Soc 133: 8525-8527. doi: 10.1021/ja202818v Ernst M, Kaup B, Muller M, et al. (2005) Enantioselective reduction of carbonyl compounds by whole-cell biotransformation, combining a formate dehydrogenase and a (R)-specific alcohol dehydrogenase. Appl Microbiol Biotechnol 66:629-634. doi: 10.1007/s00253-004-1765-5

Gabelman A, Luzio G A (1997) Enzymatic oxidation of alcohols to aldehydes in a continuous reaction system using *Candida boidinii*.

Goswami P, Chinnadayyala S S R, Chakraborty M, et al. (2013) An overview on alcohol oxidases and their potential applications. Appl Microbiol Biotechnol 97:4259-4275. doi: 10.1007/s00253-013-4842-9

Grubbs R H (2012) Synthesis of large and small molecules using olefin metathesis catalysts. PMSE Prepr No pp. given.

Hamberg M, Ponce de Leon I, Rodriguez M J, Castresana C (2005) α-Dioxygenases. Biochem Biophys Res Commun 338:169-174. doi: http://dx.doi.org/10.1016/j.bbrc.2005.08.117

Hartung J, Dornan P K, Grubbs R H (2014) Enantioselective Olefin Metathesis with Cyclometalated Ruthenium Complexes. J Am Chem Soc 136:13029-13037. doi: 10.1021/ja506611k Hartung J, Grubbs R H (2013) Highly Z-selective and enantioselective ring-opening/cross-metathesis catalyzed by a resolved stereogenic-at-Ru complex. J Am Chem Soc 135:10183-10185. doi: 10.1021/ja4046422

Herbert M B, Marx V M, Pederson R L, Grubbs R H (2013) Concise syntheses of insect pheromones using Z-selective cross metathesis. Angew Chem Int Ed Engl 52:310-314. doi: 10.1002/anie.201206079

Hommel R, Ratledge C (1990) Evidence for two fatty alcohol oxidases in the biosurfactant-producing yeast *Candida (Torulopsis) bombicola*. FEMS Microbiol Lett 58:183-186.

Hommel R K, Lassner D, Weiss J, Kleber H P (1994) The inducible microsomal fatty alcohol oxidase of *Candida (Torulopsis) apicola*. Appl Microbiol Biotechnol 40:729-734. doi: 10.1007/s002530050057

Hou C T, Patel R N, Laskin A I, et al. (1983) Thermostable NAD-linked secondary alcohol-dehydrogenase from propane-grown *pseudomonas-fluorescens* NRRL-B-1244. Appl Environ Microbiol 46:98-105.

Kaehne F, Buchhaupt M, Schrader J (2011) A recombinant alpha-dioxygenase from rice to produce fatty aldehydes using *E. coli*. Appl Microbiol Biotechnol 90:989-995. doi: 10.1007/s00253-011-3165-y Karra-Chaabouni M, Pulvin S, Meziani A, et al. (2003) Biooxidation of n-Hexanol by Alcohol Oxidase and Catalase in Biphasic and Micellar Systems Without Solvent. Biotechnol Bioeng 81:27-32. doi: 10.1002/bit.10452

Keitz B K, Endo K, Patel P R, et al. (2012a) Improved ruthenium catalysts for Z-selective olefin metathesis. J Am Chem Soc 134:693-699. doi: 10.1021/ja210225e Keitz B K, Fedorov A, Grubbs R H (2012b) Cis-selective ring-opening metathesis polymerization with ruthenium catalysts. J Am Chem Soc 134:2040-2043. doi: 10.1021/ja211676y Kemp G D, Dickinson F M, Ratledge C (1988) INDUCIBLE LONG-CHAIN ALCOHOL OXIDASE FROM ALKANE-GROWN *CANDIDA-TROPICALIS*. Appl Microbiol Biotechnol 29:370-374.

Kemp G D, Dickinson F M, Ratledge C (1991) ACTIVITY AND SUBSTRATE-SPECIFICITY OF THE FATTY ALCOHOL OXIDASE OF *CANDIDA-TROPICALIS* IN ORGANIC-SOLVENTS. Appl Microbiol Biotechnol 34:441-445.

Kemp G D, Dickinson F M, Ratledge C (1990) Light sensitivity of then-alkane-induced fatty alcohol oxidase from *Candida tropicalis* and *Yarrowia lipolytica*. Appl Microbiol Biotechnol 32:461-464. doi: 10.1007/BF00903783

Khan R K, Torker S, Hoveyda A H (2013) Readily accessible and easily modifiable Ru-based catalysts for efficient and Z-selective ring-opening metathesis polymerization and ring-opening/cross-metathesis. J Am Chem Soc 135: 10258-10261. doi: 10.1021/ja404208a Kumar A K, Goswami P (2006) Functional characterization of alcohol oxidases from *Aspergillus terreus* MTCC 6324. Appl Microbiol Biotechnol 72:906-911. doi: 10.1007/s00253-006-0381-y Liu X Q, Dong Y P, Zhang J, et al. (2009) Two novel metal-independent long-chain alkyl alcohol dehydrogenases from *Geobacillus thermodenitrificans* NG80-2. Microbiology-Sgm 155:2078-2085. doi: 10.1099/mic.0.027201-0

Lu W-H, Ness J E, Xie W-C, et al. (2010) Biosynthesis of Monomers for Plastics from Renewable Oils. J Am Chem Soc 132:15451-15455. doi: 10.1021/ja107707v Marx V M, Herbert M B, Keitz B K, Grubbs R H (2013) Stereoselective access to Z and E macrocycles by ruthenium-catalyzed Z-selective ring-closing metathesis and ethenolysis. J Am Chem Soc 135:94-97. doi: 10.1021/ja311241q Mauersberger S, Drechsler H, Oehme G, Muller H G (1992) SUBSTRATE-SPECIFICITY AND STEREOSELEC- TIVITY OF FATTY ALCOHOL OXIDASE FROM THE YEAST *CANDIDA-MALTOSA*. Appl Microbiol Biotechnol 37:66-73.

Moreau, R. A., Huang A H (1979) Oxidation of fatty alcohol in the cotyledons of jojoba seedlings. Arch Biochem Biophys 194:422-430. doi: 10.1016/0003-9861(79)90636-2

Murray W D, Duff S J B (1990) Biooxidation of aliphatic and aromatic high-molecular-weight alcohols by *pichia-pastoris* alcohol oxidase. Appl Microbiol Biotechnol 33:202-205.

Oprean I, Botar A A, Gansca L, Vasian I (2006) Synthesis of cis-7,8-epoxyoctadecane, species-specific component of the sex pheromone of nun moth *Lymantria monacha* (Lepidoptera, Limantriidae). Stud Univ Babes-Bolyai, Chem 51:33-38.

Ozimek P, Veenhuis M, Van Der Klei I J (2005) Alcohol oxidase: A complex peroxisomal, oligomeric flavoprotein. FEMS Yeast Res 5:975-983. doi: 10.1016/j.femsyr.2005.06.005

Pederson R L, Grubbs R H (2002) Metathesis syntheses of pheromones or their components. US Pat Appl Publ 63 pp., Cont.-in-part of U.S. Pat. No. 6,215,019.

Richard L. Pederson et al. Adv. Synth. Catal. 2002, 344, 728

M. Jordaan et al. *J. Mol. Catal. A: Chem.* 2006, 254, 145

Presecki A V, Makovsek K, Vasic-Racki D (2012) Coenzyme Regeneration in Hexanol Oxidation Catalyzed by Alcohol Dehydrogenase. Appl Biochem Biotechnol 167:595-611. doi: 10.1007/s12010-012-9712-x Pribisko M A, Ahmed T S, Grubbs R H (2014) Z-Selective ruthenium metathesis catalysts: Comparison of nitrate and nitrite X-type ligands. Polyhedron Ahead of Print. doi: 10.1016/j.poly.2014.06.055

Quigley B L, Grubbs R H (2014) Ruthenium-catalysed Z-selective cross metathesis of allylic-substituted olefins. Chem Sci 5:501-506. doi: 10.1039/c3sc52806e Rosebrugh L E, Herbert M B, Marx V M, et al. (2013) Highly active ruthenium metathesis catalysts exhibiting unprecedented activity and Z-selectivity. J Am Chem Soc 135:1276-1279. doi: 10.1021/ja311916m Ryland B L, Stahl S S (2014) Practical Aerobic Oxidations of Alcohols and Amines with Homogeneous Copper/TEMPO and Related Catalyst Systems. Angew Chemie Int Ed 53:8824-8838. doi: 10.1002/anie.201403110

Sato S, Sato F, Gotoh H, Yamada Y (2013) Selective Dehydration of Alkanediols into Unsaturated Alcohols over Rare Earth Oxide Catalysts. ACS Catal 3:721-734. doi: 10.1021/cs300781v Savitha J, Ratledge C (1991) Alcohol oxidase of *Aspergillus flavipes* grown on hexadecanol. FEMS Microbiol Lett 80:221-224. doi: 10.1111/j.1574-6968.1991.tb04665.x Schroer K, Mackfeld U, Tana I A W, et al. (2007) Continuous asymmetric ketone reduction processes with recombinant *Escherichia coli*. J Biotechnol 132:438-444. doi: 10.1016/j.jbiotec.2007.08.003

Shahane S, Bruneau C, Fischmeister C (2013) Z Selectivity: Recent Advances in one of the Current Major Challenges of Olefin Metathesis. Chem Cat Chem 5:3436-3459. doi: 10.1002/cctc.201300688

Smith A B, Beauchamp T J, LaMarche M J, et al. (2000) Evolution of a Gram-Scale Synthesis of (+)-Discodermolide. J Am Chem Soc 122:8654-8664. doi: 10.1021/ja0015287

Sugimoto K, Matsui K, Iijima Y, et al. (2014) Intake and transformation to a glycoside of (Z)-3-hexenol from infested neighbors reveals a mode of plant odor reception and defense. Proc Natl Acad Sci 111:7144-7149. doi: 10.1073/pnas.1320660111

Tani A, Sakai Y, Ishige T, Kato N (2000) Thermostable NADP(+)-dependent medium-chain alcohol dehydrogenase from *Acinetobacter* sp strain M-1: Purification and characterization and gene expression in *Escherichia coli*. Appl Environ Microbiol 66:5231-5235. doi: 10.1128/aem.66.12.5231-5235.2000

Van der Klei I J, Harder W, Veenhuis M (1991) Biosynthesis and assembly of alcohol oxidase, a peroxisomal matrix protein in methylotrophic yeasts: a review. Yeast 7:195-209. doi: 10.1002/yea.320070302

Vangnai A S, Arp D J (2001) An inducible 1-butanol dehydrogenase, a quinohaemoprotein, is involved in the oxidation of butane by "*Pseudomonas butanovora*." Microbiology-Uk 147:745-756.

Vanhanen S, West M, Kroon J T, et al. (2000) A consensus sequence for long-chain fatty-acid alcohol oxidases from *Candida* identifies a family of genes involved in lipid omega-oxidation in yeast with homologues in plants and bacteria. J Biol Chem 275:4445-4452. doi: 10.1074/jbc.275.6.4445

Zhao S, Lin Z, Ma W, et al. (2008) Cloning and characterization of long-chain fatty alcohol oxidase LjFAO1 in *Lotus japonicus*. Biotechnol Prog 24:773-779. doi: 10.1021/bp0703533

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

INFORMAL SEQUENCE LISTING

```
AlkB construct for DNA synthesis
Oligonucleotide Name: 1406_provivi 023
                                        SEQ ID NO: 1
AGCCATCATCATCATCATCACAGCAGC AlkB P1 construct for DNA synthesis
Oligonucleotide Name: 1406_provivi 024
                                        SEQ ID NO: 2
CACTATAGGGGAATTGTGAGCGGATAACAATTCC AlkB1A.p. construct for DNA synthesis
Oligonucleotide Name: 1406_provivi 025
                                        SEQ ID NO: 3
CTATAGGGGAATTGTGAGCGGATAACAATTCCC AlkB2A.p. construct for DNA synthesis
Oligonucleotide Name: 1406_provivi 026
                                        SEQ ID NO: 4
TGGTGGTGCTCGAGTGCGGCCGCAAGCTTCTAAT Fwd primer for alkB constructs
Oligonucleotide Name: oPV001
                                        SEQ ID NO: 5
CTTAAATCTCGTAGCGACTAATTTAATAAAAATTG Rev primer for alkB constructs
Oligonucleotide Name: oPV002
                                        SEQ ID NO: 6
AAACAGAAGCTTGGCTGCAGGTCG
```

```
Fwd primer from alkG
Oligonucleotide Name: oPV003
                                     SEQ ID NO: 7
CTTATTCCTGAGGATTGGTGCTGCC Rev primer from alkG
Oligonucleotide Name: oPV004
                                     SEQ ID NO: 8
GGCAGCACCAATCCTCAGGAATAAG Fwd primer from SfiI
Oligonucleotide Name: oPV005
                                     SEQ ID NO: 9
GATGCCGCTGGATCTGGCCTAGA CYP52A13 forward primer
Oligonucleotide Name: OPV 0042
                                     SEQ ID NO: 10
ATGACGGTTCATGACATCATCGC CYP52A13/A3 reverse primer
Oligonucleotide Name: OPV 0043
                                     SEQ ID NO: 11
CTGACATCCTCTTGAGCGGC CYP52A3 forward primer
Oligonucleotide Name: OPV 0044
                                     SEQ ID NO: 12
ATGGCTATTGAGCAGATTATCGAAG DNA sequence of the linearized construct for
expressing CYP52A3/CPR used for genome
integration
                                     SEQ ID NO: 13
AGATCCAATTCCCGCTTTGACTGCCTGAAATCTCCATCGCCTACAATGA

TGACATTTGGATTTGGTTGACTCATGTTGGTATTGTGAAATAGACGCAG

ATCGGGAACACTGAAAAATACACAGTTATTATTCATTTAAATAACATCC

AAAGACGAAAGGTTGAATGAAACCTTTTTGCCATCCGACATCCACAGGT

CCATTCTCACACATAAGTGCCAAACGCAACAGGAGGGGATACACTAGCA

GCAGACCGTTGCAAACGCAGGACCTCCACTCCTCTTCTCCTCAACACCC

ACTTTTGCCATCGAAAAACCAGCCCAGTTATTGGGCTTGATTGGAGCTC

GCTCATTCCAATTCCTTCTATTAGGCTACTAACACCATGACTTTATTAG

CCTGTCTATCCTGGCCCCCCTGGCGAGGTTCATGTTTGTTTATTTCCGA

ATGCAACAAGCTCCGCATTACACCCGAACATCACTCCAGATGAGGGCTT

TCTGAGTGTGGGGTCAAATAGTTTCATGTTCCCCAAATGGCCCAAAACT

GACAGTTTAAACGCTGTCTTGGAACCTAATATGACAAAAGCGTGATCTC

ATCCAAGATGAACTAAGTTTGGTTCGTTGAAATGCTAACGGCCAGTTGG

TCAAAAGAAACTTCCAAAGTCGGCATACCGTTTGTCTTGTTTGGTAT

TGATTGACGAATGCTCAAAAATAATCTCATTAATGCTTAGCGCAGTCTC

TCTATCGCTTCTGAACCCCGGTGCACCTGTGCCGAAACGCAAATGGGGA

ACACCCGCTTTTTGGATGATTATGCATTGTCTCCACATTGTATGCTTC

CAAGATTCTGGTGGGAATACTGCTGATAGCCTAACGTTCATGATCAAAA

TTTAACTGTTCTAACCCCTACTTGACAGCAATATATAAACAGAAGGAAG

CTGCCCTGTCTTAAACCTTTTTTTTATCATCATTATTAGCTTACTTTC

ATAATTGCGACTGGTTCCAATTGACAGCTTTTGATTTTAACGCTTTT

AACGACAACTTGAGAAGATCAAAAAACAACTAATTATTGAAAGAATTCC

GAAACGATGGCTTTGGATAAGTTGGATTTGTACGTCATCATTGTTCTTG

CTGTTGCTGTTGCTGCCTACTTTGCTAAAAACCAGTTCTTGGATCAACC

TCAGGACACTGGTTTCTTGTCAAACGATACAGCTGGTGGAAATAGTAGA

GATATCCTTGAAACTTTGAAGAAAAACAATAAGAACACATTGCTTTTGT

TCGGATCTCAAACCGGTACTGCTGAGGACTACGCCAATAAGCTTTCAAG

AGAAATCCATAGTAGATTCGGATTGAAAACTATGGTTGCCGATTTCGCA

GATTACGACTGGGATAACTTTGGTGACATCCCTAACGATATCTTGGTTT

TCTTTATCGTCGCCACCTATGGAGAGGGAGAACCAACTGACAACGCAGA

TGAGTTTCACACCTGGTTGACTGACGAAGCTGATACACTTTCCACCTTG

AGATACACCGTTTTCGGTTTGGGAAACTCAACTTACGAATTTTACAACG

CTATCGGTAGAAAGTTTGACAGACTTTTGGAAGAGAAAGGTGGAGAGAG

ATTTGCTGATTATGGTGAAGGAGATGACGGTACAGGAACCCTTGACGAG

GATTTCTTGACATGGAAGGACAACGTTTTCGATACCCTTAAAAACGATT

TGAACTTCGAAGAGAGAGTTGAAGTACGAACCTAACGTTAAGCTTAC

AGAAAGAGATGACTTGACCGTTGATGACTCTGAGGTCTCCTTGGGAGAA

CCAAATAAGAAATACATCCAATCTGAAGAGATCGACTTGACAAAGGGTC

CTTTTGATCATACCCACCCATATCTTGCAAAGATCTCTAAGACTAGAGA

GTTGTTTGCTTCCAAGGAAAGAAACTGTGTTCATGTCGAGTTCGATGTT

TCTGAATCCAATCTTAAGTACACTACAGGAGACCACTTGGCCGTTTGGC

CATCAAACAGTGATGAGAATATTGCAAAGTTCATCAAATGCTTTGGTTT

GGATGACAAGATTAACACTGTTTTCGAACTTAAAGCCTTGGATTCTACA

TACCAAATTCCATTCCCTAATCCAATCACCTATGGAGCAGTTGTCAGAC

ATCACTTGGAAATTTCAGGTCCTGTTAGTAGACAGTTTTTCCTTGCTAT

CGCCGGATTCGCTCCAGACGAAGAGACTAAGAAAACTTTTACAAGAATC

GGTAACGATAAGCAAGAATTTGCCAACAAGATCACAAGAAAGAAATTGA

ACGTTGCAGACGCTCTTTTGTTTGCTTCAAATGGTAGACCTTGGAGTGA

TGTTCCATTTGAGTTCATTATCGAAAACGTCCCTCATTTGCAACCAAGA

TACTACTCTATCTCTTCCTCAAGTTTGTCCGAGAAGCAGACTATTAATA

TCACAGCTGTTGTCGAAGTTGAAGAGGAAGCAGACGGAAGAGCTGTCAC

CGGTGTTGTCACTAACCTTTTGAAGAATATTGAGATCGAACAGAACAAG

ACTGGAGAAAAACCTGTTGTCCATTACGATTTGTCTGGTCCAAGAAACA

AGTTTAACAAGTTTAAGTTGCCTGTTCACGTCAGAAGATCCAACTTTAA

GCTTCCTAAAAATACCACTACACCAGTTATTTTGATCGGTCCTGGAACT

GGTGTTGCTCCACTTAGAGGTTTCGTCAGAGAGAGAGTTCAACAGGTCA

AGAACGGAGTTAACGTCGGTAAAACTGTTTTGTTTTATGGATGTAGAAA

CGAACATGATGACTTCTTGTACAAGCAAGAGTGGTCTGAATATGCTTCC

GTTTTGGGAGAGAATTTTGAAATGTTCACTGCCTTTTCTAGACAAGACC

CATCCAAGAAGTTTACGTCCAGGATAAGATTGCAGAAAACTCTAAAGT

TGTCAACGATCTTTTGAACGAAGGAGCTATCATCTATGTTTGCGGTGAC

GCCTCAAGAATGGCAAGAGATGTTCAAAGTACTATTGCTAAGATCGTCG

CCAAACACAGAGAGATTCAGGAAGATAAAGCTGTCGAGTTGGTTAAATC

CTGGAAAGTTCAGAATAGATATCAAGAAGATGTTTGGTAAGCGGCCGCT
```

```
CAAGAGGATGTCAGAATGCCATTTGCCTGAGAGATGCAGGCTTCATTTT
TGATACTTTTTTATTTGTAACCTATATAGTATAGGATTTTTTTGTCAT
TTTGTTTCTTCTCGTACGAGCTTGCTCCTGATCAGCCTATCTCGCAGCA
GATGAATATCTTGTGGTAGGGGTTTGGGAAAATCATTCGAGTTTGATGT
TTTTCTTGGTATTTCCCACTCCTCTTCAGAGTACAGAAGATTAAGTGAG
ACCTTCGTTTGTGCGGATCCAACATCCAAAGACGAAAGGTTGAATGAAA
CCTTTTTGCCATCCGACATCCACAGGTCCATTCTCACACATAAGTGCCA
AACGCAACAGGAGGGGATACACTAGCAGCAGACCGTTGCAAACGCAGGA
CCTCCACTCCTCTTCTCCTCAACACCCACTTTTGCCATCGAAAAACCAG
CCCAGTTATTGGGCTTGATTGGAGCTCGCTCATTCCAATTCCTTCTATT
AGGCTACTAACACCATGACTTTATTAGCCTGTCTATCCTGGCCCCCCTG
GCGAGGTTCATGTTTGTTTATTTCCGAATGCAACAAGCTCCGCATTACA
CCCGAACATCACTCCAGATGAGGGCTTTCTGAGTGTGGGGTCAAATAGT
TTCATGTTCCCCAAATGGCCCAAAACTGACAGTTTAAACGCTGTCTTGG
AACCTAATATGACAAAAGCGTGATCTCATCCAAGATGAACTAAGTTTGG
TTCGTTGAAATGCTAACGGCCAGTTGGTCAAAAAGAAACTTCCAAAAGT
CGGCATACCGTTTGTCTTGTTTGGTATTGATTGACGAATGCTCAAAAAT
AATCTCATTAATGCTTAGCGCAGTCTCTCTATCGCTTCTGAACCCCGGT
GCACCTGTGCCGAAACGCAAATGGGGAAACACCCGCTTTTTGGATGATT
ATGCATTGTCTCCACATTGTATGCTTCCAAGATTCTGGTGGGAATACTG
CTGATAGCCTAACGTTCATGATCAAAATTTAACTGTTCTAACCCCTACT
TGACAGCAATATATAAACAGAAGGAAGCTGCCCTGTCTTAAACCTTTTT
TTTTATCATCATTATTAGCTTACTTTCATAATTGCGACTGGTTCCAATT
GACAAGCTTTTGATTTTAACGACTTTTAACGACAACTTGAGAAGATCAA
AAAACAACTAATTATTGAAAGAATTCCGAAACGATGGCTATTGAGCAGA
TTATCGAAGAGGTTTTGCCTTACTTGACTAAATGGTACACTATCCTTTT
TGGTGCCGCTTTCACATACTTTTTGTCAATCGCACTTAGAAACAAATAC
TACGAGTACAAGTTGAAGTGTGAAAACCCACCTTACTTCAAGACTGCTG
GATTCGTTGGTATCCCTGGATTGATTGATGTCATCAAGGCTAAGAACGC
TGGTAAATTGGCCGATTACGCAGACCAAACATTTGACGAATACCCTCAT
CACAGTTTCTATATGACCGTTGCTGGAATGTTGAAAATTGTTCTTACTG
TCGATCCAGAAAACATCAAGGCTGTTCTTGCCACACAGTTTAATGACTT
CGCATTGGGTGCTAGACATGCCCACTTTGATCCATTGCTTGGAGACGGT
ATTTTCACCTTGGATGGAGAAGGTTGGAAACATTCCAGAGCAATGTTGA
GACCTCAATTTGCTAGAGAGCAGATTGCCCATGTTAAGGCATTGGAACC
ACACGTTCAAGTCCTTGCCAAGCAGATCAAATTGAACAAGGGAGAGACA
TTCGATTTGCAAGAATTGTTTTTCAGATTCACCGTTGACACAGCTACCG
AGTTTTTGTTCGGAGAATCAGTTCACAGTCTTTACGATGAGAAATTGGG
TGTCCCACCTCCAAACAATATTCCTGGAAGAGAAAACTTTGCTAAGGCC
TTCAATACCTCACAACATTATTTGGCTACTAGAACATACAGTCAGATGT
TCTATTTCTTGACTAACCCAAAGGAGTTTAGAGACTGCAATGCCAAAGT
```
```
TCACAAGCTTGCACAATACTTCGTCAATAAGGCATTGGATGCTTCTGAA
GACGAGGTTGCTGAGAAGTCCAAAGGTGGATACGTTTTCTTGTATGAAC
TTGTCAAACAGACTAGAGATCCTAAGGTTTTGCAAGACCAGTTGCTTAA
CATTATGGTCGCTGGTAGAGATACTACAGCCGGATTGCTTTCTTTTGCA
ATGTTCGAGCTTGCTAGAAACCCAAAGATCTGGAATAAGTTGAGAGAAG
AGATCGAAGTTAATTTTGGACTTGGTGAAGAGGCCAGAGTCGACGAAAT
CTCATTCGAGACTTTGAAGAAATGCGAGTACTTGAAGGCAGTTCTTAAC
GAAACATTGAGAATGTATCCTAGTGTTCCAGTCAATTTTAGAACCGCTA
CTAGAGATACCACTTTGCCTAGAGGTGGTGGTAAAGACGGTACTTCTCC
TATTTTCGTTCCAAAGGGATCTTCCGTTGTCTACACAGTCTATAAAACC
CATAGATTGGAAGAGTACTATGGTAAAGATGCTTACGAGTTTAGACCTG
AGAGATGGTTCGAACCATCCACTAGAAAATTGGGTTGGGCCTATGTTCC
TTTTAATGGAGGTCCAAGAATTTGCCTTGGACAACAGTTCGCTTTGACT
GAGGCCTCTTACGTTATCACAAGACTTGCTCAAATGTTTGAACACTTGG
AGTCCAAGGATGAAACTTATCCTCCAAACAAGTGTATCCATTTGACTAT
GAATCACAACGAAGGAGTTTTTATTTCTGCTAAGTAGGCGGCCGCTCAA
GAGGATGTCAGAATGCCATTTGCCTGAGAGATGCAGGCTTCATTTTTGA
TACTTTTTTATTTGTAACCTATATAGTATAGGATTTTTTTGTCATTTT
GTTTCTTCTCGTACGAGCTTGCTCCTGATCAGCCTATCTCGCAGCAGAT
GAATATCTTGTGGTAGGGGTTTGGGAAAATCATTCGAGTTTGATGTTTT
TCTTGGTATTTCCCACTCCTCTTCAGAGTACAGAAGATTAAGTGAGACC
TTCGTTTGTGCGGATCCTTCAGTAATGTCTTGTTTCTTTTGTTGCAGTG
GTGAGCCATTTTGACTTCGTGAAAGTTTCTTTAGAATAGTTGTTTCCAG
AGGCCAAACATTCCACCCGTAGTAAAGTGCAAGCGTAGGAAGACCAAGA
CTGGCATAAATCAGGTATAAGTGTCGAGCACTGGCAGGTGATCTTCTGA
AAGTTTCTACTAGCAGATAAGATCCAGTAGTCATGCATATGGCAACAAT
GTACCGTGTGGATCTAAGAACGCGTCCTACTAACCTTCGCATTCGTTGG
TCCAGTTTGTTGTTATCGATCAACGTGACAAGGTTGTCGATTCCGCGTA
AGCATGCATACCCAAGGACGCCTGTTGCAATTCCAAGTGAGCCAGTTCC
AACAATCTTTGTAATATTAGAGCACTTCATTGTGTTGCGCTTGAAAGTA
AAATGCGAACAAATTAAGAGATAATCTCGAAACCGCGACTTCAAACGCC
AATATGATGTGCGGCACACAATAAGCGTTCATATCCGCTGGGTGACTTT
CTCGCTTTAAAAAATTATCCGAAAAAATTTTCTAGAGTGTTGTTACTTT
ATACTTCCGGCTCGTATAATACGACAAGGTGTAAGGAGGACTAAACCAT
GGCTAAACTCACCTCTGCTGTTCCAGTCCTGACTGCTCGTGATGTTGCT
GGTGCTGTTGAGTTCTGGACTGATAGACTCGGTTTCTCCCGTGACTTCG
TAGAGGACGACTTTGCCGGTGTTGTACGTGACGACGTTACCCTGTTCAT
CTCCGCAGTTCAGGACCAGGTTGTGCCAGACAACACTCTGGCATGGGTA
TGGGTTCGTGGTCTGGACGAACTGTACGCTGAGTGGTCTGAGGTCGTGT
CTACCAACTTCCGTGATGCATCTGGTCCAGCTATGACCGAGATCGGTGA
```

```
ACAGCCCTGGGGTCGTGAGTTTGCACTGCGTGATCCAGCTGGTAACTGC
GTGCATTTCGTCGCAGAAGAGCAGGACTAACAATTGACACCTTACGATT
ATTTAGAGAGTATTTATTAGTTTTATTGTATGTATACGGATGTTTTATT
ATCTATTTATGCCCTTATATTCTGTAACTATCCAAAAGTCCTATCTTAT
CAAGCCAGCAATCTATGTCCGCGAACGTCAACTAAAAATAAGCTTTTTA
TGCTCTTCTCTCTTTTTTTCCCTTCGGTATAATTATACCTTGCATCCAC
AGATTCTCCTGCCAAATTTTGCATAATCCTTTACAACATGGCTATATGG
GAGCACTTAGCGCCCTCCAAAACCCATATTGCCTACGCATGTATAGGTG
TTTTTTTCCACAATATTTTCTCTGTGCTCTCTTTTTATTAAAGAGAAGCT
CTATATCGGAGAAGCTTCTGTGGCCGTTATATTCGGCCTTATCGTGGGA
CCACATTGCCTGAATTGGTTTGCCCCGGAAGATTGGGGAAACTTGGATC
TGATTACCTTAGCTGCAGGTACCACTGAGCGTCAGACCCCGTAGAAAAG
ATCAAAGGATCTTCTTGAGATCCTTTTTTTCTGCGCGTAATCTGCTGCT
TGCAAACAAAAAAACCACCGCTACCAGCGGTGGTTTGTTTGCCGGATCA
AGAGCTACCAACTCTTTTTCCGAAGGTAACTGGCTTCAGCAGAGCGCAG
ATACCAAATACTGTTCTTCTAGTGTAGCCGTAGTTAGGCCACCACTTCA
AGAACTCTGTAGCACCGCCTACATACCTCGCTCTGCTAATCCTGTTACC
AGTGGCTGCTGCCAGTGGCGATAAGTCGTGTCTTACCGGGTTGGACTCA
AGACGATAGTTACCGGATAAGGCGCAGCGGTCGGGCTGAACGGGGGGTT
CGTGCACACAGCCCAGCTTGGAGCGAACGACCTACACCGAACTGAGATA
CCTACAGCGTGAGCTATGAGAAAGCGCCACGCTTCCCGAAGGGAGAAAG
GCGGACAGGTATCCGGTAAGCGGCAGGGTCGGAACAGGAGAGCGCACGA
GGGAGCTTCCAGGGGAAACGCCTGGTATCTTTATAGTCCTGTCGGGTT
TCGCCACCTCTGACTTGAGCGTCGATTTTTGTGATGCTCGTCAGGGGGG
CGGAGCCTATGGAAAAACGCCAGCAACGCGGCCTTTTTACGGTTCCTGG
CCTTTTGCTGGCCTTTTGCTCACATGTTCTTTCCTGCGGTACCC
```

DNA sequence of the linearized construct for
expressing CYP52A13/CPR used for genome
integration
SEQ ID NO: 14

```
AGATCCAATTCCCGCTTTGACTGCCTGAAATCTCCATCGCCTACAATGA
TGACATTTGGATTTGGTTGACTCATGTTGGTATTGTGAAATAGACGCAG
ATCGGGAACACTGAAAAATACACAGTTATTATTCATTTAAATAACATCC
AAAGACGAAAGGTTGAATGAAACCTTTTTGCCATCCGACATCCACAGGT
CCATTCTCACACATAAGTGCCAAACGCAACAGGAGGGGATACACTAGCA
GCAGACCGTTGCAAACGCAGGACCTCCACTCCTCTTCTCCTCAACACCC
ACTTTTGCCATCGAAAAACCAGCCCAGTTATTGGGCTTGATTGGAGCTC
GCTCATTCCAATTCCTTCTATTAGGCTACTAACACCATGACTTTATTAG
CCTGTCTATCCTGGCCCCCTGGCGAGGTTCATGTTTGTTTATTTCCGA
ATGCAACAAGCTCCGCATTACACCCGAACATCACTCCAGATGAGGGCTT
TCTGAGTGTGGGGTCAAATAGTTTCATGTTCCCCAAATGGCCCAAAACT
GACAGTTTAAACGCTGTCTTGGAACCTAATATGACAAAAGCGTGATCTC
ATCCAAGATGAACTAAGTTTGGTTCGTTGAAATGCTAACGGCCAGTTGG
TCAAAAAGAAACTTCCAAAAGTCGGCATACCGTTTGTCTTGTTTGGTAT
TGATTGACGAATGCTCAAAAATAATCTCATTAATGCTTAGCGCAGTCTC
TCTATCGCTTCTGAACCCCGGTGCACCTGTGCCGAAACGCAAATGGGGA
AACACCCGCTTTTTGGATGATTATGCATTGTCTCCACATTGTATGCTTC
CAAGATTCTGGTGGGAATACTGCTGATAGCCTAACGTTCATGATCAAAA
TTTAACTGTTCTAACCCCTACTTGACAGCAATATATAAACAGAAGGAAG
CTGCCCTGTCTTAAACCTTTTTTTTTATCATCATTATTAGCTTACTTTC
ATAATTGCGACTGGTTCCAATTGACAAGCTTTTGATTTTAACGACTTTT
AACGACAACTTGAGAAGATCAAAAACAACTAATTATTGAAAGAATTCA
AAACGATGGCACTTGATAAACTAGATTTGTACGTGATTATCACCTTAGT
GGTTGCTATCGCTGCCTACTTCGCTAAAAACCAATTTCTGGACCAACAG
CAGGACACTGGATTTTGAATACTGATTCCGGTGATGGTAACTCCAGAG
ACATTTTACAAGCACTTAAGAAGAATAACAAAAATACTCTACTGTTATT
TGGATCACAAACTGGTACAGCTGAAGATTACGCCAACAAACTGTCCCGT
GAATTACATTCGAGGTTTGGATTGAAAACAATGGTTGCAGACTTCGCTG
ATTATGACTTCGAGAATTTCGGTGATATTACAGAGGACATTTTGGTCTT
TTTCATAGTCGCCACTTATGGTGAAGGTGAACCGACTGATAATGCTGAC
GAGTTCCACACTTGGCTGACCGAGGAGGCTGATACTTTGAGTACACTGA
AGTACACAGTTTTTGGATTGGGTAATTCTACTTACGAATTTTTCAACGC
TATTGGTAGGAAGTTCGACAGATTACTGGGTGAGAAAGGTGGCGACAGA
TTTGCTGAATACGGTGAAGGCGACGACGGTACTGGAACTTTGGATGAAG
ATTTCCTTGCTTGGAAGGACAACGTCTTTGATTCATTGAAAAATGATTT
GAATTTCGAGGAGAAAGAGCTTAAGTATGAACCAAACGTAAAATTGACC
GAAAGGGACGATTTGAGCGGTAATGATCCAGATGTATCTCTAGGTGAAC
CTAATGTGAAATACATCAAAAGTGAAGGTGTGGACCTTACCAAAGGACC
TTTCGACCATACCCATCCCTTTTTGGCAAGGATCGTGAAAACAAAAGAG
TTGTTCACAAGCGAAGATAGACACTGTGTTCATGTAGAGTTTGACATAT
CCGAATCAAACCTTAAGTACACAACAGGTGACCATCTGGCAATCTGGCC
ATCAAATTCTGATGAGAATATCAAGCAATTTGCCAAGTGTTTTGGACTG
GAGGATAAGCTCGACACTGTCATTGAATTGAAGGCATTGGACTCAACGT
ATTCTATTCCATTTCCAAATCCTATCACCTACGGTCAGTTATCAGACA
CCATCTAGAAATAAGTGGTCCTGTCTCAAGACAATTTTTCCTCTCCATC
GCCGGATTTGCTCCAGATGAGGAGACTAAAAAGTCCTTCACTAGAATTG
GTGGAGACAAACAGGAGTTCGCCAGCAAGGTAACTAGACGTAAGTTTAA
CATCGCTGATGCCCTTTTGTTCGCTTCCAACAATCGTCCGTGGTCTGAC
GTTCCATTCGAGTTTCTAATTGAAAATGTTCAACACTTGACACCACGTT
ATTACTCTATTTCCTCAAGCTCCCTATCAGAAAACAGACCATTAATGT
TACAGCTGTGGTTGAAGCTGAGGAGGAAGCAGACGGCAGGCCTGTTACG
GGAGTTGTGACAAATCTGCTTAAAAACATTGAAATTGAACAAAATAAGA
CGGGAGAAACTCCTATGGTTCACTATGACTTGAATGGTCCAAGAGGTAA
```

```
GTTCTCCAAGTTCAGACTGCCCGTTCACGTTAGAAGATCCAACTTTAAG
CTCCCAAAGAACTCGACTACACCCGTCATCTTGATTGGTCCAGGTACAG
GTGTTGCCCCTTTGAGAGGATTCGTTAGAGAACGTGTACAGCAAGTGAA
AAACGGTGTCAATGTGGGTAAAACGGTTTTGTTTTATGGATGTAGAAAT
TCCGAACAAGACTTCCTGTACAAGCAGGAATGGTCTGAGTATGCTTCGG
TGCTAGGTGAGAACTTTGAGATGTTCAATGCATTCAGTCGTCAAGACCC
TACTAAAAGGTGTACGTTCAAGATAAAATCTTAGAAAATTCTGCACTT
GTAGATGAGTTGCTCTCTTCTGGAGCCATAATCTACGTGTGCGGAGATG
CTAGTCGTATGGCAAGAGATGTCCAAGCAGCTATCGCTAAAATCGTCGC
TAAGTCACGAGACATCCATGAAGATAAGGCCGCAGAGTTGGTGAAGAGC
TGGAAAGTTCAAAATCGTTATCAGGAGGATGTTTGGTAAGCGGCCGCTC
AAGAGGATGTCAGAATGCCATTTGCCTGAGAGATGCAGGCTTCATTTTT
GATACTTTTTTATTTGTAACCTATATAGTATAGGATTTTTTTTGTCATT
TTGTTTCTTCTCGTACGAGCTTGCTCCTGATCAGCCTATCTCGCAGCAG
ATGAATATCTTGTGGTAGGGGTTTGGGAAAATCATTCGAGTTTGATGTT
TTTCTTGGTATTTCCCACTCCTCTTCAGAGTACAGAAGATTAAGTGAGA
CCTTCGTTTGTGCGGATCCAACATCCAAAGACGAAAGGTTGAATGAAAC
CTTTTTGCCATCCGACATCCACAGGTCCATTCTCACACATAAGTGCCAA
ACGCAACAGGAGGGGATACACTAGCAGCAGACCGTTGCAAACGCAGGAC
CTCCACTCCTCTTCCTCAACACCCACTTTTGCCATCGAAAAACCAGC
CCAGTTATTGGGCTTGATTGGAGCTCGCTCATTCCAATTCCTTCTATTA
GGCTACTAACACCATGACTTTATTAGCCTGTCTATCCTGGCCCCCCTGG
CGAGGTTCATGTTTGTTTATTTCCGAATGCAACAAGCTCCGCATTACAC
CCGAACATCACTCCAGATGAGGGCTTTCTGAGTGTGGGGTCAAATAGTT
TCATGTTCCCCAAATGGCCCAAAACTGACAGTTTAAACGCTGTCTTGGA
ACCTAATATGACAAAAGCGTGATCTCATCCAAGATGAACTAAGTTTGGT
TCGTTGAAATGCTAACGGCCAGTTGGTCAAAAAGAAACTTCCAAAGTC
GGCATACCGTTTGTCTTGTTTGGTATTGATTGACGAATGCTCAAAAATA
ATCTCATTAATGCTTAGCGCAGTCTCTCTATCGCTTCTGAACCCCGGTG
CACCTGTGCCGAAACGCAAATGGGGAAACACCCGCTTTTTGGATGATTA
TGCATTGTCTCCACATTGTATGCTTCCAAGATTCTGGTGGGAATACTGC
TGATAGCCTAACGTTCATGATCAAAATTTAACTGTTCTAACCCCTACTT
GACAGCAATATATAAACAGAAGGAAGCTGCCCTGTCTTAAACCTTTTTT
TTTATCATCATTATTAGCTTACTTTCATAATTGCGACTGGTTCCAATTG
ACAAGCTTTTGATTTTAACGACTTTTAACGACAACTTGAGAAGATCAAA
AAACAACTAATTATTGAAAGAATTCAAAACGATGACGGTTCATGACATC
ATCGCTACTTACTTCACAAAGTGGTACGTTATCGTTCCTTTAGCCCTTA
TTGCATACAGAGTGCTGGATTACTTCTATGGTAGGTACTTAATGTATAA
GTTGGGTGCAAAACCATTTTTCCAGAAACAGACCGACGGTTGTTTCGGT
TTTAAGGCTCCTTTGGAATTGCTTAAAAAGAAATCAGACGGTACTCTGA
TCGACTTTACATTGCAAAGGATACACGATCTGGATAGACCTGACATTCC
```
```
CACTTTTACTTTTCCAGTATTCAGCATTAATCTTGTTAACACTCTCGAA
CCAGAGAACATAAAAGCTATTTTGGCAACGCAATTCAATGATTTCTCCT
TGGGTACCAGACACTCCCACTTTGCTCCACTCCTCGGTGATGGTATTTT
CACACTGGACGGTGCAGGATGGAAGCATTCTAGATCCATGCTAAGGCCA
CAATTTGCAAGAGAGCAGATTTCCCATGTGAAGCTGTTGGAGCCACATG
TGCAGGTCTTTTTCAAGCACGTCCGTAAGGCTCAAGGAAAAACTTTTGA
TATTCAGGAGTTGTTTTTCAGATTGACTGTTGATTCAGCCACCGAATTT
TTGTTCGGAGAAAGTGTTGAATCGCTGCGTGACGAATCAATTGGAATGA
GCATCAACGCACTTGATTTCGATGGTAAAGCAGGTTTTGCTGATGCTTT
TAACTACTCTCAAAACTACCTTGCTTCAAGAGCTGTGATGCAACAACTG
TACTGGGTTTTGAATGGTAAAAAGTTTAAGGAATGCAATGCCAAGGTAC
ACAAGTTCGCTGACTATTATGTTAACAAAGCTCTTGATCTAACACCTGA
GCAATTGGAAAAACAAGACGGCTACGTTTTCCTATATGAGTTGGTTAAA
CAAACTAGAGACAAACAAGTTTTACGTGATCAGTTGTTGAATATCATGG
TAGCTGGCCGAGATACAACAGCAGGACTGTTGTCGTTCGTCTTTTTCGA
ACTGGCCAGAAATCCCGAAGTCACAAACAAACTGAGAGAAGAGATCGAG
GACAAGTTTGGTTTAGGTGAGAATGCTAGTGTTGAGGACATCAGCTTTG
AATCTTTAAAGTCCTGTGAGTACTTGAAGGCTGTGCTGAATGAAACTTT
GCGTTTATATCCATCTGTTCCTCAAAATTTCCGTGTCGCTACCAAAAAT
ACGACATTGCCAAGAGGAGGAGGCAAAGACGGTCTGAGTCCTGTACTAG
TCAGAAAAGGTCAGACTGTGATCTACGGAGTTTATGCAGCCCATAGAAA
TCCTGCCGTATATGGAAAAGATGCTTTGGAGTTTCGTCCGGAGAGATGG
TTTGAACCAGAAACCAAAAAGCTCGGATGGGCTTTCCTTCCATTCAATG
GTGGTCCCAGGATATGTTTAGGTCAACAATTCGCTTTAACTGAAGCATC
CTACGTGACAGTGCGTTTGTTACAAGAGTTTGCACATCTTTCCATGGAC
CCAGACACTGAGTATCCTCCTAAAAAGATGTCTCATTTGACTATGTCTT
TGTTCGATGGTGCAAACATTGAAATGTATTAAGCGGCCGCTCAAGAGGA
TGTCAGAATGCCATTTGCCTGAGAGATGCAGGCTTCATTTTTGATACTT
TTTTATTTGTAACCTATATAGTATAGGATTTTTTTGTCATTTTGTTTC
TTCTCGTACGAGCTTGCTCCTGATCAGCCTATCTCGCAGCAGATGAATA
TCTTGTGGTAGGGGTTTGGGAAAATCATTCGAGTTTGATGTTTTCTTG
GTATTTCCCACTCCTCTTCAGAGTACAGAAGATTAAGTGAGACCTTCGT
TTGTGCGGATCCTTCAGTAATGTCTTGTTTCTTTTGTTGCAGTGGTGAG
CCATTTTGACTTCGTGAAAGTTTCTTTAGAATAGTTGTTTCCAGAGGCC
AAACATTCCACCCGTAGTAAAGTGCAAGCGTAGGAAGACCAAGACTGGC
ATAAATCAGGTATAAGTGTCGAGCACTGGCAGGTGATCTTCTGAAAGTT
TCTACTAGCAGATAAGATCCAGTAGTCATGCATATGGCAACAATGTACC
GTGTGGATCTAAGAACGCGTCCTACTAACCTTCGCATTCGTTGGTCCAG
TTTGTTGTTATCGATCAACGTGACAAGGTTGTCGATTCCGCGTAAGCAT
GCATACCCAAGGACGCCTGTTGCAATTCCAAGTGAGCCAGTTCCAACAA
```

-continued

TCTTTGTAATATTAGAGCACTTCATTGTGTTGCGCTTGAAAGTAAAATG

CGAACAAATTAAGAGATAATCTCGAAACCGCGACTTCAAACGCCAATAT

GATGTGCGGCACACAATAAGCGTTCATATCCGCTGGGTGACTTTCTCGC

TTTAAAAAATTATCCGAAAAAATTTTCTAGAGTGTTGTTACTTTATACT

TCCGGCTCGTATAATACGACAAGGTGTAAGGAGGACTAAACCATGGCTA

AACTCACCTCTGCTGTTCCAGTCCTGACTGCTCGTGATGTTGCTGGTGC

TGTTGAGTTCTGGACTGATAGACTCGGTTTCTCCCGTGACTTCGTAGAG

GACGACTTTGCCGGTGTTGTACGTGACGACGTTACCCTGTTCATCTCCG

CAGTTCAGGACCAGGTTGTGCCAGACAACACTCTGGCATGGGTATGGGT

TCGTGGTCTGGACGAACTGTACGCTGAGTGGTCTGAGGTCGTGTCTACC

AACTTCCGTGATGCATCTGGTCCAGCTATGACCGAGATCGGTGAACAGC

CCTGGGGTCGTGAGTTTGCACTGCGTGATCCAGCTGGTAACTGCGTGCA

TTTCGTCGCAGAAGAGCAGGACTAACAATTGACACCTTACGATTATTTA

GAGAGTATTTATTAGTTTTATTGTATGTATACGGATGTTTTATTATCTA

TTTATGCCCTTATATTCTGTAACTATCCAAAAGTCCTATCTTATCAAGC

CAGCAATCTATGTCCGCGAACGTCAACTAAAAATAAGCTTTTTATGCTC

TTCTCTCTTTTTTTCCCTTCGGTATAATTATACCTTGCATCCACAGATT

CTCCTGCCAAATTTTGCATAATCCTTTACAACATGGCTATATGGGAGCA

CTTAGCGCCCTCCAAAACCCATATTGCCTACGCATGTATAGGTGTTTTT

-continued

TCCACAATATTTTCTCTGTGCTCTCTTTTTATTAAAGAGAAGCTCTATA

TCGGAGAAGCTTCTGTGGCCGTTATATTCGGCCTTATCGTGGGACCACA

TTGCCTGAATTGGTTTGCCCCGGAAGATTGGGGAAACTTGGATCTGATT

ACCTTAGCTGCAGGTACCACTGAGCGTCAGACCCCGTAGAAAAGATCAA

AGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGC

TACCAACTCTTTTTCCGAAGGTAACTGGCTTCAGCAGAGCGCAGATACC

AAATACTGTTCTTCTAGTGTAGCCGTAGTTAGGCCACCACTTCAAGAAC

TCTGTAGCACCGCCTACATACCTCGCTCTGCTAATCCTGTTACCAGTGG

CTGCTGCCAGTGGCGATAAGTCGTGTCTTACCGGGTTGGACTCAAGACG

ATAGTTACCGGATAAGGCGCAGCGGTCGGGCTGAACGGGGGGTTCGTGC

ACACAGCCCAGCTTGGAGCGAACGACCTACACCGAACTGAGATACCTAC

AGCGTGAGCTATGAGAAAGCGCCACGCTTCCCGAAGGGAGAAAGGCGGA

CAGGTATCCGGTAAGCGGCAGGGTCGGAACAGGAGAGCGCACGAGGGAG

CTTCCAGGGGAAACGCCTGGTATCTTTATAGTCCTGTCGGGTTTCGCC

ACCTCTGACTTGAGCGTCGATTTTTGTGATGCTCGTCAGGGGGGCGGAG

CCTATGGAAAAACGCCAGCAACGCGGCCTTTTTACGGTTCCTGGCCTTT

TGCTGGCCTTTTGCTCACATGTTCTTTCCTGCGGTACCC

What is claimed is:

1. A method for synthesizing an olefinic alcohol product, the method comprising incubating an unsaturated hydrocarbon substrate with an enzyme to form an unsaturated hydrocarbon alcohol;
   wherein the enzyme is a bacterial cytochrome P450 of the CYP153 family selected from the group consisting of SEQ ID NO: 15, SEQ ID NO: 16, SEQ ID NO: 17, SEQ ID NO: 18, and SEQ ID NO: 19 or a variant thereof having at least 90% identity thereto; or
   wherein the enzyme is a fungal cytochrome P450 of the CYP52 family selected from the group consisting of SEQ ID NO: 23, SEQ ID NO: 24, SEQ ID NO: 33, SEQ ID NO: 35, SEQ ID NO: 38, SEQ ID NO: 41, SEQ ID NO: 42, SEQ ID NO: 44, SEQ ID NO: 51, SEQ ID NO: 53, SEQ ID NO: 54, SEQ ID NO: 57, SEQ ID NO: 58, SEQ ID NO: 61, SEQ ID NO: 71, SEQ ID NO: 72, SEQ ID NO: 92, or a variant thereof having at least 90% identity thereto;
   wherein the unsaturated hydrocarbon substrate is a linear symmetric alkene having the formula $H(CH_2)_m(CH=CH)(CH_2)_mH$ or a linear asymmetric alkene having the formula $H(CH_2)_m(CH=CH)(CH_2)_nH$, wherein m and n are different integers between 1 and 17;
   wherein the unsaturated hydrocarbon alcohol has the formula $H(CH_2)_m(CH=CH)(CH_2)_mOH$ or the formula $H(CH_2)_m(CH=CH)(CH_2)_nOH$, wherein m and n are different integers between 1 and 17;
   wherein the unsaturated hydrocarbon substrate comprises a mixture of E alkene and Z alkene; and
   wherein the Z:E isomeric ratio of the unsaturated hydrocarbon alcohol is greater than the Z:E isomeric ratio of the unsaturated hydrocarbon substrate.

2. The method of claim 1, wherein the unsaturated hydrocarbon alcohol is the olefinic alcohol product.

3. The method of claim 1, further comprising converting the unsaturated hydrocarbon alcohol to the olefinic alcohol product.

4. The method of claim 1, wherein the Z:E isomeric ratio of the unsaturated hydrocarbon alcohol is at least about 1.25 times greater than the Z:E isomeric ratio of the unsaturated hydrocarbon substrate.

5. The method of claim 1, wherein the Z:E isomeric ratio of the unsaturated hydrocarbon alcohol is at least about 10 times greater than the Z:E isomeric ratio of the unsaturated hydrocarbon substrate.

6. The method of claim 1, wherein the olefinic alcohol product is a pheromone.

7. The method of claim 1, wherein the olefinic alcohol product is selected from Table 1.

8. A method for synthesizing an olefinic aldehyde product, the method comprising oxidizing the olefinic alcohol product synthesized in accordance with the method of claim 1 to form an olefinic aldehyde product.

9. The method of claim 8, wherein the olefinic aldehyde product is a pheromone.

10. The method of claim 8, wherein the olefinic aldehyde product is selected from Table 1.

11. A method for synthesizing an olefinic ester product, the method comprising esterifying the olefinic alcohol product synthesized in accordance with the method of claim 1 to form an olefinic ester product.

12. The method of claim 11, wherein the olefinic ester product is an acetate ester.

13. The method of claim 11, wherein the olefinic ester product is a pheromone.

14. The method of claim 11, wherein the olefinic ester product is selected from Table 1.

15. A method for synthesizing an olefinic acid product, the method comprising oxidizing the olefinic alcohol product synthesized in accordance with the method of claim 1 to form an olefinic acid product.

16. The method of claim 1, wherein the enzyme is active in a whole cell.

17. The method of claim 1, wherein the enzyme is selected from the group consisting of SEQ ID NO: 15; SEQ ID NO: 16; SEQ ID NO: 17; SEQ ID NO: 18; SEQ ID NO:

19; SEQ ID NO: 23; and SEQ ID NO: 24, or a variant thereof having at least 90% identity thereto.

18. The method of claim 1, wherein the bacterial or fungal cytochrome P450 is selected from the group consisting of SEQ ID NO: 15; SEQ ID NO: 16; SEQ ID NO: 17; SEQ ID NO: 18; SEQ ID NO: 19; SEQ ID NO: 23; and SEQ ID NO: 24, or a variant thereof having at least 95% identity thereto.

19. The method of claim 1, wherein the bacterial or fungal cytochrome P450 is selected from the group consisting of SEQ ID NO: 15; SEQ ID NO: 16; SEQ ID NO: 17; SEQ ID NO: 18; SEQ ID NO: 19; SEQ ID NO: 23; and SEQ ID NO: 24.

* * * * *

UNITED STATES PATENT AND TRADEMARK OFFICE
CERTIFICATE OF CORRECTION

PATENT NO. : 10,202,620 B2  
APPLICATION NO. : 14/845212  
DATED : February 12, 2019  
INVENTOR(S) : Pedro Coelho et al.

Page 1 of 1

It is certified that error appears in the above-identified patent and that said Letters Patent is hereby corrected as shown below:

In the Claims

In Column 437, Line 47, Claim 1, "SEQ ID NO: 72, SEQ ID NO: 92" should read -- SEQ ID NO: 72, and SEQ ID NO: 92 --

Signed and Sealed this  
Twenty-third Day of April, 2019

Andrei Iancu  
*Director of the United States Patent and Trademark Office*